US007897367B2

(12) United States Patent
Klaenhammer et al.

(10) Patent No.: US 7,897,367 B2
(45) Date of Patent: Mar. 1, 2011

(54) LACTOBACILLUS ACIDOPHILUS NUCLEIC ACID SEQUENCES ENCODING PROTEASE HOMOLOGUES AND USES THEREFORE

(75) Inventors: Todd R. Klaenhammer, Raleigh, NC (US); Eric Altermann, Palmerston North (NZ); W. Michael Russell, Newburgh, IN (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/251,501

(22) Filed: Oct. 15, 2008

(65) Prior Publication Data

US 2011/0020900 A1  Jan. 27, 2011

Related U.S. Application Data

(62) Division of application No. 11/062,665, filed on Feb. 22, 2005, now Pat. No. 7,455,992.

(60) Provisional application No. 60/546,745, filed on Feb. 23, 2004.

(51) Int. Cl.
*C12P 21/06* (2006.01)

(52) U.S. Cl. .................. 435/69.1; 435/320.1; 435/6; 435/7.1; 435/252; 530/350

(58) Field of Classification Search .................. None
See application file for complete search history.

(56) References Cited

U.S. PATENT DOCUMENTS

| 5,837,509 | A  | 11/1998 | Israelsen et al. |
| 6,451,584 | B2 | 9/2002  | Tomita et al. |
| 6,476,209 | B1 | 11/2002 | Glenn et al. |
| 6,544,772 | B1 | 4/2003  | Glenn et al. |
| 6,635,460 | B1 | 10/2003 | Van Hijum et al. |
| 2002/0159976 | A1 | 10/2002 | Glenn et al. |
| 2003/0138822 | A1 | 7/2003  | Glenn et al. |
| 2004/0009490 | A1 | 1/2004  | Glenn et al. |
| 2004/0208863 | A1 | 10/2004 | Versalovic et al. |
| 2005/0003510 | A1 | 1/2005  | Chang et al. |
| 2005/0112612 | A1 | 5/2005  | Klaenhammer et al. |
| 2005/0123941 | A1 | 6/2005  | Barrangou et al. |

FOREIGN PATENT DOCUMENTS

| EP | 633316 | 11/1995 |
| EP | 0 888 118 B1 | 1/1999 |
| WO | WO 02/12506 A1 | 2/2002 |
| WO | WO 02/074798 A2 | 9/2002 |
| WO | WO 03/084989 A2 | 10/2003 |
| WO | WO 2004/020467 A2 | 3/2004 |
| WO | WO 2004/031389 A1 | 4/2004 |
| WO | WO 2004/069178 A2 | 8/2004 |
| WO | WO 2004/096992 A2 | 11/2004 |
| WO | WO 2005/001057 A2 | 1/2005 |
| WO | WO 2005/012491 A2 | 2/2005 |

OTHER PUBLICATIONS (Wells, Biochemistry, vol. 29, pp. 8509-8517, 1990).*
Seffernick et al. (J. Bacteriology, vol. 183, pp. 2405-2410, 2001).*
Abee et al. (1994) "Kinetic studies of the action of lactacin F, a bacteriocin produced by *Lactobacillus johnsonii* that forms poration complexes in the cytoplasmic membrane" *Appl. Environ. Microbiol.* 60:1006-10013.
Allison and Klaenhammer (1996) "Functional analysis of the gene encoding immunity to lactacin F, *lafI*, and its use as a *Lactobacillus*-specific, food-grade genetic marker" *Appl. Environ. Microbiol.* 62:4450-4460.
Allison and Klaenhammer (1999) "Genetics of bacteriocins produced by lactic acid bacteria and their use in novel industrial applications" in *Manual of Industrial Microbiology and Biotechnology*. DeMain and Davies (eds.), ASM Press, Washington, D.C., pp. 789-808.
Allison et al. (1994) "Expansion of bacteriocin activity and host range upon complementation of two peptides encoded with the lactacin F operon" *J. Bacteriol.* 176:2235-2241.
Altermann et al. (2004) "Identification and phenotypic characterization of the cell-division protein CdpA" *Gene* 342:189-197.
Altermann et al. (2005) "Complete genome sequence of the probiotic lactic acid bacterium *Lactobacillus acidophilus* NCFM" *Proc. Natl. Acad. Sci. U.S.A.* Early Edition 10.1073/pnas.0409188102, online publication date Jan. 25, 2005.
Azcarate-Peril et al. (2004) "Identification and inactivation of genetic loci involved with *Lactobacillus acidophilus* acid tolerance" *Appl. Environ. Microbiol.* 70:5315-5322.
Barefoot and Klaenhammer (1983) "Detection and activity of lactacin B, a bacteriocin produced by *Lactobacillus acidophilus*" *Appl. Environ. Microbiol.* 45:1808-1815.
Barefoot and Klaenhammer (1984) "Purification and characterization of the *Lactobacillus acidophilus* bacteriocin lactacin B" *Antimicrob. Agents Chemother.* 26:328-334.
Barefoot et al. (1994) "Identification and purification of a protein that induces production of the *Lactobacillus acidophilus* bacteriocin lactacin B" *Appl. Environ. Microbiol.* 60:3522-3528.
Barrangou et al. (2003) "Functional and comparative genomic analyses of an operon involved in fructooligosaccharide utilization by *Lactobacillus acidophilus*" *Proc. Natl. Acad. Sci, U.S.A.* 100:8957-8962.
Boels et al. (2001) "Functional analysis of the *Lactococcus lactis galU* and *galE* genes and their impact on sugar nucleotide and exopolysaccharide biosynthesis" *Appl. Environ. Microbiol.* 67:3033-3040.
Bruno-Barcena et al. (2004) "Expression of heterologous manganese superoxide dismutase gene in intestinal lactobacilli provides protection against hydrogen peroxide toxicity" *Appl. Environ. Microbiol.* 70:4702-4710.

(Continued)

*Primary Examiner*—Hope A Robinson
(74) *Attorney, Agent, or Firm*—Alston & Bird LLP

(57) ABSTRACT

Protease-like nucleic acid molecules and polypeptides and fragments and variants thereof are disclosed in the current invention. In addition, protease-like fusion proteins, antigenic peptides, and anti-protease-like antibodies are encompassed. The invention also provides vectors containing a nucleic acid molecule of the invention and cells into which the vectors have been introduced. Methods for producing the polypeptides and methods of use for the polypeptides of the invention are further disclosed.

31 Claims, No Drawings

OTHER PUBLICATIONS

Christensen et al. (1999) "Peptidases and Amino Acid Catabolism in Lactic Acid Bacteria" *Antonie van Leeuwenhoek* 76: 217-246.

Coconnier et al. (1992) "Protein-mediated adhesion of *Lactobacillus acidophilus* BG2FO4 on human enterocyte and mucus-secreting cell lines in culture" *Appl. Environ. Microbiol.* 58:2034-2039.

Contreras et al. (1997) "Isolation, purification and amino acid sequence of lactobin A, one of the two bacteriocins produced by *Lactobacillus amylovorus* LMG P-13139" *Appl. Environ. Microbiol.* 63:13-20.

De Vuyst and Degeest (1998) "Heteropolysaccharides from lactic acid bacteria" *FEMS Microbiol. Rev.* 23:153-177.

Dodd and Gasson (1994) "Bacteriocins of lactic acid bacteria" in *Genetics and Biotechnology of Lactic Acid Bacteria.* Gasson and de Vos (eds.), Blackie Academic and Professional, London, pp. 211-251.

Fremaux et al. (1993) "Molecular analysis of the lactacin F operon" *Appl. Environ. Microbiol.* 59:3906-3915.

GenBank Accession No. AAA19050; filed Jan. 17, 1994; Prolinase; Source: *Lactobacillus helveticus*.

GenBank Accession No. AAA25250; filed Jan. 13, 1994;Aminopeptidase C.; Source: *Lactobacillus helveticus*.

GenBank Accession No. AAB52540; filed Nov. 1, 1996; Endopeptidase; Source: *Lactobacillus helveticus*.

GenBank Accession No. AAB66326; filed Aug. 7, 1997; GroEL; Source: *Lactobacillus zeae*.

GenBank Accession No. AAC29003; filed Aug. 7, 1998; cochaperonin GroES; Source: *Lactobacillus helveticus*.

GenBank Accession No. AAC99363; filed Sep. 10, 1999; D-lactate dehydrogenase; Source: *Lactobacillus johnsonii*.

GenBank Accession No. AAF22492; filed Aug. 30, 2001; FlF0-ATPase subunit a; Source: *Lactobacillus acidophilus*.

GenBank Accession No. AAF22493; filed Aug. 30, 2001; FlF0-ATPase subunit c; Source: *Lactobacillus acidophilus*.

GenBank Accession No. AAF22494; filed Aug. 30, 2001; FlF0-ATPase subunit b; Source: *Lactobacillus acidophilus*.

GenBank Accession No. AAF22495; filed Aug. 30, 2001; FlF0-ATPase subunit delta; Source: *Lactobacillus acidophilus*.

GenBank Accession No. AAF22496; filed Aug. 30, 2001; FlF0-ATPase subunit alpha; Source: *Lactobacillus acidophilus*.

GenBank Accession No. AAF22497; filed Aug. 30, 2001; FlF0-ATPase subunit gamma; Source: *Lactobacillus acidophilus*.

GenBank Accession No. AAF22498; filed Aug. 30, 2001; FlF0-ATPase subunit beta; Source: *Lactobacillus acidophilus*.

GenBank Accession No. AAF22499; filed Aug. 30, 2001; FlF0-ATPase subunit epsilon; Source: *Lactobacillus acidophilus*.

GenBank Accession No. AAF75593; filed Jun. 13, 2000; GroEL; Source: *Lactobacillus johnsonii*.

GenBank Accession No. AAK97217; filed Sep. 2, 2001; cochaperonin GroES; Source: *Lactobacillus acidophilus*.

GenBank Accession No. AAK97218; filed Sep. 2, 2001; chaperonin GroEL; Source: *Lactobacillus acidophilus*.

GenBank Accession No. AAK97220; filed Sep. 2, 2001; cochaperonin GrpE; Source: *Lactobacillus acidophilus*.

GenBank Accession No. AAK97221; filed Sep. 2, 2001; heat shock protein DnaK; Source: *Lactobacillus acidophilus*.

GenBank Accession No. AAQ72431; filed Aug. 11, 2003; Endopeptidase E2; Source: *Lactobacillus helveticus*.

GenBank Accession No. AAR25444; filed Dec. 3, 2003; Tuf; *Lactobacillus johnsonii*.

GenBank Accession No. AAT09141; filed Sep. 7, 2004; amino acid permease La995; Source: *Lactobacillus acidophilus*.

GenBank Accession No. AF010281; filed Aug. 9, 1997; *Lactobacillus zeae* GroES; Source: *Lactobacillus zeae*.

GenBank Accession No. AF031929; filed Aug. 8, 1998; *Lactobacillus helveticus* cochaperonin GroES and chaperonin GroEL genes, complete cds and DNA mismatch repair enzyme (hexA) gene, partial cds; Source: *Lactobacillus helveticus*.

GenBank Accession No. AF071558; filed Sep. 10, 1999; *Lactobacillus johnsonii* D-lactate dehydrogenase (ldhD) gene, complete cds; Source: *Lactobacillus johnsonii*.

GenBank Accession No. AF098522; filed Aug. 30, 2001; *Lactobacillus acidophilus* uracil phosphoribosyltransferase; Source: *Lactobacillus acidophilus*.

GenBank Accession No. AF214488; filed Jun. 13, 2000; *Lactobacillus johnsonii* groESL operon, complete sequence and unknown gene; Source: *Lactobacillus johnsonii*.

GenBank Accession No. AF300645; filed Sep. 2, 2001; *Lactobacillus acidophilus* groESL operon, complete sequence; Source: *Lactobacillus acidophilus*.

GenBank Accession No. AF300646; filed Sep. 2, 2001; *Lactobacillus acidophilus* repressor protein HrcA (hrcA) gene, partial cds; cochaperonin GrpE (grpE) and heat shock protein DnaK (dnaK) genes, complete cds, and DnaJ (dnaJ) gene, partical cds; Source: *Lactobacilus acidophilus*.

GenBank Accession No. B59088; filed Oct. 22, 1999; Prolyl Aminopeptidase; Source: *Lactobacillus helveticus*.

GenBank Accession No. CAA42781; filed Nov. 5, 1992; D-lactate dehydrogenase; Source: *Lactobacillus delbrueckii*.

GenBank Accession No. CAA59019; filed Apr. 18, 2005; heat shock induced protein HtpI; Source: *Lactobacillus leichmannii*.

GenBank Accession No. CAA61561; filed Jan. 22, 1996; SB-protein; *Lactobacillus acidophilus*.

GenBank Accession No. CAA86210; filed Oct. 10, 1994; Dipeptidase; Source: *Lactobacillus helveticus*.

GenBank Accession No. CAB72938; filed Jun. 23, 1999; Tripeptidase Enzyme; Source: *Lactobacillus helveticus*.

GenBank Accession No. NP_964658; filed Jan. 26, 2007; probable xylulose-5-phosphate/fructose-6-phosphate phosphoketolase; Source: *Lactobacillus johnsonii* NCC 533.

GenBank Accession No. NP_964694; filed Jan. 26, 2007; RecA protein; Source: *Lactobacillus johnsonii* NCC 533.

GenBank Accession No. NP_964728; filed Jan. 26, 2007; phosphoglycerate kinase; Source: *Lactobacillus johnsonii* NCC 533.

GenBank Accession No. NP_964948; filed Jan. 26, 2007; DNA-binding protein HU; Source: *Lactobacillus johsonii* NCC 533.

GenBank Accession No. NP_965314; filed Jan. 26, 2007; 50S ribosomal protein L19; Source: *Lactobacillus johnsonii* NCC 533.

GenBank Accession No. NP_965472; filed Jan. 26, 2007; thioredoxin; Source: *Lactobacillus johnsonii* NCC 533.

GenBank Accession No. NP_965500; filed Jan. 26, 2007; hypothetica protein LJ1693; Source: *Lactobacillus johnsonii* NC 533.

GenBank Accession No. O07684; filed Oct. 17, 2006; Beta-galactosidase large subunit; Source: *Lactobacillus acidophilus*.

GenBank Accession No. O07685; filed Nov. 28, 2006; Beta-galactosidase small subunit; Source: *Lactobacillus acidophilus*.

GenBank Accession No. O32755; filed Oct. 17, 2006; Glyceraldehyde-3-phosphate dehydrogenase; Source: *Lactobacillus delbrueckii* subsp. *Bulgaricus*.

GenBank Accession No. O32756; filed Apr. 18, 2006; Phosphoglycerate kinase; Source: *Lactobacillus delbrueckii* subsp. *Bulgaricus*.

GenBank Accession No. O32765; filed Nov. 28, 2006; L-lactate dehydrogenase; Source: *Lactobacillus helveticus*.

GenBank Accession No. O68324; filed Mar. 21, 2006; 60 kDa chaperonin; Source: *Lactobacillus helveticus*.

GenBank Accession No. O84913; filed Jul. 1, 1997; Xaa-Pro dipeptidase; Source: *Lactobacillus helveticus*.

GenBank Accession No. P26297; filed Jan. 23, 2007; D-lactate dehydrogenase; Source: *Lactobacillus delbrueckii* subsp. *Bulgaricus*.

GenBank Accession No. P30901; filed Jan. 23, 2007; D-lactate dehydrogenase; Source: *Lactobacillus helveticus*.

GenBank Accession No. P34038; filed Nov. 28, 2006; Pyruvate kinase; Source: *Lactobacillus delbrueckii* subsp. *Bulgaricus*.

GenBank Accession No. P35829; filed Jan. 9, 2007; S-layer protein precursor; Source: *Lactobacilus acidophilus*.

GenBank Accession No. P43451; filed Oct. 17, 2006; ATP synthase beta chain; Source: *Enterococcus hirae*.

GenBank Accession No. P94870; filed May 1, 1997; Aminopeptidase E.; Source: *Lactobacillus helveticus*.

GenBank Accession No. Q00052; filed Mar. 21, 2006; Galactokinase; Source: *Lactobacillus helveticus*.

GenBank Accession No. Q10730; filed Oct. 1, 1996; Aminopeptidase N; Source: *Lactobacillus helveticus*.
GenBank Accession No. Q10744; filed Nov. 1, 1996; Aminopeptidase C.; Source: *Lactobacillus helveticus*.
GenBank Accession No. Q48558; filed Sep. 26, 2001; Dipeptidase A.; Source: *Lactobacillus helveticus*.
GenBank Accession No. Q9Z4H7; filed Oct. 17, 2006; Serine protease do-like htrA; Source: *Lactobacillus helveticus*.
GenBank Accession No. S47274; filed Feb. 1, 1994; Membrane Alanyl Aminopeptidase; Source: *Lactobacillus helveticus*.
GenBank Accession No. S47276; filed Jan. 6, 1995; Prolinase; Source: *Lactobacillus helveticus*.
GenBank Accession No. X60220; filed Nov. 5, 1992; *L. delbrueckii* subsp. *Bulgaricus* IdhA gene for D-lactate dehydrogenase; Source: *Lactobacillus delbrueckii*.
GenBank Accession No. X84261; filed Apr. 18, 2005; *L.leichmannii* xerC, hslU and hslV; Source: *Lactobacillus leichmannii*.
GenBank Accession No. X89376; filed Jan. 22, 1996; *L. acidophilus* DNA for SB-protein gene; Source: *Lactobacillus acidophilus*.
GenBank Accession No. ZP_00046537; filed May 25, 2006; COG0124: Histidyl-tRNA sythetase; Source: *Lactobacillus gasseri*.
GenBank Accession No. ZP_00046557; filed May 25, 2006; COG0148: Enolase; Source: *Lactobacillus gasseri*.
GenBank Accession No. ZP_00046583; filed May 25, 2006; COG0195: Transcription elongation factor; Source: *Lactobacillus gasseri*.
GenBank Accession No. ZP_00047305; filed May 25, 2006; COG4690: Dipeptidase; Source: *Lactobacillus gasseri*.
GenBank Accession No. ZP_00341831; filed May 25, 2006; COG0522: Ribosomal protein S4 and related proteins; Source: *Lactobacillus gasseri*.
GenBank Accession No. Q03234; filed Oct. 17, 2006; ATP synthesis beta chain; *Lactobacillus casei*.
Girgis et al. (2002) "Stress adaptations of lactic acid bacteria" in *Microbial adaptation to stress and safety of new-generation foods*. Yousef and Juneja (eds.) CRC Press, NY, pp. 159-212.
Greene and Klaenhammer (1994) "Factors involved in adherence of lactobacilli to human Caco-2 cells" *Appl Environ. Microbiol.* 60:4487-4494.
Holzapfel et al. (2001) "Taxonomy and Important Features of Probiotic Microorganisms in Food and Nutrition" *Am J of Clil Nutr* 73 Suppl: 365S-373S.
Hugenholtz (1999) "Metabolic Engineering of Lactic Acid Bacteria: Overview of the Approaches and Results of Pathway Rerouting Involved in Food Fermentations" *Current Opinion in Biotechnology* 10: 492-497.
Joerger and Klaenhammer (1986) "Characterization and purification of helveticin J and evidence for a chromosomally determined bacteriocin produced by *Lactobacillus helveticus*" *J. Bacteriol.* 167:439-446.
Joerger et al. (1990) "Cloning, expression, and nucleotide sequence of the *Lactobacillus helveticus* 481 gene encoding the bactericin helveticin J" *J. Bacteriol.* 172:6339-6347.
Jolly et al. (2002) "Exploiting exopolysaccharides from lactic acid bacteria" *Antonie van Leeuwenhoek* 82:367-374.
Joutsjoki, V. et al., "Recombinant *Lactococcus* Starters as a Potential Source of Additional Peptidolytic Activity in Cheese Ripening," *Journal of Applied Microbiology*, 2002, pp. 1159-1166, vol. 92.
Kitazono, A., et al., "Prolyl Aminopeptidase Gene From *Flavobacterium meningosepticum*: Cloning, Purification of the Expressed Enzyme, and Analysis of Its Sequence," *Archives of Biochemistry and Biophysics*, 1996, pp. 35-41, vol. 336(1).
Klaenhammer (1988) "Bacteriocins of lactic acid bacteria" *Biochimie* 70:337-349.
Klaenhammer (1993) "Genetics of bacteriocins produced by lactic acid bacteria" *FEMS Microbiol. Rev.* 12:39-85.
Klaenhammer (2000) "Probiotic bacteria: today and tomorrow" *J. Nutr.* 130(2S Suppl.):415S-416S.
Klaenhammer and Kullen (1999) "Selection and design of probiotics" *Int. J. Food Microbiol.* 50:45-57.
Klaenhammer and Sutherland (1980) "Detection of plasmid deoxyribonucleic acid in an isolate of *Lactobacillus acidophilus*" *Appl. Environ. Microbiol.* 39:671-674.

Klaenhammer et al. (2002) "Discovering lactic acid bacteria by genomics" *Antonie van Leeuenhoek* 82:29-58.
Kleeman and Klaenhammer (1982) "Adherence of *Lactobacillus* species to human fetal intestinal cells" *J. Dairy Sci.* 65:2063-2069.
Kleerebezem et al. (1999) "Exopolysaccharides produced by *Lactococcus lactis*: from genetic engineering to improved rheological properties?" *Antonie van Leeuwenhoek* 76:357-365.
Kleerebezem et al. (2003) "Complete genome sequence of *Lactobacillus plantarum* WCFS1" *Proc. Natl. Acad. Sci. U.S.A.* 100:1990-1995.
Kok et al. (1994) "The Proteolytic System of Lactic Acid Bacteria" *Genetics and Biotechnology of Lactic Acid Bacteria* pp. 169-210.
Konigs et al. (1997) "The role of transport processes in survival of lactic acid bacteria" *Antonie van Leeuwenhoek* 71:117-128.
Konigs et al. (2000) "Lactic acid bacteria: the bugs of a new millennium" *Curr. Opin. Microbiol.* 3:276-282.
Kuipers et al. (2000) "Current Strategies for Improving Food Bacteria" *Res Microbiol* 151: 815-822.
Kullen and Klaenhammer (1999) Identification of the pH-inducible, proton-translocating $F_1F_0$-ATPase (atpBEFHAGDC) operon of *Lactobacillus acidophilus* by differential display: gene structure, cloning and characterization *Mol. Microbiol.* 33:1152-1161.
Kullen and Klaenhammer (2000) "Genetic modification of intestinal *Lactobacilli* and bifidobacteria" *Curr. Issues Mol. Biol.* 2:41-50.
Kullen et al. (2000) "Use of the DNA sequence of variable regions of the I6S rRNA gene for rapid and accurate identification of bacteria in the *Lactobacillus acidophilus* complex" *J. Appl. Microbiol.* 89:511-516.
Law et al. (1997) "Proteolytic Enzymes of Lactic Acid Bacteria" *Int Dairy Journal* 7: 1-11.
Luchansky et al. (1988) "Application of electroporation for transfer of plasmid DNA to *Lactobacillus, Lactococcus, Leuconostoc, Listeria, Pediococcus, Bacillus, Staphylococcus, Enterococcus* and *Propionobacterium*" *Mol. Microbiol.* 2:637-646.
Luchansky et al. (1989) "Genetic transfer systems for delivery of plasmid deoxyribonucleic acid to *Lactobacillus acidophilus* ADH: conjugation, electroporation, and transduction" *J. Dairy Sci.* 72:1408-1417.
Luchansky et al. (1991) "Molecular cloning and deoxyribonucleic acid polymorphisms in *Lactobacillus acidophilus* and *Lactobacillus gasseri*" *J. Dairy Sci.* 74:3293-3302.
Majhenic et al. (2004) "DNA analysis of the genes encoding acidocin LF221 A and acidocin LF221 B, two bacteriocins produced by *Lactobacillus gasseri* LF221" *Appl. Microbiol. Biotechnol.* 63:705-714.
Mohamadzadeh et al. (2005) "*Lactobacilli* activate human dendritic cells that skew T cells toward T helper 1 polarization" *Proc. Nat. Acad. Sci. USA* 102:2880-2885.
Muriana and Klaenhammer (1991) "Cloning, phenotypic expression, and DNA sequence of the gene for lactacin F, an antimicrobial peptide produced by *Lactobacillus* spp." *J. Bacteriol.* 173:1779-1788.
Muriana and Klaenhammer (1991) "Purification and partial characterization of lactacin F, a bacteriocin produced by *Lactobacillus acidophilus* 11088" *Appl. Environ. Microbiol.* 57:114-121.
Pao et al. (1998) "Major Facilitator Superfamily" *Microbiol. Mol. Biol. Rev.* 62:1-34.
Poolman (2002) "Transporters and their roles in LAB cell physiology" *Antonie van Leeuwenhoek* 82:147-164.
Pridmore et al. (2004) "The genome sequence of the probiotic intestinal bacterium *Lactobacillus johnsonii* NCC 533" *Proc. Natl. Acad. Sci. U.S.A.* 101:2512-2517.
Putman et al. (2000) "Molecular properties of bacterial multidrug transporters" *Microbiol. Mol. Biol. Rev.* 64:672-693.
Rastall et al. (2005). Modulation of the microbial ecology of the human colon by probiotics, prebiotics and synbiotics to enhance human health: An overview of enabling science and potential applications. *FEMS Microbiol. Ecol.* 52:145-152.
Roy et al. (1993) "Cloning and expression of the manganese superoxide dismutase gene of *Escherichia coli* in *Lactococcus lactis* and *Lactobacillus gasseri*" *Mol. Gen. Genet.* 239:33-40.

Russell and Klaenhammer (2001) "Efficient system for directed integration into the *Lactobacillus acidophilus* and *Lactobacillus gasseri* chromosomes via homologous recombination" *Appl. Environ. Microbiol.* 67:4361-4364.

Russell and Klaenhammer (2001) "Identification and cloning of *gus*A, encoding a new β-glucuronidase from *Lactobacillus gasseri* ADH" *Appl. Environ. Microbiol.* 67:1253-1261.

Sablon et al. (2000) "Antimicrobiol peptides of lactic acid bacteria: mode of action, genetics and biosynthesis" in *Advances in Biochemical Engineering/Biotechnology*, vol. 68. Schleper (ed.), Springer-Verlag, Berlin, pp. 21-60.

Sanders and Klaenhammer (2001) "Invited review: the scientific basis of *Lactobacillus acidophilus* NCFM functionality as a probiotic" *J. Dairy Sci.* 84:319-331.

Sanders et al. (1996) "Performance of commercial cultures in fluid milk applications" *J. Dairy Sci.* 79:943-955.

Seffernick, et al., *J. Bacteriology*, vol. 183, pp. 2405-2410 (2001).

Steidler et al. (1998) "Functional display of a heterologous protein on the surface of *Lactococcus lactis* by means of the cell wall anchor of *Staphylococcus aureus* protein A" *Appl. Environ. Microbiol.* 64:342-345.

Sturino and Klaenhammer (2004) "Bacteriophage defense systems for lactic acid bacteria" *Adv. Appl. Microbiol.* 56:331-378.

Ventura et al. (2003) "Analysis, characterization, and loci of *tuf* genes in *Lactobacillus* and *Bifidobacterium* species and their direct application for species identification" *Appl. Environ. Microbiol.* 69:6908-6922.

Walker et al. (1999) "The groESL chaperone operon of *Lactobacillus johnsonii*" *Appl. Environ. Microbiol.* 65:3033-3041.

Wells, *Biochemistry*, vol. 29, pp. 8509-8517 (1990).

Yother et al. (2002) Genetics of *Streptococci, Lactococci, and Enterococci*: review of the sixth international conference *J. Bacteriol.* 184:6085-6092.

\* cited by examiner

SEQUENCE LISTING

```
<160> NUMBER OF SEQ ID NOS: 154

<210> SEQ ID NO 1
<211> LENGTH: 879
<212> TYPE: DNA
<213> ORGANISM: Lactobacillus acidophilus
<220> FEATURE:
<221> NAME/KEY: CDS
<222> LOCATION: (1)..(879)
<223> OTHER INFORMATION: Prolyl aminopeptidase (EC3.4.11.5) ORF# 92

<400> SEQUENCE: 1 atg gaa atc att gaa gga aaa atg cct ttt atg ggc tat gaa act cac       48
Met Glu Ile Ile Glu Gly Lys Met Pro Phe Met Gly Tyr Glu Thr His
1               5                   10                  15 tat cgt att gtt ggt aga aga agc gaa aaa tcg cca cta gtt ttg ctt       96
Tyr Arg Ile Val Gly Arg Arg Ser Glu Lys Ser Pro Leu Val Leu Leu
            20                  25                  30 cat ggt ggc cct ggc tca act cat aat tat ttt gaa gtg ttg gac aaa      144
His Gly Gly Pro Gly Ser Thr His Asn Tyr Phe Glu Val Leu Asp Lys
        35                  40                  45 tta gcc aaa atc gat gat cgc cgc att att atg tat gac caa tta ggt      192
Leu Ala Lys Ile Asp Asp Arg Arg Ile Ile Met Tyr Asp Gln Leu Gly
    50                  55                  60 tgc ggc aat agt agc atc ccc gac gat cat cct gaa ctt tac aca aaa      240
Cys Gly Asn Ser Ser Ile Pro Asp Asp His Pro Glu Leu Tyr Thr Lys
65                  70                  75                  80 gaa act tgg gtg aaa gaa tta aaa aca cta cgt gaa cat cta gct ttg      288
Glu Thr Trp Val Lys Glu Leu Lys Thr Leu Arg Glu His Leu Ala Leu
                85                  90                  95 cgt aaa att cat ttg tta ggt caa agc tgg ggc ggg atg ctc gct atc      336
Arg Lys Ile His Leu Leu Gly Gln Ser Trp Gly Gly Met Leu Ala Ile
            100                 105                 110 att tat atg tgt gat tat cac cca gag ggc att caa agt ttg att tta      384
Ile Tyr Met Cys Asp Tyr His Pro Glu Gly Ile Gln Ser Leu Ile Leu
        115                 120                 125 tca agt acc ctt tca tca gct tca cta tgg tca aaa gaa ttg cac cgc      432
Ser Ser Thr Leu Ser Ser Ala Ser Leu Trp Ser Lys Glu Leu His Arg
    130                 135                 140 atg atc aag tac tta cca att gaa gaa caa gct gca att cat cgt gct      480
Met Ile Lys Tyr Leu Pro Ile Glu Glu Gln Ala Ala Ile His Arg Ala
145                 150                 155                 160
```

```
gaa tta acg gac aca ttt acg gag cct gac tat ttg aag gct aac gaa    528
Glu Leu Thr Asp Thr Phe Thr Glu Pro Asp Tyr Leu Lys Ala Asn Glu
            165                 170                 175 cac ttt atg aat caa cat gca att gat atg aag aag aaa tgg cca gaa    576
His Phe Met Asn Gln His Ala Ile Asp Met Lys Lys Lys Trp Pro Glu
        180                 185                 190 tgc gtc atg cgt gag aaa aaa ggt ggc aca gtt gct tac gaa act gcc    624
Cys Val Met Arg Glu Lys Lys Gly Gly Thr Val Ala Tyr Glu Thr Ala
    195                 200                 205 tgg ggg cct aac gaa tat acg cct gaa ggt aat tta cat gat tat gaa    672
Trp Gly Pro Asn Glu Tyr Thr Pro Glu Gly Asn Leu His Asp Tyr Glu
210                 215                 220 tac act gat caa ttg agt aaa ata aaa gtt cca act ctg att acg agt    720
Tyr Thr Asp Gln Leu Ser Lys Ile Lys Val Pro Thr Leu Ile Thr Ser
225                 230                 235                 240 gga acc gat gat ttg tgt act cca tat gtt gct aag aca atg cat gat    768
Gly Thr Asp Asp Leu Cys Thr Pro Tyr Val Ala Lys Thr Met His Asp
                245                 250                 255 cat att gcg ggc agt caa tgg aaa cta ttc gaa aat tgt agt cat atg    816
His Ile Ala Gly Ser Gln Trp Lys Leu Phe Glu Asn Cys Ser His Met
            260                 265                 270 tcc ttc gtg caa aaa act gac gaa tat att gct atg ctt aag aaa tgg    864
Ser Phe Val Gln Lys Thr Asp Glu Tyr Ile Ala Met Leu Lys Lys Trp
        275                 280                 285 ctt gat gcc aat gac                                                879
Leu Asp Ala Asn Asp
    290

<210> SEQ ID NO 2
<211> LENGTH: 293
<212> TYPE: PRT
<213> ORGANISM: Lactobacillus acidophilus

<400> SEQUENCE: 2

Met Glu Ile Ile Glu Gly Lys Met Pro Phe Met Gly Tyr Glu Thr His
1               5                   10                  15

Tyr Arg Ile Val Gly Arg Arg Ser Glu Lys Ser Pro Leu Val Leu Leu
            20                  25                  30

His Gly Gly Pro Gly Ser Thr His Asn Tyr Phe Glu Val Leu Asp Lys
        35                  40                  45

Leu Ala Lys Ile Asp Asp Arg Arg Ile Ile Met Tyr Asp Gln Leu Gly
    50                  55                  60

Cys Gly Asn Ser Ser Ile Pro Asp Asp His Pro Glu Leu Tyr Thr Lys
65                  70                  75                  80

Glu Thr Trp Val Lys Glu Leu Lys Thr Leu Arg Glu His Leu Ala Leu
                85                  90                  95

Arg Lys Ile His Leu Leu Gly Gln Ser Trp Gly Gly Met Leu Ala Ile
            100                 105                 110

Ile Tyr Met Cys Asp Tyr His Pro Glu Gly Ile Gln Ser Leu Ile Leu
        115                 120                 125

Ser Ser Thr Leu Ser Ser Ala Ser Leu Trp Ser Lys Glu Leu His Arg
    130                 135                 140

Met Ile Lys Tyr Leu Pro Ile Glu Glu Gln Ala Ala Ile His Arg Ala
145                 150                 155                 160

Glu Leu Thr Asp Thr Phe Thr Glu Pro Asp Tyr Leu Lys Ala Asn Glu
                165                 170                 175

His Phe Met Asn Gln His Ala Ile Asp Met Lys Lys Lys Trp Pro Glu
```

-continued

```
                    180                 185                 190
Cys Val Met Arg Glu Lys Lys Gly Gly Thr Val Ala Tyr Glu Thr Ala
        195                 200                 205

Trp Gly Pro Asn Glu Tyr Thr Pro Glu Gly Asn Leu His Asp Tyr Glu
    210                 215                 220

Tyr Thr Asp Gln Leu Ser Lys Ile Lys Val Pro Thr Leu Ile Thr Ser
225                 230                 235                 240

Gly Thr Asp Asp Leu Cys Thr Pro Tyr Val Ala Lys Thr Met His Asp
                245                 250                 255

His Ile Ala Gly Ser Gln Trp Lys Leu Phe Glu Asn Cys Ser His Met
            260                 265                 270

Ser Phe Val Gln Lys Thr Asp Glu Tyr Ile Ala Met Leu Lys Lys Trp
        275                 280                 285

Leu Asp Ala Asn Asp
        290

<210> SEQ ID NO 3
<211> LENGTH: 1974
<212> TYPE: DNA
<213> ORGANISM: Lactobacillus acidophilus
<220> FEATURE:
<221> NAME/KEY: CDS
<222> LOCATION: (1)..(1974)
<223> OTHER INFORMATION: pepO neutral endopeptidase (EC 3.4.-.-) ORF#
      165

<400> SEQUENCE: 3 ttg aat aaa ggg gga ttt tcc tta atg agt aat aaa gtg act gtt cgt       48
Leu Asn Lys Gly Gly Phe Ser Leu Met Ser Asn Lys Val Thr Val Arg
1               5                   10                  15 ggt ggt gct ggt aat atc ctc gaa cct aaa gtt ggt act cgt cca caa       96
Gly Gly Ala Gly Asn Ile Leu Glu Pro Lys Val Gly Thr Arg Pro Gln
            20                  25                  30 gat aat tta tat tta gct gtt aac tca gac tgg ctt gag aag gct aag      144
Asp Asn Leu Tyr Leu Ala Val Asn Ser Asp Trp Leu Glu Lys Ala Lys
        35                  40                  45 att cct tca gat cgt tca aga att gct agt ttt gat agt att gat ctt      192
Ile Pro Ser Asp Arg Ser Arg Ile Ala Ser Phe Asp Ser Ile Asp Leu
    50                  55                  60 aac gta gaa aag agc tta atg aag gat ttc gca gat ttt gcg gat ggc      240
Asn Val Glu Lys Ser Leu Met Lys Asp Phe Ala Asp Phe Ala Asp Gly
65                  70                  75                  80 aaa aaa gaa gta gcc gat gta ccg aac ttg aag aag gca gtt gaa cta      288
Lys Lys Glu Val Ala Asp Val Pro Asn Leu Lys Lys Ala Val Glu Leu
                85                  90                  95 tat aag ctt gct cgt gac ttt aag cgt cgt gat gaa gat ggc gct aag      336
Tyr Lys Leu Ala Arg Asp Phe Lys Arg Arg Asp Glu Asp Gly Ala Lys
            100                 105                 110 cct att caa gct gat ttg ttc tta ctt gaa agt atc agt gac ttt gct      384
Pro Ile Gln Ala Asp Leu Phe Leu Leu Glu Ser Ile Ser Asp Phe Ala
        115                 120                 125 gat ttc aac ttg aag gct gct gat tta ttt aag gct tca ttt tca ttg      432
Asp Phe Asn Leu Lys Ala Ala Asp Leu Phe Lys Ala Ser Phe Ser Leu
    130                 135                 140 cca ttt ggt tta gat att gat gct gat atg aag aat act aag att aat      480
Pro Phe Gly Leu Asp Ile Asp Ala Asp Met Lys Asn Thr Lys Ile Asn
145                 150                 155                 160 gtt ctt caa ttt att gga cca tca aca ttc ttg cca gat act act act      528
Val Leu Gln Phe Ile Gly Pro Ser Thr Phe Leu Pro Asp Thr Thr Thr
                165                 170                 175
```

-continued

| | |
|---|---|
| tac aag aca gaa gct gct gga aag ctt ttg gaa gtt ttg aag aag caa<br>Tyr Lys Thr Glu Ala Ala Gly Lys Leu Leu Glu Val Leu Lys Lys Gln<br>180             185                 190 | 576 |
| tca att aac ttg ctt aag atg gct ggc gtt tct gaa ggt caa gct aag<br>Ser Ile Asn Leu Leu Lys Met Ala Gly Val Ser Glu Gly Gln Ala Lys<br>        195                 200                 205 | 624 |
| gaa tac gtg gaa gat gcc tta aaa ttt gat aaa aag ctt tct gaa gta<br>Glu Tyr Val Glu Asp Ala Leu Lys Phe Asp Lys Lys Leu Ser Glu Val<br>210                 215                 220 | 672 |
| gtt aaa tca tca gaa gaa tgg gca gat tat cca gca atg tat aat cca<br>Val Lys Ser Ser Glu Glu Trp Ala Asp Tyr Pro Ala Met Tyr Asn Pro<br>225                 230                 235                 240 | 720 |
| act tca atg gaa gat ttt gaa ggc aag att aag aac ttc aag att gat<br>Thr Ser Met Glu Asp Phe Glu Gly Lys Ile Lys Asn Phe Lys Ile Asp<br>            245                 250                 255 | 768 |
| tac ttc ttg aag gaa gct tta ggt gaa gtt cct gat aga att att gtt<br>Tyr Phe Leu Lys Glu Ala Leu Gly Glu Val Pro Asp Arg Ile Ile Val<br>        260                 265                 270 | 816 |
| act gaa cca cgt ttc ttg aaa cac ttt gat gaa tta atg aat gaa gaa<br>Thr Glu Pro Arg Phe Leu Lys His Phe Asp Glu Leu Met Asn Glu Glu<br>    275                 280                 285 | 864 |
| aac ttt gat gaa att aag ggt tgg atg atc gtt aag ttt att aat aat<br>Asn Phe Asp Glu Ile Lys Gly Trp Met Ile Val Lys Phe Ile Asn Asn<br>290                 295                 300 | 912 |
| gtt gca agt tac ttg tca caa gat ttc cgt gaa gca tca ttc caa ttt<br>Val Ala Ser Tyr Leu Ser Gln Asp Phe Arg Glu Ala Ser Phe Gln Phe<br>305                 310                 315                 320 | 960 |
| agt caa gca ttg aca ggc caa ccg gaa tta caa agc caa gaa aag caa<br>Ser Gln Ala Leu Thr Gly Gln Pro Glu Leu Gln Ser Gln Glu Lys Gln<br>            325                 330                 335 | 1008 |
| gca tat cat tta gct aat ggt cta ttc agc gaa gta gtc ggt gtt tac<br>Ala Tyr His Leu Ala Asn Gly Leu Phe Ser Glu Val Val Gly Val Tyr<br>        340                 345                 350 | 1056 |
| tat ggt caa aca tac ttt ggt gaa gaa gct aaa aaa gat gtt tta act<br>Tyr Gly Gln Thr Tyr Phe Gly Glu Glu Ala Lys Lys Asp Val Leu Thr<br>    355                 360                 365 | 1104 |
| atg att cgc caa atg att gat gtt tac gaa aag cgt att aag gaa aat<br>Met Ile Arg Gln Met Ile Asp Val Tyr Glu Lys Arg Ile Lys Glu Asn<br>370                 375                 380 | 1152 |
| tca tgg ctt tct gaa gaa act aag gaa aag gct att gtt aag ctt cgt<br>Ser Trp Leu Ser Glu Glu Thr Lys Glu Lys Ala Ile Val Lys Leu Arg<br>385                 390                 395                 400 | 1200 |
| gca ttg atc tta aag att ggt tac cct gat aag att gaa gaa atc tat<br>Ala Leu Ile Leu Lys Ile Gly Tyr Pro Asp Lys Ile Glu Glu Ile Tyr<br>            405                 410                 415 | 1248 |
| aat cgc tac aat ata act cct gct agt gaa ggc ggt agt ctt tac tca<br>Asn Arg Tyr Asn Ile Thr Pro Ala Ser Glu Gly Gly Ser Leu Tyr Ser<br>        420                 425                 430 | 1296 |
| aac gta aga gca gct gat att gaa caa gtt aaa tat aac gtt gaa aag<br>Asn Val Arg Ala Ala Asp Ile Glu Gln Val Lys Tyr Asn Val Glu Lys<br>    435                 440                 445 | 1344 |
| tta cat aaa cca gtt gat cgt agc gta tgg ctc atg cca gcc aac ttg<br>Leu His Lys Pro Val Asp Arg Ser Val Trp Leu Met Pro Ala Asn Leu<br>450                 455                 460 | 1392 |
| gta aat gct tgc tat gat cca caa aga aat gac tta act ttc cca gca<br>Val Asn Ala Cys Tyr Asp Pro Gln Arg Asn Asp Leu Thr Phe Pro Ala<br>465                 470                 475                 480 | 1440 |
| gca att ttg caa gca cca ttt tat gac tta aag caa gat cgt gct gaa<br>Ala Ile Leu Gln Ala Pro Phe Tyr Asp Leu Lys Gln Asp Arg Ala Glu | 1488 |

-continued

```
                   485                 490                 495
aac ttt ggt gga att ggt act gtt att gct cat gaa att tct cat gcc    1536
Asn Phe Gly Gly Ile Gly Thr Val Ile Ala His Glu Ile Ser His Ala
            500                 505                 510 ttt gat aac aat ggt gca caa ttc gat gaa ttc ggt aat atg aag aat    1584
Phe Asp Asn Asn Gly Ala Gln Phe Asp Glu Phe Gly Asn Met Lys Asn
            515                 520                 525 tgg tgg act gaa gaa gac ttc gct gaa ttt aag aag cgt act caa gca    1632
Trp Trp Thr Glu Glu Asp Phe Ala Glu Phe Lys Lys Arg Thr Gln Ala
    530                 535                 540 gaa atc gac ttg ttc gat ggt att aaa tac ggc cct gtt act ttg aac    1680
Glu Ile Asp Leu Phe Asp Gly Ile Lys Tyr Gly Pro Val Thr Leu Asn
545                 550                 555                 560 ggt aag caa atc gtt tca gaa aat att gcc gac caa ggt ggt ctt act    1728
Gly Lys Gln Ile Val Ser Glu Asn Ile Ala Asp Gln Gly Gly Leu Thr
                565                 570                 575 gca gct att aag gca gct aag gac gaa ggc gat gat ttg aag aaa ttg    1776
Ala Ala Ile Lys Ala Ala Lys Asp Glu Gly Asp Asp Leu Lys Lys Leu
            580                 585                 590 ttt gaa aac ttt gct cgt att tgg gct aac aag caa ctt act gaa tct    1824
Phe Glu Asn Phe Ala Arg Ile Trp Ala Asn Lys Gln Leu Thr Glu Ser
            595                 600                 605 att aag aca caa gtt tct ttt gat gtt cac gca cca ggt cca gaa cgt    1872
Ile Lys Thr Gln Val Ser Phe Asp Val His Ala Pro Gly Pro Glu Arg
    610                 615                 620 gca aat gtt caa tca caa tgt caa gaa gac ttc tat gaa gta ttt gat    1920
Ala Asn Val Gln Ser Gln Cys Gln Glu Asp Phe Tyr Glu Val Phe Asp
625                 630                 635                 640 gtt aag gaa act gat ggt atg tgg tta gat cca gaa aaa cgt gta gtt    1968
Val Lys Glu Thr Asp Gly Met Trp Leu Asp Pro Glu Lys Arg Val Val
                645                 650                 655 att tgg                                                            1974
Ile Trp

<210> SEQ ID NO 4
<211> LENGTH: 658
<212> TYPE: PRT
<213> ORGANISM: Lactobacillus acidophilus

<400> SEQUENCE: 4

Leu Asn Lys Gly Gly Phe Ser Leu Met Ser Asn Lys Val Thr Val Arg
1               5                   10                  15

Gly Gly Ala Gly Asn Ile Leu Glu Pro Lys Val Gly Thr Arg Pro Gln
            20                  25                  30

Asp Asn Leu Tyr Leu Ala Val Asn Ser Asp Trp Leu Glu Lys Ala Lys
        35                  40                  45

Ile Pro Ser Asp Arg Ser Arg Ile Ala Ser Phe Asp Ser Ile Asp Leu
    50                  55                  60

Asn Val Glu Lys Ser Leu Met Lys Asp Phe Ala Asp Phe Ala Asp Gly
65                  70                  75                  80

Lys Lys Glu Val Ala Asp Val Pro Asn Leu Lys Lys Ala Val Glu Leu
                85                  90                  95

Tyr Lys Leu Ala Arg Asp Phe Lys Arg Arg Asp Glu Asp Gly Ala Lys
            100                 105                 110

Pro Ile Gln Ala Asp Leu Phe Leu Leu Glu Ser Ile Ser Asp Phe Ala
        115                 120                 125

Asp Phe Asn Leu Lys Ala Ala Asp Leu Phe Lys Ala Ser Phe Ser Leu
    130                 135                 140
```

```
Pro Phe Gly Leu Asp Ile Asp Ala Asp Met Lys Asn Thr Lys Ile Asn
145                 150                 155                 160

Val Leu Gln Phe Ile Gly Pro Ser Thr Phe Leu Pro Asp Thr Thr Thr
            165                 170                 175

Tyr Lys Thr Glu Ala Ala Gly Lys Leu Leu Glu Val Leu Lys Lys Gln
        180                 185                 190

Ser Ile Asn Leu Leu Lys Met Ala Gly Val Ser Glu Gly Gln Ala Lys
            195                 200                 205

Glu Tyr Val Glu Asp Ala Leu Lys Phe Asp Lys Lys Leu Ser Glu Val
        210                 215                 220

Val Lys Ser Ser Glu Glu Trp Ala Asp Tyr Pro Ala Met Tyr Asn Pro
225                 230                 235                 240

Thr Ser Met Glu Asp Phe Glu Gly Lys Ile Lys Asn Phe Lys Ile Asp
            245                 250                 255

Tyr Phe Leu Lys Glu Ala Leu Gly Glu Val Pro Asp Arg Ile Ile Val
        260                 265                 270

Thr Glu Pro Arg Phe Leu Lys His Phe Asp Glu Leu Met Asn Glu Glu
    275                 280                 285

Asn Phe Asp Glu Ile Lys Gly Trp Met Ile Val Lys Phe Ile Asn Asn
290                 295                 300

Val Ala Ser Tyr Leu Ser Gln Asp Phe Arg Glu Ala Ser Phe Gln Phe
305                 310                 315                 320

Ser Gln Ala Leu Thr Gly Gln Pro Glu Leu Gln Ser Gln Glu Lys Gln
            325                 330                 335

Ala Tyr His Leu Ala Asn Gly Leu Phe Ser Glu Val Val Gly Val Tyr
        340                 345                 350

Tyr Gly Gln Thr Tyr Phe Gly Glu Glu Ala Lys Lys Asp Val Leu Thr
        355                 360                 365

Met Ile Arg Gln Met Ile Asp Val Tyr Glu Lys Arg Ile Lys Glu Asn
    370                 375                 380

Ser Trp Leu Ser Glu Glu Thr Lys Glu Lys Ala Ile Val Lys Leu Arg
385                 390                 395                 400

Ala Leu Ile Leu Lys Ile Gly Tyr Pro Asp Lys Ile Glu Glu Ile Tyr
            405                 410                 415

Asn Arg Tyr Asn Ile Thr Pro Ala Ser Glu Gly Gly Ser Leu Tyr Ser
        420                 425                 430

Asn Val Arg Ala Ala Asp Ile Glu Gln Val Lys Tyr Asn Val Glu Lys
        435                 440                 445

Leu His Lys Pro Val Asp Arg Ser Val Trp Leu Met Pro Ala Asn Leu
    450                 455                 460

Val Asn Ala Cys Tyr Asp Pro Gln Arg Asn Asp Leu Thr Phe Pro Ala
465                 470                 475                 480

Ala Ile Leu Gln Ala Pro Phe Tyr Asp Leu Lys Gln Asp Arg Ala Glu
            485                 490                 495

Asn Phe Gly Gly Ile Gly Thr Val Ile Ala His Glu Ile Ser His Ala
        500                 505                 510

Phe Asp Asn Asn Gly Ala Gln Phe Asp Glu Phe Gly Asn Met Lys Asn
    515                 520                 525

Trp Trp Thr Glu Glu Asp Phe Ala Glu Phe Lys Lys Arg Thr Gln Ala
    530                 535                 540

Glu Ile Asp Leu Phe Asp Gly Ile Lys Tyr Gly Pro Val Thr Leu Asn
545                 550                 555                 560
```

```
Gly Lys Gln Ile Val Ser Glu Asn Ile Ala Asp Gln Gly Gly Leu Thr
                565                 570                 575

Ala Ala Ile Lys Ala Ala Lys Asp Glu Gly Asp Asp Leu Lys Lys Leu
            580                 585                 590

Phe Glu Asn Phe Ala Arg Ile Trp Ala Asn Lys Gln Leu Thr Glu Ser
        595                 600                 605

Ile Lys Thr Gln Val Ser Phe Asp Val His Ala Pro Gly Pro Glu Arg
    610                 615                 620

Ala Asn Val Gln Ser Gln Cys Gln Glu Asp Phe Tyr Glu Val Phe Asp
625                 630                 635                 640

Val Lys Glu Thr Asp Gly Met Trp Leu Asp Pro Glu Lys Arg Val Val
                645                 650                 655

Ile Trp

<210> SEQ ID NO 5
<211> LENGTH: 600
<212> TYPE: DNA
<213> ORGANISM: Lactobacillus acidophilus
<220> FEATURE:
<221> NAME/KEY: CDS
<222> LOCATION: (1)..(600)
<223> OTHER INFORMATION: Pyrrolidone carboxylpeptidase (EC 3.4.19.3)
      ORF# 186

<400> SEQUENCE: 5
```

| | | | | | | | | | | | | | | | | |
|---|---|---|---|---|---|---|---|---|---|---|---|---|---|---|---|---|
| atg | aaa | atc | tta | ata | act | gga | ttt | gat | cct | ttt | ggt | ggg | gaa | aaa | att | 48 |
| Met | Lys | Ile | Leu | Ile | Thr | Gly | Phe | Asp | Pro | Phe | Gly | Gly | Glu | Lys | Ile | |
| 1   |     |     |     | 5   |     |     |     |     | 10  |     |     |     |     | 15  |     | |
| aat | cct | gca | att | gaa | gct | gta | aaa | aag | tta | cct | gac | gaa | ata | gat | ggt | 96 |
| Asn | Pro | Ala | Ile | Glu | Ala | Val | Lys | Lys | Leu | Pro | Asp | Glu | Ile | Asp | Gly | |
|     |     | 20  |     |     |     |     | 25  |     |     |     |     | 30  |     |     |     | |
| cat | caa | att | att | aaa | tta | gag | gtg | ccg | act | att | ttt | tat | gaa | agt | gcc | 144 |
| His | Gln | Ile | Ile | Lys | Leu | Glu | Val | Pro | Thr | Ile | Phe | Tyr | Glu | Ser | Ala | |
|     |     |     | 35  |     |     |     |     | 40  |     |     |     |     | 45  |     |     | |
| aga | gtc | gtc | aaa | aat | gca | ata | gaa | aaa | tat | cag | cca | gat | atg | gtt | att | 192 |
| Arg | Val | Val | Lys | Asn | Ala | Ile | Glu | Lys | Tyr | Gln | Pro | Asp | Met | Val | Ile | |
| 50  |     |     |     |     | 55  |     |     |     |     | 60  |     |     |     |     |     | |
| aac | gtg | ggg | caa | gcg | gga | ggc | cgt | gca | gca | att | act | cca | gaa | cga | atc | 240 |
| Asn | Val | Gly | Gln | Ala | Gly | Gly | Arg | Ala | Ala | Ile | Thr | Pro | Glu | Arg | Ile | |
| 65  |     |     |     | 70  |     |     |     |     | 75  |     |     |     |     | 80  | | |
| gct | att | aat | ttt | caa | tct | ggt | tca | act | cct | gat | aat | tcg | ggt | aaa | gga | 288 |
| Ala | Ile | Asn | Phe | Gln | Ser | Gly | Ser | Thr | Pro | Asp | Asn | Ser | Gly | Lys | Gly | |
|     |     |     |     | 85  |     |     |     |     | 90  |     |     |     |     | 95  |     | |
| cca | aaa | gaa | ggc | aaa | att | gaa | gca | gat | ggt | gct | gat | ggt | tat | ttc | act | 336 |
| Pro | Lys | Glu | Gly | Lys | Ile | Glu | Ala | Asp | Gly | Ala | Asp | Gly | Tyr | Phe | Thr | |
|     |     |     | 100 |     |     |     |     | 105 |     |     |     |     | 110 |     |     | |
| cag | ttg | cca | atc | aaa | aaa | atg | gtg | aca | gcc | aca | aga | aaa | gcg | ggg | gtt | 384 |
| Gln | Leu | Pro | Ile | Lys | Lys | Met | Val | Thr | Ala | Thr | Arg | Lys | Ala | Gly | Val | |
|     |     | 115 |     |     |     |     | 120 |     |     |     |     | 125 |     |     |     | |
| cct | agt | gaa | att | tcc | aat | tct | gca | ggt | aat | tat | gtg | tgc | aat | cat | ctt | 432 |
| Pro | Ser | Glu | Ile | Ser | Asn | Ser | Ala | Gly | Asn | Tyr | Val | Cys | Asn | His | Leu | |
|     | 130 |     |     |     |     | 135 |     |     |     |     | 140 |     |     |     |     | |
| ttt | tat | gaa | tta | caa | tac | atg | cga | gtt | cat | gaa | ttt | cct | aat | ttg | aaa | 480 |
| Phe | Tyr | Glu | Leu | Gln | Tyr | Met | Arg | Val | His | Glu | Phe | Pro | Asn | Leu | Lys | |
| 145 |     |     |     |     | 150 |     |     |     |     | 155 |     |     |     |     | 160 | |
| acg | gga | ttt | att | cat | att | cca | ttt | ttg | cca | agc | cag | gtt | aaa | aat | gga | 528 |
| Thr | Gly | Phe | Ile | His | Ile | Pro | Phe | Leu | Pro | Ser | Gln | Val | Lys | Asn | Gly | |
|     |     |     |     | 165 |     |     |     |     | 170 |     |     |     |     | 175 |     | |
| cgg | cat | cct | tcg | atg | agt | tta | tcc | tat | atg | gtt | aaa | ggg | tta | acc | gct | 576 |
| Arg | His | Pro | Ser | Met | Ser | Leu | Ser | Tyr | Met | Val | Lys | Gly | Leu | Thr | Ala | |

-continued

```
                     180                 185                 190
tcc att aag gcg gca gta gac gcc                                          600
Ser Ile Lys Ala Ala Val Asp Ala
        195                 200

<210> SEQ ID NO 6
<211> LENGTH: 200
<212> TYPE: PRT
<213> ORGANISM: Lactobacillus acidophilus

<400> SEQUENCE: 6

Met Lys Ile Leu Ile Thr Gly Phe Asp Pro Phe Gly Gly Glu Lys Ile
1               5                   10                  15

Asn Pro Ala Ile Glu Ala Val Lys Lys Leu Pro Asp Glu Ile Asp Gly
            20                  25                  30

His Gln Ile Ile Lys Leu Glu Val Pro Thr Ile Phe Tyr Glu Ser Ala
        35                  40                  45

Arg Val Val Lys Asn Ala Ile Glu Lys Tyr Gln Pro Asp Met Val Ile
    50                  55                  60

Asn Val Gly Gln Ala Gly Gly Arg Ala Ala Ile Thr Pro Glu Arg Ile
65                  70                  75                  80

Ala Ile Asn Phe Gln Ser Gly Ser Thr Pro Asp Asn Ser Gly Lys Gly
                85                  90                  95

Pro Lys Glu Gly Lys Ile Glu Ala Asp Gly Ala Asp Gly Tyr Phe Thr
            100                 105                 110

Gln Leu Pro Ile Lys Lys Met Val Thr Ala Thr Arg Lys Ala Gly Val
        115                 120                 125

Pro Ser Glu Ile Ser Asn Ser Ala Gly Asn Tyr Val Cys Asn His Leu
    130                 135                 140

Phe Tyr Glu Leu Gln Tyr Met Arg Val His Glu Phe Pro Asn Leu Lys
145                 150                 155                 160

Thr Gly Phe Ile His Ile Pro Phe Leu Pro Ser Gln Val Lys Asn Gly
                165                 170                 175

Arg His Pro Ser Met Ser Leu Ser Tyr Met Val Lys Gly Leu Thr Ala
            180                 185                 190

Ser Ile Lys Ala Ala Val Asp Ala
        195                 200

<210> SEQ ID NO 7
<211> LENGTH: 1337
<212> TYPE: DNA
<213> ORGANISM: Lactobacillus acidophilus
<220> FEATURE:
<221> NAME/KEY: CDS
<222> LOCATION: (1)..(372)
<223> OTHER INFORMATION: Aminopeptidase G ORF# 194
<220> FEATURE:
<221> NAME/KEY: CDS
<222> LOCATION: (420)..(1337)
<223> OTHER INFORMATION: Aminopeptidase G ORF# 195

<400> SEQUENCE: 7 atg att ttt gac gag aaa gga aaa tca atg aaa cac aag ctg aca atg     48
Met Ile Phe Asp Glu Lys Gly Lys Ser Met Lys His Lys Leu Thr Met
1               5                   10                  15 gca gaa att gcc aaa ttt caa caa gaa tat gag aag caa cct aga aat     96
Ala Glu Ile Ala Lys Phe Gln Gln Glu Tyr Glu Lys Gln Pro Arg Asn
            20                  25                  30 cgt gtt gct gaa ctt gca gta gtg aat aat ggt gta caa aag gcc agc    144
Arg Val Ala Glu Leu Ala Val Val Asn Asn Gly Val Gln Lys Ala Ser
```

```
              35                  40                  45
ttt aat aat gag ggg gtt aga aag cta aat cgt aca ttt tct att gaa    192
Phe Asn Asn Glu Gly Val Arg Lys Leu Asn Arg Thr Phe Ser Ile Glu
 50                  55                  60 att ccc aca gat aat gta act gat caa aaa caa tcg ggt cgc tgc tgg    240
Ile Pro Thr Asp Asn Val Thr Asp Gln Lys Gln Ser Gly Arg Cys Trp
 65                  70                  75                  80 tta ttt gca gca ttg aat acg ctt cgc cat ggc ttt gct aaa aag caa    288
Leu Phe Ala Ala Leu Asn Thr Leu Arg His Gly Phe Ala Lys Lys Gln
                 85                  90                  95 aat gct aag aat ttt act ttt tca caa aat tat cta ttc ttc tgg gat    336
Asn Ala Lys Asn Phe Thr Phe Ser Gln Asn Tyr Leu Phe Phe Trp Asp
            100                 105                 110 aga gta gaa aga gcc aat tct tct ttg ata ata ttt taaatactgc         382
Arg Val Glu Arg Ala Asn Ser Ser Leu Ile Ile Phe
        115                 120 ggataagcca ctggatgaca gaacggttca tacctat atg caa ggt cct gat act   437
                                        Met Gln Gly Pro Asp Thr
                                                    125         130 gat ggt ggt caa tgg gct atg gct gtt tct tta att aga aag tat ggt    485
Asp Gly Gly Gln Trp Ala Met Ala Val Ser Leu Ile Arg Lys Tyr Gly
                135                 140                 145 tta gtt cca aca tat gca caa gat gaa agc ttt act gct aac aat aca    533
Leu Val Pro Thr Tyr Ala Gln Asp Glu Ser Phe Thr Ala Asn Asn Thr
            150                 155                 160 gct gcg ttt aat agc gcc tta aat atg aaa ctg cgt gaa gat ggt tta    581
Ala Ala Phe Asn Ser Ala Leu Asn Met Lys Leu Arg Glu Asp Gly Leu
        165                 170                 175 gta ttg cgt aaa ctt tat caa gaa aag aaa atg gat gaa atc gaa act    629
Val Leu Arg Lys Leu Tyr Gln Glu Lys Lys Met Asp Glu Ile Glu Thr
    180                 185                 190 aaa cgt caa gaa ttt ttg agt gaa gtt tat aga atg gct gtt att gca    677
Lys Arg Gln Glu Phe Leu Ser Glu Val Tyr Arg Met Ala Val Ile Ala
195                 200                 205                 210 ttt ggt gaa cca gtt caa aaa ttt gat ctt gaa ttt aaa gat gat aat    725
Phe Gly Glu Pro Val Gln Lys Phe Asp Leu Glu Phe Lys Asp Asp Asn
                215                 220                 225 ggc aat tat cat ttt gat ggg aat tta act cca tta gac ttc ttc cac    773
Gly Asn Tyr His Phe Asp Gly Asn Leu Thr Pro Leu Asp Phe Phe His
            230                 235                 240 aat tat ttc act gat gat cta gat gat tac att gtt ttg ttt aat gca    821
Asn Tyr Phe Thr Asp Asp Leu Asp Asp Tyr Ile Val Leu Phe Asn Ala
        245                 250                 255 cct gat cat gaa ttt gat aag ctt tat gct ctt cca ttt gaa gat aat    869
Pro Asp His Glu Phe Asp Lys Leu Tyr Ala Leu Pro Phe Glu Asp Asn
    260                 265                 270 gtt gaa ggc ggc aca cca gta caa ttt ttg aat aca gaa att gat aat    917
Val Glu Gly Gly Thr Pro Val Gln Phe Leu Asn Thr Glu Ile Asp Asn
275                 280                 285                 290 tta aaa gaa gcg gct att aag cag ctt gaa gct ggt gaa act att tgg    965
Leu Lys Glu Ala Ala Ile Lys Gln Leu Glu Ala Gly Glu Thr Ile Trp
                295                 300                 305 ttt ggt tgt gat gtt ggt aaa gag agt gat cgt caa aaa ggt atc ttg   1013
Phe Gly Cys Asp Val Gly Lys Glu Ser Asp Arg Gln Lys Gly Ile Leu
            310                 315                 320 tct aag ggt ctt tac caa aca gat tta att ttt gat att gaa act aag   1061
Ser Lys Gly Leu Tyr Gln Thr Asp Leu Ile Phe Asp Ile Glu Thr Lys
        325                 330                 335 tta aat aaa aaa gaa aga tta caa act ggt gct tca ggc tca acg cat   1109
```

```
Leu Asn Lys Lys Glu Arg Leu Gln Thr Gly Ala Ser Gly Ser Thr His
        340                 345                 350 gcc atg act tta gtg gga gtt gac gtt gta gac gga cag cct caa caa      1157
Ala Met Thr Leu Val Gly Val Asp Val Val Asp Gly Gln Pro Gln Gln
355                 360                 365                 370 tgg aag gtt gaa aat tca tgg ggc agt aag gtc ggt gaa aag ggc tac      1205
Trp Lys Val Glu Asn Ser Trp Gly Ser Lys Val Gly Glu Lys Gly Tyr
                375                 380                 385 ttt gtc atg aat gat gag tgg ttt aat gaa tac tta ttc aag gtg gtt      1253
Phe Val Met Asn Asp Glu Trp Phe Asn Glu Tyr Leu Phe Lys Val Val
            390                 395                 400 gta aaa aag caa tat gta cca gaa aaa tta att aag atc tgg gaa ggc      1301
Val Lys Lys Gln Tyr Val Pro Glu Lys Leu Ile Lys Ile Trp Glu Gly
        405                 410                 415 gaa gca aca cca gta gaa gca tgg gac tca atg gca                      1337
Glu Ala Thr Pro Val Glu Ala Trp Asp Ser Met Ala
420                 425                 430
```

<210> SEQ ID NO 8
<211> LENGTH: 124
<212> TYPE: PRT
<213> ORGANISM: Lactobacillus acidophilus

<400> SEQUENCE: 8

```
Met Ile Phe Asp Glu Lys Gly Lys Ser Met Lys His Lys Leu Thr Met
1               5                   10                  15

Ala Glu Ile Ala Lys Phe Gln Gln Glu Tyr Glu Lys Gln Pro Arg Asn
            20                  25                  30

Arg Val Ala Glu Leu Ala Val Val Asn Asn Gly Val Gln Lys Ala Ser
        35                  40                  45

Phe Asn Asn Glu Gly Val Arg Lys Leu Asn Arg Thr Phe Ser Ile Glu
    50                  55                  60

Ile Pro Thr Asp Asn Val Thr Asp Gln Lys Gln Ser Gly Arg Cys Trp
65                  70                  75                  80

Leu Phe Ala Ala Leu Asn Thr Leu Arg His Gly Phe Ala Lys Lys Gln
                85                  90                  95

Asn Ala Lys Asn Phe Thr Phe Ser Gln Asn Tyr Leu Phe Phe Trp Asp
            100                 105                 110

Arg Val Glu Arg Ala Asn Ser Ser Leu Ile Ile Phe
        115                 120
```

<210> SEQ ID NO 9
<211> LENGTH: 306
<212> TYPE: PRT
<213> ORGANISM: Lactobacillus acidophilus

<400> SEQUENCE: 9

```
Met Gln Gly Pro Asp Thr Asp Gly Gly Gln Trp Ala Met Ala Val Ser
1               5                   10                  15

Leu Ile Arg Lys Tyr Gly Leu Val Pro Thr Tyr Ala Gln Asp Glu Ser
            20                  25                  30

Phe Thr Ala Asn Asn Thr Ala Ala Phe Asn Ser Ala Leu Asn Met Lys
        35                  40                  45

Leu Arg Glu Asp Gly Leu Val Leu Arg Lys Leu Tyr Gln Glu Lys Lys
    50                  55                  60

Met Asp Glu Ile Glu Thr Lys Arg Gln Glu Phe Leu Ser Glu Val Tyr
65                  70                  75                  80

Arg Met Ala Val Ile Ala Phe Gly Glu Pro Val Gln Lys Phe Asp Leu
```

```
                85                  90                  95
Glu Phe Lys Asp Asp Asn Gly Asn Tyr His Phe Asp Gly Asn Leu Thr
            100                 105                 110

Pro Leu Asp Phe Phe His Asn Tyr Phe Thr Asp Asp Leu Asp Asp Tyr
            115                 120                 125

Ile Val Leu Phe Asn Ala Pro Asp His Glu Phe Asp Lys Leu Tyr Ala
            130                 135                 140

Leu Pro Phe Glu Asp Asn Val Glu Gly Gly Thr Pro Val Gln Phe Leu
145                 150                 155                 160

Asn Thr Glu Ile Asp Asn Leu Lys Glu Ala Ala Ile Lys Gln Leu Glu
            165                 170                 175

Ala Gly Glu Thr Ile Trp Phe Gly Cys Asp Val Gly Lys Glu Ser Asp
            180                 185                 190

Arg Gln Lys Gly Ile Leu Ser Lys Gly Leu Tyr Gln Thr Asp Leu Ile
            195                 200                 205

Phe Asp Ile Glu Thr Lys Leu Asn Lys Lys Glu Arg Leu Gln Thr Gly
            210                 215                 220

Ala Ser Gly Ser Thr His Ala Met Thr Leu Val Gly Val Asp Val Val
225                 230                 235                 240

Asp Gly Gln Pro Gln Gln Trp Lys Val Glu Asn Ser Trp Gly Ser Lys
            245                 250                 255

Val Gly Glu Lys Gly Tyr Phe Val Met Asn Asp Glu Trp Phe Asn Glu
            260                 265                 270

Tyr Leu Phe Lys Val Val Leu Lys Gln Tyr Val Pro Glu Lys Leu
            275                 280                 285

Ile Lys Ile Trp Glu Gly Glu Ala Thr Pro Val Glu Ala Trp Asp Ser
290                 295                 300

Met Ala
305

<210> SEQ ID NO 10
<211> LENGTH: 1335
<212> TYPE: DNA
<213> ORGANISM: Lactobacillus acidophilus
<220> FEATURE:
<221> NAME/KEY: CDS
<222> LOCATION: (1)..(1335)
<223> OTHER INFORMATION: pepE Aminopeptidase E ORF# 204

<400> SEQUENCE: 10 atg aga aaa gga gat ttt tta atg gct cat gaa ctc act gtg caa gaa      48
Met Arg Lys Gly Asp Phe Leu Met Ala His Glu Leu Thr Val Gln Glu
1               5                   10                  15 cta gaa aag ttc tct gct gat ttt aac aag aat cca aag aat aaa att      96
Leu Glu Lys Phe Ser Ala Asp Phe Asn Lys Asn Pro Lys Asn Lys Ile
            20                  25                  30 att gct cgt gcg gct caa cgt agc ggt gtg ctc gaa gca tct tac aac     144
Ile Ala Arg Ala Ala Gln Arg Ser Gly Val Leu Glu Ala Ser Tyr Asn
        35                  40                  45 gat cgc gta gaa ggt gaa tta act cgc gtt ttt tca acg gaa tta gat     192
Asp Arg Val Glu Gly Glu Leu Thr Arg Val Phe Ser Thr Glu Leu Asp
    50                  55                  60 act gac aac gtt act aac caa ctt cac tca ggt cgt tgc tgg gag ttt     240
Thr Asp Asn Val Thr Asn Gln Leu His Ser Gly Arg Cys Trp Glu Phe
65                  70                  75                  80 tca acc tta aat gtt ttg cgt cat gca ttt ggc aag aag tac aaa gca     288
Ser Thr Leu Asn Val Leu Arg His Ala Phe Gly Lys Lys Tyr Lys Ala
                85                  90                  95
```

```
aag aac ttt acc ttc tca caa gcc tac aac ttc ttc tgg gat aag att      336
Lys Asn Phe Thr Phe Ser Gln Ala Tyr Asn Phe Phe Trp Asp Lys Ile
            100                 105                 110 gaa cgt gct aat atg ttc tac aat cgt atc tta gat agt gct gac atg      384
Glu Arg Ala Asn Met Phe Tyr Asn Arg Ile Leu Asp Ser Ala Asp Met
115                 120                 125 cct ctt gat tct cgt caa gtg aaa gct gat ctc gac ttt gct ggt gca      432
Pro Leu Asp Ser Arg Gln Val Lys Ala Asp Leu Asp Phe Ala Gly Ala
        130                 135                 140 gac ggt gga caa ttc caa atg gct gcc gca tta gta gaa aaa tat ggc      480
Asp Gly Gly Gln Phe Gln Met Ala Ala Ala Leu Val Glu Lys Tyr Gly
145                 150                 155                 160 gtt gtt cct tca tac gca atg cct gaa act ttc aac act aat aat aca      528
Val Val Pro Ser Tyr Ala Met Pro Glu Thr Phe Asn Thr Asn Asn Thr
                165                 170                 175 act agc ttt gcg aca gct ctt ggt gac aag ctt aaa aaa gac gca tta      576
Thr Ser Phe Ala Thr Ala Leu Gly Asp Lys Leu Lys Lys Asp Ala Leu
            180                 185                 190 gtt ctt cgt gaa tta aag caa tat ggt aaa gat gac gaa atc gct aag      624
Val Leu Arg Glu Leu Lys Gln Tyr Gly Lys Asp Asp Glu Ile Ala Lys
        195                 200                 205 act cgt gaa aaa ttc ttg agt gaa gtt tac caa atg act gct atc gct      672
Thr Arg Glu Lys Phe Leu Ser Glu Val Tyr Gln Met Thr Ala Ile Ala
210                 215                 220 gtc ggt gaa cca cct aag acg ttt gat ctt gaa tat cgt gat gat gat      720
Val Gly Glu Pro Pro Lys Thr Phe Asp Leu Glu Tyr Arg Asp Asp Asp
225                 230                 235                 240 aag aaa tat cat tta gac aag aat ctt aca cca ctt gaa ttc tta cat      768
Lys Lys Tyr His Leu Asp Lys Asn Leu Thr Pro Leu Glu Phe Leu His
                245                 250                 255 aag tat atg ggt gag gtt gat ttt gat gac tat gtt gtt tta act aat      816
Lys Tyr Met Gly Glu Val Asp Phe Asp Asp Tyr Val Val Leu Thr Asn
            260                 265                 270 gca cct gat cat gaa tac aac aag tta tac ggt ctt cca gca gaa gat      864
Ala Pro Asp His Glu Tyr Asn Lys Leu Tyr Gly Leu Pro Ala Glu Asp
        275                 280                 285 aac att gaa ggc tca ctt aga atc aag ctt tta aat gta cct atg gaa      912
Asn Ile Glu Gly Ser Leu Arg Ile Lys Leu Leu Asn Val Pro Met Glu
290                 295                 300 tac tta tca tca gct gct att gct caa tta aaa gat ggt gaa gca gta      960
Tyr Leu Ser Ser Ala Ala Ile Ala Gln Leu Lys Asp Gly Glu Ala Val
305                 310                 315                 320 tgg ttt ggt aac gat gtt ctt cgt caa atg gac cgc aag act ggt tat     1008
Trp Phe Gly Asn Asp Val Leu Arg Gln Met Asp Arg Lys Thr Gly Tyr
                325                 330                 335 ctt gat act aac ctt tac aaa ctt gac gat tta ttc ggc gtt gat ctt     1056
Leu Asp Thr Asn Leu Tyr Lys Leu Asp Asp Leu Phe Gly Val Asp Leu
            340                 345                 350 aag atg tct aaa gct gac aga tta agg act ggt gtt ggt gaa gtt tca     1104
Lys Met Ser Lys Ala Asp Arg Leu Arg Thr Gly Val Gly Glu Val Ser
        355                 360                 365 cac gca atg acc ttg gtt ggt gtt gat gaa gat aat ggc gaa atc cgt     1152
His Ala Met Thr Leu Val Gly Val Asp Glu Asp Asn Gly Glu Ile Arg
370                 375                 380 caa tgg aag gtc gaa aac tca tgg ggc gaa aaa tct ggt tct aaa gga     1200
Gln Trp Lys Val Glu Asn Ser Trp Gly Glu Lys Ser Gly Ser Lys Gly
385                 390                 395                 400 ttc ttt gtt atg agt aat gac tgg ttc aac gac tat gta tat gaa gtt     1248
Phe Phe Val Met Ser Asn Asp Trp Phe Asn Asp Tyr Val Tyr Glu Val
```

```
                         405                 410                 415
gtt gtt cac aag aag tat tta acc gat aag caa aaa gaa ctt gca gaa       1296
Val Val His Lys Lys Tyr Leu Thr Asp Lys Gln Lys Glu Leu Ala Glu
            420                 425                 430 ggt cct att acc gac ttg cct gca tgg gat tca tta gct                   1335
Gly Pro Ile Thr Asp Leu Pro Ala Trp Asp Ser Leu Ala
        435                 440                 445
```

<210> SEQ ID NO 11
<211> LENGTH: 445
<212> TYPE: PRT
<213> ORGANISM: Lactobacillus acidophilus

<400> SEQUENCE: 11

```
Met Arg Lys Gly Asp Phe Leu Met Ala His Glu Leu Thr Val Gln Glu
1               5                   10                  15

Leu Glu Lys Phe Ser Ala Asp Phe Asn Lys Asn Pro Lys Asn Lys Ile
            20                  25                  30

Ile Ala Arg Ala Ala Gln Arg Ser Gly Val Leu Glu Ala Ser Tyr Asn
        35                  40                  45

Asp Arg Val Glu Gly Leu Thr Arg Val Phe Ser Thr Glu Leu Asp
    50                  55                  60

Thr Asp Asn Val Thr Asn Gln Leu His Ser Gly Arg Cys Trp Glu Phe
65                  70                  75                  80

Ser Thr Leu Asn Val Leu Arg His Ala Phe Gly Lys Lys Tyr Lys Ala
                85                  90                  95

Lys Asn Phe Thr Phe Ser Gln Ala Tyr Asn Phe Phe Trp Asp Lys Ile
            100                 105                 110

Glu Arg Ala Asn Met Phe Tyr Asn Arg Ile Leu Asp Ser Ala Asp Met
        115                 120                 125

Pro Leu Asp Ser Arg Gln Val Lys Ala Asp Leu Asp Phe Ala Gly Ala
    130                 135                 140

Asp Gly Gly Gln Phe Gln Met Ala Ala Ala Leu Val Glu Lys Tyr Gly
145                 150                 155                 160

Val Val Pro Ser Tyr Ala Met Pro Glu Thr Phe Asn Thr Asn Asn Thr
                165                 170                 175

Thr Ser Phe Ala Thr Ala Leu Gly Asp Lys Leu Lys Lys Asp Ala Leu
            180                 185                 190

Val Leu Arg Glu Leu Lys Gln Tyr Gly Lys Asp Asp Glu Ile Ala Lys
        195                 200                 205

Thr Arg Glu Lys Phe Leu Ser Glu Val Tyr Gln Met Thr Ala Ile Ala
    210                 215                 220

Val Gly Glu Pro Pro Lys Thr Phe Asp Leu Glu Tyr Arg Asp Asp
225                 230                 235                 240

Lys Lys Tyr His Leu Asp Lys Asn Leu Thr Pro Leu Glu Phe Leu His
                245                 250                 255

Lys Tyr Met Gly Glu Val Asp Phe Asp Tyr Val Val Leu Thr Asn
            260                 265                 270

Ala Pro Asp His Glu Tyr Asn Lys Leu Tyr Gly Leu Pro Ala Glu Asp
        275                 280                 285

Asn Ile Glu Gly Ser Leu Arg Ile Lys Leu Leu Asn Val Pro Met Glu
    290                 295                 300

Tyr Leu Ser Ser Ala Ala Ile Ala Gln Leu Lys Asp Gly Glu Ala Val
305                 310                 315                 320

Trp Phe Gly Asn Asp Val Leu Arg Gln Met Asp Arg Lys Thr Gly Tyr
```

```
                   325                 330                 335
Leu Asp Thr Asn Leu Tyr Lys Leu Asp Asp Leu Phe Gly Val Asp Leu
                340                 345                 350

Lys Met Ser Lys Ala Asp Arg Leu Arg Thr Gly Val Gly Glu Val Ser
            355                 360                 365

His Ala Met Thr Leu Val Gly Val Asp Glu Asp Asn Gly Glu Ile Arg
        370                 375                 380

Gln Trp Lys Val Glu Asn Ser Trp Gly Glu Lys Ser Gly Ser Lys Gly
385                 390                 395                 400

Phe Phe Val Met Ser Asn Asp Trp Phe Asn Asp Tyr Val Tyr Glu Val
                405                 410                 415

Val Val His Lys Lys Tyr Leu Thr Asp Lys Gln Lys Glu Leu Ala Glu
            420                 425                 430

Gly Pro Ile Thr Asp Leu Pro Ala Trp Asp Ser Leu Ala
        435                 440                 445

<210> SEQ ID NO 12
<211> LENGTH: 582
<212> TYPE: DNA
<213> ORGANISM: Lactobacillus acidophilus
<220> FEATURE:
<221> NAME/KEY: CDS
<222> LOCATION: (1)..(582)
<223> OTHER INFORMATION: Dipeptidase (EC 3.4.13.18) ORF# 235

<400> SEQUENCE: 12 ttg atc tca atc gaa gat att aag tgg gcc gaa agt tca cac tac caa      48
Leu Ile Ser Ile Glu Asp Ile Lys Trp Ala Glu Ser Ser His Tyr Gln
1               5                   10                  15 gac act cca tac gat gct tat ggc gac caa ggt act ccg gaa caa aag     96
Asp Thr Pro Tyr Asp Ala Tyr Gly Asp Gln Gly Thr Pro Glu Gln Lys
                20                  25                  30 aag acc ttc cgt cca att ggt att aac cgt aac ttc gaa act cac att    144
Lys Thr Phe Arg Pro Ile Gly Ile Asn Arg Asn Phe Glu Thr His Ile
            35                  40                  45 tta caa att aga aac gac gtc cct gca gaa atc gct ggt gtt caa tgg    192
Leu Gln Ile Arg Asn Asp Val Pro Ala Glu Ile Ala Gly Val Gln Trp
        50                  55                  60 ttg gca ttt ggc cct aat acc ttc aac tca atg gtg cca ttc tat act    240
Leu Ala Phe Gly Pro Asn Thr Phe Asn Ser Met Val Pro Phe Tyr Thr
65                  70                  75                  80 aat gta act act aca cca gaa agc ttc caa act act cct aag ttc aac    288
Asn Val Thr Thr Thr Pro Glu Ser Phe Gln Thr Thr Pro Lys Phe Asn
                85                  90                  95 ttg aac aag atc ttc tgg ctt aat aag tta act gcc caa ctt ggt gac    336
Leu Asn Lys Ile Phe Trp Leu Asn Lys Leu Thr Ala Gln Leu Gly Asp
            100                 105                 110 acc aat tac cgc gta tac gga gaa ctt gaa gat gct ttt gaa caa aag    384
Thr Asn Tyr Arg Val Tyr Gly Glu Leu Glu Asp Ala Phe Glu Gln Lys
        115                 120                 125 agt ttg gca caa tgc cac aag atc caa cac gac act gac aaa gaa gtt    432
Ser Leu Ala Gln Cys His Lys Ile Gln His Asp Thr Asp Lys Glu Val
    130                 135                 140 aag ggt ctt tca ggt aag gaa tta caa gat aag tta aac gca gct aac    480
Lys Gly Leu Ser Gly Lys Glu Leu Gln Asp Lys Leu Asn Ala Ala Asn
145                 150                 155                 160 cag ttg atg gcc gac act gtt tac aac aat acc gtt gaa ctt ctt ggt    528
Gln Leu Met Ala Asp Thr Val Tyr Asn Asn Thr Val Glu Leu Leu Gly
                165                 170                 175
```

```
caa atg gtt gac gaa ggt cac ggt ttg atg act ttg aag tac gac ttg      576
Gln Met Val Asp Glu Gly His Gly Leu Met Thr Leu Lys Tyr Asp Leu
            180                 185                 190 ctt gat                                                               582
Leu Asp <210> SEQ ID NO 13
<211> LENGTH: 194
<212> TYPE: PRT
<213> ORGANISM: Lactobacillus acidophilus

<400> SEQUENCE: 13

Leu Ile Ser Ile Glu Asp Ile Lys Trp Ala Glu Ser Ser His Tyr Gln
1               5                   10                  15

Asp Thr Pro Tyr Asp Ala Tyr Gly Asp Gln Gly Thr Pro Glu Gln Lys
            20                  25                  30

Lys Thr Phe Arg Pro Ile Gly Ile Asn Arg Asn Phe Glu Thr His Ile
        35                  40                  45

Leu Gln Ile Arg Asn Asp Val Pro Ala Glu Ile Ala Gly Val Gln Trp
    50                  55                  60

Leu Ala Phe Gly Pro Asn Thr Phe Asn Ser Met Val Pro Phe Tyr Thr
65                  70                  75                  80

Asn Val Thr Thr Thr Pro Glu Ser Phe Gln Thr Thr Pro Lys Phe Asn
                85                  90                  95

Leu Asn Lys Ile Phe Trp Leu Asn Lys Leu Thr Ala Gln Leu Gly Asp
            100                 105                 110

Thr Asn Tyr Arg Val Tyr Gly Glu Leu Glu Asp Ala Phe Glu Gln Lys
        115                 120                 125

Ser Leu Ala Gln Cys His Lys Ile Gln His Asp Thr Asp Lys Glu Val
    130                 135                 140

Lys Gly Leu Ser Gly Lys Glu Leu Gln Asp Lys Leu Asn Ala Ala Asn
145                 150                 155                 160

Gln Leu Met Ala Asp Thr Val Tyr Asn Asn Thr Val Glu Leu Leu Gly
                165                 170                 175

Gln Met Val Asp Glu Gly His Gly Leu Met Thr Leu Lys Tyr Asp Leu
            180                 185                 190

Leu Asp

<210> SEQ ID NO 14
<211> LENGTH: 840
<212> TYPE: DNA
<213> ORGANISM: Lactobacillus acidophilus
<220> FEATURE:
<221> NAME/KEY: CDS
<222> LOCATION: (1)..(840)
<223> OTHER INFORMATION: Dipeptidase (EC 3.4.13.18) ORF# 236

<400> SEQUENCE: 14 atg aaa caa aca gaa tgt act act atc tta gta ggt aaa aaa gca act       48
Met Lys Gln Thr Glu Cys Thr Thr Ile Leu Val Gly Lys Lys Ala Thr
1               5                   10                  15 atc gac ggt tca acc atg atc gca cgt agt gaa gac ggt ggt cgt gta       96
Ile Asp Gly Ser Thr Met Ile Ala Arg Ser Glu Asp Gly Gly Arg Val
            20                  25                  30 att atc cct gaa ggg ttc aaa gta gtt aac cct gaa gaa caa cct aag      144
Ile Ile Pro Glu Gly Phe Lys Val Val Asn Pro Glu Glu Gln Pro Lys
        35                  40                  45 cac tac act agc gct atc agt aag caa aag att gat gat aca gac tta      192
His Tyr Thr Ser Ala Ile Ser Lys Gln Lys Ile Asp Asp Thr Asp Leu
```

```
         50                  55                  60
gct gaa act cca ctt cgt tac acc tca gca cct gat gta tct ggt gaa    240
Ala Glu Thr Pro Leu Arg Tyr Thr Ser Ala Pro Asp Val Ser Gly Glu
 65                  70                  75                  80 aat ggt att tgg gga gca gct ggt att aat tct gaa aat atc gcc atg    288
Asn Gly Ile Trp Gly Ala Ala Gly Ile Asn Ser Glu Asn Ile Ala Met
                 85                  90                  95 act gct act gaa act att act act aat tca cgt att caa ggt gtt gac    336
Thr Ala Thr Glu Thr Ile Thr Thr Asn Ser Arg Ile Gln Gly Val Asp
            100                 105                 110 cca ctc ctt gac cca gct gaa ggt ggt ctt ggt gaa gaa gat ttc gtt    384
Pro Leu Leu Asp Pro Ala Glu Gly Gly Leu Gly Glu Glu Asp Phe Val
        115                 120                 125 aca cta acg ctt cca tac att cac tca gct ttt gat ggt gtt aag cgc    432
Thr Leu Thr Leu Pro Tyr Ile His Ser Ala Phe Asp Gly Val Lys Arg
    130                 135                 140 gta ggt tac cta gtt gaa aaa tac ggt act tac gaa atg aac ggc atg    480
Val Gly Tyr Leu Val Glu Lys Tyr Gly Thr Tyr Glu Met Asn Gly Met
145                 150                 155                 160 gct ttt tca gat aaa gat act att tgg tac ctt gaa act atc ggt ggt    528
Ala Phe Ser Asp Lys Asp Thr Ile Trp Tyr Leu Glu Thr Ile Gly Gly
                165                 170                 175 cac cac tgg att gca cgt cgc atc cct gac gat gca tat gtt att gct    576
His His Trp Ile Ala Arg Arg Ile Pro Asp Asp Ala Tyr Val Ile Ala
            180                 185                 190 cca aac cgt ttg aac atc gat gaa ttc gac ttc gat gat acc gac aat    624
Pro Asn Arg Leu Asn Ile Asp Glu Phe Asp Phe Asp Asp Thr Asp Asn
        195                 200                 205 ttt gct gca gct agt gac ttg aaa gac tta atc agt gaa tat cac ttg    672
Phe Ala Ala Ala Ser Asp Leu Lys Asp Leu Ile Ser Glu Tyr His Leu
    210                 215                 220 aac cca gac cgt gaa ggc tac aac atg cgc cac atc ttt ggt tca tca    720
Asn Pro Asp Arg Glu Gly Tyr Asn Met Arg His Ile Phe Gly Ser Ser
225                 230                 235                 240 act atc aag gac gct cac tac aac aat cca cgt gct ggt aca ttc aca    768
Thr Ile Lys Asp Ala His Tyr Asn Asn Pro Arg Ala Gly Thr Phe Thr
                245                 250                 255 act act tcg atc cag act tcg gcg gca ctc ccg ctg atc aag atc aac    816
Thr Thr Ser Ile Gln Thr Ser Ala Ala Leu Pro Leu Ile Lys Ile Asn
            260                 265                 270 cat tca ttt gcc acg caa atc gtt                                    840
His Ser Phe Ala Thr Gln Ile Val
        275                 280

<210> SEQ ID NO 15
<211> LENGTH: 280
<212> TYPE: PRT
<213> ORGANISM: Lactobacillus acidophilus

<400> SEQUENCE: 15

Met Lys Gln Thr Glu Cys Thr Thr Ile Leu Val Gly Lys Lys Ala Thr
 1               5                  10                  15

Ile Asp Gly Ser Thr Met Ile Ala Arg Ser Glu Asp Gly Gly Arg Val
                20                  25                  30

Ile Ile Pro Glu Gly Phe Lys Val Val Asn Pro Glu Glu Gln Pro Lys
            35                  40                  45

His Tyr Thr Ser Ala Ile Ser Lys Gln Lys Ile Asp Asp Thr Asp Leu
        50                  55                  60

Ala Glu Thr Pro Leu Arg Tyr Thr Ser Ala Pro Asp Val Ser Gly Glu
```

-continued

```
                65                  70                  75                  80
            Asn Gly Ile Trp Gly Ala Ala Gly Ile Asn Ser Glu Asn Ile Ala Met
                            85                  90                  95

Thr Ala Thr Glu Thr Ile Thr Thr Asn Ser Arg Ile Gln Gly Val Asp
                        100                 105                 110

Pro Leu Leu Asp Pro Ala Glu Gly Leu Gly Glu Glu Asp Phe Val
                    115                 120                 125

Thr Leu Thr Leu Pro Tyr Ile His Ser Ala Phe Asp Gly Val Lys Arg
                    130                 135                 140

Val Gly Tyr Leu Val Glu Lys Tyr Gly Thr Tyr Glu Met Asn Gly Met
            145                 150                 155                 160

Ala Phe Ser Asp Lys Asp Thr Ile Trp Tyr Leu Glu Thr Ile Gly Gly
                            165                 170                 175

His His Trp Ile Ala Arg Arg Ile Pro Asp Asp Ala Tyr Val Ile Ala
                        180                 185                 190

Pro Asn Arg Leu Asn Ile Asp Glu Phe Asp Phe Asp Asp Thr Asp Asn
                    195                 200                 205

Phe Ala Ala Ala Ser Asp Leu Lys Asp Leu Ile Ser Glu Tyr His Leu
                    210                 215                 220

Asn Pro Asp Arg Glu Gly Tyr Asn Met Arg His Ile Phe Gly Ser Ser
            225                 230                 235                 240

Thr Ile Lys Asp Ala His Tyr Asn Asn Pro Arg Ala Gly Thr Phe Thr
                            245                 250                 255

Thr Thr Ser Ile Gln Thr Ser Ala Ala Leu Pro Leu Ile Lys Ile Asn
                        260                 265                 270

His Ser Phe Ala Thr Gln Ile Val
                    275                 280

<210> SEQ ID NO 16
<211> LENGTH: 687
<212> TYPE: DNA
<213> ORGANISM: Lactobacillus acidophilus
<220> FEATURE:
<221> NAME/KEY: CDS
<222> LOCATION: (1)..(687)
<223> OTHER INFORMATION: Prepilin peptidase (EC 3.4.99.-) ORF# 286

<400> SEQUENCE: 16 ttg aac tca ata tat ttt tta ctt aat ttt ttc ata gga gca tgc tta         48
Leu Asn Ser Ile Tyr Phe Leu Leu Asn Phe Phe Ile Gly Ala Cys Leu
1               5                   10                  15 gct tca cat gca aac gtt ata tac gaa cga tgg gat act cgt aac ttt         96
Ala Ser His Ala Asn Val Ile Tyr Glu Arg Trp Asp Thr Arg Asn Phe
                20                  25                  30 atc ttt tct cgg tct tat tgt gat aat tgt aaa agt act ctt tca cta        144
Ile Phe Ser Arg Ser Tyr Cys Asp Asn Cys Lys Ser Thr Leu Ser Leu
            35                  40                  45 ttg gac gaa att cct cta ttc tct tat tta ctt ttg aaa ggc aaa tgt        192
Leu Asp Glu Ile Pro Leu Phe Ser Tyr Leu Leu Leu Lys Gly Lys Cys
        50                  55                  60 aag tat tgc caa aaa aat att ccg cgt gaa tta ttc ttt ttt gaa cta        240
Lys Tyr Cys Gln Lys Asn Ile Pro Arg Glu Leu Phe Phe Phe Glu Leu
65                  70                  75                  80 gtt ggt ggc ttt gct ttt tgt aca ata aat ttt agt gat aaa agt caa        288
Val Gly Gly Phe Ala Phe Cys Thr Ile Asn Phe Ser Asp Lys Ser Gln
                85                  90                  95 att atc act tct atc ttt att ttt tct ctt ctt tta att gca atc tct        336
Ile Ile Thr Ser Ile Phe Ile Phe Ser Leu Leu Leu Ile Ala Ile Ser
```

-continued

```
                  100                 105                 110
gat tat tat caa aat gaa ttt gat tta att ttt att ttt cca gca att       384
Asp Tyr Tyr Gln Asn Glu Phe Asp Leu Ile Phe Ile Phe Pro Ala Ile
            115                 120                 125 att act tct att tta ttt aat cgc att tac tta ttt aac tgg att gaa       432
Ile Thr Ser Ile Leu Phe Asn Arg Ile Tyr Leu Phe Asn Trp Ile Glu
        130                 135                 140 tgg cta tct ttt cta cca gtt ttg ata gtc ctt agt att tat tca ttt       480
Trp Leu Ser Phe Leu Pro Val Leu Ile Val Leu Ser Ile Tyr Ser Phe
145                 150                 155                 160 aaa caa aaa atg gga tta ggt gat tta tta atc tat gtc cta atc tcc       528
Lys Gln Lys Met Gly Leu Gly Asp Leu Leu Ile Tyr Val Leu Ile Ser
                165                 170                 175 act tat ttt act ccc act ttt gca aac tta act tta ctt ttt gct gct       576
Thr Tyr Phe Thr Pro Thr Phe Ala Asn Leu Thr Leu Leu Phe Ala Ala
            180                 185                 190 tta att tta ata atc att cat ttt aca gaa aat aat tta gct tca tat       624
Leu Ile Leu Ile Ile Ile His Phe Thr Glu Asn Asn Leu Ala Ser Tyr
        195                 200                 205 aat tat cca ttt att cca ttc att ttt att gga cta att att tca aaa       672
Asn Tyr Pro Phe Ile Pro Phe Ile Phe Ile Gly Leu Ile Ile Ser Lys
210                 215                 220 ttt att ttt gaa caa                                                   687
Phe Ile Phe Glu Gln
225
```

<210> SEQ ID NO 17
<211> LENGTH: 229
<212> TYPE: PRT
<213> ORGANISM: Lactobacillus acidophilus

<400> SEQUENCE: 17

```
Leu Asn Ser Ile Tyr Phe Leu Leu Asn Phe Phe Ile Gly Ala Cys Leu
1               5                   10                  15

Ala Ser His Ala Asn Val Ile Tyr Glu Arg Trp Asp Thr Arg Asn Phe
            20                  25                  30

Ile Phe Ser Arg Ser Tyr Cys Asp Asn Cys Lys Ser Thr Leu Ser Leu
        35                  40                  45

Leu Asp Glu Ile Pro Leu Phe Ser Tyr Leu Leu Leu Lys Gly Lys Cys
50                  55                  60

Lys Tyr Cys Gln Lys Asn Ile Pro Arg Glu Leu Phe Phe Glu Leu
65                  70                  75                  80

Val Gly Gly Phe Ala Phe Cys Thr Ile Asn Phe Ser Asp Lys Ser Gln
            85                  90                  95

Ile Ile Thr Ser Ile Phe Ile Phe Ser Leu Leu Leu Ile Ala Ile Ser
        100                 105                 110

Asp Tyr Tyr Gln Asn Glu Phe Asp Leu Ile Phe Ile Phe Pro Ala Ile
            115                 120                 125

Ile Thr Ser Ile Leu Phe Asn Arg Ile Tyr Leu Phe Asn Trp Ile Glu
        130                 135                 140

Trp Leu Ser Phe Leu Pro Val Leu Ile Val Leu Ser Ile Tyr Ser Phe
145                 150                 155                 160

Lys Gln Lys Met Gly Leu Gly Asp Leu Leu Ile Tyr Val Leu Ile Ser
                165                 170                 175

Thr Tyr Phe Thr Pro Thr Phe Ala Asn Leu Thr Leu Leu Phe Ala Ala
            180                 185                 190

Leu Ile Leu Ile Ile Ile His Phe Thr Glu Asn Asn Leu Ala Ser Tyr
```

```
                    195                 200                 205
Asn Tyr Pro Phe Ile Pro Phe Ile Phe Ile Gly Leu Ile Ile Ser Lys
    210                 215                 220

Phe Ile Phe Glu Gln
225

<210> SEQ ID NO 18
<211> LENGTH: 1347
<212> TYPE: DNA
<213> ORGANISM: Lactobacillus acidophilus
<220> FEATURE:
<221> NAME/KEY: CDS
<222> LOCATION: (1)..(1347)
<223> OTHER INFORMATION: Aminopeptidase C ORF# 343

<400> SEQUENCE: 18 atg tca aaa gaa att tct aag gat act att aat aaa ttt gaa caa gat         48
Met Ser Lys Glu Ile Ser Lys Asp Thr Ile Asn Lys Phe Glu Gln Asp
1               5                   10                  15 tta act aat cac cca gct tat aaa gtt gcc agc cgt gca gca caa gaa         96
Leu Thr Asn His Pro Ala Tyr Lys Val Ala Ser Arg Ala Ala Gln Glu
                20                  25                  30 aat ggc att ttt aaa gca agt caa gat tta caa act aaa att gat ctt        144
Asn Gly Ile Phe Lys Ala Ser Gln Asp Leu Gln Thr Lys Ile Asp Leu
            35                  40                  45 gat cca act ttt tca att gaa att gaa act ggt aaa cca gct gac caa        192
Asp Pro Thr Phe Ser Ile Glu Ile Glu Thr Gly Lys Pro Ala Asp Gln
        50                  55                  60 aag caa tcc ggt cgt tgc tgg atg ttc agc gca tta aat acc atg cgt        240
Lys Gln Ser Gly Arg Cys Trp Met Phe Ser Ala Leu Asn Thr Met Arg
65                  70                  75                  80 cac cca ctt caa aag aaa ttc caa ttg aag gac ttc gaa tta tct caa        288
His Pro Leu Gln Lys Lys Phe Gln Leu Lys Asp Phe Glu Leu Ser Gln
                85                  90                  95 aat tac acc aac ttc tgg gat aaa ttt gaa aag tca aac tgg ttc ttt        336
Asn Tyr Thr Asn Phe Trp Asp Lys Phe Glu Lys Ser Asn Trp Phe Phe
                100                 105                 110 gaa aat gtt att gca act gca gat aag cca ctc ggc gat cgc aaa gtt        384
Glu Asn Val Ile Ala Thr Ala Asp Lys Pro Leu Gly Asp Arg Lys Val
            115                 120                 125 tca ttc ttg ttt gcc act cca caa caa gac ggt ggt caa tgg gat atg        432
Ser Phe Leu Phe Ala Thr Pro Gln Gln Asp Gly Gly Gln Trp Asp Met
        130                 135                 140 ctt tgt ggc att att gaa aaa tac ggt atc gta cca aag agt gtt tac        480
Leu Cys Gly Ile Ile Glu Lys Tyr Gly Ile Val Pro Lys Ser Val Tyr
145                 150                 155                 160 cca gaa act gct aat gca act aac tca agt gca tta aac gac act tta        528
Pro Glu Thr Ala Asn Ala Thr Asn Ser Ser Ala Leu Asn Asp Thr Leu
                165                 170                 175 aac acc ttg ctt cgt aaa gat ggt cta gaa tta cgt aaa ttg gtt aac        576
Asn Thr Leu Leu Arg Lys Asp Gly Leu Glu Leu Arg Lys Leu Val Asn
                180                 185                 190 gat ggt aag tca gaa gaa gaa att caa act cgt aag gaa gaa atg ctt        624
Asp Gly Lys Ser Glu Glu Glu Ile Gln Thr Arg Lys Glu Glu Met Leu
            195                 200                 205 aac gat gtc ttc cgc gta cta gct gtt tca ctt ggc gtt cca cca aag        672
Asn Asp Val Phe Arg Val Leu Ala Val Ser Leu Gly Val Pro Pro Lys
        210                 215                 220 aaa ttt aac ttc gaa tat cgt gac gat gac aag aat tac cat att gat        720
Lys Phe Asn Phe Glu Tyr Arg Asp Asp Asp Lys Asn Tyr His Ile Asp
225                 230                 235                 240
```

```
aag gac att act cca aag gaa ttc ttt gat aaa tat gtt ggt atg gac      768
Lys Asp Ile Thr Pro Lys Glu Phe Phe Asp Lys Tyr Val Gly Met Asp
                245                 250                 255 ctt gaa gac cac atc tca act atc aat gct cca act agt gac aag cca      816
Leu Glu Asp His Ile Ser Thr Ile Asn Ala Pro Thr Ser Asp Lys Pro
            260                 265                 270 ttc cat aaa gta ttc tca gtt gaa tac tta ggt aat gtt gaa ggt ggt      864
Phe His Lys Val Phe Ser Val Glu Tyr Leu Gly Asn Val Glu Gly Gly
        275                 280                 285 cgt caa gtt cgt cac ttg aac tta aag gtt gat gaa atg aaa gac tta      912
Arg Gln Val Arg His Leu Asn Leu Lys Val Asp Glu Met Lys Asp Leu
    290                 295                 300 atc atc aag caa cta aag agc ggc gaa gtt gta tgg ttt ggt tca aac      960
Ile Ile Lys Gln Leu Lys Ser Gly Glu Val Val Trp Phe Gly Ser Asn
305                 310                 315                 320 gtt gtt aag gac tca gaa aga aga gct ggt ctt ctt gat act gac ctt     1008
Val Val Lys Asp Ser Glu Arg Arg Ala Gly Leu Leu Asp Thr Asp Leu
                325                 330                 335 tac aga cgt gac gaa tta ttt gac gtg gac ttt tca atg tca aag gct     1056
Tyr Arg Arg Asp Glu Leu Phe Asp Val Asp Phe Ser Met Ser Lys Ala
            340                 345                 350 gaa aag ctt gat tct ggt gaa agt atg atg gac cat gct atg gtt atc     1104
Glu Lys Leu Asp Ser Gly Glu Ser Met Met Asp His Ala Met Val Ile
        355                 360                 365 act ggt gtt gat att gtt gat ggc aaa cca act aag tgg aag atc gaa     1152
Thr Gly Val Asp Ile Val Asp Gly Lys Pro Thr Lys Trp Lys Ile Glu
    370                 375                 380 aac tca tgg ggc gaa aag cct ggc ttc aaa ggt tac ttt gta atg agc     1200
Asn Ser Trp Gly Glu Lys Pro Gly Phe Lys Gly Tyr Phe Val Met Ser
385                 390                 395                 400 gac aaa tgg ttt gat tca ttt gtt tac caa gct gtt atc aac aag aaa     1248
Asp Lys Trp Phe Asp Ser Phe Val Tyr Gln Ala Val Ile Asn Lys Lys
                405                 410                 415 ttc ttg cca gac gac tta aag aaa gcc tac gat gaa ggt gtt aaa gat     1296
Phe Leu Pro Asp Asp Leu Lys Lys Ala Tyr Asp Glu Gly Val Lys Asp
            420                 425                 430 cca atc caa tta tta cca tgg gat cca atg ggt gct tta gca ttt gat     1344
Pro Ile Gln Leu Leu Pro Trp Asp Pro Met Gly Ala Leu Ala Phe Asp
        435                 440                 445 ttt                                                                 1347
Phe

<210> SEQ ID NO 19
<211> LENGTH: 449
<212> TYPE: PRT
<213> ORGANISM: Lactobacillus acidophilus

<400> SEQUENCE: 19

Met Ser Lys Glu Ile Ser Lys Asp Thr Ile Asn Lys Phe Glu Gln Asp
1               5                   10                  15

Leu Thr Asn His Pro Ala Tyr Lys Val Ala Ser Arg Ala Ala Gln Glu
            20                  25                  30

Asn Gly Ile Phe Lys Ala Ser Gln Asp Leu Gln Thr Lys Ile Asp Leu
        35                  40                  45

Asp Pro Thr Phe Ser Ile Glu Ile Glu Thr Gly Lys Pro Ala Asp Gln
    50                  55                  60

Lys Gln Ser Gly Arg Cys Trp Met Phe Ser Ala Leu Asn Thr Met Arg
65                  70                  75                  80
```

His Pro Leu Gln Lys Lys Phe Gln Leu Lys Asp Phe Glu Leu Ser Gln
                85                  90                  95

Asn Tyr Thr Asn Phe Trp Asp Lys Phe Glu Lys Ser Asn Trp Phe Phe
            100                 105                 110

Glu Asn Val Ile Ala Thr Ala Asp Lys Pro Leu Gly Asp Arg Lys Val
        115                 120                 125

Ser Phe Leu Phe Ala Thr Pro Gln Gln Asp Gly Gly Gln Trp Asp Met
130                 135                 140

Leu Cys Gly Ile Ile Glu Lys Tyr Gly Ile Val Pro Lys Ser Val Tyr
145                 150                 155                 160

Pro Glu Thr Ala Asn Ala Thr Asn Ser Ser Ala Leu Asn Asp Thr Leu
                165                 170                 175

Asn Thr Leu Leu Arg Lys Asp Gly Leu Glu Leu Arg Lys Leu Val Asn
            180                 185                 190

Asp Gly Lys Ser Glu Glu Glu Ile Gln Thr Arg Lys Glu Met Leu
        195                 200                 205

Asn Asp Val Phe Arg Val Leu Ala Val Ser Leu Gly Val Pro Pro Lys
    210                 215                 220

Lys Phe Asn Phe Glu Tyr Arg Asp Asp Lys Asn Tyr His Ile Asp
225                 230                 235                 240

Lys Asp Ile Thr Pro Lys Glu Phe Phe Asp Lys Tyr Val Gly Met Asp
                245                 250                 255

Leu Glu Asp His Ile Ser Thr Ile Asn Ala Pro Thr Ser Asp Lys Pro
            260                 265                 270

Phe His Lys Val Phe Ser Val Glu Tyr Leu Gly Asn Val Glu Gly Gly
        275                 280                 285

Arg Gln Val Arg His Leu Asn Leu Lys Val Asp Glu Met Lys Asp Leu
    290                 295                 300

Ile Ile Lys Gln Leu Lys Ser Gly Glu Val Val Trp Phe Gly Ser Asn
305                 310                 315                 320

Val Val Lys Asp Ser Glu Arg Arg Ala Gly Leu Leu Asp Thr Asp Leu
                325                 330                 335

Tyr Arg Arg Asp Glu Leu Phe Asp Val Asp Phe Ser Met Ser Lys Ala
            340                 345                 350

Glu Lys Leu Asp Ser Gly Glu Ser Met Met Asp His Ala Met Val Ile
        355                 360                 365

Thr Gly Val Asp Ile Val Asp Gly Lys Pro Thr Lys Trp Lys Ile Glu
370                 375                 380

Asn Ser Trp Gly Glu Lys Pro Gly Phe Lys Gly Tyr Phe Val Met Ser
385                 390                 395                 400

Asp Lys Trp Phe Asp Ser Phe Val Tyr Gln Ala Val Ile Asn Lys Lys
                405                 410                 415

Phe Leu Pro Asp Asp Leu Lys Lys Ala Tyr Asp Glu Gly Val Lys Asp
            420                 425                 430

Pro Ile Gln Leu Leu Pro Trp Asp Pro Met Gly Ala Leu Ala Phe Asp
        435                 440                 445

Phe

<210> SEQ ID NO 20
<211> LENGTH: 732
<212> TYPE: DNA
<213> ORGANISM: Lactobacillus acidophilus
<220> FEATURE:
<221> NAME/KEY: CDS
<222> LOCATION: (1)..(732)

<223> OTHER INFORMATION: Putative glycoprotein endopeptidase ORF# 388

<400> SEQUENCE: 20

| | | | | | | | | | | | | | | | | |
|---|---|---|---|---|---|---|---|---|---|---|---|---|---|---|---|---|
| atg | aga | atc | tta | agc | gtt | tct | acg | gct | act | aat | cat | tta | agt | gtt | gca | 48 |
| Met | Arg | Ile | Leu | Ser | Val | Ser | Thr | Ala | Thr | Asn | His | Leu | Ser | Val | Ala | |
| 1 | | | | 5 | | | | | 10 | | | | | 15 | | |

| tta | aat | gat | agt | caa | caa | att | att | gtc | gaa | aaa | aat | gaa | caa | gat | gaa | 96 |
|---|---|---|---|---|---|---|---|---|---|---|---|---|---|---|---|---|
| Leu | Asn | Asp | Ser | Gln | Gln | Ile | Ile | Val | Glu | Lys | Asn | Glu | Gln | Asp | Glu | |
| | | | 20 | | | | | 25 | | | | | 30 | | | |

| cgt | aat | cat | agt | gaa | cat | ctt | gat | cca | tta | att | gat | gaa | att | tta | aaa | 144 |
|---|---|---|---|---|---|---|---|---|---|---|---|---|---|---|---|---|
| Arg | Asn | His | Ser | Glu | His | Leu | Asp | Pro | Leu | Ile | Asp | Glu | Ile | Leu | Lys | |
| | | 35 | | | | | 40 | | | | | 45 | | | | |

| gaa | aat | cag | tta | acc | tta | aaa | gat | att | gat | cgt | ttt | gca | gtt | gct | att | 192 |
|---|---|---|---|---|---|---|---|---|---|---|---|---|---|---|---|---|
| Glu | Asn | Gln | Leu | Thr | Leu | Lys | Asp | Ile | Asp | Arg | Phe | Ala | Val | Ala | Ile | |
| 50 | | | | | 55 | | | | | 60 | | | | | | |

| ggc | cca | ggt | tca | tat | act | ggg | ctt | aga | att | gga | att | act | act | gtt | aaa | 240 |
|---|---|---|---|---|---|---|---|---|---|---|---|---|---|---|---|---|
| Gly | Pro | Gly | Ser | Tyr | Thr | Gly | Leu | Arg | Ile | Gly | Ile | Thr | Thr | Val | Lys | |
| 65 | | | | 70 | | | | | 75 | | | | | 80 | | |

| atg | ttt | gct | agt | gtt | ttg | aat | aaa | gaa | gta | gta | gga | att | tca | aca | tta | 288 |
|---|---|---|---|---|---|---|---|---|---|---|---|---|---|---|---|---|
| Met | Phe | Ala | Ser | Val | Leu | Asn | Lys | Glu | Val | Val | Gly | Ile | Ser | Thr | Leu | |
| | | | | 85 | | | | | 90 | | | | | 95 | | |

| caa | gca | ttg | gct | aaa | tcc | gtt | aag | gaa | gat | gca | tta | gta | att | act | gga | 336 |
|---|---|---|---|---|---|---|---|---|---|---|---|---|---|---|---|---|
| Gln | Ala | Leu | Ala | Lys | Ser | Val | Lys | Glu | Asp | Ala | Leu | Val | Ile | Thr | Gly | |
| | | | | 100 | | | | | 105 | | | | | 110 | | |

| tta | gat | gca | aga | aat | aat | aat | tat | ttt | gca | gca | ggc | tat | aag | agc | ggt | 384 |
|---|---|---|---|---|---|---|---|---|---|---|---|---|---|---|---|---|
| Leu | Asp | Ala | Arg | Asn | Asn | Asn | Tyr | Phe | Ala | Ala | Gly | Tyr | Lys | Ser | Gly | |
| | | | 115 | | | | | 120 | | | | | 125 | | | |

| gat | att | cca | gat | aat | gta | att | cct | gat | ggt | cac | tat | aat | atc | gat | gtc | 432 |
|---|---|---|---|---|---|---|---|---|---|---|---|---|---|---|---|---|
| Asp | Ile | Pro | Asp | Asn | Val | Ile | Pro | Asp | Gly | His | Tyr | Asn | Ile | Asp | Val | |
| | | 130 | | | | | 135 | | | | | 140 | | | | |

| tta | att | aaa | gca | atc | caa | gat | tat | act | gct | aaa | aat | gaa | gtt | aag | aag | 480 |
|---|---|---|---|---|---|---|---|---|---|---|---|---|---|---|---|---|
| Leu | Ile | Lys | Ala | Ile | Gln | Asp | Tyr | Thr | Ala | Lys | Asn | Glu | Val | Lys | Lys | |
| 145 | | | | | 150 | | | | | 155 | | | | | 160 | |

| ctt | gtt | tta | gtg | gga | act | ggt | tta | gaa | aaa | caa | gat | gaa | aaa | ttt | aag | 528 |
|---|---|---|---|---|---|---|---|---|---|---|---|---|---|---|---|---|
| Leu | Val | Leu | Val | Gly | Thr | Gly | Leu | Glu | Lys | Gln | Asp | Glu | Lys | Phe | Lys | |
| | | | | 165 | | | | | 170 | | | | | 175 | | |

| gct | ttg | aat | att | cca | tat | aaa | tat | ggt | aat | gat | agt | caa | aat | gta | atc | 576 |
|---|---|---|---|---|---|---|---|---|---|---|---|---|---|---|---|---|
| Ala | Leu | Asn | Ile | Pro | Tyr | Lys | Tyr | Gly | Asn | Asp | Ser | Gln | Asn | Val | Ile | |
| | | | 180 | | | | | 185 | | | | | 190 | | | |

| cat | gca | ggc | tta | att | gga | caa | tta | gct | gaa | tac | tca | gaa | cca | gtt | gat | 624 |
|---|---|---|---|---|---|---|---|---|---|---|---|---|---|---|---|---|
| His | Ala | Gly | Leu | Ile | Gly | Gln | Leu | Ala | Glu | Tyr | Ser | Glu | Pro | Val | Asp | |
| | | 195 | | | | | 200 | | | | | 205 | | | | |

| cca | gat | aag | tta | ttg | cca | cgc | tat | cta | cgt | aga | act | caa | gct | gaa | gta | 672 |
|---|---|---|---|---|---|---|---|---|---|---|---|---|---|---|---|---|
| Pro | Asp | Lys | Leu | Leu | Pro | Arg | Tyr | Leu | Arg | Arg | Thr | Gln | Ala | Glu | Val | |
| 210 | | | | | 215 | | | | | 220 | | | | | | |

| gat | tgg | cac | aag | aag | aca | gga | aaa | cca | ttc | gaa | cca | gat | agt | cat | tat | 720 |
|---|---|---|---|---|---|---|---|---|---|---|---|---|---|---|---|---|
| Asp | Trp | His | Lys | Lys | Thr | Gly | Lys | Pro | Phe | Glu | Pro | Asp | Ser | His | Tyr | |
| 225 | | | | | 230 | | | | | 235 | | | | | 240 | |

| gtt | gaa | gaa | gtt | | | | | | | | | | | | | 732 |
|---|---|---|---|---|---|---|---|---|---|---|---|---|---|---|---|---|
| Val | Glu | Glu | Val | | | | | | | | | | | | | |

<210> SEQ ID NO 21
<211> LENGTH: 244
<212> TYPE: PRT
<213> ORGANISM: Lactobacillus acidophilus

<400> SEQUENCE: 21

Met Arg Ile Leu Ser Val Ser Thr Ala Thr Asn His Leu Ser Val Ala
1               5                   10                  15

Leu Asn Asp Ser Gln Gln Ile Ile Val Glu Lys Asn Glu Gln Asp Glu

```
                    20                  25                  30
Arg Asn His Ser Glu His Leu Asp Pro Leu Ile Asp Glu Ile Leu Lys
             35                  40                  45
Glu Asn Gln Leu Thr Leu Lys Asp Ile Asp Arg Phe Ala Val Ala Ile
         50                  55                  60
Gly Pro Gly Ser Tyr Thr Gly Leu Arg Ile Gly Ile Thr Thr Val Lys
65                  70                  75                  80
Met Phe Ala Ser Val Leu Asn Lys Glu Val Gly Ile Ser Thr Leu
                 85                  90                  95
Gln Ala Leu Ala Lys Ser Val Lys Glu Asp Ala Leu Val Ile Thr Gly
             100                 105                 110
Leu Asp Ala Arg Asn Asn Tyr Phe Ala Ala Gly Tyr Lys Ser Gly
             115                 120                 125
Asp Ile Pro Asp Asn Val Ile Pro Asp Gly His Tyr Asn Ile Asp Val
             130                 135                 140
Leu Ile Lys Ala Ile Gln Asp Tyr Thr Ala Lys Asn Glu Val Lys Lys
145                 150                 155                 160
Leu Val Leu Val Gly Thr Gly Leu Glu Lys Gln Asp Glu Lys Phe Lys
                 165                 170                 175
Ala Leu Asn Ile Pro Tyr Lys Tyr Gly Asn Asp Ser Gln Asn Val Ile
             180                 185                 190
His Ala Gly Leu Ile Gly Gln Leu Ala Glu Tyr Ser Glu Pro Val Asp
             195                 200                 205
Pro Asp Lys Leu Leu Pro Arg Tyr Leu Arg Arg Thr Gln Ala Glu Val
             210                 215                 220
Asp Trp His Lys Lys Thr Gly Lys Pro Phe Glu Pro Asp Ser His Tyr
225                 230                 235                 240
Val Glu Glu Val

<210> SEQ ID NO 22
<211> LENGTH: 1047
<212> TYPE: DNA
<213> ORGANISM: Lactobacillus acidophilus
<220> FEATURE:
<221> NAME/KEY: CDS
<222> LOCATION: (1)..(1047)
<223> OTHER INFORMATION: Endopeptidase (E.C. 3.4.24.57) ORF# 390

<400> SEQUENCE: 22 ttg agt gaa aag aaa gac gtt cgc att tta gct tat gaa agt tca tgt      48
Leu Ser Glu Lys Lys Asp Val Arg Ile Leu Ala Tyr Glu Ser Ser Cys
1               5                   10                  15 gat gaa act tca act gct gtt ata aaa aat gga cgt gaa att gaa agt      96
Asp Glu Thr Ser Thr Ala Val Ile Lys Asn Gly Arg Glu Ile Glu Ser
            20                  25                  30 tta att gtt gca acc caa att aaa agt cat caa cgt ttt ggt gga gtt     144
Leu Ile Val Ala Thr Gln Ile Lys Ser His Gln Arg Phe Gly Gly Val
        35                  40                  45 gta cct gaa gtt gct agt cga cat cac att gaa gta gtt agc caa att     192
Val Pro Glu Val Ala Ser Arg His His Ile Glu Val Val Ser Gln Ile
    50                  55                  60 act aaa gaa gct cta aat gaa gca aat tgc agt tgg aaa gat att gac     240
Thr Lys Glu Ala Leu Asn Glu Ala Asn Cys Ser Trp Lys Asp Ile Asp
65                  70                  75                  80 gca att gct gta act tat ggt cca ggc ctt gta ggt gcc ctt ttg att     288
Ala Ile Ala Val Thr Tyr Gly Pro Gly Leu Val Gly Ala Leu Leu Ile
                85                  90                  95
```

```
gga gtt agc gct gct aag gct gta tct atg gca aca gga att cca ttg      336
Gly Val Ser Ala Ala Lys Ala Val Ser Met Ala Thr Gly Ile Pro Leu
            100                 105                 110 att ggt gtt gat cat att atg gga cat att atg gct gct caa tta aaa      384
Ile Gly Val Asp His Ile Met Gly His Ile Met Ala Ala Gln Leu Lys
        115                 120                 125 gac gaa att gaa tat cca gct att gct ttg caa gtg tct ggt ggt cat      432
Asp Glu Ile Glu Tyr Pro Ala Ile Ala Leu Gln Val Ser Gly Gly His
130                 135                 140 act gaa att gtc tta tta aag gat cct act cat ttt gaa att att ggt      480
Thr Glu Ile Val Leu Leu Lys Asp Pro Thr His Phe Glu Ile Ile Gly
145                 150                 155                 160 gat act cgt gat gat gct gca ggt gaa gca tat gac aag att ggt cgt      528
Asp Thr Arg Asp Asp Ala Ala Gly Glu Ala Tyr Asp Lys Ile Gly Arg
                165                 170                 175 gtg ctt ggt gta aat tat cct gca ggt aag acg att gat gcg tgg gca      576
Val Leu Gly Val Asn Tyr Pro Ala Gly Lys Thr Ile Asp Ala Trp Ala
            180                 185                 190 cat caa ggt aag gat act ttt aat ttc cca cgt gcg atg ctg gaa gat      624
His Gln Gly Lys Asp Thr Phe Asn Phe Pro Arg Ala Met Leu Glu Asp
        195                 200                 205 gat gat tat gat ttt tca ttt tcg ggt ctt aag tca gct ttt att aat      672
Asp Asp Tyr Asp Phe Ser Phe Ser Gly Leu Lys Ser Ala Phe Ile Asn
210                 215                 220 act tgt cat cat gca gat caa atc cat gaa aag ttg aat aaa tat gac      720
Thr Cys His His Ala Asp Gln Ile His Glu Lys Leu Asn Lys Tyr Asp
225                 230                 235                 240 ttg gct gct agc ttt caa gct gct gta atc gat gtt ctt gct cat aag      768
Leu Ala Ala Ser Phe Gln Ala Ala Val Ile Asp Val Leu Ala His Lys
                245                 250                 255 act att aga gca atc aaa gag tat aaa cct aag aca ttt att atg ggt      816
Thr Ile Arg Ala Ile Lys Glu Tyr Lys Pro Lys Thr Phe Ile Met Gly
            260                 265                 270 ggc ggg gtt gcc gca aat caa ggt tta cgt gat cga atg agt gaa gag      864
Gly Gly Val Ala Ala Asn Gln Gly Leu Arg Asp Arg Met Ser Glu Glu
        275                 280                 285 att gct aag ctt cct aaa gca gat caa cca aaa gtt att ttg cct gat      912
Ile Ala Lys Leu Pro Lys Ala Asp Gln Pro Lys Val Ile Leu Pro Asp
290                 295                 300 ctt aaa ctt tgt ggt gat aat gct gct atg att ggt gca gct gct tat      960
Leu Lys Leu Cys Gly Asp Asn Ala Ala Met Ile Gly Ala Ala Ala Tyr
305                 310                 315                 320 aat ctt tat aat ggt ggg caa ttt gct gat ctg act tta aat gca gat     1008
Asn Leu Tyr Asn Gly Gly Gln Phe Ala Asp Leu Thr Leu Asn Ala Asp
                325                 330                 335 cca tca tta gaa ttg cca tat gct aaa agt atg ttg aat                 1047
Pro Ser Leu Glu Leu Pro Tyr Ala Lys Ser Met Leu Asn
            340                 345

<210> SEQ ID NO 23
<211> LENGTH: 349
<212> TYPE: PRT
<213> ORGANISM: Lactobacillus acidophilus

<400> SEQUENCE: 23

Leu Ser Glu Lys Lys Asp Val Arg Ile Leu Ala Tyr Glu Ser Ser Cys
1               5                   10                  15

Asp Glu Thr Ser Thr Ala Val Ile Lys Asn Gly Arg Glu Ile Glu Ser
            20                  25                  30

Leu Ile Val Ala Thr Gln Ile Lys Ser His Gln Arg Phe Gly Gly Val
```

```
                35                  40                  45
Val Pro Glu Val Ala Ser Arg His His Ile Glu Val Ser Gln Ile
 50                  55                  60

Thr Lys Glu Ala Leu Asn Glu Ala Asn Cys Ser Trp Lys Asp Ile Asp
 65                  70                  75                  80

Ala Ile Ala Val Thr Tyr Gly Pro Gly Leu Val Gly Ala Leu Leu Ile
                 85                  90                  95

Gly Val Ser Ala Ala Lys Ala Val Ser Met Ala Thr Gly Ile Pro Leu
                100                 105                 110

Ile Gly Val Asp His Ile Met Gly His Ile Met Ala Ala Gln Leu Lys
                115                 120                 125

Asp Glu Ile Glu Tyr Pro Ala Ile Ala Leu Gln Val Ser Gly Gly His
130                 135                 140

Thr Glu Ile Val Leu Leu Lys Asp Pro Thr His Phe Glu Ile Ile Gly
145                 150                 155                 160

Asp Thr Arg Asp Asp Ala Ala Gly Glu Ala Tyr Asp Lys Ile Gly Arg
                165                 170                 175

Val Leu Gly Val Asn Tyr Pro Ala Gly Lys Thr Ile Asp Ala Trp Ala
                180                 185                 190

His Gln Gly Lys Asp Thr Phe Asn Phe Pro Arg Ala Met Leu Glu Asp
                195                 200                 205

Asp Asp Tyr Asp Phe Ser Phe Ser Gly Leu Lys Ser Ala Phe Ile Asn
210                 215                 220

Thr Cys His His Ala Asp Gln Ile His Glu Lys Leu Asn Lys Tyr Asp
225                 230                 235                 240

Leu Ala Ala Ser Phe Gln Ala Ala Val Ile Asp Val Leu Ala His Lys
                245                 250                 255

Thr Ile Arg Ala Ile Lys Glu Tyr Lys Pro Lys Thr Phe Ile Met Gly
                260                 265                 270

Gly Gly Val Ala Ala Asn Gln Gly Leu Arg Asp Arg Met Ser Glu Glu
                275                 280                 285

Ile Ala Lys Leu Pro Lys Ala Asp Gln Pro Lys Val Ile Leu Pro Asp
290                 295                 300

Leu Lys Leu Cys Gly Asp Asn Ala Ala Met Ile Gly Ala Ala Ala Tyr
305                 310                 315                 320

Asn Leu Tyr Asn Gly Gly Gln Phe Ala Asp Leu Thr Leu Asn Ala Asp
                325                 330                 335

Pro Ser Leu Glu Leu Pro Tyr Ala Lys Ser Met Leu Asn
                340                 345
```

<210> SEQ ID NO 24
<211> LENGTH: 1104
<212> TYPE: DNA
<213> ORGANISM: Lactobacillus acidophilus
<220> FEATURE:
<221> NAME/KEY: CDS
<222> LOCATION: (1)..(1104)
<223> OTHER INFORMATION: Xaa-Pro dipeptidase (EC 3.4.13.9) ORF# 430

<400> SEQUENCE: 24

```
atg aac tta gat aaa cta caa cag tgg ttg caa gat tcc aat aat gat    48
Met Asn Leu Asp Lys Leu Gln Gln Trp Leu Gln Asp Ser Asn Asn Asp
 1               5                  10                  15 att gca tat atc tcc aat cca att aca att tca tac ttt act gga tat    96
Ile Ala Tyr Ile Ser Asn Pro Ile Thr Ile Ser Tyr Phe Thr Gly Tyr
                20                  25                  30
```

```
tca atg gaa cca cat gaa aga att ttt gct tta att gcg ttt aaa gat      144
Ser Met Glu Pro His Glu Arg Ile Phe Ala Leu Ile Ala Phe Lys Asp
     35              40                  45 gca gaa cct ttt atc ttc tgc cct gct tta aat gta gaa gaa gct aaa      192
Ala Glu Pro Phe Ile Phe Cys Pro Ala Leu Asn Val Glu Glu Ala Lys
 50              55                  60 gct tca gaa tgg aat ggt gac gtt gtt ggg tat ctc gac tca gaa gac      240
Ala Ser Glu Trp Asn Gly Asp Val Val Gly Tyr Leu Asp Ser Glu Asp
 65              70                  75              80 cct tgg caa ata atc gca gat aac atc aga aag aga acc agc gat att      288
Pro Trp Gln Ile Ile Ala Asp Asn Ile Arg Lys Arg Thr Ser Asp Ile
                 85                  90                  95 cat aac tgg gca att gag aaa gat gat tta tct gta agt cat tat caa      336
His Asn Trp Ala Ile Glu Lys Asp Asp Leu Ser Val Ser His Tyr Gln
             100                 105                 110 ctt tta cgt ggc gaa ttt cct aat gcc agt tta acc aac gat gtt tca      384
Leu Leu Arg Gly Glu Phe Pro Asn Ala Ser Leu Thr Asn Asp Val Ser
         115                 120                 125 cct ttt att gaa aga ctt cgt ctt ttc aag aca ccc gaa gaa att aag      432
Pro Phe Ile Glu Arg Leu Arg Leu Phe Lys Thr Pro Glu Glu Ile Lys
    130                 135                 140 aaa tta caa ggt gct gga gca gaa gct gac ttt gcc ttt caa atc ggt      480
Lys Leu Gln Gly Ala Gly Ala Glu Ala Asp Phe Ala Phe Gln Ile Gly
145                 150                 155                 160 ttt gat gca atc aga act ggc gta act gaa aga agt atc gct gga caa      528
Phe Asp Ala Ile Arg Thr Gly Val Thr Glu Arg Ser Ile Ala Gly Gln
                 165                 170                 175 ata gat tat caa tta aag att caa aaa ggc gta atg cac gag agt ttt      576
Ile Asp Tyr Gln Leu Lys Ile Gln Lys Gly Val Met His Glu Ser Phe
             180                 185                 190 gaa act att gtt caa gct ggt aaa aat gct gct aac cca cac ttg gga      624
Glu Thr Ile Val Gln Ala Gly Lys Asn Ala Ala Asn Pro His Leu Gly
         195                 200                 205 cca act atg aat aaa att caa ccc aat gaa tta gta tta ttc gat tta      672
Pro Thr Met Asn Lys Ile Gln Pro Asn Glu Leu Val Leu Phe Asp Leu
    210                 215                 220 ggt act atg cat gat ggt tac gca tca gat gca agt aga act gta gct      720
Gly Thr Met His Asp Gly Tyr Ala Ser Asp Ala Ser Arg Thr Val Ala
225                 230                 235                 240 tat ggc aca cct agc gac aaa caa cgt gaa att tac gaa gtt gat aga      768
Tyr Gly Thr Pro Ser Asp Lys Gln Arg Glu Ile Tyr Glu Val Asp Arg
                 245                 250                 255 gaa gct cag caa gca gct att gaa gca gca aaa cct ggc att act gcc      816
Glu Ala Gln Gln Ala Ala Ile Glu Ala Ala Lys Pro Gly Ile Thr Ala
             260                 265                 270 gaa gaa ctt gac agt gtt gct cgt gat att att act aaa gcc ggt tat      864
Glu Glu Leu Asp Ser Val Ala Arg Asp Ile Ile Thr Lys Ala Gly Tyr
         275                 280                 285 ggc gaa tac ttc att cac cgt tta ggt cac ggt atc ggt aaa aat gtt      912
Gly Glu Tyr Phe Ile His Arg Leu Gly His Gly Ile Gly Lys Asn Val
    290                 295                 300 cac gaa ttt cca tca att gtt caa ggt aat gat tta gta att caa gaa      960
His Glu Phe Pro Ser Ile Val Gln Gly Asn Asp Leu Val Ile Gln Glu
305                 310                 315                 320 ggt atg tgc ttc tcc atc gaa cca gga att tac atc ccc ggc ttt gcg     1008
Gly Met Cys Phe Ser Ile Glu Pro Gly Ile Tyr Ile Pro Gly Phe Ala
                 325                 330                 335 gga gtg cga att gaa gat tgt ggg gtt gta act aaa gat ggc ttc aaa     1056
Gly Val Arg Ile Glu Asp Cys Gly Val Val Thr Lys Asp Gly Phe Lys
             340                 345                 350
```

```
cca ttt act cac acc gac aaa gaa ctt aaa atc tta cca ctt aaa gat      1104
Pro Phe Thr His Thr Asp Lys Glu Leu Lys Ile Leu Pro Leu Lys Asp
    355                 360                 365
```

<210> SEQ ID NO 25
<211> LENGTH: 368
<212> TYPE: PRT
<213> ORGANISM: Lactobacillus acidophilus

<400> SEQUENCE: 25

```
Met Asn Leu Asp Lys Leu Gln Gln Trp Leu Gln Asp Ser Asn Asn Asp
1               5                   10                  15

Ile Ala Tyr Ile Ser Asn Pro Ile Thr Ile Ser Tyr Phe Thr Gly Tyr
            20                  25                  30

Ser Met Glu Pro His Glu Arg Ile Phe Ala Leu Ile Ala Phe Lys Asp
        35                  40                  45

Ala Glu Pro Phe Ile Phe Cys Pro Ala Leu Asn Val Glu Glu Ala Lys
    50                  55                  60

Ala Ser Glu Trp Asn Gly Asp Val Val Gly Tyr Leu Asp Ser Glu Asp
65                  70                  75                  80

Pro Trp Gln Ile Ile Ala Asp Asn Ile Arg Lys Arg Thr Ser Asp Ile
                85                  90                  95

His Asn Trp Ala Ile Glu Lys Asp Asp Leu Ser Val Ser His Tyr Gln
            100                 105                 110

Leu Leu Arg Gly Glu Phe Pro Asn Ala Ser Leu Thr Asn Asp Val Ser
        115                 120                 125

Pro Phe Ile Glu Arg Leu Arg Leu Phe Lys Thr Pro Glu Glu Ile Lys
    130                 135                 140

Lys Leu Gln Gly Ala Gly Ala Glu Ala Asp Phe Ala Phe Gln Ile Gly
145                 150                 155                 160

Phe Asp Ala Ile Arg Thr Gly Val Thr Glu Arg Ser Ile Ala Gly Gln
                165                 170                 175

Ile Asp Tyr Gln Leu Lys Ile Gln Lys Gly Val Met His Glu Ser Phe
            180                 185                 190

Glu Thr Ile Val Gln Ala Gly Lys Asn Ala Ala Asn Pro His Leu Gly
        195                 200                 205

Pro Thr Met Asn Lys Ile Gln Pro Asn Glu Leu Val Leu Phe Asp Leu
    210                 215                 220

Gly Thr Met His Asp Gly Tyr Ala Ser Asp Ala Ser Arg Thr Val Ala
225                 230                 235                 240

Tyr Gly Thr Pro Ser Asp Lys Gln Arg Glu Ile Tyr Glu Val Asp Arg
                245                 250                 255

Glu Ala Gln Gln Ala Ala Ile Glu Ala Ala Lys Pro Gly Ile Thr Ala
            260                 265                 270

Glu Glu Leu Asp Ser Val Ala Arg Asp Ile Ile Thr Lys Ala Gly Tyr
        275                 280                 285

Gly Glu Tyr Phe Ile His Arg Leu Gly His Gly Ile Gly Lys Asn Val
    290                 295                 300

His Glu Phe Pro Ser Ile Val Gln Gly Asn Asp Leu Val Ile Gln Glu
305                 310                 315                 320

Gly Met Cys Phe Ser Ile Glu Pro Gly Ile Tyr Ile Pro Gly Phe Ala
                325                 330                 335

Gly Val Arg Ile Glu Asp Cys Gly Val Val Thr Lys Asp Gly Phe Lys
            340                 345                 350
```

| Pro | Phe | Thr | His | Thr | Asp | Lys | Glu | Leu | Lys | Ile | Leu | Pro | Leu | Lys | Asp |
|---|---|---|---|---|---|---|---|---|---|---|---|---|---|---|---|
| | | | 355 | | | | 360 | | | | | 365 | | | |

<210> SEQ ID NO 26
<211> LENGTH: 825
<212> TYPE: DNA
<213> ORGANISM: Lactobacillus acidophilus
<220> FEATURE:
<221> NAME/KEY: CDS
<222> LOCATION: (1)..(825)
<223> OTHER INFORMATION: ampM methionine aminopeptidase (EC 3.4.11.18) ORF# 623

<400> SEQUENCE: 26

```
ttg att aca att aaa tca att cgt gaa ctt aaa ggt atg caa gct tca      48
Leu Ile Thr Ile Lys Ser Ile Arg Glu Leu Lys Gly Met Gln Ala Ser
1               5                   10                  15 ggc cat ctt ctt gca aca atg ttt gaa ggc tta cgt gat gtt atc aaa      96
Gly His Leu Leu Ala Thr Met Phe Glu Gly Leu Arg Asp Val Ile Lys
            20                  25                  30 cca gga att tca act tgg gaa att gaa gaa ttt tgt caa gat ttt gtt     144
Pro Gly Ile Ser Thr Trp Glu Ile Glu Glu Phe Cys Gln Asp Phe Val
        35                  40                  45 aaa agt cgt ggt ggt cgt ctt tca gaa caa ggt ttt gaa ggc tac aaa     192
Lys Ser Arg Gly Gly Arg Leu Ser Glu Gln Gly Phe Glu Gly Tyr Lys
    50                  55                  60 tat ggt act tgt att tca gtt aat gat gaa att gct cac caa acc cca     240
Tyr Gly Thr Cys Ile Ser Val Asn Asp Glu Ile Ala His Gln Thr Pro
65                  70                  75                  80 aga aaa gat cgt atc tta aag gag ggc gac atc gtt aag gtt gat gtt     288
Arg Lys Asp Arg Ile Leu Lys Glu Gly Asp Ile Val Lys Val Asp Val
                85                  90                  95 act tgc aac ttg aat ggc tat gaa tca gat tct tgt act act tac cca     336
Thr Cys Asn Leu Asn Gly Tyr Glu Ser Asp Ser Cys Thr Thr Tyr Pro
            100                 105                 110 gta ggt aaa att tca gaa gct gat aag aag ttg att gaa gta act aag     384
Val Gly Lys Ile Ser Glu Ala Asp Lys Lys Leu Ile Glu Val Thr Lys
        115                 120                 125 aag gca atg tat ctt gga atc gat caa gct gtt ttg ggt aac cgt att     432
Lys Ala Met Tyr Leu Gly Ile Asp Gln Ala Val Leu Gly Asn Arg Ile
    130                 135                 140 ggt gac att ggt gct gca att caa cat tat gtt gaa gta gaa aat cat     480
Gly Asp Ile Gly Ala Ala Ile Gln His Tyr Val Glu Val Glu Asn His
145                 150                 155                 160 tat ggt gac gtt cgt gaa tta att ggt cat ggt att caa cct tca att     528
Tyr Gly Asp Val Arg Glu Leu Ile Gly His Gly Ile Gln Pro Ser Ile
                165                 170                 175 cac gaa gat ccg gaa gtt cct cac tgg ggt aaa gct ggt cat ggt ctt     576
His Glu Asp Pro Glu Val Pro His Trp Gly Lys Ala Gly His Gly Leu
            180                 185                 190 cgt ctt cgt gaa ggt atg act att act tgt gaa cca atg gta gaa gct     624
Arg Leu Arg Glu Gly Met Thr Ile Thr Cys Glu Pro Met Val Glu Ala
        195                 200                 205 ggt gga gac tgg cat att gat caa aga aca gtt gat gat cca aac gat     672
Gly Gly Asp Trp His Ile Asp Gln Arg Thr Val Asp Asp Pro Asn Asp
    210                 215                 220 gat tgg gta tat tac gca act cca gat ggt tca aat gct gca cag ttt     720
Asp Trp Val Tyr Tyr Ala Thr Pro Asp Gly Ser Asn Ala Ala Gln Phe
225                 230                 235                 240 gaa cat act ttt gct att act aaa gat ggt cct aag att tta act tta     768
Glu His Thr Phe Ala Ile Thr Lys Asp Gly Pro Lys Ile Leu Thr Leu
                245                 250                 255
```

```
caa cgt cct tat gat ggc tta gaa aag tac atc cca cac ttt gat gaa    816
Gln Arg Pro Tyr Asp Gly Leu Glu Lys Tyr Ile Pro His Phe Asp Glu
        260                 265                 270 atg gat gac                                                        825
Met Asp Asp
    275
```

<210> SEQ ID NO 27
<211> LENGTH: 275
<212> TYPE: PRT
<213> ORGANISM: Lactobacillus acidophilus

<400> SEQUENCE: 27

```
Leu Ile Thr Ile Lys Ser Ile Arg Glu Leu Lys Gly Met Gln Ala Ser
1               5                   10                  15

Gly His Leu Leu Ala Thr Met Phe Glu Gly Leu Arg Asp Val Ile Lys
            20                  25                  30

Pro Gly Ile Ser Thr Trp Glu Ile Glu Glu Phe Cys Gln Asp Phe Val
        35                  40                  45

Lys Ser Arg Gly Gly Arg Leu Ser Glu Gln Gly Phe Glu Gly Tyr Lys
    50                  55                  60

Tyr Gly Thr Cys Ile Ser Val Asn Asp Glu Ile Ala His Gln Thr Pro
65                  70                  75                  80

Arg Lys Asp Arg Ile Leu Lys Glu Gly Asp Ile Val Lys Val Asp Val
                85                  90                  95

Thr Cys Asn Leu Asn Gly Tyr Glu Ser Asp Ser Cys Thr Thr Tyr Pro
            100                 105                 110

Val Gly Lys Ile Ser Glu Ala Asp Lys Lys Leu Ile Glu Val Thr Lys
        115                 120                 125

Lys Ala Met Tyr Leu Gly Ile Asp Gln Ala Val Leu Gly Asn Arg Ile
    130                 135                 140

Gly Asp Ile Gly Ala Ala Ile Gln His Tyr Val Glu Val Glu Asn His
145                 150                 155                 160

Tyr Gly Asp Val Arg Glu Leu Ile Gly His Gly Ile Gln Pro Ser Ile
                165                 170                 175

His Glu Asp Pro Glu Val Pro His Trp Gly Lys Ala Gly His Gly Leu
            180                 185                 190

Arg Leu Arg Glu Gly Met Thr Ile Thr Cys Glu Pro Met Val Glu Ala
        195                 200                 205

Gly Gly Asp Trp His Ile Asp Gln Arg Thr Val Asp Pro Asn Asp
    210                 215                 220

Asp Trp Val Tyr Tyr Ala Thr Pro Asp Gly Ser Asn Ala Ala Gln Phe
225                 230                 235                 240

Glu His Thr Phe Ala Ile Thr Lys Asp Gly Pro Lys Ile Leu Thr Leu
                245                 250                 255

Gln Arg Pro Tyr Asp Gly Leu Glu Lys Tyr Ile Pro His Phe Asp Glu
            260                 265                 270

Met Asp Asp
    275
```

<210> SEQ ID NO 28
<211> LENGTH: 1311
<212> TYPE: DNA
<213> ORGANISM: Lactobacillus acidophilus
<220> FEATURE:
<221> NAME/KEY: CDS
<222> LOCATION: (1)..(1311)

<223> OTHER INFORMATION: Aminopeptidase ORF# 911

<400> SEQUENCE: 28

```
atg gca att att tca gat caa gaa att gcg gat ttt tcc gca gat ttt      48
Met Ala Ile Ile Ser Asp Gln Glu Ile Ala Asp Phe Ser Ala Asp Phe
1               5                   10                  15 aat tct aat agt gaa aac tta gtt gca tct tgt gca gct cgg cgt aat      96
Asn Ser Asn Ser Glu Asn Leu Val Ala Ser Cys Ala Ala Arg Arg Asn
            20                  25                  30 gga tta tta gaa gct tct ttc aat gat cga gtt tca gaa aaa tta aat     144
Gly Leu Leu Glu Ala Ser Phe Asn Asp Arg Val Ser Glu Lys Leu Asn
        35                  40                  45 cat gtt ttt tca act gaa ctt gat att ggt ggt gta act aat caa aaa     192
His Val Phe Ser Thr Glu Leu Asp Ile Gly Gly Val Thr Asn Gln Lys
    50                  55                  60 caa tct ggg cgt tgt tgg gag ttt gcc aca tta aat gtt tta cga cat     240
Gln Ser Gly Arg Cys Trp Glu Phe Ala Thr Leu Asn Val Leu Arg His
65                  70                  75                  80 tat ttt ggt aag aaa aat aat gtg aaa gat ttc act ttt tct caa gca     288
Tyr Phe Gly Lys Lys Asn Asn Val Lys Asp Phe Thr Phe Ser Gln Ala
                85                  90                  95 tat aat ttc ttt tgg gat aaa att gaa cgg gca aat gca ttt tat gat     336
Tyr Asn Phe Phe Trp Asp Lys Ile Glu Arg Ala Asn Ala Phe Tyr Asp
            100                 105                 110 gca atg att cgc tta gcc gat aaa ccg att aat gat cgt gaa gtt caa     384
Ala Met Ile Arg Leu Ala Asp Lys Pro Ile Asn Asp Arg Glu Val Gln
        115                 120                 125 tca tgg tta tct ttt gca ggt gaa gat ggc gga tta tgg agt atg gca     432
Ser Trp Leu Ser Phe Ala Gly Glu Asp Gly Gly Leu Trp Ser Met Ala
    130                 135                 140 att aat ttg gtt aaa aaa tat ggg gta gta cca tca tat gca atg cca     480
Ile Asn Leu Val Lys Lys Tyr Gly Val Val Pro Ser Tyr Ala Met Pro
145                 150                 155                 160 gaa agt ttt aat tct aat cat aca gct gga ttg att gat tca ctt gct     528
Glu Ser Phe Asn Ser Asn His Thr Ala Gly Leu Ile Asp Ser Leu Ala
                165                 170                 175 cgt aaa gaa aga aaa gat gca att ctt tta cgt aaa tta gtg aat gaa     576
Arg Lys Glu Arg Lys Asp Ala Ile Leu Leu Arg Lys Leu Val Asn Glu
            180                 185                 190 aat agg caa aat gag att gca gaa act aag aaa aag gct tta aat gaa     624
Asn Arg Gln Asn Glu Ile Ala Glu Thr Lys Lys Lys Ala Leu Asn Glu
        195                 200                 205 gtt tat cga atg gtt tct gta gca tta gga gaa cca cct aaa aag ttt     672
Val Tyr Arg Met Val Ser Val Ala Leu Gly Glu Pro Pro Lys Lys Phe
    210                 215                 220 gat tta gaa tat cgt gat gat gat aaa aaa tat cat ttg gaa aaa gac     720
Asp Leu Glu Tyr Arg Asp Asp Asp Lys Lys Tyr His Leu Glu Lys Asp
225                 230                 235                 240 tta act cca cgt gct ttt gtt caa aag tat ttt aaa gac ttt aaa ttt     768
Leu Thr Pro Arg Ala Phe Val Gln Lys Tyr Phe Lys Asp Phe Lys Phe
                245                 250                 255 gac gat tat gta gtg tta tct aat tgt cca aat cat gag ttt aac aaa     816
Asp Asp Tyr Val Val Leu Ser Asn Cys Pro Asn His Glu Phe Asn Lys
            260                 265                 270 ttg tat cat atg ccg ctt tat gac aat gtg gat ggt ggt gat cag att     864
Leu Tyr His Met Pro Leu Tyr Asp Asn Val Asp Gly Gly Asp Gln Ile
        275                 280                 285 aag ttt tta aat gta cca att gaa tat ctt tct caa gcc gct gta gct     912
Lys Phe Leu Asn Val Pro Ile Glu Tyr Leu Ser Gln Ala Ala Val Ala
    290                 295                 300
```

```
cag ctt aaa tca ggg gat gcc gta att ttt ggc aat gat gtt tcc aaa         960
Gln Leu Lys Ser Gly Asp Ala Val Ile Phe Gly Asn Asp Val Ser Lys
305                 310                 315                 320 caa atg gag cga aaa act gga tat tta gat aca aat ctt tat gaa aca        1008
Gln Met Glu Arg Lys Thr Gly Tyr Leu Asp Thr Asn Leu Tyr Glu Thr
            325                 330                 335 gat aaa tta ttt ggt gta gat act aaa atg agt aaa gca gat cgc ttg        1056
Asp Lys Leu Phe Gly Val Asp Thr Lys Met Ser Lys Ala Asp Arg Leu
        340                 345                 350 gca acg gga gaa gga ttt gct aca cat gat atg act tta gtt ggt gtt        1104
Ala Thr Gly Glu Gly Phe Ala Thr His Asp Met Thr Leu Val Gly Val
    355                 360                 365 gat gaa gat aat ggt cat att cgc aag tgg aaa gta gaa aat tct tgg        1152
Asp Glu Asp Asn Gly His Ile Arg Lys Trp Lys Val Glu Asn Ser Trp
370                 375                 380 ggt gat aaa ttt ggt cat aat gga ttc tat gaa atg agt caa caa tgg        1200
Gly Asp Lys Phe Gly His Asn Gly Phe Tyr Glu Met Ser Gln Gln Trp
385                 390                 395                 400 ttt gaa gat tat gtc tat gac gta gta gtc aga aaa gaa ttt tta act        1248
Phe Glu Asp Tyr Val Tyr Asp Val Val Val Arg Lys Glu Phe Leu Thr
                405                 410                 415 gac gaa caa tta aaa ttg gca gaa ggt cct gca att gat ctt aaa cca        1296
Asp Glu Gln Leu Lys Leu Ala Glu Gly Pro Ala Ile Asp Leu Lys Pro
            420                 425                 430 tgg gat aac att ggc                                                    1311
Trp Asp Asn Ile Gly
                435

<210> SEQ ID NO 29
<211> LENGTH: 437
<212> TYPE: PRT
<213> ORGANISM: Lactobacillus acidophilus

<400> SEQUENCE: 29

Met Ala Ile Ile Ser Asp Gln Glu Ile Ala Asp Phe Ser Ala Asp Phe
1               5                   10                  15

Asn Ser Asn Ser Glu Asn Leu Val Ala Ser Cys Ala Ala Arg Arg Asn
            20                  25                  30

Gly Leu Leu Glu Ala Ser Phe Asn Asp Arg Val Ser Glu Lys Leu Asn
        35                  40                  45

His Val Phe Ser Thr Glu Leu Asp Ile Gly Gly Val Thr Asn Gln Lys
    50                  55                  60

Gln Ser Gly Arg Cys Trp Glu Phe Ala Thr Leu Asn Val Leu Arg His
65                  70                  75                  80

Tyr Phe Gly Lys Lys Asn Asn Val Lys Asp Phe Thr Phe Ser Gln Ala
                85                  90                  95

Tyr Asn Phe Phe Trp Asp Lys Ile Glu Arg Ala Asn Ala Phe Tyr Asp
            100                 105                 110

Ala Met Ile Arg Leu Ala Asp Lys Pro Ile Asn Asp Arg Glu Val Gln
        115                 120                 125

Ser Trp Leu Ser Phe Ala Gly Glu Asp Gly Gly Leu Trp Ser Met Ala
    130                 135                 140

Ile Asn Leu Val Lys Lys Tyr Gly Val Val Pro Ser Tyr Ala Met Pro
145                 150                 155                 160

Glu Ser Phe Asn Ser Asn His Thr Ala Gly Leu Ile Asp Ser Leu Ala
                165                 170                 175

Arg Lys Glu Arg Lys Asp Ala Ile Leu Leu Arg Lys Leu Val Asn Glu
```

```
                    180                 185                 190
Asn Arg Gln Asn Glu Ile Ala Glu Thr Lys Lys Ala Leu Asn Glu
            195                 200                 205

Val Tyr Arg Met Val Ser Val Ala Leu Gly Glu Pro Pro Lys Lys Phe
        210                 215                 220

Asp Leu Glu Tyr Arg Asp Asp Lys Lys Tyr His Leu Glu Lys Asp
225                 230                 235                 240

Leu Thr Pro Arg Ala Phe Val Gln Lys Tyr Phe Lys Asp Phe Lys Phe
                    245                 250                 255

Asp Asp Tyr Val Val Leu Ser Asn Cys Pro Asn His Glu Phe Asn Lys
            260                 265                 270

Leu Tyr His Met Pro Leu Tyr Asp Asn Val Asp Gly Asp Gln Ile
            275                 280                 285

Lys Phe Leu Asn Val Pro Ile Glu Tyr Leu Ser Gln Ala Ala Val Ala
        290                 295                 300

Gln Leu Lys Ser Gly Asp Ala Val Ile Phe Gly Asn Asp Val Ser Lys
305                 310                 315                 320

Gln Met Glu Arg Lys Thr Gly Tyr Leu Asp Thr Asn Leu Tyr Glu Thr
                    325                 330                 335

Asp Lys Leu Phe Gly Val Asp Thr Lys Met Ser Lys Ala Asp Arg Leu
            340                 345                 350

Ala Thr Gly Glu Gly Phe Ala Thr His Asp Met Thr Leu Val Gly Val
            355                 360                 365

Asp Glu Asp Asn Gly His Ile Arg Lys Trp Lys Val Glu Asn Ser Trp
370                 375                 380

Gly Asp Lys Phe Gly His Asn Gly Phe Tyr Glu Met Ser Gln Gln Trp
385                 390                 395                 400

Phe Glu Asp Tyr Val Tyr Asp Val Val Arg Lys Glu Phe Leu Thr
                    405                 410                 415

Asp Glu Gln Leu Lys Leu Ala Glu Gly Pro Ala Ile Asp Leu Lys Pro
            420                 425                 430

Trp Asp Asn Ile Gly
            435

<210> SEQ ID NO 30
<211> LENGTH: 1401
<212> TYPE: DNA
<213> ORGANISM: Lactobacillus acidophilus
<220> FEATURE:
<221> NAME/KEY: CDS
<222> LOCATION: (1)..(1401)
<223> OTHER INFORMATION: pepD aminoacyl-histidine dipeptidase
      (EC 3.4.13.3) ORF# 994

<400> SEQUENCE: 30 atg aat tta gat tat aag gaa tta gct caa gct aaa aaa gaa gat att        48
Met Asn Leu Asp Tyr Lys Glu Leu Ala Gln Ala Lys Lys Glu Asp Ile
1               5                   10                  15 ctt cgt gat ctt ggc gaa tta att gca att gac tcg tca gaa gat tta       96
Leu Arg Asp Leu Gly Glu Leu Ile Ala Ile Asp Ser Ser Glu Asp Leu
            20                  25                  30 gac aat aca tct att gaa tat cct gtt ggt cct gga cca gtt aag gca      144
Asp Asn Thr Ser Ile Glu Tyr Pro Val Gly Pro Gly Pro Val Lys Ala
        35                  40                  45 atg aag aag ttt tta tca ttt gct gaa cgt gat ggt ttc cac gtt aaa      192
Met Lys Lys Phe Leu Ser Phe Ala Glu Arg Asp Gly Phe His Val Lys
    50                  55                  60
```

```
                                                     -continued aac gtt gat aac tat gct ggt cgc gtt gat tac ggt gaa ggt gaa aag     240
Asn Val Asp Asn Tyr Ala Gly Arg Val Asp Tyr Gly Glu Gly Glu Lys
 65                  70                  75                  80 cgt tta ggc gtt att ggg cat atg gat gta gtt cct gcc ggt gat ggc     288
Arg Leu Gly Val Ile Gly His Met Asp Val Val Pro Ala Gly Asp Gly
                 85                  90                  95 tgg gtt aca gat cca ttt aag atg att att aaa gat gga aaa atc att     336
Trp Val Thr Asp Pro Phe Lys Met Ile Ile Lys Asp Gly Lys Ile Ile
            100                 105                 110 ggt cgt ggt tca gct gat gac aaa gga cct gct ttg gca gct tat tac     384
Gly Arg Gly Ser Ala Asp Asp Lys Gly Pro Ala Leu Ala Ala Tyr Tyr
        115                 120                 125 ggt atg ctt tta ctt aaa gaa gct ggc ttt aaa cct aaa aag aaa att     432
Gly Met Leu Leu Leu Lys Glu Ala Gly Phe Lys Pro Lys Lys Lys Ile
    130                 135                 140 gac ttt att gtc ggt act aat gaa gaa act aat tgg gtt ggt att aat     480
Asp Phe Ile Val Gly Thr Asn Glu Glu Thr Asn Trp Val Gly Ile Asn
145                 150                 155                 160 tac tac tta aaa cat gaa ccg act cct gat caa gtt ttc tca cct gat     528
Tyr Tyr Leu Lys His Glu Pro Thr Pro Asp Gln Val Phe Ser Pro Asp
                165                 170                 175 gcg gaa tat cca att att aat ggt gaa caa ggc atc tac aca tta gaa     576
Ala Glu Tyr Pro Ile Ile Asn Gly Glu Gln Gly Ile Tyr Thr Leu Glu
            180                 185                 190 ctt aat ttc aaa gac gat aag cca aaa ggc tca gta gtc ctc aag aaa     624
Leu Asn Phe Lys Asp Asp Lys Pro Lys Gly Ser Val Val Leu Lys Lys
        195                 200                 205 ttt aaa gcc ggt att gct aca aat gtt aca cca caa aag gct ttt gcc     672
Phe Lys Ala Gly Ile Ala Thr Asn Val Thr Pro Gln Lys Ala Phe Ala
    210                 215                 220 act att caa gct gac aat ctt gac gaa att aaa gct aaa ttt ggt gaa     720
Thr Ile Gln Ala Asp Asn Leu Asp Glu Ile Lys Ala Lys Phe Gly Glu
225                 230                 235                 240 ttt ctg gcg gaa aat aat cta gag gga cat ttt gaa att gat gat aat     768
Phe Leu Ala Glu Asn Asn Leu Glu Gly His Phe Glu Ile Asp Asp Asn
                245                 250                 255 att gct cag att gaa tta act ggc caa ggt gct cat gca tct gct cca     816
Ile Ala Gln Ile Glu Leu Thr Gly Gln Gly Ala His Ala Ser Ala Pro
            260                 265                 270 caa gtt ggg cgt aat gct gct acc ttt tta gct tta ttc tta gat caa     864
Gln Val Gly Arg Asn Ala Ala Thr Phe Leu Ala Leu Phe Leu Asp Gln
        275                 280                 285 ttt gac ttt gca ggt cgt gat aaa aat tat att cac ttc tta gca gac     912
Phe Asp Phe Ala Gly Arg Asp Lys Asn Tyr Ile His Phe Leu Ala Asp
    290                 295                 300 gtt gaa cat gaa gac ttc caa ggt aag aaa tta ggt gta ttt cat cat     960
Val Glu His Glu Asp Phe Gln Gly Lys Lys Leu Gly Val Phe His His
305                 310                 315                 320 gat gac tta atg ggt gat ttg tca tcc gct cct tct atc ttt gaa tat    1008
Asp Asp Leu Met Gly Asp Leu Ser Ser Ala Pro Ser Ile Phe Glu Tyr
                325                 330                 335 gaa gaa gac ggt gtt gcc att ctt aaa gac aat att cgt tat cct caa    1056
Glu Glu Asp Gly Val Ala Ile Leu Lys Asp Asn Ile Arg Tyr Pro Gln
            340                 345                 350 ggt aca gat cca agt aca atg gta aaa caa gtt acc gaa aaa ttt agc    1104
Gly Thr Asp Pro Ser Thr Met Val Lys Gln Val Thr Glu Lys Phe Ser
        355                 360                 365 gat att tta agt gct agt ttt gac tca ttt gaa aaa cct cac tat gta    1152
Asp Ile Leu Ser Ala Ser Phe Asp Ser Phe Glu Lys Pro His Tyr Val
    370                 375                 380
```

-continued

```
cct ggt gat gat cca cta gtt caa act tta ctt aag gtt tac gaa cgt    1200
Pro Gly Asp Asp Pro Leu Val Gln Thr Leu Leu Lys Val Tyr Glu Arg
385                 390                 395                 400 caa act ggt aaa aaa gga cat gaa gtt gtt atc ggt ggt ggt act tat    1248
Gln Thr Gly Lys Lys Gly His Glu Val Val Ile Gly Gly Gly Thr Tyr
            405                 410                 415 ggc cga tta ttc gag cac ggt gtt gca tat ggt gct caa cct gaa gat    1296
Gly Arg Leu Phe Glu His Gly Val Ala Tyr Gly Ala Gln Pro Glu Asp
        420                 425                 430 gcg cca atg gtt atg cac caa gca aat gaa tac atg aaa gtt gat gac    1344
Ala Pro Met Val Met His Gln Ala Asn Glu Tyr Met Lys Val Asp Asp
    435                 440                 445 tta att gat tct att gct atc tat gct gaa gca att tat gaa ttg act    1392
Leu Ile Asp Ser Ile Ala Ile Tyr Ala Glu Ala Ile Tyr Glu Leu Thr
450                 455                 460 aaa gaa gct                                                        1401
Lys Glu Ala
465
```

<210> SEQ ID NO 31
<211> LENGTH: 467
<212> TYPE: PRT
<213> ORGANISM: Lactobacillus acidophilus

<400> SEQUENCE: 31

```
Met Asn Leu Asp Tyr Lys Glu Leu Ala Gln Ala Lys Lys Glu Asp Ile
1               5                   10                  15

Leu Arg Asp Leu Gly Glu Leu Ile Ala Ile Asp Ser Ser Glu Asp Leu
            20                  25                  30

Asp Asn Thr Ser Ile Glu Tyr Pro Val Gly Pro Gly Pro Val Lys Ala
        35                  40                  45

Met Lys Lys Phe Leu Ser Phe Ala Glu Arg Asp Gly Phe His Val Lys
    50                  55                  60

Asn Val Asp Asn Tyr Ala Gly Arg Val Asp Tyr Gly Glu Gly Glu Lys
65                  70                  75                  80

Arg Leu Gly Val Ile Gly His Met Asp Val Val Pro Ala Gly Asp Gly
                85                  90                  95

Trp Val Thr Asp Pro Phe Lys Met Ile Ile Lys Asp Gly Lys Ile Ile
            100                 105                 110

Gly Arg Gly Ser Ala Asp Asp Lys Gly Pro Ala Leu Ala Ala Tyr Tyr
        115                 120                 125

Gly Met Leu Leu Leu Lys Glu Ala Gly Phe Lys Pro Lys Lys Lys Ile
    130                 135                 140

Asp Phe Ile Val Gly Thr Asn Glu Glu Thr Asn Trp Val Gly Ile Asn
145                 150                 155                 160

Tyr Tyr Leu Lys His Glu Pro Thr Pro Asp Gln Val Phe Ser Pro Asp
                165                 170                 175

Ala Glu Tyr Pro Ile Ile Asn Gly Glu Gln Gly Ile Tyr Thr Leu Glu
            180                 185                 190

Leu Asn Phe Lys Asp Asp Lys Pro Lys Gly Ser Val Val Leu Lys Lys
        195                 200                 205

Phe Lys Ala Gly Ile Ala Thr Asn Val Thr Pro Gln Lys Ala Phe Ala
    210                 215                 220

Thr Ile Gln Ala Asp Asn Leu Asp Glu Ile Lys Ala Lys Phe Gly Glu
225                 230                 235                 240

Phe Leu Ala Glu Asn Asn Leu Glu Gly His Phe Glu Ile Asp Asp Asn
```

-continued

```
                    245                 250                 255
Ile Ala Gln Ile Glu Leu Thr Gly Gln Gly Ala His Ala Ser Ala Pro
            260                 265                 270

Gln Val Gly Arg Asn Ala Ala Thr Phe Leu Ala Leu Phe Leu Asp Gln
        275                 280                 285

Phe Asp Phe Ala Gly Arg Asp Lys Asn Tyr Ile His Phe Leu Ala Asp
    290                 295                 300

Val Glu His Glu Asp Phe Gln Gly Lys Lys Leu Gly Val Phe His His
305                 310                 315                 320

Asp Asp Leu Met Gly Asp Leu Ser Ser Ala Pro Ser Ile Phe Glu Tyr
                325                 330                 335

Glu Glu Asp Gly Val Ala Ile Leu Lys Asp Asn Ile Arg Tyr Pro Gln
            340                 345                 350

Gly Thr Asp Pro Ser Thr Met Val Lys Gln Val Thr Glu Lys Phe Ser
        355                 360                 365

Asp Ile Leu Ser Ala Ser Phe Asp Ser Phe Glu Lys Pro His Tyr Val
    370                 375                 380

Pro Gly Asp Asp Pro Leu Val Gln Thr Leu Leu Lys Val Tyr Glu Arg
385                 390                 395                 400

Gln Thr Gly Lys Lys Gly His Glu Val Val Ile Gly Gly Thr Tyr
                405                 410                 415

Gly Arg Leu Phe Glu His Gly Val Ala Tyr Gly Ala Gln Pro Glu Asp
            420                 425                 430

Ala Pro Met Val Met His Gln Ala Asn Glu Tyr Met Lys Val Asp Asp
        435                 440                 445

Leu Ile Asp Ser Ile Ala Ile Tyr Ala Glu Ala Ile Tyr Glu Leu Thr
    450                 455                 460

Lys Glu Ala
465
```

```
<210> SEQ ID NO 32
<211> LENGTH: 501
<212> TYPE: DNA
<213> ORGANISM: Lactobacillus acidophilus
<220> FEATURE:
<221> NAME/KEY: CDS
<222> LOCATION: (1)..(501)
<223> OTHER INFORMATION: lspA Lipoprotein signal peptidase A
      (EC 3.4.23.36) ORF# 1152

<400> SEQUENCE: 32
```

```
atg atg gta aga tta gtg gat tat ttt aga aaa aat tat atg caa ttt     48
Met Met Val Arg Leu Val Asp Tyr Phe Arg Lys Asn Tyr Met Gln Phe
1               5                   10                  15 tta tat tta att att aca tta ttt gtt gtt tta gca gat cag ggg tta     96
Leu Tyr Leu Ile Ile Thr Leu Phe Val Val Leu Ala Asp Gln Gly Leu
            20                  25                  30 aag aat tat ata gta agt aat tat tca gtt ggt gag gtt cac cag att    144
Lys Asn Tyr Ile Val Ser Asn Tyr Ser Val Gly Glu Val His Gln Ile
        35                  40                  45 att cca gga atc ttg tca ttt aat tat ttg caa aat aat ggt gca gct    192
Ile Pro Gly Ile Leu Ser Phe Asn Tyr Leu Gln Asn Asn Gly Ala Ala
    50                  55                  60 tgg aat att tta act aat caa atg tgg cta ttt tat ttt att agt att    240
Trp Asn Ile Leu Thr Asn Gln Met Trp Leu Phe Tyr Phe Ile Ser Ile
65                  70                  75                  80 att gca att ggt gtt tgt tta tac ttt ctt ttt aat aaa aag tat aag    288
Ile Ala Ile Gly Val Cys Leu Tyr Phe Leu Phe Asn Lys Lys Tyr Lys
```

-continued

```
                  85                  90                  95
aat gtt tta ttt gat ata gga tta tct ttt gta ctt ggt ggt att att      336
Asn Val Leu Phe Asp Ile Gly Leu Ser Phe Val Leu Gly Gly Ile Ile
                100                 105                 110 ggt aac ttt atc gat aga ctc aga cta aaa tat gta gtc gat atg ttg      384
Gly Asn Phe Ile Asp Arg Leu Arg Leu Lys Tyr Val Val Asp Met Leu
            115                 120                 125 cag tta gat ttt gtt cat ttc aac att ttt aat atc gca gat tca gca      432
Gln Leu Asp Phe Val His Phe Asn Ile Phe Asn Ile Ala Asp Ser Ala
        130                 135                 140 att act att ggc gta att ctt att ttt att tac tta ata att ttt gca      480
Ile Thr Ile Gly Val Ile Leu Ile Phe Ile Tyr Leu Ile Ile Phe Ala
145                 150                 155                 160 gac aag gat gaa aaa cat gcc                                          501
Asp Lys Asp Glu Lys His Ala
                165
```

```
<210> SEQ ID NO 33
<211> LENGTH: 167
<212> TYPE: PRT
<213> ORGANISM: Lactobacillus acidophilus

<400> SEQUENCE: 33

Met Met Val Arg Leu Val Asp Tyr Phe Arg Lys Asn Tyr Met Gln Phe
1               5                   10                  15

Leu Tyr Leu Ile Ile Thr Leu Phe Val Val Leu Ala Asp Gln Gly Leu
            20                  25                  30

Lys Asn Tyr Ile Val Ser Asn Tyr Ser Val Gly Glu Val His Gln Ile
        35                  40                  45

Ile Pro Gly Ile Leu Ser Phe Asn Tyr Leu Gln Asn Asn Gly Ala Ala
    50                  55                  60

Trp Asn Ile Leu Thr Asn Gln Met Trp Leu Phe Tyr Phe Ile Ser Ile
65                  70                  75                  80

Ile Ala Ile Gly Val Cys Leu Tyr Phe Leu Phe Asn Lys Lys Tyr Lys
                85                  90                  95

Asn Val Leu Phe Asp Ile Gly Leu Ser Phe Val Leu Gly Gly Ile Ile
            100                 105                 110

Gly Asn Phe Ile Asp Arg Leu Arg Leu Lys Tyr Val Val Asp Met Leu
        115                 120                 125

Gln Leu Asp Phe Val His Phe Asn Ile Phe Asn Ile Ala Asp Ser Ala
    130                 135                 140

Ile Thr Ile Gly Val Ile Leu Ile Phe Ile Tyr Leu Ile Ile Phe Ala
145                 150                 155                 160

Asp Lys Asp Glu Lys His Ala
                165
```

```
<210> SEQ ID NO 34
<211> LENGTH: 186
<212> TYPE: DNA
<213> ORGANISM: Lactobacillus acidophilus
<220> FEATURE:
<221> NAME/KEY: CDS
<222> LOCATION: (1)..(186)
<223> OTHER INFORMATION: Consensus hypothetical protein ORF# 1183

<400> SEQUENCE: 34 atg aat gag caa aac gaa tta tct gac gca att atc gat ttt caa gta      48
Met Asn Glu Gln Asn Glu Leu Ser Asp Ala Ile Ile Asp Phe Gln Val
1               5                   10                  15
```

```
aaa cat cac gtt aat gat aca gac tta gct ttt gca agt cat ctt tcc         96
Lys His His Val Asn Asp Thr Asp Leu Ala Phe Ala Ser His Leu Ser
             20                  25                  30 gta gag aaa gta cac gca atg aaa act ggt gac ggc aat tat aca gcc        144
Val Glu Lys Val His Ala Met Lys Thr Gly Asp Gly Asn Tyr Thr Ala
         35                  40                  45 gaa gaa gtt aac caa ctt tat gat tac atg tct gca aat gct                186
Glu Glu Val Asn Gln Leu Tyr Asp Tyr Met Ser Ala Asn Ala
     50                  55                  60

<210> SEQ ID NO 35
<211> LENGTH: 62
<212> TYPE: PRT
<213> ORGANISM: Lactobacillus acidophilus

<400> SEQUENCE: 35

Met Asn Glu Gln Asn Glu Leu Ser Asp Ala Ile Ile Asp Phe Gln Val
1               5                   10                  15

Lys His His Val Asn Asp Thr Asp Leu Ala Phe Ala Ser His Leu Ser
             20                  25                  30

Val Glu Lys Val His Ala Met Lys Thr Gly Asp Gly Asn Tyr Thr Ala
         35                  40                  45

Glu Glu Val Asn Gln Leu Tyr Asp Tyr Met Ser Ala Asn Ala
     50                  55                  60

<210> SEQ ID NO 36
<211> LENGTH: 1245
<212> TYPE: DNA
<213> ORGANISM: Lactobacillus acidophilus
<220> FEATURE:
<221> NAME/KEY: CDS
<222> LOCATION: (1)..(1245)
<223> OTHER INFORMATION: pepT amino tripeptidase T (EC 3.411.-) ORF#
      1190

<400> SEQUENCE: 36 atg gaa tat cca aat tta tta cca aga ttt tta aaa tac gtt aaa gtt         48
Met Glu Tyr Pro Asn Leu Leu Pro Arg Phe Leu Lys Tyr Val Lys Val
1               5                   10                  15 aat tca cgt tct gat gaa cat tca gat cgt ttc cca tca act gaa aga         96
Asn Ser Arg Ser Asp Glu His Ser Asp Arg Phe Pro Ser Thr Glu Arg
             20                  25                  30 gaa gag aac ttt caa aag aat gta att atg aaa gat ctt gag gaa tta        144
Glu Glu Asn Phe Gln Lys Asn Val Ile Met Lys Asp Leu Glu Glu Leu
         35                  40                  45 ggc ttg aaa gat att cac tac aat caa aag gct ggt agt gta atc gct        192
Gly Leu Lys Asp Ile His Tyr Asn Gln Lys Ala Gly Ser Val Ile Ala
     50                  55                  60 gaa att cct tca aat gtt gat tat gat gta cct gta atg gga ttc ttg        240
Glu Ile Pro Ser Asn Val Asp Tyr Asp Val Pro Val Met Gly Phe Leu
65                  70                  75                  80 gca cat agt gat aca gct gat ttc aat tca gaa aat gtt aaa cca caa        288
Ala His Ser Asp Thr Ala Asp Phe Asn Ser Glu Asn Val Lys Pro Gln
                 85                  90                  95 att cat aaa aac tat gat ggt gaa agt aga att cga tta ggg gat tca        336
Ile His Lys Asn Tyr Asp Gly Glu Ser Arg Ile Arg Leu Gly Asp Ser
            100                 105                 110 gaa ttt tat ctt gat cct gaa gtt ttc cca cat ttg aaa aac tat aaa        384
Glu Phe Tyr Leu Asp Pro Glu Val Phe Pro His Leu Lys Asn Tyr Lys
        115                 120                 125 ggt caa act att atc act gct tcg ggt gat act tta ctt ggt ggt gac        432
Gly Gln Thr Ile Ile Thr Ala Ser Gly Asp Thr Leu Leu Gly Gly Asp
```

-continued

```
              130                 135                 140
gat aag tgt ggt gtt tct gaa tta atg acc ttt gca gaa tat ttg atg    480
Asp Lys Cys Gly Val Ser Glu Leu Met Thr Phe Ala Glu Tyr Leu Met
145                 150                 155                 160 aat cat cca gaa gta aaa cat gga aag atc cgt tta gca ttt act cca    528
Asn His Pro Glu Val Lys His Gly Lys Ile Arg Leu Ala Phe Thr Pro
                165                 170                 175 gat gaa gaa att gga acc ggc gct gaa cat ttc gat gtt aaa gat ttt    576
Asp Glu Glu Ile Gly Thr Gly Ala Glu His Phe Asp Val Lys Asp Phe
            180                 185                 190 ggt gct gat ttt gct ttt act gtt gat ggt gag gct cct ggt aag ctt    624
Gly Ala Asp Phe Ala Phe Thr Val Asp Gly Glu Ala Pro Gly Lys Leu
        195                 200                 205 gat tgg gga act ttc tca gcc gct caa ttt agt ctg gat att caa ggg    672
Asp Trp Gly Thr Phe Ser Ala Ala Gln Phe Ser Leu Asp Ile Gln Gly
    210                 215                 220 gta aat gtt cat cca gct gta gct aaa ggt caa atg att aat gct gtt    720
Val Asn Val His Pro Ala Val Ala Lys Gly Gln Met Ile Asn Ala Val
225                 230                 235                 240 caa gtg ggg att gat ttt cat aat caa ttg cca gaa cat gat cgt cca    768
Gln Val Gly Ile Asp Phe His Asn Gln Leu Pro Glu His Asp Arg Pro
                245                 250                 255 gaa cat act gat ggt cgt gaa ggt ttc ttc cat ttg atg agt ttt gat    816
Glu His Thr Asp Gly Arg Glu Gly Phe Phe His Leu Met Ser Phe Asp
            260                 265                 270 gga act gtt gat aat gca cat ttg gat tac att att cgt gat ttt gaa    864
Gly Thr Val Asp Asn Ala His Leu Asp Tyr Ile Ile Arg Asp Phe Glu
        275                 280                 285 cgt gat ggt cta gaa gca cgt aag aat tta gtt aag tct act gta gat    912
Arg Asp Gly Leu Glu Ala Arg Lys Asn Leu Val Lys Ser Thr Val Asp
    290                 295                 300 aaa atg aat gca gaa ttt ggt aca gaa cgt atc aaa tta aag atg tgg    960
Lys Met Asn Ala Glu Phe Gly Thr Glu Arg Ile Lys Leu Lys Met Trp
305                 310                 315                 320 gat caa tac tac aac atg gct gat gaa tta aag aaa cac atg gat atc   1008
Asp Gln Tyr Tyr Asn Met Ala Asp Glu Leu Lys Lys His Met Asp Ile
                325                 330                 335 gtt gat ttg gca aga gat gca tat aaa gca gag ggc ctt gaa atc aat   1056
Val Asp Leu Ala Arg Asp Ala Tyr Lys Ala Glu Gly Leu Glu Ile Asn
            340                 345                 350 gaa gat cca gtc cgt ggc ggt act gat ggc tca caa tta act tat atg   1104
Glu Asp Pro Val Arg Gly Gly Thr Asp Gly Ser Gln Leu Thr Tyr Met
        355                 360                 365 ggt ctt cct tgt cct aat att ttt gct ggt gaa gaa aat atg cat ggc   1152
Gly Leu Pro Cys Pro Asn Ile Phe Ala Gly Glu Glu Asn Met His Gly
    370                 375                 380 cgt tat gaa tat act gtc ctt gaa tct atg tat aaa gct gtc gat gtc   1200
Arg Tyr Glu Tyr Thr Val Leu Glu Ser Met Tyr Lys Ala Val Asp Val
385                 390                 395                 400 atg att aaa atg gca gaa tta aat gct gaa aga gca aga aaa gct       1245
Met Ile Lys Met Ala Glu Leu Asn Ala Glu Arg Ala Arg Lys Ala
                405                 410                 415
```

<210> SEQ ID NO 37
<211> LENGTH: 415
<212> TYPE: PRT
<213> ORGANISM: Lactobacillus acidophilus

<400> SEQUENCE: 37

Met Glu Tyr Pro Asn Leu Leu Pro Arg Phe Leu Lys Tyr Val Lys Val

```
1               5                  10                 15
Asn Ser Arg Ser Asp Glu His Ser Asp Arg Phe Pro Ser Thr Glu Arg
                20                 25                 30

Glu Glu Asn Phe Gln Lys Asn Val Ile Met Lys Asp Leu Glu Glu Leu
                35                 40                 45

Gly Leu Lys Asp Ile His Tyr Asn Gln Lys Ala Gly Ser Val Ile Ala
            50                 55                 60

Glu Ile Pro Ser Asn Val Asp Tyr Asp Val Pro Val Met Gly Phe Leu
65                      70                 75                 80

Ala His Ser Asp Thr Ala Asp Phe Asn Ser Glu Asn Val Lys Pro Gln
                    85                 90                 95

Ile His Lys Asn Tyr Asp Gly Glu Ser Arg Ile Arg Leu Gly Asp Ser
                100                105                110

Glu Phe Tyr Leu Asp Pro Glu Val Phe Pro His Leu Lys Asn Tyr Lys
            115                120                125

Gly Gln Thr Ile Ile Thr Ala Ser Gly Asp Thr Leu Leu Gly Gly Asp
        130                135                140

Asp Lys Cys Gly Val Ser Glu Leu Met Thr Phe Ala Glu Tyr Leu Met
145                 150                155                160

Asn His Pro Glu Val Lys His Gly Lys Ile Arg Leu Ala Phe Thr Pro
                165                170                175

Asp Glu Glu Ile Gly Thr Gly Ala Glu His Phe Asp Val Lys Asp Phe
                180                185                190

Gly Ala Asp Phe Ala Phe Thr Val Asp Gly Glu Ala Pro Gly Lys Leu
            195                200                205

Asp Trp Gly Thr Phe Ser Ala Ala Gln Phe Ser Leu Asp Ile Gln Gly
        210                215                220

Val Asn Val His Pro Ala Val Ala Lys Gly Gln Met Ile Asn Ala Val
225                 230                235                240

Gln Val Gly Ile Asp Phe His Asn Gln Leu Pro Glu His Asp Arg Pro
                245                250                255

Glu His Thr Asp Gly Arg Glu Gly Phe Phe His Leu Met Ser Phe Asp
                260                265                270

Gly Thr Val Asp Asn Ala His Leu Asp Tyr Ile Ile Arg Asp Phe Glu
            275                280                285

Arg Asp Gly Leu Glu Ala Arg Lys Asn Leu Val Lys Ser Thr Val Asp
        290                295                300

Lys Met Asn Ala Glu Phe Gly Thr Glu Arg Ile Lys Leu Lys Met Trp
305                 310                315                320

Asp Gln Tyr Tyr Asn Met Ala Asp Glu Leu Lys Lys His Met Asp Ile
                325                330                335

Val Asp Leu Ala Arg Asp Ala Tyr Lys Ala Glu Gly Leu Glu Ile Asn
            340                345                350

Glu Asp Pro Val Arg Gly Gly Thr Asp Gly Ser Gln Leu Thr Tyr Met
        355                360                365

Gly Leu Pro Cys Pro Asn Ile Phe Ala Gly Glu Glu Asn Met His Gly
        370                375                380

Arg Tyr Glu Tyr Thr Val Leu Glu Ser Met Tyr Lys Ala Val Asp Val
385                 390                395                400

Met Ile Lys Met Ala Glu Leu Asn Ala Glu Arg Ala Arg Lys Ala
                405                410                415

<210> SEQ ID NO 38
```

```
<211> LENGTH: 1941
<212> TYPE: DNA
<213> ORGANISM: Lactobacillus acidophilus
<220> FEATURE:
<221> NAME/KEY: CDS
<222> LOCATION: (1)..(1941)
<223> OTHER INFORMATION: pepO neutral endopepdidase O (EC 3.4.-.-)
      ORF# 1275

<400> SEQUENCE: 38
```

| | | | | | | | | | | | | | | | | |
|---|---|---|---|---|---|---|---|---|---|---|---|---|---|---|---|---|
| atg | aga | aga | tat | ttt | gct | gtt | cgt | ggc | ggt | gca | gga | gat | gtc | gct | gaa | 48 |
| Met | Arg | Arg | Tyr | Phe | Ala | Val | Arg | Gly | Gly | Ala | Gly | Asp | Val | Ala | Glu | |
| 1 | | | | 5 | | | | | 10 | | | | | 15 | | |
| ccg | gat | gtc | aat | gct | aaa | cct | caa | gat | aat | tta | tat | tta | gca | gtt | aat | 96 |
| Pro | Asp | Val | Asn | Ala | Lys | Pro | Gln | Asp | Asn | Leu | Tyr | Leu | Ala | Val | Asn | |
| | | | 20 | | | | | 25 | | | | | 30 | | | |
| tca | gaa | tgg | tta | tcc | aaa | gct | gag | att | cca | gca | gat | aga | ata | tct | acc | 144 |
| Ser | Glu | Trp | Leu | Ser | Lys | Ala | Glu | Ile | Pro | Ala | Asp | Arg | Ile | Ser | Thr | |
| | | | 35 | | | | | 40 | | | | | 45 | | | |
| gga | gta | aac | tct | gag | tta | gat | atc | aag | att | gaa | aag | cga | atg | atg | aaa | 192 |
| Gly | Val | Asn | Ser | Glu | Leu | Asp | Ile | Lys | Ile | Glu | Lys | Arg | Met | Met | Lys | |
| | 50 | | | | | 55 | | | | | 60 | | | | | |
| gac | ttt | gct | gat | att | gct | tct | ggt | aaa | gaa | aaa | atg | ccc | gat | att | aaa | 240 |
| Asp | Phe | Ala | Asp | Ile | Ala | Ser | Gly | Lys | Glu | Lys | Met | Pro | Asp | Ile | Lys | |
| 65 | | | | | 70 | | | | | 75 | | | | | 80 | |
| gat | ttt | gat | aag | gca | att | gct | ttg | tac | aag | att | gct | aaa | aac | ttt | gag | 288 |
| Asp | Phe | Asp | Lys | Ala | Ile | Ala | Leu | Tyr | Lys | Ile | Ala | Lys | Asn | Phe | Glu | |
| | | | | 85 | | | | | 90 | | | | | 95 | | |
| aag | agg | gat | gca | gaa | gaa | gct | aat | cca | att | caa | aag | gat | tta | caa | aaa | 336 |
| Lys | Arg | Asp | Ala | Glu | Glu | Ala | Asn | Pro | Ile | Gln | Lys | Asp | Leu | Gln | Lys | |
| | | | 100 | | | | | 105 | | | | | 110 | | | |
| ctt | tta | tca | ttg | ggt | agc | ttt | gta | gag | ttg | gta | aaa | cag | gct | aaa | gat | 384 |
| Leu | Leu | Ser | Leu | Gly | Ser | Phe | Val | Glu | Leu | Val | Lys | Gln | Ala | Lys | Asp | |
| | | | | 115 | | | | | 120 | | | | | 125 | | |
| tta | ttt | atg | gga | ccc | tat | gtc | ttt | cca | ttt | gta | ttt | gac | gtc | gat | gcc | 432 |
| Leu | Phe | Met | Gly | Pro | Tyr | Val | Phe | Pro | Phe | Val | Phe | Asp | Val | Asp | Ala | |
| | 130 | | | | | 135 | | | | | 140 | | | | | |
| gat | atg | aag | aat | act | gat | gtg | aat | gct | cta | tac | ttt | ggt | ggt | cct | agt | 480 |
| Asp | Met | Lys | Asn | Thr | Asp | Val | Asn | Ala | Leu | Tyr | Phe | Gly | Gly | Pro | Ser | |
| 145 | | | | | 150 | | | | | 155 | | | | | 160 | |
| aca | ttt | tta | ccg | gat | aca | act | act | tac | aaa | aca | gat | gat | gct | aag | aag | 528 |
| Thr | Phe | Leu | Pro | Asp | Thr | Thr | Thr | Tyr | Lys | Thr | Asp | Asp | Ala | Lys | Lys | |
| | | | | 165 | | | | | 170 | | | | | 175 | | |
| ttg | cta | gat | gta | ttg | caa | gac | cag | agc | att | aac | ttg | ttg | atg | atg | gca | 576 |
| Leu | Leu | Asp | Val | Leu | Gln | Asp | Gln | Ser | Ile | Asn | Leu | Leu | Met | Met | Ala | |
| | | | 180 | | | | | 185 | | | | | 190 | | | |
| gga | att | ggt | aag | act | gaa | gca | agg | atg | tat | gtt | gat | aat | gct | ttg | gca | 624 |
| Gly | Ile | Gly | Lys | Thr | Glu | Ala | Arg | Met | Tyr | Val | Asp | Asn | Ala | Leu | Ala | |
| | | | | 195 | | | | | 200 | | | | | 205 | | |
| ttt | gat | gca | aaa | att | gct | aag | gtt | gtt | aaa | tca | act | gaa | gaa | tgg | gct | 672 |
| Phe | Asp | Ala | Lys | Ile | Ala | Lys | Val | Val | Lys | Ser | Thr | Glu | Glu | Trp | Ala | |
| | 210 | | | | | 215 | | | | | 220 | | | | | |
| gac | tac | gct | gct | att | tat | aat | ccg | gtt | tca | tat | gac | gaa | ttt | att | tct | 720 |
| Asp | Tyr | Ala | Ala | Ile | Tyr | Asn | Pro | Val | Ser | Tyr | Asp | Glu | Phe | Ile | Ser | |
| 225 | | | | | 230 | | | | | 235 | | | | | 240 | |
| aaa | ttt | aag | tca | ttt | aag | atg | gat | gaa | ttc | tta | ggt | aaa | att | tta | cct | 768 |
| Lys | Phe | Lys | Ser | Phe | Lys | Met | Asp | Glu | Phe | Leu | Gly | Lys | Ile | Leu | Pro | |
| | | | | 245 | | | | | 250 | | | | | 255 | | |
| gaa | aag | cca | gag | agt | gta | att | gtg | atg | gag | ccg | cgt | ttt | ctt | gat | tat | 816 |
| Glu | Lys | Pro | Glu | Ser | Val | Ile | Val | Met | Glu | Pro | Arg | Phe | Leu | Asp | Tyr | |
| | | | 260 | | | | | 265 | | | | | 270 | | | |

-continued

| | |
|---|---|
| gca gaa gaa ttg att aat gca gat aac ttt gct gaa att aag ggc tgg<br>Ala Glu Glu Leu Ile Asn Ala Asp Asn Phe Ala Glu Ile Lys Gly Trp<br>              275                  280                  285 | 864 |
| ttg tta gtt aaa tat att aat agc gta gct aaa tac tta tca cag aag<br>Leu Leu Val Lys Tyr Ile Asn Ser Val Ala Lys Tyr Leu Ser Gln Lys<br>    290                  295                  300 | 912 |
| ttt cgt gaa gca tca ttc cca ttt gct cat gca att agt ggt att cct<br>Phe Arg Glu Ala Ser Phe Pro Phe Ala His Ala Ile Ser Gly Ile Pro<br>305                  310                  315                  320 | 960 |
| gaa ctt cct tca caa att aaa caa gca tac cgt gtt gcc aat ggt gca<br>Glu Leu Pro Ser Gln Ile Lys Gln Ala Tyr Arg Val Ala Asn Gly Ala<br>              325                  330                  335 | 1008 |
| ttc gat gaa gta gtc ggt att ttt tat ggt aag aaa tac ttt ggc gaa<br>Phe Asp Glu Val Val Gly Ile Phe Tyr Gly Lys Lys Tyr Phe Gly Glu<br>                340                  345                  350 | 1056 |
| aag gca aaa cac gat gtt gaa gat atg att cat aat atg ctt aaa gta<br>Lys Ala Lys His Asp Val Glu Asp Met Ile His Asn Met Leu Lys Val<br>    355                  360                  365 | 1104 |
| tat gaa gaa cgt atc ggc agc aat gat tgg ctt tca gaa gac acc aag<br>Tyr Glu Glu Arg Ile Gly Ser Asn Asp Trp Leu Ser Glu Asp Thr Lys<br>370                  375                  380 | 1152 |
| aag caa gct atc att aag ttg aaa gct tta gtt ctt aag atc ggt tat<br>Lys Gln Ala Ile Ile Lys Leu Lys Ala Leu Val Leu Lys Ile Gly Tyr<br>385                  390                  395                  400 | 1200 |
| cca gaa aag att gaa aag att ttc gat tta ctt caa gtt gat tca gaa<br>Pro Glu Lys Ile Glu Lys Ile Phe Asp Leu Leu Gln Val Asp Ser Glu<br>              405                  410                  415 | 1248 |
| aag agc ctt tat gaa aat gaa gct gct atg gat aaa gtt cgt acc aaa<br>Lys Ser Leu Tyr Glu Asn Glu Ala Ala Met Asp Lys Val Arg Thr Lys<br>        420                  425                  430 | 1296 |
| tat atg ctt gat aaa tta acc aaa ccg gtt gat cgt tcg gta tgg ctg<br>Tyr Met Leu Asp Lys Leu Thr Lys Pro Val Asp Arg Ser Val Trp Leu<br>              435                  440                  445 | 1344 |
| atg cca ggt aat ttg aat aat gct tgt tat gat cca caa aga aat gat<br>Met Pro Gly Asn Leu Asn Asn Ala Cys Tyr Asp Pro Gln Arg Asn Asp<br>    450                  455                  460 | 1392 |
| tta act ttc cca gcg ggt att ttg caa gcg cca ttt tat gat att aat<br>Leu Thr Phe Pro Ala Gly Ile Leu Gln Ala Pro Phe Tyr Asp Ile Asn<br>465                  470                  475                  480 | 1440 |
| caa tct cgt ggt gct aac tac ggt ggt att ggt gca act atc ggt cac<br>Gln Ser Arg Gly Ala Asn Tyr Gly Gly Ile Gly Ala Thr Ile Gly His<br>              485                  490                  495 | 1488 |
| gaa gtt tct cat gct ttt gat aat gag ggc gct aag ttc gac gaa cac<br>Glu Val Ser His Ala Phe Asp Asn Glu Gly Ala Lys Phe Asp Glu His<br>        500                  505                  510 | 1536 |
| ggt aat atg aat aac tgg tgg acg aag gaa gat ttc gaa gaa ttt aat<br>Gly Asn Met Asn Asn Trp Trp Thr Lys Glu Asp Phe Glu Glu Phe Asn<br>              515                  520                  525 | 1584 |
| aag cgc gtt ggt aag atg gtt gat atc ttt gac ggt ctt caa tat ggc<br>Lys Arg Val Gly Lys Met Val Asp Ile Phe Asp Gly Leu Gln Tyr Gly<br>    530                  535                  540 | 1632 |
| cca gct aag att aat ggt aaa caa gtt gtt tct gaa aat att gcc gac<br>Pro Ala Lys Ile Asn Gly Lys Gln Val Val Ser Glu Asn Ile Ala Asp<br>545                  550                  555                  560 | 1680 |
| tta gca ggt ctt gct tgt gct gtc caa acc ggt aaa aat gat ggt gtt<br>Leu Ala Gly Leu Ala Cys Ala Val Gln Thr Gly Lys Asn Asp Gly Val<br>              565                  570                  575 | 1728 |
| gac tta aaa gat ttg ttt gaa aat tat gcg aga agc tgg atg gaa aag<br>Asp Leu Lys Asp Leu Phe Glu Asn Tyr Ala Arg Ser Trp Met Glu Lys<br>        580                  585                  590 | 1776 |

```
caa cgt cca gaa gca att aaa act gag gtt caa aca gat gtt cat gcg    1824
Gln Arg Pro Glu Ala Ile Lys Thr Glu Val Gln Thr Asp Val His Ala
        595                 600                 605 cca cag cca act agg gtt aat atc cct gtt caa tgt cag gat gaa ttc    1872
Pro Gln Pro Thr Arg Val Asn Ile Pro Val Gln Cys Gln Asp Glu Phe
610                 615                 620 tat gag gcc ttt ggt gtt aaa gat aca gat ggt atg tgg ctt gac ccg    1920
Tyr Glu Ala Phe Gly Val Lys Asp Thr Asp Gly Met Trp Leu Asp Pro
625                 630                 635                 640 aaa gat aga att aca att tgg                                        1941
Lys Asp Arg Ile Thr Ile Trp
                645

<210> SEQ ID NO 39
<211> LENGTH: 647
<212> TYPE: PRT
<213> ORGANISM: Lactobacillus acidophilus

<400> SEQUENCE: 39

Met Arg Arg Tyr Phe Ala Val Arg Gly Gly Ala Gly Asp Val Ala Glu
1               5                   10                  15

Pro Asp Val Asn Ala Lys Pro Gln Asp Asn Leu Tyr Leu Ala Val Asn
            20                  25                  30

Ser Glu Trp Leu Ser Lys Ala Glu Ile Pro Ala Asp Arg Ile Ser Thr
        35                  40                  45

Gly Val Asn Ser Glu Leu Asp Ile Lys Ile Glu Lys Arg Met Met Lys
    50                  55                  60

Asp Phe Ala Asp Ile Ala Ser Gly Lys Glu Lys Met Pro Asp Ile Lys
65                  70                  75                  80

Asp Phe Asp Lys Ala Ile Ala Leu Tyr Lys Ile Ala Lys Asn Phe Glu
                85                  90                  95

Lys Arg Asp Ala Glu Glu Ala Asn Pro Ile Gln Lys Asp Leu Gln Lys
            100                 105                 110

Leu Leu Ser Leu Gly Ser Phe Val Glu Leu Val Lys Gln Ala Lys Asp
        115                 120                 125

Leu Phe Met Gly Pro Tyr Val Phe Pro Phe Val Phe Asp Val Asp Ala
    130                 135                 140

Asp Met Lys Asn Thr Asp Val Asn Ala Leu Tyr Phe Gly Gly Pro Ser
145                 150                 155                 160

Thr Phe Leu Pro Asp Thr Thr Thr Tyr Lys Thr Asp Asp Ala Lys Lys
                165                 170                 175

Leu Leu Asp Val Leu Gln Asp Gln Ser Ile Asn Leu Leu Met Met Ala
            180                 185                 190

Gly Ile Gly Lys Thr Glu Ala Arg Met Tyr Val Asp Asn Ala Leu Ala
        195                 200                 205

Phe Asp Ala Lys Ile Ala Lys Val Val Lys Ser Thr Glu Glu Trp Ala
    210                 215                 220

Asp Tyr Ala Ala Ile Tyr Asn Pro Val Ser Tyr Asp Glu Phe Ile Ser
225                 230                 235                 240

Lys Phe Lys Ser Phe Lys Met Asp Glu Phe Leu Gly Lys Ile Leu Pro
                245                 250                 255

Glu Lys Pro Glu Ser Val Ile Val Met Glu Pro Arg Phe Leu Asp Tyr
            260                 265                 270

Ala Glu Glu Leu Ile Asn Ala Asp Asn Phe Ala Glu Ile Lys Gly Trp
        275                 280                 285
```

```
Leu Leu Val Lys Tyr Ile Asn Ser Val Ala Lys Tyr Leu Ser Gln Lys
    290                 295                 300

Phe Arg Glu Ala Ser Phe Pro Phe Ala His Ala Ile Ser Gly Ile Pro
305                 310                 315                 320

Glu Leu Pro Ser Gln Ile Lys Gln Ala Tyr Arg Val Ala Asn Gly Ala
                325                 330                 335

Phe Asp Glu Val Val Gly Ile Phe Tyr Gly Lys Lys Tyr Phe Gly Glu
            340                 345                 350

Lys Ala Lys His Asp Val Glu Asp Met Ile His Asn Met Leu Lys Val
        355                 360                 365

Tyr Glu Glu Arg Ile Gly Ser Asn Asp Trp Leu Ser Glu Asp Thr Lys
    370                 375                 380

Lys Gln Ala Ile Ile Lys Leu Lys Ala Leu Val Leu Lys Ile Gly Tyr
385                 390                 395                 400

Pro Glu Lys Ile Glu Lys Ile Phe Asp Leu Leu Gln Val Asp Ser Glu
                405                 410                 415

Lys Ser Leu Tyr Glu Asn Glu Ala Ala Met Asp Lys Val Arg Thr Lys
            420                 425                 430

Tyr Met Leu Asp Lys Leu Thr Lys Pro Val Asp Arg Ser Val Trp Leu
        435                 440                 445

Met Pro Gly Asn Leu Asn Asn Ala Cys Tyr Asp Pro Gln Arg Asn Asp
450                 455                 460

Leu Thr Phe Pro Ala Gly Ile Leu Gln Ala Pro Phe Tyr Asp Ile Asn
465                 470                 475                 480

Gln Ser Arg Gly Ala Asn Tyr Gly Gly Ile Gly Ala Thr Ile Gly His
                485                 490                 495

Glu Val Ser His Ala Phe Asp Asn Glu Gly Ala Lys Phe Asp Glu His
            500                 505                 510

Gly Asn Met Asn Asn Trp Trp Thr Lys Glu Asp Phe Glu Glu Phe Asn
        515                 520                 525

Lys Arg Val Gly Lys Met Val Asp Ile Phe Asp Gly Leu Gln Tyr Gly
    530                 535                 540

Pro Ala Lys Ile Asn Gly Lys Gln Val Val Ser Glu Asn Ile Ala Asp
545                 550                 555                 560

Leu Ala Gly Leu Ala Cys Ala Val Gln Thr Gly Lys Asn Asp Gly Val
                565                 570                 575

Asp Leu Lys Asp Leu Phe Glu Asn Tyr Ala Arg Ser Trp Met Glu Lys
            580                 585                 590

Gln Arg Pro Glu Ala Ile Lys Thr Glu Val Gln Thr Asp Val His Ala
        595                 600                 605

Pro Gln Pro Thr Arg Val Asn Ile Pro Val Gln Cys Gln Asp Glu Phe
    610                 615                 620

Tyr Glu Ala Phe Gly Val Lys Asp Thr Asp Gly Met Trp Leu Asp Pro
625                 630                 635                 640

Lys Asp Arg Ile Thr Ile Trp
                645

<210> SEQ ID NO 40
<211> LENGTH: 624
<212> TYPE: DNA
<213> ORGANISM: Lactobacillus acidophilus
<220> FEATURE:
<221> NAME/KEY: CDS
<222> LOCATION: (1)..(624)
<223> OTHER INFORMATION: Transcriptional repressor protein ORF# 1280
```

<400> SEQUENCE: 40

```
atg tct aga aaa aat agt gac acc aaa caa ctg gaa att cta cgc tat      48
Met Ser Arg Lys Asn Ser Asp Thr Lys Gln Leu Glu Ile Leu Arg Tyr
1               5                   10                  15 atc tac gat aca gta gaa aat cgt gga ttt cct cca aca gtt cgt gaa      96
Ile Tyr Asp Thr Val Glu Asn Arg Gly Phe Pro Pro Thr Val Arg Glu
                20                  25                  30 att tgt gct gcg gtt ggc tta tct tcc act tca aca gtt cat ggc cat     144
Ile Cys Ala Ala Val Gly Leu Ser Ser Thr Ser Thr Val His Gly His
            35                  40                  45 tta tct cgg ctt gaa cgc aag ggt ttt tta atc aaa gac gct act aag     192
Leu Ser Arg Leu Glu Arg Lys Gly Phe Leu Ile Lys Asp Ala Thr Lys
        50                  55                  60 cct cgc gcc ctt gaa att aca gct gaa ggt aag act gaa ctg ggt att     240
Pro Arg Ala Leu Glu Ile Thr Ala Glu Gly Lys Thr Glu Leu Gly Ile
65                  70                  75                  80 aag cca aaa gaa att cct gtt gtc gga gta gtc act gca ggt caa cct     288
Lys Pro Lys Glu Ile Pro Val Val Gly Val Val Thr Ala Gly Gln Pro
                85                  90                  95 att tta gca gtt gaa gac att agc gaa tat ttc cca ctt cct cct gat     336
Ile Leu Ala Val Glu Asp Ile Ser Glu Tyr Phe Pro Leu Pro Pro Asp
            100                 105                 110 tta gag agt gat gca ggc gaa tta ttc atg ctt aaa gtc cac ggt aac     384
Leu Glu Ser Asp Ala Gly Glu Leu Phe Met Leu Lys Val His Gly Asn
        115                 120                 125 agt atg att aaa gct ggc att tta aat ggt gac aat gta atc gta aga     432
Ser Met Ile Lys Ala Gly Ile Leu Asn Gly Asp Asn Val Ile Val Arg
    130                 135                 140 aaa caa agt act gcc aat aac gga gaa ata gta gtt gca atg aca gat     480
Lys Gln Ser Thr Ala Asn Asn Gly Glu Ile Val Val Ala Met Thr Asp
145                 150                 155                 160 gaa aat gag gcc acg gtt aaa cgt ttc ttc aaa gaa gat gat cat tat     528
Glu Asn Glu Ala Thr Val Lys Arg Phe Phe Lys Glu Asp Asp His Tyr
                165                 170                 175 cgt ctt caa cca gaa aat gat aca atg gca cct att att ttg caa caa     576
Arg Leu Gln Pro Glu Asn Asp Thr Met Ala Pro Ile Ile Leu Gln Gln
            180                 185                 190 gta agc att tta ggt aaa gtg gtt ggt ctt tac cgt aac aat att caa     624
Val Ser Ile Leu Gly Lys Val Val Gly Leu Tyr Arg Asn Asn Ile Gln
        195                 200                 205
```

<210> SEQ ID NO 41
<211> LENGTH: 208
<212> TYPE: PRT
<213> ORGANISM: Lactobacillus acidophilus

<400> SEQUENCE: 41

```
Met Ser Arg Lys Asn Ser Asp Thr Lys Gln Leu Glu Ile Leu Arg Tyr
1               5                   10                  15

Ile Tyr Asp Thr Val Glu Asn Arg Gly Phe Pro Pro Thr Val Arg Glu
                20                  25                  30

Ile Cys Ala Ala Val Gly Leu Ser Ser Thr Ser Thr Val His Gly His
            35                  40                  45

Leu Ser Arg Leu Glu Arg Lys Gly Phe Leu Ile Lys Asp Ala Thr Lys
        50                  55                  60

Pro Arg Ala Leu Glu Ile Thr Ala Glu Gly Lys Thr Glu Leu Gly Ile
65                  70                  75                  80

Lys Pro Lys Glu Ile Pro Val Val Gly Val Val Thr Ala Gly Gln Pro
                85                  90                  95
```

```
Ile Leu Ala Val Glu Asp Ile Ser Glu Tyr Phe Pro Leu Pro Pro Asp
                100                 105                 110

Leu Glu Ser Asp Ala Gly Glu Leu Phe Met Leu Lys Val His Gly Asn
            115                 120                 125

Ser Met Ile Lys Ala Gly Ile Leu Asn Gly Asp Asn Val Ile Val Arg
        130                 135                 140

Lys Gln Ser Thr Ala Asn Asn Gly Glu Ile Val Val Ala Met Thr Asp
145                 150                 155                 160

Glu Asn Glu Ala Thr Val Lys Arg Phe Phe Lys Glu Asp Asp His Tyr
                165                 170                 175

Arg Leu Gln Pro Glu Asn Asp Thr Met Ala Pro Ile Ile Leu Gln Gln
            180                 185                 190

Val Ser Ile Leu Gly Lys Val Val Gly Leu Tyr Arg Asn Asn Ile Gln
        195                 200                 205

<210> SEQ ID NO 42
<211> LENGTH: 1461
<212> TYPE: DNA
<213> ORGANISM: Lactobacillus acidophilus
<220> FEATURE:
<221> NAME/KEY: CDS
<222> LOCATION: (1)..(1461)
<223> OTHER INFORMATION: Dipeptidase (EC 3.4.13.18) ORF# 1294

<400> SEQUENCE: 42 gtg tta aag tta aga ggt aat aga att tat aag gag aat ttt atg aaa      48
Val Leu Lys Leu Arg Gly Asn Arg Ile Tyr Lys Glu Asn Phe Met Lys
1               5                   10                  15 gaa tat agt gct tgt act acc atc tta gtt ggt aaa aat gcc tca att      96
Glu Tyr Ser Ala Cys Thr Thr Ile Leu Val Gly Lys Asn Ala Ser Ile
                20                  25                  30 gat ggc aca act atg att gct cgt aat gat gat acc ttc cgc cca att     144
Asp Gly Thr Thr Met Ile Ala Arg Asn Asp Asp Thr Phe Arg Pro Ile
            35                  40                  45 act cca caa aag ttt att att gag cca gct cgt cat ggc gaa aag aaa     192
Thr Pro Gln Lys Phe Ile Ile Glu Pro Ala Arg His Gly Glu Lys Lys
        50                  55                  60 cat att aaa tca tgg ctt aat aag ttt gag atg gat ctt cca gaa gat     240
His Ile Lys Ser Trp Leu Asn Lys Phe Glu Met Asp Leu Pro Glu Asp
65                  70                  75                  80 gca caa cga gtt cct gcc gta cca aat gtt gat tat aaa cat cgt ggt     288
Ala Gln Arg Val Pro Ala Val Pro Asn Val Asp Tyr Lys His Arg Gly
                85                  90                  95 tac tac gat gaa agt ggt att aac caa gaa aat gtt gct atg tca tgt     336
Tyr Tyr Asp Glu Ser Gly Ile Asn Gln Glu Asn Val Ala Met Ser Cys
                100                 105                 110 act gaa tca act tat ggt aat gaa aga act tta gca ttt gat cca ttg     384
Thr Glu Ser Thr Tyr Gly Asn Glu Arg Thr Leu Ala Phe Asp Pro Leu
            115                 120                 125 gtt aaa gat gga tta gat gaa gac tgt atg caa acc gta gtt ttg cca     432
Val Lys Asp Gly Leu Asp Glu Asp Cys Met Gln Thr Val Val Leu Pro
        130                 135                 140 tac att cat tca gca cgt gat ggt gtt aag tat tta ggt aag tta att     480
Tyr Ile His Ser Ala Arg Asp Gly Val Lys Tyr Leu Gly Lys Leu Ile
145                 150                 155                 160 gct aag tat ggc tca cca gct ggt aac tct gtt ttg ttc agt gat aaa     528
Ala Lys Tyr Gly Ser Pro Ala Gly Asn Ser Val Leu Phe Ser Asp Lys
                165                 170                 175 gat gaa att tgg tac atg gaa att gta act ggt cac cac tgg gta gca     576
```

```
                                                                                        -continued Asp Glu Ile Trp Tyr Met Glu Ile Val Thr Gly His His Trp Val Ala
            180                 185                 190 gaa cgt att cct gat gat tgc tat gct gca act ggt aac cgt gta gct              624
Glu Arg Ile Pro Asp Asp Cys Tyr Ala Ala Thr Gly Asn Arg Val Ala
        195                 200                 205 att gaa caa gtc gat ttc gat aat cct gaa tac ttc atg tgg agt gaa              672
Ile Glu Gln Val Asp Phe Asp Asn Pro Glu Tyr Phe Met Trp Ser Glu
    210                 215                 220 gga att caa gaa ttt gtt gaa gaa cat cac ttg aat cca gat cat gaa              720
Gly Ile Gln Glu Phe Val Glu Glu His His Leu Asn Pro Asp His Glu
225                 230                 235                 240 ggt tgg aat ttc cgt cat atc ttt ggt act tac act gaa caa gat cgc              768
Gly Trp Asn Phe Arg His Ile Phe Gly Thr Tyr Thr Glu Gln Asp Arg
                245                 250                 255 cac tac aat act aac cgt caa tgg tat att caa aag ttg ttc aac cca              816
His Tyr Asn Thr Asn Arg Gln Trp Tyr Ile Gln Lys Leu Phe Asn Pro
            260                 265                 270 gaa att gaa caa gat cca caa gat ggc gat att cca ttt att cgt aag              864
Glu Ile Glu Gln Asp Pro Gln Asp Gly Asp Ile Pro Phe Ile Arg Lys
        275                 280                 285 gca gct aag aag att acc aag gaa gat att gaa ttt gcc tta ggt tca              912
Ala Ala Lys Lys Ile Thr Lys Glu Asp Ile Glu Phe Ala Leu Gly Ser
    290                 295                 300 cat tat caa gat act cca tat gat cca ttt ggt aag ggt acc gaa gaa              960
His Tyr Gln Asp Thr Pro Tyr Asp Pro Phe Gly Lys Gly Thr Glu Glu
305                 310                 315                 320 gaa aag cac cgc tac cgt cct att ggt ttg aac cgt acg caa aat gct             1008
Glu Lys His Arg Tyr Arg Pro Ile Gly Leu Asn Arg Thr Gln Asn Ala
                325                 330                 335 cat att tta caa ata aga agt gat gta cca gca gac cgt gca gca att             1056
His Ile Leu Gln Ile Arg Ser Asp Val Pro Ala Asp Arg Ala Ala Ile
            340                 345                 350 atg tgg tta tgt att ggt ggt cca acg ttt act cca ttt atc cca ttc             1104
Met Trp Leu Cys Ile Gly Gly Pro Thr Phe Thr Pro Phe Ile Pro Phe
        355                 360                 365 ttt gct aat atg aat gaa act gat cct tca ttt aac aat act tca atg             1152
Phe Ala Asn Met Asn Glu Thr Asp Pro Ser Phe Asn Asn Thr Ser Met
    370                 375                 380 gat tac aat atg agt gat gca tgg tgg tac tac aag tca ttt gct gca             1200
Asp Tyr Asn Met Ser Asp Ala Trp Trp Tyr Tyr Lys Ser Phe Ala Ala
385                 390                 395                 400 ctt gtt gaa agc cac tat cca caa ttt gtt caa ctt gat act act tat             1248
Leu Val Glu Ser His Tyr Pro Gln Phe Val Gln Leu Asp Thr Thr Tyr
                405                 410                 415 ctt act gaa ctt aat cgt tac ttc aga ggt cgt gtt gaa gaa att att             1296
Leu Thr Glu Leu Asn Arg Tyr Phe Arg Gly Arg Val Glu Glu Ile Ile
            420                 425                 430 aag aat tca gaa ggt aaa tca ggc gat gaa tta act gaa tac tta act             1344
Lys Asn Ser Glu Gly Lys Ser Gly Asp Glu Leu Thr Glu Tyr Leu Thr
        435                 440                 445 aaa gaa aat caa aag act gtt gct cat act cgc aag gaa act gaa aag             1392
Lys Glu Asn Gln Lys Thr Val Ala His Thr Arg Lys Glu Thr Glu Lys
    450                 455                 460 tta tgg gga gaa atg atg att gat tca att aat atg tct aag ttg act             1440
Leu Trp Gly Glu Met Met Ile Asp Ser Ile Asn Met Ser Lys Leu Thr
465                 470                 475                 480 ttt aat atg gat gaa aat ctc                                                 1461
Phe Asn Met Asp Glu Asn Leu
                485
```

<210> SEQ ID NO 43
<211> LENGTH: 487
<212> TYPE: PRT
<213> ORGANISM: Lactobacillus acidophilus

<400> SEQUENCE: 43

```
Val Leu Lys Leu Arg Gly Asn Arg Ile Tyr Lys Glu Asn Phe Met Lys
  1               5                  10                  15

Glu Tyr Ser Ala Cys Thr Thr Ile Leu Val Gly Lys Asn Ala Ser Ile
             20                  25                  30

Asp Gly Thr Thr Met Ile Ala Arg Asn Asp Asp Thr Phe Arg Pro Ile
         35                  40                  45

Thr Pro Gln Lys Phe Ile Ile Glu Pro Ala Arg His Gly Glu Lys Lys
     50                  55                  60

His Ile Lys Ser Trp Leu Asn Lys Phe Glu Met Asp Leu Pro Glu Asp
 65                  70                  75                  80

Ala Gln Arg Val Pro Ala Val Pro Asn Val Asp Tyr Lys His Arg Gly
                 85                  90                  95

Tyr Tyr Asp Glu Ser Gly Ile Asn Gln Glu Asn Val Ala Met Ser Cys
            100                 105                 110

Thr Glu Ser Thr Tyr Gly Asn Glu Arg Thr Leu Ala Phe Asp Pro Leu
        115                 120                 125

Val Lys Asp Gly Leu Asp Glu Asp Cys Met Gln Thr Val Val Leu Pro
    130                 135                 140

Tyr Ile His Ser Ala Arg Asp Gly Val Lys Tyr Leu Gly Lys Leu Ile
145                 150                 155                 160

Ala Lys Tyr Gly Ser Pro Ala Gly Asn Ser Val Leu Phe Ser Asp Lys
                165                 170                 175

Asp Glu Ile Trp Tyr Met Glu Ile Val Thr Gly His His Trp Val Ala
            180                 185                 190

Glu Arg Ile Pro Asp Asp Cys Tyr Ala Ala Thr Gly Asn Arg Val Ala
        195                 200                 205

Ile Glu Gln Val Asp Phe Asp Asn Pro Glu Tyr Phe Met Trp Ser Glu
    210                 215                 220

Gly Ile Gln Glu Phe Val Glu His His Leu Asn Pro Asp His Glu
225                 230                 235                 240

Gly Trp Asn Phe Arg His Ile Phe Gly Thr Tyr Thr Glu Gln Asp Arg
                245                 250                 255

His Tyr Asn Thr Asn Arg Gln Trp Tyr Ile Gln Lys Leu Phe Asn Pro
            260                 265                 270

Glu Ile Glu Gln Asp Pro Gln Asp Gly Asp Ile Pro Phe Ile Arg Lys
        275                 280                 285

Ala Ala Lys Lys Ile Thr Lys Glu Asp Ile Glu Phe Ala Leu Gly Ser
    290                 295                 300

His Tyr Gln Asp Thr Pro Tyr Asp Pro Phe Lys Gly Thr Glu Glu
305                 310                 315                 320

Glu Lys His Arg Tyr Arg Pro Ile Gly Leu Asn Arg Thr Gln Asn Ala
                325                 330                 335

His Ile Leu Gln Ile Arg Ser Asp Val Pro Ala Asp Arg Ala Ala Ile
            340                 345                 350

Met Trp Leu Cys Ile Gly Gly Pro Thr Phe Thr Pro Phe Ile Pro Phe
        355                 360                 365

Phe Ala Asn Met Asn Glu Thr Asp Pro Ser Phe Asn Asn Thr Ser Met
    370                 375                 380
```

```
Asp Tyr Asn Met Ser Asp Ala Trp Trp Tyr Tyr Lys Ser Phe Ala Ala
385                 390                 395                 400

Leu Val Glu Ser His Tyr Pro Gln Phe Val Gln Leu Asp Thr Thr Tyr
            405                 410                 415

Leu Thr Glu Leu Asn Arg Tyr Phe Arg Gly Arg Val Glu Glu Ile Ile
                420                 425                 430

Lys Asn Ser Glu Gly Lys Ser Gly Asp Glu Leu Thr Gly Tyr Leu Thr
            435                 440                 445

Lys Glu Asn Gln Lys Thr Val Ala His Thr Arg Lys Glu Thr Glu Lys
        450                 455                 460

Leu Trp Gly Glu Met Met Ile Asp Ser Ile Asn Met Ser Lys Leu Thr
465                 470                 475                 480

Phe Asn Met Asp Glu Asn Leu
                485

<210> SEQ ID NO 44
<211> LENGTH: 1107
<212> TYPE: DNA
<213> ORGANISM: Lactobacillus acidophilus
<220> FEATURE:
<221> NAME/KEY: CDS
<222> LOCATION: (1)..(1107)
<223> OTHER INFORMATION: Xaa-pro dipeptidase (EC 3.4.13.9) ORF# 1336

<400> SEQUENCE: 44 atg gaa gaa cga caa gaa tta ctt act tta att aat aat cga att gat    48
Met Glu Glu Arg Gln Glu Leu Leu Thr Leu Ile Asn Asn Arg Ile Asp
1               5                   10                  15 caa gtt acc tct tta gtt aaa gaa cat gat gct gat gca atg att att    96
Gln Val Thr Ser Leu Val Lys Glu His Asp Ala Asp Ala Met Ile Ile
            20                  25                  30 ttt aat caa gca aat tat cgt tac tta act aac ttt act ggt gaa gaa   144
Phe Asn Gln Ala Asn Tyr Arg Tyr Leu Thr Asn Phe Thr Gly Glu Glu
        35                  40                  45 gca cag ctt att tta aat gct aat ggt gat cgt act ctt tta tca gat   192
Ala Gln Leu Ile Leu Asn Ala Asn Gly Asp Arg Thr Leu Leu Ser Asp
    50                  55                  60 tca cga ttt gca gga caa att aag gcc cag gct ccc ggt gaa ttg aat   240
Ser Arg Phe Ala Gly Gln Ile Lys Ala Gln Ala Pro Gly Glu Leu Asn
65                  70                  75                  80 gta gta atg aaa cgt tca agt gat tat gaa gaa cta act aaa gca ctt   288
Val Val Met Lys Arg Ser Ser Asp Tyr Glu Glu Leu Thr Lys Ala Leu
                85                  90                  95 aaa aaa atg aac gtt aag aaa gtt tta gta gag ggt gaa ttt gtt tca   336
Lys Lys Met Asn Val Lys Lys Val Leu Val Glu Gly Glu Phe Val Ser
            100                 105                 110 gct agc gaa tat gaa aaa ttg aag gaa tta aat cct gat att aaa ttt   384
Ala Ser Glu Tyr Glu Lys Leu Lys Glu Leu Asn Pro Asp Ile Lys Phe
        115                 120                 125 gaa atg gtt gaa gaa tta gtt gaa cgt gtt cgt aat gtt aaa gat gaa   432
Glu Met Val Glu Glu Leu Val Glu Arg Val Arg Asn Val Lys Asp Glu
    130                 135                 140 ctt gaa ata gct gca tta cgc aga gca atc gat att tcc atg gaa agc   480
Leu Glu Ile Ala Ala Leu Arg Arg Ala Ile Asp Ile Ser Met Glu Ser
145                 150                 155                 160 ttt aaa gca atc tta cca atg att aag cca gga gta aaa gaa cga gca   528
Phe Lys Ala Ile Leu Pro Met Ile Lys Pro Gly Val Lys Glu Arg Ala
                165                 170                 175 gtt ggt gcg aaa ttg gat tat ttg ttt aag gtc aat ggt ggc gat ggc   576
```

```
                                                           -continued

Val Gly Ala Lys Leu Asp Tyr Leu Phe Lys Val Asn Gly Asp Gly
        180                 185                 190 cca gat ttt gaa acc att att gct tca gga gta cgt tca gct tgg gct      624
Pro Asp Phe Glu Thr Ile Ile Ala Ser Gly Val Arg Ser Ala Trp Ala
        195                 200                 205 cat ggt gtt gct agt gat aaa gaa att gaa gaa ggc gac atg atc gtt      672
His Gly Val Ala Ser Asp Lys Glu Ile Glu Glu Gly Asp Met Ile Val
210                 215                 220 atc gat ttt ggt agt ttt tat cat ggt tat gct gca gat ata acc aga      720
Ile Asp Phe Gly Ser Phe Tyr His Gly Tyr Ala Ala Asp Ile Thr Arg
225                 230                 235                 240 act gtt gca tta ggt gaa gtc gat tct gaa atg cat aaa att tat aat      768
Thr Val Ala Leu Gly Glu Val Asp Ser Glu Met His Lys Ile Tyr Asn
                245                 250                 255 att gtt cat gaa gca caa cgt cgc ggc atc gaa gct gca gta gta ggc      816
Ile Val His Glu Ala Gln Arg Arg Gly Ile Glu Ala Ala Val Val Gly
                260                 265                 270 aat act ggt cgt gat gtt gat aaa gca gca cgt gat tac att act gaa      864
Asn Thr Gly Arg Asp Val Asp Lys Ala Ala Arg Asp Tyr Ile Thr Glu
            275                 280                 285 caa gga tat gga gaa tat ttt ggc cat gga att ggt cac gga atc ggt      912
Gln Gly Tyr Gly Glu Tyr Phe Gly His Gly Ile Gly His Gly Ile Gly
290                 295                 300 cta gaa att cac gaa tta tgt caa ccg gct ttg cca ttc aga act act      960
Leu Glu Ile His Glu Leu Cys Gln Pro Ala Leu Pro Phe Arg Thr Thr
305                 310                 315                 320 aaa ctg gtg aac aat atg gtt cat aca gtt gaa cct ggg att tat tta     1008
Lys Leu Val Asn Asn Met Val His Thr Val Glu Pro Gly Ile Tyr Leu
                325                 330                 335 cca gat aaa ggc gga gtt aga att gaa gac gat att tta gtg aat ggt     1056
Pro Asp Lys Gly Gly Val Arg Ile Glu Asp Asp Ile Leu Val Asn Gly
            340                 345                 350 gaa aca cca gaa act ctg tca act ttg ccc aaa gat gaa tta att tct     1104
Glu Thr Pro Glu Thr Leu Ser Thr Leu Pro Lys Asp Glu Leu Ile Ser
        355                 360                 365 tta                                                                  1107
Leu

<210> SEQ ID NO 45
<211> LENGTH: 369
<212> TYPE: PRT
<213> ORGANISM: Lactobacillus acidophilus

<400> SEQUENCE: 45

Met Glu Glu Arg Gln Glu Leu Leu Thr Leu Ile Asn Asn Arg Ile Asp
1               5                   10                  15

Gln Val Thr Ser Leu Val Lys Glu His Asp Ala Asp Ala Met Ile Ile
            20                  25                  30

Phe Asn Gln Ala Asn Tyr Arg Tyr Leu Thr Asn Phe Thr Gly Glu Glu
        35                  40                  45

Ala Gln Leu Ile Leu Asn Ala Asn Gly Asp Arg Thr Leu Leu Ser Asp
    50                  55                  60

Ser Arg Phe Ala Gly Gln Ile Lys Ala Gln Ala Pro Gly Glu Leu Asn
65                  70                  75                  80

Val Val Met Lys Arg Ser Ser Asp Tyr Glu Glu Leu Thr Lys Ala Leu
                85                  90                  95

Lys Lys Met Asn Val Lys Lys Val Leu Val Glu Gly Glu Phe Val Ser
            100                 105                 110
```

-continued

```
Ala Ser Glu Tyr Glu Lys Leu Lys Glu Leu Asn Pro Asp Ile Lys Phe
        115                 120                 125

Glu Met Val Glu Glu Leu Val Glu Arg Val Arg Asn Val Lys Asp Glu
    130                 135                 140

Leu Glu Ile Ala Ala Leu Arg Arg Ala Ile Asp Ile Ser Met Glu Ser
145                 150                 155                 160

Phe Lys Ala Ile Leu Pro Met Ile Lys Pro Gly Val Lys Glu Arg Ala
                165                 170                 175

Val Gly Ala Lys Leu Asp Tyr Leu Phe Lys Val Asn Gly Gly Asp Gly
            180                 185                 190

Pro Asp Phe Glu Thr Ile Ile Ala Ser Gly Val Arg Ser Ala Trp Ala
        195                 200                 205

His Gly Val Ala Ser Asp Lys Glu Ile Glu Gly Asp Met Ile Val
    210                 215                 220

Ile Asp Phe Gly Ser Phe Tyr His Gly Tyr Ala Ala Asp Ile Thr Arg
225                 230                 235                 240

Thr Val Ala Leu Gly Glu Val Asp Ser Glu Met His Lys Ile Tyr Asn
                245                 250                 255

Ile Val His Glu Ala Gln Arg Arg Gly Ile Glu Ala Ala Val Val Gly
            260                 265                 270

Asn Thr Gly Arg Asp Val Asp Lys Ala Ala Arg Asp Tyr Ile Thr Glu
        275                 280                 285

Gln Gly Tyr Gly Glu Tyr Phe Gly His Gly Ile Gly His Gly Ile Gly
    290                 295                 300

Leu Glu Ile His Glu Leu Cys Gln Pro Ala Leu Pro Phe Arg Thr Thr
305                 310                 315                 320

Lys Leu Val Asn Asn Met Val His Thr Val Glu Pro Gly Ile Tyr Leu
                325                 330                 335

Pro Asp Lys Gly Gly Val Arg Ile Glu Asp Asp Ile Leu Val Asn Gly
            340                 345                 350

Glu Thr Pro Glu Thr Leu Ser Thr Leu Pro Lys Asp Glu Leu Ile Ser
        355                 360                 365

Leu
```

<210> SEQ ID NO 46
<211> LENGTH: 1197
<212> TYPE: DNA
<213> ORGANISM: Lactobacillus acidophilus
<220> FEATURE:
<221> NAME/KEY: CDS
<222> LOCATION: (1)..(579)
<223> OTHER INFORMATION: pepQ ORF# 1344
<220> FEATURE:
<221> NAME/KEY: CDS
<222> LOCATION: (604)..(1197)
<223> OTHER INFORMATION: pepQ ORF# 1343

<400> SEQUENCE: 46

```
atg agt aaa aca gtt ttt aag aat tgt aat ttg ttt gta ggg aca aaa      48
Met Ser Lys Thr Val Phe Lys Asn Cys Asn Leu Phe Val Gly Thr Lys
1               5                   10                  15 gat gaa ttg cta cat aag gca tgg ttc gta gtt gac gaa gaa acg ggt      96
Asp Glu Leu Leu His Lys Ala Trp Phe Val Val Asp Glu Glu Thr Gly
            20                  25                  30 aag tta ctc caa gtg gga aca ggg aca aac ccg aag gaa gat aaa aat     144
Lys Leu Leu Gln Val Gly Thr Gly Thr Asn Pro Lys Glu Asp Lys Asn
        35                  40                  45 gtt gac ttg cat ggt caa tat gta atg tct gga ttg att aat gct cat     192
```

```
                Val Asp Leu His Gly Gln Tyr Val Met Ser Gly Leu Ile Asn Ala His
                     50                  55                  60 aca cat gta ggg ttg gtt aat gca gcc aaa gaa cat tat cct gag act             240
Thr His Val Gly Leu Val Asn Ala Ala Lys Glu His Tyr Pro Glu Thr
 65                  70                  75                  80 gaa act ttg gtt act tat aag gcc tta aaa gat tta aaa agt gga tta             288
Glu Thr Leu Val Thr Tyr Lys Ala Leu Lys Asp Leu Lys Ser Gly Leu
                 85                  90                  95 cgt ggg ggc gtt aca tat att aga agc tgt ggt gta gct ttt gat gtt             336
Arg Gly Gly Val Thr Tyr Ile Arg Ser Cys Gly Val Ala Phe Asp Val
            100                 105                 110 gat gtt aag cta aat aaa atg agg gat gca tat cct ttt gaa gga cct             384
Asp Val Lys Leu Asn Lys Met Arg Asp Ala Tyr Pro Phe Glu Gly Pro
            115                 120                 125 gaa att gaa ccg gct ggg atg cca atc tct ata tta ggt ggc cat gct             432
Glu Ile Glu Pro Ala Gly Met Pro Ile Ser Ile Leu Gly Gly His Ala
        130                 135                 140 gat cag cca ttg gaa gat aat aag tta aat gtt gct cac ttg gtt aat             480
Asp Gln Pro Leu Glu Asp Asn Lys Leu Asn Val Ala His Leu Val Asn
145                 150                 155                 160 tca cca gat gat gtg aga aaa gca gtg cgt gag cag ttt aaa aaa ggc             528
Ser Pro Asp Asp Val Arg Lys Ala Val Arg Glu Gln Phe Lys Lys Gly
                165                 170                 175 cct gaa aat att aaa tta atg gcg ata ggt ggt gtt atg tca caa ggt             576
Pro Glu Asn Ile Lys Leu Met Ala Ile Gly Gly Val Met Ser Gln Gly
            180                 185                 190 gat taaatagatg atacggaact ttcc ttg gaa gaa atg caa atg gca gtt               627
Asp                           Leu Glu Glu Met Gln Met Ala Val
                                           195                 200 aaa gag gca cat tct aag cac atg act gta tgt gca cat gca gaa gga             675
Lys Glu Ala His Ser Lys His Met Thr Val Cys Ala His Ala Glu Gly
                205                 210                 215 aaa atg gaa att cat tat gct gtt gtt gcc gga gta gat tct gtt gag             723
Lys Met Glu Ile His Tyr Ala Val Val Ala Gly Val Asp Ser Val Glu
            220                 225                 230 cat ggt ttt tat gta agt gat gaa gat att gaa tta atg aaa aaa caa             771
His Gly Phe Tyr Val Ser Asp Glu Asp Ile Glu Leu Met Lys Lys Gln
        235                 240                 245 ggt aca ttt tta tca cca acg tta att gct gga cat caa att gtg gaa             819
Gly Thr Phe Leu Ser Pro Thr Leu Ile Ala Gly His Gln Ile Val Glu
250                 255                 260                 265 tat ggt aaa gga aaa atg acc gat ttt tca tat cag aag atg tgt cag             867
Tyr Gly Lys Gly Lys Met Thr Asp Phe Ser Tyr Gln Lys Met Cys Gln
                270                 275                 280 cat gta gag gca ttt tat gaa cat gtt ggt aaa gca att aaa gca ggt             915
His Val Glu Ala Phe Tyr Glu His Val Gly Lys Ala Ile Lys Ala Gly
            285                 290                 295 gtt aaa tta gcg tta gga acc gat gca ggc aca ttt atg aat cca tta             963
Val Lys Leu Ala Leu Gly Thr Asp Ala Gly Thr Phe Met Asn Pro Leu
        300                 305                 310 gaa gat act gct aaa gaa tta aaa gaa tta act aga gct ggt aca agc            1011
Glu Asp Thr Ala Lys Glu Leu Lys Glu Leu Thr Arg Ala Gly Thr Ser
315                 320                 325 aat tac caa gcc tta cgt gct gca gga tta gga tct gct gaa tta tta            1059
Asn Tyr Gln Ala Leu Arg Ala Ala Gly Leu Gly Ser Ala Glu Leu Leu
330                 335                 340                 345 aaa att gat cga aat tat gga tcg ctt gaa gtt gga aaa tat gca gat            1107
Lys Ile Asp Arg Asn Tyr Gly Ser Leu Glu Val Gly Lys Tyr Ala Asp
                350                 355                 360
```

```
ttt tta gta tta aag aat aat cca cta act gat gta acg gct gtt gag      1155
Phe Leu Val Leu Lys Asn Asn Pro Leu Thr Asp Val Thr Ala Val Glu
            365                 370                 375 caa gtt gat aag caa gtt tat cag cat ggt aag cga aaa tat              1197
Gln Val Asp Lys Gln Val Tyr Gln His Gly Lys Arg Lys Tyr
        380                 385                 390
```

<210> SEQ ID NO 47
<211> LENGTH: 193
<212> TYPE: PRT
<213> ORGANISM: Lactobacillus acidophilus

<400> SEQUENCE: 47

```
Met Ser Lys Thr Val Phe Lys Asn Cys Asn Leu Phe Val Gly Thr Lys
1               5                   10                  15

Asp Glu Leu Leu His Lys Ala Trp Phe Val Val Asp Glu Glu Thr Gly
                20                  25                  30

Lys Leu Leu Gln Val Gly Thr Gly Thr Asn Pro Lys Glu Asp Lys Asn
            35                  40                  45

Val Asp Leu His Gly Gln Tyr Val Met Ser Gly Leu Ile Asn Ala His
        50                  55                  60

Thr His Val Gly Leu Val Asn Ala Ala Lys Glu His Tyr Pro Glu Thr
65                  70                  75                  80

Glu Thr Leu Val Thr Tyr Lys Ala Leu Lys Asp Leu Lys Ser Gly Leu
                85                  90                  95

Arg Gly Gly Val Thr Tyr Ile Arg Ser Cys Gly Val Ala Phe Asp Val
            100                 105                 110

Asp Val Lys Leu Asn Lys Met Arg Asp Ala Tyr Pro Phe Glu Gly Pro
        115                 120                 125

Glu Ile Glu Pro Ala Gly Met Pro Ile Ser Ile Leu Gly Gly His Ala
    130                 135                 140

Asp Gln Pro Leu Glu Asp Asn Lys Leu Asn Val Ala His Leu Val Asn
145                 150                 155                 160

Ser Pro Asp Asp Val Arg Lys Ala Val Arg Glu Gln Phe Lys Lys Gly
                165                 170                 175

Pro Glu Asn Ile Lys Leu Met Ala Ile Gly Gly Val Met Ser Gln Gly
            180                 185                 190

Asp
```

<210> SEQ ID NO 48
<211> LENGTH: 198
<212> TYPE: PRT
<213> ORGANISM: Lactobacillus acidophilus

<400> SEQUENCE: 48

```
Leu Glu Glu Met Gln Met Ala Val Lys Glu Ala His Ser Lys His Met
1               5                   10                  15

Thr Val Cys Ala His Ala Glu Gly Lys Met Glu Ile His Tyr Ala Val
                20                  25                  30

Val Ala Gly Val Asp Ser Val Glu His Gly Phe Tyr Val Ser Asp Glu
            35                  40                  45

Asp Ile Glu Leu Met Lys Lys Gln Gly Thr Phe Leu Ser Pro Thr Leu
        50                  55                  60

Ile Ala Gly His Gln Ile Val Glu Tyr Gly Lys Gly Lys Met Thr Asp
65                  70                  75                  80

Phe Ser Tyr Gln Lys Met Cys Gln His Val Glu Ala Phe Tyr Glu His
                85                  90                  95
```

-continued

```
Val Gly Lys Ala Ile Lys Ala Gly Val Lys Leu Ala Leu Gly Thr Asp
            100                 105                 110

Ala Gly Thr Phe Met Asn Pro Leu Glu Asp Thr Ala Lys Glu Leu Lys
        115                 120                 125

Glu Leu Thr Arg Ala Gly Thr Ser Asn Tyr Gln Ala Leu Arg Ala Ala
    130                 135                 140

Gly Leu Gly Ser Ala Glu Leu Lys Ile Asp Arg Asn Tyr Gly Ser
145                 150                 155                 160

Leu Glu Val Gly Lys Tyr Ala Asp Phe Leu Val Leu Lys Asn Asn Pro
                165                 170                 175

Leu Thr Asp Val Thr Ala Val Glu Gln Val Asp Lys Gln Val Tyr Gln
            180                 185                 190

His Gly Lys Arg Lys Tyr
        195
```

<210> SEQ ID NO 49
<211> LENGTH: 2379
<212> TYPE: DNA
<213> ORGANISM: Lactobacillus acidophilus
<220> FEATURE:
<221> NAME/KEY: CDS
<222> LOCATION: (1)..(2379)
<223> OTHER INFORMATION: pepX X-Pro dipeptidyl peptidase (EC 3.4.14.11) ORF# 1373

<400> SEQUENCE: 49

```
atg aaa tat aat caa tac gcc tac gtt gaa act gac ttt gac aac caa      48
Met Lys Tyr Asn Gln Tyr Ala Tyr Val Glu Thr Asp Phe Asp Asn Gln
1               5                   10                  15 gtt aga gaa ctt atc gac att aac ttt tta cct aga aac tac gaa gat      96
Val Arg Glu Leu Ile Asp Ile Asn Phe Leu Pro Arg Asn Tyr Glu Asp
                20                  25                  30 tgg tca ttt agc gac ctt tta gct aaa ttg gtc aaa aac gcg atc gct     144
Trp Ser Phe Ser Asp Leu Leu Ala Lys Leu Val Lys Asn Ala Ile Ala
            35                  40                  45 gaa gca aag act gat gct gct aaa agt gct aaa ctc agc gaa ttt gcc     192
Glu Ala Lys Thr Asp Ala Ala Lys Ser Ala Lys Leu Ser Glu Phe Ala
        50                  55                  60 gtt tct gat cac gaa acc tta act gat ttt ctt aag caa aag cca gaa     240
Val Ser Asp His Glu Thr Leu Thr Asp Phe Leu Lys Gln Lys Pro Glu
65                  70                  75                  80 tct atc ggt acc gca caa ttc tat aat gtt gca tta caa cta ctt ggc     288
Ser Ile Gly Thr Ala Gln Phe Tyr Asn Val Ala Leu Gln Leu Leu Gly
                85                  90                  95 tac cat gtt cat tat gac tat gac ttt gcc gat cca act ggt ttt atg     336
Tyr His Val His Tyr Asp Tyr Asp Phe Ala Asp Pro Thr Gly Phe Met
            100                 105                 110 caa aaa aca gcg ctg cct ttt gtt caa gat att aac gat acc cat aag     384
Gln Lys Thr Ala Leu Pro Phe Val Gln Asp Ile Asn Asp Thr His Lys
        115                 120                 125 ttg atc tcc gct ttc tat cgt ttg ctc aat acc cgt act aaa aac ggt     432
Leu Ile Ser Ala Phe Tyr Arg Leu Leu Asn Thr Arg Thr Lys Asn Gly
    130                 135                 140 caa att tta ctt gat gtg atg gct ggt aaa ggt tac ttc act caa ttc     480
Gln Ile Leu Leu Asp Val Met Ala Gly Lys Gly Tyr Phe Thr Gln Phe
145                 150                 155                 160 tgg ggt caa aat caa ttc aaa ttt ttc aat ggt aaa tct atc cct gtc     528
Trp Gly Gln Asn Gln Phe Lys Phe Phe Asn Gly Lys Ser Ile Pro Val
                165                 170                 175
```

-continued

| | |
|---|---:|
| ttt gat act tca aaa gta atc cgc gaa gtt gtt tat gta gaa acc gac<br>Phe Asp Thr Ser Lys Val Ile Arg Glu Val Val Tyr Val Glu Thr Asp<br>          180                     185                        190 | 576 |
| tta gat act gat cat gat gga aag agc gac tta att caa gtt act gtt<br>Leu Asp Thr Asp His Asp Gly Lys Ser Asp Leu Ile Gln Val Thr Val<br>          195                     200                        205 | 624 |
| ttc cgt cca gtt gaa act aac aac ggt ctt aag gta cca gca ctt tat<br>Phe Arg Pro Val Glu Thr Asn Asn Gly Leu Lys Val Pro Ala Leu Tyr<br>210                     215                     220 | 672 |
| act gca tcc cca tat ttc ggc gga atc atc gct aac gaa aag cgt aat<br>Thr Ala Ser Pro Tyr Phe Gly Gly Ile Ile Ala Asn Glu Lys Arg Asn<br>225                   230                     235                 240 | 720 |
| cac agc gtc gat gaa aat cta tct gat gct act gaa tgg aat gat cca<br>His Ser Val Asp Glu Asn Leu Ser Asp Ala Thr Glu Trp Asn Asp Pro<br>                   245                     250                    255 | 768 |
| caa tac gtt cat tct cca atc gtt aaa gca gaa aag cct gat ggc tca<br>Gln Tyr Val His Ser Pro Ile Val Lys Ala Glu Lys Pro Asp Gly Ser<br>                   260                     265                   270 | 816 |
| aat cat cca act act gaa gaa gca gtt cac aag tct tct tac cca ttg<br>Asn His Pro Thr Thr Glu Glu Ala Val His Lys Ser Ser Tyr Pro Leu<br>          275                     280                        285 | 864 |
| aac gaa tat atg ctt gct cgc ggt ttt gct agt gtc ttt gcc ggc gca<br>Asn Glu Tyr Met Leu Ala Arg Gly Phe Ala Ser Val Phe Ala Gly Ala<br>          290                     295                     300 | 912 |
| atc ggt act cgc ggt agt gac ggt gtc aga atc act ggt gcc cct gaa<br>Ile Gly Thr Arg Gly Ser Asp Gly Val Arg Ile Thr Gly Ala Pro Glu<br>305                     310                     315                 320 | 960 |
| gaa acc gaa tca gca gct gct gta atc gaa tgg ctt cac ggc gac cgt<br>Glu Thr Glu Ser Ala Ala Ala Val Ile Glu Trp Leu His Gly Asp Arg<br>                   325                     330                    335 | 1008 |
| att gcc tac act gac cgt acc aga act atg caa aca aaa gct gat tgg<br>Ile Ala Tyr Thr Asp Arg Thr Arg Thr Met Gln Thr Lys Ala Asp Trp<br>                   340                     345                    350 | 1056 |
| tgt aac ggc aac atc ggt atg acc ggc cgc tca tac ttg ggc act ttg<br>Cys Asn Gly Asn Ile Gly Met Thr Gly Arg Ser Tyr Leu Gly Thr Leu<br>          355                     360                     365 | 1104 |
| caa att gct atc gct acc acc ggt gtc aag gga ctt aag act gtt gtc<br>Gln Ile Ala Ile Ala Thr Thr Gly Val Lys Gly Leu Lys Thr Val Val<br>          370                     375                     380 | 1152 |
| tca gaa gct gca att tct tca tgg tac gac tac tat cgc gaa cac ggt<br>Ser Glu Ala Ala Ile Ser Ser Trp Tyr Asp Tyr Tyr Arg Glu His Gly<br>385                     390                     395                 400 | 1200 |
| ttg gtc atc gct cca gaa gca tgt caa ggt gaa gac ttg gat ctt ctt<br>Leu Val Ile Ala Pro Glu Ala Cys Gln Gly Glu Asp Leu Asp Leu Leu<br>                   405                     410                    415 | 1248 |
| gca gaa act tgt gaa tct aac tta tgg gat gct gga tca tac ctc aag<br>Ala Glu Thr Cys Glu Ser Asn Leu Trp Asp Ala Gly Ser Tyr Leu Lys<br>                   420                     425                    430 | 1296 |
| atc aag cca gaa tac gac aaa atg caa aag cag ttg cta gaa aaa gag<br>Ile Lys Pro Glu Tyr Asp Lys Met Gln Lys Gln Leu Leu Glu Lys Glu<br>          435                     440                     445 | 1344 |
| gat cgg aca act ggc caa tat tct gat ttc tgg gaa gct aga aac tat<br>Asp Arg Thr Thr Gly Gln Tyr Ser Asp Phe Trp Glu Ala Arg Asn Tyr<br>          450                     455                     460 | 1392 |
| cgt cat cac gct gac ggt atc aag tgt tca tgg att tcc gtt cat ggt<br>Arg His His Ala Asp Gly Ile Lys Cys Ser Trp Ile Ser Val His Gly<br>465                     470                     475                 480 | 1440 |
| tta aac gac tgg aac gtt aaa cca aag aac gtt tac aag att tgg caa<br>Leu Asn Asp Trp Asn Val Lys Pro Lys Asn Val Tyr Lys Ile Trp Gln<br>                   485                     490                    495 | 1488 |

```
ctt gtt tct aag atg cca atg aag cat cac ctc ttc ttg cac caa ggt    1536
Leu Val Ser Lys Met Pro Met Lys His His Leu Phe Leu His Gln Gly
        500                 505                 510 cca cac tat aat atg aac aat ttt gtt tct atc gac ttc act gac ttg    1584
Pro His Tyr Asn Met Asn Asn Phe Val Ser Ile Asp Phe Thr Asp Leu
        515                 520                 525 atg aac ctt tgg ttt gtc cac gaa tta ttg gat gtt gaa aac aat gct    1632
Met Asn Leu Trp Phe Val His Glu Leu Leu Asp Val Glu Asn Asn Ala
        530                 535                 540 tac aac caa tgg cca act gtt atg att caa gac aac ttg caa gcc gac    1680
Tyr Asn Gln Trp Pro Thr Val Met Ile Gln Asp Asn Leu Gln Ala Asp
545                 550                 555                 560 aag tgg cat gaa gaa aaa gat tgg aac gat aaa tta ggt cgt gaa aag    1728
Lys Trp His Glu Glu Lys Asp Trp Asn Asp Lys Leu Gly Arg Glu Lys
                565                 570                 575 atc tac ttc cct acc gat gat gat gaa ctt ttg caa gat ggt gat agc    1776
Ile Tyr Phe Pro Thr Asp Asp Asp Glu Leu Leu Gln Asp Gly Asp Ser
                    580                 585                 590 cat gcc gaa aag tcc ttc act gat gta ggt ggt att gaa ttt aag aag    1824
His Ala Glu Lys Ser Phe Thr Asp Val Gly Gly Ile Glu Phe Lys Lys
                595                 600                 605 gcc ggt att tct gaa agt gaa tgg gaa tac aaa ttt atc agc ggg gat    1872
Ala Gly Ile Ser Glu Ser Glu Trp Glu Tyr Lys Phe Ile Ser Gly Asp
        610                 615                 620 gaa aaa tgg gct aag cca agt ttg cgc ttt act act gat gaa ttc atc    1920
Glu Lys Trp Ala Lys Pro Ser Leu Arg Phe Thr Thr Asp Glu Phe Ile
625                 630                 635                 640 cac cct act act att gta ggc cga cct gaa gtt aaa gtt aga gtt aaa    1968
His Pro Thr Thr Ile Val Gly Arg Pro Glu Val Lys Val Arg Val Lys
                645                 650                 655 gga tca cta cct aag ggg caa atc tcc gtt gct tta gtt gaa ctt ggt    2016
Gly Ser Leu Pro Lys Gly Gln Ile Ser Val Ala Leu Val Glu Leu Gly
                660                 665                 670 gaa aga caa cgt ttg act gct act cct aag ttc ttg atg cgt ggt ggt    2064
Glu Arg Gln Arg Leu Thr Ala Thr Pro Lys Phe Leu Met Arg Gly Gly
        675                 680                 685 caa gaa tta ggc tac aag ttc ggt act gat aca ctt caa gaa ttt gtt    2112
Gln Glu Leu Gly Tyr Lys Phe Gly Thr Asp Thr Leu Gln Glu Phe Val
        690                 695                 700 cct gat aaa aag act aag gct aag ttg att act aag gca cac atg aac    2160
Pro Asp Lys Lys Thr Lys Ala Lys Leu Ile Thr Lys Ala His Met Asn
705                 710                 715                 720 ttg caa aac tac aag gat atg aaa aag cct gag cat att gat gca gac    2208
Leu Gln Asn Tyr Lys Asp Met Lys Lys Pro Glu His Ile Asp Ala Asp
                725                 730                 735 aag ttc tat gat ctt gat ttc tta ctt caa cct acc tac tac act att    2256
Lys Phe Tyr Asp Leu Asp Phe Leu Leu Gln Pro Thr Tyr Tyr Thr Ile
                740                 745                 750 cca tcc gga agc aag tta gct ttg atc att tac tca act gat gaa ggg    2304
Pro Ser Gly Ser Lys Leu Ala Leu Ile Ile Tyr Ser Thr Asp Glu Gly
        755                 760                 765 atg act aag cga cca ctt gaa gaa gaa act tac act att gat tta gct    2352
Met Thr Lys Arg Pro Leu Glu Glu Glu Thr Tyr Thr Ile Asp Leu Ala
        770                 775                 780 aat act gaa atc aag ttt tat gaa aag                                2379
Asn Thr Glu Ile Lys Phe Tyr Glu Lys
785                 790

<210> SEQ ID NO 50
```

```
<211> LENGTH: 793
<212> TYPE: PRT
<213> ORGANISM: Lactobacillus acidophilus

<400> SEQUENCE: 50
```

| | | | | | | | | | | | | | | |
|---|---|---|---|---|---|---|---|---|---|---|---|---|---|---|
| Met | Lys | Tyr | Asn | Gln | Tyr | Ala | Tyr | Val | Glu | Thr | Asp | Phe | Asp | Asn | Gln |
| 1 | | | | 5 | | | | | 10 | | | | | 15 | |

Val Arg Glu Leu Ile Asp Ile Asn Phe Leu Pro Arg Asn Tyr Glu Asp
            20                  25                  30

Trp Ser Phe Ser Asp Leu Leu Ala Lys Leu Val Lys Asn Ala Ile Ala
        35                  40                  45

Glu Ala Lys Thr Asp Ala Ala Lys Ser Ala Lys Leu Ser Glu Phe Ala
    50                  55                  60

Val Ser Asp His Glu Thr Leu Thr Asp Phe Leu Lys Gln Lys Pro Glu
65                  70                  75                  80

Ser Ile Gly Thr Ala Gln Phe Tyr Asn Val Ala Leu Gln Leu Leu Gly
                85                  90                  95

Tyr His Val His Tyr Asp Tyr Asp Phe Ala Asp Pro Thr Gly Phe Met
            100                 105                 110

Gln Lys Thr Ala Leu Pro Phe Val Gln Asp Ile Asn Asp Thr His Lys
        115                 120                 125

Leu Ile Ser Ala Phe Tyr Arg Leu Leu Asn Thr Arg Thr Lys Asn Gly
130                 135                 140

Gln Ile Leu Leu Asp Val Met Ala Gly Lys Gly Tyr Phe Thr Gln Phe
145                 150                 155                 160

Trp Gly Gln Asn Gln Phe Lys Phe Phe Asn Gly Lys Ser Ile Pro Val
                165                 170                 175

Phe Asp Thr Ser Lys Val Ile Arg Glu Val Val Tyr Val Glu Thr Asp
            180                 185                 190

Leu Asp Thr Asp His Asp Gly Lys Ser Asp Leu Ile Gln Val Thr Val
        195                 200                 205

Phe Arg Pro Val Glu Thr Asn Asn Gly Leu Lys Val Pro Ala Leu Tyr
210                 215                 220

Thr Ala Ser Pro Tyr Phe Gly Gly Ile Ile Ala Asn Glu Lys Arg Asn
225                 230                 235                 240

His Ser Val Asp Glu Asn Leu Ser Asp Ala Thr Glu Trp Asn Asp Pro
                245                 250                 255

Gln Tyr Val His Ser Pro Ile Val Lys Ala Glu Lys Pro Asp Gly Ser
            260                 265                 270

Asn His Pro Thr Thr Glu Glu Ala Val His Lys Ser Ser Tyr Pro Leu
        275                 280                 285

Asn Glu Tyr Met Leu Ala Arg Gly Phe Ala Ser Val Phe Ala Gly Ala
    290                 295                 300

Ile Gly Thr Arg Gly Ser Asp Gly Val Arg Ile Thr Gly Ala Pro Glu
305                 310                 315                 320

Glu Thr Glu Ser Ala Ala Ala Val Ile Glu Trp Leu His Gly Asp Arg
                325                 330                 335

Ile Ala Tyr Thr Asp Arg Thr Arg Thr Met Gln Thr Lys Ala Asp Trp
            340                 345                 350

Cys Asn Gly Asn Ile Gly Met Thr Gly Arg Ser Tyr Leu Gly Thr Leu
        355                 360                 365

Gln Ile Ala Ile Ala Thr Thr Gly Val Lys Gly Leu Lys Thr Val Val
    370                 375                 380

Ser Glu Ala Ala Ile Ser Ser Trp Tyr Asp Tyr Tyr Arg Glu His Gly

```
            385                 390                 395                 400
Leu Val Ile Ala Pro Glu Ala Cys Gln Gly Glu Asp Leu Asp Leu Leu
                405                 410                 415
Ala Glu Thr Cys Glu Ser Asn Leu Trp Asp Ala Gly Ser Tyr Leu Lys
                420                 425                 430
Ile Lys Pro Glu Tyr Asp Lys Met Gln Lys Gln Leu Leu Glu Lys Glu
                435                 440                 445
Asp Arg Thr Thr Gly Gln Tyr Ser Asp Phe Trp Glu Ala Arg Asn Tyr
            450                 455                 460
Arg His His Ala Asp Gly Ile Lys Cys Ser Trp Ile Ser Val His Gly
465                 470                 475                 480
Leu Asn Asp Trp Asn Val Lys Pro Lys Asn Val Tyr Lys Ile Trp Gln
                485                 490                 495
Leu Val Ser Lys Met Pro Met Lys His His Leu Phe Leu His Gln Gly
                500                 505                 510
Pro His Tyr Asn Met Asn Asn Phe Val Ser Ile Asp Phe Thr Asp Leu
                515                 520                 525
Met Asn Leu Trp Phe Val His Glu Leu Leu Asp Val Glu Asn Asn Ala
            530                 535                 540
Tyr Asn Gln Trp Pro Thr Val Met Ile Gln Asp Asn Leu Gln Ala Asp
545                 550                 555                 560
Lys Trp His Glu Glu Lys Asp Trp Asn Asp Lys Leu Gly Arg Glu Lys
                565                 570                 575
Ile Tyr Phe Pro Thr Asp Asp Glu Leu Leu Gln Asp Gly Asp Ser
                580                 585                 590
His Ala Glu Lys Ser Phe Thr Asp Val Gly Gly Ile Glu Phe Lys Lys
            595                 600                 605
Ala Gly Ile Ser Glu Ser Glu Trp Glu Tyr Lys Phe Ile Ser Gly Asp
        610                 615                 620
Glu Lys Trp Ala Lys Pro Ser Leu Arg Phe Thr Thr Asp Glu Phe Ile
625                 630                 635                 640
His Pro Thr Thr Ile Val Gly Arg Pro Glu Val Lys Val Arg Val Lys
                645                 650                 655
Gly Ser Leu Pro Lys Gly Gln Ile Ser Val Ala Leu Val Glu Leu Gly
                660                 665                 670
Glu Arg Gln Arg Leu Thr Ala Thr Pro Lys Phe Leu Met Arg Gly Gly
            675                 680                 685
Gln Glu Leu Gly Tyr Lys Phe Gly Thr Asp Thr Leu Gln Glu Phe Val
            690                 695                 700
Pro Asp Lys Lys Thr Lys Ala Lys Leu Ile Thr Lys Ala His Met Asn
705                 710                 715                 720
Leu Gln Asn Tyr Lys Asp Met Lys Pro Glu His Ile Asp Ala Asp
                725                 730                 735
Lys Phe Tyr Asp Leu Asp Phe Leu Gln Pro Thr Tyr Tyr Thr Ile
                740                 745                 750
Pro Ser Gly Ser Lys Leu Ala Leu Ile Ile Tyr Ser Thr Asp Glu Gly
                755                 760                 765
Met Thr Lys Arg Pro Leu Glu Glu Thr Tyr Thr Ile Asp Leu Ala
            770                 775                 780
Asn Thr Glu Ile Lys Phe Tyr Glu Lys
785                 790

<210> SEQ ID NO 51
```

<211> LENGTH: 4881
<212> TYPE: DNA
<213> ORGANISM: Lactobacillus acidophilus
<220> FEATURE:
<221> NAME/KEY: CDS
<222> LOCATION: (1)..(4881)
<223> OTHER INFORMATION: prtP precursor ORF# 1512

<400> SEQUENCE: 51

```
atg aga aat aaa aaa gtg ggg agt gta act aca gac tac agt tac ctt       48
Met Arg Asn Lys Lys Val Gly Ser Val Thr Thr Asp Tyr Ser Tyr Leu
1               5                   10                  15 aat caa tct agg aac cat tta aat tta gta act ggt aaa gaa aat gat       96
Asn Gln Ser Arg Asn His Leu Asn Leu Val Thr Gly Lys Glu Asn Asp
            20                  25                  30 agt aaa tta aaa att tgg cga aaa aat ttt gct aca gct gct att att      144
Ser Lys Leu Lys Ile Trp Arg Lys Asn Phe Ala Thr Ala Ala Ile Ile
        35                  40                  45 gca tta gca tct ggc act aca atg ttg ttt tca gct cat tct gta aag      192
Ala Leu Ala Ser Gly Thr Thr Met Leu Phe Ser Ala His Ser Val Lys
    50                  55                  60 gca gat gaa gtt gat gat att act gtt caa aat gat aaa caa gta aat      240
Ala Asp Glu Val Asp Asp Ile Thr Val Gln Asn Asp Lys Gln Val Asn
65                  70                  75                  80 act acg att gta caa aat aat aaa gat caa caa tca tct gat aca caa      288
Thr Thr Ile Val Gln Asn Asn Lys Asp Gln Gln Ser Ser Asp Thr Gln
                85                  90                  95 caa aat gta aat gag aat agg gca agc agc cag caa gct ata aga aga      336
Gln Asn Val Asn Glu Asn Arg Ala Ser Ser Gln Gln Ala Ile Arg Arg
            100                 105                 110 cca ggg act ggt aac aag tta aca gat caa tgg cct gat aat tat caa      384
Pro Gly Thr Gly Asn Lys Leu Thr Asp Gln Trp Pro Asp Asn Tyr Gln
        115                 120                 125 tca gat caa caa aat aat agt tct caa gct gaa act aca aaa att tct      432
Ser Asp Gln Gln Asn Asn Ser Ser Gln Ala Glu Thr Thr Lys Ile Ser
    130                 135                 140 acc act ggt tat tct aat caa act gaa cag caa tca aat aat act gta      480
Thr Thr Gly Tyr Ser Asn Gln Thr Glu Gln Gln Ser Asn Asn Thr Val
145                 150                 155                 160 ccg tct aca gta gcc agt tcg aca gta tat aaa gaa tca agc gat gat      528
Pro Ser Thr Val Ala Ser Ser Thr Val Tyr Lys Glu Ser Ser Asp Asp
                165                 170                 175 caa gct gga caa aaa gat act aat ggt gtt gag ctt cca gct aat aac      576
Gln Ala Gly Gln Lys Asp Thr Asn Gly Val Glu Leu Pro Ala Asn Asn
            180                 185                 190 caa gac cat att aag gga aat gtt cag gat gct tgg gat caa ggc tat      624
Gln Asp His Ile Lys Gly Asn Val Gln Asp Ala Trp Asp Gln Gly Tyr
        195                 200                 205 aag gga caa cat act gta gtt gca gtt att gat tca ggt gtt gat aca      672
Lys Gly Gln His Thr Val Val Ala Val Ile Asp Ser Gly Val Asp Thr
    210                 215                 220 agt cat aaa gac ttt caa acg atg cct gaa aat cct aag ctt tct caa      720
Ser His Lys Asp Phe Gln Thr Met Pro Glu Asn Pro Lys Leu Ser Gln
225                 230                 235                 240 gct gaa ata gaa gcg ttg atc gca aaa tta ggt tac ggt act tat ata      768
Ala Glu Ile Glu Ala Leu Ile Ala Lys Leu Gly Tyr Gly Thr Tyr Ile
                245                 250                 255 aat tct aag ttt cct ttt gtg tac aat gca gta gat cat gaa aac caa      816
Asn Ser Lys Phe Pro Phe Val Tyr Asn Ala Val Asp His Glu Asn Gln
            260                 265                 270 agt atg aaa ggg cct gat ggt gag cct cac ggt caa cat gtt tca gga      864
```

```
                Ser Met Lys Gly Pro Asp Gly Glu Pro His Gly Gln His Val Ser Gly
                        275                 280                 285 att ata gct gct gat ggt caa cca aat ggt gat caa gaa tat gtg gtt              912
Ile Ile Ala Ala Asp Gly Gln Pro Asn Gly Asp Gln Glu Tyr Val Val
        290                 295                 300 gga gtt gct cca gaa gca caa tta atg cat ttt aaa gtc ttt ggc gac              960
Gly Val Ala Pro Glu Ala Gln Leu Met His Phe Lys Val Phe Gly Asp
305                 310                 315                 320 aat gct act tca tta gac tta gca cag gaa atc tat gat gca act aat             1008
Asn Ala Thr Ser Leu Asp Leu Ala Gln Glu Ile Tyr Asp Ala Thr Asn
                325                 330                 335 tta gga gca gac gta att caa atg tct tta ggt gga ggg gtt gca gct             1056
Leu Gly Ala Asp Val Ile Gln Met Ser Leu Gly Gly Gly Val Ala Ala
            340                 345                 350 gct gat ctc aat gtt gca gat caa aga gcg gtt caa tat gct att gat             1104
Ala Asp Leu Asn Val Ala Asp Gln Arg Ala Val Gln Tyr Ala Ile Asp
        355                 360                 365 cat ggt gta att gtt tct atc tca gct tct aat aac ggt aat gct gct             1152
His Gly Val Ile Val Ser Ile Ser Ala Ser Asn Asn Gly Asn Ala Ala
370                 375                 380 tca att caa aat cca agc aat gtt act gac tta gat aat tat gaa gct             1200
Ser Ile Gln Asn Pro Ser Asn Val Thr Asp Leu Asp Asn Tyr Glu Ala
385                 390                 395                 400 ggt aca cat gtg ggt aac tat gaa cct ttc agc tct agt act gtt gcg             1248
Gly Thr His Val Gly Asn Tyr Glu Pro Phe Ser Ser Ser Thr Val Ala
                405                 410                 415 gat ccc ggt gct gct cgt ggt gcc att act gga gca gca gaa aca tca             1296
Asp Pro Gly Ala Ala Arg Gly Ala Ile Thr Gly Ala Ala Glu Thr Ser
            420                 425                 430 ggc ttg ggt gat aaa agt gat atg gca aca ttc aca tct tgg gga cca             1344
Gly Leu Gly Asp Lys Ser Asp Met Ala Thr Phe Thr Ser Trp Gly Pro
        435                 440                 445 tta cca gat ttt act ttg aaa cct gat gtc tct gcg cct ggt agc aat             1392
Leu Pro Asp Phe Thr Leu Lys Pro Asp Val Ser Ala Pro Gly Ser Asn
    450                 455                 460 gtg att tct ttg gct aat gac aac ggt tat act act atg agt ggt act             1440
Val Ile Ser Leu Ala Asn Asp Asn Gly Tyr Thr Thr Met Ser Gly Thr
465                 470                 475                 480 tca atg gca ggt ccg ttt att gcc ggt gct gct gca tta gtt aga caa             1488
Ser Met Ala Gly Pro Phe Ile Ala Gly Ala Ala Ala Leu Val Arg Gln
                485                 490                 495 aga ttg caa caa act aat cct gaa tta aaa ggt gca gat ttg gta gca             1536
Arg Leu Gln Gln Thr Asn Pro Glu Leu Lys Gly Ala Asp Leu Val Ala
            500                 505                 510 gct gta aaa gca cta tta atg aat act gct gat ccg caa att caa caa             1584
Ala Val Lys Ala Leu Leu Met Asn Thr Ala Asp Pro Gln Ile Gln Gln
        515                 520                 525 ggc ttc aca act att gtt tct cca aga aga caa ggt gct ggt cag att             1632
Gly Phe Thr Thr Ile Val Ser Pro Arg Arg Gln Gly Ala Gly Gln Ile
    530                 535                 540 aat gtt ggt gca gca act aaa gca cct gtt tat att tta gct aat gat             1680
Asn Val Gly Ala Ala Thr Lys Ala Pro Val Tyr Ile Leu Ala Asn Asp
545                 550                 555                 560 ggt aca ggc tct gtt agt tta cgt aac att aaa gaa acg act aat ttt             1728
Gly Thr Gly Ser Val Ser Leu Arg Asn Ile Lys Glu Thr Thr Asn Phe
                565                 570                 575 gaa cta act ttc cac aat tta act gat aat aca gaa act tat act ttt             1776
Glu Leu Thr Phe His Asn Leu Thr Asp Asn Thr Glu Thr Tyr Thr Phe
            580                 585                 590
```

```
gat gat tta ggt ggt ggt ttt acc gag gtt aga gat act gat act gga    1824
Asp Asp Leu Gly Gly Gly Phe Thr Glu Val Arg Asp Thr Asp Thr Gly
            595                 600                 605 tta ttc cat gat gtt caa tta gcg ggc gca cga gtt act ggc ccc aat    1872
Leu Phe His Asp Val Gln Leu Ala Gly Ala Arg Val Thr Gly Pro Asn
    610                 615                 620 act att acg gta aat cct aaa gag act aaa aaa ata gta ttt act tta    1920
Thr Ile Thr Val Asn Pro Lys Glu Thr Lys Lys Ile Val Phe Thr Leu
625                 630                 635                 640 aat tta act ggc tta aag cag aat caa ttg gtt gaa gga tat ttg aat    1968
Asn Leu Thr Gly Leu Lys Gln Asn Gln Leu Val Glu Gly Tyr Leu Asn
            645                 650                 655 ttt act aat tct aag gat aag ttg tct ctg tca gta cct tat tta ggc    2016
Phe Thr Asn Ser Lys Asp Lys Leu Ser Leu Ser Val Pro Tyr Leu Gly
    660                 665                 670 tac tat ggt gac atg aca tct gag gat gtc ttt gac aag aaa gct aac    2064
Tyr Tyr Gly Asp Met Thr Ser Glu Asp Val Phe Asp Lys Lys Ala Asn
675                 680                 685 gaa gat aag cca gat att aaa ggt aat cgc tta aca aat gaa gac aat    2112
Glu Asp Lys Pro Asp Ile Lys Gly Asn Arg Leu Thr Asn Glu Asp Asn
            690                 695                 700 tac cca cgt ggg att gct gat gaa gaa tca ctt aaa gaa tta gtt aat    2160
Tyr Pro Arg Gly Ile Ala Asp Glu Glu Ser Leu Lys Glu Leu Val Asn
705                 710                 715                 720 att gaa ggt aac tat aat tgg caa gaa gtt gct aag ctg tat gaa agc    2208
Ile Glu Gly Asn Tyr Asn Trp Gln Glu Val Ala Lys Leu Tyr Glu Ser
            725                 730                 735 ggt aag gtt gca ttt tct cct aat ggt gac aat aag agc gac tta att    2256
Gly Lys Val Ala Phe Ser Pro Asn Gly Asp Asn Lys Ser Asp Leu Ile
    740                 745                 750 atg cca tat gta tat tta aag cag aat ctt caa gat tta aag gta gaa    2304
Met Pro Tyr Val Tyr Leu Lys Gln Asn Leu Gln Asp Leu Lys Val Glu
            755                 760                 765 att cta gat gct aaa gga aat gtt gtt cgt gta tta gca gat gca cat    2352
Ile Leu Asp Ala Lys Gly Asn Val Val Arg Val Leu Ala Asp Ala His
770                 775                 780 ggt gtt caa aaa tct tat aac gaa gat ggt act ggt acc gtt gat gcc    2400
Gly Val Gln Lys Ser Tyr Asn Glu Asp Gly Thr Gly Thr Val Asp Ala
785                 790                 795                 800 tta att agt gtt gat tct ggt aaa ttt aat tgg gat ggt aaa gtt tat    2448
Leu Ile Ser Val Asp Ser Gly Lys Phe Asn Trp Asp Gly Lys Val Tyr
            805                 810                 815 aat tac aaa acg ggt aaa atg gaa gtt gca cca gat ggt caa tat act    2496
Asn Tyr Lys Thr Gly Lys Met Glu Val Ala Pro Asp Gly Gln Tyr Thr
    820                 825                 830 tat cgc ttt gtt gct acg ctt tac aat gat gga cca cat aag gtt caa    2544
Tyr Arg Phe Val Ala Thr Leu Tyr Asn Asp Gly Pro His Lys Val Gln
            835                 840                 845 acc aat gat acg tca gta att att gat act act gct cca att tta aaa    2592
Thr Asn Asp Thr Ser Val Ile Ile Asp Thr Thr Ala Pro Ile Leu Lys
850                 855                 860 gat gta gaa tat gat gtt act act aaa act att act gga aca tat tct    2640
Asp Val Glu Tyr Asp Val Thr Thr Lys Thr Ile Thr Gly Thr Tyr Ser
865                 870                 875                 880 gat gca ggt gca gga ttt act gat tat tca tat gct act gta act ata    2688
Asp Ala Gly Ala Gly Phe Thr Asp Tyr Ser Tyr Ala Thr Val Thr Ile
            885                 890                 895 aat gat cga gtt ttt ggt ttt aaa tta aac gat aat gat aat tca aca    2736
Asn Asp Arg Val Phe Gly Phe Lys Leu Asn Asp Asn Asp Asn Ser Thr
900                 905                 910
```

```
ttt gat aat act gac aag act ata gga cat ttt agt ttt gct tta act      2784
Phe Asp Asn Thr Asp Lys Thr Ile Gly His Phe Ser Phe Ala Leu Thr
        915                 920                 925 cct tta gaa caa cag gct cta act gct gct cat aat aaa gtg agt gtt      2832
Pro Leu Glu Gln Gln Ala Leu Thr Ala Ala His Asn Lys Val Ser Val
    930                 935                 940 tgt tta agc gat gtg gca gat aat act gct gtt aaa aca ctt gat gta      2880
Cys Leu Ser Asp Val Ala Asp Asn Thr Ala Val Lys Thr Leu Asp Val
945                 950                 955                 960 gca agt gtg ggt gat ggt aac aag att gct att tgg aat gct gtt aat      2928
Ala Ser Val Gly Asp Gly Asn Lys Ile Ala Ile Trp Asn Ala Val Asn
                965                 970                 975 ggt gta cca ttt aat tcc aat tct caa gat tat agt gat aag aat aat      2976
Gly Val Pro Phe Asn Ser Asn Ser Gln Asp Tyr Ser Asp Lys Asn Asn
            980                 985                 990 agt tac tta tta cgt ggt agt gct  act gaa aac ttc tac  gtt aat ggt    3024
Ser Tyr Leu Leu Arg Gly Ser Ala  Thr Glu Asn Phe Tyr  Val Asn Gly
                995             1000                1005 aag tta gtg caa gtt gct cca  aat ggt gaa ttt gtt  tta ccg gtt        3069
Lys Leu Val Gln Val Ala Pro  Asn Gly Glu Phe Val  Leu Pro Val
    1010                1015                1020 tct tta gat gaa caa aat tta  gta ttt act tct gat  gaa aat ggc        3114
Ser Leu Asp Glu Gln Asn Leu  Val Phe Thr Ser Asp  Glu Asn Gly
1025                1030                1035 caa aat gtg cta aga caa ttt  acc acc tat act cct  aaa gct gat        3159
Gln Asn Val Leu Arg Gln Phe  Thr Thr Tyr Thr Pro  Lys Ala Asp
        1040                1045                1050 ttt gct tgg cag cat att gat  ggt agt gaa aga tca  ttt ggt gtt        3204
Phe Ala Trp Gln His Ile Asp  Gly Ser Glu Arg Ser  Phe Gly Val
    1055                1060                1065 tca gtt tat tca att gat gca  gct gat cca aat gat  gca ata gtt        3249
Ser Val Tyr Ser Ile Asp Ala  Ala Asp Pro Asn Asp  Ala Ile Val
1070                1075                1080 caa gca gca gtg cca aaa gga  aat aat gtt aag gct  ttt gca aaa        3294
Gln Ala Ala Val Pro Lys Gly  Asn Asn Val Lys Ala  Phe Ala Lys
        1085                1090                1095 gat tac ttt act ggt gaa aca  tat gtt ggt gaa gta  aaa gat ggt        3339
Asp Tyr Phe Thr Gly Glu Thr  Tyr Val Gly Glu Val  Lys Asp Gly
    1100                1105                1110 gta gca aca ttc cat att cat  act tca att aat ccg  gat cct caa        3384
Val Ala Thr Phe His Ile His  Thr Ser Ile Asn Pro  Asp Pro Gln
1115                1120                1125 acg ggt att aat cgt cga gcc  ctt tta caa ggt tgg  gtt gaa att        3429
Thr Gly Ile Asn Arg Arg Ala  Leu Leu Gln Gly Trp  Val Glu Ile
        1130                1135                1140 gat gga cca act tat aat gct  aag caa gta aca gat  ccg act gcc        3474
Asp Gly Pro Thr Tyr Asn Ala  Lys Gln Val Thr Asp  Pro Thr Ala
    1145                1150                1155 att agt gat aga aat tat att  ggt gtt tat tac aaa  cca gat gct        3519
Ile Ser Asp Arg Asn Tyr Ile  Gly Val Tyr Tyr Lys  Pro Asp Ala
1160                1165                1170 tca tct cat gtt tat agt aat  cgt gat gag cta ggc  gta gat gat        3564
Ser Ser His Val Tyr Ser Asn  Arg Asp Glu Leu Gly  Val Asp Asp
        1175                1180                1185 ttt act gat gaa caa gca gat  gtg tcg gat ttt gga  cca agt aaa        3609
Phe Thr Asp Glu Gln Ala Asp  Val Ser Asp Phe Gly  Pro Ser Lys
    1190                1195                1200 ttc ctg tat cca ggc cac aat  gcc cca agt gat ggt  aat gca aat        3654
Phe Leu Tyr Pro Gly His Asn  Ala Pro Ser Asp Gly  Asn Ala Asn
```

-continued

|     |     |     |     |     |     |     |     |     |     |     |     |     |     |     |     |
| --- | --- | --- | --- | --- | --- | --- | --- | --- | --- | --- | --- | --- | --- | --- | --- |
|     |     | 1205 |     |     |     | 1210 |     |     |     | 1215 |     |     |     |     |     |
| att | tca | ttt | gat | tat | gta | aat | gat | aat | aat | ata | agt | acg | ttt | gga | 3699 |
| Ile | Ser | Phe | Asp | Tyr | Val | Asn | Asp | Asn | Asn | Ile | Ser | Thr | Phe | Gly |     |
|     | 1220 |     |     |     | 1225 |     |     |     |     | 1230 |     |     |     |     |     |
| caa | gaa | gca | gtt | aaa | gca | ggt | tat | tat | gat | cct | att | gct | aaa | gta | 3744 |
| Gln | Glu | Ala | Val | Lys | Ala | Gly | Tyr | Tyr | Asp | Pro | Ile | Ala | Lys | Val |     |
|     | 1235 |     |     |     | 1240 |     |     |     |     | 1245 |     |     |     |     |     |
| ttc | act | att | aca | ggt | cat | gta | gat | aaa | gat | gta | gtt | agt | ttg | gtt | 3789 |
| Phe | Thr | Ile | Thr | Gly | His | Val | Asp | Lys | Asp | Val | Val | Ser | Leu | Val |     |
|     | 1250 |     |     |     | 1255 |     |     |     |     | 1260 |     |     |     |     |     |
| gct | tta | caa | gat | aat | cca | aat | gaa | gat | gca | cct | gaa | aat | cgg | gtt | 3834 |
| Ala | Leu | Gln | Asp | Asn | Pro | Asn | Glu | Asp | Ala | Pro | Glu | Asn | Arg | Val |     |
|     | 1265 |     |     |     | 1270 |     |     |     |     | 1275 |     |     |     |     |     |
| gca | att | gat | aaa | gat | ggt | aat | ttt | ata | att | aaa | ttc | cac | atg | gat | 3879 |
| Ala | Ile | Asp | Lys | Asp | Gly | Asn | Phe | Ile | Ile | Lys | Phe | His | Met | Asp |     |
|     | 1280 |     |     |     | 1285 |     |     |     |     | 1290 |     |     |     |     |     |
| gat | ccg | tct | aca | aga | caa | ctt | act | tat | att | tat | aag | gta | aag | gat | 3924 |
| Asp | Pro | Ser | Thr | Arg | Gln | Leu | Thr | Tyr | Ile | Tyr | Lys | Val | Lys | Asp |     |
|     | 1295 |     |     |     | 1300 |     |     |     |     | 1305 |     |     |     |     |     |
| tca | tca | aca | gat | aag | att | gat | acg | gtt | aaa | ggt | tcg | att | act | ctt | 3969 |
| Ser | Ser | Thr | Asp | Lys | Ile | Asp | Thr | Val | Lys | Gly | Ser | Ile | Thr | Leu |     |
|     | 1310 |     |     |     | 1315 |     |     |     |     | 1320 |     |     |     |     |     |
| att | ctt | gat | aca | gtt | ttg | cca | act | ttg | cat | gtt | gat | caa | tta | aat | 4014 |
| Ile | Leu | Asp | Thr | Val | Leu | Pro | Thr | Leu | His | Val | Asp | Gln | Leu | Asn |     |
|     | 1325 |     |     |     | 1330 |     |     |     |     | 1335 |     |     |     |     |     |
| ggt | gct | gac | aac | tta | aca | att | aca | act | aat | aat | cca | aca | ttt | aaa | 4059 |
| Gly | Ala | Asp | Asn | Leu | Thr | Ile | Thr | Thr | Asn | Asn | Pro | Thr | Phe | Lys |     |
|     | 1340 |     |     |     | 1345 |     |     |     |     | 1350 |     |     |     |     |     |
| att | tct | ggt | aat | gct | aac | gat | gac | ttg | gat | gac | tat | agt | gta | tac | 4104 |
| Ile | Ser | Gly | Asn | Ala | Asn | Asp | Asp | Leu | Asp | Asp | Tyr | Ser | Val | Tyr |     |
|     | 1355 |     |     |     | 1360 |     |     |     |     | 1365 |     |     |     |     |     |
| att | aat | ggt | gat | aat | gta | ttt | act | caa | ttt | aat | ggt | tca | agc | ttc | 4149 |
| Ile | Asn | Gly | Asp | Asn | Val | Phe | Thr | Gln | Phe | Asn | Gly | Ser | Ser | Phe |     |
|     | 1370 |     |     |     | 1375 |     |     |     |     | 1380 |     |     |     |     |     |
| aat | tat | att | cca | gga | atg | tat | ggt | gac | cca | aat | caa | aaa | aca | cct | 4194 |
| Asn | Tyr | Ile | Pro | Gly | Met | Tyr | Gly | Asp | Pro | Asn | Gln | Lys | Thr | Pro |     |
|     | 1385 |     |     |     | 1390 |     |     |     |     | 1395 |     |     |     |     |     |
| aac | tta | tat | gga | ggc | tat | gac | ttt | gag | caa | gaa | gta | aat | ctt | gat | 4239 |
| Asn | Leu | Tyr | Gly | Gly | Tyr | Asp | Phe | Glu | Gln | Glu | Val | Asn | Leu | Asp |     |
|     | 1400 |     |     |     | 1405 |     |     |     |     | 1410 |     |     |     |     |     |
| gat | gag | aat | gga | aag | cca | act | aca | cat | atc | ttt | aat | att | gaa | tta | 4284 |
| Asp | Glu | Asn | Gly | Lys | Pro | Thr | Thr | His | Ile | Phe | Asn | Ile | Glu | Leu |     |
|     | 1415 |     |     |     | 1420 |     |     |     |     | 1425 |     |     |     |     |     |
| att | gat | caa | gtg | ggt | aat | aaa | gta | ttc | aaa | act | tta | acg | gtc | aac | 4329 |
| Ile | Asp | Gln | Val | Gly | Asn | Lys | Val | Phe | Lys | Thr | Leu | Thr | Val | Asn |     |
|     | 1430 |     |     |     | 1435 |     |     |     |     | 1440 |     |     |     |     |     |
| tac | gat | cca | aat | gcc | act | aac | tct | gaa | gac | cca | agt | aac | ggt | aca | 4374 |
| Tyr | Asp | Pro | Asn | Ala | Thr | Asn | Ser | Glu | Asp | Pro | Ser | Asn | Gly | Thr |     |
|     | 1445 |     |     |     | 1450 |     |     |     |     | 1455 |     |     |     |     |     |
| ggt | gac | agt | gga | att | gaa | gtt | gtt | cca | act | gta | cca | aga | aaa | gtt | 4419 |
| Gly | Asp | Ser | Gly | Ile | Glu | Val | Val | Pro | Thr | Val | Pro | Arg | Lys | Val |     |
|     | 1460 |     |     |     | 1465 |     |     |     |     | 1470 |     |     |     |     |     |
| caa | cct | ctt | tcg | gat | gat | aat | tca | act | aac | att | aat | gat | aag | caa | 4464 |
| Gln | Pro | Leu | Ser | Asp | Asp | Asn | Ser | Thr | Asn | Ile | Asn | Asp | Lys | Gln |     |
|     | 1475 |     |     |     | 1480 |     |     |     |     | 1485 |     |     |     |     |     |
| act | tta | tct | act | gaa | tta | acg | att | act | ttg | cca | aga | aat | atc | ttt | 4509 |
| Thr | Leu | Ser | Thr | Glu | Leu | Thr | Ile | Thr | Leu | Pro | Arg | Asn | Ile | Phe |     |
|     | 1490 |     |     |     | 1495 |     |     |     |     | 1500 |     |     |     |     |     |
| gca | ttt | gat | tat | caa | ggt | aaa | gta | gcc | aga | aaa | cat | ggt | aaa | gat | 4554 |

-continued

```
Ala Phe Asp Tyr Gln Gly Lys Val Ala Arg Lys His Gly Lys Asp
    1505                1510                1515 att att ttg aag aag ggc gtt gtt tta tac aat cct aaa gaa gta      4599
Ile Ile Leu Lys Lys Gly Val Val Leu Tyr Asn Pro Lys Glu Val
    1520                1525                1530 aat att aga aaa cat aaa tat tat aaa gta agt aag aat gtc tac      4644
Asn Ile Arg Lys His Lys Tyr Tyr Lys Val Ser Lys Asn Val Tyr
    1535                1540                1545 att aag gtg aca tca acg aga gta aat aaa aaa ctt aag cga ctt      4689
Ile Lys Val Thr Ser Thr Arg Val Asn Lys Lys Leu Lys Arg Leu
    1550                1555                1560 att ttg atc aag aat tct tat gtt tat aat tta aac gga aaa gca      4734
Ile Leu Ile Lys Asn Ser Tyr Val Tyr Asn Leu Asn Gly Lys Ala
    1565                1570                1575 aat aaa gtt cat aat aaa cgt gtt cta ctt aag cgg gga tta gcc      4779
Asn Lys Val His Asn Lys Arg Val Leu Leu Lys Arg Gly Leu Ala
    1580                1585                1590 gtt gat gtc tta cat ggt ggt aag att act aaa gta ggc aaa tat      4824
Val Asp Val Leu His Gly Gly Lys Ile Thr Lys Val Gly Lys Tyr
    1595                1600                1605 gat tgt tat caa att ggt atc aat caa tac att aaa gta gct aat      4869
Asp Cys Tyr Gln Ile Gly Ile Asn Gln Tyr Ile Lys Val Ala Asn
    1610                1615                1620 aca gct ttg aaa                                                  4881
Thr Ala Leu Lys
    1625

<210> SEQ ID NO 52
<211> LENGTH: 1627
<212> TYPE: PRT
<213> ORGANISM: Lactobacillus acidophilus

<400> SEQUENCE: 52

Met Arg Asn Lys Lys Val Gly Ser Val Thr Thr Asp Tyr Ser Tyr Leu
1               5                   10                  15

Asn Gln Ser Arg Asn His Leu Asn Leu Val Thr Gly Lys Glu Asn Asp
            20                  25                  30

Ser Lys Leu Lys Ile Trp Arg Lys Asn Phe Ala Thr Ala Ala Ile Ile
        35                  40                  45

Ala Leu Ala Ser Gly Thr Thr Met Leu Phe Ser Ala His Ser Val Lys
    50                  55                  60

Ala Asp Glu Val Asp Asp Ile Thr Val Gln Asn Asp Lys Gln Val Asn
65                  70                  75                  80

Thr Thr Ile Val Gln Asn Asn Lys Asp Gln Gln Ser Ser Asp Thr Gln
                85                  90                  95

Gln Asn Val Asn Glu Asn Arg Ala Ser Ser Gln Gln Ala Ile Arg Arg
            100                 105                 110

Pro Gly Thr Gly Asn Lys Leu Thr Asp Gln Trp Pro Asp Asn Tyr Gln
        115                 120                 125

Ser Asp Gln Gln Asn Asn Ser Ser Gln Ala Glu Thr Thr Lys Ile Ser
    130                 135                 140

Thr Thr Gly Tyr Ser Asn Gln Thr Glu Gln Gln Ser Asn Asn Thr Val
145                 150                 155                 160

Pro Ser Thr Val Ala Ser Ser Thr Val Tyr Lys Glu Ser Ser Asp Asp
                165                 170                 175

Gln Ala Gly Gln Lys Asp Thr Asn Gly Val Glu Leu Pro Ala Asn Asn
            180                 185                 190
```

-continued

```
Gln Asp His Ile Lys Gly Asn Val Gln Asp Ala Trp Asp Gln Gly Tyr
        195                 200                 205
Lys Gly Gln His Thr Val Val Ala Val Ile Asp Ser Gly Val Asp Thr
    210                 215                 220
Ser His Lys Asp Phe Gln Thr Met Pro Glu Asn Pro Lys Leu Ser Gln
225                 230                 235                 240
Ala Glu Ile Glu Ala Leu Ile Ala Lys Leu Gly Tyr Gly Thr Tyr Ile
                245                 250                 255
Asn Ser Lys Phe Pro Phe Val Tyr Asn Ala Val Asp His Glu Asn Gln
            260                 265                 270
Ser Met Lys Gly Pro Asp Gly Glu Pro His Gly Gln His Val Ser Gly
        275                 280                 285
Ile Ile Ala Ala Asp Gly Gln Pro Asn Gly Asp Gln Glu Tyr Val Val
    290                 295                 300
Gly Val Ala Pro Glu Ala Gln Leu Met His Phe Lys Val Phe Gly Asp
305                 310                 315                 320
Asn Ala Thr Ser Leu Asp Leu Ala Gln Glu Ile Tyr Asp Ala Thr Asn
                325                 330                 335
Leu Gly Ala Asp Val Ile Gln Met Ser Leu Gly Gly Val Ala Ala
            340                 345                 350
Ala Asp Leu Asn Val Ala Asp Gln Arg Ala Val Gln Tyr Ala Ile Asp
        355                 360                 365
His Gly Val Ile Val Ser Ile Ser Ala Ser Asn Asn Gly Asn Ala Ala
    370                 375                 380
Ser Ile Gln Asn Pro Ser Asn Val Thr Asp Leu Asp Asn Tyr Glu Ala
385                 390                 395                 400
Gly Thr His Val Gly Asn Tyr Glu Pro Phe Ser Ser Thr Val Ala
                405                 410                 415
Asp Pro Gly Ala Ala Arg Gly Ala Ile Thr Gly Ala Ala Glu Thr Ser
            420                 425                 430
Gly Leu Gly Asp Lys Ser Asp Met Ala Thr Phe Thr Ser Trp Gly Pro
        435                 440                 445
Leu Pro Asp Phe Thr Leu Lys Pro Asp Val Ser Ala Pro Gly Ser Asn
    450                 455                 460
Val Ile Ser Leu Ala Asn Asp Asn Gly Tyr Thr Thr Met Ser Gly Thr
465                 470                 475                 480
Ser Met Ala Gly Pro Phe Ile Ala Gly Ala Ala Leu Val Arg Gln
                485                 490                 495
Arg Leu Gln Gln Thr Asn Pro Glu Leu Lys Gly Ala Asp Leu Val Ala
            500                 505                 510
Ala Val Lys Ala Leu Leu Met Asn Thr Ala Asp Pro Gln Ile Gln Gln
        515                 520                 525
Gly Phe Thr Thr Ile Val Ser Pro Arg Arg Gln Gly Ala Gly Gln Ile
    530                 535                 540
Asn Val Gly Ala Ala Thr Lys Ala Pro Val Tyr Ile Leu Ala Asn Asp
545                 550                 555                 560
Gly Thr Gly Ser Val Ser Leu Arg Asn Ile Lys Glu Thr Thr Asn Phe
                565                 570                 575
Glu Leu Thr Phe His Asn Leu Thr Asp Asn Thr Glu Tyr Thr Phe
            580                 585                 590
Asp Asp Leu Gly Gly Gly Phe Thr Glu Val Arg Asp Thr Asp Thr Gly
        595                 600                 605
Leu Phe His Asp Val Gln Leu Ala Gly Ala Arg Val Thr Gly Pro Asn
```

-continued

```
            610                 615                 620
Thr Ile Thr Val Asn Pro Lys Glu Thr Lys Ile Val Phe Thr Leu
625                 630                 635                 640

Asn Leu Thr Gly Leu Lys Gln Asn Gln Leu Val Glu Gly Tyr Leu Asn
                645                 650                 655

Phe Thr Asn Ser Lys Asp Lys Leu Ser Leu Ser Val Pro Tyr Leu Gly
                660                 665                 670

Tyr Tyr Gly Asp Met Thr Ser Glu Asp Val Phe Asp Lys Ala Asn
                675                 680                 685

Glu Asp Lys Pro Asp Ile Lys Gly Asn Arg Leu Thr Asn Glu Asp Asn
690                 695                 700

Tyr Pro Arg Gly Ile Ala Asp Glu Glu Ser Leu Lys Glu Leu Val Asn
705                 710                 715                 720

Ile Glu Gly Asn Tyr Asn Trp Gln Glu Val Ala Lys Leu Tyr Glu Ser
                725                 730                 735

Gly Lys Val Ala Phe Ser Pro Asn Gly Asp Asn Lys Ser Asp Leu Ile
                740                 745                 750

Met Pro Tyr Val Tyr Leu Lys Gln Asn Leu Gln Asp Leu Lys Val Glu
                755                 760                 765

Ile Leu Asp Ala Lys Gly Asn Val Val Arg Val Leu Ala Asp Ala His
770                 775                 780

Gly Val Gln Lys Ser Tyr Asn Glu Asp Gly Thr Gly Thr Val Asp Ala
785                 790                 795                 800

Leu Ile Ser Val Asp Ser Gly Lys Phe Asn Trp Asp Gly Lys Val Tyr
                805                 810                 815

Asn Tyr Lys Thr Gly Lys Met Glu Val Ala Pro Asp Gly Gln Tyr Thr
                820                 825                 830

Tyr Arg Phe Val Ala Thr Leu Tyr Asn Asp Gly Pro His Lys Val Gln
                835                 840                 845

Thr Asn Asp Thr Ser Val Ile Ile Asp Thr Thr Ala Pro Ile Leu Lys
                850                 855                 860

Asp Val Glu Tyr Asp Val Thr Thr Lys Thr Ile Thr Gly Thr Tyr Ser
865                 870                 875                 880

Asp Ala Gly Ala Gly Phe Thr Asp Tyr Ser Tyr Ala Thr Val Thr Ile
                885                 890                 895

Asn Asp Arg Val Phe Gly Phe Lys Leu Asn Asp Asn Asp Asn Ser Thr
                900                 905                 910

Phe Asp Asn Thr Asp Lys Thr Ile Gly His Phe Ser Phe Ala Leu Thr
                915                 920                 925

Pro Leu Glu Gln Gln Ala Leu Thr Ala Ala His Asn Lys Val Ser Val
                930                 935                 940

Cys Leu Ser Asp Val Ala Asp Asn Thr Ala Val Lys Thr Leu Asp Val
945                 950                 955                 960

Ala Ser Val Gly Asp Gly Asn Lys Ile Ala Ile Trp Asn Ala Val Asn
                965                 970                 975

Gly Val Pro Phe Asn Ser Asn Ser Gln Asp Tyr Ser Lys Asn Asn
                980                 985                 990

Ser Tyr Leu Leu Arg Gly Ser Ala Thr Glu Asn Phe Tyr Val Asn Gly
                995                 1000                1005

Lys Leu Val Gln Val Ala Pro Asn Gly Glu Phe Val Leu Pro Val
                1010                1015                1020

Ser Leu Asp Glu Gln Asn Leu Val Phe Thr Ser Asp Glu Asn Gly
                1025                1030                1035
```

-continued

```
Gln Asn Val Leu Arg Gln Phe Thr Thr Tyr Thr Pro Lys Ala Asp
    1040                1045                1050

Phe Ala Trp Gln His Ile Asp Gly Ser Glu Arg Ser Phe Gly Val
    1055                1060                1065

Ser Val Tyr Ser Ile Asp Ala Ala Asp Pro Asn Asp Ala Ile Val
    1070                1075                1080

Gln Ala Ala Val Pro Lys Gly Asn Asn Val Lys Ala Phe Ala Lys
    1085                1090                1095

Asp Tyr Phe Thr Gly Glu Thr Tyr Val Gly Glu Val Lys Asp Gly
    1100                1105                1110

Val Ala Thr Phe His Ile His Thr Ser Ile Asn Pro Asp Pro Gln
    1115                1120                1125

Thr Gly Ile Asn Arg Arg Ala Leu Leu Gln Gly Trp Val Glu Ile
    1130                1135                1140

Asp Gly Pro Thr Tyr Asn Ala Lys Gln Val Thr Asp Pro Thr Ala
    1145                1150                1155

Ile Ser Asp Arg Asn Tyr Ile Gly Val Tyr Tyr Lys Pro Asp Ala
    1160                1165                1170

Ser Ser His Val Tyr Ser Asn Arg Asp Glu Leu Gly Val Asp Asp
    1175                1180                1185

Phe Thr Asp Glu Gln Ala Asp Val Ser Asp Phe Gly Pro Ser Lys
    1190                1195                1200

Phe Leu Tyr Pro Gly His Asn Ala Pro Ser Asp Gly Asn Ala Asn
    1205                1210                1215

Ile Ser Phe Asp Tyr Val Asn Asp Asn Asn Ile Ser Thr Phe Gly
    1220                1225                1230

Gln Glu Ala Val Lys Ala Gly Tyr Tyr Asp Pro Ile Ala Lys Val
    1235                1240                1245

Phe Thr Ile Thr Gly His Val Asp Lys Asp Val Val Ser Leu Val
    1250                1255                1260

Ala Leu Gln Asp Asn Pro Asn Glu Asp Ala Pro Glu Asn Arg Val
    1265                1270                1275

Ala Ile Asp Lys Asp Gly Asn Phe Ile Ile Lys Phe His Met Asp
    1280                1285                1290

Asp Pro Ser Thr Arg Gln Leu Thr Tyr Ile Tyr Lys Val Lys Asp
    1295                1300                1305

Ser Ser Thr Asp Lys Ile Asp Thr Val Lys Gly Ser Ile Thr Leu
    1310                1315                1320

Ile Leu Asp Thr Val Leu Pro Thr Leu His Val Asp Gln Leu Asn
    1325                1330                1335

Gly Ala Asp Asn Leu Thr Ile Thr Thr Asn Asn Pro Thr Phe Lys
    1340                1345                1350

Ile Ser Gly Asn Ala Asn Asp Asp Leu Asp Tyr Ser Val Tyr
    1355                1360                1365

Ile Asn Gly Asp Asn Val Phe Thr Gln Phe Asn Gly Ser Ser Phe
    1370                1375                1380

Asn Tyr Ile Pro Gly Met Tyr Gly Asp Pro Asn Gln Lys Thr Pro
    1385                1390                1395

Asn Leu Tyr Gly Gly Tyr Asp Phe Glu Gln Glu Val Asn Leu Asp
    1400                1405                1410

Asp Glu Asn Gly Lys Pro Thr Thr His Ile Phe Asn Ile Glu Leu
    1415                1420                1425
```

-continued

```
Ile Asp Gln Val Gly Asn Lys Val Phe Lys Thr Leu Thr Val Asn
    1430                1435                1440

Tyr Asp Pro Asn Ala Thr Asn Ser Glu Asp Pro Ser Asn Gly Thr
    1445                1450                1455

Gly Asp Ser Gly Ile Glu Val Val Pro Thr Val Pro Arg Lys Val
    1460                1465                1470

Gln Pro Leu Ser Asp Asp Asn Ser Thr Asn Ile Asn Asp Lys Gln
    1475                1480                1485

Thr Leu Ser Thr Glu Leu Thr Ile Thr Leu Pro Arg Asn Ile Phe
    1490                1495                1500

Ala Phe Asp Tyr Gln Gly Lys Val Ala Arg Lys His Gly Lys Asp
    1505                1510                1515

Ile Ile Leu Lys Lys Gly Val Val Leu Tyr Asn Pro Lys Glu Val
    1520                1525                1530

Asn Ile Arg Lys His Lys Tyr Tyr Lys Val Ser Lys Asn Val Tyr
    1535                1540                1545

Ile Lys Val Thr Ser Thr Arg Val Asn Lys Lys Leu Lys Arg Leu
    1550                1555                1560

Ile Leu Ile Lys Asn Ser Tyr Val Tyr Asn Leu Asn Gly Lys Ala
    1565                1570                1575

Asn Lys Val His Asn Lys Arg Val Leu Leu Lys Arg Gly Leu Ala
    1580                1585                1590

Val Asp Val Leu His Gly Gly Lys Ile Thr Lys Val Gly Lys Tyr
    1595                1600                1605

Asp Cys Tyr Gln Ile Gly Ile Asn Gln Tyr Ile Lys Val Ala Asn
    1610                1615                1620

Thr Ala Leu Lys
    1625
```

```
<210> SEQ ID NO 53
<211> LENGTH: 1281
<212> TYPE: DNA
<213> ORGANISM: Lactobacillus acidophilus
<220> FEATURE:
<221> NAME/KEY: CDS
<222> LOCATION: (1)..(1281)
<223> OTHER INFORMATION: Peptidase T ORF# 1515

<400> SEQUENCE: 53
```

```
atg gct ttt tat gat ttg aaa tat tta gaa gac act ttt att cat tat      48
Met Ala Phe Tyr Asp Leu Lys Tyr Leu Glu Asp Thr Phe Ile His Tyr
1               5                   10                  15 gtt aag caa aat act aga tct tat gaa gaa aat cat gat cag gtt ccc      96
Val Lys Gln Asn Thr Arg Ser Tyr Glu Glu Asn His Asp Gln Val Pro
            20                  25                  30 tca tca cct aat caa gtt aag atg gga aaa gaa ctt gcg aaa gct cta    144
Ser Ser Pro Asn Gln Val Lys Met Gly Lys Glu Leu Ala Lys Ala Leu
        35                  40                  45 aaa gaa ata ggt ctt gtt gca tat tat aat gaa aaa aat ggt ttt gcc    192
Lys Glu Ile Gly Leu Val Ala Tyr Tyr Asn Glu Lys Asn Gly Phe Ala
    50                  55                  60 att ggg tat tta aag aaa aat gtt gaa gac gat gta aca ccg att ggc    240
Ile Gly Tyr Leu Lys Lys Asn Val Glu Asp Asp Val Thr Pro Ile Gly
65                  70                  75                  80 ttt ttc tca cat att gat acg gct gat ttc aat gcc gaa aat att aag    288
Phe Phe Ser His Ile Asp Thr Ala Asp Phe Asn Ala Glu Asn Ile Lys
                85                  90                  95 cct caa att cat cgc aat tat gat ggt aag agg att gct tta gat aaa    336
```

```
                Pro Gln Ile His Arg Asn Tyr Asp Gly Lys Arg Ile Ala Leu Asp Lys
                                100                 105                 110 gag aat aat att tat ctt gat ccc aaa gaa ttc cct gcc ttg gct agt              384
Glu Asn Asn Ile Tyr Leu Asp Pro Lys Glu Phe Pro Ala Leu Ala Ser
            115                 120                 125 tgt aaa ggc gaa act ttg att act tct gat ggt cac act ttg ctt gga              432
Cys Lys Gly Glu Thr Leu Ile Thr Ser Asp Gly His Thr Leu Leu Gly
130                 135                 140 aca gat gat aaa gca ggg att gtt ggg att tta ggg atg ctt aag tat              480
Thr Asp Asp Lys Ala Gly Ile Val Gly Ile Leu Gly Met Leu Lys Tyr
145                 150                 155                 160 ttg agc gaa cat cct gag att gag cat ggt gat att tat att ggc ttt              528
Leu Ser Glu His Pro Glu Ile Glu His Gly Asp Ile Tyr Ile Gly Phe
                165                 170                 175 ggt cca gat gaa gaa att gga tat ggt ggt caa aga ttt gat ccc caa              576
Gly Pro Asp Glu Glu Ile Gly Tyr Gly Gly Gln Arg Phe Asp Pro Gln
            180                 185                 190 gat ttt cct ggt gtc gaa tta gcc tat act tta gaa aat gga cga cca              624
Asp Phe Pro Gly Val Glu Leu Ala Tyr Thr Leu Glu Asn Gly Arg Pro
        195                 200                 205 ggt gac ttt gaa tat gag act ttt aat gca act gaa gca caa att cac              672
Gly Asp Phe Glu Tyr Glu Thr Phe Asn Ala Thr Glu Ala Gln Ile His
    210                 215                 220 att cgc ggt acg gtc gtt cat cca ggt gag gcg tat ggc tta atg gtg              720
Ile Arg Gly Thr Val Val His Pro Gly Glu Ala Tyr Gly Leu Met Val
225                 230                 235                 240 aat gcg acc agc cta atg aac gaa ttt ttg aat caa ttg cca aaa gat              768
Asn Ala Thr Ser Leu Met Asn Glu Phe Leu Asn Gln Leu Pro Lys Asp
                245                 250                 255 gaa gtt ccg gaa aaa tct aaa aat cat gat ggc ttt att ttg gta tta              816
Glu Val Pro Glu Lys Ser Lys Asn His Asp Gly Phe Ile Leu Val Leu
            260                 265                 270 aat gcc gca ggt tca gta gat cat gca gat att agt tta att att agg              864
Asn Ala Ala Gly Ser Val Asp His Ala Asp Ile Ser Leu Ile Ile Arg
        275                 280                 285 gat ttt gac tgg gat aaa ttt acc gct aaa gag caa cta att gag gaa              912
Asp Phe Asp Trp Asp Lys Phe Thr Ala Lys Glu Gln Leu Ile Glu Glu
    290                 295                 300 att gtt gca aaa ctt aat cag aaa tat ggc gaa cgt ttt tca tta aag              960
Ile Val Ala Lys Leu Asn Gln Lys Tyr Gly Glu Arg Phe Ser Leu Lys
305                 310                 315                 320 atg cgt cgg caa tat gaa aat atc tat aat gtg att aaa gac aag cct             1008
Met Arg Arg Gln Tyr Glu Asn Ile Tyr Asn Val Ile Lys Asp Lys Pro
                325                 330                 335 tat gtg gtt aat cta gct ctt gat gcg tat aaa aag ttg ggg att aag             1056
Tyr Val Val Asn Leu Ala Leu Asp Ala Tyr Lys Lys Leu Gly Ile Lys
            340                 345                 350 cct cac att caa aca ttt aga ggt gga aca gat ggt aac ttt atc acg             1104
Pro His Ile Gln Thr Phe Arg Gly Gly Thr Asp Gly Asn Phe Ile Thr
        355                 360                 365 caa aaa ggt atc cca act cct aat tta ttc aat ggt ggt ggg aat tat             1152
Gln Lys Gly Ile Pro Thr Pro Asn Leu Phe Asn Gly Gly Gly Asn Tyr
    370                 375                 380 cat ggt cgc tat gaa tat gca act gtt gag caa ata gat aag tta gcg             1200
His Gly Arg Tyr Glu Tyr Ala Thr Val Glu Gln Ile Asp Lys Leu Ala
385                 390                 395                 400 gaa gta tta act gaa att gtc aaa gaa cat tta tat caa acg cgt cat             1248
Glu Val Leu Thr Glu Ile Val Lys Glu His Leu Tyr Gln Thr Arg His
                405                 410                 415
```

```
gga cgt aat aat tca cca ttg atc aaa tat tgg                    1281
Gly Arg Asn Asn Ser Pro Leu Ile Lys Tyr Trp
            420                 425
```

<210> SEQ ID NO 54
<211> LENGTH: 427
<212> TYPE: PRT
<213> ORGANISM: Lactobacillus acidophilus

<400> SEQUENCE: 54

```
Met Ala Phe Tyr Asp Leu Lys Tyr Leu Glu Asp Thr Phe Ile His Tyr
1               5                   10                  15

Val Lys Gln Asn Thr Arg Ser Tyr Glu Glu Asn His Asp Gln Val Pro
            20                  25                  30

Ser Ser Pro Asn Gln Val Lys Met Gly Lys Glu Leu Ala Lys Ala Leu
        35                  40                  45

Lys Glu Ile Gly Leu Val Ala Tyr Tyr Asn Glu Lys Asn Gly Phe Ala
    50                  55                  60

Ile Gly Tyr Leu Lys Lys Asn Val Glu Asp Val Thr Pro Ile Gly
65                  70                  75                  80

Phe Phe Ser His Ile Asp Thr Ala Asp Phe Asn Ala Glu Asn Ile Lys
                85                  90                  95

Pro Gln Ile His Arg Asn Tyr Asp Gly Lys Arg Ile Ala Leu Asp Lys
            100                 105                 110

Glu Asn Asn Ile Tyr Leu Asp Pro Lys Glu Phe Pro Ala Leu Ala Ser
        115                 120                 125

Cys Lys Gly Glu Thr Leu Ile Thr Ser Asp Gly His Thr Leu Leu Gly
    130                 135                 140

Thr Asp Asp Lys Ala Gly Ile Val Gly Ile Leu Gly Met Leu Lys Tyr
145                 150                 155                 160

Leu Ser Glu His Pro Glu Ile Glu His Gly Asp Ile Tyr Ile Gly Phe
                165                 170                 175

Gly Pro Asp Glu Glu Ile Gly Tyr Gly Gly Gln Arg Phe Asp Pro Gln
            180                 185                 190

Asp Phe Pro Gly Val Glu Leu Ala Tyr Thr Leu Glu Asn Gly Arg Pro
        195                 200                 205

Gly Asp Phe Glu Tyr Glu Thr Phe Asn Ala Thr Glu Ala Gln Ile His
    210                 215                 220

Ile Arg Gly Thr Val Val His Pro Gly Glu Ala Tyr Gly Leu Met Val
225                 230                 235                 240

Asn Ala Thr Ser Leu Met Asn Glu Phe Leu Asn Gln Leu Pro Lys Asp
                245                 250                 255

Glu Val Pro Glu Lys Ser Lys Asn His Asp Gly Phe Ile Leu Val Leu
            260                 265                 270

Asn Ala Ala Gly Ser Val Asp His Ala Asp Ile Ser Leu Ile Ile Arg
        275                 280                 285

Asp Phe Asp Trp Asp Lys Phe Thr Ala Lys Glu Gln Leu Ile Glu Glu
    290                 295                 300

Ile Val Ala Lys Leu Asn Gln Lys Tyr Gly Glu Arg Phe Ser Leu Lys
305                 310                 315                 320

Met Arg Arg Gln Tyr Glu Asn Ile Tyr Asn Val Ile Lys Asp Lys Pro
                325                 330                 335

Tyr Val Val Asn Leu Ala Leu Asp Ala Tyr Lys Lys Leu Gly Ile Lys
            340                 345                 350

Pro His Ile Gln Thr Phe Arg Gly Gly Thr Asp Gly Asn Phe Ile Thr
```

-continued

```
                    355                 360                 365
Gln Lys Gly Ile Pro Thr Pro Asn Leu Phe Asn Gly Gly Asn Tyr
        370                 375                 380

His Gly Arg Tyr Glu Tyr Ala Thr Val Glu Gln Ile Asp Lys Leu Ala
385                 390                 395                 400

Glu Val Leu Thr Glu Ile Val Lys Glu His Leu Tyr Gln Thr Arg His
                405                 410                 415

Gly Arg Asn Asn Ser Pro Leu Ile Lys Tyr Trp
            420                 425

<210> SEQ ID NO 55
<211> LENGTH: 1530
<212> TYPE: DNA
<213> ORGANISM: Lactobacillus acidophilus
<220> FEATURE:
<221> NAME/KEY: CDS
<222> LOCATION: (1)..(1530)
<223> OTHER INFORMATION: Aminopeptidase ORF# 1567

<400> SEQUENCE: 55 ttg gag gta aaa cgt atg aaa aaa aga aca aca ctt tta tta tca agt      48
Leu Glu Val Lys Arg Met Lys Lys Arg Thr Thr Leu Leu Leu Ser Ser
1               5                   10                  15 gca ata aca att gca gca tta ttt agt ttt aat tca aag gct cag gcc      96
Ala Ile Thr Ile Ala Ala Leu Phe Ser Phe Asn Ser Lys Ala Gln Ala
            20                  25                  30 gct gcc gat ccc gca gtc aaa gca acc aac tac aat atg act gta aaa    144
Ala Ala Asp Pro Ala Val Lys Ala Thr Asn Tyr Asn Met Thr Val Lys
        35                  40                  45 cta aat act cgc aaa aat caa cta acc gaa aaa gtt acc atg cat gtc    192
Leu Asn Thr Arg Lys Asn Gln Leu Thr Glu Lys Val Thr Met His Val
    50                  55                  60 gtt aat aac ggc aat gaa cca gtt aag aac tta ctg atc aga aat att    240
Val Asn Asn Gly Asn Glu Pro Val Lys Asn Leu Leu Ile Arg Asn Ile
65                  70                  75                  80 gct aat ggt gtt tta aag tat gac cat cag cat ttt aaa att gcc aaa    288
Ala Asn Gly Val Leu Lys Tyr Asp His Gln His Phe Lys Ile Ala Lys
                85                  90                  95 aat gca aaa act aca gtt aaa agt att tcc tca gct gga gaa aat ctt    336
Asn Ala Lys Thr Thr Val Lys Ser Ile Ser Ser Ala Gly Glu Asn Leu
            100                 105                 110 tcc tat acc act ggc aaa gat aag agc aac cta ttc gtt gat aaa agc    384
Ser Tyr Thr Thr Gly Lys Asp Lys Ser Asn Leu Phe Val Asp Lys Ser
        115                 120                 125 tta aat gca ggt gaa tct acc gac tta act gtt aat gta gtc acc agc    432
Leu Asn Ala Gly Glu Ser Thr Asp Leu Thr Val Asn Val Val Thr Ser
    130                 135                 140 gtt ccc aaa aga caa gat cgt ttt ggc tac caa aat att aat ggc ggt    480
Val Pro Lys Arg Gln Asp Arg Phe Gly Tyr Gln Asn Ile Asn Gly Gly
145                 150                 155                 160 aaa gtt tat aac tta tcc ttc tgt ttt cct tac cta agc gat tat cgc    528
Lys Val Tyr Asn Leu Ser Phe Cys Phe Pro Tyr Leu Ser Asp Tyr Arg
                165                 170                 175 aac gga aaa tgg aat tac cat cca tat tat gac ggt ggt gaa aac cgt    576
Asn Gly Lys Trp Asn Tyr His Pro Tyr Tyr Asp Gly Gly Glu Asn Arg
            180                 185                 190 aat acc act gtc agc aat ttt cat gtt agc ttt tat gca cca aag agt    624
Asn Thr Thr Val Ser Asn Phe His Val Ser Phe Tyr Ala Pro Lys Ser
        195                 200                 205 tac aag gtt gct gct tca gga caa aat agc acc aaa aat ggc aag act    672
```

-continued

```
            Tyr Lys Val Ala Ala Ser Gly Gln Asn Ser Thr Lys Asn Gly Lys Thr
                210             215                 220 aca atc gtt gcg gaa aat atg aga gat ttt gct atc gtt gct tct aat        720
Thr Ile Val Ala Glu Asn Met Arg Asp Phe Ala Ile Val Ala Ser Asn
225                 230                 235                 240 aaa ttc aag gtt tct cat act tat gca gat ggt ata aga att aat aat        768
Lys Phe Lys Val Ser His Thr Tyr Ala Asp Gly Ile Arg Ile Asn Asn
                245                 250                 255 tat tat ttt gcc ggt aaa aat agt aag caa tat aac aaa ctt gcc tta        816
Tyr Tyr Phe Ala Gly Lys Asn Ser Lys Gln Tyr Asn Lys Leu Ala Leu
            260                 265                 270 ttg act gct aaa gat agt ttc aat att ttc acc aag aaa att ggt aaa        864
Leu Thr Ala Lys Asp Ser Phe Asn Ile Phe Thr Lys Lys Ile Gly Lys
        275                 280                 285 tat cct tat aaa gaa atc gat atg act gaa ggc tta ctt ggt aaa gat        912
Tyr Pro Tyr Lys Glu Ile Asp Met Thr Glu Gly Leu Leu Gly Lys Asp
    290                 295                 300 acc ggt gga atg gaa tat cct agt tta att atg atc gat gcg agt ggc        960
Thr Gly Gly Met Glu Tyr Pro Ser Leu Ile Met Ile Asp Ala Ser Gly
305                 310                 315                 320 ttt gta caa aag aaa cac cca atc aac aga tac aat gaa tta acc gaa       1008
Phe Val Gln Lys Lys His Pro Ile Asn Arg Tyr Asn Glu Leu Thr Glu
                325                 330                 335 gat gtt tcc cat gaa att ggt cac caa tgg ttc tac gct act gtt ggc       1056
Asp Val Ser His Glu Ile Gly His Gln Trp Phe Tyr Ala Thr Val Gly
            340                 345                 350 aat gac gaa tac acc gag cca tgg ctt gat gaa gga ctt act aat ttc       1104
Asn Asp Glu Tyr Thr Glu Pro Trp Leu Asp Glu Gly Leu Thr Asn Phe
        355                 360                 365 ctt gaa aac agt gtt tat gat tta act tat act aag agt aaa gcc tat       1152
Leu Glu Asn Ser Val Tyr Asp Leu Thr Tyr Thr Lys Ser Lys Ala Tyr
    370                 375                 380 act gct aaa ctt atg cac aac aaa ctt tat aat cgt aaa aca gtg aaa       1200
Thr Ala Lys Leu Met His Asn Lys Leu Tyr Asn Arg Lys Thr Val Lys
385                 390                 395                 400 aag gca aat caa gtt ctg gct aac tta gct aat acc ttt tta acc gat       1248
Lys Ala Asn Gln Val Leu Ala Asn Leu Ala Asn Thr Phe Leu Thr Asp
                405                 410                 415 cat cgt caa aaa ggt atc tac gtt aac cgt cct ctc aac aat cca cca       1296
His Arg Gln Lys Gly Ile Tyr Val Asn Arg Pro Leu Asn Asn Pro Pro
            420                 425                 430 aaa gga atc gat act gac gag atg gct tat gaa gcc ggt agt tct ttc       1344
Lys Gly Ile Asp Thr Asp Glu Met Ala Tyr Glu Ala Gly Ser Ser Phe
        435                 440                 445 cca gca atc tta atg atc gct atg ggt aaa aag aaa ttc ttt aat gct       1392
Pro Ala Ile Leu Met Ile Ala Met Gly Lys Lys Lys Phe Phe Asn Ala
    450                 455                 460 ttg cat gat tac tat gaa acc tac tac tta aaa caa gct act aca cag       1440
Leu His Asp Tyr Tyr Glu Thr Tyr Tyr Leu Lys Gln Ala Thr Thr Gln
465                 470                 475                 480 gat ttt ttg aat atc att cgt aag tat gac aac tca aag aaa gta aac       1488
Asp Phe Leu Asn Ile Ile Arg Lys Tyr Asp Asn Ser Lys Lys Val Asn
                485                 490                 495 tat gtg att aat caa ttt atc gat cct gat tat ttg aac aaa              1530
Tyr Val Ile Asn Gln Phe Ile Asp Pro Asp Tyr Leu Asn Lys
            500                 505                 510

<210> SEQ ID NO 56
<211> LENGTH: 510
<212> TYPE: PRT
```

<213> ORGANISM: Lactobacillus acidophilus

<400> SEQUENCE: 56

| | | | | | | | | | | | | | | | |
|---|---|---|---|---|---|---|---|---|---|---|---|---|---|---|---|
| Leu | Glu | Val | Lys | Arg | Met | Lys | Lys | Arg | Thr | Thr | Leu | Leu | Leu | Ser | Ser |
| 1 | | | | 5 | | | | | 10 | | | | | 15 | |
| Ala | Ile | Thr | Ile | Ala | Ala | Leu | Phe | Ser | Phe | Asn | Ser | Lys | Ala | Gln | Ala |
| | | | 20 | | | | | 25 | | | | | 30 | | |
| Ala | Ala | Asp | Pro | Ala | Val | Lys | Ala | Thr | Asn | Tyr | Asn | Met | Thr | Val | Lys |
| | | 35 | | | | | 40 | | | | | 45 | | | |
| Leu | Asn | Thr | Arg | Lys | Asn | Gln | Leu | Thr | Glu | Lys | Val | Thr | Met | His | Val |
| | 50 | | | | | 55 | | | | | 60 | | | | |
| Val | Asn | Asn | Gly | Asn | Glu | Pro | Val | Lys | Asn | Leu | Leu | Ile | Arg | Asn | Ile |
| 65 | | | | | 70 | | | | | 75 | | | | | 80 |
| Ala | Asn | Gly | Val | Leu | Lys | Tyr | Asp | His | Gln | His | Phe | Lys | Ile | Ala | Lys |
| | | | | 85 | | | | | 90 | | | | | 95 | |
| Asn | Ala | Lys | Thr | Thr | Val | Lys | Ser | Ile | Ser | Ser | Ala | Gly | Glu | Asn | Leu |
| | | | 100 | | | | | 105 | | | | | 110 | | |
| Ser | Tyr | Thr | Thr | Gly | Lys | Asp | Lys | Ser | Asn | Leu | Phe | Val | Asp | Lys | Ser |
| | | 115 | | | | | 120 | | | | | 125 | | | |
| Leu | Asn | Ala | Gly | Glu | Ser | Thr | Asp | Leu | Thr | Val | Asn | Val | Val | Thr | Ser |
| | 130 | | | | | 135 | | | | | 140 | | | | |
| Val | Pro | Lys | Arg | Gln | Asp | Arg | Phe | Gly | Tyr | Gln | Asn | Ile | Asn | Gly | Gly |
| 145 | | | | | 150 | | | | | 155 | | | | | 160 |
| Lys | Val | Tyr | Asn | Leu | Ser | Phe | Cys | Phe | Pro | Tyr | Leu | Ser | Asp | Tyr | Arg |
| | | | | 165 | | | | | 170 | | | | | 175 | |
| Asn | Gly | Lys | Trp | Asn | Tyr | His | Pro | Tyr | Tyr | Asp | Gly | Gly | Glu | Asn | Arg |
| | | | 180 | | | | | 185 | | | | | 190 | | |
| Asn | Thr | Thr | Val | Ser | Asn | Phe | His | Val | Ser | Phe | Tyr | Ala | Pro | Lys | Ser |
| | | 195 | | | | | 200 | | | | | 205 | | | |
| Tyr | Lys | Val | Ala | Ala | Ser | Gly | Gln | Asn | Ser | Thr | Lys | Asn | Gly | Lys | Thr |
| | 210 | | | | | 215 | | | | | 220 | | | | |
| Thr | Ile | Val | Ala | Glu | Asn | Met | Arg | Asp | Phe | Ala | Ile | Val | Ala | Ser | Asn |
| 225 | | | | | 230 | | | | | 235 | | | | | 240 |
| Lys | Phe | Lys | Val | Ser | His | Thr | Tyr | Ala | Asp | Gly | Ile | Arg | Ile | Asn | Asn |
| | | | | 245 | | | | | 250 | | | | | 255 | |
| Tyr | Tyr | Phe | Ala | Gly | Lys | Asn | Ser | Lys | Gln | Tyr | Asn | Lys | Leu | Ala | Leu |
| | | | 260 | | | | | 265 | | | | | 270 | | |
| Leu | Thr | Ala | Lys | Asp | Ser | Phe | Asn | Ile | Phe | Thr | Lys | Lys | Ile | Gly | Lys |
| | | 275 | | | | | 280 | | | | | 285 | | | |
| Tyr | Pro | Tyr | Lys | Glu | Ile | Asp | Met | Thr | Glu | Gly | Leu | Leu | Gly | Lys | Asp |
| | 290 | | | | | 295 | | | | | 300 | | | | |
| Thr | Gly | Gly | Met | Glu | Tyr | Pro | Ser | Leu | Ile | Met | Ile | Asp | Ala | Ser | Gly |
| 305 | | | | | 310 | | | | | 315 | | | | | 320 |
| Phe | Val | Gln | Lys | Lys | His | Pro | Ile | Asn | Arg | Tyr | Asn | Glu | Leu | Thr | Glu |
| | | | | 325 | | | | | 330 | | | | | 335 | |
| Asp | Val | Ser | His | Glu | Ile | Gly | His | Gln | Trp | Phe | Tyr | Ala | Thr | Val | Gly |
| | | | 340 | | | | | 345 | | | | | 350 | | |
| Asn | Asp | Glu | Tyr | Thr | Glu | Pro | Trp | Leu | Asp | Glu | Gly | Leu | Thr | Asn | Phe |
| | | 355 | | | | | 360 | | | | | 365 | | | |
| Leu | Glu | Asn | Ser | Val | Tyr | Asp | Leu | Thr | Tyr | Thr | Lys | Ser | Lys | Ala | Tyr |
| | 370 | | | | | 375 | | | | | 380 | | | | |
| Thr | Ala | Lys | Leu | Met | His | Asn | Lys | Leu | Tyr | Asn | Arg | Lys | Thr | Val | Lys |
| 385 | | | | | 390 | | | | | 395 | | | | | 400 |

```
Lys Ala Asn Gln Val Leu Ala Asn Leu Ala Asn Thr Phe Leu Thr Asp
                405                 410                 415

His Arg Gln Lys Gly Ile Tyr Val Asn Arg Pro Leu Asn Asn Pro Pro
                420                 425                 430

Lys Gly Ile Asp Thr Asp Glu Met Ala Tyr Glu Ala Gly Ser Ser Phe
                435                 440                 445

Pro Ala Ile Leu Met Ile Ala Met Gly Lys Lys Phe Phe Asn Ala
        450                 455                 460

Leu His Asp Tyr Tyr Glu Thr Tyr Tyr Leu Lys Gln Ala Thr Thr Gln
465                 470                 475                 480

Asp Phe Leu Asn Ile Ile Arg Lys Tyr Asp Asn Ser Lys Lys Val Asn
                485                 490                 495

Tyr Val Ile Asn Gln Phe Ile Asp Pro Asp Tyr Leu Asn Lys
                500                 505                 510

<210> SEQ ID NO 57
<211> LENGTH: 1296
<212> TYPE: DNA
<213> ORGANISM: Lactobacillus acidophilus
<220> FEATURE:
<221> NAME/KEY: CDS
<222> LOCATION: (1)..(1296)
<223> OTHER INFORMATION: D-alanyl D-alanine carboxypeptidase ORF# 1603

<400> SEQUENCE: 57 atg gtt ttt agt aaa aaa ata aaa cgg aca tta att agt ctt gtt gct      48
Met Val Phe Ser Lys Lys Ile Lys Arg Thr Leu Ile Ser Leu Val Ala
1               5                   10                  15 tta gtt tct tta gtt tct tgt ggt gca gta ttt aca aca ccg gtt agt      96
Leu Val Ser Leu Val Ser Cys Gly Ala Val Phe Thr Thr Pro Val Ser
            20                  25                  30 gca gat aca tca agt agt tat cgc aat aat gaa gtg aat tta gat gtt     144
Ala Asp Thr Ser Ser Ser Tyr Arg Asn Asn Glu Val Asn Leu Asp Val
        35                  40                  45 aaa tct gca att gca att gat agt aat tcg ggg caa att ttg tat gct     192
Lys Ser Ala Ile Ala Ile Asp Ser Asn Ser Gly Gln Ile Leu Tyr Ala
    50                  55                  60 aaa aat gct gat aag act tta cca att gct tca atg aca aag tta att     240
Lys Asn Ala Asp Lys Thr Leu Pro Ile Ala Ser Met Thr Lys Leu Ile
65                  70                  75                  80 aca gtt tat tta act tta aat gca att aaa aat aaa aaa tta tct tgg     288
Thr Val Tyr Leu Thr Leu Asn Ala Ile Lys Asn Lys Lys Leu Ser Trp
                85                  90                  95 aat caa aag gtg aag cca act gct tca att gta aaa gta gct aat aat     336
Asn Gln Lys Val Lys Pro Thr Ala Ser Ile Val Lys Val Ala Asn Asn
            100                 105                 110 gcg gaa tat tca aat gta ccg ctt aag atg ggg cat tct tat act att     384
Ala Glu Tyr Ser Asn Val Pro Leu Lys Met Gly His Ser Tyr Thr Ile
        115                 120                 125 cgt cag ctt tat caa gca act tta att gaa tca gct aat ggg gcc gca     432
Arg Gln Leu Tyr Gln Ala Thr Leu Ile Glu Ser Ala Asn Gly Ala Ala
    130                 135                 140 atg ctt ttg ggc caa act att gct ggt tca caa aag aaa ttt att gat     480
Met Leu Leu Gly Gln Thr Ile Ala Gly Ser Gln Lys Lys Phe Ile Asp
145                 150                 155                 160 caa atg cgt gcc caa gtt aaa aaa tgg ggg att gaa gat gcc gag att     528
Gln Met Arg Ala Gln Val Lys Lys Trp Gly Ile Glu Asp Ala Glu Ile
                165                 170                 175 tat acg gca tgt ggt tta cct aat ggt aat gta ggt aaa gat gcc tat     576
Tyr Thr Ala Cys Gly Leu Pro Asn Gly Asn Val Gly Lys Asp Ala Tyr
```

-continued

```
                180                 185                 190
cct ggt gta aat aag aat gct gaa aat act atg tca gct aag gat atg      624
Pro Gly Val Asn Lys Asn Ala Glu Asn Thr Met Ser Ala Lys Asp Met
            195                 200                 205 gcc att gtt gga caa cat tta ctt aaa gaa tac cca gaa att tta gat      672
Ala Ile Val Gly Gln His Leu Leu Lys Glu Tyr Pro Glu Ile Leu Asp
    210                 215                 220 act act aaa tta gct cat tta gat ttt aaa gac ggt aat aaa act act      720
Thr Thr Lys Leu Ala His Leu Asp Phe Lys Asp Gly Asn Lys Thr Thr
225                 230                 235                 240 aaa atg gcc aac ttt aac tgg atg ctt aaa gga ctt tct caa tat gat      768
Lys Met Ala Asn Phe Asn Trp Met Leu Lys Gly Leu Ser Gln Tyr Asp
                245                 250                 255 caa gca tat cca gtt gat gga tta aag act ggt acc act gat gca gca      816
Gln Ala Tyr Pro Val Asp Gly Leu Lys Thr Gly Thr Thr Asp Ala Ala
            260                 265                 270 ggt gca tgt ttt att ggt aca gtt gaa cat aat ggt gct cgt ttg att      864
Gly Ala Cys Phe Ile Gly Thr Val Glu His Asn Gly Ala Arg Leu Ile
    275                 280                 285 act gtt gtc atg ggt gca cgt cac caa gat ggt acg gat cct tca cgt      912
Thr Val Val Met Gly Ala Arg His Gln Asp Gly Thr Asp Pro Ser Arg
290                 295                 300 ttt att caa act aag aaa tta atg agt ttt att ttc aac aaa tac cgt      960
Phe Ile Gln Thr Lys Lys Leu Met Ser Phe Ile Phe Asn Lys Tyr Arg
305                 310                 315                 320 cca gtt aca atg act gct gga agt caa ata aat ggt gca aaa agt att     1008
Pro Val Thr Met Thr Ala Gly Ser Gln Ile Asn Gly Ala Lys Ser Ile
                325                 330                 335 aaa gtt act gat ggt aaa gac gct aca act aat att ggt tta aag aat     1056
Lys Val Thr Asp Gly Lys Asp Ala Thr Thr Asn Ile Gly Leu Lys Asn
            340                 345                 350 aag aca act att tgg gat cca gca gat ggt aaa aca ttg act gct agt     1104
Lys Thr Thr Ile Trp Asp Pro Ala Asp Gly Lys Thr Leu Thr Ala Ser
    355                 360                 365 tta aac aaa aaa aca ata gat gcg cct ctt gaa aag aat cag aca gtt     1152
Leu Asn Lys Lys Thr Ile Asp Ala Pro Leu Glu Lys Asn Gln Thr Val
370                 375                 380 ggt aat tat caa tta aaa tca ggt agt gaa aaa att gtt tca ttg gat     1200
Gly Asn Tyr Gln Leu Lys Ser Gly Ser Glu Lys Ile Val Ser Leu Asp
385                 390                 395                 400 aat cct aat gga atg aat gta aaa gct aaa gct tta tca gct aat gga     1248
Asn Pro Asn Gly Met Asn Val Lys Ala Lys Ala Leu Ser Ala Asn Gly
                405                 410                 415 aaa gtt aat ttc ttt gtt aga att tgg cgt tgg ctt ttc ggg ggc aga     1296
Lys Val Asn Phe Phe Val Arg Ile Trp Arg Trp Leu Phe Gly Gly Arg
            420                 425                 430
```

<210> SEQ ID NO 58
<211> LENGTH: 432
<212> TYPE: PRT
<213> ORGANISM: Lactobacillus acidophilus

<400> SEQUENCE: 58

```
Met Val Phe Ser Lys Lys Ile Lys Arg Thr Leu Ile Ser Leu Val Ala
1               5                   10                  15

Leu Val Ser Leu Val Ser Cys Gly Ala Val Phe Thr Thr Pro Val Ser
                20                  25                  30

Ala Asp Thr Ser Ser Ser Tyr Arg Asn Asn Glu Val Asn Leu Asp Val
        35                  40                  45
```

-continued

```
Lys Ser Ala Ile Ala Ile Asp Ser Asn Ser Gly Gln Ile Leu Tyr Ala
 50                  55                  60

Lys Asn Ala Asp Lys Thr Leu Pro Ile Ala Ser Met Thr Lys Leu Ile
 65                  70                  75                  80

Thr Val Tyr Leu Thr Leu Asn Ala Ile Lys Asn Lys Lys Leu Ser Trp
                 85                  90                  95

Asn Gln Lys Val Lys Pro Thr Ala Ser Ile Val Lys Val Ala Asn Asn
            100                 105                 110

Ala Glu Tyr Ser Asn Val Pro Leu Lys Met Gly His Ser Tyr Thr Ile
            115                 120                 125

Arg Gln Leu Tyr Gln Ala Thr Leu Ile Glu Ser Ala Asn Gly Ala Ala
        130                 135                 140

Met Leu Leu Gly Gln Thr Ile Ala Gly Ser Gln Lys Lys Phe Ile Asp
145                 150                 155                 160

Gln Met Arg Ala Gln Val Lys Lys Trp Gly Ile Glu Asp Ala Glu Ile
                165                 170                 175

Tyr Thr Ala Cys Gly Leu Pro Asn Gly Asn Val Gly Lys Asp Ala Tyr
            180                 185                 190

Pro Gly Val Asn Lys Asn Ala Glu Asn Thr Met Ser Ala Lys Asp Met
            195                 200                 205

Ala Ile Val Gly Gln His Leu Leu Lys Glu Tyr Pro Glu Ile Leu Asp
        210                 215                 220

Thr Thr Lys Leu Ala His Leu Asp Phe Lys Asp Gly Asn Lys Thr Thr
225                 230                 235                 240

Lys Met Ala Asn Phe Asn Trp Met Leu Lys Gly Leu Ser Gln Tyr Asp
                245                 250                 255

Gln Ala Tyr Pro Val Asp Gly Leu Lys Thr Gly Thr Thr Asp Ala Ala
            260                 265                 270

Gly Ala Cys Phe Ile Gly Thr Val Glu His Asn Gly Ala Arg Leu Ile
            275                 280                 285

Thr Val Val Met Gly Ala Arg His Gln Asp Gly Thr Asp Pro Ser Arg
        290                 295                 300

Phe Ile Gln Thr Lys Lys Leu Met Ser Phe Ile Phe Asn Lys Tyr Arg
305                 310                 315                 320

Pro Val Thr Met Thr Ala Gly Ser Gln Ile Asn Gly Ala Lys Ser Ile
                325                 330                 335

Lys Val Thr Asp Gly Lys Asp Ala Thr Thr Asn Ile Gly Leu Lys Asn
            340                 345                 350

Lys Thr Thr Ile Trp Asp Pro Ala Asp Gly Lys Thr Leu Thr Ala Ser
        355                 360                 365

Leu Asn Lys Lys Thr Ile Asp Ala Pro Leu Glu Lys Asn Gln Thr Val
    370                 375                 380

Gly Asn Tyr Gln Leu Lys Ser Gly Ser Glu Lys Ile Val Ser Leu Asp
385                 390                 395                 400

Asn Pro Asn Gly Met Asn Val Lys Ala Lys Ala Leu Ser Ala Asn Gly
                405                 410                 415

Lys Val Asn Phe Phe Val Arg Ile Trp Arg Trp Leu Phe Gly Gly Arg
            420                 425                 430
```

<210> SEQ ID NO 59
<211> LENGTH: 1425
<212> TYPE: DNA
<213> ORGANISM: Lactobacillus acidophilus
<220> FEATURE:
<221> NAME/KEY: CDS
<222> LOCATION: (1)..(1425)
<223> OTHER INFORMATION: Dipeptidase (EC 3.4.13.18) ORF# 1646

<400> SEQUENCE: 59

| | | | | | | | | | | | | | | | | |
|---|---|---|---|---|---|---|---|---|---|---|---|---|---|---|---|---|
| atg | aaa | aaa | gat | aat | tgt | act | gca | atc | cta | gta | ggt | aaa | gac | gct | tca | 48 |
| Met | Lys | Lys | Asp | Asn | Cys | Thr | Ala | Ile | Leu | Val | Gly | Lys | Asp | Ala | Ser | |
| 1 | | | | 5 | | | | | 10 | | | | | 15 | | |

| att | gat | ggt | tca | acc | atg | att | gct | cgt | gat | gaa | gat | ggg | tac | ggc | ggc | 96 |
|---|---|---|---|---|---|---|---|---|---|---|---|---|---|---|---|---|
| Ile | Asp | Gly | Ser | Thr | Met | Ile | Ala | Arg | Asp | Glu | Asp | Gly | Tyr | Gly | Gly | |
| | | | 20 | | | | | 25 | | | | | 30 | | | |

| atc | aac | gaa | aag | ctt | ttt | gtc | gta | aat | aag | gct | cgt | cac | tac | gat | gaa | 144 |
|---|---|---|---|---|---|---|---|---|---|---|---|---|---|---|---|---|
| Ile | Asn | Glu | Lys | Leu | Phe | Val | Val | Asn | Lys | Ala | Arg | His | Tyr | Asp | Glu | |
| | | 35 | | | | | 40 | | | | | 45 | | | | |

| gac | tat | gtt | tca | aaa | tac | aac | ggc | ttt | aag | atg | cac | ctt | gaa | gga | gat | 192 |
|---|---|---|---|---|---|---|---|---|---|---|---|---|---|---|---|---|
| Asp | Tyr | Val | Ser | Lys | Tyr | Asn | Gly | Phe | Lys | Met | His | Leu | Glu | Gly | Asp | |
| | 50 | | | | | 55 | | | | | 60 | | | | | |

| ggc | tgc | aag | tgg | act | gct | gct | cca | acg | gca | gat | gat | tca | gaa | ggt | cgc | 240 |
|---|---|---|---|---|---|---|---|---|---|---|---|---|---|---|---|---|
| Gly | Cys | Lys | Trp | Thr | Ala | Ala | Pro | Thr | Ala | Asp | Asp | Ser | Glu | Gly | Arg | |
| 65 | | | | 70 | | | | | 75 | | | | | 80 | | |

| tgg | gat | gaa | caa | ggt | atc | aac | gaa | tat | aac | gtg | gct | atg | tct | gct | acg | 288 |
|---|---|---|---|---|---|---|---|---|---|---|---|---|---|---|---|---|
| Trp | Asp | Glu | Gln | Gly | Ile | Asn | Glu | Tyr | Asn | Val | Ala | Met | Ser | Ala | Thr | |
| | | | | 85 | | | | | 90 | | | | | 95 | | |

| gaa | act | gaa | gca | act | aat | gcg | cgt | tgc | tta | ggc | cat | gat | cca | cta | gtg | 336 |
|---|---|---|---|---|---|---|---|---|---|---|---|---|---|---|---|---|
| Glu | Thr | Glu | Ala | Thr | Asn | Ala | Arg | Cys | Leu | Gly | His | Asp | Pro | Leu | Val | |
| | | | | 100 | | | | | 105 | | | | | 110 | | |

| gca | gat | gga | att | aac | gaa | gac | tcc | atg | gtt | tac | att | acc | ttg | cct | ttt | 384 |
|---|---|---|---|---|---|---|---|---|---|---|---|---|---|---|---|---|
| Ala | Asp | Gly | Ile | Asn | Glu | Asp | Ser | Met | Val | Tyr | Ile | Thr | Leu | Pro | Phe | |
| | | | 115 | | | | | 120 | | | | | 125 | | | |

| gtt | aaa | act | gct | cgt | gaa | ggg | gtt | aag | cgt | tta | ggc | cgc | ttg | att | gaa | 432 |
|---|---|---|---|---|---|---|---|---|---|---|---|---|---|---|---|---|
| Val | Lys | Thr | Ala | Arg | Glu | Gly | Val | Lys | Arg | Leu | Gly | Arg | Leu | Ile | Glu | |
| | 130 | | | | | 135 | | | | | 140 | | | | | |

| aag | tat | ggt | act | ggt | gaa | agt | aat | ggg | att | gcc | ttt | tcc | gat | aat | aaa | 480 |
|---|---|---|---|---|---|---|---|---|---|---|---|---|---|---|---|---|
| Lys | Tyr | Gly | Thr | Gly | Glu | Ser | Asn | Gly | Ile | Ala | Phe | Ser | Asp | Asn | Lys | |
| 145 | | | | | 150 | | | | | 155 | | | | | 160 | |

| gaa | gtt | tgg | tat | ctt | gaa | act | ggt | gcg | ggt | cac | caa | tgg | gta | gct | gca | 528 |
|---|---|---|---|---|---|---|---|---|---|---|---|---|---|---|---|---|
| Glu | Val | Trp | Tyr | Leu | Glu | Thr | Gly | Ala | Gly | His | Gln | Trp | Val | Ala | Ala | |
| | | | | 165 | | | | | 170 | | | | | 175 | | |

| cgt | att | cct | gat | aat | tct | tat | gct | att | tgc | cct | aac | att | atg | gta | att | 576 |
|---|---|---|---|---|---|---|---|---|---|---|---|---|---|---|---|---|
| Arg | Ile | Pro | Asp | Asn | Ser | Tyr | Ala | Ile | Cys | Pro | Asn | Ile | Met | Val | Ile | |
| | | | 180 | | | | | 185 | | | | | 190 | | | |

| caa | gat | gtt | gat | ttt | tct | gat | cct | gat | aac | ttt | atg | tgg | agt | gaa | ggt | 624 |
|---|---|---|---|---|---|---|---|---|---|---|---|---|---|---|---|---|
| Gln | Asp | Val | Asp | Phe | Ser | Asp | Pro | Asp | Asn | Phe | Met | Trp | Ser | Glu | Gly | |
| | | 195 | | | | | 200 | | | | | 205 | | | | |

| atc | cag | gaa | ttt | gtc | gaa | aag | aat | cac | tta | aat | aat | agt | aca | gat | ggt | 672 |
|---|---|---|---|---|---|---|---|---|---|---|---|---|---|---|---|---|
| Ile | Gln | Glu | Phe | Val | Glu | Lys | Asn | His | Leu | Asn | Asn | Ser | Thr | Asp | Gly | |
| | 210 | | | | | 215 | | | | | 220 | | | | | |

| agt | ttt | tca | ttt | aga | gat | att | ttt | ggc | acc | aag | gat | gaa | gct | gat | gct | 720 |
|---|---|---|---|---|---|---|---|---|---|---|---|---|---|---|---|---|
| Ser | Phe | Ser | Phe | Arg | Asp | Ile | Phe | Gly | Thr | Lys | Asp | Glu | Ala | Asp | Ala | |
| 225 | | | | | 230 | | | | | 235 | | | | | 240 | |

| ttt | tac | aac | aca | cca | aga | act | tgg | tat | ggt | caa | aag | ttg | ttc | aac | cca | 768 |
|---|---|---|---|---|---|---|---|---|---|---|---|---|---|---|---|---|
| Phe | Tyr | Asn | Thr | Pro | Arg | Thr | Trp | Tyr | Gly | Gln | Lys | Leu | Phe | Asn | Pro | |
| | | | | 245 | | | | | 250 | | | | | 255 | | |

| agt | att | gaa | caa | gac | cca | acc | agt | caa | gaa | atg | cca | ttt | act | cgc | gtt | 816 |
|---|---|---|---|---|---|---|---|---|---|---|---|---|---|---|---|---|
| Ser | Ile | Glu | Gln | Asp | Pro | Thr | Ser | Gln | Glu | Met | Pro | Phe | Thr | Arg | Val | |
| | | | 260 | | | | | 265 | | | | | 270 | | | |

| cct | gaa | aag | aag | att | ggc | gtt | gaa | gat | gta | caa | aag | ttt | tta | act | agt | 864 |
|---|---|---|---|---|---|---|---|---|---|---|---|---|---|---|---|---|
| Pro | Glu | Lys | Lys | Ile | Gly | Val | Glu | Asp | Val | Gln | Lys | Phe | Leu | Thr | Ser | |
| | | 275 | | | | | 280 | | | | | 285 | | | | |

| cac | tat | aac | ggt | acg | cca | tat | gat | cca | atg | gat | act | ttc | tca | tcc | ggc | 912 |
|---|---|---|---|---|---|---|---|---|---|---|---|---|---|---|---|---|
| His | Tyr | Asn | Gly | Thr | Pro | Tyr | Asp | Pro | Met | Asp | Thr | Phe | Ser | Ser | Gly | |

```
                 290                 295                 300
agc gaa aaa gaa caa aag atg ttc cgt tca att gcg ttg gat aga aac    960
Ser Glu Lys Glu Gln Lys Met Phe Arg Ser Ile Ala Leu Asp Arg Asn
305                 310                 315                 320 caa gaa tcc agt atc ttg caa att aga aat gat gtt cct gct aag att   1008
Gln Glu Ser Ser Ile Leu Gln Ile Arg Asn Asp Val Pro Ala Lys Ile
                325                 330                 335 gct ggt gtt caa tgg gta aac ttt ggc ttt tat gca tat tct cca tat   1056
Ala Gly Val Gln Trp Val Asn Phe Gly Phe Tyr Ala Tyr Ser Pro Tyr
            340                 345                 350 gtt cct ttc tac acg aac att gaa gat act cca ctt aac tac aaa gtg   1104
Val Pro Phe Tyr Thr Asn Ile Glu Asp Thr Pro Leu Asn Tyr Lys Val
        355                 360                 365 gca gaa cat aca gtt gat cca gat agc agt gct tac tgg ctt tac aag   1152
Ala Glu His Thr Val Asp Pro Asp Ser Ser Ala Tyr Trp Leu Tyr Lys
    370                 375                 380 act ttg caa gta att gtt gaa cca cgt tat cac caa tac att tat gaa   1200
Thr Leu Gln Val Ile Val Glu Pro Arg Tyr His Gln Tyr Ile Tyr Glu
385                 390                 395                 400 gta aat gct tac cgt gat gat tgt caa agt tat ggt att ggt cgt att   1248
Val Asn Ala Tyr Arg Asp Asp Cys Gln Ser Tyr Gly Ile Gly Arg Ile
                405                 410                 415 gat gaa atc gac gaa aaa gcc aaa gac tta gaa ggt act gaa tta att   1296
Asp Glu Ile Asp Glu Lys Ala Lys Asp Leu Glu Gly Thr Glu Leu Ile
            420                 425                 430 aat tat tta act aat gct aat gat gct act gct ggt gta att act aaa   1344
Asn Tyr Leu Thr Asn Ala Asn Asp Ala Thr Ala Gly Val Ile Thr Lys
        435                 440                 445 aag act aag act tta atg agt aat tta gta aga caa gct tta aat agt   1392
Lys Thr Lys Thr Leu Met Ser Asn Leu Val Arg Gln Ala Leu Asn Ser
    450                 455                 460 tca aaa tat caa ttt gaa cgt ggt gat aat tta                       1425
Ser Lys Tyr Gln Phe Glu Arg Gly Asp Asn Leu
465                 470                 475

<210> SEQ ID NO 60
<211> LENGTH: 475
<212> TYPE: PRT
<213> ORGANISM: Lactobacillus acidophilus

<400> SEQUENCE: 60

Met Lys Lys Asp Asn Cys Thr Ala Ile Leu Val Gly Lys Asp Ala Ser
1               5                   10                  15

Ile Asp Gly Ser Thr Met Ile Ala Arg Asp Glu Asp Gly Tyr Gly Gly
            20                  25                  30

Ile Asn Glu Lys Leu Phe Val Val Asn Lys Ala Arg His Tyr Asp Glu
        35                  40                  45

Asp Tyr Val Ser Lys Tyr Asn Gly Phe Lys Met His Leu Glu Gly Asp
    50                  55                  60

Gly Cys Lys Trp Thr Ala Ala Pro Thr Ala Asp Asp Ser Glu Gly Arg
65                  70                  75                  80

Trp Asp Glu Gln Gly Ile Asn Glu Tyr Asn Val Ala Met Ser Ala Thr
                85                  90                  95

Glu Thr Glu Ala Thr Asn Ala Arg Cys Leu Gly His Asp Pro Leu Val
            100                 105                 110

Ala Asp Gly Ile Asn Glu Asp Ser Met Val Tyr Ile Thr Leu Pro Phe
        115                 120                 125

Val Lys Thr Ala Arg Glu Gly Val Lys Arg Leu Gly Arg Leu Ile Glu
```

```
            130                 135                 140
Lys Tyr Gly Thr Gly Glu Ser Asn Gly Ile Ala Phe Ser Asp Asn Lys
145                 150                 155                 160

Glu Val Trp Tyr Leu Glu Thr Gly Ala Gly His Gln Trp Val Ala Ala
                165                 170                 175

Arg Ile Pro Asp Asn Ser Tyr Ala Ile Cys Pro Asn Ile Met Val Ile
            180                 185                 190

Gln Asp Val Asp Phe Ser Asp Pro Asp Asn Phe Met Trp Ser Glu Gly
        195                 200                 205

Ile Gln Glu Phe Val Glu Lys Asn His Leu Asn Asn Ser Thr Asp Gly
210                 215                 220

Ser Phe Ser Phe Arg Asp Ile Phe Gly Thr Lys Asp Glu Ala Asp Ala
225                 230                 235                 240

Phe Tyr Asn Thr Pro Arg Thr Trp Tyr Gly Gln Lys Leu Phe Asn Pro
                245                 250                 255

Ser Ile Glu Gln Asp Pro Thr Ser Gln Glu Met Pro Phe Thr Arg Val
            260                 265                 270

Pro Glu Lys Lys Ile Gly Val Glu Asp Val Gln Lys Phe Leu Thr Ser
        275                 280                 285

His Tyr Asn Gly Thr Pro Tyr Asp Pro Met Asp Thr Phe Ser Ser Gly
290                 295                 300

Ser Glu Lys Glu Gln Lys Met Phe Arg Ser Ile Ala Leu Asp Arg Asn
305                 310                 315                 320

Gln Glu Ser Ser Ile Leu Gln Ile Arg Asn Asp Val Pro Ala Lys Ile
                325                 330                 335

Ala Gly Val Gln Trp Val Asn Phe Gly Phe Tyr Ala Tyr Ser Pro Tyr
            340                 345                 350

Val Pro Phe Tyr Thr Asn Ile Glu Asp Thr Pro Leu Asn Tyr Lys Val
        355                 360                 365

Ala Glu His Thr Val Asp Pro Asp Ser Ser Ala Tyr Trp Leu Tyr Lys
        370                 375                 380

Thr Leu Gln Val Ile Val Glu Pro Arg Tyr His Gln Tyr Ile Tyr Glu
385                 390                 395                 400

Val Asn Ala Tyr Arg Asp Asp Cys Gln Ser Tyr Gly Ile Gly Arg Ile
                405                 410                 415

Asp Glu Ile Asp Glu Lys Ala Lys Asp Leu Glu Gly Thr Glu Leu Ile
            420                 425                 430

Asn Tyr Leu Thr Asn Ala Asn Asp Ala Thr Ala Gly Val Ile Thr Lys
        435                 440                 445

Lys Thr Lys Thr Leu Met Ser Asn Leu Val Arg Gln Ala Leu Asn Ser
450                 455                 460

Ser Lys Tyr Gln Phe Glu Arg Gly Asp Asn Leu
465                 470                 475

<210> SEQ ID NO 61
<211> LENGTH: 915
<212> TYPE: DNA
<213> ORGANISM: Lactobacillus acidophilus
<220> FEATURE:
<221> NAME/KEY: CDS
<222> LOCATION: (1)..(915)
<223> OTHER INFORMATION: Prolyl aminopeptidase (EC 3.4.11.5) ORF# 1658

<400> SEQUENCE: 61 atg aaa act ggt act aaa att atc act tta gac aac ggt tac cac tta      48
Met Lys Thr Gly Thr Lys Ile Ile Thr Leu Asp Asn Gly Tyr His Leu
```

-continued

```
1               5                   10                  15 tgg act aat act caa ggt gaa ggc gac att cac tta tta gct ctt cac        96
Trp Thr Asn Thr Gln Gly Glu Gly Asp Ile His Leu Leu Ala Leu His
             20                  25                  30 ggt ggt cct ggc ggc aac cac gaa tat tgg gaa gac act gca gaa caa       144
Gly Gly Pro Gly Gly Asn His Glu Tyr Trp Glu Asp Thr Ala Glu Gln
         35                  40                  45 cta aaa aaa caa ggc tta gac gtc caa gtt acc atg tac gat caa ctt       192
Leu Lys Lys Gln Gly Leu Asp Val Gln Val Thr Met Tyr Asp Gln Leu
     50                  55                  60 ggc tca ctc tac tca gat caa cct gac tat tct aat cct gaa att gct       240
Gly Ser Leu Tyr Ser Asp Gln Pro Asp Tyr Ser Asn Pro Glu Ile Ala
 65                  70                  75                  80 aaa aag tat tta act tat gaa tac ttc tta gat gaa gtt gat gaa gtt       288
Lys Lys Tyr Leu Thr Tyr Glu Tyr Phe Leu Asp Glu Val Asp Glu Val
                 85                  90                  95 cgt gaa aag ctc ggt tta gac aat att tac tta atc ggt caa agt tgg       336
Arg Glu Lys Leu Gly Leu Asp Asn Ile Tyr Leu Ile Gly Gln Ser Trp
            100                 105                 110 ggt ggg tta tta gtt caa gaa tac gcc gtt aaa tat ggt cag cac tta       384
Gly Gly Leu Leu Val Gln Glu Tyr Ala Val Lys Tyr Gly Gln His Leu
        115                 120                 125 aag ggt gcg atc att tca tca atg gtt gat gaa atc gac gaa tat gtt       432
Lys Gly Ala Ile Ile Ser Ser Met Val Asp Glu Ile Asp Glu Tyr Val
    130                 135                 140 gca tca gtt aat cgt aga cgt caa gaa gtt cta cca cag act gaa att       480
Ala Ser Val Asn Arg Arg Arg Gln Glu Val Leu Pro Gln Thr Glu Ile
145                 150                 155                 160 gat ttt atg cat gaa tgt gaa aag aac aat gat tac gac aac aaa cgt       528
Asp Phe Met His Glu Cys Glu Lys Asn Asn Asp Tyr Asp Asn Lys Arg
                165                 170                 175 tac caa gat gac gtt caa atc ttg aac att aac ttt gtt gat cgt aag       576
Tyr Gln Asp Asp Val Gln Ile Leu Asn Ile Asn Phe Val Asp Arg Lys
            180                 185                 190 caa cct tca aag ctt tac cat cta aag gac ctt ggt ggt tct gct gtt       624
Gln Pro Ser Lys Leu Tyr His Leu Lys Asp Leu Gly Gly Ser Ala Val
        195                 200                 205 tac aac gcc ttc caa ggt gat aat gag ttt gtt atc acc ggt aag tta       672
Tyr Asn Ala Phe Gln Gly Asp Asn Glu Phe Val Ile Thr Gly Lys Leu
    210                 215                 220 aag gac tgg cac ttc aga gat caa tta cac aag atc aat gtt cca act       720
Lys Asp Trp His Phe Arg Asp Gln Leu His Lys Ile Asn Val Pro Thr
225                 230                 235                 240 ttg ctt act ttt ggt gaa aac gaa act atg cct att tca act gct aag       768
Leu Leu Thr Phe Gly Glu Asn Glu Thr Met Pro Ile Ser Thr Ala Lys
                245                 250                 255 att atg caa aag gaa att cct aac tca cgt tta gtt act act cca gat       816
Ile Met Gln Lys Glu Ile Pro Asn Ser Arg Leu Val Thr Thr Pro Asp
            260                 265                 270 ggt gga cac cac cac atg gtt gat aat cct aca gtt tac tat aaa cac       864
Gly Gly His His His Met Val Asp Asn Pro Thr Val Tyr Tyr Lys His
        275                 280                 285 ttg gct gac ttc att cgt gaa gta gaa aac ggc acc ttt aaa ggc caa       912
Leu Ala Asp Phe Ile Arg Glu Val Glu Asn Gly Thr Phe Lys Gly Gln
    290                 295                 300 aat                                                                   915
Asn
305
```

<210> SEQ ID NO 62
<211> LENGTH: 305
<212> TYPE: PRT
<213> ORGANISM: Lactobacillus acidophilus

<400> SEQUENCE: 62

```
Met Lys Thr Gly Thr Lys Ile Ile Thr Leu Asp Asn Gly Tyr His Leu
1               5                   10                  15
Trp Thr Asn Thr Gln Gly Glu Gly Asp Ile His Leu Leu Ala Leu His
            20                  25                  30
Gly Gly Pro Gly Gly Asn His Glu Tyr Trp Glu Asp Thr Ala Glu Gln
        35                  40                  45
Leu Lys Lys Gln Gly Leu Asp Val Gln Val Thr Met Tyr Asp Gln Leu
    50                  55                  60
Gly Ser Leu Tyr Ser Asp Gln Pro Asp Tyr Ser Asn Pro Glu Ile Ala
65                  70                  75                  80
Lys Lys Tyr Leu Thr Tyr Glu Tyr Phe Leu Asp Glu Val Asp Glu Val
                85                  90                  95
Arg Glu Lys Leu Gly Leu Asp Asn Ile Tyr Leu Ile Gly Gln Ser Trp
            100                 105                 110
Gly Gly Leu Leu Val Gln Glu Tyr Ala Val Lys Tyr Gly Gln His Leu
        115                 120                 125
Lys Gly Ala Ile Ile Ser Ser Met Val Asp Glu Ile Asp Glu Tyr Val
    130                 135                 140
Ala Ser Val Asn Arg Arg Arg Gln Glu Val Leu Pro Gln Thr Glu Ile
145                 150                 155                 160
Asp Phe Met His Glu Cys Glu Lys Asn Asn Asp Tyr Asp Asn Lys Arg
                165                 170                 175
Tyr Gln Asp Asp Val Gln Ile Leu Asn Ile Asn Phe Val Asp Arg Lys
            180                 185                 190
Gln Pro Ser Lys Leu Tyr His Leu Lys Asp Leu Gly Gly Ser Ala Val
        195                 200                 205
Tyr Asn Ala Phe Gln Gly Asp Asn Glu Phe Val Ile Thr Gly Lys Leu
    210                 215                 220
Lys Asp Trp His Phe Arg Asp Gln Leu His Lys Ile Asn Val Pro Thr
225                 230                 235                 240
Leu Leu Thr Phe Gly Glu Asn Glu Thr Met Pro Ile Ser Thr Ala Lys
                245                 250                 255
Ile Met Gln Lys Glu Ile Pro Asn Ser Arg Leu Val Thr Thr Pro Asp
            260                 265                 270
Gly Gly His His His Met Val Asp Asn Pro Thr Val Tyr Tyr Lys His
        275                 280                 285
Leu Ala Asp Phe Ile Arg Glu Val Glu Asn Gly Thr Phe Lys Gly Gln
    290                 295                 300
Asn
305
```

<210> SEQ ID NO 63
<211> LENGTH: 1794
<212> TYPE: DNA
<213> ORGANISM: Lactobacillus acidophilus
<220> FEATURE:
<221> NAME/KEY: CDS
<222> LOCATION: (1)..(1794)
<223> OTHER INFORMATION: pepF oligopeptidase (EC 3.4.24.15)

<400> SEQUENCE: 63

-continued

| | | |
|---|---|---|
| atg gca att cca aca aga agt gaa gtt cca gaa gaa tta aaa tgg gac<br>Met Ala Ile Pro Thr Arg Ser Glu Val Pro Glu Glu Leu Lys Trp Asp<br>1               5                   10                  15 | 48 | |
| tta acc cgt gtt ttt aag aca gat gaa gac tgg gaa gca gcc ttt gat<br>Leu Thr Arg Val Phe Lys Thr Asp Glu Asp Trp Glu Ala Ala Phe Asp<br>            20                  25                  30 | 96 | |
| aat gca aaa gat gaa gta gaa aaa tta ggt gat ttt aaa aaa atc ctt<br>Asn Ala Lys Asp Glu Val Glu Lys Leu Gly Asp Phe Lys Lys Ile Leu<br>        35                  40                  45 | 144 | |
| act aaa tct ggc aaa gac tta tac gaa agt ttg acc caa att tta gca<br>Thr Lys Ser Gly Lys Asp Leu Tyr Glu Ser Leu Thr Gln Ile Leu Ala<br>    50                  55                  60 | 192 | |
| gtt aaa cgt caa gta gaa aat att tac gtt tat gca act atg tct agt<br>Val Lys Arg Gln Val Glu Asn Ile Tyr Val Tyr Ala Thr Met Ser Ser<br>65                  70                  75                  80 | 240 | |
| gat gtt gat act tca aat tct cac tat tta ggt tat gta agc cgc gca<br>Asp Val Asp Thr Ser Asn Ser His Tyr Leu Gly Tyr Val Ser Arg Ala<br>            85                  90                  95 | 288 | |
| caa aat tta gtt aac caa ttt gag gca gta act agt ttt atc agc cca<br>Gln Asn Leu Val Asn Gln Phe Glu Ala Val Thr Ser Phe Ile Ser Pro<br>        100                 105                 110 | 336 | |
| gaa att ctg agt atc cct gcc gat aag ttt gaa caa ttc aaa aag gat<br>Glu Ile Leu Ser Ile Pro Ala Asp Lys Phe Glu Gln Phe Lys Lys Asp<br>    115                 120                 125 | 384 | |
| gaa cct cgt tta aac gat tat gct cac tat ctt gag aca atc act aat<br>Glu Pro Arg Leu Asn Asp Tyr Ala His Tyr Leu Glu Thr Ile Thr Asn<br>130                 135                 140 | 432 | |
| aag cgt ccc cac act tta cct gct gaa gag gaa aaa att atc gca gat<br>Lys Arg Pro His Thr Leu Pro Ala Glu Glu Glu Lys Ile Ile Ala Asp<br>145                 150                 155                 160 | 480 | |
| gcc agt gat gcc atg ggc gtt tca gaa aat acc ttt aac gtt tta act<br>Ala Ser Asp Ala Met Gly Val Ser Glu Asn Thr Phe Asn Val Leu Thr<br>            165                 170                 175 | 528 | |
| aat tca gac atg gaa tat ggc tac gtt caa gat gac gat ggt aat atg<br>Asn Ser Asp Met Glu Tyr Gly Tyr Val Gln Asp Asp Asp Gly Asn Met<br>        180                 185                 190 | 576 | |
| gaa caa ttg tct gac ggt ttg tac tca ctt tta atc caa tca caa aac<br>Glu Gln Leu Ser Asp Gly Leu Tyr Ser Leu Leu Ile Gln Ser Gln Asn<br>    195                 200                 205 | 624 | |
| cgt gat gtc aga aaa ggc gct ttt gat acg ctt tat gca agc tat ggt<br>Arg Asp Val Arg Lys Gly Ala Phe Asp Thr Leu Tyr Ala Ser Tyr Gly<br>210                 215                 220 | 672 | |
| caa ttc caa aat tca ctt gct tct acg ctt tcc ggc gtt gta aag aag<br>Gln Phe Gln Asn Ser Leu Ala Ser Thr Leu Ser Gly Val Val Lys Lys<br>225                 230                 235                 240 | 720 | |
| cac aat tat aac gct aaa gtt cac aag tat gat tca gct cgt gaa gca<br>His Asn Tyr Asn Ala Lys Val His Lys Tyr Asp Ser Ala Arg Glu Ala<br>            245                 250                 255 | 768 | |
| gct tta gct gaa aac aac gta cct acc aag gtt tac gac act ttg att<br>Ala Leu Ala Glu Asn Asn Val Pro Thr Lys Val Tyr Asp Thr Leu Ile<br>        260                 265                 270 | 816 | |
| cga gaa gtt gac tcc cat ctt gat tta ctt cac cgt tat gta gca ctt<br>Arg Glu Val Asp Ser His Leu Asp Leu Leu His Arg Tyr Val Ala Leu<br>    275                 280                 285 | 864 | |
| cgg aag aaa att ttg gga ctt aaa gat tta caa atg tgg gac atg tac<br>Arg Lys Lys Ile Leu Gly Leu Lys Asp Leu Gln Met Trp Asp Met Tyr<br>290                 295                 300 | 912 | |
| gtg cca cta act ggt aag cct gct ctt tca tat aat ttt gaa gaa gca<br>Val Pro Leu Thr Gly Lys Pro Ala Leu Ser Tyr Asn Phe Glu Glu Ala<br>305                 310                 315                 320 | 960 | |

```
aag gaa gta gct aag aaa gct tta gct cca ctg ggc gaa gat tac tta   1008
Lys Glu Val Ala Lys Lys Ala Leu Ala Pro Leu Gly Glu Asp Tyr Leu
            325                 330                 335 aag cat gtt gat tat atc ttt aat aat cgc gta att gat gta gtt gaa   1056
Lys His Val Asp Tyr Ile Phe Asn Asn Arg Val Ile Asp Val Val Glu
        340                 345                 350 tca aag aat aaa gta act ggc gca tat tct ggc ggt gct tat gat aca   1104
Ser Lys Asn Lys Val Thr Gly Ala Tyr Ser Gly Gly Ala Tyr Asp Thr
    355                 360                 365 gat cca tat gaa ctt tta aac tgg gaa aac aac att gac tcc tta tat   1152
Asp Pro Tyr Glu Leu Leu Asn Trp Glu Asn Asn Ile Asp Ser Leu Tyr
370                 375                 380 act cta gtt cac gaa act ggt cac tca gtt cac tct tgg tac act cgc   1200
Thr Leu Val His Glu Thr Gly His Ser Val His Ser Trp Tyr Thr Arg
385                 390                 395                 400 aat agc caa cct tac gtt tat ggg gat tat cct att ttc gta gca gaa   1248
Asn Ser Gln Pro Tyr Val Tyr Gly Asp Tyr Pro Ile Phe Val Ala Glu
                405                 410                 415 att gct tca acc act aac gaa aat att ttg act gaa tac ttc tta gat   1296
Ile Ala Ser Thr Thr Asn Glu Asn Ile Leu Thr Glu Tyr Phe Leu Asp
            420                 425                 430 cat att act gat tct aag aca cgc gcc ttt att ttg aac tac tat ctt   1344
His Ile Thr Asp Ser Lys Thr Arg Ala Phe Ile Leu Asn Tyr Tyr Leu
        435                 440                 445 gat tca ttt aag ggg aca ttg ttc cgt caa acc caa ttt gcg gtg ttt   1392
Asp Ser Phe Lys Gly Thr Leu Phe Arg Gln Thr Gln Phe Ala Val Phe
    450                 455                 460 gaa caa ttt att cat gaa gca gat gct aaa ggt gaa cca ctt act gct   1440
Glu Gln Phe Ile His Glu Ala Asp Ala Lys Gly Glu Pro Leu Thr Ala
465                 470                 475                 480 gat atc ttg gat gaa gtt tat gga caa ctt aac caa cac tat tac ggt   1488
Asp Ile Leu Asp Glu Val Tyr Gly Gln Leu Asn Gln His Tyr Tyr Gly
                485                 490                 495 gac agc gtt gag cca ggc ggc gat att gca ctt gaa tgg tca cgt atc   1536
Asp Ser Val Glu Pro Gly Gly Asp Ile Ala Leu Glu Trp Ser Arg Ile
            500                 505                 510 ccg cac ttc tac tac gac ttt tac gtt tac caa tat gca aca gga ttt   1584
Pro His Phe Tyr Tyr Asp Phe Tyr Val Tyr Gln Tyr Ala Thr Gly Phe
        515                 520                 525 gcg gct gca aca gct ctt gcc aac aag gtg gtt cat ggt tct gaa gct   1632
Ala Ala Ala Thr Ala Leu Ala Asn Lys Val Val His Gly Ser Glu Ala
    530                 535                 540 gat agg gat gca tat ctt ggt ttt ctt aag gct ggt tca agt aac tat   1680
Asp Arg Asp Ala Tyr Leu Gly Phe Leu Lys Ala Gly Ser Ser Asn Tyr
545                 550                 555                 560 cca acc gaa att atg aag cat gct ggc gtt gat atg act aag cca gac   1728
Pro Thr Glu Ile Met Lys His Ala Gly Val Asp Met Thr Lys Pro Asp
                565                 570                 575 tac ttg gaa gat gca ttt aag aca ttt gaa aaa cgt tta gcc gaa ttt   1776
Tyr Leu Glu Asp Ala Phe Lys Thr Phe Glu Lys Arg Leu Ala Glu Phe
            580                 585                 590 gaa agt ttg att gaa aaa                                           1794
Glu Ser Leu Ile Glu Lys
        595

<210> SEQ ID NO 64
<211> LENGTH: 598
<212> TYPE: PRT
<213> ORGANISM: Lactobacillus acidophilus
```

```
<400> SEQUENCE: 64

Met Ala Ile Pro Thr Arg Ser Glu Val Pro Glu Glu Leu Lys Trp Asp
1               5                   10                  15

Leu Thr Arg Val Phe Lys Thr Asp Glu Asp Trp Glu Ala Ala Phe Asp
            20                  25                  30

Asn Ala Lys Asp Glu Val Glu Lys Leu Gly Asp Phe Lys Lys Ile Leu
        35                  40                  45

Thr Lys Ser Gly Lys Asp Leu Tyr Glu Ser Leu Thr Gln Ile Leu Ala
    50                  55                  60

Val Lys Arg Gln Val Glu Asn Ile Tyr Val Tyr Ala Thr Met Ser Ser
65                  70                  75                  80

Asp Val Asp Thr Ser Asn Ser His Tyr Leu Gly Tyr Val Ser Arg Ala
                85                  90                  95

Gln Asn Leu Val Asn Gln Phe Glu Ala Val Thr Ser Phe Ile Ser Pro
            100                 105                 110

Glu Ile Leu Ser Ile Pro Ala Asp Lys Phe Glu Gln Phe Lys Lys Asp
        115                 120                 125

Glu Pro Arg Leu Asn Asp Tyr Ala His Tyr Leu Glu Thr Ile Thr Asn
    130                 135                 140

Lys Arg Pro His Thr Leu Pro Ala Glu Glu Lys Ile Ile Ala Asp
145                 150                 155                 160

Ala Ser Asp Ala Met Gly Val Ser Glu Asn Thr Phe Asn Val Leu Thr
                165                 170                 175

Asn Ser Asp Met Glu Tyr Gly Tyr Val Gln Asp Asp Gly Asn Met
            180                 185                 190

Glu Gln Leu Ser Asp Gly Leu Tyr Ser Leu Leu Ile Gln Ser Gln Asn
        195                 200                 205

Arg Asp Val Arg Lys Gly Ala Phe Asp Thr Leu Tyr Ala Ser Tyr Gly
    210                 215                 220

Gln Phe Gln Asn Ser Leu Ala Ser Thr Leu Ser Gly Val Val Lys Lys
225                 230                 235                 240

His Asn Tyr Asn Ala Lys Val His Lys Tyr Asp Ser Ala Arg Glu Ala
                245                 250                 255

Ala Leu Ala Glu Asn Asn Val Pro Thr Lys Val Tyr Asp Thr Leu Ile
            260                 265                 270

Arg Glu Val Asp Ser His Leu Asp Leu Leu His Arg Tyr Val Ala Leu
        275                 280                 285

Arg Lys Lys Ile Leu Gly Leu Lys Asp Leu Gln Met Trp Asp Met Tyr
    290                 295                 300

Val Pro Leu Thr Gly Lys Pro Ala Leu Ser Tyr Asn Phe Glu Glu Ala
305                 310                 315                 320

Lys Glu Val Ala Lys Lys Ala Leu Ala Pro Leu Gly Glu Asp Tyr Leu
                325                 330                 335

Lys His Val Asp Tyr Ile Phe Asn Asn Arg Val Ile Asp Val Val Glu
            340                 345                 350

Ser Lys Asn Lys Val Thr Gly Ala Tyr Ser Gly Gly Ala Tyr Asp Thr
        355                 360                 365

Asp Pro Tyr Glu Leu Leu Asn Trp Glu Asn Asn Ile Asp Ser Leu Tyr
    370                 375                 380

Thr Leu Val His Glu Thr Gly His Ser Val His Ser Trp Tyr Thr Arg
385                 390                 395                 400

Asn Ser Gln Pro Tyr Val Tyr Gly Asp Tyr Pro Ile Phe Val Ala Glu
                405                 410                 415
```

```
Ile Ala Ser Thr Thr Asn Glu Asn Ile Leu Thr Glu Tyr Phe Leu Asp
        420                 425                 430

His Ile Thr Asp Ser Lys Thr Arg Ala Phe Ile Leu Asn Tyr Tyr Leu
        435                 440                 445

Asp Ser Phe Lys Gly Thr Leu Phe Arg Gln Thr Gln Phe Ala Val Phe
        450                 455                 460

Glu Gln Phe Ile His Glu Ala Asp Ala Lys Gly Glu Pro Leu Thr Ala
465                 470                 475                 480

Asp Ile Leu Asp Glu Val Tyr Gly Gln Leu Asn Gln His Tyr Tyr Gly
                485                 490                 495

Asp Ser Val Glu Pro Gly Gly Asp Ile Ala Leu Glu Trp Ser Arg Ile
            500                 505                 510

Pro His Phe Tyr Tyr Asp Phe Val Tyr Gln Tyr Ala Thr Gly Phe
        515                 520                 525

Ala Ala Ala Thr Ala Leu Ala Asn Lys Val Val His Gly Ser Glu Ala
        530                 535                 540

Asp Arg Asp Ala Tyr Leu Gly Phe Leu Lys Ala Gly Ser Ser Asn Tyr
545                 550                 555                 560

Pro Thr Glu Ile Met Lys His Ala Gly Val Asp Met Thr Lys Pro Asp
                565                 570                 575

Tyr Leu Glu Asp Ala Phe Lys Thr Phe Glu Lys Arg Leu Ala Glu Phe
            580                 585                 590

Glu Ser Leu Ile Glu Lys
        595
```

```
<210> SEQ ID NO 65
<211> LENGTH: 1419
<212> TYPE: DNA
<213> ORGANISM: Lactobacillus acidophilus
<220> FEATURE:
<221> NAME/KEY: CDS
<222> LOCATION: (1)..(1419)
<223> OTHER INFORMATION: Cytosol non-specific dipeptidase
      (EC 3.4.13.18) ORF# 1837

<400> SEQUENCE: 65
```

```
gtg aat ttt atg aat act aca gtc gtt ggt cgt tcg tct tgt acc tca      48
Val Asn Phe Met Asn Thr Thr Val Val Gly Arg Ser Ser Cys Thr Ser
1               5                   10                  15 atc tta att ggt aag aaa gca tcc ctt tca ggc agt gta att att ggc      96
Ile Leu Ile Gly Lys Lys Ala Ser Leu Ser Gly Ser Val Ile Ile Gly
            20                  25                  30 cgc aat gag gat gca aaa act gct tgg cca aaa cat ctt gca ttc aat    144
Arg Asn Glu Asp Ala Lys Thr Ala Trp Pro Lys His Leu Ala Phe Asn
        35                  40                  45 cac cat aag aat gtt aag aat aac cat ttt aag tca aaa gac aat aaa    192
His His Lys Asn Val Lys Asn Asn His Phe Lys Ser Lys Asp Asn Lys
    50                  55                  60 ttt gaa att gat tta cct gaa aag ata ttc agc tat tct tcc aca cca    240
Phe Glu Ile Asp Leu Pro Glu Lys Ile Phe Ser Tyr Ser Ser Thr Pro
65                  70                  75                  80 gaa tgg aca gat aaa tac ggt gtt ttt gaa gaa gat ggc att aat gag    288
Glu Trp Thr Asp Lys Tyr Gly Val Phe Glu Glu Asp Gly Ile Asn Glu
                85                  90                  95 tat cat gtg gca atg agt gct act gaa agt gcc tat gcc aat gat cgt    336
Tyr His Val Ala Met Ser Ala Thr Glu Ser Ala Tyr Ala Asn Asp Arg
            100                 105                 110 gta atg gca gtt gat cca ttc aat aca gaa aag ggc atc cta gaa gaa    384
```

```
                Val Met Ala Val Asp Pro Phe Asn Thr Glu Lys Gly Ile Leu Glu Glu
                        115                 120                 125 gct atg gta acg gta gta ttg cca tat att aaa aca gca aaa gaa ggc         432
Ala Met Val Thr Val Val Leu Pro Tyr Ile Lys Thr Ala Lys Glu Gly
130                 135                 140 gtt att cgc tta ggc aaa atc gtt gaa aaa cat ggt gcc gct gaa gca         480
Val Ile Arg Leu Gly Lys Ile Val Glu Lys His Gly Ala Ala Glu Ala
145                 150                 155                 160 gac ggg atc tta ttt gct gac cgc gac gaa gca tgg tac atg gaa att         528
Asp Gly Ile Leu Phe Ala Asp Arg Asp Glu Ala Trp Tyr Met Glu Ile
                        165                 170                 175 gga tca ggt cac cac tgg gtt gct caa aga att cca gat gat tca tat         576
Gly Ser Gly His His Trp Val Ala Gln Arg Ile Pro Asp Asp Ser Tyr
                        180                 185                 190 gca gta gtt gct aac caa tta gca att caa gaa att gac ttt gac agt         624
Ala Val Val Ala Asn Gln Leu Ala Ile Gln Glu Ile Asp Phe Asp Ser
                        195                 200                 205 gac aat ttc tta tat tca aat aat tta caa aat ttt gtt tat aac aat         672
Asp Asn Phe Leu Tyr Ser Asn Asn Leu Gln Asn Phe Val Tyr Asn Asn
210                 215                 220 caa ctt tgg cca aaa gat aaa cca ttt att tgg cgt gat att ttt ggt         720
Gln Leu Trp Pro Lys Asp Lys Pro Phe Ile Trp Arg Asp Ile Phe Gly
225                 230                 235                 240 aca cat gac gat agt gat ctt cat tac aat acg cca cgt gtt tgg agc         768
Thr His Asp Asp Ser Asp Leu His Tyr Asn Thr Pro Arg Val Trp Ser
                        245                 250                 255 ggt cag cgt ctt tta acg cca tct gct gaa caa aag cct caa gac ttc         816
Gly Gln Arg Leu Leu Thr Pro Ser Ala Glu Gln Lys Pro Gln Asp Phe
                        260                 265                 270 aat tta cca ttt acc aga aag cct gat gcg cct att tct gcc caa gat         864
Asn Leu Pro Phe Thr Arg Lys Pro Asp Ala Pro Ile Ser Ala Gln Asp
                        275                 280                 285 gct caa cat gtt tta agt gat cac ttt aat aat aca gtt tat gat cta         912
Ala Gln His Val Leu Ser Asp His Phe Asn Asn Thr Val Tyr Asp Leu
                        290                 295                 300 aca aat aag aaa aat aaa gat cag cct gca ttt cgt cca att tct gta         960
Thr Asn Lys Lys Asn Lys Asp Gln Pro Ala Phe Arg Pro Ile Ser Val
305                 310                 315                 320 gct act act caa gaa tca cat ttg ctt gaa tta aac ggc gaa gac atg        1008
Ala Thr Thr Gln Glu Ser His Leu Leu Glu Leu Asn Gly Glu Asp Met
                        325                 330                 335 att cat tgg cta gca atg ggc gtt gcc gca caa agc gta tat att ccg        1056
Ile His Trp Leu Ala Met Gly Val Ala Ala Gln Ser Val Tyr Ile Pro
                        340                 345                 350 ttc tat cca caa ggt act aaa gtt cct agt acc tgg aaa aac ggt aaa        1104
Phe Tyr Pro Gln Gly Thr Lys Val Pro Ser Thr Trp Lys Asn Gly Lys
                        355                 360                 365 gag act tat tca ccg aat tct gcc tac tgg gta ttt aag ctt gcc agc        1152
Glu Thr Tyr Ser Pro Asn Ser Ala Tyr Trp Val Phe Lys Leu Ala Ser
                        370                 375                 380 gtt tta gtt gat cgc gat tgg agt aag tac ggt act gca ttg agt aat        1200
Val Leu Val Asp Arg Asp Trp Ser Lys Tyr Gly Thr Ala Leu Ser Asn
385                 390                 395                 400 acc caa aac tct act aat gag aaa tta ttg caa att aga cat caa tat        1248
Thr Gln Asn Ser Thr Asn Glu Lys Leu Leu Gln Ile Arg His Gln Tyr
                        405                 410                 415 gat gaa aaa tta gct aag gaa aat gat cct gct aaa cga act gat tta        1296
Asp Glu Lys Leu Ala Lys Glu Asn Asp Pro Ala Lys Arg Thr Asp Leu
                        420                 425                 430
```

```
att aat gaa gca aat gct aaa ctg gct aag aca gct aca gac gca tat       1344
Ile Asn Glu Ala Asn Ala Lys Leu Ala Lys Thr Ala Thr Asp Ala Tyr
            435                 440                 445 aaa gaa tta act gca aaa ttg att act gaa caa act ggt gat tca cca       1392
Lys Glu Leu Thr Ala Lys Leu Ile Thr Glu Gln Thr Gly Asp Ser Pro
450                 455                 460 ctt aga ttc caa atg gat cct aac cta                                   1419
Leu Arg Phe Gln Met Asp Pro Asn Leu
465                 470

<210> SEQ ID NO 66
<211> LENGTH: 473
<212> TYPE: PRT
<213> ORGANISM: Lactobacillus acidophilus

<400> SEQUENCE: 66

Val Asn Phe Met Asn Thr Thr Val Val Gly Arg Ser Ser Cys Thr Ser
1               5                   10                  15

Ile Leu Ile Gly Lys Lys Ala Ser Leu Ser Gly Ser Val Ile Ile Gly
            20                  25                  30

Arg Asn Glu Asp Ala Lys Thr Ala Trp Pro Lys His Leu Ala Phe Asn
        35                  40                  45

His His Lys Asn Val Lys Asn His Phe Lys Ser Lys Asp Asn Lys
    50                  55                  60

Phe Glu Ile Asp Leu Pro Glu Lys Ile Phe Ser Tyr Ser Ser Thr Pro
65                  70                  75                  80

Glu Trp Thr Asp Lys Tyr Gly Val Phe Glu Glu Asp Gly Ile Asn Glu
                85                  90                  95

Tyr His Val Ala Met Ser Ala Thr Glu Ser Ala Tyr Ala Asn Asp Arg
            100                 105                 110

Val Met Ala Val Asp Pro Phe Asn Thr Glu Lys Gly Ile Leu Glu Glu
        115                 120                 125

Ala Met Val Thr Val Val Leu Pro Tyr Ile Lys Thr Ala Lys Glu Gly
    130                 135                 140

Val Ile Arg Leu Gly Lys Ile Val Glu Lys His Gly Ala Ala Glu Ala
145                 150                 155                 160

Asp Gly Ile Leu Phe Ala Asp Arg Asp Glu Ala Trp Tyr Met Glu Ile
                165                 170                 175

Gly Ser Gly His His Trp Val Ala Gln Arg Ile Pro Asp Asp Ser Tyr
            180                 185                 190

Ala Val Val Ala Asn Gln Leu Ala Ile Gln Ile Asp Phe Asp Ser
        195                 200                 205

Asp Asn Phe Leu Tyr Ser Asn Asn Leu Gln Asn Phe Val Tyr Asn Asn
    210                 215                 220

Gln Leu Trp Pro Lys Asp Lys Pro Phe Ile Trp Arg Asp Ile Phe Gly
225                 230                 235                 240

Thr His Asp Asp Ser Asp Leu His Tyr Asn Thr Pro Arg Val Trp Ser
                245                 250                 255

Gly Gln Arg Leu Leu Thr Pro Ser Ala Glu Gln Lys Pro Gln Asp Phe
            260                 265                 270

Asn Leu Pro Phe Thr Arg Lys Pro Asp Ala Pro Ile Ser Ala Gln Asp
        275                 280                 285

Ala Gln His Val Leu Ser Asp His Phe Asn Asn Thr Val Tyr Asp Leu
    290                 295                 300

Thr Asn Lys Lys Asn Lys Asp Gln Pro Ala Phe Arg Pro Ile Ser Val
305                 310                 315                 320
```

```
Ala Thr Thr Gln Glu Ser His Leu Leu Glu Leu Asn Gly Glu Asp Met
            325                 330                 335

Ile His Trp Leu Ala Met Gly Val Ala Ala Gln Ser Val Tyr Ile Pro
            340                 345                 350

Phe Tyr Pro Gln Gly Thr Lys Val Pro Ser Thr Trp Lys Asn Gly Lys
            355                 360                 365

Glu Thr Tyr Ser Pro Asn Ser Ala Tyr Trp Val Phe Lys Leu Ala Ser
            370                 375                 380

Val Leu Val Asp Arg Asp Trp Ser Lys Tyr Gly Thr Ala Leu Ser Asn
385                 390                 395                 400

Thr Gln Asn Ser Thr Asn Glu Lys Leu Leu Gln Ile Arg His Gln Tyr
            405                 410                 415

Asp Glu Lys Leu Ala Lys Glu Asn Asp Pro Ala Lys Arg Thr Asp Leu
            420                 425                 430

Ile Asn Glu Ala Asn Ala Lys Leu Ala Lys Thr Ala Thr Asp Ala Tyr
            435                 440                 445

Lys Glu Leu Thr Ala Lys Leu Ile Thr Glu Gln Thr Gly Asp Ser Pro
            450                 455                 460

Leu Arg Phe Gln Met Asp Pro Asn Leu
465                 470

<210> SEQ ID NO 67
<211> LENGTH: 2532
<212> TYPE: DNA
<213> ORGANISM: Lactobacillus acidophilus
<220> FEATURE:
<221> NAME/KEY: CDS
<222> LOCATION: (1)..(2532)
<223> OTHER INFORMATION: Aminopeptidase N (EC 3.4.11.2)

<400> SEQUENCE: 67 atg gca gta aaa cgt ttt tat gaa act ttc cat cca gaa cat tac gat      48
Met Ala Val Lys Arg Phe Tyr Glu Thr Phe His Pro Glu His Tyr Asp
1               5                   10                  15 tta cgt att gat gta aac cgt aaa aat aag gaa att aat ggt act tct      96
Leu Arg Ile Asp Val Asn Arg Lys Asn Lys Glu Ile Asn Gly Thr Ser
            20                  25                  30 act att act ggt gat gta gtt gag aat cca gta ttt att aat cag aag     144
Thr Ile Thr Gly Asp Val Val Glu Asn Pro Val Phe Ile Asn Gln Lys
        35                  40                  45 ttt atg act atc gac agt gtt aaa gtt gag gga aaa gac gtt gat ttt     192
Phe Met Thr Ile Asp Ser Val Lys Val Glu Gly Lys Asp Val Asp Phe
    50                  55                  60 gaa gta gtt gaa aaa gac gaa gca att aaa att gaa acc ggc gta act     240
Glu Val Val Glu Lys Asp Glu Ala Ile Lys Ile Glu Thr Gly Val Thr
65                  70                  75                  80 ggt aaa gcc atc atc gaa att gct tat agt gca cct ttg aca gat act     288
Gly Lys Ala Ile Ile Glu Ile Ala Tyr Ser Ala Pro Leu Thr Asp Thr
                85                  90                  95 atg atg ggt att tat cct tca tat tac gaa ttg gaa ggt aaa aag aag     336
Met Met Gly Ile Tyr Pro Ser Tyr Tyr Glu Leu Glu Gly Lys Lys Lys
            100                 105                 110 caa att att ggt acg caa ttt gaa acc act ttt gcg cgt caa gca ttt     384
Gln Ile Ile Gly Thr Gln Phe Glu Thr Thr Phe Ala Arg Gln Ala Phe
        115                 120                 125 ccg tgt gtt gac gaa cca gaa gct aaa gcg acc ttt acg ctt gct ctt     432
Pro Cys Val Asp Glu Pro Glu Ala Lys Ala Thr Phe Thr Leu Ala Leu
    130                 135                 140
```

-continued

| | |
|---|---|
| aaa tgg gat gaa caa gat ggc gaa att gct ctt gcc aac atg cct gaa<br>Lys Trp Asp Glu Gln Asp Gly Glu Ile Ala Leu Ala Asn Met Pro Glu<br>145                    150                   155                 160 | 480 |
| atc gaa gtt gat aaa gat ggt tac cac cat ttt gaa gaa act gtt cgt<br>Ile Glu Val Asp Lys Asp Gly Tyr His His Phe Glu Glu Thr Val Arg<br>                 165                   170                 175 | 528 |
| atg tct agt tac ctt gtt gca ttt gcc ttt ggt gaa ttg caa tca aag<br>Met Ser Ser Tyr Leu Val Ala Phe Ala Phe Gly Glu Leu Gln Ser Lys<br>            180                   185                 190 | 576 |
| act gat cat act aaa gac ggc gtt tta gta ggt gtt tat gca act aag<br>Thr Asp His Thr Lys Asp Gly Val Leu Val Gly Val Tyr Ala Thr Lys<br>        195                   200                 205 | 624 |
| gct cac aag cct aag gaa ttg gat ttt gca tta gat att gct act cgt<br>Ala His Lys Pro Lys Glu Leu Asp Phe Ala Leu Asp Ile Ala Thr Arg<br>210                    215                   220 | 672 |
| gca att gaa ttt tac gaa gac ttc tac caa act aag tac cca ctt cca<br>Ala Ile Glu Phe Tyr Glu Asp Phe Tyr Gln Thr Lys Tyr Pro Leu Pro<br>225                    230                   235                 240 | 720 |
| caa tca ttg caa ctt gca ttg cca gat ttt agt gcc ggt gcg atg gaa<br>Gln Ser Leu Gln Leu Ala Leu Pro Asp Phe Ser Ala Gly Ala Met Glu<br>                 245                   250                 255 | 768 |
| aac tgg gga ctt ata act tat cgt gaa gct tac ttg ttg ctt gat cca<br>Asn Trp Gly Leu Ile Thr Tyr Arg Glu Ala Tyr Leu Leu Leu Asp Pro<br>            260                   265                 270 | 816 |
| gac aat act agt ttg gaa atg aag aag ttg gta gct aca gtt att act<br>Asp Asn Thr Ser Leu Glu Met Lys Lys Leu Val Ala Thr Val Ile Thr<br>        275                   280                 285 | 864 |
| cac gaa ttg gct cac caa tgg ttt ggt gac tta gta acc atg aag tgg<br>His Glu Leu Ala His Gln Trp Phe Gly Asp Leu Val Thr Met Lys Trp<br>290                    295                   300 | 912 |
| tgg gat aac tta tgg ctt aac gaa agt ttt gct aac atg atg gaa tac<br>Trp Asp Asn Leu Trp Leu Asn Glu Ser Phe Ala Asn Met Met Glu Tyr<br>305                    310                   315                 320 | 960 |
| ttg tca gtt gat ggc ttg gaa cca gat tgg cac att tgg gaa atg ttc<br>Leu Ser Val Asp Gly Leu Glu Pro Asp Trp His Ile Trp Glu Met Phe<br>                 325                   330                 335 | 1008 |
| caa act aat gaa gct tct tca gca tta tca cgt gat gct aca gat ggt<br>Gln Thr Asn Glu Ala Ser Ser Ala Leu Ser Arg Asp Ala Thr Asp Gly<br>            340                   345                 350 | 1056 |
| gtt caa cca att caa atg gaa att aac gat cca gca gat att gat tca<br>Val Gln Pro Ile Gln Met Glu Ile Asn Asp Pro Ala Asp Ile Asp Ser<br>        355                   360                 365 | 1104 |
| gta ttt gat ggt gcg att gtt tat gct aag ggt tca aga atg ttg gtc<br>Val Phe Asp Gly Ala Ile Val Tyr Ala Lys Gly Ser Arg Met Leu Val<br>370                    375                   380 | 1152 |
| atg gtt cgt tca ctt ctt ggc gat gaa gct ttg aga aag ggt ctt aag<br>Met Val Arg Ser Leu Leu Gly Asp Glu Ala Leu Arg Lys Gly Leu Lys<br>385                    390                   395                 400 | 1200 |
| tac tac ttc gat cac cac aag ttt ggt aat gcc aca ggt gac gat ctt<br>Tyr Tyr Phe Asp His His Lys Phe Gly Asn Ala Thr Gly Asp Asp Leu<br>                 405                   410                 415 | 1248 |
| tgg gat gca ctt tca act gca act gac ctt aat att ggt gaa att atg<br>Trp Asp Ala Leu Ser Thr Ala Thr Asp Leu Asn Ile Gly Glu Ile Met<br>            420                   425                 430 | 1296 |
| cat tca tgg cta aaa caa cca ggt tac cca gta gtt agt gcc ttt gtt<br>His Ser Trp Leu Lys Gln Pro Gly Tyr Pro Val Val Ser Ala Phe Val<br>        435                   440                 445 | 1344 |
| gat aaa gat ggc cat ttg aag ctt act caa aag caa ttc ttc att ggt<br>Asp Lys Asp Gly His Leu Lys Leu Thr Gln Lys Gln Phe Phe Ile Gly<br>450                    455                   460 | 1392 |

-continued

```
gaa ggt gaa gat aag ggg aga tta tgg cag att cca ttg aac gct aac        1440
Glu Gly Glu Asp Lys Gly Arg Leu Trp Gln Ile Pro Leu Asn Ala Asn
465             470                 475                 480 ttt gat gct cct aag att atg tca gaa aag gaa att gat cta ggc aac        1488
Phe Asp Ala Pro Lys Ile Met Ser Glu Lys Glu Ile Asp Leu Gly Asn
                485                 490                 495 tac aag gtt ctt cgt gaa gaa gcg ggt cac cca ctt aga ctt aac gtt        1536
Tyr Lys Val Leu Arg Glu Glu Ala Gly His Pro Leu Arg Leu Asn Val
            500                 505                 510 ggt aat aat tct cac ttc atc gtt gaa tat gat gaa acc tta ctt aac        1584
Gly Asn Asn Ser His Phe Ile Val Glu Tyr Asp Glu Thr Leu Leu Asn
        515                 520                 525 gat att ttg gca gac gtt aat gca ctt gat cca atc gat aag ttg caa        1632
Asp Ile Leu Ala Asp Val Asn Ala Leu Asp Pro Ile Asp Lys Leu Gln
    530                 535                 540 tta tta caa gac ctt aga ctt tta gca gaa ggt aag caa att tct tac        1680
Leu Leu Gln Asp Leu Arg Leu Leu Ala Glu Gly Lys Gln Ile Ser Tyr
545                 550                 555                 560 gct gta att gtg cca ctt ctt act aag ttc gca gat tct aaa tca agt        1728
Ala Val Ile Val Pro Leu Leu Thr Lys Phe Ala Asp Ser Lys Ser Ser
                565                 570                 575 ttg gta att aac gct ttg tac act act gct aac aag ctt cgt caa ttt        1776
Leu Val Ile Asn Ala Leu Tyr Thr Thr Ala Asn Lys Leu Arg Gln Phe
            580                 585                 590 gtt aaa cca gaa tca gaa gaa gaa aag aac ctg aag aag ctt tac gat        1824
Val Lys Pro Glu Ser Glu Glu Glu Lys Asn Leu Lys Lys Leu Tyr Asp
        595                 600                 605 ctc tta tca aag aag caa gtt gct cgt tta ggc tgg gaa gtt aag aag        1872
Leu Leu Ser Lys Lys Gln Val Ala Arg Leu Gly Trp Glu Val Lys Lys
    610                 615                 620 ggc gaa agc gat gaa gat gct caa att cgt cca tac gaa tta agc gca        1920
Gly Glu Ser Asp Glu Asp Ala Gln Ile Arg Pro Tyr Glu Leu Ser Ala
625                 630                 635                 640 agt ctc tac gca gat aat act gat tca att aag gca gct cac caa atc        1968
Ser Leu Tyr Ala Asp Asn Thr Asp Ser Ile Lys Ala Ala His Gln Ile
                645                 650                 655 ttc act gaa aat gaa gat aac ttg gaa gca atg aac gct gat gtt cgc        2016
Phe Thr Glu Asn Glu Asp Asn Leu Glu Ala Met Asn Ala Asp Val Arg
            660                 665                 670 cca tac gtt ttg att aac gaa gta aag aat ttt gga agc cat aac tta        2064
Pro Tyr Val Leu Ile Asn Glu Val Lys Asn Phe Gly Ser His Asn Leu
        675                 680                 685 att gcc aag tta att aag gaa tac caa aga act gct gat gct tca tac        2112
Ile Ala Lys Leu Ile Lys Glu Tyr Gln Arg Thr Ala Asp Ala Ser Tyr
    690                 695                 700 aag gta gac ctt cgt tct gct att acc agc aca att gat aag gca gaa        2160
Lys Val Asp Leu Arg Ser Ala Ile Thr Ser Thr Ile Asp Lys Ala Glu
705                 710                 715                 720 gta gct aca att gta gaa gat ttc gaa aat gca gat att att aag cca        2208
Val Ala Thr Ile Val Glu Asp Phe Glu Asn Ala Asp Ile Ile Lys Pro
                725                 730                 735 caa gac ctt cgc ggc tgg tac cgc ggc tta ctt gct aac cat cat ggt        2256
Gln Asp Leu Arg Gly Trp Tyr Arg Gly Leu Leu Ala Asn His His Gly
            740                 745                 750 caa caa gct gct tgg gac tgg atc aga gaa gat tgg gac tgg ctt gat        2304
Gln Gln Ala Ala Trp Asp Trp Ile Arg Glu Asp Trp Asp Trp Leu Asp
        755                 760                 765 aag act gtt ggt ggt gac atg gaa ttt gct aca ttc atc act gtt act        2352
Lys Thr Val Gly Gly Asp Met Glu Phe Ala Thr Phe Ile Thr Val Thr
```

```
                    770                 775                 780
gct ggt gtg ttc cac act cct gaa aga ctt aag gaa ttc aag gaa ttc      2400
Ala Gly Val Phe His Thr Pro Glu Arg Leu Lys Glu Phe Lys Glu Phe
785                 790                 795                 800 ttt gaa cca aag gta aat gtt cca ctt ctt agt cgt gaa att aag atg      2448
Phe Glu Pro Lys Val Asn Val Pro Leu Leu Ser Arg Glu Ile Lys Met
            805                 810                 815 gac act aag gtt atc gaa agc aag gtt aac ttg atc gaa gct gaa aaa      2496
Asp Thr Lys Val Ile Glu Ser Lys Val Asn Leu Ile Glu Ala Glu Lys
        820                 825                 830 gat gct gta aat agc gca att gct aag gcg att gat                      2532
Asp Ala Val Asn Ser Ala Ile Ala Lys Ala Ile Asp
        835                 840

<210> SEQ ID NO 68
<211> LENGTH: 844
<212> TYPE: PRT
<213> ORGANISM: Lactobacillus acidophilus

<400> SEQUENCE: 68

Met Ala Val Lys Arg Phe Tyr Glu Thr Phe His Pro Glu His Tyr Asp
1               5                   10                  15

Leu Arg Ile Asp Val Asn Arg Lys Asn Lys Glu Ile Asn Gly Thr Ser
            20                  25                  30

Thr Ile Thr Gly Asp Val Val Glu Asn Pro Val Phe Ile Asn Gln Lys
        35                  40                  45

Phe Met Thr Ile Asp Ser Val Lys Val Glu Gly Lys Asp Val Asp Phe
    50                  55                  60

Glu Val Val Glu Lys Asp Glu Ala Ile Lys Ile Glu Thr Gly Val Thr
65                  70                  75                  80

Gly Lys Ala Ile Ile Glu Ile Ala Tyr Ser Ala Pro Leu Thr Asp Thr
                85                  90                  95

Met Met Gly Ile Tyr Pro Ser Tyr Tyr Glu Leu Glu Gly Lys Lys Lys
            100                 105                 110

Gln Ile Ile Gly Thr Gln Phe Glu Thr Thr Phe Ala Arg Gln Ala Phe
        115                 120                 125

Pro Cys Val Asp Glu Pro Glu Ala Lys Ala Thr Phe Thr Leu Ala Leu
    130                 135                 140

Lys Trp Asp Glu Gln Asp Gly Glu Ile Ala Leu Ala Asn Met Pro Glu
145                 150                 155                 160

Ile Glu Val Asp Lys Asp Gly Tyr His His Phe Glu Glu Thr Val Arg
                165                 170                 175

Met Ser Ser Tyr Leu Val Ala Phe Ala Phe Gly Glu Leu Gln Ser Lys
            180                 185                 190

Thr Asp His Thr Lys Asp Gly Val Leu Val Gly Val Tyr Ala Thr Lys
        195                 200                 205

Ala His Lys Pro Lys Glu Leu Asp Phe Ala Leu Asp Ile Ala Thr Arg
    210                 215                 220

Ala Ile Glu Phe Tyr Glu Asp Phe Tyr Gln Thr Lys Tyr Pro Leu Pro
225                 230                 235                 240

Gln Ser Leu Gln Leu Ala Leu Pro Asp Phe Ser Ala Gly Ala Met Glu
                245                 250                 255

Asn Trp Gly Leu Ile Thr Tyr Arg Glu Ala Tyr Leu Leu Asp Pro
            260                 265                 270

Asp Asn Thr Ser Leu Glu Met Lys Lys Leu Val Ala Thr Val Ile Thr
        275                 280                 285
```

-continued

```
His Glu Leu Ala His Gln Trp Phe Gly Asp Leu Val Thr Met Lys Trp
    290                 295                 300

Trp Asp Asn Leu Trp Leu Asn Glu Ser Phe Ala Asn Met Met Glu Tyr
305                 310                 315                 320

Leu Ser Val Asp Gly Leu Glu Pro Asp Trp His Ile Trp Glu Met Phe
                325                 330                 335

Gln Thr Asn Glu Ala Ser Ser Ala Leu Ser Arg Asp Ala Thr Asp Gly
            340                 345                 350

Val Gln Pro Ile Gln Met Glu Ile Asn Asp Pro Ala Asp Ile Asp Ser
        355                 360                 365

Val Phe Asp Gly Ala Ile Val Tyr Ala Lys Gly Ser Arg Met Leu Val
    370                 375                 380

Met Val Arg Ser Leu Leu Gly Asp Glu Ala Leu Arg Lys Gly Leu Lys
385                 390                 395                 400

Tyr Tyr Phe Asp His His Lys Phe Gly Asn Ala Thr Gly Asp Asp Leu
                405                 410                 415

Trp Asp Ala Leu Ser Thr Ala Thr Asp Leu Asn Ile Gly Glu Ile Met
            420                 425                 430

His Ser Trp Leu Lys Gln Pro Gly Tyr Pro Val Val Ser Ala Phe Val
        435                 440                 445

Asp Lys Asp Gly His Leu Lys Leu Thr Gln Lys Gln Phe Phe Ile Gly
    450                 455                 460

Glu Gly Glu Asp Lys Gly Arg Leu Trp Gln Ile Pro Leu Asn Ala Asn
465                 470                 475                 480

Phe Asp Ala Pro Lys Ile Met Ser Glu Lys Glu Ile Asp Leu Gly Asn
                485                 490                 495

Tyr Lys Val Leu Arg Glu Glu Ala Gly His Pro Leu Arg Leu Asn Val
            500                 505                 510

Gly Asn Asn Ser His Phe Ile Val Glu Tyr Asp Glu Thr Leu Leu Asn
        515                 520                 525

Asp Ile Leu Ala Asp Val Asn Ala Leu Asp Pro Ile Asp Lys Leu Gln
    530                 535                 540

Leu Leu Gln Asp Leu Arg Leu Leu Ala Glu Gly Lys Gln Ile Ser Tyr
545                 550                 555                 560

Ala Val Ile Val Pro Leu Leu Thr Lys Phe Ala Asp Ser Lys Ser Ser
                565                 570                 575

Leu Val Ile Asn Ala Leu Tyr Thr Thr Ala Asn Lys Leu Arg Gln Phe
            580                 585                 590

Val Lys Pro Glu Ser Glu Glu Lys Asn Leu Lys Lys Leu Tyr Asp
        595                 600                 605

Leu Leu Ser Lys Lys Gln Val Ala Arg Leu Gly Trp Glu Val Lys Lys
    610                 615                 620

Gly Glu Ser Asp Glu Asp Ala Gln Ile Arg Pro Tyr Glu Leu Ser Ala
625                 630                 635                 640

Ser Leu Tyr Ala Asp Asn Thr Asp Ser Ile Lys Ala Ala His Gln Ile
                645                 650                 655

Phe Thr Glu Asn Glu Asp Asn Leu Glu Ala Met Asn Ala Asp Val Arg
            660                 665                 670

Pro Tyr Val Leu Ile Asn Glu Val Lys Asn Phe Gly Ser His Asn Leu
        675                 680                 685

Ile Ala Lys Leu Ile Lys Glu Tyr Gln Arg Thr Ala Asp Ala Ser Tyr
    690                 695                 700
```

```
Lys Val Asp Leu Arg Ser Ala Ile Thr Ser Thr Ile Asp Lys Ala Glu
705                 710                 715                 720

Val Ala Thr Ile Val Glu Asp Phe Glu Asn Ala Asp Ile Ile Lys Pro
                725                 730                 735

Gln Asp Leu Arg Gly Trp Tyr Arg Gly Leu Leu Ala Asn His His Gly
            740                 745                 750

Gln Gln Ala Ala Trp Asp Trp Ile Arg Glu Asp Trp Asp Trp Leu Asp
        755                 760                 765

Lys Thr Val Gly Gly Asp Met Glu Phe Ala Thr Phe Ile Thr Val Thr
    770                 775                 780

Ala Gly Val Phe His Thr Pro Glu Arg Leu Lys Glu Phe Lys Glu Phe
785                 790                 795                 800

Phe Glu Pro Lys Val Asn Val Pro Leu Leu Ser Arg Glu Ile Lys Met
                805                 810                 815

Asp Thr Lys Val Ile Glu Ser Lys Val Asn Leu Ile Glu Ala Glu Lys
            820                 825                 830

Asp Ala Val Asn Ser Ala Ile Ala Lys Ala Ile Asp
        835                 840

<210> SEQ ID NO 69
<211> LENGTH: 630
<212> TYPE: DNA
<213> ORGANISM: Lactobacillus acidophilus
<220> FEATURE:
<221> NAME/KEY: CDS
<222> LOCATION: (1)..(630)
<223> OTHER INFORMATION: Signal peptidase I ORF# 1909

<400> SEQUENCE: 69 atg tct aaa caa aaa gaa gaa aat gaa tct tgg ggc aga ttt gtc ctt        48
Met Ser Lys Gln Lys Glu Glu Asn Glu Ser Trp Gly Arg Phe Val Leu
1               5                   10                  15 gat att gtg att att tgg gcc gtt ttg atg gga atc ttt ttc ctg ctc        96
Asp Ile Val Ile Ile Trp Ala Val Leu Met Gly Ile Phe Phe Leu Leu
                20                  25                  30 ttt cgt ttt gta ttg agt aac gat act gta tct ggc cca tca atg cag       144
Phe Arg Phe Val Leu Ser Asn Asp Thr Val Ser Gly Pro Ser Met Gln
            35                  40                  45 cct agt ttt gag aat ggt caa cgt tta att tct gtg cgt cat gca caa       192
Pro Ser Phe Glu Asn Gly Gln Arg Leu Ile Ser Val Arg His Ala Gln
        50                  55                  60 att aaa cgt ggc gaa gta gtc att gtt aaa gca cca gat gaa cca gga       240
Ile Lys Arg Gly Glu Val Val Ile Val Lys Ala Pro Asp Glu Pro Gly
65                  70                  75                  80 gct tta tac att aag cga gtt att ggt atg cct ggt gaa aag att gtc       288
Ala Leu Tyr Ile Lys Arg Val Ile Gly Met Pro Gly Glu Lys Ile Val
                85                  90                  95 agc aag aac aat caa atc tat att aat aac aaa aaa ttg tct caa cca       336
Ser Lys Asn Asn Gln Ile Tyr Ile Asn Asn Lys Lys Leu Ser Gln Pro
                100                 105                 110 tgg ttg act caa ggc aaa aag atg att gat gct ggt agc gat aca ttc       384
Trp Leu Thr Gln Gly Lys Lys Met Ile Asp Ala Gly Ser Asp Thr Phe
            115                 120                 125 tat tca gct act caa aac ttt aca atg aaa tct ctt gct cga tca cgc       432
Tyr Ser Ala Thr Gln Asn Phe Thr Met Lys Ser Leu Ala Arg Ser Arg
        130                 135                 140 caa ttc cag caa tat tac act aag tca caa ttg aat tat att aat aaa       480
Gln Phe Gln Gln Tyr Tyr Thr Lys Ser Gln Leu Asn Tyr Ile Asn Lys
145                 150                 155                 160
```

```
tat aat cga att cct aag gaa aca tat ttt gtg atg ggt gat cat aga       528
Tyr Asn Arg Ile Pro Lys Glu Thr Tyr Phe Val Met Gly Asp His Arg
                165                 170                 175 agt gtt tca aaa gat agt cgt tat att gga acg att aag cgt aag aat       576
Ser Val Ser Lys Asp Ser Arg Tyr Ile Gly Thr Ile Lys Arg Lys Asn
            180                 185                 190 gtt gta ggt gtg gta aaa cta aga tat tgg cca ctt aat gaa ttt aag       624
Val Val Gly Val Val Lys Leu Arg Tyr Trp Pro Leu Asn Glu Phe Lys
        195                 200                 205 att tat                                                                630
Ile Tyr
    210

<210> SEQ ID NO 70
<211> LENGTH: 210
<212> TYPE: PRT
<213> ORGANISM: Lactobacillus acidophilus

<400> SEQUENCE: 70

Met Ser Lys Gln Lys Glu Glu Asn Glu Ser Trp Gly Arg Phe Val Leu
1               5                   10                  15

Asp Ile Val Ile Ile Trp Ala Val Leu Met Gly Ile Phe Phe Leu Leu
            20                  25                  30

Phe Arg Phe Val Leu Ser Asn Asp Thr Val Ser Gly Pro Ser Met Gln
        35                  40                  45

Pro Ser Phe Glu Asn Gly Gln Arg Leu Ile Ser Val Arg His Ala Gln
    50                  55                  60

Ile Lys Arg Gly Glu Val Val Ile Val Lys Ala Pro Asp Glu Pro Gly
65                  70                  75                  80

Ala Leu Tyr Ile Lys Arg Val Ile Gly Met Pro Gly Glu Lys Ile Val
                85                  90                  95

Ser Lys Asn Asn Gln Ile Tyr Ile Asn Asn Lys Lys Leu Ser Gln Pro
            100                 105                 110

Trp Leu Thr Gln Gly Lys Lys Met Ile Asp Ala Gly Ser Asp Thr Phe
        115                 120                 125

Tyr Ser Ala Thr Gln Asn Phe Thr Met Lys Ser Leu Ala Arg Ser Arg
    130                 135                 140

Gln Phe Gln Gln Tyr Tyr Thr Lys Ser Gln Leu Asn Tyr Ile Asn Lys
145                 150                 155                 160

Tyr Asn Arg Ile Pro Lys Glu Thr Tyr Phe Val Met Gly Asp His Arg
                165                 170                 175

Ser Val Ser Lys Asp Ser Arg Tyr Ile Gly Thr Ile Lys Arg Lys Asn
            180                 185                 190

Val Val Gly Val Val Lys Leu Arg Tyr Trp Pro Leu Asn Glu Phe Lys
        195                 200                 205

Ile Tyr
    210

<210> SEQ ID NO 71
<211> LENGTH: 903
<212> TYPE: DNA
<213> ORGANISM: Lactobacillus acidophilus
<220> FEATURE:
<221> NAME/KEY: CDS
<222> LOCATION: (1)..(903)
<223> OTHER INFORMATION: Prolyl aminopeptidase (EC 3.4.11.5)

<400> SEQUENCE: 71 ttg gca atg gat caa aca aga tta gta act tta gat aat ggt tat cac        48
```

```
Leu Ala Met Asp Gln Thr Arg Leu Val Thr Leu Asp Asn Gly Tyr His
1               5                   10                  15 cta ttt aca cga aaa gtc aat gaa gga cct att aaa ctg ctt tgc tta       96
Leu Phe Thr Arg Lys Val Asn Glu Gly Pro Ile Lys Leu Leu Cys Leu
                20                  25                  30 cat ggt ggc cct ggc gga aca cat gaa act ttt gat aat ttt aaa gat      144
His Gly Gly Pro Gly Gly Thr His Glu Thr Phe Asp Asn Phe Lys Asp
            35                  40                  45 ggc tta aaa ggg caa ggc gtt gaa gtt tat tca tat gat caa tta gga      192
Gly Leu Lys Gly Gln Gly Val Glu Val Tyr Ser Tyr Asp Gln Leu Gly
    50                  55                  60 tct tac tat tct gat caa cct gat ttt act aaa aaa gaa aat aaa tca      240
Ser Tyr Tyr Ser Asp Gln Pro Asp Phe Thr Lys Lys Glu Asn Lys Ser
65                  70                  75                  80 tta ctt tct atc cct cga tat gtc gac gaa gtc gaa gaa gta aga caa      288
Leu Leu Ser Ile Pro Arg Tyr Val Asp Glu Val Glu Glu Val Arg Gln
                85                  90                  95 aag tta ggc tta gat aac ttt tac ttg ttg gga cat tca tgg ggt gga      336
Lys Leu Gly Leu Asp Asn Phe Tyr Leu Leu Gly His Ser Trp Gly Gly
            100                 105                 110 ctt ctt gct caa gaa tat gct tac aaa tat ggc aaa cac cta aag ggc      384
Leu Leu Ala Gln Glu Tyr Ala Tyr Lys Tyr Gly Lys His Leu Lys Gly
        115                 120                 125 cta gtt cta atg tca atg att gat aac tta gat gaa tat aca gaa aat      432
Leu Val Leu Met Ser Met Ile Asp Asn Leu Asp Glu Tyr Thr Glu Asn
    130                 135                 140 att aat cat gaa cgt gaa gaa act ttt tca cct gaa caa gtt gat tac      480
Ile Asn His Glu Arg Glu Glu Thr Phe Ser Pro Glu Gln Val Asp Tyr
145                 150                 155                 160 atg aaa gaa tgt gaa aaa gct gag aac ttt act gac cct atg tat cag      528
Met Lys Glu Cys Glu Lys Ala Glu Asn Phe Thr Asp Pro Met Tyr Gln
                165                 170                 175 caa tta gtt gct cat ctt tat tcc ctc ttt tta aca aga cat ccc aca      576
Gln Leu Val Ala His Leu Tyr Ser Leu Phe Leu Thr Arg His Pro Thr
            180                 185                 190 ggt aca gct cat cct gta aat act cac aat aat gtg att tac aac tat      624
Gly Thr Ala His Pro Val Asn Thr His Asn Asn Val Ile Tyr Asn Tyr
        195                 200                 205 ttc caa gga aat aat gaa ttt gtt atg gtg ggt gag ctt acc aaa tgg      672
Phe Gln Gly Asn Asn Glu Phe Val Met Val Gly Glu Leu Thr Lys Trp
    210                 215                 220 gat ttc aga gag aaa cta gca agt ttg aag atg cca act tta tta acc      720
Asp Phe Arg Glu Lys Leu Ala Ser Leu Lys Met Pro Thr Leu Leu Thr
225                 230                 235                 240 ttt gga gaa ttc gat act atg cca ctt tca gct gct cgc aga atg cat      768
Phe Gly Glu Phe Asp Thr Met Pro Leu Ser Ala Ala Arg Arg Met His
                245                 250                 255 caa aca cta agt aat tca cgc tta act tta act ccg gat ggc gga cat      816
Gln Thr Leu Ser Asn Ser Arg Leu Thr Leu Thr Pro Asp Gly Gly His
            260                 265                 270 tgt cat aat act gat aat cca aaa gca ttc ttc acg tct tta act aag      864
Cys His Asn Thr Asp Asn Pro Lys Ala Phe Phe Thr Ser Leu Thr Lys
        275                 280                 285 ttt tta cac gat gtt gag aac aac aca ttc aag gga gaa                  903
Phe Leu His Asp Val Glu Asn Asn Thr Phe Lys Gly Glu
    290                 295                 300

<210> SEQ ID NO 72
<211> LENGTH: 301
<212> TYPE: PRT
```

<213> ORGANISM: Lactobacillus acidophilus

<400> SEQUENCE: 72

| | | | | | | | | | | | | | | | |
|---|---|---|---|---|---|---|---|---|---|---|---|---|---|---|---|
| Leu | Ala | Met | Asp | Gln | Thr | Arg | Leu | Val | Thr | Leu | Asp | Asn | Gly | Tyr | His |
| 1 | | | | 5 | | | | | 10 | | | | | 15 | |
| Leu | Phe | Thr | Arg | Lys | Val | Asn | Glu | Gly | Pro | Ile | Lys | Leu | Leu | Cys | Leu |
| | | | 20 | | | | | 25 | | | | | 30 | | |
| His | Gly | Gly | Pro | Gly | Gly | Thr | His | Glu | Thr | Phe | Asp | Asn | Phe | Lys | Asp |
| | | 35 | | | | | 40 | | | | | 45 | | | |
| Gly | Leu | Lys | Gly | Gln | Gly | Val | Glu | Val | Tyr | Ser | Tyr | Asp | Gln | Leu | Gly |
| | 50 | | | | | 55 | | | | | 60 | | | | |
| Ser | Tyr | Tyr | Ser | Asp | Gln | Pro | Asp | Phe | Thr | Lys | Lys | Glu | Asn | Lys | Ser |
| 65 | | | | | 70 | | | | | 75 | | | | | 80 |
| Leu | Leu | Ser | Ile | Pro | Arg | Tyr | Val | Asp | Glu | Val | Glu | Glu | Val | Arg | Gln |
| | | | | 85 | | | | | 90 | | | | | 95 | |
| Lys | Leu | Gly | Leu | Asp | Asn | Phe | Tyr | Leu | Leu | Gly | His | Ser | Trp | Gly | Gly |
| | | | 100 | | | | | 105 | | | | | 110 | | |
| Leu | Leu | Ala | Gln | Glu | Tyr | Ala | Tyr | Lys | Tyr | Gly | Lys | His | Leu | Lys | Gly |
| | | 115 | | | | | 120 | | | | | 125 | | | |
| Leu | Val | Leu | Met | Ser | Met | Ile | Asp | Asn | Leu | Asp | Glu | Tyr | Thr | Glu | Asn |
| | 130 | | | | | 135 | | | | | 140 | | | | |
| Ile | Asn | His | Glu | Arg | Glu | Glu | Thr | Phe | Ser | Pro | Glu | Gln | Val | Asp | Tyr |
| 145 | | | | | 150 | | | | | 155 | | | | | 160 |
| Met | Lys | Glu | Cys | Glu | Lys | Ala | Glu | Asn | Phe | Thr | Asp | Pro | Met | Tyr | Gln |
| | | | | 165 | | | | | 170 | | | | | 175 | |
| Gln | Leu | Val | Ala | His | Leu | Tyr | Ser | Leu | Phe | Leu | Thr | Arg | His | Pro | Thr |
| | | | 180 | | | | | 185 | | | | | 190 | | |
| Gly | Thr | Ala | His | Pro | Val | Asn | Thr | His | Asn | Asn | Val | Ile | Tyr | Asn | Tyr |
| | | 195 | | | | | 200 | | | | | 205 | | | |
| Phe | Gln | Gly | Asn | Asn | Glu | Phe | Val | Met | Val | Gly | Glu | Leu | Thr | Lys | Trp |
| | 210 | | | | | 215 | | | | | 220 | | | | |
| Asp | Phe | Arg | Glu | Lys | Leu | Ala | Ser | Leu | Lys | Met | Pro | Thr | Leu | Leu | Thr |
| 225 | | | | | 230 | | | | | 235 | | | | | 240 |
| Phe | Gly | Glu | Phe | Asp | Thr | Met | Pro | Leu | Ser | Ala | Ala | Arg | Arg | Met | His |
| | | | | 245 | | | | | 250 | | | | | 255 | |
| Gln | Thr | Leu | Ser | Asn | Ser | Arg | Leu | Thr | Leu | Thr | Pro | Asp | Gly | Gly | His |
| | | | 260 | | | | | 265 | | | | | 270 | | |
| Cys | His | Asn | Thr | Asp | Asn | Pro | Lys | Ala | Phe | Phe | Thr | Ser | Leu | Thr | Lys |
| | | 275 | | | | | 280 | | | | | 285 | | | |
| Phe | Leu | His | Asp | Val | Glu | Asn | Asn | Thr | Phe | Lys | Gly | Glu | | | |
| | 290 | | | | | 295 | | | | | 300 | | | | |

<210> SEQ ID NO 73
<211> LENGTH: 1455
<212> TYPE: DNA
<213> ORGANISM: Lactobacillus acidophilus
<220> FEATURE:
<221> NAME/KEY: CDS
<222> LOCATION: (1)..(1455)
<223> OTHER INFORMATION: Unknown (PFAM: protease) ORF# 87

<400> SEQUENCE: 73

| | | | | | | | | | | | | | | | | |
|---|---|---|---|---|---|---|---|---|---|---|---|---|---|---|---|---|
| atg | gta | gaa | aat | aaa | tgg | ctg | cat | gct | aga | aaa | atg | gaa | gta | aga | atg | 48 |
| Met | Val | Glu | Asn | Lys | Trp | Leu | His | Ala | Arg | Lys | Met | Glu | Val | Arg | Met | |
| 1 | | | | 5 | | | | | 10 | | | | | 15 | | |
| ctg | att | att | gaa | gca | atc | tat | gtt | ttt | agc | atg | ttt | ctt | tcc | tta | gtt | 96 |
| Leu | Ile | Ile | Glu | Ala | Ile | Tyr | Val | Phe | Ser | Met | Phe | Leu | Ser | Leu | Val | |

|  |  |
|---|---|
| ttt tac ttt cca ctt ttt gtc att gaa ttt aaa att gca att gcc ttt<br>Phe Tyr Phe Pro Leu Phe Val Ile Glu Phe Lys Ile Ala Ile Ala Phe<br>            35                  40                  45 | 144 |
| act ttc ctg gta atg att gga gaa tta ttt gaa att aag ttc aaa aac<br>Thr Phe Leu Val Met Ile Gly Glu Leu Phe Glu Ile Lys Phe Lys Asn<br>50                  55                  60 | 192 |
| gaa gaa agc aaa gac aga ata gat att aag gaa cat ggt ttg atg aaa<br>Glu Glu Ser Lys Asp Arg Ile Asp Ile Lys Glu His Gly Leu Met Lys<br>65                  70                  75                  80 | 240 |
| cca tgt ttt ttt cat aag gag gaa aag cgt gtg aaa gca aaa agt tgg<br>Pro Cys Phe Phe His Lys Glu Glu Lys Arg Val Lys Ala Lys Ser Trp<br>            85                  90                  95 | 288 |
| aat tgg aat atg ata ctg aat att cag tta atc ata aat att ttg ata<br>Asn Trp Asn Met Ile Leu Asn Ile Gln Leu Ile Ile Asn Ile Leu Ile<br>                100              105              110 | 336 |
| gca gga tat tta ctg gta aga gaa aac aag aac tta gat att caa att<br>Ala Gly Tyr Leu Leu Val Arg Glu Asn Lys Asn Leu Asp Ile Gln Ile<br>                115              120              125 | 384 |
| atc ttt ggc att att ctg ttg tat ata att att gct aga tta ttc att<br>Ile Phe Gly Ile Ile Leu Leu Tyr Ile Ile Ile Ala Arg Leu Phe Ile<br>                130              135              140 | 432 |
| aaa aat cag tac ata gaa aag ttt aat ttg gta cta gaa ata atc tgc<br>Lys Asn Gln Tyr Ile Glu Lys Phe Asn Leu Val Leu Glu Ile Ile Cys<br>145                150              155              160 | 480 |
| ttg ccg att ttg tta aca tat tat ttg aat tgg cta gtc att tca ttg<br>Leu Pro Ile Leu Leu Thr Tyr Tyr Leu Asn Trp Leu Val Ile Ser Leu<br>                165              170              175 | 528 |
| gta cac ttt tta cca gca ata aaa tta gag att att acc att tat cta<br>Val His Phe Leu Pro Ala Ile Lys Leu Glu Ile Ile Thr Ile Tyr Leu<br>                180              185              190 | 576 |
| gtg gtg att ttg cta tat ttg ctt ccg aca tct gtg gtt gct ttt ggc<br>Val Val Ile Leu Leu Tyr Leu Leu Pro Thr Ser Val Val Ala Phe Gly<br>                195              200              205 | 624 |
| aaa att cat aat gga tat tta cgc att gcg gca agt atc tat ttg ttc<br>Lys Ile His Asn Gly Tyr Leu Arg Ile Ala Ala Ser Ile Tyr Leu Phe<br>                210              215              220 | 672 |
| cta gtt ttt ttg tct agt atc aac tca agc ttg tcc gta aat gtt gat<br>Leu Val Phe Leu Ser Ser Ile Asn Ser Ser Leu Ser Val Asn Val Asp<br>225                230              235              240 | 720 |
| ttt att gat aat tta ctg aag gtg aat gtt gtt tct ggc atg gct ttt<br>Phe Ile Asp Asn Leu Leu Lys Val Asn Val Val Ser Gly Met Ala Phe<br>                245              250              255 | 768 |
| cta att ttg act cca ttt ttg tta aga cag tgg gga ttc aag ttt cgg<br>Leu Ile Leu Thr Pro Phe Leu Leu Arg Gln Trp Gly Phe Lys Phe Arg<br>                260              265              270 | 816 |
| atg aat gta ttt ccc aga aag cag gaa aat ttt caa tta cta gtt tta<br>Met Asn Val Phe Pro Arg Lys Gln Glu Asn Phe Gln Leu Leu Val Leu<br>                275              280              285 | 864 |
| att tta ctg gtg ctt ttt gct gca tgg ctt aca ttt ttt aat act tac<br>Ile Leu Leu Val Leu Phe Ala Ala Trp Leu Thr Phe Phe Asn Thr Tyr<br>                290              295              300 | 912 |
| gta tat atc gcg act gtg cca gag caa tta ttc ttt aat tgg gat ttg<br>Val Tyr Ile Ala Thr Val Pro Glu Gln Leu Phe Phe Asn Trp Asp Leu<br>305                310              315              320 | 960 |
| agt att tta gct cca act caa tgg acg gta ctc aga agt gct ggt gct<br>Ser Ile Leu Ala Pro Thr Gln Trp Thr Val Leu Arg Ser Ala Gly Ala<br>                325              330              335 | 1008 |
| gcg att ttt gaa gaa act gaa cgc tat tta att ttg att tta ctc ttg | 1056 |

```
Ala Ile Phe Glu Glu Thr Glu Arg Tyr Leu Ile Leu Ile Leu Leu Leu
                340                 345                 350 tat att gca cgt aat tcc agg ttt caa att cag ata gct att ttc ttc   1104
Tyr Ile Ala Arg Asn Ser Arg Phe Gln Ile Gln Ile Ala Ile Phe Phe
            355                 360                 365 agc gct gta caa ttt ggt ctg ctt cat atg acc cac ttt ctt gat gca   1152
Ser Ala Val Gln Phe Gly Leu Leu His Met Thr His Phe Leu Asp Ala
        370                 375                 380 gat gcg aat gta tct agc att ttc tat gaa gta cta tac act ttc ggc   1200
Asp Ala Asn Val Ser Ser Ile Phe Tyr Glu Val Leu Tyr Thr Phe Gly
385                 390                 395                 400 tat ggt tgt ttt tta gct gtt ttg tac ttg tat agt ggg caa atc tgg   1248
Tyr Gly Cys Phe Leu Ala Val Leu Tyr Leu Tyr Ser Gly Gln Ile Trp
                405                 410                 415 cta tca atg ttg tcc cac ttt aca ttg gat ttg gtc tcg tac tcg gta   1296
Leu Ser Met Leu Ser His Phe Thr Leu Asp Leu Val Ser Tyr Ser Val
            420                 425                 430 ggt aat gga ggc gtc gga ttt tta tcg ctt tat ggc aac gtt gaa gga   1344
Gly Asn Gly Gly Val Gly Phe Leu Ser Leu Tyr Gly Asn Val Glu Gly
        435                 440                 445 atc ggt gca gcg tta gtt ttg gca gtt aac tta tta gtt gtc ttt ctg   1392
Ile Gly Ala Ala Leu Val Leu Ala Val Asn Leu Leu Val Val Phe Leu
450                 455                 460 atg ttg tgg gga aaa cga aaa ata gtt atg caa aat aat gcg aga ata   1440
Met Leu Trp Gly Lys Arg Lys Ile Val Met Gln Asn Asn Ala Arg Ile
465                 470                 475                 480 tta att gaa aga atc                                               1455
Leu Ile Glu Arg Ile
                485

<210> SEQ ID NO 74
<211> LENGTH: 485
<212> TYPE: PRT
<213> ORGANISM: Lactobacillus acidophilus

<400> SEQUENCE: 74

Met Val Glu Asn Lys Trp Leu His Ala Arg Lys Met Glu Val Arg Met
1               5                   10                  15

Leu Ile Ile Glu Ala Ile Tyr Val Phe Ser Met Phe Leu Ser Leu Val
            20                  25                  30

Phe Tyr Phe Pro Leu Phe Val Ile Glu Phe Lys Ile Ala Ile Ala Phe
        35                  40                  45

Thr Phe Leu Val Met Ile Gly Glu Leu Phe Glu Ile Lys Phe Lys Asn
    50                  55                  60

Glu Glu Ser Lys Asp Arg Ile Asp Ile Lys Glu His Gly Leu Met Lys
65                  70                  75                  80

Pro Cys Phe Phe His Lys Glu Lys Arg Val Lys Ala Lys Ser Trp
                85                  90                  95

Asn Trp Asn Met Ile Leu Asn Ile Gln Leu Ile Ile Asn Ile Leu Ile
            100                 105                 110

Ala Gly Tyr Leu Leu Val Arg Glu Asn Lys Asn Leu Asp Ile Gln Ile
        115                 120                 125

Ile Phe Gly Ile Ile Leu Leu Tyr Ile Ile Ala Arg Leu Phe Ile
    130                 135                 140

Lys Asn Gln Tyr Ile Glu Lys Phe Asn Leu Val Leu Glu Ile Ile Cys
145                 150                 155                 160

Leu Pro Ile Leu Leu Thr Tyr Tyr Leu Asn Trp Leu Val Ile Ser Leu
                165                 170                 175
```

```
Val His Phe Leu Pro Ala Ile Lys Leu Glu Ile Thr Ile Tyr Leu
            180                 185                 190

Val Val Ile Leu Leu Tyr Leu Leu Pro Thr Ser Val Val Ala Phe Gly
        195                 200                 205

Lys Ile His Asn Gly Tyr Leu Arg Ile Ala Ala Ser Ile Tyr Leu Phe
        210                 215                 220

Leu Val Phe Leu Ser Ser Ile Asn Ser Ser Leu Ser Val Asn Val Asp
225                 230                 235                 240

Phe Ile Asp Asn Leu Leu Lys Val Asn Val Val Ser Gly Met Ala Phe
                245                 250                 255

Leu Ile Leu Thr Pro Phe Leu Leu Arg Gln Trp Gly Phe Lys Phe Arg
            260                 265                 270

Met Asn Val Phe Pro Arg Lys Gln Glu Asn Phe Gln Leu Leu Val Leu
        275                 280                 285

Ile Leu Leu Val Leu Phe Ala Ala Trp Leu Thr Phe Phe Asn Thr Tyr
        290                 295                 300

Val Tyr Ile Ala Thr Val Pro Glu Gln Leu Phe Phe Asn Trp Asp Leu
305                 310                 315                 320

Ser Ile Leu Ala Pro Thr Gln Trp Thr Val Leu Arg Ser Ala Gly Ala
                325                 330                 335

Ala Ile Phe Glu Glu Thr Glu Arg Tyr Leu Ile Leu Ile Leu Leu Leu
            340                 345                 350

Tyr Ile Ala Arg Asn Ser Arg Phe Gln Ile Gln Ile Ala Ile Phe Phe
        355                 360                 365

Ser Ala Val Gln Phe Gly Leu Leu His Met Thr His Phe Leu Asp Ala
        370                 375                 380

Asp Ala Asn Val Ser Ser Ile Phe Tyr Glu Val Leu Tyr Thr Phe Gly
385                 390                 395                 400

Tyr Gly Cys Phe Leu Ala Val Leu Tyr Leu Tyr Ser Gly Gln Ile Trp
                405                 410                 415

Leu Ser Met Leu Ser His Phe Thr Leu Asp Leu Val Ser Tyr Ser Val
            420                 425                 430

Gly Asn Gly Gly Val Gly Phe Leu Ser Leu Tyr Gly Asn Val Glu Gly
        435                 440                 445

Ile Gly Ala Ala Leu Val Leu Ala Val Asn Leu Val Val Phe Leu
        450                 455                 460

Met Leu Trp Gly Lys Arg Lys Ile Val Met Gln Asn Asn Ala Arg Ile
465                 470                 475                 480

Leu Ile Glu Arg Ile
            485

<210> SEQ ID NO 75
<211> LENGTH: 792
<212> TYPE: DNA
<213> ORGANISM: Lactobacillus acidophilus
<220> FEATURE:
<221> NAME/KEY: CDS
<222> LOCATION: (1)..(792)
<223> OTHER INFORMATION: plnI PRF# 553

<400> SEQUENCE: 75 atg cgc aaa aac aca tta tgt tat agg aga aat aag atg att gaa aaa      48
Met Arg Lys Asn Thr Leu Cys Tyr Arg Arg Asn Lys Met Ile Glu Lys
1               5                   10                  15 cga aat ttc aag aaa tca att gct atc tgg atc tgt tta tta tta gtg      96
Arg Asn Phe Lys Lys Ser Ile Ala Ile Trp Ile Cys Leu Leu Leu Val
```

-continued

```
                20                  25                  30
tat aca ttg gct ggt cta gta ctg cga cca atc aat aat tta acc tta    144
Tyr Thr Leu Ala Gly Leu Val Leu Arg Pro Ile Asn Asn Leu Thr Leu
         35                  40                  45 cgc tta gcg atc cgt tgt ttt att gct cta gtt att aca gga ttc tgt    192
Arg Leu Ala Ile Arg Cys Phe Ile Ala Leu Val Ile Thr Gly Phe Cys
 50                  55                  60 ttt tat ttt atg cat ggc agc aag ctt tat tct aac gag ctt aat ttg    240
Phe Tyr Phe Met His Gly Ser Lys Leu Tyr Ser Asn Glu Leu Asn Leu
 65                  70                  75                  80 cga cac att aaa att tat aac act att ttt att att att gtt gct atc    288
Arg His Ile Lys Ile Tyr Asn Thr Ile Phe Ile Ile Ile Val Ala Ile
                 85                  90                  95 ttc tat tta ttt ttt cgc ctg cca att tgg att gaa tta ttt act act    336
Phe Tyr Leu Phe Phe Arg Leu Pro Ile Trp Ile Glu Leu Phe Thr Thr
            100                 105                 110 caa aga agc gga tta atc aat tct tta ctg att gca gtt tgt gca gga    384
Gln Arg Ser Gly Leu Ile Asn Ser Leu Leu Ile Ala Val Cys Ala Gly
            115                 120                 125 ttt tgt gaa gaa gcc ttg ttt aga gga atg ttg ttt aat atc tgc gct    432
Phe Cys Glu Glu Ala Leu Phe Arg Gly Met Leu Phe Asn Ile Cys Ala
        130                 135                 140 aat tat ttg aaa aaa cat cgg tat att tgg ctt gaa aca gct tta gtt    480
Asn Tyr Leu Lys Lys His Arg Tyr Ile Trp Leu Glu Thr Ala Leu Val
145                 150                 155                 160 act tca att ctt ttt gga cta atg cac tca gtc aat ttg ctt tcc agt    528
Thr Ser Ile Leu Phe Gly Leu Met His Ser Val Asn Leu Leu Ser Ser
                165                 170                 175 gag cca cta ccc tct gta ggt aca caa gtt ttt tac gct ttt gcc agc    576
Glu Pro Leu Pro Ser Val Gly Thr Gln Val Phe Tyr Ala Phe Ala Ser
            180                 185                 190 gga tta atg ttt gca tac ctg cgt tta atg tct aac cat ctt tgg cca    624
Gly Leu Met Phe Ala Tyr Leu Arg Leu Met Ser Asn His Leu Trp Pro
            195                 200                 205 gct atc ttg gct cat gct gcc ttt gat ttt aca atc gta cct aaa aat    672
Ala Ile Leu Ala His Ala Ala Phe Asp Phe Thr Ile Val Pro Lys Asn
        210                 215                 220 gcg gta ttt gca atc aac gct caa gga tta tca cta gtt tac ata att    720
Ala Val Phe Ala Ile Asn Ala Gln Gly Leu Ser Leu Val Tyr Ile Ile
225                 230                 235                 240 ttt ggt att ctt acc gtt atc tat tta ttg ttc att tgg agc ttc aac    768
Phe Gly Ile Leu Thr Val Ile Tyr Leu Leu Phe Ile Trp Ser Phe Asn
                245                 250                 255 aga ttg tac aat gaa act aaa gcc                                    792
Arg Leu Tyr Asn Glu Thr Lys Ala
            260

<210> SEQ ID NO 76
<211> LENGTH: 264
<212> TYPE: PRT
<213> ORGANISM: Lactobacillus acidophilus

<400> SEQUENCE: 76

Met Arg Lys Asn Thr Leu Cys Tyr Arg Arg Asn Lys Met Ile Glu Lys
1               5                   10                  15

Arg Asn Phe Lys Lys Ser Ile Ala Ile Trp Ile Cys Leu Leu Leu Val
            20                  25                  30

Tyr Thr Leu Ala Gly Leu Val Leu Arg Pro Ile Asn Asn Leu Thr Leu
        35                  40                  45
```

```
Arg Leu Ala Ile Arg Cys Phe Ile Ala Leu Val Ile Thr Gly Phe Cys
    50                  55                  60

Phe Tyr Phe Met His Gly Ser Lys Leu Tyr Ser Asn Glu Leu Asn Leu
 65                  70                  75                  80

Arg His Ile Lys Ile Tyr Asn Thr Ile Phe Ile Ile Val Ala Ile
                85                  90                  95

Phe Tyr Leu Phe Phe Arg Leu Pro Ile Trp Ile Glu Leu Phe Thr Thr
                100                 105                 110

Gln Arg Ser Gly Leu Ile Asn Ser Leu Leu Ile Ala Val Cys Ala Gly
            115                 120                 125

Phe Cys Glu Glu Ala Leu Phe Arg Gly Met Leu Phe Asn Ile Cys Ala
        130                 135                 140

Asn Tyr Leu Lys Lys His Arg Tyr Ile Trp Leu Glu Thr Ala Leu Val
145                 150                 155                 160

Thr Ser Ile Leu Phe Gly Leu Met His Ser Val Asn Leu Leu Ser Ser
                165                 170                 175

Glu Pro Leu Pro Ser Val Gly Thr Gln Val Phe Tyr Ala Phe Ala Ser
            180                 185                 190

Gly Leu Met Phe Ala Tyr Leu Arg Leu Met Ser Asn His Leu Trp Pro
        195                 200                 205

Ala Ile Leu Ala His Ala Ala Phe Asp Phe Thr Ile Val Pro Lys Asn
    210                 215                 220

Ala Val Phe Ala Ile Asn Ala Gln Gly Leu Ser Leu Val Tyr Ile Ile
225                 230                 235                 240

Phe Gly Ile Leu Thr Val Ile Tyr Leu Leu Phe Ile Trp Ser Phe Asn
                245                 250                 255

Arg Leu Tyr Asn Glu Thr Lys Ala
            260

<210> SEQ ID NO 77
<211> LENGTH: 858
<212> TYPE: DNA
<213> ORGANISM: Lactobacillus acidophilus
<220> FEATURE:
<221> NAME/KEY: CDS
<222> LOCATION: (1)..(858)
<223> OTHER INFORMATION: Serine protease ORF# 601

<400> SEQUENCE: 77 ttg gag gaa aaa atg aaa act ggg tta gtg tta gaa ggc ggt gca atg      48
Leu Glu Glu Lys Met Lys Thr Gly Leu Val Leu Glu Gly Gly Ala Met
 1               5                  10                  15 cgt gga tta ttt acc gct ggt gtg atc gat gtc tta atg gaa aac aag      96
Arg Gly Leu Phe Thr Ala Gly Val Ile Asp Val Leu Met Glu Asn Lys
                20                  25                  30 att aat ttt gat gta gca att gga gtt tcc gct gga gct gct ttt ggc     144
Ile Asn Phe Asp Val Ala Ile Gly Val Ser Ala Gly Ala Ala Phe Gly
            35                  40                  45 gtt aat ctg aaa tcc aaa caa att ggc cga gtt ctg cgt tat aat tta     192
Val Asn Leu Lys Ser Lys Gln Ile Gly Arg Val Leu Arg Tyr Asn Leu
        50                  55                  60 cgt ttt gca ggt aaa tct tat tat gca agt tgg aag tca tgg cgt aga     240
Arg Phe Ala Gly Lys Ser Tyr Tyr Ala Ser Trp Lys Ser Trp Arg Arg
65                  70                  75                  80 tct ggt aat ttg tat gct gct aat ttt tgc tat cat att ttg cca gat     288
Ser Gly Asn Leu Tyr Ala Ala Asn Phe Cys Tyr His Ile Leu Pro Asp
                85                  90                  95 aag tta gat att ttt gat aaa gaa act ttt atg gct aat cca atg cga     336
```

```
Lys Leu Asp Ile Phe Asp Lys Glu Thr Phe Met Ala Asn Pro Met Arg
            100                 105                 110 ttc tgt tgt gta gcg act gat gct gca acg gga gag cct gtt tat cat    384
Phe Cys Cys Val Ala Thr Asp Ala Ala Thr Gly Glu Pro Val Tyr His
            115                 120                 125 gag ttg tac gat gct ggg tat gta gat tta gag tgg att agg gca tcc    432
Glu Leu Tyr Asp Ala Gly Tyr Val Asp Leu Glu Trp Ile Arg Ala Ser
130                 135                 140 tct tca att cca ttt ttt gct cat cct gtt gct att ggt ggc cat tat    480
Ser Ser Ile Pro Phe Phe Ala His Pro Val Ala Ile Gly Gly His Tyr
145                 150                 155                 160 tat ttt gac ggc gga gtt tct gat tct att cca tat gat ttt ttg ata    528
Tyr Phe Asp Gly Gly Val Ser Asp Ser Ile Pro Tyr Asp Phe Leu Ile
                165                 170                 175 aag aac ggt gtt tct aaa agg gta gta att aca acg caa cct aaa gaa    576
Lys Asn Gly Val Ser Lys Arg Val Val Ile Thr Thr Gln Pro Lys Glu
            180                 185                 190 tat cgt aaa aag caa agt aag cta tat cca att gaa aaa att gta cta    624
Tyr Arg Lys Lys Gln Ser Lys Leu Tyr Pro Ile Glu Lys Ile Val Leu
        195                 200                 205 cgt gaa tat cct gct gtt tta aag aaa tta gct act aga gca gaa gat    672
Arg Glu Tyr Pro Ala Val Leu Lys Lys Leu Ala Thr Arg Ala Glu Asp
210                 215                 220 tat aat gcg gtt tta gat aag atg gaa gaa gat gaa aat cag ggg aat    720
Tyr Asn Ala Val Leu Asp Lys Met Glu Glu Asp Glu Asn Gln Gly Asn
225                 230                 235                 240 gca ttt att att cgt ccg cca tat ccg cta gaa att ggt act gtt gaa    768
Ala Phe Ile Ile Arg Pro Pro Tyr Pro Leu Glu Ile Gly Thr Val Glu
                245                 250                 255 caa aat aaa gaa gag att aaa cgg gta tat gag atc gga cga aaa aag    816
Gln Asn Lys Glu Glu Ile Lys Arg Val Tyr Glu Ile Gly Arg Lys Lys
            260                 265                 270 gca gaa gaa att ctg cca gat ttg gtt gaa tat ttg aaa gac              858
Ala Glu Glu Ile Leu Pro Asp Leu Val Glu Tyr Leu Lys Asp
        275                 280                 285

<210> SEQ ID NO 78
<211> LENGTH: 286
<212> TYPE: PRT
<213> ORGANISM: Lactobacillus acidophilus

<400> SEQUENCE: 78

Leu Glu Glu Lys Met Lys Thr Gly Leu Val Leu Glu Gly Gly Ala Met
1               5                   10                  15

Arg Gly Leu Phe Thr Ala Gly Val Ile Asp Val Leu Met Glu Asn Lys
            20                  25                  30

Ile Asn Phe Asp Val Ala Ile Gly Val Ser Ala Gly Ala Ala Phe Gly
        35                  40                  45

Val Asn Leu Lys Ser Lys Gln Ile Gly Arg Val Leu Arg Tyr Asn Leu
    50                  55                  60

Arg Phe Ala Gly Lys Ser Tyr Tyr Ala Ser Trp Lys Ser Trp Arg Arg
65                  70                  75                  80

Ser Gly Asn Leu Tyr Ala Ala Asn Phe Cys Tyr His Ile Leu Pro Asp
                85                  90                  95

Lys Leu Asp Ile Phe Asp Lys Glu Thr Phe Met Ala Asn Pro Met Arg
            100                 105                 110

Phe Cys Cys Val Ala Thr Asp Ala Ala Thr Gly Glu Pro Val Tyr His
        115                 120                 125
```

-continued

```
Glu Leu Tyr Asp Ala Gly Tyr Val Asp Leu Glu Trp Ile Arg Ala Ser
    130                 135                 140

Ser Ser Ile Pro Phe Phe Ala His Pro Val Ala Ile Gly Gly His Tyr
145                 150                 155                 160

Tyr Phe Asp Gly Gly Val Ser Asp Ser Ile Pro Tyr Asp Phe Leu Ile
                165                 170                 175

Lys Asn Gly Val Ser Lys Arg Val Val Ile Thr Thr Gln Pro Lys Glu
            180                 185                 190

Tyr Arg Lys Lys Gln Ser Lys Leu Tyr Pro Ile Glu Lys Ile Val Leu
        195                 200                 205

Arg Glu Tyr Pro Ala Val Leu Lys Lys Leu Ala Thr Arg Ala Glu Asp
    210                 215                 220

Tyr Asn Ala Val Leu Asp Lys Met Glu Glu Asp Glu Asn Gln Gly Asn
225                 230                 235                 240

Ala Phe Ile Ile Arg Pro Pro Tyr Pro Leu Glu Ile Gly Thr Val Glu
                245                 250                 255

Gln Asn Lys Glu Glu Ile Lys Arg Val Tyr Glu Ile Gly Arg Lys Lys
            260                 265                 270

Ala Glu Glu Ile Leu Pro Asp Leu Val Glu Tyr Leu Lys Asp
        275                 280                 285
```

```
<210> SEQ ID NO 79
<211> LENGTH: 1206
<212> TYPE: DNA
<213> ORGANISM: Lactobacillus acidophilus
<220> FEATURE:
<221> NAME/KEY: CDS
<222> LOCATION: (1)..(1206)
<223> OTHER INFORMATION: plnI ORF# 604

<400> SEQUENCE: 79
```

| | | | | | | | | | | | | | | | | |
|---|---|---|---|---|---|---|---|---|---|---|---|---|---|---|---|---|
| gtg | aag | caa | aga | aaa | atg | aac | tta | aaa | aag | tgg | gat | ttt | gga | ttt | agg | 48 |
| Val | Lys | Gln | Arg | Lys | Met | Asn | Leu | Lys | Lys | Trp | Asp | Phe | Gly | Phe | Arg | |
| 1 | | | | 5 | | | | | 10 | | | | | 15 | | |
| tat | gaa | act | gcc | atc | gtt | atc | cta | gtt | tgg | tgg | gga | atg | gca | atc | ttt | 96 |
| Tyr | Glu | Thr | Ala | Ile | Val | Ile | Leu | Val | Trp | Trp | Gly | Met | Ala | Ile | Phe | |
| | | | 20 | | | | | 25 | | | | | 30 | | | |
| aat | att | agt | aaa | gga | aaa | tca | gct | aca | gca | gga | tta | tgt | att | gca | gct | 144 |
| Asn | Ile | Ser | Lys | Gly | Lys | Ser | Ala | Thr | Ala | Gly | Leu | Cys | Ile | Ala | Ala | |
| | | 35 | | | | | 40 | | | | | 45 | | | | |
| agt | gtt | ttg | cca | gta | ctt | gtc | ttt | gtg | ttt | gat | tta | ctc | aag | cgg | cat | 192 |
| Ser | Val | Leu | Pro | Val | Leu | Val | Phe | Val | Phe | Asp | Leu | Leu | Lys | Arg | His | |
| | 50 | | | | | 55 | | | | | 60 | | | | | |
| tca | gac | aaa | tgg | aca | gtg | gca | gca | aat | tgg | ctg | gca | att | gta | tta | atg | 240 |
| Ser | Asp | Lys | Trp | Thr | Val | Ala | Ala | Asn | Trp | Leu | Ala | Ile | Val | Leu | Met | |
| 65 | | | | 70 | | | | | 75 | | | | | 80 | | |
| cca | gca | att | ttg | tcg | att | acg | tgg | tac | ata | ctt | ttt | aga | aat | att | ttg | 288 |
| Pro | Ala | Ile | Leu | Ser | Ile | Thr | Trp | Tyr | Ile | Leu | Phe | Arg | Asn | Ile | Leu | |
| | | | | 85 | | | | | 90 | | | | | 95 | | |
| cag | cat | gtc | att | ttt | aaa | atg | ttc | att | acg | atc | gtt | ttt | agt | tta | att | 336 |
| Gln | His | Val | Ile | Phe | Lys | Met | Phe | Ile | Thr | Ile | Val | Phe | Ser | Leu | Ile | |
| | | | 100 | | | | | 105 | | | | | 110 | | | |
| tta | ctg | gtg | atg | gac | tta | ccg | gtt | gca | gtt | gta | gca | att | gga | caa | ttg | 384 |
| Leu | Leu | Val | Met | Asp | Leu | Pro | Val | Ala | Val | Val | Ala | Ile | Gly | Gln | Leu | |
| | | | 115 | | | | | 120 | | | | | 125 | | | |
| aga | aat | tgg | ctt | gga | cga | tta | att | gca | gta | tgt | tat | ttc | aac | atg | gta | 432 |
| Arg | Asn | Trp | Leu | Gly | Arg | Leu | Ile | Ala | Val | Cys | Tyr | Phe | Asn | Met | Val | |
| | | 130 | | | | | 135 | | | | | 140 | | | | |
| ctt | tta | tca | tct | act | gta | att | gaa | tta | aag | ccc | cag | gga | att | aat | gtt | 480 |

-continued

```
Leu Leu Ser Ser Thr Val Ile Glu Leu Lys Pro Gln Gly Ile Asn Val
145                 150                 155                 160 tta att act tca ggc tta atg gca gca atc gct acc ttt tta gct gca     528
Leu Ile Thr Ser Gly Leu Met Ala Ala Ile Ala Thr Phe Leu Ala Ala
                165                 170                 175 ata tta att gca aaa agg tgg agc ttt agt ttt aat ccc gat ttg aaa     576
Ile Leu Ile Ala Lys Arg Trp Ser Phe Ser Phe Asn Pro Asp Leu Lys
            180                 185                 190 tgg cag ggg tca aac gta act tta att tgg ttg gta cta ttt tgt ctt     624
Trp Gln Gly Ser Asn Val Thr Leu Ile Trp Leu Val Leu Phe Cys Leu
        195                 200                 205 att ttc gcc ttc tgg gca gaa ttt tgc ggt caa gga aat agt cta gga     672
Ile Phe Ala Phe Trp Ala Glu Phe Cys Gly Gln Gly Asn Ser Leu Gly
    210                 215                 220 gaa att tta tta aaa cca gat ctt gct ccg cta aaa cca act tgg gtg     720
Glu Ile Leu Leu Lys Pro Asp Leu Ala Pro Leu Lys Pro Thr Trp Val
225                 230                 235                 240 tca ttt tgt aga gca ata gaa gca ggg gtc ttt gag gaa act aac cgc     768
Ser Phe Cys Arg Ala Ile Glu Ala Gly Val Phe Glu Glu Thr Asn Arg
                245                 250                 255 tat tta acg att tta gct ttg att gct ggt ttt gct tat agt aga tat     816
Tyr Leu Thr Ile Leu Ala Leu Ile Ala Gly Phe Ala Tyr Ser Arg Tyr
            260                 265                 270 cgg gtt caa att gct ttg att gtc agt gcc ata ttc ttt ggt tta cta     864
Arg Val Gln Ile Ala Leu Ile Val Ser Ala Ile Phe Phe Gly Leu Leu
        275                 280                 285 cat ttt act aat ttg ggt ggt caa gct ttt gcg gct acg cta aac caa     912
His Phe Thr Asn Leu Gly Gly Gln Ala Phe Ala Ala Thr Leu Asn Gln
    290                 295                 300 gct gtc tat gcc gca gca ctg ggc tta gtt ttc gca att atg tat tta     960
Ala Val Tyr Ala Ala Ala Leu Gly Leu Val Phe Ala Ile Met Tyr Leu
305                 310                 315                 320 tat act ggt aaa tta tgg cta gcc atg ttg tat cac ttc ggg atc gat    1008
Tyr Thr Gly Lys Leu Trp Leu Ala Met Leu Tyr His Phe Gly Ile Asp
                325                 330                 335 ttt ctt aat tat gca gtt aat ggt gga gtt aaa gca cag gtt tgg tct    1056
Phe Leu Asn Tyr Ala Val Asn Gly Gly Val Lys Ala Gln Val Trp Ser
            340                 345                 350 ggt acg ctt agt gat tgg gtc agc tca ttt gta tta gtt ctg gtg cca    1104
Gly Thr Leu Ser Asp Trp Val Ser Ser Phe Val Leu Val Leu Val Pro
        355                 360                 365 gta gct att gcc gtc tgg atg atg aca ggt aag aga aag caa gtt atg    1152
Val Ala Ile Ala Val Trp Met Met Thr Gly Lys Arg Lys Gln Val Met
    370                 375                 380 gat gaa aat att gat gaa aaa ttg aaa acg aat gaa tgg caa ata gga    1200
Asp Glu Asn Ile Asp Glu Lys Leu Lys Thr Asn Glu Trp Gln Ile Gly
385                 390                 395                 400 ctt agt                                                             1206
Leu Ser <210> SEQ ID NO 80
<211> LENGTH: 402
<212> TYPE: PRT
<213> ORGANISM: Lactobacillus acidophilus

<400> SEQUENCE: 80

Val Lys Gln Arg Lys Met Asn Leu Lys Lys Trp Asp Phe Gly Phe Arg
1               5                   10                  15

Tyr Glu Thr Ala Ile Val Ile Leu Val Trp Trp Gly Met Ala Ile Phe
            20                  25                  30
```

```
Asn Ile Ser Lys Gly Lys Ser Ala Thr Ala Gly Leu Cys Ile Ala Ala
         35                  40                  45

Ser Val Leu Pro Val Leu Val Phe Val Phe Asp Leu Leu Lys Arg His
 50                  55                  60

Ser Asp Lys Trp Thr Val Ala Ala Asn Trp Leu Ala Ile Val Leu Met
 65                  70                  75                  80

Pro Ala Ile Leu Ser Ile Thr Trp Tyr Ile Leu Phe Arg Asn Ile Leu
                 85                  90                  95

Gln His Val Ile Phe Lys Met Phe Ile Thr Ile Val Phe Ser Leu Ile
                100                 105                 110

Leu Leu Val Met Asp Leu Pro Val Ala Val Ala Ile Gly Gln Leu
145                 150                 155                 160

Arg Asn Trp Leu Gly Arg Leu Ile Ala Val Cys Tyr Phe Asn Met Val
        130                 135                 140

Leu Leu Ser Ser Thr Val Ile Glu Leu Lys Pro Gln Gly Ile Asn Val
145                 150                 155                 160

Leu Ile Thr Ser Gly Leu Met Ala Ala Ile Ala Thr Phe Leu Ala Ala
                165                 170                 175

Ile Leu Ile Ala Lys Arg Trp Ser Phe Ser Phe Asn Pro Asp Leu Lys
                180                 185                 190

Trp Gln Gly Ser Asn Val Thr Leu Ile Trp Leu Val Leu Phe Cys Leu
        195                 200                 205

Ile Phe Ala Phe Trp Ala Glu Phe Cys Gly Gln Gly Asn Ser Leu Gly
        210                 215                 220

Glu Ile Leu Leu Lys Pro Asp Leu Ala Pro Leu Lys Pro Thr Trp Val
225                 230                 235                 240

Ser Phe Cys Arg Ala Ile Glu Ala Gly Val Phe Glu Glu Thr Asn Arg
                245                 250                 255

Tyr Leu Thr Ile Leu Ala Leu Ile Ala Gly Phe Ala Tyr Ser Arg Tyr
                260                 265                 270

Arg Val Gln Ile Ala Leu Ile Val Ser Ala Ile Phe Phe Gly Leu Leu
        275                 280                 285

His Phe Thr Asn Leu Gly Gly Gln Ala Phe Ala Ala Thr Leu Asn Gln
        290                 295                 300

Ala Val Tyr Ala Ala Ala Leu Gly Leu Val Phe Ala Ile Met Tyr Leu
305                 310                 315                 320

Tyr Thr Gly Lys Leu Trp Leu Ala Met Leu Tyr His Phe Gly Ile Asp
                325                 330                 335

Phe Leu Asn Tyr Ala Val Asn Gly Gly Val Lys Ala Gln Val Trp Ser
                340                 345                 350

Gly Thr Leu Ser Asp Trp Val Ser Ser Phe Val Leu Val Leu Val Pro
        355                 360                 365

Val Ala Ile Ala Val Trp Met Met Thr Gly Lys Arg Lys Gln Val Met
        370                 375                 380

Asp Glu Asn Ile Asp Glu Lys Leu Lys Thr Asn Glu Trp Gln Ile Gly
385                 390                 395                 400

Leu Ser

<210> SEQ ID NO 81
<211> LENGTH: 2184
<212> TYPE: DNA
<213> ORGANISM: Lactobacillus acidophilus
<220> FEATURE:
<221> NAME/KEY: CDS
```

<222> LOCATION: (1)..(2184)
<223> OTHER INFORMATION: clpE protease ORF# 638

<400> SEQUENCE: 81

| | | | | | | | | | | | | | | | | |
|---|---|---|---|---|---|---|---|---|---|---|---|---|---|---|---|---|
| ttg | ctt | tgc | caa | aat | tgt | cat | caa | cgg | cct | gcc | gct | att | cac | ctt | ttt | 48 |
| Leu | Leu | Cys | Gln | Asn | Cys | His | Gln | Arg | Pro | Ala | Ala | Ile | His | Leu | Phe | |
| 1 | | | | 5 | | | | | 10 | | | | | 15 | | |
| aca | aag | gta | aat | ggt | caa | agc | cgt | gaa | att | gat | tta | tgt | caa | caa | tgt | 96 |
| Thr | Lys | Val | Asn | Gly | Gln | Ser | Arg | Glu | Ile | Asp | Leu | Cys | Gln | Gln | Cys | |
| | | | 20 | | | | | 25 | | | | | 30 | | | |
| tat | caa | gaa | tta | aga | aat | caa | caa | gga | aat | cta | gaa | aat | atg | aac | aac | 144 |
| Tyr | Gln | Glu | Leu | Arg | Asn | Gln | Gln | Gly | Asn | Leu | Glu | Asn | Met | Asn | Asn | |
| | | 35 | | | | | 40 | | | | | 45 | | | | |
| aat | aac | gaa | ttt | ttt | ggc | gac | ttt | gat | gat | tta | ttt | aac | gca | tta | aac | 192 |
| Asn | Asn | Glu | Phe | Phe | Gly | Asp | Phe | Asp | Asp | Leu | Phe | Asn | Ala | Leu | Asn | |
| 50 | | | | | 55 | | | | | 60 | | | | | | |
| gga | aat | aac | aac | aac | gcc | gca | aat | aac | aat | aat | aat | atg | aaa | aat | aac | 240 |
| Gly | Asn | Asn | Asn | Asn | Ala | Ala | Asn | Asn | Asn | Asn | Asn | Met | Lys | Asn | Asn | |
| 65 | | | | | 70 | | | | | 75 | | | | | 80 | |
| gac | cca | aga | atg | caa | atg | ggt | ggt | gga | aat | ggt | ggt | caa | ggt | ggt | aga | 288 |
| Asp | Pro | Arg | Met | Gln | Met | Gly | Gly | Gly | Asn | Gly | Gly | Gln | Gly | Gly | Arg | |
| | | | | 85 | | | | | 90 | | | | | 95 | | |
| agc | tta | ctt | gat | caa | tat | ggt | act | gat | tta | act | gct | ctt | gct | aaa | aaa | 336 |
| Ser | Leu | Leu | Asp | Gln | Tyr | Gly | Thr | Asp | Leu | Thr | Ala | Leu | Ala | Lys | Lys | |
| | | | | 100 | | | | | 105 | | | | | 110 | | |
| ggt | aaa | atc | gat | cca | gtt | atc | ggt | cgt | gat | aaa | gaa | atc | gct | cgc | gta | 384 |
| Gly | Lys | Ile | Asp | Pro | Val | Ile | Gly | Arg | Asp | Lys | Glu | Ile | Ala | Arg | Val | |
| | | | 115 | | | | | 120 | | | | | 125 | | | |
| att | gaa | att | tta | aac | aga | agg | act | aag | aat | aat | cca | gtt | tta | att | ggt | 432 |
| Ile | Glu | Ile | Leu | Asn | Arg | Arg | Thr | Lys | Asn | Asn | Pro | Val | Leu | Ile | Gly | |
| 130 | | | | | 135 | | | | | 140 | | | | | | |
| gaa | gcc | ggt | gtt | ggt | aag | aca | gct | gta | gtt | gaa | ggc | ctt | gct | caa | gaa | 480 |
| Glu | Ala | Gly | Val | Gly | Lys | Thr | Ala | Val | Val | Glu | Gly | Leu | Ala | Gln | Glu | |
| 145 | | | | | 150 | | | | | 155 | | | | | 160 | |
| att | gta | gat | ggt | tct | gtt | cca | gct | aaa | ctt | cag | aat | aaa | cgt | att | att | 528 |
| Ile | Val | Asp | Gly | Ser | Val | Pro | Ala | Lys | Leu | Gln | Asn | Lys | Arg | Ile | Ile | |
| | | | | 165 | | | | | 170 | | | | | 175 | | |
| tca | tta | aat | gtt | gta | tca | ctt | gtt | caa | ggt | act | ggc | att | cgt | ggt | caa | 576 |
| Ser | Leu | Asn | Val | Val | Ser | Leu | Val | Gln | Gly | Thr | Gly | Ile | Arg | Gly | Gln | |
| | | | | 180 | | | | | 185 | | | | | 190 | | |
| ttt | gaa | caa | aga | atg | gaa | caa | ttg | att | aga | gaa | tta | caa | caa | aat | gat | 624 |
| Phe | Glu | Gln | Arg | Met | Glu | Gln | Leu | Ile | Arg | Glu | Leu | Gln | Gln | Asn | Asp | |
| | | 195 | | | | | 200 | | | | | 205 | | | | |
| gat | atc | atc | ctc | ttt | att | gat | gaa | att | cat | gaa | att | gta | ggc | gcc | gga | 672 |
| Asp | Ile | Ile | Leu | Phe | Ile | Asp | Glu | Ile | His | Glu | Ile | Val | Gly | Ala | Gly | |
| | 210 | | | | | 215 | | | | | 220 | | | | | |
| aat | gcc | gaa | ggc | ggt | atg | gac | gca | ggt | aat | att | atc | aaa | cct | gct | tta | 720 |
| Asn | Ala | Glu | Gly | Gly | Met | Asp | Ala | Gly | Asn | Ile | Ile | Lys | Pro | Ala | Leu | |
| 225 | | | | | 230 | | | | | 235 | | | | | 240 | |
| gct | cgt | ggt | gaa | ctc | caa | tta | gtt | ggt | gct | act | act | att | aaa | gaa | tat | 768 |
| Ala | Arg | Gly | Glu | Leu | Gln | Leu | Val | Gly | Ala | Thr | Thr | Ile | Lys | Glu | Tyr | |
| | | | | 245 | | | | | 250 | | | | | 255 | | |
| cgt | gat | att | gaa | aaa | gat | tca | gct | tta | gca | cgt | aga | ttc | caa | cca | gtt | 816 |
| Arg | Asp | Ile | Glu | Lys | Asp | Ser | Ala | Leu | Ala | Arg | Arg | Phe | Gln | Pro | Val | |
| | | | | 260 | | | | | 265 | | | | | 270 | | |
| gaa | gta | aaa | gag | cct | tca | att | gat | gaa | acg | att | cgc | att | ttg | aag | gga | 864 |
| Glu | Val | Lys | Glu | Pro | Ser | Ile | Asp | Glu | Thr | Ile | Arg | Ile | Leu | Lys | Gly | |
| | | 275 | | | | | 280 | | | | | 285 | | | | |
| atc | caa | caa | cgt | tat | gaa | gac | tat | cat | cat | gtt | caa | tac | tcc | gat | gat | 912 |
| Ile | Gln | Gln | Arg | Tyr | Glu | Asp | Tyr | His | His | Val | Gln | Tyr | Ser | Asp | Asp | |

```
              290                 295                 300
tcc att gag tct gct gtt aaa tta tca gct aga tac att caa gat aga         960
Ser Ile Glu Ser Ala Val Lys Leu Ser Ala Arg Tyr Ile Gln Asp Arg
305                 310                 315                 320 ttc tta cct gac aag gct att gat ctt tta gat gaa gcc ggt tca aga        1008
Phe Leu Pro Asp Lys Ala Ile Asp Leu Leu Asp Glu Ala Gly Ser Arg
                325                 330                 335 atg aat tta act att cct tat att gat aaa gga aaa atg caa gaa cgt        1056
Met Asn Leu Thr Ile Pro Tyr Ile Asp Lys Gly Lys Met Gln Glu Arg
            340                 345                 350 att aac gct gca gaa caa tta aaa gag gaa tct tta aag aac gaa gac        1104
Ile Asn Ala Ala Glu Gln Leu Lys Glu Glu Ser Leu Lys Asn Glu Asp
        355                 360                 365 tac gaa aaa gca gct tat tat cgt gat caa atc gaa aaa tat gaa aag        1152
Tyr Glu Lys Ala Ala Tyr Tyr Arg Asp Gln Ile Glu Lys Tyr Glu Lys
    370                 375                 380 atg aag gat caa aaa gtt gat cct gat aaa tca cca att att acc gat        1200
Met Lys Asp Gln Lys Val Asp Pro Asp Lys Ser Pro Ile Ile Thr Asp
385                 390                 395                 400 aag att atg aac aag att gtc gaa gaa aag aca gga att cct gtt ggt        1248
Lys Ile Met Asn Lys Ile Val Glu Glu Lys Thr Gly Ile Pro Val Gly
                405                 410                 415 gat att caa aag caa gaa gaa aat caa ttg caa aac ttg gct agt gat        1296
Asp Ile Gln Lys Gln Glu Glu Asn Gln Leu Gln Asn Leu Ala Ser Asp
            420                 425                 430 tta aag tct aat gtt att ggt caa gac aag gca gtc gaa aaa gtt gct        1344
Leu Lys Ser Asn Val Ile Gly Gln Asp Lys Ala Val Glu Lys Val Ala
        435                 440                 445 cga gct att cga cgt aac aga atc ggt ttc aat aag tca gga cgt cca        1392
Arg Ala Ile Arg Arg Asn Arg Ile Gly Phe Asn Lys Ser Gly Arg Pro
    450                 455                 460 att ggt tcc ttc cta ttt gtt ggg cca acc ggt gtt ggt aag acc gaa        1440
Ile Gly Ser Phe Leu Phe Val Gly Pro Thr Gly Val Gly Lys Thr Glu
465                 470                 475                 480 tta gct aaa caa cta gcc aag caa atg ttt ggt tca gaa gat gcc atg        1488
Leu Ala Lys Gln Leu Ala Lys Gln Met Phe Gly Ser Glu Asp Ala Met
                485                 490                 495 att cgt ttc gat atg tca gaa tac atg gaa caa tat tct gtc tcc aaa        1536
Ile Arg Phe Asp Met Ser Glu Tyr Met Glu Gln Tyr Ser Val Ser Lys
            500                 505                 510 tta atc ggc tct gct cca ggt tac gta ggt tat gaa gaa gct ggt caa        1584
Leu Ile Gly Ser Ala Pro Gly Tyr Val Gly Tyr Glu Glu Ala Gly Gln
        515                 520                 525 tta act gaa caa gtt cgc cat aat cca tat agc ttg att cta ctt gat        1632
Leu Thr Glu Gln Val Arg His Asn Pro Tyr Ser Leu Ile Leu Leu Asp
    530                 535                 540 gaa att gaa aaa gct cat cca gat gtt ttg aat ctt ttc tta caa atc        1680
Glu Ile Glu Lys Ala His Pro Asp Val Leu Asn Leu Phe Leu Gln Ile
545                 550                 555                 560 tta gac gac ggc cgc tta act gac tct caa ggt aga acc gtt tca ttt        1728
Leu Asp Asp Gly Arg Leu Thr Asp Ser Gln Gly Arg Thr Val Ser Phe
                565                 570                 575 aag gat act att att att atg act tct aac gca ggc caa ggt atc aag        1776
Lys Asp Thr Ile Ile Ile Met Thr Ser Asn Ala Gly Gln Gly Ile Lys
            580                 585                 590 aat gcc agc gtt ggt ttt act gct gaa aat gat gac gaa tct agc gaa        1824
Asn Ala Ser Val Gly Phe Thr Ala Glu Asn Asp Asp Glu Ser Ser Glu
        595                 600                 605 tca gca aga aat aat atg agt caa ttc ttt aaa cca gaa ttt tta aat        1872
```

```
Ser Ala Arg Asn Asn Met Ser Gln Phe Phe Lys Pro Glu Phe Leu Asn
    610                 615                 620 cgt cta gat gat gta att gaa ttc aat gaa ttg act aag cca gac tta    1920
Arg Leu Asp Asp Val Ile Glu Phe Asn Glu Leu Thr Lys Pro Asp Leu
625                 630                 635                 640 ttg gaa att gta gat ctt atg ctt caa aac act aac aat atg gtt aag    1968
Leu Glu Ile Val Asp Leu Met Leu Gln Asn Thr Asn Asn Met Val Lys
                645                 650                 655 gat caa ggc tta cat att gac gta acc tca gct gct aaa aat aag ctt    2016
Asp Gln Gly Leu His Ile Asp Val Thr Ser Ala Ala Lys Asn Lys Leu
        660                 665                 670 gtt gaa gaa ggc ttt aat cct gct tta ggt gcc cgt cct ctt cgt cgt    2064
Val Glu Glu Gly Phe Asn Pro Ala Leu Gly Ala Arg Pro Leu Arg Arg
            675                 680                 685 aca att caa gaa gaa att gaa gat aaa gtt gca gat tac aag ctt gac    2112
Thr Ile Gln Glu Glu Ile Glu Asp Lys Val Ala Asp Tyr Lys Leu Asp
690                 695                 700 cat act gaa agt aaa aac tta aag gct gac gta att aat gat caa atc    2160
His Thr Glu Ser Lys Asn Leu Lys Ala Asp Val Ile Asn Asp Gln Ile
705                 710                 715                 720 gta atc agt gac gaa aca gct caa                                    2184
Val Ile Ser Asp Glu Thr Ala Gln
                725

<210> SEQ ID NO 82
<211> LENGTH: 728
<212> TYPE: PRT
<213> ORGANISM: Lactobacillus acidophilus

<400> SEQUENCE: 82

Leu Leu Cys Gln Asn Cys His Gln Arg Pro Ala Ala Ile His Leu Phe
1               5                   10                  15

Thr Lys Val Asn Gly Gln Ser Arg Glu Ile Asp Leu Cys Gln Gln Cys
            20                  25                  30

Tyr Gln Glu Leu Arg Asn Gln Gln Gly Asn Leu Glu Asn Met Asn Asn
        35                  40                  45

Asn Asn Glu Phe Phe Gly Asp Phe Asp Asp Leu Phe Asn Ala Leu Asn
    50                  55                  60

Gly Asn Asn Asn Ala Ala Asn Asn Asn Asn Met Lys Asn Asn
65                  70                  75                  80

Asp Pro Arg Met Gln Met Gly Gly Asn Gly Gln Gly Arg
                85                  90                  95

Ser Leu Leu Asp Gln Tyr Gly Thr Asp Leu Thr Ala Leu Ala Lys Lys
            100                 105                 110

Gly Lys Ile Asp Pro Val Ile Gly Arg Asp Lys Glu Ile Ala Arg Val
        115                 120                 125

Ile Glu Ile Leu Asn Arg Arg Thr Lys Asn Asn Pro Val Leu Ile Gly
    130                 135                 140

Glu Ala Gly Val Gly Lys Thr Ala Val Val Glu Gly Leu Ala Gln Glu
145                 150                 155                 160

Ile Val Asp Gly Ser Val Pro Ala Lys Leu Gln Asn Lys Arg Ile Ile
                165                 170                 175

Ser Leu Asn Val Val Ser Leu Val Gln Gly Thr Gly Ile Arg Gly Gln
            180                 185                 190

Phe Glu Gln Arg Met Glu Gln Leu Ile Arg Glu Leu Gln Gln Asn Asp
        195                 200                 205

Asp Ile Ile Leu Phe Ile Asp Glu Ile His Glu Ile Val Gly Ala Gly
```

-continued

```
            210                 215                 220
Asn Ala Glu Gly Gly Met Asp Ala Gly Asn Ile Ile Lys Pro Ala Leu
225                 230                 235                 240

Ala Arg Gly Glu Leu Gln Leu Val Gly Ala Thr Thr Ile Lys Glu Tyr
                245                 250                 255

Arg Asp Ile Glu Lys Asp Ser Ala Leu Ala Arg Arg Phe Gln Pro Val
                260                 265                 270

Glu Val Lys Glu Pro Ser Ile Asp Glu Thr Ile Arg Ile Leu Lys Gly
                275                 280                 285

Ile Gln Gln Arg Tyr Glu Asp Tyr His His Val Gln Tyr Ser Asp Asp
290                 295                 300

Ser Ile Glu Ser Ala Val Lys Leu Ser Ala Arg Tyr Ile Gln Asp Arg
305                 310                 315                 320

Phe Leu Pro Asp Lys Ala Ile Asp Leu Leu Asp Glu Ala Gly Ser Arg
                325                 330                 335

Met Asn Leu Thr Ile Pro Tyr Ile Asp Lys Gly Lys Met Gln Glu Arg
                340                 345                 350

Ile Asn Ala Ala Glu Gln Leu Lys Glu Ser Leu Lys Asn Glu Asp
                355                 360                 365

Tyr Glu Lys Ala Ala Tyr Tyr Arg Asp Gln Ile Glu Lys Tyr Glu Lys
                370                 375                 380

Met Lys Asp Gln Lys Val Asp Pro Asp Lys Ser Pro Ile Ile Thr Asp
385                 390                 395                 400

Lys Ile Met Asn Lys Ile Val Glu Glu Lys Thr Gly Ile Pro Val Gly
                405                 410                 415

Asp Ile Gln Lys Gln Glu Glu Asn Gln Leu Gln Asn Leu Ala Ser Asp
                420                 425                 430

Leu Lys Ser Asn Val Ile Gly Gln Asp Lys Ala Val Glu Lys Val Ala
                435                 440                 445

Arg Ala Ile Arg Arg Asn Arg Ile Gly Phe Asn Lys Ser Gly Arg Pro
                450                 455                 460

Ile Gly Ser Phe Leu Phe Val Gly Pro Thr Gly Val Gly Lys Thr Glu
465                 470                 475                 480

Leu Ala Lys Gln Leu Ala Lys Gln Met Phe Gly Ser Glu Asp Ala Met
                485                 490                 495

Ile Arg Phe Asp Met Ser Glu Tyr Met Glu Gln Tyr Ser Val Ser Lys
                500                 505                 510

Leu Ile Gly Ser Ala Pro Gly Tyr Val Gly Tyr Glu Glu Ala Gly Gln
                515                 520                 525

Leu Thr Glu Gln Val Arg His Asn Pro Tyr Ser Leu Ile Leu Leu Asp
                530                 535                 540

Glu Ile Glu Lys Ala His Pro Asp Val Leu Asn Leu Phe Leu Gln Ile
545                 550                 555                 560

Leu Asp Asp Gly Arg Leu Thr Asp Ser Gln Gly Arg Thr Val Ser Phe
                565                 570                 575

Lys Asp Thr Ile Ile Met Thr Ser Asn Ala Gly Gln Gly Ile Lys
                580                 585                 590

Asn Ala Ser Val Gly Phe Thr Ala Glu Asn Asp Asp Glu Ser Ser Glu
                595                 600                 605

Ser Ala Arg Asn Asn Met Ser Gln Phe Phe Lys Pro Glu Phe Leu Asn
                610                 615                 620

Arg Leu Asp Asp Val Ile Glu Phe Asn Glu Leu Thr Lys Pro Asp Leu
625                 630                 635                 640
```

| | | | | | | | |
|---|---|---|---|---|---|---|---|
Leu Glu Ile Val Asp Leu Met Leu Gln Asn Thr Asn Met Val Lys
                645                      650                  655

Asp Gln Gly Leu His Ile Asp Val Thr Ser Ala Ala Lys Asn Lys Leu
            660                      665                    670

Val Glu Glu Gly Phe Asn Pro Ala Leu Gly Ala Arg Pro Leu Arg Arg
            675                      680                    685

Thr Ile Gln Glu Glu Ile Glu Asp Lys Val Ala Asp Tyr Lys Leu Asp
            690                      695                    700

His Thr Glu Ser Lys Asn Leu Lys Ala Asp Val Ile Asn Asp Gln Ile
705                  710                      715                    720

Val Ile Ser Asp Glu Thr Ala Gln
            725

```
<210> SEQ ID NO 83
<211> LENGTH: 1230
<212> TYPE: DNA
<213> ORGANISM: Lactobacillus acidophilus
<220> FEATURE:
<221> NAME/KEY: CDS
<222> LOCATION: (1)..(1230)
<223> OTHER INFORMATION: Hypothetical protease ORF# 660

<400> SEQUENCE: 83
```

| | |
|---|---|
| atg aag gta att caa acg atg cta aca act aat ata aca att aga aaa<br>Met Lys Val Ile Gln Thr Met Leu Thr Thr Asn Ile Thr Ile Arg Lys<br>1                   5                      10                 15 | 48 |
| aat aaa aaa ttt aca aca gcc gga ata ggc tgt ttt ttg cgt tta ccg<br>Asn Lys Lys Phe Thr Thr Ala Gly Ile Gly Cys Phe Leu Arg Leu Pro<br>            20                      25                    30 | 96 |
| tta act aat cat aat tta gct ttt gct agt tta ctt tcg cga ttg caa<br>Leu Thr Asn His Asn Leu Ala Phe Ala Ser Leu Leu Ser Arg Leu Gln<br>                35                      40                    45 | 144 |
| atg aat act agt ttg tca tat cca aca att gct gct caa caa aga aag<br>Met Asn Thr Ser Leu Ser Tyr Pro Thr Ile Ala Ala Gln Gln Arg Lys<br> 50                      55                      60 | 192 |
| tta gcc caa tta tat gat ttg cag ctt gat att atg ccg caa ctt ttt<br>Leu Ala Gln Leu Tyr Asp Leu Gln Leu Asp Ile Met Pro Gln Leu Phe<br>65                  70                      75                    80 | 240 |
| ggc aac caa att att ttg atg tat tat gct aat ttt gtt gaa ccg att<br>Gly Asn Gln Ile Ile Leu Met Tyr Tyr Ala Asn Phe Val Glu Pro Ile<br>                        85                      90                    95 | 288 |
| gaa gta ttg gat cca gat tat act tat gaa gaa ata atc caa act att<br>Glu Val Leu Asp Pro Asp Tyr Thr Tyr Glu Glu Ile Ile Gln Thr Ile<br>            100                      105                    110 | 336 |
| agc caa att atc aga ttt cca gca tat gat aat aat tta ttc gat tat<br>Ser Gln Ile Ile Arg Phe Pro Ala Tyr Asp Asn Asn Leu Phe Asp Tyr<br>                115                      120                    125 | 384 |
| gct aaa aga caa ctt gaa gat gaa tat cgt gaa att atg gtt caa cct<br>Ala Lys Arg Gln Leu Glu Asp Glu Tyr Arg Glu Ile Met Val Gln Pro<br> 130                      135                      140 | 432 |
| tca aat tat gct ctc gat cgc ttt ttt aaa tta tgg tat gaa gat caa<br>Ser Asn Tyr Ala Leu Asp Arg Phe Phe Lys Leu Trp Tyr Glu Asp Gln<br>145                 150                      155                    160 | 480 |
| cca gaa tat gct gaa aac ttt atg ggg cca att gat gaa ata aaa aat<br>Pro Glu Tyr Ala Glu Asn Phe Met Gly Pro Ile Asp Glu Ile Lys Asn<br>                        165                      170                    175 | 528 |
| act acg att gtt gag atg cgt gat ttt att gaa aat ttg cgt gat ata<br>Thr Thr Ile Val Glu Met Arg Asp Phe Ile Glu Asn Leu Arg Asp Ile<br>                180                      185                    190 | 576 |

```
cca atg gcg gta att ggc atg gga cga gac aat caa tta atg act aaa    624
Pro Met Ala Val Ile Gly Met Gly Arg Asp Asn Gln Leu Met Thr Lys
        195                 200                 205 ata ctc aga aat att ttt aaa ggg gct gga att att aaa aaa ttc caa    672
Ile Leu Arg Asn Ile Phe Lys Gly Ala Gly Ile Ile Lys Lys Phe Gln
    210                 215                 220 gtt agt gat tta gtt att cca gct aaa aga aaa tta att gaa aaa gtt    720
Val Ser Asp Leu Val Ile Pro Ala Lys Arg Lys Leu Ile Glu Lys Val
225                 230                 235                 240 gat gag caa gac aat att caa gct caa tta ttg atg gga ttt ggt ttt    768
Asp Glu Gln Asp Asn Ile Gln Ala Gln Leu Leu Met Gly Phe Gly Phe
                245                 250                 255 aaa cag aga att agt tat caa gaa caa gtt gtt ggt ttg ctt tta gaa    816
Lys Gln Arg Ile Ser Tyr Gln Glu Gln Val Val Gly Leu Leu Leu Glu
            260                 265                 270 caa tat tta gct ggt gat cag tct tca aaa tta ttt agt cag att aga    864
Gln Tyr Leu Ala Gly Asp Gln Ser Ser Lys Leu Phe Ser Gln Ile Arg
        275                 280                 285 gaa gag tta ggt gcg gct tat gat gtt caa gca agt gac ttt gct aat    912
Glu Glu Leu Gly Ala Ala Tyr Asp Val Gln Ala Ser Asp Phe Ala Asn
    290                 295                 300 aat tct ctc ttt tta att aat gct gga att gat cct caa aaa gta gaa    960
Asn Ser Leu Phe Leu Ile Asn Ala Gly Ile Asp Pro Gln Lys Val Glu
305                 310                 315                 320 cca gcc aaa aga att att ctt aat gaa atg caa aaa tta atg gat ggt    1008
Pro Ala Lys Arg Ile Ile Leu Asn Glu Met Gln Lys Leu Met Asp Gly
                325                 330                 335 aat ata gat gaa gag cta ttt aga aaa tcc aaa aag gct gta tat cga    1056
Asn Ile Asp Glu Glu Leu Phe Arg Lys Ser Lys Lys Ala Val Tyr Arg
            340                 345                 350 aac act agg att ggg tta gac aat caa aat tgg caa tta gga cag gcc    1104
Asn Thr Arg Ile Gly Leu Asp Asn Gln Asn Trp Gln Leu Gly Gln Ala
        355                 360                 365 ttg cgt gcc gaa tta tta cca gat tat tta gat ttt gat aga gaa gct    1152
Leu Arg Ala Glu Leu Leu Pro Asp Tyr Leu Asp Phe Asp Arg Glu Ala
    370                 375                 380 gct ata aaa aaa gca acg cca cat caa tta att aat ttt gtt caa aat    1200
Ala Ile Lys Lys Ala Thr Pro His Gln Leu Ile Asn Phe Val Gln Asn
385                 390                 395                 400 tta ttc ttt aat gaa agt tat att tta aaa                            1230
Leu Phe Phe Asn Glu Ser Tyr Ile Leu Lys
                405                 410

<210> SEQ ID NO 84
<211> LENGTH: 410
<212> TYPE: PRT
<213> ORGANISM: Lactobacillus acidophilus

<400> SEQUENCE: 84

Met Lys Val Ile Gln Thr Met Leu Thr Thr Asn Ile Thr Ile Arg Lys
1               5                   10                  15

Asn Lys Lys Phe Thr Thr Ala Gly Ile Gly Cys Phe Leu Arg Leu Pro
            20                  25                  30

Leu Thr Asn His Asn Leu Ala Phe Ala Ser Leu Leu Ser Arg Leu Gln
        35                  40                  45

Met Asn Thr Ser Leu Ser Tyr Pro Thr Ile Ala Ala Gln Gln Arg Lys
    50                  55                  60

Leu Ala Gln Leu Tyr Asp Leu Gln Leu Asp Ile Met Pro Gln Leu Phe
65                  70                  75                  80
```

Gly Asn Gln Ile Ile Leu Met Tyr Tyr Ala Asn Phe Val Glu Pro Ile
               85                  90                  95

Glu Val Leu Asp Pro Asp Tyr Thr Tyr Glu Ile Ile Gln Thr Ile
               100                 105                 110

Ser Gln Ile Ile Arg Phe Pro Ala Tyr Asp Asn Leu Phe Asp Tyr
               115                 120                 125

Ala Lys Arg Gln Leu Glu Asp Glu Tyr Arg Glu Ile Met Val Gln Pro
130                 135                 140

Ser Asn Tyr Ala Leu Asp Arg Phe Phe Lys Leu Trp Tyr Glu Asp Gln
145                 150                 155                 160

Pro Glu Tyr Ala Glu Asn Phe Met Gly Pro Ile Asp Glu Ile Lys Asn
                165                 170                 175

Thr Thr Ile Val Glu Met Arg Asp Phe Ile Glu Asn Leu Arg Asp Ile
                180                 185                 190

Pro Met Ala Val Ile Gly Met Gly Arg Asp Asn Gln Leu Met Thr Lys
                195                 200                 205

Ile Leu Arg Asn Ile Phe Lys Gly Ala Gly Ile Ile Lys Lys Phe Gln
210                 215                 220

Val Ser Asp Leu Val Ile Pro Ala Lys Arg Lys Leu Ile Glu Lys Val
225                 230                 235                 240

Asp Glu Gln Asp Asn Ile Gln Ala Gln Leu Leu Met Gly Phe Gly Phe
                245                 250                 255

Lys Gln Arg Ile Ser Tyr Gln Glu Gln Val Val Gly Leu Leu Leu Glu
                260                 265                 270

Gln Tyr Leu Ala Gly Asp Gln Ser Ser Lys Leu Phe Ser Gln Ile Arg
                275                 280                 285

Glu Glu Leu Gly Ala Ala Tyr Asp Val Gln Ala Ser Asp Phe Ala Asn
                290                 295                 300

Asn Ser Leu Phe Leu Ile Asn Ala Gly Ile Asp Pro Gln Lys Val Glu
305                 310                 315                 320

Pro Ala Lys Arg Ile Ile Leu Asn Glu Met Gln Lys Leu Met Asp Gly
                325                 330                 335

Asn Ile Asp Glu Glu Leu Phe Arg Lys Ser Lys Lys Ala Val Tyr Arg
                340                 345                 350

Asn Thr Arg Ile Gly Leu Asp Asn Gln Asn Trp Gln Leu Gly Gln Ala
                355                 360                 365

Leu Arg Ala Glu Leu Leu Pro Asp Tyr Leu Asp Phe Asp Arg Glu Ala
370                 375                 380

Ala Ile Lys Lys Ala Thr Pro His Gln Leu Ile Asn Phe Val Gln Asn
385                 390                 395                 400

Leu Phe Phe Asn Glu Ser Tyr Ile Leu Lys
                405                 410

<210> SEQ ID NO 85
<211> LENGTH: 1251
<212> TYPE: DNA
<213> ORGANISM: Lactobacillus acidophilus
<220> FEATURE:
<221> NAME/KEY: CDS
<222> LOCATION: (1)..(1251)
<223> OTHER INFORMATION: Protease ORF# 661

<400> SEQUENCE: 85 atg att aca cct aaa att ata aaa aga gaa tat aaa tct ggc ttt aaa    48
Met Ile Thr Pro Lys Ile Ile Lys Arg Glu Tyr Lys Ser Gly Phe Lys
1               5                   10                  15

-continued

```
gca gaa gtt atc tta aaa ccg cat ttt tat cag cgt ttt ttt ggt att      96
Ala Glu Val Ile Leu Lys Pro His Phe Tyr Gln Arg Phe Phe Gly Ile
         20                  25                  30 att atc gac ttt ggt agt agt gat gca caa aaa ata gct ggg tca gcc     144
Ile Ile Asp Phe Gly Ser Ser Asp Ala Gln Lys Ile Ala Gly Ser Ala
     35                  40                  45 cat ttt tta gaa cat aaa tta ttt gct aaa aaa gat ggc gat att tca     192
His Phe Leu Glu His Lys Leu Phe Ala Lys Lys Asp Gly Asp Ile Ser
 50                  55                  60 cat aag ttt gaa gaa att ggt gcg gat gtt aat gca ttt aca tca ttt     240
His Lys Phe Glu Glu Ile Gly Ala Asp Val Asn Ala Phe Thr Ser Phe
 65                  70                  75                  80 aat gaa act atg ttt tat tgc agt ggt att gac cat acg cct aaa atg     288
Asn Glu Thr Met Phe Tyr Cys Ser Gly Ile Asp His Thr Pro Lys Met
                 85                  90                  95 ctc gat ttg ttg ttt gaa tta gtt gga aaa cca tac ttt act aag caa     336
Leu Asp Leu Leu Phe Glu Leu Val Gly Lys Pro Tyr Phe Thr Lys Gln
            100                 105                 110 aat att gct caa gaa gcc cca att att caa caa gaa ttg gct atg tat     384
Asn Ile Ala Gln Glu Ala Pro Ile Ile Gln Gln Glu Leu Ala Met Tyr
        115                 120                 125 aaa aat gat ccg att tgg agt ata aat aat gcg att atg act gca atg     432
Lys Asn Asp Pro Ile Trp Ser Ile Asn Asn Ala Ile Met Thr Ala Met
    130                 135                 140 ttt gat cat tca aat tta ggt act gaa gtt gtg gga aca gaa aaa tcg     480
Phe Asp His Ser Asn Leu Gly Thr Glu Val Val Gly Thr Glu Lys Ser
145                 150                 155                 160 att aat gag att act gtt caa aac tta act aag gca tat aag aat aac     528
Ile Asn Glu Ile Thr Val Gln Asn Leu Thr Lys Ala Tyr Lys Asn Asn
                165                 170                 175 tat ata cca agt aaa atg cag ttt gta gca tgc ggt gat ttt tca gat     576
Tyr Ile Pro Ser Lys Met Gln Phe Val Ala Cys Gly Asp Phe Ser Asp
            180                 185                 190 aat caa gtc caa aca att tta cgt aca gtt ggt aag ctg caa gaa aag     624
Asn Gln Val Gln Thr Ile Leu Arg Thr Val Gly Lys Leu Gln Glu Lys
        195                 200                 205 tac ttt caa aat aga aaa gcg act cca act aaa att gaa atg cca att     672
Tyr Phe Gln Asn Arg Lys Ala Thr Pro Thr Lys Ile Glu Met Pro Ile
    210                 215                 220 gga aat tta aag gat caa gtt att cct act aaa agt ggt tct aat gtt     720
Gly Asn Leu Lys Asp Gln Val Ile Pro Thr Lys Ser Gly Ser Asn Val
225                 230                 235                 240 ttt gga ttg ggt att cgt ttt aaa aat ttt aag aaa gta tta tca agc     768
Phe Gly Leu Gly Ile Arg Phe Lys Asn Phe Lys Lys Val Leu Ser Ser
                245                 250                 255 ttt gat ttg act caa att ctg tta gaa ata atg tta gaa tca aaa cta     816
Phe Asp Leu Thr Gln Ile Leu Leu Glu Ile Met Leu Glu Ser Lys Leu
            260                 265                 270 agt gta atg ggc cca tgg ttt gaa agg atg cga aaa aat aag tta tta     864
Ser Val Met Gly Pro Trp Phe Glu Arg Met Arg Lys Asn Lys Leu Leu
        275                 280                 285 act aat cca ctt caa att tcg gtt aat tac act aga cag ggt gat ttt     912
Thr Asn Pro Leu Gln Ile Ser Val Asn Tyr Thr Arg Gln Gly Asp Phe
    290                 295                 300 gca acc att ttt ggt act agt ccg caa gga cag gaa gta att aat gaa     960
Ala Thr Ile Phe Gly Thr Ser Pro Gln Gly Gln Glu Val Ile Asn Glu
305                 310                 315                 320 ata aag cat gtt tta act aag cca tta gtt aaa aat tct gaa caa tat    1008
Ile Lys His Val Leu Thr Lys Pro Leu Val Lys Asn Ser Glu Gln Tyr
                325                 330                 335
```

```
cgc ttt atc gaa gaa aat ttt gaa ttg caa aaa aga gaa tgg cat gca      1056
Arg Phe Ile Glu Glu Asn Phe Glu Leu Gln Lys Arg Glu Trp His Ala
            340                 345                 350 cgc act gtc aga aca att aat aat ctt tca tca tat gct att gaa atg      1104
Arg Thr Val Arg Thr Ile Asn Asn Leu Ser Ser Tyr Ala Ile Glu Met
        355                 360                 365 gta gaa gaa aat tta gat cat gaa gac tta gat tta aat tta aag aaa      1152
Val Glu Glu Asn Leu Asp His Glu Asp Leu Asp Leu Asn Leu Lys Lys
    370                 375                 380 tta caa gca atg ggt ttt gaa gaa ttc tat caa act tgt caa tta att      1200
Leu Gln Ala Met Gly Phe Glu Glu Phe Tyr Gln Thr Cys Gln Leu Ile
385                 390                 395                 400 atg aaa gat agt gca att tgt tcc gct tat tta gat cct aac agg gag      1248
Met Lys Asp Ser Ala Ile Cys Ser Ala Tyr Leu Asp Pro Asn Arg Glu
                405                 410                 415 gga                                                                  1251
Gly
```

<210> SEQ ID NO 86
<211> LENGTH: 417
<212> TYPE: PRT
<213> ORGANISM: Lactobacillus acidophilus

<400> SEQUENCE: 86

```
Met Ile Thr Pro Lys Ile Ile Lys Arg Glu Tyr Lys Ser Gly Phe Lys
1               5                   10                  15

Ala Glu Val Ile Leu Lys Pro His Phe Tyr Gln Arg Phe Phe Gly Ile
            20                  25                  30

Ile Ile Asp Phe Gly Ser Ser Asp Ala Gln Lys Ile Ala Gly Ser Ala
        35                  40                  45

His Phe Leu Glu His Lys Leu Phe Ala Lys Lys Asp Gly Asp Ile Ser
    50                  55                  60

His Lys Phe Glu Glu Ile Gly Ala Asp Val Asn Ala Phe Thr Ser Phe
65                  70                  75                  80

Asn Glu Thr Met Phe Tyr Cys Ser Gly Ile Asp His Thr Pro Lys Met
                85                  90                  95

Leu Asp Leu Leu Phe Glu Leu Val Gly Lys Pro Tyr Phe Thr Lys Gln
            100                 105                 110

Asn Ile Ala Gln Glu Ala Pro Ile Ile Gln Gln Glu Leu Ala Met Tyr
        115                 120                 125

Lys Asn Asp Pro Ile Trp Ser Ile Asn Asn Ala Ile Met Thr Ala Met
    130                 135                 140

Phe Asp His Ser Asn Leu Gly Thr Glu Val Val Gly Thr Glu Lys Ser
145                 150                 155                 160

Ile Asn Glu Ile Thr Val Gln Asn Leu Thr Lys Ala Tyr Lys Asn Asn
                165                 170                 175

Tyr Ile Pro Ser Lys Met Gln Phe Val Ala Cys Gly Asp Phe Ser Asp
            180                 185                 190

Asn Gln Val Gln Thr Ile Leu Arg Thr Val Gly Lys Leu Gln Glu Lys
        195                 200                 205

Tyr Phe Gln Asn Arg Lys Ala Thr Pro Thr Lys Ile Glu Met Pro Ile
    210                 215                 220

Gly Asn Leu Lys Asp Gln Val Ile Pro Thr Lys Ser Gly Ser Asn Val
225                 230                 235                 240

Phe Gly Leu Gly Ile Arg Phe Lys Asn Phe Lys Lys Val Leu Ser Ser
                245                 250                 255
```

```
Phe Asp Leu Thr Gln Ile Leu Leu Glu Ile Met Leu Glu Ser Lys Leu
            260                 265                 270

Ser Val Met Gly Pro Trp Phe Glu Arg Met Arg Lys Asn Lys Leu Leu
        275                 280                 285

Thr Asn Pro Leu Gln Ile Ser Val Asn Tyr Thr Arg Gln Gly Asp Phe
    290                 295                 300

Ala Thr Ile Phe Gly Thr Ser Pro Gln Gly Gln Glu Val Ile Asn Glu
305                 310                 315                 320

Ile Lys His Val Leu Thr Lys Pro Leu Val Lys Asn Ser Glu Gln Tyr
                325                 330                 335

Arg Phe Ile Glu Glu Asn Phe Glu Leu Gln Lys Arg Glu Trp His Ala
            340                 345                 350

Arg Thr Val Arg Thr Ile Asn Asn Leu Ser Ser Tyr Ala Ile Glu Met
        355                 360                 365

Val Glu Glu Asn Leu Asp His Glu Asp Leu Asp Leu Asn Leu Lys Lys
    370                 375                 380

Leu Gln Ala Met Gly Phe Glu Glu Phe Tyr Gln Thr Cys Gln Leu Ile
385                 390                 395                 400

Met Lys Asp Ser Ala Ile Cys Ser Ala Tyr Leu Asp Pro Asn Arg Glu
                405                 410                 415

Gly

<210> SEQ ID NO 87
<211> LENGTH: 591
<212> TYPE: DNA
<213> ORGANISM: Lactobacillus acidophilus
<220> FEATURE:
<221> NAME/KEY: CDS
<222> LOCATION: (1)..(591)
<223> OTHER INFORMATION: Hypothetical PFAM protease ORF# 1808

<400> SEQUENCE: 87 gtg cta ctg ctc ctt ttc tca gct tat ttc cca ttt ttt aat gtg ttt      48
Val Leu Leu Leu Leu Phe Ser Ala Tyr Phe Pro Phe Phe Asn Val Phe
1               5                   10                  15 ttg ggg ata gca caa aca ccg gta caa atc ttt aac tgg gat ttt agt      96
Leu Gly Ile Ala Gln Thr Pro Val Gln Ile Phe Asn Trp Asp Phe Ser
            20                  25                  30 act ttt gaa gta acg ttg act gga ttt ctt tca gca gta gaa gcc gga     144
Thr Phe Glu Val Thr Leu Thr Gly Phe Leu Ser Ala Val Glu Ala Gly
        35                  40                  45 atc atg gaa gaa acg caa cgt tgt tta gat att gtt gta ctt tta ttt     192
Ile Met Glu Glu Thr Gln Arg Cys Leu Asp Ile Val Val Leu Leu Phe
    50                  55                  60 gtc ttt cgt aat ttt aaa gga aaa gta gtg tgg gct acc gta att tct     240
Val Phe Arg Asn Phe Lys Gly Lys Val Val Trp Ala Thr Val Ile Ser
65                  70                  75                  80 tca cta tta ttt agc ttg gat cat ttg act aat ttg ggt tca acg caa     288
Ser Leu Leu Phe Ser Leu Asp His Leu Thr Asn Leu Gly Ser Thr Gln
                85                  90                  95 ttt ggc gtt ctt tat aat ttg aca aaa gtt gaa cag caa atg atc tat     336
Phe Gly Val Leu Tyr Asn Leu Thr Lys Val Glu Gln Gln Met Ile Tyr
            100                 105                 110 acc ttt gga ttt ggc atg tta gct gca gtt tgt tac tta tat act ggt     384
Thr Phe Gly Phe Gly Met Leu Ala Ala Val Cys Tyr Leu Tyr Thr Gly
        115                 120                 125 aaa tta tgg tta agc atg ttg gtt cac ttt ggc tta gat ttc att gtc     432
Lys Leu Trp Leu Ser Met Leu Val His Phe Gly Leu Asp Phe Ile Val
```

```
                130                 135                 140
ttt agt gaa acg cca tta act gtg tcg ata tct cca ttt ttt gat aat        480
Phe Ser Glu Thr Pro Leu Thr Val Ser Ile Ser Pro Phe Phe Asp Asn
145                 150                 155                 160 tgg gct tgt gct ttt att gta atg gca gca tca tcc ttg gta gcc atc        528
Trp Ala Cys Ala Phe Ile Val Met Ala Ala Ser Ser Leu Val Ala Ile
                165                 170                 175 ttc atg tta tta gga aaa aga tgt aag ttt atg gat gat aat gca gat        576
Phe Met Leu Leu Gly Lys Arg Cys Lys Phe Met Asp Asp Asn Ala Asp
                180                 185                 190 aga att atg aaa atg                                                    591
Arg Ile Met Lys Met
        195

<210> SEQ ID NO 88
<211> LENGTH: 197
<212> TYPE: PRT
<213> ORGANISM: Lactobacillus acidophilus

<400> SEQUENCE: 88

Val Leu Leu Leu Leu Phe Ser Ala Tyr Phe Pro Phe Phe Asn Val Phe
1               5                   10                  15

Leu Gly Ile Ala Gln Thr Pro Val Gln Ile Phe Asn Trp Asp Phe Ser
                20                  25                  30

Thr Phe Glu Val Thr Leu Thr Gly Phe Leu Ser Ala Val Glu Ala Gly
                35                  40                  45

Ile Met Glu Glu Thr Gln Arg Cys Leu Asp Ile Val Val Leu Leu Phe
50                  55                  60

Val Phe Arg Asn Phe Lys Gly Lys Val Val Trp Ala Thr Val Ile Ser
65                  70                  75                  80

Ser Leu Leu Phe Ser Leu Asp His Leu Thr Asn Leu Gly Ser Thr Gln
                85                  90                  95

Phe Gly Val Leu Tyr Asn Leu Thr Lys Val Glu Gln Gln Met Ile Tyr
                100                 105                 110

Thr Phe Gly Phe Gly Met Leu Ala Ala Val Leu Tyr Leu Tyr Thr Gly
                115                 120                 125

Lys Leu Trp Leu Ser Met Leu Val His Phe Gly Leu Asp Phe Ile Val
130                 135                 140

Phe Ser Glu Thr Pro Leu Thr Val Ser Ile Ser Pro Phe Phe Asp Asn
145                 150                 155                 160

Trp Ala Cys Ala Phe Ile Val Met Ala Ala Ser Ser Leu Val Ala Ile
                165                 170                 175

Phe Met Leu Leu Gly Lys Arg Cys Lys Phe Met Asp Asp Asn Ala Asp
                180                 185                 190

Arg Ile Met Lys Met
        195

<210> SEQ ID NO 89
<211> LENGTH: 1194
<212> TYPE: DNA
<213> ORGANISM: Lactobacillus acidophilus
<220> FEATURE:
<221> NAME/KEY: CDS
<222> LOCATION: (1)..(1194)
<223> OTHER INFORMATION: Hypothetical PFAM protease ORF# 1810

<400> SEQUENCE: 89 atg aaa aat aga att tat caa ttg att tta aaa att caa ttg ata gta        48
Met Lys Asn Arg Ile Tyr Gln Leu Ile Leu Lys Ile Gln Leu Ile Val
```

```
1               5                  10                 15
gga ata ctg ctc atg ctt tgc ctt aat ctg aat gtg gta cat aca ttt    96
Gly Ile Leu Leu Met Leu Cys Leu Asn Leu Asn Val Val His Thr Phe
            20                  25                  30 aag atg cct aaa cta gta tat cca act att cta tgt gca tta gta gta   144
Lys Met Pro Lys Leu Val Tyr Pro Thr Ile Leu Cys Ala Leu Val Val
        35                  40                  45 ata ttt gtt ttg act ctc ttt gaa aat aaa aac cgt tat ata cag gca   192
Ile Phe Val Leu Thr Leu Phe Glu Asn Lys Asn Arg Tyr Ile Gln Ala
    50                  55                  60 gcg gca aaa tgg ctt ggc gtt cta gca tta cca tat gca tct aat ttc   240
Ala Ala Lys Trp Leu Gly Val Leu Ala Leu Pro Tyr Ala Ser Asn Phe
65                  70                  75                  80 tta gtt tat act gga att tca gtt ctt aat att gca ttt cca agc tat   288
Leu Val Tyr Thr Gly Ile Ser Val Leu Asn Ile Ala Phe Pro Ser Tyr
                85                  90                  95 gca atg ttt ttc tca atc ata ggc tgt att ctt tta ctt gta gta aat   336
Ala Met Phe Phe Ser Ile Ile Gly Cys Ile Leu Leu Leu Val Val Asn
            100                 105                 110 att ccc tgg gta atg gtt gat ttg ccg ata gta aag aat ggt ttt ctc   384
Ile Pro Trp Val Met Val Asp Leu Pro Ile Val Lys Asn Gly Phe Leu
        115                 120                 125 cgt gtg cta agt atc gct ctt att gat atg agc ttt aca ttt aat gcc   432
Arg Val Leu Ser Ile Ala Leu Ile Asp Met Ser Phe Thr Phe Asn Ala
    130                 135                 140 aat gac ttt att aat ttg ccg gag tcg ctt cat ttt ctt gta tac gat   480
Asn Asp Phe Ile Asn Leu Pro Glu Ser Leu His Phe Leu Val Tyr Asp
145                 150                 155                 160 gcc gtg ata gtt gcc ata gaa atc ttt gtt tta ggc ttt ttt att acg   528
Ala Val Ile Val Ala Ile Glu Ile Phe Val Leu Gly Phe Phe Ile Thr
                165                 170                 175 aag gca tgg ggc ttg aaa ttc agt tgg aat ttg aag ttt gtt aaa aca   576
Lys Ala Trp Gly Leu Lys Phe Ser Trp Asn Leu Lys Phe Val Lys Thr
            180                 185                 190 agt aat ttt caa tta gga tcc tgg att gta tta att ctg gta atg atc   624
Ser Asn Phe Gln Leu Gly Ser Trp Ile Val Leu Ile Leu Val Met Ile
        195                 200                 205 tgg ctt att ttc ttt aat acg tat tta aat ctt gta aat aac tgg gca   672
Trp Leu Ile Phe Phe Asn Thr Tyr Leu Asn Leu Val Asn Asn Trp Ala
    210                 215                 220 gaa ttg ctt gct ttt tgg aac tgg aat agc ttt gaa att tca tat cac   720
Glu Leu Leu Ala Phe Trp Asn Trp Asn Ser Phe Glu Ile Ser Tyr His
225                 230                 235                 240 ttt act gca gat ata gtg agt ttt gca gct aga gcg ggt att tat gag   768
Phe Thr Ala Asp Ile Val Ser Phe Ala Ala Arg Ala Gly Ile Tyr Glu
                245                 250                 255 gaa atg ttt cgc gga cta gaa ata att gtt ttg ctt tat gct atg cgt   816
Glu Met Phe Arg Gly Leu Glu Ile Ile Val Leu Leu Tyr Ala Met Arg
            260                 265                 270 aac ttc aaa gac aga ata atg gtg gct gta gta ata tca gct att ttg   864
Asn Phe Lys Asp Arg Ile Met Val Ala Val Val Ile Ser Ala Ile Leu
        275                 280                 285 ttc agt tta ggg cat ttg agt aat ctg ggt act att acc aat ggt act   912
Phe Ser Leu Gly His Leu Ser Asn Leu Gly Thr Ile Thr Asn Gly Thr
    290                 295                 300 ttt tat tct gct gat atg atg gcg cag caa ctt ata tat gcg ttt ggt   960
Phe Tyr Ser Ala Asp Met Met Ala Gln Gln Leu Ile Tyr Ala Phe Gly
305                 310                 315                 320 ctg ggc ttg gcg ttt ggt gta ctg tat ttg tat act gga aaa tta tgg  1008
```

```
Leu Gly Leu Ala Phe Gly Val Leu Tyr Leu Tyr Thr Gly Lys Leu Trp
                325                 330                 335 cta ggg atg ctg atc cac ttt ttg tat gat tta gag act ttg agt act    1056
Leu Gly Met Leu Ile His Phe Leu Tyr Asp Leu Glu Thr Leu Ser Thr
                340                 345                 350 gat gtc aca aca ggc ttg ttt aca ggt tgg ccg gct tca att atg ttg    1104
Asp Val Thr Thr Gly Leu Phe Thr Gly Trp Pro Ala Ser Ile Met Leu
            355                 360                 365 tta atc att ggc gta gcg att ttt gtc tgg atg tta aca ggt aag aga    1152
Leu Ile Ile Gly Val Ala Ile Phe Val Trp Met Leu Thr Gly Lys Arg
        370                 375                 380 cgt aag ttc atg gaa gat aat gta gat cga att gtt ggc gga            1194
Arg Lys Phe Met Glu Asp Asn Val Asp Arg Ile Val Gly Gly
385                 390                 395

<210> SEQ ID NO 90
<211> LENGTH: 398
<212> TYPE: PRT
<213> ORGANISM: Lactobacillus acidophilus

<400> SEQUENCE: 90

Met Lys Asn Arg Ile Tyr Gln Leu Ile Leu Lys Ile Gln Leu Ile Val
1               5                   10                  15

Gly Ile Leu Leu Met Leu Cys Leu Asn Leu Asn Val Val His Thr Phe
            20                  25                  30

Lys Met Pro Lys Leu Val Tyr Pro Thr Ile Leu Cys Ala Leu Val Val
        35                  40                  45

Ile Phe Val Leu Thr Leu Phe Glu Asn Lys Asn Arg Tyr Ile Gln Ala
    50                  55                  60

Ala Ala Lys Trp Leu Gly Val Leu Ala Leu Pro Tyr Ala Ser Asn Phe
65                  70                  75                  80

Leu Val Tyr Thr Gly Ile Ser Val Leu Asn Ile Ala Phe Pro Ser Tyr
                85                  90                  95

Ala Met Phe Phe Ser Ile Ile Gly Cys Ile Leu Leu Leu Val Val Asn
            100                 105                 110

Ile Pro Trp Val Met Val Asp Leu Pro Ile Val Lys Asn Gly Phe Leu
        115                 120                 125

Arg Val Leu Ser Ile Ala Leu Ile Asp Met Ser Phe Thr Phe Asn Ala
    130                 135                 140

Asn Asp Phe Ile Asn Leu Pro Glu Ser Leu His Phe Leu Val Tyr Asp
145                 150                 155                 160

Ala Val Ile Val Ala Ile Glu Ile Phe Val Leu Gly Phe Phe Ile Thr
                165                 170                 175

Lys Ala Trp Gly Leu Lys Phe Ser Trp Asn Leu Lys Phe Val Lys Thr
            180                 185                 190

Ser Asn Phe Gln Leu Gly Ser Trp Ile Val Leu Ile Leu Val Met Ile
        195                 200                 205

Trp Leu Ile Phe Phe Asn Thr Tyr Leu Asn Leu Val Asn Asn Trp Ala
    210                 215                 220

Glu Leu Leu Ala Phe Trp Asn Trp Asn Ser Phe Glu Ile Ser Tyr His
225                 230                 235                 240

Phe Thr Ala Asp Ile Val Ser Phe Ala Ala Arg Ala Gly Ile Tyr Glu
                245                 250                 255

Glu Met Phe Arg Gly Leu Glu Ile Ile Val Leu Leu Tyr Ala Met Arg
            260                 265                 270

Asn Phe Lys Asp Arg Ile Met Val Ala Val Val Ile Ser Ala Ile Leu
```

-continued

```
                275                 280                 285
Phe Ser Leu Gly His Leu Ser Asn Leu Gly Thr Ile Thr Asn Gly Thr
    290                 295                 300

Phe Tyr Ser Ala Asp Met Met Ala Gln Gln Leu Ile Tyr Ala Phe Gly
305                 310                 315                 320

Leu Gly Leu Ala Phe Gly Val Leu Tyr Leu Tyr Thr Gly Lys Leu Trp
                325                 330                 335

Leu Gly Met Leu Ile His Phe Leu Tyr Asp Leu Glu Thr Leu Ser Thr
                340                 345                 350

Asp Val Thr Thr Gly Leu Phe Thr Gly Trp Pro Ala Ser Ile Met Leu
                355                 360                 365

Leu Ile Ile Gly Val Ala Ile Phe Val Trp Met Leu Thr Gly Lys Arg
    370                 375                 380

Arg Lys Phe Met Glu Asp Asn Val Asp Arg Ile Val Gly Gly
385                 390                 395

<210> SEQ ID NO 91
<211> LENGTH: 651
<212> TYPE: DNA
<213> ORGANISM: Lactobacillus acidophilus
<220> FEATURE:
<221> NAME/KEY: CDS
<222> LOCATION: (1)..(651)
<223> OTHER INFORMATION: Hypothetical PFAM protease ORF# 1937

<400> SEQUENCE: 91 atg aga aaa ttt tgg cat tac ctg gga aat att gca ggg ata att gtc       48
Met Arg Lys Phe Trp His Tyr Leu Gly Asn Ile Ala Gly Ile Ile Val
1               5                   10                  15 gca tta att tta tat agt agg ctt gag ata ttc tat ttt gct ccg caa       96
Ala Leu Ile Leu Tyr Ser Arg Leu Glu Ile Phe Tyr Phe Ala Pro Gln
            20                  25                  30 agg ata cat tta ggt aat ctt cgt gtt ata gta act gct tta gta act      144
Arg Ile His Leu Gly Asn Leu Arg Val Ile Val Thr Ala Leu Val Thr
        35                  40                  45 gtc gca att tta ttt gtg att ttt tat tta tat cga agt cag tta aga      192
Val Ala Ile Leu Phe Val Ile Phe Tyr Leu Tyr Arg Ser Gln Leu Arg
    50                  55                  60 gaa aga aat tat tgg gga ttt aat gag agt cct cac tgg gat atg aga      240
Glu Arg Asn Tyr Trp Gly Phe Asn Glu Ser Pro His Trp Asp Met Arg
65                  70                  75                  80 aga att gga ata gct gcg att ggt ttt gta tta att acg atc ggc tca      288
Arg Ile Gly Ile Ala Ala Ile Gly Phe Val Leu Ile Thr Ile Gly Ser
                85                  90                  95 att gta atg tta aat ata gtg ggt ggc ggt gtt tcc gaa aat cag cag      336
Ile Val Met Leu Asn Ile Val Gly Gly Gly Val Ser Glu Asn Gln Gln
            100                 105                 110 gct tta aat aga atc cag caa cag aat act gga atg ttt aag att ctg      384
Ala Leu Asn Arg Ile Gln Gln Gln Asn Thr Gly Met Phe Lys Ile Leu
        115                 120                 125 gta gta ttc att gca ccg ttt tgc gaa gaa aca att ttt aga ggg atg      432
Val Val Phe Ile Ala Pro Phe Cys Glu Glu Thr Ile Phe Arg Gly Met
    130                 135                 140 ttt ttc aat atc ttc ttt act aaa cct acg cgt ttg aat aag tgg ctg      480
Phe Phe Asn Ile Phe Phe Thr Lys Pro Thr Arg Leu Asn Lys Trp Leu
145                 150                 155                 160 gga ata gtt aca agt ggc ttt ttg ttt ggc tac atg cat gat ccg atg      528
Gly Ile Val Thr Ser Gly Phe Leu Phe Gly Tyr Met His Asp Pro Met
                165                 170                 175
```

```
tta agc aga ttt att ttt gta tat tgg gtg ttg ggg ata gtc tta gcc      576
Leu Ser Arg Phe Ile Phe Val Tyr Trp Val Leu Gly Ile Val Leu Ala
        180                 185                 190 tgg gta tat acg aca act aag gac ttg cgc tat tcg atg ctg gta cac      624
Trp Val Tyr Thr Thr Thr Lys Asp Leu Arg Tyr Ser Met Leu Val His
            195                 200                 205 atg tgt tat aac gca tta ggt ttt att                                  651
Met Cys Tyr Asn Ala Leu Gly Phe Ile
    210                 215

<210> SEQ ID NO 92
<211> LENGTH: 217
<212> TYPE: PRT
<213> ORGANISM: Lactobacillus acidophilus

<400> SEQUENCE: 92

Met Arg Lys Phe Trp His Tyr Leu Gly Asn Ile Ala Gly Ile Ile Val
1               5                   10                  15

Ala Leu Ile Leu Tyr Ser Arg Leu Glu Ile Phe Tyr Phe Ala Pro Gln
            20                  25                  30

Arg Ile His Leu Gly Asn Leu Arg Val Ile Val Thr Ala Leu Val Thr
        35                  40                  45

Val Ala Ile Leu Phe Val Ile Phe Tyr Leu Tyr Arg Ser Gln Leu Arg
    50                  55                  60

Glu Arg Asn Tyr Trp Gly Phe Asn Glu Ser Pro His Trp Asp Met Arg
65                  70                  75                  80

Arg Ile Gly Ile Ala Ala Ile Gly Phe Val Leu Ile Thr Ile Gly Ser
                85                  90                  95

Ile Val Met Leu Asn Ile Val Gly Gly Gly Val Ser Glu Asn Gln Gln
            100                 105                 110

Ala Leu Asn Arg Ile Gln Gln Gln Asn Thr Gly Met Phe Lys Ile Leu
        115                 120                 125

Val Val Phe Ile Ala Pro Phe Cys Glu Glu Thr Ile Phe Arg Gly Met
    130                 135                 140

Phe Phe Asn Ile Phe Phe Thr Lys Pro Thr Arg Leu Asn Lys Trp Leu
145                 150                 155                 160

Gly Ile Val Thr Ser Gly Phe Leu Phe Gly Tyr Met His Asp Pro Met
                165                 170                 175

Leu Ser Arg Phe Ile Phe Val Tyr Trp Val Leu Gly Ile Val Leu Ala
            180                 185                 190

Trp Val Tyr Thr Thr Thr Lys Asp Leu Arg Tyr Ser Met Leu Val His
        195                 200                 205

Met Cys Tyr Asn Ala Leu Gly Phe Ile
    210                 215

<210> SEQ ID NO 93
<211> LENGTH: 540
<212> TYPE: DNA
<213> ORGANISM: Lactobacillus acidophilus
<220> FEATURE:
<221> NAME/KEY: CDS
<222> LOCATION: (1)..(540)
<223> OTHER INFORMATION: Cell envelope-associated protease ORF# 1235

<400> SEQUENCE: 93 atg aaa ata gca gat att att ata cgg ggg gta gga act atg tta aaa      48
Met Lys Ile Ala Asp Ile Ile Ile Arg Gly Val Gly Thr Met Leu Lys
1               5                   10                  15 aag aaa ata atc tat ctt gca gga gta gca ttg ttc aca gct gga tta      96
Lys Lys Ile Ile Tyr Leu Ala Gly Val Ala Leu Phe Thr Ala Gly Leu
```

```
                Lys Lys Ile Ile Tyr Leu Ala Gly Val Ala Leu Phe Thr Ala Gly Leu
                            20                  25                  30 ggg gta gca gcc aat act cat ata aca gaa gct gct gtt gct aat cct             144
Gly Val Ala Ala Asn Thr His Ile Thr Glu Ala Ala Val Ala Asn Pro
         35                  40                  45 att aag caa gga aaa aaa tta agt ttg act aga agt aca tac gtc tat             192
Ile Lys Gln Gly Lys Lys Leu Ser Leu Thr Arg Ser Thr Tyr Val Tyr
 50                  55                  60 aat aaa gat ggt gtt aga gtt gga cgc tta aag aaa ggg aat ctt tgc             240
Asn Lys Asp Gly Val Arg Val Gly Arg Leu Lys Lys Gly Asn Leu Cys
 65                  70                  75                  80 aaa gtt tat atc att aaa gtg att aat ggg aat agt tat gtt aag gtt             288
Lys Val Tyr Ile Ile Lys Val Ile Asn Gly Asn Ser Tyr Val Lys Val
                 85                  90                  95 ggc aag aat aga ttt gta aaa caa gag gca ttt tta cca tat gta aaa             336
Gly Lys Asn Arg Phe Val Lys Gln Glu Ala Phe Leu Pro Tyr Val Lys
             100                 105                 110 tct acg gct aag gta gag aat caa att aaa aaa tct tca ttt gtt tat             384
Ser Thr Ala Lys Val Glu Asn Gln Ile Lys Lys Ser Ser Phe Val Tyr
         115                 120                 125 gat gaa aat ggt gaa aaa ata cca ggc aaa ttt gtc aag cgt ggg gaa             432
Asp Glu Asn Gly Glu Lys Ile Pro Gly Lys Phe Val Lys Arg Gly Glu
130                 135                 140 aaa gta aac tat tta ggt cat aaa gaa att aat gaa aag cca ttt atc             480
Lys Val Asn Tyr Leu Gly His Lys Glu Ile Asn Glu Lys Pro Phe Ile
145                 150                 155                 160 aaa att ggt gat ggc gaa tat gtt aaa gct ttt aat gtt tta act att             528
Lys Ile Gly Asp Gly Glu Tyr Val Lys Ala Phe Asn Val Leu Thr Ile
                 165                 170                 175 atg att aat aac                                                             540
Met Ile Asn Asn
            180

<210> SEQ ID NO 94
<211> LENGTH: 180
<212> TYPE: PRT
<213> ORGANISM: Lactobacillus acidophilus

<400> SEQUENCE: 94

Met Lys Ile Ala Asp Ile Ile Arg Gly Val Gly Thr Met Leu Lys
 1               5                  10                  15

Lys Lys Ile Ile Tyr Leu Ala Gly Val Ala Leu Phe Thr Ala Gly Leu
             20                  25                  30

Gly Val Ala Ala Asn Thr His Ile Thr Glu Ala Ala Val Ala Asn Pro
         35                  40                  45

Ile Lys Gln Gly Lys Lys Leu Ser Leu Thr Arg Ser Thr Tyr Val Tyr
 50                  55                  60

Asn Lys Asp Gly Val Arg Val Gly Arg Leu Lys Lys Gly Asn Leu Cys
 65                  70                  75                  80

Lys Val Tyr Ile Ile Lys Val Ile Asn Gly Asn Ser Tyr Val Lys Val
                 85                  90                  95

Gly Lys Asn Arg Phe Val Lys Gln Glu Ala Phe Leu Pro Tyr Val Lys
             100                 105                 110

Ser Thr Ala Lys Val Glu Asn Gln Ile Lys Lys Ser Ser Phe Val Tyr
         115                 120                 125

Asp Glu Asn Gly Glu Lys Ile Pro Gly Lys Phe Val Lys Arg Gly Glu
130                 135                 140

Lys Val Asn Tyr Leu Gly His Lys Glu Ile Asn Glu Lys Pro Phe Ile
```

```
                145                 150                 155                 160
Lys Ile Gly Asp Gly Glu Tyr Val Lys Ala Phe Asn Val Leu Thr Ile
                165                 170                 175

Met Ile Asn Asn
            180

<210> SEQ ID NO 95
<211> LENGTH: 198
<212> TYPE: DNA
<213> ORGANISM: Lactobacillus acidophilus
<220> FEATURE:
<221> NAME/KEY: CDS
<222> LOCATION: (1)..(198)
<223> OTHER INFORMATION: Cell envelope protease ORF# 1378

<400> SEQUENCE: 95 atg aga aga gac tta cat aat tta gac gta ggg gac gtt aaa gaa aaa      48
Met Arg Arg Asp Leu His Asn Leu Asp Val Gly Asp Val Lys Glu Lys
1               5                   10                  15 caa cgt ttt tca att cgc aag tta act gta ggt act gct agt gta ttg      96
Gln Arg Phe Ser Ile Arg Lys Leu Thr Val Gly Thr Ala Ser Val Leu
            20                  25                  30 ctg ggt act aca ttc ttg ttt ggt gca ggt cag act gct tac gct gat     144
Leu Gly Thr Thr Phe Leu Phe Gly Ala Gly Gln Thr Ala Tyr Ala Asp
        35                  40                  45 act act gct tca ggt gct att act agt gaa gat tcc caa aac caa att     192
Thr Thr Ala Ser Gly Ala Ile Thr Ser Glu Asp Ser Gln Asn Gln Ile
    50                  55                  60 ggg ggg                                                              198
Gly Gly
65

<210> SEQ ID NO 96
<211> LENGTH: 66
<212> TYPE: PRT
<213> ORGANISM: Lactobacillus acidophilus

<400> SEQUENCE: 96

Met Arg Arg Asp Leu His Asn Leu Asp Val Gly Asp Val Lys Glu Lys
1               5                   10                  15

Gln Arg Phe Ser Ile Arg Lys Leu Thr Val Gly Thr Ala Ser Val Leu
            20                  25                  30

Leu Gly Thr Thr Phe Leu Phe Gly Ala Gly Gln Thr Ala Tyr Ala Asp
        35                  40                  45

Thr Thr Ala Ser Gly Ala Ile Thr Ser Glu Asp Ser Gln Asn Gln Ile
    50                  55                  60

Gly Gly
65

<210> SEQ ID NO 97
<211> LENGTH: 1398
<212> TYPE: DNA
<213> ORGANISM: Lactobacillus acidophilus
<220> FEATURE:
<221> NAME/KEY: CDS
<222> LOCATION: (1)..(1398)
<223> OTHER INFORMATION: Cytosol non-specific dipeptidase
      (EC3.4.13.18) ORF# 35

<400> SEQUENCE: 97 atg cca tgt aca aca att tta gcc ggt aaa aag gct act gca gac ggt      48
Met Pro Cys Thr Thr Ile Leu Ala Gly Lys Lys Ala Thr Ala Asp Gly
1               5                   10                  15
```

```
tca acc tta gtt gcc aga aac gaa gac tat ggt cac gca ttt aat ccc      96
Ser Thr Leu Val Ala Arg Asn Glu Asp Tyr Gly His Ala Phe Asn Pro
        20                  25                  30 aag cgt ttt atc gtt gta acg cca gac aag caa cct aag gat tat caa     144
Lys Arg Phe Ile Val Val Thr Pro Asp Lys Gln Pro Lys Asp Tyr Gln
    35                  40                  45 tct gta act tct aaa tgc aag gtg gat ttg cca gat aat cca atg cgt     192
Ser Val Thr Ser Lys Cys Lys Val Asp Leu Pro Asp Asn Pro Met Arg
50                  55                  60 tac acc gct gtg cct gaa ctt gaa tca act atc aaa aaa gta ggc tgg     240
Tyr Thr Ala Val Pro Glu Leu Glu Ser Thr Ile Lys Lys Val Gly Trp
65                  70                  75                  80 tgg ggt gaa gca ggt att aac gaa gca aac gtt gct atg tct gct act     288
Trp Gly Glu Ala Gly Ile Asn Glu Ala Asn Val Ala Met Ser Ala Thr
                85                  90                  95 gaa act agc act act aat tca cgt gta tta ggt atc gat cca atg aat     336
Glu Thr Ser Thr Thr Asn Ser Arg Val Leu Gly Ile Asp Pro Met Asn
            100                 105                 110 aaa aag ggt atc ggt gaa gaa gac ttt gtt act atc gtt ttg cct tac     384
Lys Lys Gly Ile Gly Glu Glu Asp Phe Val Thr Ile Val Leu Pro Tyr
        115                 120                 125 att cgt tct gct cgt gaa ggt gtg aag cta tta ggt aaa tac tta gaa     432
Ile Arg Ser Ala Arg Glu Gly Val Lys Leu Leu Gly Lys Tyr Leu Glu
    130                 135                 140 aaa tac ggt acc tac gaa tca aat ggt gtt gcc ttc tcg gat aaa gat     480
Lys Tyr Gly Thr Tyr Glu Ser Asn Gly Val Ala Phe Ser Asp Lys Asp
145                 150                 155                 160 gaa gtt tgg tac atg gaa act att ggt ggt cgt cac tgg gcc gct att     528
Glu Val Trp Tyr Met Glu Thr Ile Gly Gly Arg His Trp Ala Ala Ile
                165                 170                 175 aag gtg cca gat gat agt tat atc gtt gca ccg aac tgg ttt agc att     576
Lys Val Pro Asp Asp Ser Tyr Ile Val Ala Pro Asn Trp Phe Ser Ile
            180                 185                 190 acc aat ttt gac ttt aat agt gac gat aca atg gct tca gat gat ttg     624
Thr Asn Phe Asp Phe Asn Ser Asp Asp Thr Met Ala Ser Asp Asp Leu
        195                 200                 205 gaa aag atg att caa gat aat cac atg gat att gat cat agt ggt aat     672
Glu Lys Met Ile Gln Asp Asn His Met Asp Ile Asp His Ser Gly Asn
    210                 215                 220 cca tat aat ttg cgt cat atc ttc ggc agt cat gac gat tca gat tat     720
Pro Tyr Asn Leu Arg His Ile Phe Gly Ser His Asp Asp Ser Asp Tyr
225                 230                 235                 240 gaa tac aat att cca cgt caa tgg tat att caa aag ctg ttc aat ccg     768
Glu Tyr Asn Ile Pro Arg Gln Trp Tyr Ile Gln Lys Leu Phe Asn Pro
                245                 250                 255 agc gat gtt cat gaa cct gat gat cca gat ttg cca ttt gct aaa aag     816
Ser Asp Val His Glu Pro Asp Asp Pro Asp Leu Pro Phe Ala Lys Lys
            260                 265                 270 cca gag cat tta ctt act att gaa gac tta aag tat gct ttg tca tca     864
Pro Glu His Leu Leu Thr Ile Glu Asp Leu Lys Tyr Ala Leu Ser Ser
        275                 280                 285 cac tat caa cac act aaa tac gat cca tac ggc tta gag ggc aca gat     912
His Tyr Gln His Thr Lys Tyr Asp Pro Tyr Gly Leu Glu Gly Thr Asp
    290                 295                 300 gcg gat cgc cac gct ttt cgt cca att ggc tta caa cgt aat caa gaa     960
Ala Asp Arg His Ala Phe Arg Pro Ile Gly Leu Gln Arg Asn Gln Glu
305                 310                 315                 320 tta tct att tta caa att aga aat gat gtc cca gcc aaa att gct ggt    1008
Leu Ser Ile Leu Gln Ile Arg Asn Asp Val Pro Ala Lys Ile Ala Gly
```

-continued

```
                    325                 330                 335
gtg caa tgg att gcc ttt gga cct aat act ttt aat ggt att gca cca      1056
Val Gln Trp Ile Ala Phe Gly Pro Asn Thr Phe Asn Gly Ile Ala Pro
                340                 345                 350 tac tat acc aac gtt ctt gat acg ccg gaa aca tat cgt gat act aaa      1104
Tyr Tyr Thr Asn Val Leu Asp Thr Pro Glu Thr Tyr Arg Asp Thr Lys
                355                 360                 365 gag cat ttc aat att caa aac atg tat tgg tta act cat gca att act      1152
Glu His Phe Asn Ile Gln Asn Met Tyr Trp Leu Thr His Ala Ile Thr
            370                 375                 380 aca att gct gat gag cac cca ttc cgc tac agt gct tcg att gaa gca      1200
Thr Ile Ala Asp Glu His Pro Phe Arg Tyr Ser Ala Ser Ile Glu Ala
385                 390                 395                 400 atg aag caa agc act tta gct gct ggt cgt cat gtt ttg ctt gaa acc      1248
Met Lys Gln Ser Thr Leu Ala Ala Gly Arg His Val Leu Leu Glu Thr
                405                 410                 415 gat caa gaa gtt caa gaa ctt gcc ggt gaa gaa tta caa aga aaa ctt      1296
Asp Gln Glu Val Gln Glu Leu Ala Gly Glu Glu Leu Gln Arg Lys Leu
                420                 425                 430 caa cag gct aat gat aaa act gct aaa gct gct tat gat acc gca atg      1344
Gln Gln Ala Asn Asp Lys Thr Ala Lys Ala Ala Tyr Asp Thr Ala Met
            435                 440                 445 aaa tgc ttt ggc gaa tgt gtt gag act gga tca ctt aag atc aga ttg      1392
Lys Cys Phe Gly Glu Cys Val Glu Thr Gly Ser Leu Lys Ile Arg Leu
450                 455                 460 aat tat                                                              1398
Asn Tyr
465
```

<210> SEQ ID NO 98
<211> LENGTH: 466
<212> TYPE: PRT
<213> ORGANISM: Lactobacillus acidophilus

<400> SEQUENCE: 98

```
Met Pro Cys Thr Thr Ile Leu Ala Gly Lys Lys Ala Thr Ala Asp Gly
1               5                   10                  15

Ser Thr Leu Val Ala Arg Asn Glu Asp Tyr Gly His Ala Phe Asn Pro
            20                  25                  30

Lys Arg Phe Ile Val Val Thr Pro Asp Lys Gln Pro Lys Asp Tyr Gln
        35                  40                  45

Ser Val Thr Ser Lys Cys Lys Val Asp Leu Pro Asp Asn Pro Met Arg
    50                  55                  60

Tyr Thr Ala Val Pro Glu Leu Glu Ser Thr Ile Lys Lys Val Gly Trp
65                  70                  75                  80

Trp Gly Glu Ala Gly Ile Asn Glu Ala Asn Val Ala Met Ser Ala Thr
                85                  90                  95

Glu Thr Ser Thr Thr Asn Ser Arg Val Leu Gly Ile Asp Pro Met Asn
            100                 105                 110

Lys Lys Gly Ile Gly Glu Glu Asp Phe Val Thr Ile Val Leu Pro Tyr
        115                 120                 125

Ile Arg Ser Ala Arg Glu Gly Val Lys Leu Leu Gly Lys Tyr Leu Glu
    130                 135                 140

Lys Tyr Gly Thr Tyr Glu Ser Asn Gly Val Ala Phe Ser Asp Lys Asp
145                 150                 155                 160

Glu Val Trp Tyr Met Glu Thr Ile Gly Gly Arg His Trp Ala Ala Ile
                165                 170                 175
```

-continued

```
Lys Val Pro Asp Asp Ser Tyr Ile Val Ala Pro Asn Trp Phe Ser Ile
            180                 185                 190

Thr Asn Phe Asp Phe Asn Ser Asp Asp Thr Met Ala Ser Asp Asp Leu
        195                 200                 205

Glu Lys Met Ile Gln Asp Asn His Met Asp Ile Asp His Ser Gly Asn
    210                 215                 220

Pro Tyr Asn Leu Arg His Ile Phe Gly Ser His Asp Ser Asp Tyr
225                 230                 235                 240

Glu Tyr Asn Ile Pro Arg Gln Trp Tyr Ile Gln Lys Leu Phe Asn Pro
                245                 250                 255

Ser Asp Val His Glu Pro Asp Pro Asp Leu Pro Phe Ala Lys Lys
            260                 265                 270

Pro Glu His Leu Leu Thr Ile Glu Asp Leu Lys Tyr Ala Leu Ser Ser
        275                 280                 285

His Tyr Gln His Thr Lys Tyr Asp Pro Tyr Gly Leu Glu Gly Thr Asp
    290                 295                 300

Ala Asp Arg His Ala Phe Arg Pro Ile Gly Leu Gln Arg Asn Gln Glu
305                 310                 315                 320

Leu Ser Ile Leu Gln Ile Arg Asn Asp Val Pro Ala Lys Ile Ala Gly
                325                 330                 335

Val Gln Trp Ile Ala Phe Gly Pro Asn Thr Phe Asn Gly Ile Ala Pro
            340                 345                 350

Tyr Tyr Thr Asn Val Leu Asp Thr Pro Glu Thr Tyr Arg Asp Thr Lys
        355                 360                 365

Glu His Phe Asn Ile Gln Asn Met Tyr Trp Leu Thr His Ala Ile Thr
    370                 375                 380

Thr Ile Ala Asp Glu His Pro Phe Arg Tyr Ser Ala Ser Ile Glu Ala
385                 390                 395                 400

Met Lys Gln Ser Thr Leu Ala Ala Gly Arg His Val Leu Leu Glu Thr
                405                 410                 415

Asp Gln Glu Val Gln Glu Leu Ala Gly Glu Glu Leu Gln Arg Lys Leu
            420                 425                 430

Gln Gln Ala Asn Asp Lys Thr Ala Lys Ala Ala Tyr Asp Thr Ala Met
        435                 440                 445

Lys Cys Phe Gly Glu Cys Val Glu Thr Gly Ser Leu Lys Ile Arg Leu
    450                 455                 460

Asn Tyr
465
```

<210> SEQ ID NO 99
<211> LENGTH: 894
<212> TYPE: DNA
<213> ORGANISM: Lactobacillus acidophilus
<220> FEATURE:
<221> NAME/KEY: CDS
<222> LOCATION: (1)..(894)
<223> OTHER INFORMATION: htpX heat shock protease ORF# 96

<400> SEQUENCE: 99

```
atg ttg tac caa caa att gcc cgt aac aag cgt aaa act gcg cta att      48
Met Leu Tyr Gln Gln Ile Ala Arg Asn Lys Arg Lys Thr Ala Leu Ile
1               5                   10                  15 atg gtt ctt ttt gtg gta atc ttg acc tta gtt ggt gct gga ctg ggc      96
Met Val Leu Phe Val Val Ile Leu Thr Leu Val Gly Ala Gly Leu Gly
            20                  25                  30 tat ctt ttt agc aat agt cca tgg acg gga ata atc att gca tta gct     144
Tyr Leu Phe Ser Asn Ser Pro Trp Thr Gly Ile Ile Ile Ala Leu Ala
```

```
              35                  40                  45
ggt agc tta atc tat cta tta att atg tgg caa aac cca gct aac atg     192
Gly Ser Leu Ile Tyr Leu Leu Ile Met Trp Gln Asn Pro Ala Asn Met
     50                  55                  60 att atg agt ctc aat cat gct cag gaa att caa gaa gct gat aac cct     240
Ile Met Ser Leu Asn His Ala Gln Glu Ile Gln Glu Ala Asp Asn Pro
 65                  70                  75                  80 gag ttg tgg cat att gta gaa gat atg gca atg gta gct cgt gta cca     288
Glu Leu Trp His Ile Val Glu Asp Met Ala Met Val Ala Arg Val Pro
                     85                  90                  95 atg cca cgc gtt ttt att att cct gat cct agc ccg aat gct ttt gca     336
Met Pro Arg Val Phe Ile Ile Pro Asp Pro Ser Pro Asn Ala Phe Ala
                100                 105                 110 acg ggg cgt gat cct gaa cac agc gct gtt gcc gta acg caa gga att     384
Thr Gly Arg Asp Pro Glu His Ser Ala Val Ala Val Thr Gln Gly Ile
            115                 120                 125 ctt gaa tta atg aat cga gaa gag ctt gaa ggc gtt ctg ggt cat gaa     432
Leu Glu Leu Met Asn Arg Glu Glu Leu Glu Gly Val Leu Gly His Glu
        130                 135                 140 tta tca cac gta cgt aat tac gat att tta tta tca aca atc ggt gta     480
Leu Ser His Val Arg Asn Tyr Asp Ile Leu Leu Ser Thr Ile Gly Val
145                 150                 155                 160 gtt ttg gtg ggt gtt att tcc ttt att tct gga ata gct tct cgc tat     528
Val Leu Val Gly Val Ile Ser Phe Ile Ser Gly Ile Ala Ser Arg Tyr
                165                 170                 175 att tgg ttt ttc ggt ggt aat cgt cga gac gat gaa gat cga gac acc     576
Ile Trp Phe Phe Gly Gly Asn Arg Arg Asp Asp Glu Asp Arg Asp Thr
            180                 185                 190 aat gca ttt gaa ata att ttt aaa gtc atc gct att gtc ttt gta tta     624
Asn Ala Phe Glu Ile Ile Phe Lys Val Ile Ala Ile Val Phe Val Leu
        195                 200                 205 att tta ggt cct att tct gca tcc ctc gca caa atg gcc cta tca cgt     672
Ile Leu Gly Pro Ile Ser Ala Ser Leu Ala Gln Met Ala Leu Ser Arg
    210                 215                 220 aat cga gaa tat tta gct gat gct tct tct gtt gaa tta acc cgt aat     720
Asn Arg Glu Tyr Leu Ala Asp Ala Ser Ser Val Glu Leu Thr Arg Asn
225                 230                 235                 240 cca caa ggc tta atc tcc gca tta aga aag att gaa ggc agt cag cct     768
Pro Gln Gly Leu Ile Ser Ala Leu Arg Lys Ile Glu Gly Ser Gln Pro
                245                 250                 255 atg cgt caa gca gat cgt agt agt gcc ggg tta tat att gag aac cca     816
Met Arg Gln Ala Asp Arg Ser Ser Ala Gly Leu Tyr Ile Glu Asn Pro
            260                 265                 270 ttt cac aat cac ggt cta tct cac tta ttt gac aca cat cca ccg aca     864
Phe His Asn His Gly Leu Ser His Leu Phe Asp Thr His Pro Pro Thr
        275                 280                 285 gaa gat aga atc aaa cga tta gaa cac atg                             894
Glu Asp Arg Ile Lys Arg Leu Glu His Met
    290                 295

<210> SEQ ID NO 100
<211> LENGTH: 298
<212> TYPE: PRT
<213> ORGANISM: Lactobacillus acidophilus

<400> SEQUENCE: 100

Met Leu Tyr Gln Gln Ile Ala Arg Asn Lys Arg Lys Thr Ala Leu Ile
1               5                   10                  15

Met Val Leu Phe Val Val Ile Leu Thr Leu Val Gly Ala Gly Leu Gly
            20                  25                  30
```

```
Tyr Leu Phe Ser Asn Ser Pro Trp Thr Gly Ile Ile Ile Ala Leu Ala
            35                  40                  45

Gly Ser Leu Ile Tyr Leu Leu Ile Met Trp Gln Asn Pro Ala Asn Met
 50                  55                  60

Ile Met Ser Leu Asn His Ala Gln Glu Ile Gln Glu Ala Asp Asn Pro
 65                  70                  75                  80

Glu Leu Trp His Ile Val Glu Asp Met Ala Met Val Ala Arg Val Pro
                 85                  90                  95

Met Pro Arg Val Phe Ile Ile Pro Asp Pro Ser Pro Asn Ala Phe Ala
            100                 105                 110

Thr Gly Arg Asp Pro Glu His Ser Ala Val Ala Val Thr Gln Gly Ile
            115                 120                 125

Leu Glu Leu Met Asn Arg Glu Leu Glu Gly Val Leu Gly His Glu
            130                 135                 140

Leu Ser His Val Arg Asn Tyr Asp Ile Leu Leu Ser Thr Ile Gly Val
145                 150                 155                 160

Val Leu Val Gly Val Ile Ser Phe Ile Ser Gly Ile Ala Ser Arg Tyr
                165                 170                 175

Ile Trp Phe Phe Gly Gly Asn Arg Arg Asp Asp Glu Asp Arg Asp Thr
            180                 185                 190

Asn Ala Phe Glu Ile Ile Phe Lys Val Ile Ala Ile Val Phe Val Leu
            195                 200                 205

Ile Leu Gly Pro Ile Ser Ala Ser Leu Ala Gln Met Ala Leu Ser Arg
            210                 215                 220

Asn Arg Glu Tyr Leu Ala Asp Ala Ser Ser Val Glu Leu Thr Arg Asn
225                 230                 235                 240

Pro Gln Gly Leu Ile Ser Ala Leu Arg Lys Ile Glu Gly Ser Gln Pro
                245                 250                 255

Met Arg Gln Ala Asp Arg Ser Ser Ala Gly Leu Tyr Ile Glu Asn Pro
            260                 265                 270

Phe His Asn His Gly Leu Ser His Leu Phe Asp Thr His Pro Pro Thr
            275                 280                 285

Glu Asp Arg Ile Lys Arg Leu Glu His Met
290                 295

<210> SEQ ID NO 101
<211> LENGTH: 1080
<212> TYPE: DNA
<213> ORGANISM: Lactobacillus acidophilus
<220> FEATURE:
<221> NAME/KEY: CDS
<222> LOCATION: (1)..(1080)
<223> OTHER INFORMATION: Aminopeptidase M42 family ORF# 569

<400> SEQUENCE: 101 atg gaa aaa gca caa gaa att gag atg ctt aaa gat ttt tca gat gct      48
Met Glu Lys Ala Gln Glu Ile Glu Met Leu Lys Asp Phe Ser Asp Ala
 1               5                  10                  15 aat gct aca tct ggc ttt gaa gaa gaa ttc gtt aaa ctt ttt att agc      96
Asn Ala Thr Ser Gly Phe Glu Glu Glu Phe Val Lys Leu Phe Ile Ser
             20                  25                  30 tac gca gaa aaa act gcc aat att gag act gac ggg atg ctg aat gta     144
Tyr Ala Glu Lys Thr Ala Asn Ile Glu Thr Asp Gly Met Leu Asn Val
         35                  40                  45 tat gca gca aag aag gaa aat aaa ggc aat cgc cca gta att caa ctt     192
Tyr Ala Ala Lys Lys Glu Asn Lys Gly Asn Arg Pro Val Ile Gln Leu
     50                  55                  60
```

```
gat gca cac tca gat gct gtt ggt ttt att act caa gct gtt cgt cca      240
Asp Ala His Ser Asp Ala Val Gly Phe Ile Thr Gln Ala Val Arg Pro
 65              70                  75                  80 aat ggt tta att aaa ttt gtg cca ctt ggt ggt tgg gta aaa tac aac      288
Asn Gly Leu Ile Lys Phe Val Pro Leu Gly Gly Trp Val Lys Tyr Asn
                 85                  90                  95 att cct gct cta aaa gtg aag gtg aga aat cgt gat ggt gaa tat atc      336
Ile Pro Ala Leu Lys Val Lys Val Arg Asn Arg Asp Gly Glu Tyr Ile
            100                 105                 110 cct ggc gtt gta gct act aaa cca cca cat ttt atg act gtt gct gaa      384
Pro Gly Val Val Ala Thr Lys Pro Pro His Phe Met Thr Val Ala Glu
            115                 120                 125 aga aat aat gtc cct gat gta gca gat atg tca att gat gtt ggt tca      432
Arg Asn Asn Val Pro Asp Val Ala Asp Met Ser Ile Asp Val Gly Ser
130                 135                 140 agt agc cgc gaa gaa acc att aat gat tat aag atc gat acg ggc tgt      480
Ser Ser Arg Glu Glu Thr Ile Asn Asp Tyr Lys Ile Asp Thr Gly Cys
145                 150                 155                 160 cca atc ttt gtc gat gtt aag tgt gaa tat cat gaa aaa tca ggg tta      528
Pro Ile Phe Val Asp Val Lys Cys Glu Tyr His Glu Lys Ser Gly Leu
                165                 170                 175 ttc ttt ggt aaa gac ttc gat gat cgt ttc ggt gct gga gca atg att      576
Phe Phe Gly Lys Asp Phe Asp Asp Arg Phe Gly Ala Gly Ala Met Ile
            180                 185                 190 gat gtt ttg gat aat tta aag gat gaa gaa act aac ttt gat gtt gtg      624
Asp Val Leu Asp Asn Leu Lys Asp Glu Glu Thr Asn Phe Asp Val Val
            195                 200                 205 gca gcc ttg tct agt caa gag gaa gta ggg ctt cgc gga gct tac gta      672
Ala Ala Leu Ser Ser Gln Glu Glu Val Gly Leu Arg Gly Ala Tyr Val
210                 215                 220 act gct aga aaa gtt aag cca gat cta tgt att gtg ctt gaa agc tgt      720
Thr Ala Arg Lys Val Lys Pro Asp Leu Cys Ile Val Leu Glu Ser Cys
225                 230                 235                 240 cca gca gat gat act ttt act ccg gac tgg ctt tct caa act ggt tta      768
Pro Ala Asp Asp Thr Phe Thr Pro Asp Trp Leu Ser Gln Thr Gly Leu
                245                 250                 255 aag cgg gga cca atg tta cgt gat atg gat act act ttc ttg cca aat      816
Lys Arg Gly Pro Met Leu Arg Asp Met Asp Thr Thr Phe Leu Pro Asn
            260                 265                 270 cct aag ttc caa caa tat gct tgc gac cta gct gac aag aac aac att      864
Pro Lys Phe Gln Gln Tyr Ala Cys Asp Leu Ala Asp Lys Asn Asn Ile
            275                 280                 285 cca tac act cgt tca gtt aga acc ggt ggt gga caa gat ggt gcc gca      912
Pro Tyr Thr Arg Ser Val Arg Thr Gly Gly Gly Gln Asp Gly Ala Ala
290                 295                 300 att tac tac gaa aac ggt gca cca act att gtt atc ggt atc cca gtt      960
Ile Tyr Tyr Glu Asn Gly Ala Pro Thr Ile Val Ile Gly Ile Pro Val
305                 310                 315                 320 cgt tat gaa cac tca cca tat tgc ttc agt agc tat aag gac ttc aag     1008
Arg Tyr Glu His Ser Pro Tyr Cys Phe Ser Ser Tyr Lys Asp Phe Lys
                325                 330                 335 gct tct gta gat ttg gct act gca att atc cgt gat att acc cag gaa     1056
Ala Ser Val Asp Leu Ala Thr Ala Ile Ile Arg Asp Ile Thr Gln Glu
            340                 345                 350 aag ttg gat agt ttc aag aag ttt                                     1080
Lys Leu Asp Ser Phe Lys Lys Phe
            355                 360

<210> SEQ ID NO 102
```

<211> LENGTH: 360
<212> TYPE: PRT
<213> ORGANISM: Lactobacillus acidophilus

<400> SEQUENCE: 102

```
Met Glu Lys Ala Gln Glu Ile Glu Met Leu Lys Asp Phe Ser Asp Ala
1               5                   10                  15

Asn Ala Thr Ser Gly Phe Glu Glu Phe Val Lys Leu Phe Ile Ser
            20                  25                  30

Tyr Ala Glu Lys Thr Ala Asn Ile Glu Thr Asp Gly Met Leu Asn Val
        35                  40                  45

Tyr Ala Ala Lys Lys Glu Asn Lys Gly Asn Arg Pro Val Ile Gln Leu
    50                  55                  60

Asp Ala His Ser Asp Ala Val Gly Phe Ile Thr Gln Ala Val Arg Pro
65                  70                  75                  80

Asn Gly Leu Ile Lys Phe Val Pro Leu Gly Gly Trp Val Lys Tyr Asn
                85                  90                  95

Ile Pro Ala Leu Lys Val Lys Val Arg Asn Arg Asp Gly Glu Tyr Ile
            100                 105                 110

Pro Gly Val Val Ala Thr Lys Pro Pro His Phe Met Thr Val Ala Glu
        115                 120                 125

Arg Asn Asn Val Pro Asp Val Ala Asp Met Ser Ile Asp Val Gly Ser
    130                 135                 140

Ser Ser Arg Glu Glu Thr Ile Asn Asp Tyr Lys Ile Asp Thr Gly Cys
145                 150                 155                 160

Pro Ile Phe Val Asp Val Lys Cys Glu Tyr His Glu Lys Ser Gly Leu
                165                 170                 175

Phe Phe Gly Lys Asp Phe Asp Asp Arg Phe Gly Ala Gly Ala Met Ile
            180                 185                 190

Asp Val Leu Asp Asn Leu Lys Asp Glu Glu Thr Asn Phe Asp Val Val
        195                 200                 205

Ala Ala Leu Ser Ser Gln Glu Glu Val Gly Leu Arg Gly Ala Tyr Val
    210                 215                 220

Thr Ala Arg Lys Val Lys Pro Asp Leu Cys Ile Val Leu Glu Ser Cys
225                 230                 235                 240

Pro Ala Asp Asp Thr Phe Thr Pro Asp Trp Leu Ser Gln Thr Gly Leu
                245                 250                 255

Lys Arg Gly Pro Met Leu Arg Asp Met Asp Thr Thr Phe Leu Pro Asn
            260                 265                 270

Pro Lys Phe Gln Gln Tyr Ala Cys Asp Leu Ala Asp Lys Asn Asn Ile
        275                 280                 285

Pro Tyr Thr Arg Ser Val Arg Thr Gly Gly Gln Asp Gly Ala Ala
    290                 295                 300

Ile Tyr Tyr Glu Asn Gly Ala Pro Thr Ile Val Ile Gly Ile Pro Val
305                 310                 315                 320

Arg Tyr Glu His Ser Pro Tyr Cys Phe Ser Ser Tyr Lys Asp Phe Lys
                325                 330                 335

Ala Ser Val Asp Leu Ala Thr Ala Ile Ile Arg Asp Ile Thr Gln Glu
            340                 345                 350

Lys Leu Asp Ser Phe Lys Lys Phe
        355                 360
```

<210> SEQ ID NO 103
<211> LENGTH: 1149
<212> TYPE: DNA

<213> ORGANISM: Lactobacillus acidophilus
<220> FEATURE:
<221> NAME/KEY: CDS
<222> LOCATION: (1)..(1149)
<223> OTHER INFORMATION: Amino acid amidohydrolase (EC3.5.-.-) ORF# 853

<400> SEQUENCE: 103

```
atg aca gtt tta agt gaa aaa gaa tta att caa att cgg cgg cat tta         48
Met Thr Val Leu Ser Glu Lys Glu Leu Ile Gln Ile Arg Arg His Leu
 1               5                  10                  15 cat gaa att cct gaa tta gct ctc caa gaa aaa gaa acg cat gat tat         96
His Glu Ile Pro Glu Leu Ala Leu Gln Glu Lys Glu Thr His Asp Tyr
             20                  25                  30 tta cta aag gta att aaa aat tta aaa caa gat cat tta act att gta        144
Leu Leu Lys Val Ile Lys Asn Leu Lys Gln Asp His Leu Thr Ile Val
         35                  40                  45 gtg cct aag aca tta cca act gca ata tta ggt tta gtt aaa gga att        192
Val Pro Lys Thr Leu Pro Thr Ala Ile Leu Gly Leu Val Lys Gly Ile
     50                  55                  60 aat cct aaa aaa aca atc ggc tat aga act gat att gat gca tta cct        240
Asn Pro Lys Lys Thr Ile Gly Tyr Arg Thr Asp Ile Asp Ala Leu Pro
 65                  70                  75                  80 gta caa gaa aag act ggc tta cct ttt act tca aaa cat tct gga ata        288
Val Gln Glu Lys Thr Gly Leu Pro Phe Thr Ser Lys His Ser Gly Ile
                 85                  90                  95 atg cat gcc tgc gga cat gat att cat atg acc gta gct tta ggc tta        336
Met His Ala Cys Gly His Asp Ile His Met Thr Val Ala Leu Gly Leu
            100                 105                 110 tta agc tat ttt agt gaa aat caa cct aaa gat aat ttg cta ttt ttc        384
Leu Ser Tyr Phe Ser Glu Asn Gln Pro Lys Asp Asn Leu Leu Phe Phe
        115                 120                 125 ttt caa cca gct gaa gaa agt gag agt gga gga aaa cag gca tac gaa        432
Phe Gln Pro Ala Glu Glu Ser Glu Ser Gly Gly Lys Gln Ala Tyr Glu
    130                 135                 140 aaa ggc tta ttt cag gga aaa ttt aaa cca gat gaa ttt tat ggg ttg        480
Lys Gly Leu Phe Gln Gly Lys Phe Lys Pro Asp Glu Phe Tyr Gly Leu
145                 150                 155                 160 cat gat aat cca gaa cta cct gct ggt agt att ggc tgt aga atg gga        528
His Asp Asn Pro Glu Leu Pro Ala Gly Ser Ile Gly Cys Arg Met Gly
                165                 170                 175 acc tta ttt gct gga aca act gaa ata aat att gat gta att ggt aaa        576
Thr Leu Phe Ala Gly Thr Thr Glu Ile Asn Ile Asp Val Ile Gly Lys
            180                 185                 190 agc ggc cat gct gct ttt ccg caa aat gct aat gat aca gtt gta gcg        624
Ser Gly His Ala Ala Phe Pro Gln Asn Ala Asn Asp Thr Val Val Ala
        195                 200                 205 gcc gca aat tta att atg caa att caa act atc att tca cga agt att        672
Ala Ala Asn Leu Ile Met Gln Ile Gln Thr Ile Ile Ser Arg Ser Ile
    210                 215                 220 gat cca att caa agt ggt gtc att act ttg ggt aag gtt aat gca gga        720
Asp Pro Ile Gln Ser Gly Val Ile Thr Leu Gly Lys Val Asn Ala Gly
225                 230                 235                 240 gtt att aga aat gta att gca ggt cat act aga att gag gga act att        768
Val Ile Arg Asn Val Ile Ala Gly His Thr Arg Ile Glu Gly Thr Ile
                245                 250                 255 cgt ggg tta act caa aaa atg att cta caa ata gat aga cgt ttg caa        816
Arg Gly Leu Thr Gln Lys Met Ile Leu Gln Ile Asp Arg Arg Leu Gln
            260                 265                 270 gat gta tgt gat gga att gca cat agc tat aat gta gaa gta aat ttg        864
Asp Val Cys Asp Gly Ile Ala His Ser Tyr Asn Val Glu Val Asn Leu
```

```
                   275                 280                 285
gaa tta aat caa ggt ggc tat tgg cca gta gaa aat gat cct aag ata      912
Glu Leu Asn Gln Gly Gly Tyr Trp Pro Val Glu Asn Asp Pro Lys Ile
    290                 295                 300 act aaa aat ttc att tct tat atg aag aaa aat cct aag gtt aac ttt      960
Thr Lys Asn Phe Ile Ser Tyr Met Lys Lys Asn Pro Lys Val Asn Phe
305                 310                 315                 320 ata gaa aca gag cct aaa atg aca gga gaa gat ttt ggc ttt ttg cta     1008
Ile Glu Thr Glu Pro Lys Met Thr Gly Glu Asp Phe Gly Phe Leu Leu
                325                 330                 335 gcg aag ttc cca gga aca atg ttt tgg tta gga gtt ggt gat cca agt     1056
Ala Lys Phe Pro Gly Thr Met Phe Trp Leu Gly Val Gly Asp Pro Ser
            340                 345                 350 tca caa tta cat tca tct aca ctt aat ccg gat gaa aaa agt att caa     1104
Ser Gln Leu His Ser Ser Thr Leu Asn Pro Asp Glu Lys Ser Ile Gln
        355                 360                 365 agt gga att gat gca att aaa gga ttt tta att gat aga atg ggg         1149
Ser Gly Ile Asp Ala Ile Lys Gly Phe Leu Ile Asp Arg Met Gly
    370                 375                 380
```

<210> SEQ ID NO 104
<211> LENGTH: 383
<212> TYPE: PRT
<213> ORGANISM: Lactobacillus acidophilus

<400> SEQUENCE: 104

```
Met Thr Val Leu Ser Glu Lys Glu Leu Ile Gln Ile Arg Arg His Leu
1               5                   10                  15

His Glu Ile Pro Glu Leu Ala Leu Gln Glu Lys Glu Thr His Asp Tyr
            20                  25                  30

Leu Leu Lys Val Ile Lys Asn Leu Lys Gln Asp His Leu Thr Ile Val
        35                  40                  45

Val Pro Lys Thr Leu Pro Thr Ala Ile Leu Gly Leu Val Lys Gly Ile
    50                  55                  60

Asn Pro Lys Lys Thr Ile Gly Tyr Arg Thr Asp Ile Asp Ala Leu Pro
65                  70                  75                  80

Val Gln Glu Lys Thr Gly Leu Pro Phe Thr Ser Lys His Ser Gly Ile
                85                  90                  95

Met His Ala Cys Gly His Asp Ile His Met Thr Val Ala Leu Gly Leu
            100                 105                 110

Leu Ser Tyr Phe Ser Glu Asn Gln Pro Lys Asp Asn Leu Leu Phe Phe
        115                 120                 125

Phe Gln Pro Ala Glu Glu Ser Glu Ser Gly Gly Lys Gln Ala Tyr Glu
    130                 135                 140

Lys Gly Leu Phe Gln Gly Lys Phe Lys Pro Asp Glu Phe Tyr Gly Leu
145                 150                 155                 160

His Asp Asn Pro Glu Leu Pro Ala Gly Ser Ile Gly Cys Arg Met Gly
                165                 170                 175

Thr Leu Phe Ala Gly Thr Thr Glu Ile Asn Ile Asp Val Ile Gly Lys
            180                 185                 190

Ser Gly His Ala Ala Phe Pro Gln Asn Ala Asn Asp Thr Val Val Ala
        195                 200                 205

Ala Ala Asn Leu Ile Met Gln Ile Gln Thr Ile Ile Ser Arg Ser Ile
    210                 215                 220

Asp Pro Ile Gln Ser Gly Val Ile Thr Leu Gly Lys Val Asn Ala Gly
225                 230                 235                 240
```

```
Val Ile Arg Asn Val Ile Ala Gly His Thr Arg Ile Glu Gly Thr Ile
                245                 250                 255

Arg Gly Leu Thr Gln Lys Met Ile Leu Gln Ile Asp Arg Arg Leu Gln
            260                 265                 270

Asp Val Cys Asp Gly Ile Ala His Ser Tyr Asn Val Glu Val Asn Leu
        275                 280                 285

Glu Leu Asn Gln Gly Gly Tyr Trp Pro Val Glu Asn Asp Pro Lys Ile
    290                 295                 300

Thr Lys Asn Phe Ile Ser Tyr Met Lys Lys Asn Pro Lys Val Asn Phe
305                 310                 315                 320

Ile Glu Thr Glu Pro Lys Met Thr Gly Glu Asp Phe Gly Phe Leu Leu
                325                 330                 335

Ala Lys Phe Pro Gly Thr Met Phe Trp Leu Gly Val Gly Asp Pro Ser
            340                 345                 350

Ser Gln Leu His Ser Ser Thr Leu Asn Pro Asp Glu Lys Ser Ile Gln
        355                 360                 365

Ser Gly Ile Asp Ala Ile Lys Gly Phe Leu Ile Asp Arg Met Gly
    370                 375                 380

<210> SEQ ID NO 105
<211> LENGTH: 540
<212> TYPE: DNA
<213> ORGANISM: Lactobacillus acidophilus
<220> FEATURE:
<221> NAME/KEY: CDS
<222> LOCATION: (1)..(540)
<223> OTHER INFORMATION: Consensus hypothetical protein ORF# 1661

<400> SEQUENCE: 105 atg aaa gct atc aac tta aag aaa att ata att gct agt gca gca tta      48
Met Lys Ala Ile Asn Leu Lys Lys Ile Ile Ile Ala Ser Ala Ala Leu
1               5                   10                  15 atc ggc cta ggc gct gct gct atc act act att aat caa gca gaa cct      96
Ile Gly Leu Gly Ala Ala Ala Ile Thr Thr Ile Asn Gln Ala Glu Pro
            20                  25                  30 act act gtt caa gca gct acc ggc aaa att aaa gtt tct caa agt tct     144
Thr Thr Val Gln Ala Ala Thr Gly Lys Ile Lys Val Ser Gln Ser Ser
        35                  40                  45 gca gta aag aaa ttc caa gct aaa tat aac gct aaa atc aaa tct att     192
Ala Val Lys Lys Phe Gln Ala Lys Tyr Asn Ala Lys Ile Lys Ser Ile
    50                  55                  60 aat tta gaa aaa gaa aat ggt cgc tat gtt tat gaa att gaa gga ttt     240
Asn Leu Glu Lys Glu Asn Gly Arg Tyr Val Tyr Glu Ile Glu Gly Phe
65                  70                  75                  80 agc tca act aga gaa tac gaa atg aaa atc aat gct tct agt ggc aag     288
Ser Ser Thr Arg Glu Tyr Glu Met Lys Ile Asn Ala Ser Ser Gly Lys
                85                  90                  95 act att tct tct cat tct gaa aaa tta gaa gcc ggt tat aaa aaa gca     336
Thr Ile Ser Ser His Ser Glu Lys Leu Glu Ala Gly Tyr Lys Lys Ala
            100                 105                 110 gct ttg aat tta aat aag act att tct cgt tca act gcc aca aaa att     384
Ala Leu Asn Leu Asn Lys Thr Ile Ser Arg Ser Thr Ala Thr Lys Ile
        115                 120                 125 gct cag aaa cgt gtt tct ggt agc aaa gct atc gaa tgg aac ctt gaa     432
Ala Gln Lys Arg Val Ser Gly Ser Lys Ala Ile Glu Trp Asn Leu Glu
    130                 135                 140 cgt gaa aac tct aga agc gta tgg gaa gta acc gtt act aaa aat ggt     480
Arg Glu Asn Ser Arg Ser Val Trp Glu Val Thr Val Thr Lys Asn Gly
145                 150                 155                 160
```

```
aaa aag agc gac gtg aaa atc aat gct tta act aaa aag att att agc      528
Lys Lys Ser Asp Val Lys Ile Asn Ala Leu Thr Lys Lys Ile Ile Ser
            165                 170                 175 gtc gaa cgt gac                                                      540
Val Glu Arg Asp
            180

<210> SEQ ID NO 106
<211> LENGTH: 180
<212> TYPE: PRT
<213> ORGANISM: Lactobacillus acidophilus

<400> SEQUENCE: 106

Met Lys Ala Ile Asn Leu Lys Lys Ile Ile Ala Ser Ala Ala Leu
1               5                   10                  15

Ile Gly Leu Gly Ala Ala Ala Ile Thr Thr Ile Asn Gln Ala Glu Pro
                20                  25                  30

Thr Thr Val Gln Ala Ala Thr Gly Lys Ile Lys Val Ser Gln Ser Ser
            35                  40                  45

Ala Val Lys Lys Phe Gln Ala Lys Tyr Asn Ala Lys Ile Lys Ser Ile
        50                  55                  60

Asn Leu Glu Lys Glu Asn Gly Arg Tyr Val Tyr Glu Ile Glu Gly Phe
65                  70                  75                  80

Ser Ser Thr Arg Glu Tyr Glu Met Lys Ile Asn Ala Ser Ser Gly Lys
                85                  90                  95

Thr Ile Ser Ser His Ser Glu Lys Leu Glu Ala Gly Tyr Lys Lys Ala
            100                 105                 110

Ala Leu Asn Leu Asn Lys Thr Ile Ser Arg Ser Thr Ala Thr Lys Ile
        115                 120                 125

Ala Gln Lys Arg Val Ser Gly Ser Lys Ala Ile Glu Trp Asn Leu Glu
    130                 135                 140

Arg Glu Asn Ser Arg Ser Val Trp Glu Val Thr Val Thr Lys Asn Gly
145                 150                 155                 160

Lys Lys Ser Asp Val Lys Ile Asn Ala Leu Thr Lys Lys Ile Ile Ser
                165                 170                 175

Val Glu Arg Asp
            180

<210> SEQ ID NO 107
<211> LENGTH: 606
<212> TYPE: DNA
<213> ORGANISM: Lactobacillus acidophilus
<220> FEATURE:
<221> NAME/KEY: CDS
<222> LOCATION: (1)..(606)
<223> OTHER INFORMATION: Consensus hypothetical protein ORF# 1662

<400> SEQUENCE: 107 atg aaa ctg aaa tta gct agt tta acc tta tta tcc gta gca tta att      48
Met Lys Leu Lys Leu Ala Ser Leu Thr Leu Leu Ser Val Ala Leu Ile
1               5                   10                  15 gct act gct tgt tct aat aac gat aac agt aca aca caa agt agt cgg      96
Ala Thr Ala Cys Ser Asn Asn Asp Asn Ser Thr Thr Gln Ser Ser Arg
                20                  25                  30 act att gaa aat tct aaa aaa agt aca gtt act gaa aaa aga agt tct      144
Thr Ile Glu Asn Ser Lys Lys Ser Thr Val Thr Glu Lys Arg Ser Ser
            35                  40                  45 gtt gct tca aac caa gta caa tca agc gtt aat aaa att aag cta agc      192
Val Ala Ser Asn Gln Val Gln Ser Ser Val Asn Lys Ile Lys Leu Ser
        50                  55                  60
```

```
caa caa gaa gct atc gat aaa ttt cat aac caa ttt aac aat aaa aaa    240
Gln Gln Glu Ala Ile Asp Lys Phe His Asn Gln Phe Asn Asn Lys Lys
 65                  70                  75                  80 atc cat agt att gat tta aaa ctt gaa ggc agc caa tac atc tac gaa    288
Ile His Ser Ile Asp Leu Lys Leu Glu Gly Ser Gln Tyr Ile Tyr Glu
                 85                  90                  95 att gaa ggt ttc gac act acc cat aaa tat tct gcc gag att aat gcc    336
Ile Glu Gly Phe Asp Thr Thr His Lys Tyr Ser Ala Glu Ile Asn Ala
            100                 105                 110 gaa act ggt cat gcc agc agt gtt cat tca gag aaa tta gaa cat gat    384
Glu Thr Gly His Ala Ser Ser Val His Ser Glu Lys Leu Glu His Asp
        115                 120                 125 gat caa gat gat caa caa gaa tta aat ctt aac ggt gta atc agc cgt    432
Asp Gln Asp Asp Gln Gln Glu Leu Asn Leu Asn Gly Val Ile Ser Arg
130                 135                 140 gat gaa gct agt act att gct gaa gag cac gct aaa ggt aca agt cgt    480
Asp Glu Ala Ser Thr Ile Ala Glu Glu His Ala Lys Gly Thr Ser Arg
145                 150                 155                 160 gaa tgg aat ctt gaa caa gaa cat ggt aaa act tac tgg aat gta gaa    528
Glu Trp Asn Leu Glu Gln Glu His Gly Lys Thr Tyr Trp Asn Val Glu
                165                 170                 175 gta ggt gaa aga tac cat agt tct gaa gtt aaa att gat gct cat agt    576
Val Gly Glu Arg Tyr His Ser Ser Glu Val Lys Ile Asp Ala His Ser
            180                 185                 190 aaa aaa gta att tca gtt gaa aat gat gac                            606
Lys Lys Val Ile Ser Val Glu Asn Asp Asp
        195                 200

<210> SEQ ID NO 108
<211> LENGTH: 202
<212> TYPE: PRT
<213> ORGANISM: Lactobacillus acidophilus

<400> SEQUENCE: 108

Met Lys Leu Lys Leu Ala Ser Leu Thr Leu Leu Ser Val Ala Leu Ile
  1               5                  10                  15

Ala Thr Ala Cys Ser Asn Asn Asp Asn Ser Thr Thr Gln Ser Ser Arg
             20                  25                  30

Thr Ile Glu Asn Ser Lys Lys Ser Thr Val Thr Glu Lys Arg Ser Ser
         35                  40                  45

Val Ala Ser Asn Gln Val Gln Ser Ser Val Asn Lys Ile Lys Leu Ser
     50                  55                  60

Gln Gln Glu Ala Ile Asp Lys Phe His Asn Gln Phe Asn Asn Lys Lys
 65                  70                  75                  80

Ile His Ser Ile Asp Leu Lys Leu Glu Gly Ser Gln Tyr Ile Tyr Glu
                 85                  90                  95

Ile Glu Gly Phe Asp Thr Thr His Lys Tyr Ser Ala Glu Ile Asn Ala
            100                 105                 110

Glu Thr Gly His Ala Ser Ser Val His Ser Glu Lys Leu Glu His Asp
        115                 120                 125

Asp Gln Asp Asp Gln Gln Glu Leu Asn Leu Asn Gly Val Ile Ser Arg
130                 135                 140

Asp Glu Ala Ser Thr Ile Ala Glu Glu His Ala Lys Gly Thr Ser Arg
145                 150                 155                 160

Glu Trp Asn Leu Glu Gln Glu His Gly Lys Thr Tyr Trp Asn Val Glu
                165                 170                 175

Val Gly Glu Arg Tyr His Ser Ser Glu Val Lys Ile Asp Ala His Ser
```

```
                    180                 185                 190
Lys Lys Val Ile Ser Val Glu Asn Asp Asp
        195                 200

<210> SEQ ID NO 109
<211> LENGTH: 579
<212> TYPE: DNA
<213> ORGANISM: Lactobacillus acidophilus
<220> FEATURE:
<221> NAME/KEY: CDS
<222> LOCATION: (1)..(579)
<223> OTHER INFORMATION: Hypothetical ORF# 1667

<400> SEQUENCE: 109 atg aaa aga ttt ctg aca ttc att tta agt att ttt gcc ggt att gct      48
Met Lys Arg Phe Leu Thr Phe Ile Leu Ser Ile Phe Ala Gly Ile Ala
1               5                   10                  15 att gga att gct att tct cat gca aat caa gag acc cga aag aca agc      96
Ile Gly Ile Ala Ile Ser His Ala Asn Gln Glu Thr Arg Lys Thr Ser
            20                  25                  30 aac gtt act gtt cat gtc gga gat ttt tta aat aaa aca cag gca gtt     144
Asn Val Thr Val His Val Gly Asp Phe Leu Asn Lys Thr Gln Ala Val
        35                  40                  45 agt tat tca act gat aaa ttg cca acg att aga gtt aat caa gct agt     192
Ser Tyr Ser Thr Asp Lys Leu Pro Thr Ile Arg Val Asn Gln Ala Ser
    50                  55                  60 gca att cgc aaa ttt aaa tcg tta tac tct aac gca gtg ata aaa tct     240
Ala Ile Arg Lys Phe Lys Ser Leu Tyr Ser Asn Ala Val Ile Lys Ser
65                  70                  75                  80 att tca tta act tta aat aaa gat ata tat gtc tat aac atc ata ggc     288
Ile Ser Leu Thr Leu Asn Lys Asp Ile Tyr Val Tyr Asn Ile Ile Gly
                85                  90                  95 ttt gat gat cga aaa gac tgt atg att caa gtc gat gca act aat aat     336
Phe Asp Asp Arg Lys Asp Cys Met Ile Gln Val Asp Ala Thr Asn Asn
            100                 105                 110 aaa atc ata ggt caa tca act caa gtc ttg aac tat gat ttt gat aaa     384
Lys Ile Ile Gly Gln Ser Thr Gln Val Leu Asn Tyr Asp Phe Asp Lys
        115                 120                 125 gaa tcc tat tta aat ttg aat aaa aca att tca cgt agt gaa gct tca     432
Glu Ser Tyr Leu Asn Leu Asn Lys Thr Ile Ser Arg Ser Glu Ala Ser
    130                 135                 140 gaa att gct act aaa gaa ttt aat aat gaa act cct att tct tgg aaa     480
Glu Ile Ala Thr Lys Glu Phe Asn Asn Glu Thr Pro Ile Ser Trp Lys
145                 150                 155                 160 tta gaa gat gtt aat gat caa gct att tgg aaa att gtt tta atc cgt     528
Leu Glu Asp Val Asn Asp Gln Ala Ile Trp Lys Ile Val Leu Ile Arg
                165                 170                 175 aat gaa caa aaa cgt gaa ata aaa att aat gcc gaa aca aaa gaa tta     576
Asn Glu Gln Lys Arg Glu Ile Lys Ile Asn Ala Glu Thr Lys Glu Leu
            180                 185                 190 tta                                                                  579
Leu

<210> SEQ ID NO 110
<211> LENGTH: 193
<212> TYPE: PRT
<213> ORGANISM: Lactobacillus acidophilus

<400> SEQUENCE: 110

Met Lys Arg Phe Leu Thr Phe Ile Leu Ser Ile Phe Ala Gly Ile Ala
1               5                   10                  15
```

```
Ile Gly Ile Ala Ile Ser His Ala Asn Gln Glu Thr Arg Lys Thr Ser
            20                  25                  30

Asn Val Thr Val His Val Gly Asp Phe Leu Asn Lys Thr Gln Ala Val
        35                  40                  45

Ser Tyr Ser Thr Asp Lys Leu Pro Thr Ile Arg Val Asn Gln Ala Ser
    50                  55                  60

Ala Ile Arg Lys Phe Lys Ser Leu Tyr Ser Asn Ala Val Ile Lys Ser
65                  70                  75                  80

Ile Ser Leu Thr Leu Asn Lys Asp Ile Tyr Val Tyr Asn Ile Ile Gly
                85                  90                  95

Phe Asp Asp Arg Lys Asp Cys Met Ile Gln Val Asp Ala Thr Asn Asn
            100                 105                 110

Lys Ile Ile Gly Gln Ser Thr Gln Val Leu Asn Tyr Asp Phe Asp Lys
        115                 120                 125

Glu Ser Tyr Leu Asn Leu Asn Lys Thr Ile Ser Arg Ser Glu Ala Ser
    130                 135                 140

Glu Ile Ala Thr Lys Glu Phe Asn Asn Glu Thr Pro Ile Ser Trp Lys
145                 150                 155                 160

Leu Glu Asp Val Asn Asp Gln Ala Ile Trp Lys Ile Val Leu Ile Arg
                165                 170                 175

Asn Glu Gln Lys Arg Glu Ile Lys Ile Asn Ala Glu Thr Lys Glu Leu
            180                 185                 190

Leu

<210> SEQ ID NO 111
<211> LENGTH: 900
<212> TYPE: DNA
<213> ORGANISM: Lactobacillus acidophilus
<220> FEATURE:
<221> NAME/KEY: CDS
<222> LOCATION: (1)..(900)
<223> OTHER INFORMATION: PrtM precursor ORF# 1588

<400> SEQUENCE: 111 atg aag agt tat atg aaa aaa gtt gct gca gtc gtc gct gta gct ggt      48
Met Lys Ser Tyr Met Lys Lys Val Ala Ala Val Val Ala Val Ala Gly
1               5                   10                  15 gtt gca tta tct act gcc gct tgt tca aac agt ggt agc aat tct act      96
Val Ala Leu Ser Thr Ala Ala Cys Ser Asn Ser Gly Ser Asn Ser Thr
            20                  25                  30 gtt gct tct tac aaa ggt ggt aag att act caa caa caa tac tat gat     144
Val Ala Ser Tyr Lys Gly Gly Lys Ile Thr Gln Gln Gln Tyr Tyr Asp
        35                  40                  45 gaa atg aaa aag tca caa gct ggt aaa tca act ttg gct aac atg att     192
Glu Met Lys Lys Ser Gln Ala Gly Lys Ser Thr Leu Ala Asn Met Ile
    50                  55                  60 atc aac cgt gct ttg gaa caa caa tac ggc aaa tac gta tca tca aag     240
Ile Asn Arg Ala Leu Glu Gln Gln Tyr Gly Lys Tyr Val Ser Ser Lys
65                  70                  75                  80 aaa gtt gac aag caa tac aac aac tac aag aag caa tat ggc tca caa     288
Lys Val Asp Lys Gln Tyr Asn Asn Tyr Lys Lys Gln Tyr Gly Ser Gln
                85                  90                  95 ttt agt gct gtt tta caa caa aat ggt atg act gct tca agt ttc aaa     336
Phe Ser Ala Val Leu Gln Gln Asn Gly Met Thr Ala Ser Ser Phe Lys
            100                 105                 110 gaa aac tta aag act aat ctt ctt tct gaa caa gca tta aag cat att     384
Glu Asn Leu Lys Thr Asn Leu Leu Ser Glu Gln Ala Leu Lys His Ile
        115                 120                 125
```

```
aag aag att act aaa aag caa gaa caa caa gct tgg aag agc tac caa      432
Lys Lys Ile Thr Lys Lys Gln Glu Gln Gln Ala Trp Lys Ser Tyr Gln
        130                 135                 140 cct aag gta act gtt caa cat att ttg gtt gct aag aag tca act gct      480
Pro Lys Val Thr Val Gln His Ile Leu Val Ala Lys Lys Ser Thr Ala
145                 150                 155                 160 caa gac att atc aag caa tta aaa gat ggt aag agc ttc agt agc tta      528
Gln Asp Ile Ile Lys Gln Leu Lys Asp Gly Lys Ser Phe Ser Ser Leu
                165                 170                 175 gct aag aaa tac tca ctc gat act gca act aag aat aaa gct ggt aag      576
Ala Lys Lys Tyr Ser Leu Asp Thr Ala Thr Lys Asn Lys Ala Gly Lys
            180                 185                 190 ctt cct tca ttt gac tca act gac aac act ctt gac tca gca ttc aag      624
Leu Pro Ser Phe Asp Ser Thr Asp Asn Thr Leu Asp Ser Ala Phe Lys
        195                 200                 205 act gct gca ttt aag ctt aag act ggt gaa gtt act tca act cca gtt      672
Thr Ala Ala Phe Lys Leu Lys Thr Gly Glu Val Thr Ser Thr Pro Val
210                 215                 220 aaa tca caa tca ggc tac cac gta att aag atg att aac cac cca gct      720
Lys Ser Gln Ser Gly Tyr His Val Ile Lys Met Ile Asn His Pro Ala
225                 230                 235                 240 aag ggt aaa ttt gct gat cac aag aag gct att gat gat gaa att tat      768
Lys Gly Lys Phe Ala Asp His Lys Lys Ala Ile Asp Asp Glu Ile Tyr
                245                 250                 255 gca tca atg gct caa gat caa tca act atg aaa gac gtt atc gca act      816
Ala Ser Met Ala Gln Asp Gln Ser Thr Met Lys Asp Val Ile Ala Thr
            260                 265                 270 gta ttg aag cgt gct gat gtt tca att aag gat agc gac ttg aag gac      864
Val Leu Lys Arg Ala Asp Val Ser Ile Lys Asp Ser Asp Leu Lys Asp
        275                 280                 285 gta tta tca gct tac gta tca act ggt gct act aag                      900
Val Leu Ser Ala Tyr Val Ser Thr Gly Ala Thr Lys
290                 295                 300

<210> SEQ ID NO 112
<211> LENGTH: 300
<212> TYPE: PRT
<213> ORGANISM: Lactobacillus acidophilus

<400> SEQUENCE: 112

Met Lys Ser Tyr Met Lys Lys Val Ala Ala Val Ala Val Ala Gly
1               5                   10                  15

Val Ala Leu Ser Thr Ala Ala Cys Ser Asn Ser Gly Ser Asn Ser Thr
            20                  25                  30

Val Ala Ser Tyr Lys Gly Gly Lys Ile Thr Gln Gln Tyr Tyr Asp
        35                  40                  45

Glu Met Lys Lys Ser Gln Ala Gly Lys Ser Thr Leu Ala Asn Met Ile
    50                  55                  60

Ile Asn Arg Ala Leu Glu Gln Gln Tyr Gly Lys Tyr Val Ser Ser Lys
65                  70                  75                  80

Lys Val Asp Lys Gln Tyr Asn Asn Tyr Lys Lys Gln Tyr Gly Ser Gln
                85                  90                  95

Phe Ser Ala Val Leu Gln Gln Asn Gly Met Thr Ala Ser Ser Phe Lys
            100                 105                 110

Glu Asn Leu Lys Thr Asn Leu Leu Ser Glu Gln Ala Leu Lys His Ile
        115                 120                 125

Lys Lys Ile Thr Lys Lys Gln Glu Gln Gln Ala Trp Lys Ser Tyr Gln
    130                 135                 140
```

```
Pro Lys Val Thr Val Gln His Ile Leu Val Ala Lys Lys Ser Thr Ala
145                 150                 155                 160

Gln Asp Ile Ile Lys Gln Leu Lys Asp Gly Lys Ser Phe Ser Ser Leu
            165                 170                 175

Ala Lys Lys Tyr Ser Leu Asp Thr Ala Thr Lys Asn Lys Ala Gly Lys
        180                 185                 190

Leu Pro Ser Phe Asp Ser Thr Asp Asn Thr Leu Asp Ser Ala Phe Lys
    195                 200                 205

Thr Ala Ala Phe Lys Leu Lys Thr Gly Glu Val Thr Ser Thr Pro Val
210                 215                 220

Lys Ser Gln Ser Gly Tyr His Val Ile Lys Met Ile Asn His Pro Ala
225                 230                 235                 240

Lys Gly Lys Phe Ala Asp His Lys Lys Ala Ile Asp Asp Glu Ile Tyr
            245                 250                 255

Ala Ser Met Ala Gln Asp Gln Ser Thr Met Lys Asp Val Ile Ala Thr
        260                 265                 270

Val Leu Lys Arg Ala Asp Val Ser Ile Lys Asp Ser Asp Leu Lys Asp
    275                 280                 285

Val Leu Ser Ala Tyr Val Ser Thr Gly Ala Thr Lys
    290                 295                 300

<210> SEQ ID NO 113
<211> LENGTH: 1311
<212> TYPE: DNA
<213> ORGANISM: Lactobacillus acidophilus
<220> FEATURE:
<221> NAME/KEY: CDS
<222> LOCATION: (1)..(1311)
<223> OTHER INFORMATION: Aminopeptidase G ORF# 195

<400> SEQUENCE: 113 atg aaa cac aag ctg aca atg gca gaa att gcc aaa ttt caa caa gaa      48
Met Lys His Lys Leu Thr Met Ala Glu Ile Ala Lys Phe Gln Gln Glu
1               5                   10                  15 tat gag aag caa cct aga aat cgt gtt gct gaa ctt gca gta gtg aat      96
Tyr Glu Lys Gln Pro Arg Asn Arg Val Ala Glu Leu Ala Val Val Asn
            20                  25                  30 aat ggt gta caa aag gcc agc ttt aat aat gag ggg gtt aga aag cta     144
Asn Gly Val Gln Lys Ala Ser Phe Asn Asn Glu Gly Val Arg Lys Leu
        35                  40                  45 aat cgt aca ttt tct att gaa att ccc aca gat aat gta act gat caa     192
Asn Arg Thr Phe Ser Ile Glu Ile Pro Thr Asp Asn Val Thr Asp Gln
50                  55                  60 aaa caa tcg ggt cgc tgc tgg tta ttt gca gca ttg aat acg ctt cgc     240
Lys Gln Ser Gly Arg Cys Trp Leu Phe Ala Ala Leu Asn Thr Leu Arg
65                  70                  75                  80 cat ggc ttt gct aaa aag caa aat gct aag aat ttt act ttt tca caa     288
His Gly Phe Ala Lys Lys Gln Asn Ala Lys Asn Phe Thr Phe Ser Gln
            85                  90                  95 aat tat cta ttc ttc tgg gat aga gta gaa aga gcc aat atc ttc ttt     336
Asn Tyr Leu Phe Phe Trp Asp Arg Val Glu Arg Ala Asn Ile Phe Phe
        100                 105                 110 gat aat att tta aat act gcg gat aag cca ctg gat gac aga acg gtt     384
Asp Asn Ile Leu Asn Thr Ala Asp Lys Pro Leu Asp Asp Arg Thr Val
    115                 120                 125 cat acc tat atg caa ggt cct gat act gat ggt ggt caa tgg gct atg     432
His Thr Tyr Met Gln Gly Pro Asp Thr Asp Gly Gly Gln Trp Ala Met
130                 135                 140 gct gtt tct tta att aga aag tat ggt tta gtt cca aca tat gca caa     480
```

```
Ala Val Ser Leu Ile Arg Lys Tyr Gly Leu Val Pro Thr Tyr Ala Gln
145                 150                 155                 160 gat gaa agc ttt act gct aac aat aca gct gcg ttt aat agc gcc tta      528
Asp Glu Ser Phe Thr Ala Asn Asn Thr Ala Ala Phe Asn Ser Ala Leu
                165                 170                 175 aat atg aaa ctg cgt gaa gat ggt tta gta ttg cgt aaa ctt tat caa      576
Asn Met Lys Leu Arg Glu Asp Gly Leu Val Leu Arg Lys Leu Tyr Gln
            180                 185                 190 gaa aag aaa atg gat gaa atc gaa act aaa cgt caa gaa ttt ttg agt      624
Glu Lys Lys Met Asp Glu Ile Glu Thr Lys Arg Gln Glu Phe Leu Ser
        195                 200                 205 gaa gtt tat aga atg gct gtt att gca ttt ggt gaa cca gtt caa aaa      672
Glu Val Tyr Arg Met Ala Val Ile Ala Phe Gly Glu Pro Val Gln Lys
    210                 215                 220 ttt gat ctt gaa ttt aaa gat gat aat ggc aat tat cat ttt gat ggg      720
Phe Asp Leu Glu Phe Lys Asp Asp Asn Gly Asn Tyr His Phe Asp Gly
225                 230                 235                 240 aat tta act cca tta gac ttc ttc cac aat tat ttc act gat gat cta      768
Asn Leu Thr Pro Leu Asp Phe Phe His Asn Tyr Phe Thr Asp Asp Leu
                245                 250                 255 gat gat tac att gtt ttg ttt aat gca cct gat cat gaa ttt gat aag      816
Asp Asp Tyr Ile Val Leu Phe Asn Ala Pro Asp His Glu Phe Asp Lys
            260                 265                 270 ctt tat gct ctt cca ttt gaa gat aat gtt gaa ggc ggc aca cca gta      864
Leu Tyr Ala Leu Pro Phe Glu Asp Asn Val Glu Gly Gly Thr Pro Val
        275                 280                 285 caa ttt ttg aat aca gaa att gat aat tta aaa gaa gcg gct att aag      912
Gln Phe Leu Asn Thr Glu Ile Asp Asn Leu Lys Glu Ala Ala Ile Lys
    290                 295                 300 cag ctt gaa gct ggt gaa act att tgg ttt ggt tgt gat gtt ggt aaa      960
Gln Leu Glu Ala Gly Glu Thr Ile Trp Phe Gly Cys Asp Val Gly Lys
305                 310                 315                 320 gag agt gat cgt caa aaa ggt atc ttg tct aag ggt ctt tac caa aca     1008
Glu Ser Asp Arg Gln Lys Gly Ile Leu Ser Lys Gly Leu Tyr Gln Thr
                325                 330                 335 gat tta att ttt gat att gaa act aag tta aat aaa aaa gaa aga tta     1056
Asp Leu Ile Phe Asp Ile Glu Thr Lys Leu Asn Lys Lys Glu Arg Leu
            340                 345                 350 caa act ggt gct tca ggc tca acg cat gcc atg act tta gtg gga gtt     1104
Gln Thr Gly Ala Ser Gly Ser Thr His Ala Met Thr Leu Val Gly Val
        355                 360                 365 gac gtt gta gac gga cag cct caa caa tgg aag gtt gaa aat tca tgg     1152
Asp Val Val Asp Gly Gln Pro Gln Gln Trp Lys Val Glu Asn Ser Trp
    370                 375                 380 ggc agt aag gtc ggt gaa aag ggc tac ttt gtc atg aat gat gag tgg     1200
Gly Ser Lys Val Gly Glu Lys Gly Tyr Phe Val Met Asn Asp Glu Trp
385                 390                 395                 400 ttt aat gaa tac tta ttc aag gtg gtt gta aaa aag caa tat gta cca     1248
Phe Asn Glu Tyr Leu Phe Lys Val Val Val Lys Lys Gln Tyr Val Pro
                405                 410                 415 gaa aaa tta att aag atc tgg gaa ggc gaa gca aca cca gta gaa gca     1296
Glu Lys Leu Ile Lys Ile Trp Glu Gly Glu Ala Thr Pro Val Glu Ala
            420                 425                 430 tgg gac tca atg gca                                                 1311
Trp Asp Ser Met Ala
        435

<210> SEQ ID NO 114
<211> LENGTH: 437
<212> TYPE: PRT
```

<213> ORGANISM: Lactobacillus acidophilus

<400> SEQUENCE: 114

```
Met Lys His Lys Leu Thr Met Ala Glu Ile Ala Lys Phe Gln Gln Glu
1               5                   10                  15

Tyr Glu Lys Gln Pro Arg Asn Arg Val Ala Glu Leu Ala Val Val Asn
            20                  25                  30

Asn Gly Val Gln Lys Ala Ser Phe Asn Asn Glu Gly Val Arg Lys Leu
        35                  40                  45

Asn Arg Thr Phe Ser Ile Glu Ile Pro Thr Asp Asn Val Thr Asp Gln
    50                  55                  60

Lys Gln Ser Gly Arg Cys Trp Leu Phe Ala Ala Leu Asn Thr Leu Arg
65                  70                  75                  80

His Gly Phe Ala Lys Lys Gln Asn Ala Lys Asn Phe Thr Phe Ser Gln
                85                  90                  95

Asn Tyr Leu Phe Phe Trp Asp Arg Val Glu Arg Ala Asn Ile Phe Phe
            100                 105                 110

Asp Asn Ile Leu Asn Thr Ala Asp Lys Pro Leu Asp Asp Arg Thr Val
        115                 120                 125

His Thr Tyr Met Gln Gly Pro Asp Thr Asp Gly Gly Gln Trp Ala Met
    130                 135                 140

Ala Val Ser Leu Ile Arg Lys Tyr Gly Leu Val Pro Thr Tyr Ala Gln
145                 150                 155                 160

Asp Glu Ser Phe Thr Ala Asn Asn Thr Ala Ala Phe Asn Ser Ala Leu
                165                 170                 175

Asn Met Lys Leu Arg Glu Asp Gly Leu Val Leu Arg Lys Leu Tyr Gln
            180                 185                 190

Glu Lys Lys Met Asp Glu Ile Glu Thr Lys Arg Gln Glu Phe Leu Ser
        195                 200                 205

Glu Val Tyr Arg Met Ala Val Ile Ala Phe Gly Glu Pro Val Gln Lys
    210                 215                 220

Phe Asp Leu Glu Phe Lys Asp Asp Asn Gly Asn Tyr His Phe Asp Gly
225                 230                 235                 240

Asn Leu Thr Pro Leu Asp Phe Phe His Asn Tyr Phe Thr Asp Asp Leu
                245                 250                 255

Asp Asp Tyr Ile Val Leu Phe Asn Ala Pro Asp His Glu Phe Asp Lys
            260                 265                 270

Leu Tyr Ala Leu Pro Phe Glu Asp Asn Val Glu Gly Gly Thr Pro Val
        275                 280                 285

Gln Phe Leu Asn Thr Glu Ile Asp Asn Leu Lys Glu Ala Ala Ile Lys
    290                 295                 300

Gln Leu Glu Ala Gly Glu Thr Ile Trp Phe Gly Cys Asp Val Gly Lys
305                 310                 315                 320

Glu Ser Asp Arg Gln Lys Gly Ile Leu Ser Lys Gly Leu Tyr Gln Thr
                325                 330                 335

Asp Leu Ile Phe Asp Ile Glu Thr Lys Leu Asn Lys Lys Glu Arg Leu
            340                 345                 350

Gln Thr Gly Ala Ser Gly Ser Thr His Ala Met Thr Leu Val Gly Val
        355                 360                 365

Asp Val Val Asp Gly Gln Pro Gln Gln Trp Lys Val Glu Asn Ser Trp
    370                 375                 380

Gly Ser Lys Val Gly Glu Lys Gly Tyr Phe Val Met Asn Asp Glu Trp
385                 390                 395                 400
```

```
                Phe Asn Glu Tyr Leu Phe Lys Val Val Lys Lys Gln Tyr Val Pro
                                405                 410                 415

Glu Lys Leu Ile Lys Ile Trp Glu Gly Glu Ala Thr Pro Val Glu Ala
                            420                 425                 430

Trp Asp Ser Met Ala
                        435

<210> SEQ ID NO 115
<211> LENGTH: 1950
<212> TYPE: DNA
<213> ORGANISM: Lactobacillus acidophilus
<220> FEATURE:
<221> NAME/KEY: CDS
<222> LOCATION: (1)..(1950)
<223> OTHER INFORMATION: PepO neutral endopeptidase (EC3.4.-.-) ORF#
      165

<400> SEQUENCE: 115 atg agt aat aaa gtg act gtt cgt ggt ggt gct ggt aat atc ctc gaa      48
Met Ser Asn Lys Val Thr Val Arg Gly Gly Ala Gly Asn Ile Leu Glu
1               5                   10                  15 cct aaa gtt ggt act cgt cca caa gat aat tta tat tta gct gtt aac      96
Pro Lys Val Gly Thr Arg Pro Gln Asp Asn Leu Tyr Leu Ala Val Asn
            20                  25                  30 tca gac tgg ctt gag aag gct aag att cct tca gat cgt tca aga att     144
Ser Asp Trp Leu Glu Lys Ala Lys Ile Pro Ser Asp Arg Ser Arg Ile
        35                  40                  45 gct agt ttt gat agt att gat ctt aac gta gaa aag agc tta atg aag     192
Ala Ser Phe Asp Ser Ile Asp Leu Asn Val Glu Lys Ser Leu Met Lys
    50                  55                  60 gat ttc gca gat ttt gcg gat ggc aaa aaa gaa gta gcc gat gta ccg     240
Asp Phe Ala Asp Phe Ala Asp Gly Lys Lys Glu Val Ala Asp Val Pro
65                  70                  75                  80 aac ttg aag aag gca gtt gaa cta tat aag ctt gct cgt gac ttt aag     288
Asn Leu Lys Lys Ala Val Glu Leu Tyr Lys Leu Ala Arg Asp Phe Lys
                85                  90                  95 cgt cgt gat gaa gat ggc gct aag cct att caa gct gat ttg ttc tta     336
Arg Arg Asp Glu Asp Gly Ala Lys Pro Ile Gln Ala Asp Leu Phe Leu
            100                 105                 110 ctt gaa agt atc agt gac ttt gct gat ttc aac ttg aag gct gct gat     384
Leu Glu Ser Ile Ser Asp Phe Ala Asp Phe Asn Leu Lys Ala Ala Asp
        115                 120                 125 tta ttt aag gct tca ttt tca ttg cca ttt ggt tta gat att gat gct     432
Leu Phe Lys Ala Ser Phe Ser Leu Pro Phe Gly Leu Asp Ile Asp Ala
    130                 135                 140 gat atg aag aat act aag att aat gtt ctt caa ttt att gga cca tca     480
Asp Met Lys Asn Thr Lys Ile Asn Val Leu Gln Phe Ile Gly Pro Ser
145                 150                 155                 160 aca ttc ttg cca gat act act act tac aag aca gaa gct gct gga aag     528
Thr Phe Leu Pro Asp Thr Thr Thr Tyr Lys Thr Glu Ala Ala Gly Lys
                165                 170                 175 ctt ttg gaa gtt ttg aag aag caa tca att aac ttg ctt aag atg gct     576
Leu Leu Glu Val Leu Lys Lys Gln Ser Ile Asn Leu Leu Lys Met Ala
            180                 185                 190 ggc gtt tct gaa ggt caa gct aag gaa tac gtg gaa gat gcc tta aaa     624
Gly Val Ser Glu Gly Gln Ala Lys Glu Tyr Val Glu Asp Ala Leu Lys
        195                 200                 205 ttt gat aaa aag ctt tct gaa gta gtt aaa tca tca gaa gaa tgg gca     672
Phe Asp Lys Lys Leu Ser Glu Val Val Lys Ser Ser Glu Glu Trp Ala
    210                 215                 220 gat tat cca gca atg tat aat cca act tca atg gaa gat ttt gaa ggc     720
```

```
                -continued

Asp Tyr Pro Ala Met Tyr Asn Pro Thr Ser Met Glu Asp Phe Glu Gly
225             230              235              240 aag att aag aac ttc aag att gat tac ttc ttg aag gaa gct tta ggt      768
Lys Ile Lys Asn Phe Lys Ile Asp Tyr Phe Leu Lys Glu Ala Leu Gly
                245              250              255 gaa gtt cct gat aga att att gtt act gaa cca cgt ttc ttg aaa cac      816
Glu Val Pro Asp Arg Ile Ile Val Thr Glu Pro Arg Phe Leu Lys His
            260              265              270 ttt gat gaa tta atg aat gaa gaa aac ttt gat gaa att aag ggt tgg      864
Phe Asp Glu Leu Met Asn Glu Glu Asn Phe Asp Glu Ile Lys Gly Trp
        275              280              285 atg atc gtt aag ttt att aat aat gtt gca agt tac ttg tca caa gat      912
Met Ile Val Lys Phe Ile Asn Asn Val Ala Ser Tyr Leu Ser Gln Asp
    290              295              300 ttc cgt gaa gca tca ttc caa ttt agt caa gca ttg aca ggc caa ccg      960
Phe Arg Glu Ala Ser Phe Gln Phe Ser Gln Ala Leu Thr Gly Gln Pro
305             310              315              320 gaa tta caa agc caa gaa aag caa gca tat cat tta gct aat ggt cta     1008
Glu Leu Gln Ser Gln Glu Lys Gln Ala Tyr His Leu Ala Asn Gly Leu
                325              330              335 ttc agc gaa gta gtc ggt gtt tac tat ggt caa aca tac ttt ggt gaa     1056
Phe Ser Glu Val Val Gly Val Tyr Tyr Gly Gln Thr Tyr Phe Gly Glu
            340              345              350 gaa gct aaa aaa gat gtt tta act atg att cgc caa atg att gat gtt     1104
Glu Ala Lys Lys Asp Val Leu Thr Met Ile Arg Gln Met Ile Asp Val
        355              360              365 tac gaa aag cgt att aag gaa aat tca tgg ctt tct gaa gaa act aag     1152
Tyr Glu Lys Arg Ile Lys Glu Asn Ser Trp Leu Ser Glu Glu Thr Lys
370             375              380 gaa aag gct att gtt aag ctt cgt gca ttg atc tta aag att ggt tac     1200
Glu Lys Ala Ile Val Lys Leu Arg Ala Leu Ile Leu Lys Ile Gly Tyr
385             390              395              400 cct gat aag att gaa gaa atc tat aat cgc tac aat ata act cct gct     1248
Pro Asp Lys Ile Glu Glu Ile Tyr Asn Arg Tyr Asn Ile Thr Pro Ala
                405              410              415 agt gaa ggc ggt agt ctt tac tca aac gta aga gca gct gat att gaa     1296
Ser Glu Gly Gly Ser Leu Tyr Ser Asn Val Arg Ala Ala Asp Ile Glu
            420              425              430 caa gtt aaa tat aac gtt gaa aag tta cat aaa cca gtt gat cgt agc     1344
Gln Val Lys Tyr Asn Val Glu Lys Leu His Lys Pro Val Asp Arg Ser
        435              440              445 gta tgg ctc atg cca gcc aac ttg gta aat gct tgc tat gat cca caa     1392
Val Trp Leu Met Pro Ala Asn Leu Val Asn Ala Cys Tyr Asp Pro Gln
450             455              460 aga aat gac tta act ttc cca gca gca att ttg caa gca cca ttt tat     1440
Arg Asn Asp Leu Thr Phe Pro Ala Ala Ile Leu Gln Ala Pro Phe Tyr
465             470              475              480 gac tta aag caa gat cgt gct gaa aac ttt ggt gga att ggt act gtt     1488
Asp Leu Lys Gln Asp Arg Ala Glu Asn Phe Gly Gly Ile Gly Thr Val
                485              490              495 att gct cat gaa att tct cat gcc ttt gat aac aat ggt gca caa ttc     1536
Ile Ala His Glu Ile Ser His Ala Phe Asp Asn Asn Gly Ala Gln Phe
            500              505              510 gat gaa ttc ggt aat atg aag aat tgg tgg act gaa gaa gac ttc gct     1584
Asp Glu Phe Gly Asn Met Lys Asn Trp Trp Thr Glu Glu Asp Phe Ala
        515              520              525 gaa ttt aag aag cgt act caa gca gaa atc gac ttg ttc gat ggt att     1632
Glu Phe Lys Lys Arg Thr Gln Ala Glu Ile Asp Leu Phe Asp Gly Ile
530             535              540
```

```
aaa tac ggc cct gtt act ttg aac ggt aag caa atc gtt tca gaa aat    1680
Lys Tyr Gly Pro Val Thr Leu Asn Gly Lys Gln Ile Val Ser Glu Asn
545                 550                 555                 560 att gcc gac caa ggt ggt ctt act gca gct att aag gca gct aag gac    1728
Ile Ala Asp Gln Gly Gly Leu Thr Ala Ala Ile Lys Ala Ala Lys Asp
                565                 570                 575 gaa ggc gat gat ttg aag aaa ttg ttt gaa aac ttt gct cgt att tgg    1776
Glu Gly Asp Asp Leu Lys Lys Leu Phe Glu Asn Phe Ala Arg Ile Trp
            580                 585                 590 gct aac aag caa ctt act gaa tct att aag aca caa gtt tct ttt gat    1824
Ala Asn Lys Gln Leu Thr Glu Ser Ile Lys Thr Gln Val Ser Phe Asp
        595                 600                 605 gtt cac gca cca ggt cca gaa cgt gca aat gtt caa tca caa tgt caa    1872
Val His Ala Pro Gly Pro Glu Arg Ala Asn Val Gln Ser Gln Cys Gln
    610                 615                 620 gaa gac ttc tat gaa gta ttt gat gtt aag gaa act gat ggt atg tgg    1920
Glu Asp Phe Tyr Glu Val Phe Asp Val Lys Glu Thr Asp Gly Met Trp
625                 630                 635                 640 tta gat cca gaa aaa cgt gta gtt att tgg                            1950
Leu Asp Pro Glu Lys Arg Val Val Ile Trp
                645                 650

<210> SEQ ID NO 116
<211> LENGTH: 650
<212> TYPE: PRT
<213> ORGANISM: Lactobacillus acidophilus

<400> SEQUENCE: 116

Met Ser Asn Lys Val Thr Val Arg Gly Gly Ala Gly Asn Ile Leu Glu
1               5                   10                  15

Pro Lys Val Gly Thr Arg Pro Gln Asp Asn Leu Tyr Leu Ala Val Asn
            20                  25                  30

Ser Asp Trp Leu Glu Lys Ala Lys Ile Pro Ser Asp Arg Ser Arg Ile
        35                  40                  45

Ala Ser Phe Asp Ser Ile Asp Leu Asn Val Glu Lys Ser Leu Met Lys
    50                  55                  60

Asp Phe Ala Asp Phe Ala Asp Gly Lys Lys Glu Val Ala Asp Val Pro
65                  70                  75                  80

Asn Leu Lys Lys Ala Val Glu Leu Tyr Lys Leu Ala Arg Asp Phe Lys
                85                  90                  95

Arg Arg Asp Glu Asp Gly Ala Lys Pro Ile Gln Ala Asp Leu Phe Leu
            100                 105                 110

Leu Glu Ser Ile Ser Asp Phe Ala Asp Phe Asn Leu Lys Ala Ala Asp
        115                 120                 125

Leu Phe Lys Ala Ser Phe Ser Leu Pro Phe Gly Leu Asp Ile Asp Ala
    130                 135                 140

Asp Met Lys Asn Thr Lys Ile Asn Val Leu Gln Phe Ile Gly Pro Ser
145                 150                 155                 160

Thr Phe Leu Pro Asp Thr Thr Tyr Lys Thr Glu Ala Ala Gly Lys
                165                 170                 175

Leu Leu Glu Val Leu Lys Lys Gln Ser Ile Asn Leu Leu Lys Met Ala
            180                 185                 190

Gly Val Ser Glu Gly Gln Ala Lys Glu Tyr Val Glu Asp Ala Leu Lys
        195                 200                 205

Phe Asp Lys Lys Leu Ser Glu Val Val Lys Ser Ser Glu Glu Trp Ala
    210                 215                 220

Asp Tyr Pro Ala Met Tyr Asn Pro Thr Ser Met Glu Asp Phe Glu Gly
```

-continued

```
            225                 230                 235                 240
Lys Ile Lys Asn Phe Lys Ile Asp Tyr Phe Leu Lys Glu Ala Leu Gly
                245                 250                 255
Glu Val Pro Asp Arg Ile Val Thr Glu Pro Arg Phe Leu Lys His
            260                 265                 270
Phe Asp Glu Leu Met Asn Glu Asn Phe Asp Glu Ile Lys Gly Trp
        275                 280                 285
Met Ile Val Lys Phe Ile Asn Asn Val Ala Ser Tyr Leu Ser Gln Asp
    290                 295                 300
Phe Arg Glu Ala Ser Phe Gln Phe Ser Gln Ala Leu Thr Gly Gln Pro
305                 310                 315                 320
Glu Leu Gln Ser Gln Glu Lys Gln Ala Tyr His Leu Ala Asn Gly Leu
                325                 330                 335
Phe Ser Glu Val Val Gly Val Tyr Tyr Gly Gln Thr Tyr Phe Gly Glu
                340                 345                 350
Glu Ala Lys Lys Asp Val Leu Thr Met Ile Arg Gln Met Ile Asp Val
                355                 360                 365
Tyr Glu Lys Arg Ile Lys Glu Asn Ser Trp Leu Ser Glu Glu Thr Lys
            370                 375                 380
Glu Lys Ala Ile Val Lys Leu Arg Ala Leu Ile Leu Lys Ile Gly Tyr
385                 390                 395                 400
Pro Asp Lys Ile Glu Glu Ile Tyr Asn Arg Tyr Asn Ile Thr Pro Ala
                405                 410                 415
Ser Glu Gly Gly Ser Leu Tyr Ser Asn Val Arg Ala Ala Asp Ile Glu
            420                 425                 430
Gln Val Lys Tyr Asn Val Glu Lys Leu His Lys Pro Val Asp Arg Ser
            435                 440                 445
Val Trp Leu Met Pro Ala Asn Leu Val Asn Ala Cys Tyr Asp Pro Gln
        450                 455                 460
Arg Asn Asp Leu Thr Phe Pro Ala Ala Ile Leu Gln Ala Pro Phe Tyr
465                 470                 475                 480
Asp Leu Lys Gln Asp Arg Ala Glu Asn Phe Gly Gly Ile Gly Thr Val
                485                 490                 495
Ile Ala His Glu Ile Ser His Ala Phe Asp Asn Asn Gly Ala Gln Phe
                500                 505                 510
Asp Glu Phe Gly Asn Met Lys Asn Trp Trp Thr Glu Glu Asp Phe Ala
            515                 520                 525
Glu Phe Lys Lys Arg Thr Gln Ala Glu Ile Asp Leu Phe Asp Gly Ile
        530                 535                 540
Lys Tyr Gly Pro Val Thr Leu Asn Gly Lys Gln Ile Val Ser Glu Asn
545                 550                 555                 560
Ile Ala Asp Gln Gly Gly Leu Thr Ala Ala Ile Lys Ala Ala Lys Asp
                565                 570                 575
Glu Gly Asp Asp Leu Lys Lys Leu Phe Glu Asn Phe Ala Arg Ile Trp
            580                 585                 590
Ala Asn Lys Gln Leu Thr Glu Ser Ile Lys Thr Gln Val Ser Phe Asp
            595                 600                 605
Val His Ala Pro Gly Pro Glu Arg Ala Asn Val Gln Ser Gln Cys Gln
        610                 615                 620
Glu Asp Phe Tyr Glu Val Phe Asp Val Lys Glu Thr Asp Gly Met Trp
625                 630                 635                 640
Leu Asp Pro Glu Lys Arg Val Val Ile Trp
                645                 650
```

<210> SEQ ID NO 117
<211> LENGTH: 1314
<212> TYPE: DNA
<213> ORGANISM: Lactobacillus acidophilus
<220> FEATURE:
<221> NAME/KEY: CDS
<222> LOCATION: (1)..(1314)
<223> OTHER INFORMATION: Aminopeptidase E ORF# 204

<400> SEQUENCE: 117

```
atg gct cat gaa ctc act gtg caa gaa cta gaa aag ttc tct gct gat      48
Met Ala His Glu Leu Thr Val Gln Glu Leu Glu Lys Phe Ser Ala Asp
1               5                   10                  15 ttt aac aag aat cca aag aat aaa att att gct cgt gcg gct caa cgt      96
Phe Asn Lys Asn Pro Lys Asn Lys Ile Ile Ala Arg Ala Ala Gln Arg
            20                  25                  30 agc ggt gtg ctc gaa gca tct tac aac gat cgc gta gaa ggt gaa tta     144
Ser Gly Val Leu Glu Ala Ser Tyr Asn Asp Arg Val Glu Gly Glu Leu
        35                  40                  45 act cgc gtt ttt tca acg gaa tta gat act gac aac gtt act aac caa     192
Thr Arg Val Phe Ser Thr Glu Leu Asp Thr Asp Asn Val Thr Asn Gln
50                  55                  60 ctt cac tca ggt cgt tgc tgg gag ttt tca acc tta aat gtt ttg cgt     240
Leu His Ser Gly Arg Cys Trp Glu Phe Ser Thr Leu Asn Val Leu Arg
65                  70                  75                  80 cat gca ttt ggc aag aag tac aaa gca aag aac ttt acc ttc tca caa     288
His Ala Phe Gly Lys Lys Tyr Lys Ala Lys Asn Phe Thr Phe Ser Gln
                85                  90                  95 gcc tac aac ttc ttc tgg gat aag att gaa cgt gct aat atg ttc tac     336
Ala Tyr Asn Phe Phe Trp Asp Lys Ile Glu Arg Ala Asn Met Phe Tyr
            100                 105                 110 aat cgt atc tta gat agt gct gac atg cct ctt gat tct cgt caa gtg     384
Asn Arg Ile Leu Asp Ser Ala Asp Met Pro Leu Asp Ser Arg Gln Val
        115                 120                 125 aaa gct gat ctc gac ttt gct ggt gca gac ggt gga caa ttc caa atg     432
Lys Ala Asp Leu Asp Phe Ala Gly Ala Asp Gly Gly Gln Phe Gln Met
130                 135                 140 gct gcc gca tta gta gaa aaa tat ggc gtt gtt cct tca tac gca atg     480
Ala Ala Ala Leu Val Glu Lys Tyr Gly Val Val Pro Ser Tyr Ala Met
145                 150                 155                 160 cct gaa act ttc aac act aat aat aca act agc ttt gcg aca gct ctt     528
Pro Glu Thr Phe Asn Thr Asn Asn Thr Thr Ser Phe Ala Thr Ala Leu
                165                 170                 175 ggt gac aag ctt aaa aaa gac gca tta gtt ctt cgt gaa tta aag caa     576
Gly Asp Lys Leu Lys Lys Asp Ala Leu Val Leu Arg Glu Leu Lys Gln
            180                 185                 190 tat ggt aaa gat gac gaa atc gct aag act cgt gaa aaa ttc ttg agt     624
Tyr Gly Lys Asp Asp Glu Ile Ala Lys Thr Arg Glu Lys Phe Leu Ser
        195                 200                 205 gaa gtt tac caa atg act gct atc gct gtc ggt gaa cca cct aag acg     672
Glu Val Tyr Gln Met Thr Ala Ile Ala Val Gly Glu Pro Pro Lys Thr
    210                 215                 220 ttt gat ctt gaa tat cgt gat gat gat aag aaa tat cat tta gac aag     720
Phe Asp Leu Glu Tyr Arg Asp Asp Asp Lys Lys Tyr His Leu Asp Lys
225                 230                 235                 240 aat ctt aca cca ctt gaa ttc tta cat aag tat atg ggt gag gtt gat     768
Asn Leu Thr Pro Leu Glu Phe Leu His Lys Tyr Met Gly Glu Val Asp
                245                 250                 255 ttt gat gac tat gtt gtt tta act aat gca cct gat cat gaa tac aac     816
Phe Asp Asp Tyr Val Val Leu Thr Asn Ala Pro Asp His Glu Tyr Asn
```

```
                260                 265                 270
aag tta tac ggt ctt cca gca gaa gat aac att gaa ggc tca ctt aga      864
Lys Leu Tyr Gly Leu Pro Ala Glu Asp Asn Ile Glu Gly Ser Leu Arg
        275                 280                 285 atc aag ctt tta aat gta cct atg gaa tac tta tca tca gct gct att      912
Ile Lys Leu Leu Asn Val Pro Met Glu Tyr Leu Ser Ser Ala Ala Ile
    290                 295                 300 gct caa tta aaa gat ggt gaa gca gta tgg ttt ggt aac gat gtt ctt      960
Ala Gln Leu Lys Asp Gly Glu Ala Val Trp Phe Gly Asn Asp Val Leu
305                 310                 315                 320 cgt caa atg gac cgc aag act ggt tat ctt gat act aac ctt tac aaa     1008
Arg Gln Met Asp Arg Lys Thr Gly Tyr Leu Asp Thr Asn Leu Tyr Lys
                325                 330                 335 ctt gac gat tta ttc ggc gtt gat ctt aag atg tct aaa gct gac aga     1056
Leu Asp Asp Leu Phe Gly Val Asp Leu Lys Met Ser Lys Ala Asp Arg
            340                 345                 350 tta agg act ggt gtt ggt gaa gtt tca cac gca atg acc ttg gtt ggt     1104
Leu Arg Thr Gly Val Gly Glu Val Ser His Ala Met Thr Leu Val Gly
        355                 360                 365 gtt gat gaa gat aat ggc gaa atc cgt caa tgg aag gtc gaa aac tca     1152
Val Asp Glu Asp Asn Gly Glu Ile Arg Gln Trp Lys Val Glu Asn Ser
370                 375                 380 tgg ggc gaa aaa tct ggt tct aaa gga ttc ttt gtt atg agt aat gac     1200
Trp Gly Glu Lys Ser Gly Ser Lys Gly Phe Phe Val Met Ser Asn Asp
385                 390                 395                 400 tgg ttc aac gac tat gta tat gaa gtt gtt gtt cac aag aag tat tta     1248
Trp Phe Asn Asp Tyr Val Tyr Glu Val Val Val His Lys Lys Tyr Leu
                405                 410                 415 acc gat aag caa aaa gaa ctt gca gaa ggt cct att acc gac ttg cct     1296
Thr Asp Lys Gln Lys Glu Leu Ala Glu Gly Pro Ile Thr Asp Leu Pro
            420                 425                 430 gca tgg gat tca tta gct                                              1314
Ala Trp Asp Ser Leu Ala
        435

<210> SEQ ID NO 118
<211> LENGTH: 438
<212> TYPE: PRT
<213> ORGANISM: Lactobacillus acidophilus

<400> SEQUENCE: 118

Met Ala His Glu Leu Thr Val Gln Glu Leu Glu Lys Phe Ser Ala Asp
1               5                   10                  15

Phe Asn Lys Asn Pro Lys Asn Lys Ile Ile Ala Arg Ala Ala Gln Arg
            20                  25                  30

Ser Gly Val Leu Glu Ala Ser Tyr Asn Asp Arg Val Glu Gly Glu Leu
        35                  40                  45

Thr Arg Val Phe Ser Thr Glu Leu Asp Thr Asp Asn Val Thr Asn Gln
    50                  55                  60

Leu His Ser Gly Arg Cys Trp Glu Phe Ser Thr Leu Asn Val Leu Arg
65                  70                  75                  80

His Ala Phe Gly Lys Lys Tyr Lys Ala Lys Asn Phe Thr Phe Ser Gln
                85                  90                  95

Ala Tyr Asn Phe Phe Trp Asp Lys Ile Glu Arg Ala Asn Met Phe Tyr
            100                 105                 110

Asn Arg Ile Leu Asp Ser Ala Asp Met Pro Leu Asp Ser Arg Gln Val
        115                 120                 125

Lys Ala Asp Leu Asp Phe Ala Gly Ala Asp Gly Gly Gln Phe Gln Met
```

```
                        130                 135                 140
Ala Ala Ala Leu Val Glu Lys Tyr Gly Val Val Pro Ser Tyr Ala Met
145                 150                 155                 160

Pro Glu Thr Phe Asn Thr Asn Thr Thr Ser Phe Ala Thr Ala Leu
                165                 170                 175

Gly Asp Lys Leu Lys Lys Asp Ala Leu Val Leu Arg Glu Leu Lys Gln
                180                 185                 190

Tyr Gly Lys Asp Asp Glu Ile Ala Lys Thr Arg Glu Lys Phe Leu Ser
                195                 200                 205

Glu Val Tyr Gln Met Thr Ala Ile Ala Val Gly Glu Pro Pro Lys Thr
210                 215                 220

Phe Asp Leu Glu Tyr Arg Asp Asp Lys Lys Tyr His Leu Asp Lys
225                 230                 235                 240

Asn Leu Thr Pro Leu Glu Phe Leu His Lys Tyr Met Gly Glu Val Asp
                245                 250                 255

Phe Asp Asp Tyr Val Val Leu Thr Asn Ala Pro Asp His Glu Tyr Asn
                260                 265                 270

Lys Leu Tyr Gly Leu Pro Ala Glu Asp Asn Ile Glu Gly Ser Leu Arg
                275                 280                 285

Ile Lys Leu Leu Asn Val Pro Met Glu Tyr Leu Ser Ser Ala Ala Ile
                290                 295                 300

Ala Gln Leu Lys Asp Gly Glu Ala Val Trp Phe Gly Asn Asp Val Leu
305                 310                 315                 320

Arg Gln Met Asp Arg Lys Thr Gly Tyr Leu Asp Thr Asn Leu Tyr Lys
                325                 330                 335

Leu Asp Asp Leu Phe Gly Val Asp Leu Lys Met Ser Lys Ala Asp Arg
                340                 345                 350

Leu Arg Thr Gly Val Gly Glu Val Ser His Ala Met Thr Leu Val Gly
                355                 360                 365

Val Asp Glu Asp Asn Gly Glu Ile Arg Gln Trp Lys Val Glu Asn Ser
370                 375                 380

Trp Gly Glu Lys Ser Gly Ser Lys Gly Phe Phe Val Met Ser Asn Asp
385                 390                 395                 400

Trp Phe Asn Asp Tyr Val Tyr Glu Val Val His Lys Lys Tyr Leu
                405                 410                 415

Thr Asp Lys Gln Lys Glu Leu Ala Glu Gly Pro Ile Thr Asp Leu Pro
                420                 425                 430

Ala Trp Asp Ser Leu Ala
            435

<210> SEQ ID NO 119
<211> LENGTH: 1419
<212> TYPE: DNA
<213> ORGANISM: Lactobacillus acidophilus
<220> FEATURE:
<221> NAME/KEY: CDS
<222> LOCATION: (1)..(1419)
<223> OTHER INFORMATION: Dipeptidase (EC3.4.13.18) ORF# 1294

<400> SEQUENCE: 119 atg aaa gaa tat agt gct tgt act acc atc tta gtt ggt aaa aat gcc      48
Met Lys Glu Tyr Ser Ala Cys Thr Thr Ile Leu Val Gly Lys Asn Ala
1               5                   10                  15 tca att gat ggc aca act atg att gct cgt aat gat gat acc ttc cgc      96
Ser Ile Asp Gly Thr Thr Met Ile Ala Arg Asn Asp Asp Thr Phe Arg
            20                  25                  30
```

-continued

```
cca att act cca caa aag ttt att att gag cca gct cgt cat ggc gaa    144
Pro Ile Thr Pro Gln Lys Phe Ile Ile Glu Pro Ala Arg His Gly Glu
         35                  40                  45 aag aaa cat att aaa tca tgg ctt aat aag ttt gag atg gat ctt cca    192
Lys Lys His Ile Lys Ser Trp Leu Asn Lys Phe Glu Met Asp Leu Pro
 50                  55                  60 gaa gat gca caa cga gtt cct gcc gta cca aat gtt gat tat aaa cat    240
Glu Asp Ala Gln Arg Val Pro Ala Val Pro Asn Val Asp Tyr Lys His
 65                  70                  75                  80 cgt ggt tac tac gat gaa agt ggt att aac caa gaa aat gtt gct atg    288
Arg Gly Tyr Tyr Asp Glu Ser Gly Ile Asn Gln Glu Asn Val Ala Met
                 85                  90                  95 tca tgt act gaa tca act tat ggt aat gaa aga act tta gca ttt gat    336
Ser Cys Thr Glu Ser Thr Tyr Gly Asn Glu Arg Thr Leu Ala Phe Asp
            100                 105                 110 cca ttg gtt aaa gat gga tta gat gaa gac tgt atg caa acc gta gtt    384
Pro Leu Val Lys Asp Gly Leu Asp Glu Asp Cys Met Gln Thr Val Val
        115                 120                 125 ttg cca tac att cat tca gca cgt gat ggt gtt aag tat tta ggt aag    432
Leu Pro Tyr Ile His Ser Ala Arg Asp Gly Val Lys Tyr Leu Gly Lys
    130                 135                 140 tta att gct aag tat ggc tca cca gct ggt aac tct gtt ttg ttc agt    480
Leu Ile Ala Lys Tyr Gly Ser Pro Ala Gly Asn Ser Val Leu Phe Ser
145                 150                 155                 160 gat aaa gat gaa att tgg tac atg gaa att gta act ggt cac cac tgg    528
Asp Lys Asp Glu Ile Trp Tyr Met Glu Ile Val Thr Gly His His Trp
                165                 170                 175 gta gca gaa cgt att cct gat gat tgc tat gct gca act ggt aac cgt    576
Val Ala Glu Arg Ile Pro Asp Asp Cys Tyr Ala Ala Thr Gly Asn Arg
            180                 185                 190 gta gct att gaa caa gtc gat ttc gat aat cct gaa tac ttc atg tgg    624
Val Ala Ile Glu Gln Val Asp Phe Asp Asn Pro Glu Tyr Phe Met Trp
        195                 200                 205 agt gaa gga att caa gaa ttt gtt gaa gaa cat cac ttg aat cca gat    672
Ser Glu Gly Ile Gln Glu Phe Val Glu Glu His His Leu Asn Pro Asp
    210                 215                 220 cat gaa ggt tgg aat ttc cgt cat atc ttt ggt act tac act gaa caa    720
His Glu Gly Trp Asn Phe Arg His Ile Phe Gly Thr Tyr Thr Glu Gln
225                 230                 235                 240 gat cgc cac tac aat act aac cgt caa tgg tat att caa aag ttg ttc    768
Asp Arg His Tyr Asn Thr Asn Arg Gln Trp Tyr Ile Gln Lys Leu Phe
                245                 250                 255 aac cca gaa att gaa caa gat cca caa gat ggc gat att cca ttt att    816
Asn Pro Glu Ile Glu Gln Asp Pro Gln Asp Gly Asp Ile Pro Phe Ile
            260                 265                 270 cgt aag gca gct aag aag att acc aag gaa gat att gaa ttt gcc tta    864
Arg Lys Ala Ala Lys Lys Ile Thr Lys Glu Asp Ile Glu Phe Ala Leu
        275                 280                 285 ggt tca cat tat caa gat act cca tat gat cca ttt ggt aag ggt acc    912
Gly Ser His Tyr Gln Asp Thr Pro Tyr Asp Pro Phe Gly Lys Gly Thr
    290                 295                 300 gaa gaa gaa aag cac cgc tac cgt cct att ggt ttg aac cgt acg caa    960
Glu Glu Glu Lys His Arg Tyr Arg Pro Ile Gly Leu Asn Arg Thr Gln
305                 310                 315                 320 aat gct cat att tta caa ata aga agt gat gta cca gca gac cgt gca   1008
Asn Ala His Ile Leu Gln Ile Arg Ser Asp Val Pro Ala Asp Arg Ala
                325                 330                 335 gca att atg tgg tta tgt att ggt ggt cca acg ttt act cca ttt atc   1056
Ala Ile Met Trp Leu Cys Ile Gly Gly Pro Thr Phe Thr Pro Phe Ile
            340                 345                 350
```

```
cca ttc ttt gct aat atg aat gaa act gat cct tca ttt aac aat act    1104
Pro Phe Phe Ala Asn Met Asn Glu Thr Asp Pro Ser Phe Asn Asn Thr
    355                 360                 365 tca atg gat tac aat atg agt gat gca tgg tgg tac tac aag tca ttt    1152
Ser Met Asp Tyr Asn Met Ser Asp Ala Trp Trp Tyr Tyr Lys Ser Phe
370                 375                 380 gct gca ctt gtt gaa agc cac tat cca caa ttt gtt caa ctt gat act    1200
Ala Ala Leu Val Glu Ser His Tyr Pro Gln Phe Val Gln Leu Asp Thr
385                 390                 395                 400 act tat ctt act gaa ctt aat cgt tac ttc aga ggt cgt gtt gaa gaa    1248
Thr Tyr Leu Thr Glu Leu Asn Arg Tyr Phe Arg Gly Arg Val Glu Glu
            405                 410                 415 att att aag aat tca gaa ggt aaa tca ggc gat gaa tta act gaa tac    1296
Ile Ile Lys Asn Ser Glu Gly Lys Ser Gly Asp Glu Leu Thr Glu Tyr
            420                 425                 430 tta act aaa gaa aat caa aag act gtt gct cat act cgc aag gaa act    1344
Leu Thr Lys Glu Asn Gln Lys Thr Val Ala His Thr Arg Lys Glu Thr
            435                 440                 445 gaa aag tta tgg gga gaa atg atg att gat tca att aat atg tct aag    1392
Glu Lys Leu Trp Gly Glu Met Met Ile Asp Ser Ile Asn Met Ser Lys
450                 455                 460 ttg act ttt aat atg gat gaa aat ctc                                1419
Leu Thr Phe Asn Met Asp Glu Asn Leu
465                 470

<210> SEQ ID NO 120
<211> LENGTH: 473
<212> TYPE: PRT
<213> ORGANISM: Lactobacillus acidophilus

<400> SEQUENCE: 120

Met Lys Glu Tyr Ser Ala Cys Thr Thr Ile Leu Val Gly Lys Asn Ala
1               5                   10                  15

Ser Ile Asp Gly Thr Thr Met Ile Ala Arg Asn Asp Thr Phe Arg
            20                  25                  30

Pro Ile Thr Pro Gln Lys Phe Ile Ile Glu Pro Ala Arg His Gly Glu
        35                  40                  45

Lys Lys His Ile Lys Ser Trp Leu Asn Lys Phe Glu Met Asp Leu Pro
    50                  55                  60

Glu Asp Ala Gln Arg Val Pro Ala Val Pro Asn Val Asp Tyr Lys His
65                  70                  75                  80

Arg Gly Tyr Tyr Asp Glu Ser Gly Ile Asn Gln Glu Asn Val Ala Met
                85                  90                  95

Ser Cys Thr Glu Ser Thr Tyr Gly Asn Glu Arg Thr Leu Ala Phe Asp
            100                 105                 110

Pro Leu Val Lys Asp Gly Leu Asp Glu Asp Cys Met Gln Thr Val Val
        115                 120                 125

Leu Pro Tyr Ile His Ser Ala Arg Asp Gly Val Lys Tyr Leu Gly Lys
    130                 135                 140

Leu Ile Ala Lys Tyr Gly Ser Pro Ala Gly Asn Ser Val Leu Phe Ser
145                 150                 155                 160

Asp Lys Asp Glu Ile Trp Tyr Met Glu Ile Val Thr Gly His His Trp
                165                 170                 175

Val Ala Glu Arg Ile Pro Asp Asp Cys Tyr Ala Ala Thr Gly Asn Arg
            180                 185                 190

Val Ala Ile Glu Gln Val Asp Phe Asp Asn Pro Glu Tyr Phe Met Trp
        195                 200                 205
```

Ser Glu Gly Ile Gln Glu Phe Val Glu His His Leu Asn Pro Asp
210                 215                 220

His Glu Gly Trp Asn Phe Arg His Ile Phe Gly Thr Tyr Thr Glu Gln
225                 230                 235                 240

Asp Arg His Tyr Asn Thr Asn Arg Gln Trp Tyr Ile Gln Lys Leu Phe
            245                 250                 255

Asn Pro Glu Ile Glu Gln Asp Pro Gln Asp Gly Asp Ile Pro Phe Ile
        260                 265                 270

Arg Lys Ala Ala Lys Lys Ile Thr Lys Glu Asp Ile Glu Phe Ala Leu
    275                 280                 285

Gly Ser His Tyr Gln Asp Thr Pro Tyr Asp Pro Phe Gly Lys Gly Thr
290                 295                 300

Glu Glu Lys His Arg Tyr Arg Pro Ile Gly Leu Asn Arg Thr Gln
305                 310                 315                 320

Asn Ala His Ile Leu Gln Ile Arg Ser Asp Val Pro Ala Asp Arg Ala
            325                 330                 335

Ala Ile Met Trp Leu Cys Ile Gly Gly Pro Thr Phe Thr Pro Phe Ile
        340                 345                 350

Pro Phe Phe Ala Asn Met Asn Glu Thr Asp Pro Ser Phe Asn Asn Thr
    355                 360                 365

Ser Met Asp Tyr Asn Met Ser Asp Ala Trp Trp Tyr Tyr Lys Ser Phe
370                 375                 380

Ala Ala Leu Val Glu Ser His Tyr Pro Gln Phe Val Gln Leu Asp Thr
385                 390                 395                 400

Thr Tyr Leu Thr Glu Leu Asn Arg Tyr Phe Arg Gly Arg Val Glu Glu
            405                 410                 415

Ile Ile Lys Asn Ser Glu Gly Lys Ser Gly Asp Glu Leu Thr Glu Tyr
        420                 425                 430

Leu Thr Lys Glu Asn Gln Lys Thr Val Ala His Thr Arg Lys Glu Thr
    435                 440                 445

Glu Lys Leu Trp Gly Glu Met Met Ile Asp Ser Ile Asn Met Ser Lys
450                 455                 460

Leu Thr Phe Asn Met Asp Glu Asn Leu
465                 470

<210> SEQ ID NO 121
<211> LENGTH: 579
<212> TYPE: DNA
<213> ORGANISM: Lactobacillus acidophilus
<220> FEATURE:
<221> NAME/KEY: CDS
<222> LOCATION: (1)..(579)
<223> OTHER INFORMATION: PepQ ORF# 1343

<400> SEQUENCE: 121

```
atg gca gtt aaa gag gca cat tct aag cac atg act gta tgt gca cat        48
Met Ala Val Lys Glu Ala His Ser Lys His Met Thr Val Cys Ala His
1               5                  10                  15 gca gaa gga aaa atg gaa att cat tat gct gtt gtt gcc gga gta gat        96
Ala Glu Gly Lys Met Glu Ile His Tyr Ala Val Val Ala Gly Val Asp
                20                  25                  30 tct gtt gag cat ggt ttt tat gta agt gat gaa gat att gaa tta atg       144
Ser Val Glu His Gly Phe Tyr Val Ser Asp Glu Asp Ile Glu Leu Met
            35                  40                  45 aaa aaa caa ggt aca ttt tta tca cca acg tta att gct gga cat caa       192
Lys Lys Gln Gly Thr Phe Leu Ser Pro Thr Leu Ile Ala Gly His Gln
        50                  55                  60
```

```
att gtg gaa tat ggt aaa gga aaa atg acc gat ttt tca tat cag aag        240
Ile Val Glu Tyr Gly Lys Gly Lys Met Thr Asp Phe Ser Tyr Gln Lys
 65                  70                  75                  80 atg tgt cag cat gta gag gca ttt tat gaa cat gtt ggt aaa gca att        288
Met Cys Gln His Val Glu Ala Phe Tyr Glu His Val Gly Lys Ala Ile
                 85                  90                  95 aaa gca ggt gtt aaa tta gcg tta gga acc gat gca ggc aca ttt atg        336
Lys Ala Gly Val Lys Leu Ala Leu Gly Thr Asp Ala Gly Thr Phe Met
            100                 105                 110 aat cca tta gaa gat act gct aaa gaa tta aaa gaa tta act aga gct        384
Asn Pro Leu Glu Asp Thr Ala Lys Glu Leu Lys Glu Leu Thr Arg Ala
        115                 120                 125 ggt aca agc aat tac caa gcc tta cgt gct gca gga tta gga tct gct        432
Gly Thr Ser Asn Tyr Gln Ala Leu Arg Ala Ala Gly Leu Gly Ser Ala
    130                 135                 140 gaa tta tta aaa att gat cga aat tat gga tcg ctt gaa gtt gga aaa        480
Glu Leu Leu Lys Ile Asp Arg Asn Tyr Gly Ser Leu Glu Val Gly Lys
145                 150                 155                 160 tat gca gat ttt tta gta tta aag aat aat cca cta act gat gta acg        528
Tyr Ala Asp Phe Leu Val Leu Lys Asn Asn Pro Leu Thr Asp Val Thr
                165                 170                 175 gct gtt gag caa gtt gat aag caa gtt tat cag cat ggt aag cga aaa        576
Ala Val Glu Gln Val Asp Lys Gln Val Tyr Gln His Gly Lys Arg Lys
            180                 185                 190 tat                                                                    579
Tyr

<210> SEQ ID NO 122
<211> LENGTH: 193
<212> TYPE: PRT
<213> ORGANISM: Lactobacillus acidophilus

<400> SEQUENCE: 122

Met Ala Val Lys Glu Ala His Ser Lys His Met Thr Val Cys Ala His
 1               5                  10                  15

Ala Glu Gly Lys Met Glu Ile His Tyr Ala Val Val Ala Gly Val Asp
                20                  25                  30

Ser Val Glu His Gly Phe Tyr Val Ser Asp Glu Asp Ile Glu Leu Met
            35                  40                  45

Lys Lys Gln Gly Thr Phe Leu Ser Pro Thr Leu Ile Ala Gly His Gln
        50                  55                  60

Ile Val Glu Tyr Gly Lys Gly Lys Met Thr Asp Phe Ser Tyr Gln Lys
 65                  70                  75                  80

Met Cys Gln His Val Glu Ala Phe Tyr Glu His Val Gly Lys Ala Ile
                 85                  90                  95

Lys Ala Gly Val Lys Leu Ala Leu Gly Thr Asp Ala Gly Thr Phe Met
            100                 105                 110

Asn Pro Leu Glu Asp Thr Ala Lys Glu Leu Lys Glu Leu Thr Arg Ala
        115                 120                 125

Gly Thr Ser Asn Tyr Gln Ala Leu Arg Ala Ala Gly Leu Gly Ser Ala
    130                 135                 140

Glu Leu Leu Lys Ile Asp Arg Asn Tyr Gly Ser Leu Glu Val Gly Lys
145                 150                 155                 160

Tyr Ala Asp Phe Leu Val Leu Lys Asn Asn Pro Leu Thr Asp Val Thr
                165                 170                 175

Ala Val Glu Gln Val Asp Lys Gln Val Tyr Gln His Gly Lys Arg Lys
            180                 185                 190
```

Tyr

<210> SEQ ID NO 123
<211> LENGTH: 1515
<212> TYPE: DNA
<213> ORGANISM: Lactobacillus acidophilus
<220> FEATURE:
<221> NAME/KEY: CDS
<222> LOCATION: (1)..(1515)
<223> OTHER INFORMATION: Aminopeptidase N ORF# 1567

<400> SEQUENCE: 123

| | | | | | | | | | | | | | | | | |
|---|---|---|---|---|---|---|---|---|---|---|---|---|---|---|---|---|
| atg | aaa | aaa | aga | aca | aca | ctt | tta | tta | tca | agt | gca | ata | aca | att | gca | 48 |
| Met | Lys | Lys | Arg | Thr | Thr | Leu | Leu | Leu | Ser | Ser | Ala | Ile | Thr | Ile | Ala | |
| 1 | | | | 5 | | | | | 10 | | | | | 15 | | |
| gca | tta | ttt | agt | ttt | aat | tca | aag | gct | cag | gcc | gct | gcc | gat | ccc | gca | 96 |
| Ala | Leu | Phe | Ser | Phe | Asn | Ser | Lys | Ala | Gln | Ala | Ala | Ala | Asp | Pro | Ala | |
| | | | 20 | | | | | 25 | | | | | 30 | | | |
| gtc | aaa | gca | acc | aac | tac | aat | atg | act | gta | aaa | cta | aat | act | cgc | aaa | 144 |
| Val | Lys | Ala | Thr | Asn | Tyr | Asn | Met | Thr | Val | Lys | Leu | Asn | Thr | Arg | Lys | |
| | | 35 | | | | | 40 | | | | | 45 | | | | |
| aat | caa | cta | acc | gaa | aaa | gtt | acc | atg | cat | gtc | gtt | aat | aac | ggc | aat | 192 |
| Asn | Gln | Leu | Thr | Glu | Lys | Val | Thr | Met | His | Val | Val | Asn | Asn | Gly | Asn | |
| 50 | | | | | 55 | | | | | 60 | | | | | | |
| gaa | cca | gtt | aag | aac | tta | ctg | atc | aga | aat | att | gct | aat | ggt | gtt | tta | 240 |
| Glu | Pro | Val | Lys | Asn | Leu | Leu | Ile | Arg | Asn | Ile | Ala | Asn | Gly | Val | Leu | |
| 65 | | | | | 70 | | | | | 75 | | | | | 80 | |
| aag | tat | gac | cat | cag | cat | ttt | aaa | att | gcc | aaa | aat | gca | aaa | act | aca | 288 |
| Lys | Tyr | Asp | His | Gln | His | Phe | Lys | Ile | Ala | Lys | Asn | Ala | Lys | Thr | Thr | |
| | | | | 85 | | | | | 90 | | | | | 95 | | |
| gtt | aaa | agt | att | tcc | tca | gct | gga | gaa | aat | ctt | tcc | tat | acc | act | ggc | 336 |
| Val | Lys | Ser | Ile | Ser | Ser | Ala | Gly | Glu | Asn | Leu | Ser | Tyr | Thr | Thr | Gly | |
| | | | 100 | | | | | 105 | | | | | 110 | | | |
| aaa | gat | aag | agc | aac | cta | ttc | gtt | gat | aaa | agc | tta | aat | gca | ggt | gaa | 384 |
| Lys | Asp | Lys | Ser | Asn | Leu | Phe | Val | Asp | Lys | Ser | Leu | Asn | Ala | Gly | Glu | |
| | | 115 | | | | | 120 | | | | | 125 | | | | |
| tct | acc | gac | tta | act | gtt | aat | gta | gtc | acc | agc | gtt | ccc | aaa | aga | caa | 432 |
| Ser | Thr | Asp | Leu | Thr | Val | Asn | Val | Val | Thr | Ser | Val | Pro | Lys | Arg | Gln | |
| 130 | | | | | 135 | | | | | 140 | | | | | | |
| gat | cgt | ttt | ggc | tac | caa | aat | att | aat | ggc | ggt | aaa | gtt | tat | aac | tta | 480 |
| Asp | Arg | Phe | Gly | Tyr | Gln | Asn | Ile | Asn | Gly | Gly | Lys | Val | Tyr | Asn | Leu | |
| 145 | | | | | 150 | | | | | 155 | | | | | 160 | |
| tcc | ttc | tgt | ttt | cct | tac | cta | agc | gat | tat | cgc | aac | gga | aaa | tgg | aat | 528 |
| Ser | Phe | Cys | Phe | Pro | Tyr | Leu | Ser | Asp | Tyr | Arg | Asn | Gly | Lys | Trp | Asn | |
| | | | | 165 | | | | | 170 | | | | | 175 | | |
| tac | cat | cca | tat | tat | gac | ggt | ggt | gaa | aac | cgt | aat | acc | act | gtc | agc | 576 |
| Tyr | His | Pro | Tyr | Tyr | Asp | Gly | Gly | Glu | Asn | Arg | Asn | Thr | Thr | Val | Ser | |
| | | | 180 | | | | | 185 | | | | | 190 | | | |
| aat | ttt | cat | gtt | agc | ttt | tat | gca | cca | aag | agt | tac | aag | gtt | gct | gct | 624 |
| Asn | Phe | His | Val | Ser | Phe | Tyr | Ala | Pro | Lys | Ser | Tyr | Lys | Val | Ala | Ala | |
| | | 195 | | | | | 200 | | | | | 205 | | | | |
| tca | gga | caa | aat | agc | acc | aaa | aat | ggc | aag | act | aca | atc | gtt | gcg | gaa | 672 |
| Ser | Gly | Gln | Asn | Ser | Thr | Lys | Asn | Gly | Lys | Thr | Thr | Ile | Val | Ala | Glu | |
| | | 210 | | | | | 215 | | | | | 220 | | | | |
| aat | atg | aga | gat | ttt | gct | atc | gtt | gct | tct | aat | aaa | ttc | aag | gtt | tct | 720 |
| Asn | Met | Arg | Asp | Phe | Ala | Ile | Val | Ala | Ser | Asn | Lys | Phe | Lys | Val | Ser | |
| 225 | | | | | 230 | | | | | 235 | | | | | 240 | |
| cat | act | tat | gca | gat | ggt | ata | aga | att | aat | aat | tat | tat | ttt | gcc | ggt | 768 |
| His | Thr | Tyr | Ala | Asp | Gly | Ile | Arg | Ile | Asn | Asn | Tyr | Tyr | Phe | Ala | Gly | |
| | | | | 245 | | | | | 250 | | | | | 255 | | |

```
aaa aat agt aag caa tat aac aaa ctt gcc tta ttg act gct aaa gat         816
Lys Asn Ser Lys Gln Tyr Asn Lys Leu Ala Leu Leu Thr Ala Lys Asp
        260                 265                 270 agt ttc aat att ttc acc aag aaa att ggt aaa tat cct tat aaa gaa         864
Ser Phe Asn Ile Phe Thr Lys Lys Ile Gly Lys Tyr Pro Tyr Lys Glu
    275                 280                 285 atc gat atg act gaa ggc tta ctt ggt aaa gat acc ggt gga atg gaa         912
Ile Asp Met Thr Glu Gly Leu Leu Gly Lys Asp Thr Gly Gly Met Glu
290                 295                 300 tat cct agt tta att atg atc gat gcg agt ggc ttt gta caa aag aaa         960
Tyr Pro Ser Leu Ile Met Ile Asp Ala Ser Gly Phe Val Gln Lys Lys
305                 310                 315                 320 cac cca atc aac aga tac aat gaa tta acc gaa gat gtt tcc cat gaa        1008
His Pro Ile Asn Arg Tyr Asn Glu Leu Thr Glu Asp Val Ser His Glu
                325                 330                 335 att ggt cac caa tgg ttc tac gct act gtt ggc aat gac gaa tac acc        1056
Ile Gly His Gln Trp Phe Tyr Ala Thr Val Gly Asn Asp Glu Tyr Thr
            340                 345                 350 gag cca tgg ctt gat gaa gga ctt act aat ttc ctt gaa aac agt gtt        1104
Glu Pro Trp Leu Asp Glu Gly Leu Thr Asn Phe Leu Glu Asn Ser Val
        355                 360                 365 tat gat tta act tat act aag agt aaa gcc tat act gct aaa ctt atg        1152
Tyr Asp Leu Thr Tyr Thr Lys Ser Lys Ala Tyr Thr Ala Lys Leu Met
    370                 375                 380 cac aac aaa ctt tat aat cgt aaa aca gtg aaa aag gca aat caa gtt        1200
His Asn Lys Leu Tyr Asn Arg Lys Thr Val Lys Lys Ala Asn Gln Val
385                 390                 395                 400 ctg gct aac tta gct aat acc ttt tta acc gat cat cgt caa aaa ggt        1248
Leu Ala Asn Leu Ala Asn Thr Phe Leu Thr Asp His Arg Gln Lys Gly
                405                 410                 415 atc tac gtt aac cgt cct ctc aac aat cca cca aaa gga atc gat act        1296
Ile Tyr Val Asn Arg Pro Leu Asn Asn Pro Pro Lys Gly Ile Asp Thr
            420                 425                 430 gac gag atg gct tat gaa gcc ggt agt tct ttc cca gca atc tta atg        1344
Asp Glu Met Ala Tyr Glu Ala Gly Ser Ser Phe Pro Ala Ile Leu Met
        435                 440                 445 atc gct atg ggt aaa aag aaa ttc ttt aat gct ttg cat gat tac tat        1392
Ile Ala Met Gly Lys Lys Lys Phe Phe Asn Ala Leu His Asp Tyr Tyr
    450                 455                 460 gaa acc tac tac tta aaa caa gct act aca cag gat ttt ttg aat atc        1440
Glu Thr Tyr Tyr Leu Lys Gln Ala Thr Thr Gln Asp Phe Leu Asn Ile
465                 470                 475                 480 att cgt aag tat gac aac tca aag aaa gta aac tat gtg att aat caa        1488
Ile Arg Lys Tyr Asp Asn Ser Lys Lys Val Asn Tyr Val Ile Asn Gln
                485                 490                 495 ttt atc gat cct gat tat ttg aac aaa                                    1515
Phe Ile Asp Pro Asp Tyr Leu Asn Lys
                500                 505

<210> SEQ ID NO 124
<211> LENGTH: 505
<212> TYPE: PRT
<213> ORGANISM: Lactobacillus acidophilus

<400> SEQUENCE: 124

Met Lys Lys Arg Thr Thr Leu Leu Leu Ser Ser Ala Ile Thr Ile Ala
1               5                   10                  15

Ala Leu Phe Ser Phe Asn Ser Lys Ala Gln Ala Ala Ala Asp Pro Ala
            20                  25                  30

Val Lys Ala Thr Asn Tyr Asn Met Thr Val Lys Leu Asn Thr Arg Lys
```

-continued

```
                35                  40                  45
Asn Gln Leu Thr Glu Lys Val Thr Met His Val Asn Asn Gly Asn
 50                  55                  60

Glu Pro Val Lys Asn Leu Leu Ile Arg Asn Ile Ala Asn Gly Val Leu
 65                  70                  75                  80

Lys Tyr Asp His Gln His Phe Lys Ile Ala Lys Asn Ala Lys Thr Thr
                 85                  90                  95

Val Lys Ser Ile Ser Ser Ala Gly Glu Asn Leu Ser Tyr Thr Thr Gly
                100                 105                 110

Lys Asp Lys Ser Asn Leu Phe Val Asp Lys Ser Leu Asn Ala Gly Glu
                115                 120                 125

Ser Thr Asp Leu Thr Val Asn Val Val Thr Ser Val Pro Lys Arg Gln
                130                 135                 140

Asp Arg Phe Gly Tyr Gln Asn Ile Asn Gly Gly Lys Val Tyr Asn Leu
145                 150                 155                 160

Ser Phe Cys Phe Pro Tyr Leu Ser Asp Tyr Arg Asn Gly Lys Trp Asn
                165                 170                 175

Tyr His Pro Tyr Tyr Asp Gly Gly Glu Asn Arg Asn Thr Thr Val Ser
                180                 185                 190

Asn Phe His Val Ser Phe Tyr Ala Pro Lys Ser Tyr Lys Val Ala Ala
                195                 200                 205

Ser Gly Gln Asn Ser Thr Lys Asn Gly Lys Thr Thr Ile Val Ala Glu
                210                 215                 220

Asn Met Arg Asp Phe Ala Ile Val Ala Ser Asn Lys Phe Lys Val Ser
225                 230                 235                 240

His Thr Tyr Ala Asp Gly Ile Arg Ile Asn Asn Tyr Tyr Phe Ala Gly
                245                 250                 255

Lys Asn Ser Lys Gln Tyr Asn Lys Leu Ala Leu Leu Thr Ala Lys Asp
                260                 265                 270

Ser Phe Asn Ile Phe Thr Lys Lys Ile Gly Lys Tyr Pro Tyr Lys Glu
                275                 280                 285

Ile Asp Met Thr Glu Gly Leu Leu Gly Lys Asp Thr Gly Gly Met Glu
290                 295                 300

Tyr Pro Ser Leu Ile Met Ile Asp Ala Ser Gly Phe Val Gln Lys Lys
305                 310                 315                 320

His Pro Ile Asn Arg Tyr Asn Glu Leu Thr Glu Asp Val Ser His Glu
                325                 330                 335

Ile Gly His Gln Trp Phe Tyr Ala Thr Val Gly Asn Asp Glu Tyr Thr
                340                 345                 350

Glu Pro Trp Leu Asp Glu Gly Leu Thr Asn Phe Leu Glu Asn Ser Val
                355                 360                 365

Tyr Asp Leu Thr Tyr Thr Lys Ser Lys Ala Tyr Thr Ala Lys Leu Met
370                 375                 380

His Asn Lys Leu Tyr Asn Arg Lys Thr Val Lys Lys Ala Asn Gln Val
385                 390                 395                 400

Leu Ala Asn Leu Ala Asn Thr Phe Leu Thr Asp His Arg Gln Lys Gly
                405                 410                 415

Ile Tyr Val Asn Arg Pro Leu Asn Asn Pro Lys Gly Ile Asp Thr
                420                 425                 430 Thr

Asp Glu Met Ala Tyr Glu Ala Gly Ser Ser Phe Pro Ala Ile Leu Met
                435                 440                 445

Ile Ala Met Gly Lys Lys Phe Phe Asn Ala Leu His Asp Tyr Tyr
450                 455                 460
```

```
Glu Thr Tyr Tyr Leu Lys Gln Ala Thr Thr Gln Asp Phe Leu Asn Ile
465                 470                 475                 480

Ile Arg Lys Tyr Asp Asn Ser Lys Lys Val Asn Tyr Val Ile Asn Gln
            485                 490                 495

Phe Ile Asp Pro Asp Tyr Leu Asn Lys
            500                 505

<210> SEQ ID NO 125
<211> LENGTH: 1410
<212> TYPE: DNA
<213> ORGANISM: Lactobacillus acidophilus
<220> FEATURE:
<221> NAME/KEY: CDS
<222> LOCATION: (1)..(1410)
<223> OTHER INFORMATION: Cytosol non-specific dipeptidase ORF# 1837

<400> SEQUENCE: 125
```

| | | |
|---|---|---|
| atg aat act aca gtc gtt ggt cgt tcg tct tgt acc tca atc tta att<br>Met Asn Thr Thr Val Val Gly Arg Ser Ser Cys Thr Ser Ile Leu Ile<br>1               5                   10                  15 | | 48 |
| ggt aag aaa gca tcc ctt tca ggc agt gta att att ggc cgc aat gag<br>Gly Lys Lys Ala Ser Leu Ser Gly Ser Val Ile Ile Gly Arg Asn Glu<br>            20                  25                  30 | | 96 |
| gat gca aaa act gct tgg cca aaa cat ctt gca ttc aat cac cat aag<br>Asp Ala Lys Thr Ala Trp Pro Lys His Leu Ala Phe Asn His His Lys<br>        35                  40                  45 | | 144 |
| aat gtt aag aat aac cat ttt aag tca aaa gac aat aaa ttt gaa att<br>Asn Val Lys Asn Asn His Phe Lys Ser Lys Asp Asn Lys Phe Glu Ile<br>    50                  55                  60 | | 192 |
| gat tta cct gaa aag ata ttc agc tat tct tcc aca cca gaa tgg aca<br>Asp Leu Pro Glu Lys Ile Phe Ser Tyr Ser Ser Thr Pro Glu Trp Thr<br>65                  70                  75                  80 | | 240 |
| gat aaa tac ggt gtt ttt gaa gaa gat ggc att aat gag tat cat gtg<br>Asp Lys Tyr Gly Val Phe Glu Glu Asp Gly Ile Asn Glu Tyr His Val<br>                85                  90                  95 | | 288 |
| gca atg agt gct act gaa agt gcc tat gcc aat gat cgt gta atg gca<br>Ala Met Ser Ala Thr Glu Ser Ala Tyr Ala Asn Asp Arg Val Met Ala<br>            100                 105                 110 | | 336 |
| gtt gat cca ttc aat aca gaa aag ggc atc cta gaa gaa gct atg gta<br>Val Asp Pro Phe Asn Thr Glu Lys Gly Ile Leu Glu Glu Ala Met Val<br>        115                 120                 125 | | 384 |
| acg gta gta ttg cca tat att aaa aca gca aaa gaa ggc gtt att cgc<br>Thr Val Val Leu Pro Tyr Ile Lys Thr Ala Lys Glu Gly Val Ile Arg<br>    130                 135                 140 | | 432 |
| tta ggc aaa atc gtt gaa aaa cat ggt gcc gct gaa gca gac ggg atc<br>Leu Gly Lys Ile Val Glu Lys His Gly Ala Ala Glu Ala Asp Gly Ile<br>145                 150                 155                 160 | | 480 |
| tta ttt gct gac cgc gac gaa gca tgg tac atg gaa att gga tca ggt<br>Leu Phe Ala Asp Arg Asp Glu Ala Trp Tyr Met Glu Ile Gly Ser Gly<br>                165                 170                 175 | | 528 |
| cac cac tgg gtt gct caa aga att cca gat gat tca tat gca gta gtt<br>His His Trp Val Ala Gln Arg Ile Pro Asp Asp Ser Tyr Ala Val Val<br>            180                 185                 190 | | 576 |
| gct aac caa tta gca att caa gaa att gac ttt gac agt gac aat ttc<br>Ala Asn Gln Leu Ala Ile Gln Glu Ile Asp Phe Asp Ser Asp Asn Phe<br>        195                 200                 205 | | 624 |
| tta tat tca aat aat tta caa aat ttt gtt tat aac aat caa ctt tgg<br>Leu Tyr Ser Asn Asn Leu Gln Asn Phe Val Tyr Asn Asn Gln Leu Trp<br>    210                 215                 220 | | 672 |
| cca aaa gat aaa cca ttt att tgg cgt gat att ttt ggt aca cat gac | | 720 |

```
Pro Lys Asp Lys Pro Phe Ile Trp Arg Asp Ile Phe Gly Thr His Asp
225                 230                 235                 240 gat agt gat ctt cat tac aat acg cca cgt gtt tgg agc ggt cag cgt    768
Asp Ser Asp Leu His Tyr Asn Thr Pro Arg Val Trp Ser Gly Gln Arg
                245                 250                 255 ctt tta acg cca tct gct gaa caa aag cct caa gac ttc aat tta cca    816
Leu Leu Thr Pro Ser Ala Glu Gln Lys Pro Gln Asp Phe Asn Leu Pro
            260                 265                 270 ttt acc aga aag cct gat gcg cct att tct gcc caa gat gct caa cat    864
Phe Thr Arg Lys Pro Asp Ala Pro Ile Ser Ala Gln Asp Ala Gln His
        275                 280                 285 gtt tta agt gat cac ttt aat aat aca gtt tat gat cta aca aat aag    912
Val Leu Ser Asp His Phe Asn Asn Thr Val Tyr Asp Leu Thr Asn Lys
    290                 295                 300 aaa aat aaa gat cag cct gca ttt cgt cca att tct gta gct act act    960
Lys Asn Lys Asp Gln Pro Ala Phe Arg Pro Ile Ser Val Ala Thr Thr
305                 310                 315                 320 caa gaa tca cat ttg ctt gaa tta aac ggc gaa gac atg att cat tgg   1008
Gln Glu Ser His Leu Leu Glu Leu Asn Gly Glu Asp Met Ile His Trp
                325                 330                 335 cta gca atg ggc gtt gcc gca caa agc gta tat att ccg ttc tat cca   1056
Leu Ala Met Gly Val Ala Ala Gln Ser Val Tyr Ile Pro Phe Tyr Pro
            340                 345                 350 caa ggt act aaa gtt cct agt acc tgg aaa aac ggt aaa gag act tat   1104
Gln Gly Thr Lys Val Pro Ser Thr Trp Lys Asn Gly Lys Glu Thr Tyr
        355                 360                 365 tca ccg aat tct gcc tac tgg gta ttt aag ctt gcc agc gtt tta gtt   1152
Ser Pro Asn Ser Ala Tyr Trp Val Phe Lys Leu Ala Ser Val Leu Val
370                 375                 380 gat cgc gat tgg agt aag tac ggt act gca ttg agt aat acc caa aac   1200
Asp Arg Asp Trp Ser Lys Tyr Gly Thr Ala Leu Ser Asn Thr Gln Asn
385                 390                 395                 400 tct act aat gag aaa tta ttg caa att aga cat caa tat gat gaa aaa   1248
Ser Thr Asn Glu Lys Leu Leu Gln Ile Arg His Gln Tyr Asp Glu Lys
                405                 410                 415 tta gct aag gaa aat gat cct gct aaa cga act gat tta att aat gaa   1296
Leu Ala Lys Glu Asn Asp Pro Ala Lys Arg Thr Asp Leu Ile Asn Glu
            420                 425                 430 gca aat gct aaa ctg gct aag aca gct aca gac gca tat aaa gaa tta   1344
Ala Asn Ala Lys Leu Ala Lys Thr Ala Thr Asp Ala Tyr Lys Glu Leu
        435                 440                 445 act gca aaa ttg att act gaa caa act ggt gat tca cca ctt aga ttc   1392
Thr Ala Lys Leu Ile Thr Glu Gln Thr Gly Asp Ser Pro Leu Arg Phe
    450                 455                 460 caa atg gat cct aac cta                                           1410
Gln Met Asp Pro Asn Leu
465                 470

<210> SEQ ID NO 126
<211> LENGTH: 470
<212> TYPE: PRT
<213> ORGANISM: Lactobacillus acidophilus

<400> SEQUENCE: 126

Met Asn Thr Thr Val Val Gly Arg Ser Ser Cys Thr Ser Ile Leu Ile
1               5                   10                  15

Gly Lys Lys Ala Ser Leu Ser Gly Ser Val Ile Ile Gly Arg Asn Glu
            20                  25                  30

Asp Ala Lys Thr Ala Trp Pro Lys His Leu Ala Phe Asn His His Lys
        35                  40                  45
```

```
Asn Val Lys Asn Asn His Phe Lys Ser Lys Asp Asn Lys Phe Glu Ile
     50                  55                  60

Asp Leu Pro Glu Lys Ile Phe Ser Tyr Ser Ser Thr Pro Glu Trp Thr
 65                  70                  75                  80

Asp Lys Tyr Gly Val Phe Glu Glu Asp Gly Ile Asn Glu Tyr His Val
                 85                  90                  95

Ala Met Ser Ala Thr Glu Ser Ala Tyr Ala Asn Asp Arg Val Met Ala
            100                 105                 110

Val Asp Pro Phe Asn Thr Glu Lys Gly Ile Leu Glu Glu Ala Met Val
        115                 120                 125

Thr Val Val Leu Pro Tyr Ile Lys Thr Ala Lys Glu Gly Val Ile Arg
    130                 135                 140

Leu Gly Lys Ile Val Glu Lys His Gly Ala Ala Glu Ala Asp Gly Ile
145                 150                 155                 160

Leu Phe Ala Asp Arg Asp Glu Ala Trp Tyr Met Glu Ile Gly Ser Gly
                165                 170                 175

His His Trp Val Ala Gln Arg Ile Pro Asp Asp Ser Tyr Ala Val Val
            180                 185                 190

Ala Asn Gln Leu Ala Ile Gln Glu Ile Asp Phe Asp Ser Asp Asn Phe
        195                 200                 205

Leu Tyr Ser Asn Asn Leu Gln Asn Phe Val Tyr Asn Asn Gln Leu Trp
    210                 215                 220

Pro Lys Asp Lys Pro Phe Ile Trp Arg Asp Ile Phe Gly Thr His Asp
225                 230                 235                 240

Asp Ser Asp Leu His Tyr Asn Thr Pro Arg Val Trp Ser Gly Gln Arg
                245                 250                 255

Leu Leu Thr Pro Ser Ala Glu Gln Lys Pro Gln Asp Phe Asn Leu Pro
            260                 265                 270

Phe Thr Arg Lys Pro Asp Ala Pro Ile Ser Ala Gln Asp Ala Gln His
        275                 280                 285

Val Leu Ser Asp His Phe Asn Asn Thr Val Tyr Asp Leu Thr Asn Lys
    290                 295                 300

Lys Asn Lys Asp Gln Pro Ala Phe Arg Pro Ile Ser Val Ala Thr Thr
305                 310                 315                 320

Gln Glu Ser His Leu Leu Glu Leu Asn Gly Glu Asp Met Ile His Trp
                325                 330                 335

Leu Ala Met Gly Val Ala Ala Gln Ser Val Tyr Ile Pro Phe Tyr Pro
            340                 345                 350

Gln Gly Thr Lys Val Pro Ser Thr Trp Lys Asn Gly Lys Glu Thr Tyr
        355                 360                 365

Ser Pro Asn Ser Ala Tyr Trp Val Phe Lys Leu Ala Ser Val Leu Val
    370                 375                 380

Asp Arg Asp Trp Ser Lys Tyr Gly Thr Ala Leu Ser Asn Thr Gln Asn
385                 390                 395                 400

Ser Thr Asn Glu Lys Leu Leu Gln Ile Arg His Gln Tyr Asp Glu Lys
                405                 410                 415

Leu Ala Lys Glu Asn Asp Pro Ala Lys Arg Thr Asp Leu Ile Asn Glu
            420                 425                 430

Ala Asn Ala Lys Leu Ala Lys Thr Ala Thr Asp Ala Tyr Lys Glu Leu
        435                 440                 445

Thr Ala Lys Leu Ile Thr Glu Gln Thr Gly Asp Ser Pro Leu Arg Phe
    450                 455                 460
```

```
Gln Met Asp Pro Asn Leu
465                 470

<210> SEQ ID NO 127
<211> LENGTH: 897
<212> TYPE: DNA
<213> ORGANISM: Lactobacillus acidophilus
<220> FEATURE:
<221> NAME/KEY: CDS
<222> LOCATION: (1)..(897)
<223> OTHER INFORMATION: Prolyl aminopeptidase (EC3.4.11.5) ORF# 1957

<400> SEQUENCE: 127 atg gat caa aca aga tta gta act tta gat aat ggt tat cac cta ttt      48
Met Asp Gln Thr Arg Leu Val Thr Leu Asp Asn Gly Tyr His Leu Phe
1               5                   10                  15 aca cga aaa gtc aat gaa gga cct att aaa ctg ctt tgc tta cat ggt      96
Thr Arg Lys Val Asn Glu Gly Pro Ile Lys Leu Leu Cys Leu His Gly
                20                  25                  30 ggc cct ggc gga aca cat gaa act ttt gat aat ttt aaa gat ggc tta     144
Gly Pro Gly Gly Thr His Glu Thr Phe Asp Asn Phe Lys Asp Gly Leu
            35                  40                  45 aaa ggg caa ggc gtt gaa gtt tat tca tat gat caa tta gga tct tac     192
Lys Gly Gln Gly Val Glu Val Tyr Ser Tyr Asp Gln Leu Gly Ser Tyr
        50                  55                  60 tat tct gat caa cct gat ttt act aaa aaa gaa aat aaa tca tta ctt     240
Tyr Ser Asp Gln Pro Asp Phe Thr Lys Lys Glu Asn Lys Ser Leu Leu
65                  70                  75                  80 tct atc cct cga tat gtc gac gaa gtc gaa gaa gta aga caa aag tta     288
Ser Ile Pro Arg Tyr Val Asp Glu Val Glu Glu Val Arg Gln Lys Leu
                85                  90                  95 ggc tta gat aac ttt tac ttg ttg gga cat tca tgg ggt gga ctt ctt     336
Gly Leu Asp Asn Phe Tyr Leu Leu Gly His Ser Trp Gly Gly Leu Leu
            100                 105                 110 gct caa gaa tat gct tac aaa tat ggc aaa cac cta aag ggc cta gtt     384
Ala Gln Glu Tyr Ala Tyr Lys Tyr Gly Lys His Leu Lys Gly Leu Val
        115                 120                 125 cta atg tca atg att gat aac tta gat gaa tat aca gaa aat att aat     432
Leu Met Ser Met Ile Asp Asn Leu Asp Glu Tyr Thr Glu Asn Ile Asn
130                 135                 140 cat gaa cgt gaa gaa act ttt tca cct gaa caa gtt gat tac atg aaa     480
His Glu Arg Glu Glu Thr Phe Ser Pro Glu Gln Val Asp Tyr Met Lys
145                 150                 155                 160 gaa tgt gaa aaa gct gag aac ttt act gac cct atg tat cag caa tta     528
Glu Cys Glu Lys Ala Glu Asn Phe Thr Asp Pro Met Tyr Gln Gln Leu
                165                 170                 175 gtt gct cat ctt tat tcc ctc ttt tta aca aga cat ccc aca ggt aca     576
Val Ala His Leu Tyr Ser Leu Phe Leu Thr Arg His Pro Thr Gly Thr
            180                 185                 190 gct cat cct gta aat act cac aat aat gtg att tac aac tat ttc caa     624
Ala His Pro Val Asn Thr His Asn Asn Val Ile Tyr Asn Tyr Phe Gln
        195                 200                 205 gga aat aat gaa ttt gtt atg gtg ggt gag ctt acc aaa tgg gat ttc     672
Gly Asn Asn Glu Phe Val Met Val Gly Glu Leu Thr Lys Trp Asp Phe
        210                 215                 220 aga gag aaa cta gca agt ttg aag atg cca act tta tta acc ttt gga     720
Arg Glu Lys Leu Ala Ser Leu Lys Met Pro Thr Leu Leu Thr Phe Gly
225                 230                 235                 240 gaa ttc gat act atg cca ctt tca gct gct cgc aga atg cat caa aca     768
Glu Phe Asp Thr Met Pro Leu Ser Ala Ala Arg Arg Met His Gln Thr
                245                 250                 255
```

```
cta agt aat tca cgc tta act tta act ccg gat ggc gga cat tgt cat    816
Leu Ser Asn Ser Arg Leu Thr Leu Thr Pro Asp Gly Gly His Cys His
        260                 265                 270 aat act gat aat cca aaa gca ttc ttc acg tct tta act aag ttt tta    864
Asn Thr Asp Asn Pro Lys Ala Phe Phe Thr Ser Leu Thr Lys Phe Leu
    275                 280                 285 cac gat gtt gag aac aac aca ttc aag gga gaa                        897
His Asp Val Glu Asn Asn Thr Phe Lys Gly Glu
    290                 295
```

<210> SEQ ID NO 128
<211> LENGTH: 299
<212> TYPE: PRT
<213> ORGANISM: Lactobacillus acidophilus

<400> SEQUENCE: 128

```
Met Asp Gln Thr Arg Leu Val Thr Leu Asp Asn Gly Tyr His Leu Phe
1               5                   10                  15

Thr Arg Lys Val Asn Glu Gly Pro Ile Lys Leu Leu Cys Leu His Gly
            20                  25                  30

Gly Pro Gly Gly Thr His Glu Thr Phe Asp Asn Phe Lys Asp Gly Leu
        35                  40                  45

Lys Gly Gln Gly Val Glu Val Tyr Ser Tyr Asp Gln Leu Gly Ser Tyr
    50                  55                  60

Tyr Ser Asp Gln Pro Asp Phe Thr Lys Glu Asn Lys Ser Leu Leu
65                  70                  75                  80

Ser Ile Pro Arg Tyr Val Asp Glu Val Glu Val Arg Gln Lys Leu
                85                  90                  95

Gly Leu Asp Asn Phe Tyr Leu Leu Gly His Ser Trp Gly Gly Leu Leu
            100                 105                 110

Ala Gln Glu Tyr Ala Tyr Lys Tyr Gly Lys His Leu Lys Gly Leu Val
        115                 120                 125

Leu Met Ser Met Ile Asp Asn Leu Asp Glu Tyr Thr Glu Asn Ile Asn
    130                 135                 140

His Glu Arg Glu Glu Thr Phe Ser Pro Glu Gln Val Asp Tyr Met Lys
145                 150                 155                 160

Glu Cys Glu Lys Ala Glu Asn Phe Thr Asp Pro Met Tyr Gln Gln Leu
                165                 170                 175

Val Ala His Leu Tyr Ser Leu Phe Leu Thr Arg His Pro Thr Gly Thr
            180                 185                 190

Ala His Pro Val Asn Thr His Asn Asn Val Ile Tyr Asn Tyr Phe Gln
        195                 200                 205

Gly Asn Asn Glu Phe Val Met Val Gly Glu Leu Thr Lys Trp Asp Phe
    210                 215                 220

Arg Glu Lys Leu Ala Ser Leu Lys Met Pro Thr Leu Leu Thr Phe Gly
225                 230                 235                 240

Glu Phe Asp Thr Met Pro Leu Ser Ala Ala Arg Arg Met His Gln Thr
                245                 250                 255

Leu Ser Asn Ser Arg Leu Thr Leu Thr Pro Asp Gly Gly His Cys His
            260                 265                 270

Asn Thr Asp Asn Pro Lys Ala Phe Phe Thr Ser Leu Thr Lys Phe Leu
        275                 280                 285

His Asp Val Glu Asn Asn Thr Phe Lys Gly Glu
    290                 295
```

<210> SEQ ID NO 129

-continued

```
<211> LENGTH: 756
<212> TYPE: DNA
<213> ORGANISM: Lactobacillus acidophilus
<220> FEATURE:
<221> NAME/KEY: CDS
<222> LOCATION: (1)..(756)
<223> OTHER INFORMATION: Conserved membrane protein plnI ORF# 553

<400> SEQUENCE: 129 atg att gaa aaa cga aat ttc aag aaa tca att gct atc tgg atc tgt      48
Met Ile Glu Lys Arg Asn Phe Lys Lys Ser Ile Ala Ile Trp Ile Cys
1               5                   10                  15 tta tta tta gtg tat aca ttg gct ggt cta gta ctg cga cca atc aat      96
Leu Leu Leu Val Tyr Thr Leu Ala Gly Leu Val Leu Arg Pro Ile Asn
            20                  25                  30 aat tta acc tta cgc tta gcg atc cgt tgt ttt att gct cta gtt att     144
Asn Leu Thr Leu Arg Leu Ala Ile Arg Cys Phe Ile Ala Leu Val Ile
        35                  40                  45 aca gga ttc tgt ttt tat ttt atg cat ggc agc aag ctt tat tct aac     192
Thr Gly Phe Cys Phe Tyr Phe Met His Gly Ser Lys Leu Tyr Ser Asn
    50                  55                  60 gag ctt aat ttg cga cac att aaa att tat aac act att ttt att att     240
Glu Leu Asn Leu Arg His Ile Lys Ile Tyr Asn Thr Ile Phe Ile Ile
65                  70                  75                  80 att gtt gct atc ttc tat tta ttt ttt cgc ctg cca att tgg att gaa     288
Ile Val Ala Ile Phe Tyr Leu Phe Phe Arg Leu Pro Ile Trp Ile Glu
                85                  90                  95 tta ttt act act caa aga agc gga tta atc aat tct tta ctg att gca     336
Leu Phe Thr Thr Gln Arg Ser Gly Leu Ile Asn Ser Leu Leu Ile Ala
            100                 105                 110 gtt tgt gca gga ttt tgt gaa gaa gcc ttg ttt aga gga atg ttg ttt     384
Val Cys Ala Gly Phe Cys Glu Glu Ala Leu Phe Arg Gly Met Leu Phe
        115                 120                 125 aat atc tgc gct aat tat ttg aaa aaa cat cgg tat att tgg ctt gaa     432
Asn Ile Cys Ala Asn Tyr Leu Lys Lys His Arg Tyr Ile Trp Leu Glu
    130                 135                 140 aca gct tta gtt act tca att ctt ttt gga cta atg cac tca gtc aat     480
Thr Ala Leu Val Thr Ser Ile Leu Phe Gly Leu Met His Ser Val Asn
145                 150                 155                 160 ttg ctt tcc agt gag cca cta ccc tct gta ggt aca caa gtt ttt tac     528
Leu Leu Ser Ser Glu Pro Leu Pro Ser Val Gly Thr Gln Val Phe Tyr
                165                 170                 175 gct ttt gcc agc gga tta atg ttt gca tac ctg cgt tta atg tct aac     576
Ala Phe Ala Ser Gly Leu Met Phe Ala Tyr Leu Arg Leu Met Ser Asn
            180                 185                 190 cat ctt tgg cca gct atc ttg gct cat gct gcc ttt gat ttt aca atc     624
His Leu Trp Pro Ala Ile Leu Ala His Ala Ala Phe Asp Phe Thr Ile
        195                 200                 205 gta cct aaa aat gcg gta ttt gca atc aac gct caa gga tta tca cta     672
Val Pro Lys Asn Ala Val Phe Ala Ile Asn Ala Gln Gly Leu Ser Leu
    210                 215                 220 gtt tac ata att ttt ggt att ctt acc gtt atc tat tta ttg ttc att     720
Val Tyr Ile Ile Phe Gly Ile Leu Thr Val Ile Tyr Leu Leu Phe Ile
225                 230                 235                 240 tgg agc ttc aac aga ttg tac aat gaa act aaa gcc                     756
Trp Ser Phe Asn Arg Leu Tyr Asn Glu Thr Lys Ala
                245                 250

<210> SEQ ID NO 130
<211> LENGTH: 252
<212> TYPE: PRT
<213> ORGANISM: Lactobacillus acidophilus
```

```
<400> SEQUENCE: 130

Met Ile Glu Lys Arg Asn Phe Lys Lys Ser Ile Ala Ile Trp Ile Cys
1               5                   10                  15

Leu Leu Leu Val Tyr Thr Leu Ala Gly Leu Val Leu Arg Pro Ile Asn
            20                  25                  30

Asn Leu Thr Leu Arg Leu Ala Ile Arg Cys Phe Ile Ala Leu Val Ile
        35                  40                  45

Thr Gly Phe Cys Phe Tyr Phe Met His Gly Ser Lys Leu Tyr Ser Asn
    50                  55                  60

Glu Leu Asn Leu Arg His Ile Lys Ile Tyr Asn Thr Ile Phe Ile Ile
65              70                  75                  80

Ile Val Ala Ile Phe Tyr Leu Phe Phe Arg Leu Pro Ile Trp Ile Glu
                85                  90                  95

Leu Phe Thr Thr Gln Arg Ser Gly Leu Ile Asn Ser Leu Leu Ile Ala
            100                 105                 110

Val Cys Ala Gly Phe Cys Glu Glu Ala Leu Phe Arg Gly Met Leu Phe
        115                 120                 125

Asn Ile Cys Ala Asn Tyr Leu Lys Lys His Arg Tyr Ile Trp Leu Glu
    130                 135                 140

Thr Ala Leu Val Thr Ser Ile Leu Phe Gly Leu Met His Ser Val Asn
145                 150                 155                 160

Leu Leu Ser Ser Glu Pro Leu Pro Ser Val Gly Thr Gln Val Phe Tyr
                165                 170                 175

Ala Phe Ala Ser Gly Leu Met Phe Ala Tyr Leu Arg Leu Met Ser Asn
            180                 185                 190

His Leu Trp Pro Ala Ile Leu Ala His Ala Ala Phe Asp Phe Thr Ile
        195                 200                 205

Val Pro Lys Asn Ala Val Phe Ala Ile Asn Ala Gln Gly Leu Ser Leu
    210                 215                 220

Val Tyr Ile Ile Phe Gly Ile Leu Thr Val Ile Tyr Leu Leu Phe Ile
225                 230                 235                 240

Trp Ser Phe Asn Arg Leu Tyr Asn Glu Thr Lys Ala
                245                 250

<210> SEQ ID NO 131
<211> LENGTH: 846
<212> TYPE: DNA
<213> ORGANISM: Lactobacillus acidophilus
<220> FEATURE:
<221> NAME/KEY: CDS
<222> LOCATION: (1)..(846)
<223> OTHER INFORMATION: Serine protease ORF# 601

<400> SEQUENCE: 131 atg aaa act ggg tta gtg tta gaa ggc ggt gca atg cgt gga tta ttt     48
Met Lys Thr Gly Leu Val Leu Glu Gly Gly Ala Met Arg Gly Leu Phe
1               5                   10                  15 acc gct ggt gtg atc gat gtc tta atg gaa aac aag att aat ttt gat     96
Thr Ala Gly Val Ile Asp Val Leu Met Glu Asn Lys Ile Asn Phe Asp
            20                  25                  30 gta gca att gga gtt tcc gct gga gct gct ttt ggc gtt aat ctg aaa    144
Val Ala Ile Gly Val Ser Ala Gly Ala Ala Phe Gly Val Asn Leu Lys
        35                  40                  45 tcc aaa caa att ggc cga gtt ctg cgt tat aat tta cgt ttt gca ggt    192
Ser Lys Gln Ile Gly Arg Val Leu Arg Tyr Asn Leu Arg Phe Ala Gly
    50                  55                  60
```

```
aaa tct tat tat gca agt tgg aag tca tgg cgt aga tct ggt aat ttg      240
Lys Ser Tyr Tyr Ala Ser Trp Lys Ser Trp Arg Arg Ser Gly Asn Leu
 65              70                  75                  80 tat gct gct aat ttt tgc tat cat att ttg cca gat aag tta gat att      288
Tyr Ala Ala Asn Phe Cys Tyr His Ile Leu Pro Asp Lys Leu Asp Ile
                 85                  90                  95 ttt gat aaa gaa act ttt atg gct aat cca atg cga ttc tgt tgt gta      336
Phe Asp Lys Glu Thr Phe Met Ala Asn Pro Met Arg Phe Cys Cys Val
            100                 105                 110 gcg act gat gct gca acg gga gag cct gtt tat cat gag ttg tac gat      384
Ala Thr Asp Ala Ala Thr Gly Glu Pro Val Tyr His Glu Leu Tyr Asp
        115                 120                 125 gct ggg tat gta gat tta gag tgg att agg gca tcc tct tca att cca      432
Ala Gly Tyr Val Asp Leu Glu Trp Ile Arg Ala Ser Ser Ser Ile Pro
    130                 135                 140 ttt ttt gct cat cct gtt gct att ggt ggc cat tat tat ttt gac ggc      480
Phe Phe Ala His Pro Val Ala Ile Gly Gly His Tyr Tyr Phe Asp Gly
145                 150                 155                 160 gga gtt tct gat tct att cca tat gat ttt ttg ata aag aac ggt gtt      528
Gly Val Ser Asp Ser Ile Pro Tyr Asp Phe Leu Ile Lys Asn Gly Val
                165                 170                 175 tct aaa agg gta gta att aca acg caa cct aaa gaa tat cgt aaa aag      576
Ser Lys Arg Val Val Ile Thr Thr Gln Pro Lys Glu Tyr Arg Lys Lys
            180                 185                 190 caa agt aag cta tat cca att gaa aaa att gta cta cgt gaa tat cct      624
Gln Ser Lys Leu Tyr Pro Ile Glu Lys Ile Val Leu Arg Glu Tyr Pro
        195                 200                 205 gct gtt tta aag aaa tta gct act aga gca gaa gat tat aat gcg gtt      672
Ala Val Leu Lys Lys Leu Ala Thr Arg Ala Glu Asp Tyr Asn Ala Val
    210                 215                 220 tta gat aag atg gaa gaa gat gaa aat cag ggg aat gca ttt att att      720
Leu Asp Lys Met Glu Glu Asp Glu Asn Gln Gly Asn Ala Phe Ile Ile
225                 230                 235                 240 cgt ccg cca tat ccg cta gaa att ggt act gtt gaa caa aat aaa gaa      768
Arg Pro Pro Tyr Pro Leu Glu Ile Gly Thr Val Glu Gln Asn Lys Glu
                245                 250                 255 gag att aaa cgg gta tat gag atc gga cga aaa aag gca gaa gaa att      816
Glu Ile Lys Arg Val Tyr Glu Ile Gly Arg Lys Lys Ala Glu Glu Ile
            260                 265                 270 ctg cca gat ttg gtt gaa tat ttg aaa gac                              846
Leu Pro Asp Leu Val Glu Tyr Leu Lys Asp
        275                 280

<210> SEQ ID NO 132
<211> LENGTH: 282
<212> TYPE: PRT
<213> ORGANISM: Lactobacillus acidophilus

<400> SEQUENCE: 132

Met Lys Thr Gly Leu Val Leu Glu Gly Gly Ala Met Arg Gly Leu Phe
 1               5                  10                  15

Thr Ala Gly Val Ile Asp Val Leu Met Glu Asn Lys Ile Asn Phe Asp
                20                  25                  30

Val Ala Ile Gly Val Ser Ala Gly Ala Phe Gly Val Asn Leu Lys
            35                  40                  45

Ser Lys Gln Ile Gly Arg Val Leu Arg Tyr Asn Leu Arg Phe Ala Gly
        50                  55                  60

Lys Ser Tyr Tyr Ala Ser Trp Lys Ser Trp Arg Arg Ser Gly Asn Leu
 65              70                  75                  80
```

```
                Tyr Ala Ala Asn Phe Cys Tyr His Ile Leu Pro Asp Lys Leu Asp Ile
                                85                  90                  95

Phe Asp Lys Glu Thr Phe Met Ala Asn Pro Met Arg Phe Cys Cys Val
                            100                 105                 110

Ala Thr Asp Ala Ala Thr Gly Glu Pro Val Tyr His Glu Leu Tyr Asp
                        115                 120                 125

Ala Gly Tyr Val Asp Leu Glu Trp Ile Arg Ala Ser Ser Ser Ile Pro
                    130                 135                 140

Phe Phe Ala His Pro Val Ala Ile Gly Gly His Tyr Tyr Phe Asp Gly
                145                 150                 155                 160

Gly Val Ser Asp Ser Ile Pro Tyr Asp Phe Leu Ile Lys Asn Gly Val
                                165                 170                 175

Ser Lys Arg Val Val Ile Thr Thr Gln Pro Lys Glu Tyr Arg Lys Lys
                            180                 185                 190

Gln Ser Lys Leu Tyr Pro Ile Glu Lys Ile Val Leu Arg Glu Tyr Pro
                        195                 200                 205

Ala Val Leu Lys Lys Leu Ala Thr Arg Ala Glu Asp Tyr Asn Ala Val
                    210                 215                 220

Leu Asp Lys Met Glu Glu Asp Glu Asn Gln Gly Asn Ala Phe Ile Ile
                225                 230                 235                 240

Arg Pro Pro Tyr Pro Leu Glu Ile Gly Thr Val Glu Gln Asn Lys Glu
                                245                 250                 255

Glu Ile Lys Arg Val Tyr Glu Ile Gly Arg Lys Lys Ala Glu Glu Ile
                            260                 265                 270

Leu Pro Asp Leu Val Glu Tyr Leu Lys Asp
                        275                 280

<210> SEQ ID NO 133
<211> LENGTH: 1212
<212> TYPE: DNA
<213> ORGANISM: Lactobacillus acidophilus
<220> FEATURE:
<221> NAME/KEY: CDS
<222> LOCATION: (1)..(1212)
<223> OTHER INFORMATION: Zn-dependent peptidase ORF# 660

<400> SEQUENCE: 133 atg cta aca act aat ata aca att aga aaa aat aaa aaa ttt aca aca         48
Met Leu Thr Thr Asn Ile Thr Ile Arg Lys Asn Lys Lys Phe Thr Thr
1               5                   10                  15 gcc gga ata ggc tgt ttt ttg cgt tta ccg tta act aat cat aat tta         96
Ala Gly Ile Gly Cys Phe Leu Arg Leu Pro Leu Thr Asn His Asn Leu
            20                  25                  30 gct ttt gct agt tta ctt tcg cga ttg caa atg aat act agt ttg tca        144
Ala Phe Ala Ser Leu Leu Ser Arg Leu Gln Met Asn Thr Ser Leu Ser
        35                  40                  45 tat cca aca att gct gct caa caa aga aag tta gcc caa tta tat gat        192
Tyr Pro Thr Ile Ala Ala Gln Gln Arg Lys Leu Ala Gln Leu Tyr Asp
    50                  55                  60 ttg cag ctt gat att atg ccg caa ctt ttt ggc aac caa att att ttg        240
Leu Gln Leu Asp Ile Met Pro Gln Leu Phe Gly Asn Gln Ile Ile Leu
65                  70                  75                  80 atg tat tat gct aat ttt gtt gaa ccg att gaa gta ttg gat cca gat        288
Met Tyr Tyr Ala Asn Phe Val Glu Pro Ile Glu Val Leu Asp Pro Asp
                85                  90                  95 tat act tat gaa gaa ata atc caa act att agc caa att atc aga ttt        336
Tyr Thr Tyr Glu Glu Ile Ile Gln Thr Ile Ser Gln Ile Ile Arg Phe
            100                 105                 110
```

```
cca gca tat gat aat aat tta ttc gat tat gct aaa aga caa ctt gaa      384
Pro Ala Tyr Asp Asn Asn Leu Phe Asp Tyr Ala Lys Arg Gln Leu Glu
    115                 120                 125 gat gaa tat cgt gaa att atg gtt caa cct tca aat tat gct ctc gat      432
Asp Glu Tyr Arg Glu Ile Met Val Gln Pro Ser Asn Tyr Ala Leu Asp
130                 135                 140 cgc ttt ttt aaa tta tgg tat gaa gat caa cca gaa tat gct gaa aac      480
Arg Phe Phe Lys Leu Trp Tyr Glu Asp Gln Pro Glu Tyr Ala Glu Asn
145                 150                 155                 160 ttt atg ggg cca att gat gaa ata aaa aat act acg att gtt gag atg      528
Phe Met Gly Pro Ile Asp Glu Ile Lys Asn Thr Thr Ile Val Glu Met
                165                 170                 175 cgt gat ttt att gaa aat ttg cgt gat ata cca atg gcg gta att ggc      576
Arg Asp Phe Ile Glu Asn Leu Arg Asp Ile Pro Met Ala Val Ile Gly
            180                 185                 190 atg gga cga gac aat caa tta atg act aaa ata ctc aga aat att ttt      624
Met Gly Arg Asp Asn Gln Leu Met Thr Lys Ile Leu Arg Asn Ile Phe
        195                 200                 205 aaa ggg gct gga att att aaa aaa ttc caa gtt agt gat tta gtt att      672
Lys Gly Ala Gly Ile Ile Lys Lys Phe Gln Val Ser Asp Leu Val Ile
    210                 215                 220 cca gct aaa aga aaa tta att gaa aaa gtt gat gag caa gac aat att      720
Pro Ala Lys Arg Lys Leu Ile Glu Lys Val Asp Glu Gln Asp Asn Ile
225                 230                 235                 240 caa gct caa tta ttg atg gga ttt ggt ttt aaa cag aga att agt tat      768
Gln Ala Gln Leu Leu Met Gly Phe Gly Phe Lys Gln Arg Ile Ser Tyr
                245                 250                 255 caa gaa caa gtt gtt ggt ttg ctt tta gaa caa tat tta gct ggt gat      816
Gln Glu Gln Val Val Gly Leu Leu Leu Glu Gln Tyr Leu Ala Gly Asp
            260                 265                 270 cag tct tca aaa tta ttt agt cag att aga gaa gag tta ggt gcg gct      864
Gln Ser Ser Lys Leu Phe Ser Gln Ile Arg Glu Glu Leu Gly Ala Ala
        275                 280                 285 tat gat gtt caa gca agt gac ttt gct aat aat tct ctc ttt tta att      912
Tyr Asp Val Gln Ala Ser Asp Phe Ala Asn Asn Ser Leu Phe Leu Ile
    290                 295                 300 aat gct gga att gat cct caa aaa gta gaa cca gcc aaa aga att att      960
Asn Ala Gly Ile Asp Pro Gln Lys Val Glu Pro Ala Lys Arg Ile Ile
305                 310                 315                 320 ctt aat gaa atg caa aaa tta atg gat ggt aat ata gat gaa gag cta     1008
Leu Asn Glu Met Gln Lys Leu Met Asp Gly Asn Ile Asp Glu Glu Leu
                325                 330                 335 ttt aga aaa tcc aaa aag gct gta tat cga aac act agg att ggg tta     1056
Phe Arg Lys Ser Lys Lys Ala Val Tyr Arg Asn Thr Arg Ile Gly Leu
            340                 345                 350 gac aat caa aat tgg caa tta gga cag gcc ttg cgt gcc gaa tta tta     1104
Asp Asn Gln Asn Trp Gln Leu Gly Gln Ala Leu Arg Ala Glu Leu Leu
        355                 360                 365 cca gat tat tta gat ttt gat aga gaa gct gct ata aaa aaa gca acg     1152
Pro Asp Tyr Leu Asp Phe Asp Arg Glu Ala Ala Ile Lys Lys Ala Thr
    370                 375                 380 cca cat caa tta att aat ttt gtt caa aat tta ttc ttt aat gaa agt     1200
Pro His Gln Leu Ile Asn Phe Val Gln Asn Leu Phe Phe Asn Glu Ser
385                 390                 395                 400 tat att tta aaa                                                      1212
Tyr Ile Leu Lys

<210> SEQ ID NO 134
<211> LENGTH: 404
<212> TYPE: PRT
```

<213> ORGANISM: Lactobacillus acidophilus

<400> SEQUENCE: 134

```
Met Leu Thr Thr Asn Ile Thr Ile Arg Lys Asn Lys Phe Thr Thr
1               5                   10                  15

Ala Gly Ile Gly Cys Phe Leu Arg Leu Pro Leu Thr Asn His Asn Leu
            20                  25                  30

Ala Phe Ala Ser Leu Leu Ser Arg Leu Gln Met Asn Thr Ser Leu Ser
        35                  40                  45

Tyr Pro Thr Ile Ala Ala Gln Gln Arg Lys Leu Ala Gln Leu Tyr Asp
    50                  55                  60

Leu Gln Leu Asp Ile Met Pro Gln Leu Phe Gly Asn Gln Ile Ile Leu
65                  70                  75                  80

Met Tyr Tyr Ala Asn Phe Val Glu Pro Ile Glu Val Leu Asp Pro Asp
                85                  90                  95

Tyr Thr Tyr Glu Glu Ile Ile Gln Thr Ile Ser Gln Ile Ile Arg Phe
            100                 105                 110

Pro Ala Tyr Asp Asn Asn Leu Phe Asp Tyr Ala Lys Arg Gln Leu Glu
        115                 120                 125

Asp Glu Tyr Arg Glu Ile Met Val Gln Pro Ser Asn Tyr Ala Leu Asp
    130                 135                 140

Arg Phe Phe Lys Leu Trp Tyr Glu Asp Gln Pro Glu Tyr Ala Glu Asn
145                 150                 155                 160

Phe Met Gly Pro Ile Asp Glu Ile Lys Asn Thr Thr Ile Val Glu Met
                165                 170                 175

Arg Asp Phe Ile Glu Asn Leu Arg Asp Ile Pro Met Ala Val Ile Gly
            180                 185                 190

Met Gly Arg Asp Asn Gln Leu Met Thr Lys Ile Leu Arg Asn Ile Phe
        195                 200                 205

Lys Gly Ala Gly Ile Ile Lys Lys Phe Gln Val Ser Asp Leu Val Ile
    210                 215                 220

Pro Ala Lys Arg Lys Leu Ile Glu Lys Val Asp Glu Gln Asp Asn Ile
225                 230                 235                 240

Gln Ala Gln Leu Leu Met Gly Phe Gly Phe Lys Gln Arg Ile Ser Tyr
                245                 250                 255

Gln Glu Gln Val Val Gly Leu Leu Leu Glu Gln Tyr Leu Ala Gly Asp
            260                 265                 270

Gln Ser Ser Lys Leu Phe Ser Gln Ile Arg Glu Glu Leu Gly Ala Ala
        275                 280                 285

Tyr Asp Val Gln Ala Ser Asp Phe Ala Asn Asn Ser Leu Phe Leu Ile
    290                 295                 300

Asn Ala Gly Ile Asp Pro Gln Lys Val Glu Pro Ala Lys Arg Ile Ile
305                 310                 315                 320

Leu Asn Glu Met Gln Lys Leu Met Asp Gly Asn Ile Asp Glu Glu Leu
                325                 330                 335

Phe Arg Lys Ser Lys Lys Ala Val Tyr Arg Asn Thr Arg Ile Gly Leu
            340                 345                 350

Asp Asn Gln Asn Trp Gln Leu Gly Gln Ala Leu Arg Ala Glu Leu Leu
        355                 360                 365

Pro Asp Tyr Leu Asp Phe Asp Arg Glu Ala Ala Ile Lys Lys Ala Thr
    370                 375                 380

Pro His Gln Leu Ile Asn Phe Val Gln Asn Leu Phe Phe Asn Glu Ser
385                 390                 395                 400
```

Tyr Ile Leu Lys

```
<210> SEQ ID NO 135
<211> LENGTH: 5
<212> TYPE: PRT
<213> ORGANISM: Artificial
<220> FEATURE:
<223> OTHER INFORMATION: Consensus peptide sequence
<220> FEATURE:
<221> NAME/KEY: misc_feature
<222> LOCATION: (3)..(3)
<223> OTHER INFORMATION: Xaa can be any naturally occurring amino
      acid

<400> SEQUENCE: 135

Leu Pro Xaa Thr Gly
1               5

<210> SEQ ID NO 136
<211> LENGTH: 10
<212> TYPE: PRT
<213> ORGANISM: Artificial
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa can be valine or threonine
<220> FEATURE:
<221> NAME/KEY: MISC_FEATURE
<222> LOCATION: (2)..(2)
<223> OTHER INFORMATION: Xaa can be any uncharged amino acid
<220> FEATURE:
<221> NAME/KEY: misc_feature
<222> LOCATION: (3)..(3)
<223> OTHER INFORMATION: Xaa can be any naturally occurring amino
      acid
<220> FEATURE:
<221> NAME/KEY: MISC_FEATURE
<222> LOCATION: (6)..(6)
<223> OTHER INFORMATION: Xaa can be any uncharged amino acid
<220> FEATURE:
<221> NAME/KEY: MISC_FEATURE
<222> LOCATION: (7)..(7)
<223> OTHER INFORMATION: Xaa can be any uncharged amino acid
<220> FEATURE:
<221> NAME/KEY: MISC_FEATURE
<222> LOCATION: (9)..(9)
<223> OTHER INFORMATION: Xaa can be any uncharged amino acid
<220> FEATURE:
<221> NAME/KEY: MISC_FEATURE
<222> LOCATION: (10)..(10)
<223> OTHER INFORMATION: Xaa can be any hydrophobic amino acid

<400> SEQUENCE: 136

Xaa Xaa Xaa His Glu Xaa Xaa His Xaa Xaa
1               5                   10

<210> SEQ ID NO 137
<211> LENGTH: 5
<212> TYPE: PRT
<213> ORGANISM: Artificial
<220> FEATURE:
<223> OTHER INFORMATION: Consensus peptide sequence

<400> SEQUENCE: 137

His Met Glu Gly His
1               5

<210> SEQ ID NO 138
<211> LENGTH: 5
<212> TYPE: PRT
```

```
<213> ORGANISM: Artificial
<220> FEATURE:
<223> OTHER INFORMATION: Consensus peptide sequence
<220> FEATURE:
<221> NAME/KEY: MISC_FEATURE
<222> LOCATION: (4)..(4)
<223> OTHER INFORMATION: Xaa can be aspartic acid or glutamic acid

<400> SEQUENCE: 138

His Asp Glu Xaa His
1               5

<210> SEQ ID NO 139
<211> LENGTH: 6
<212> TYPE: PRT
<213> ORGANISM: Artificial
<220> FEATURE:
<223> OTHER INFORMATION: Consensus peptide sequence
<220> FEATURE:
<221> NAME/KEY: misc_feature
<222> LOCATION: (3)..(4)
<223> OTHER INFORMATION: Xaa can be any naturally occurring amino
      acid

<400> SEQUENCE: 139

His Glu Xaa Xaa His Glu
1               5

<210> SEQ ID NO 140
<211> LENGTH: 5
<212> TYPE: PRT
<213> ORGANISM: Artificial
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa can be histidine or aspartic acid
<220> FEATURE:
<221> NAME/KEY: MISC_FEATURE
<222> LOCATION: (4)..(4)
<223> OTHER INFORMATION: Xaa can be aspartic acid or glutamic acid

<400> SEQUENCE: 140

Xaa Asp Glu Xaa His
1               5

<210> SEQ ID NO 141
<211> LENGTH: 7
<212> TYPE: PRT
<213> ORGANISM: Artificial
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa can be histidine or aspartic acid
<220> FEATURE:
<221> NAME/KEY: MISC_FEATURE
<222> LOCATION: (6)..(6)
<223> OTHER INFORMATION: Xaa can be aspartic acid or glutamic acid

<400> SEQUENCE: 141

Xaa Asp Asp Glu Glu Xaa His
1               5

<210> SEQ ID NO 142
<211> LENGTH: 4
<212> TYPE: PRT
<213> ORGANISM: Artificial
<220> FEATURE:
```

```
<223> OTHER INFORMATION: Consensus peptide sequence
<220> FEATURE:
<221> NAME/KEY: MISC_FEATURE
<222> LOCATION: (1)..(4)
<223> OTHER INFORMATION: Xaa can be leucine or isoleucine

<400> SEQUENCE: 142

Gly Phe Thr Xaa
1

<210> SEQ ID NO 143
<211> LENGTH: 7
<212> TYPE: PRT
<213> ORGANISM: Artificial
<220> FEATURE:
<223> OTHER INFORMATION: Consensus peptide sequence
<220> FEATURE:
<221> NAME/KEY: MISC_FEATURE
<222> LOCATION: (3)..(3)
<223> OTHER INFORMATION: Xaa can be any hydrophobic amino acid
<220> FEATURE:
<221> NAME/KEY: MISC_FEATURE
<222> LOCATION: (4)..(4)
<223> OTHER INFORMATION: Xaa can be any hydrophobic amino acid
<220> FEATURE:
<221> NAME/KEY: MISC_FEATURE
<222> LOCATION: (7)..(7)
<223> OTHER INFORMATION: Xaa can be any hydrophobic amino acid

<400> SEQUENCE: 143

Gly Asn Xaa Xaa Asp Arg Xaa
1               5

<210> SEQ ID NO 144
<211> LENGTH: 5
<212> TYPE: PRT
<213> ORGANISM: Artificial
<220> FEATURE:
<223> OTHER INFORMATION: Consensus peptide sequence
<220> FEATURE:
<221> NAME/KEY: MISC_FEATURE
<222> LOCATION: (3)..(3)
<223> OTHER INFORMATION: Xaa can be any hydrophobic amino acid

<400> SEQUENCE: 144

Phe Asn Xaa Ala Asp
1               5

<210> SEQ ID NO 145
<211> LENGTH: 16
<212> TYPE: PRT
<213> ORGANISM: Artificial
<220> FEATURE:
<223> OTHER INFORMATION: Consensus peptide sequence
<220> FEATURE:
<221> NAME/KEY: MISC_FEATURE
<222> LOCATION: (1)..(2)
<223> OTHER INFORMATION: Tyr-Phe is optionally present
<220> FEATURE:
<221> NAME/KEY: misc_feature
<222> LOCATION: (7)..(9)
<223> OTHER INFORMATION: Xaa can be any naturally occurring amino
      acid
<220> FEATURE:
<221> NAME/KEY: misc_feature
<222> LOCATION: (11)..(12)
<223> OTHER INFORMATION: Xaa can be any naturally occurring amino
      acid
<220> FEATURE:
<221> NAME/KEY: MISC_FEATURE
<222> LOCATION: (14)..(16)
<223> OTHER INFORMATION: Val-Ile-Ala is optionally present
```

```
<400> SEQUENCE: 145

Tyr Phe Ser Ile Arg Lys Xaa Xaa Xaa Gly Xaa Xaa Ser Val Ile Ala
1               5                   10                  15

<210> SEQ ID NO 146
<211> LENGTH: 240
<212> TYPE: DNA
<213> ORGANISM: Lactobacillus acidophilus
<220> FEATURE:
<221> NAME/KEY: CDS
<222> LOCATION: (1)..(240)
<223> OTHER INFORMATION: Signal peptidase I ORF# 1182

<400> SEQUENCE: 146 atg gta gaa aac cta aag aag aaa aaa gac gat aac gaa agt att ggt      48
Met Val Glu Asn Leu Lys Lys Lys Lys Asp Asp Asn Glu Ser Ile Gly
1               5                   10                  15 cgc ttt gtt tta gac ata gtt att atg ttt gca atc tta atg gga att      96
Arg Phe Val Leu Asp Ile Val Ile Met Phe Ala Ile Leu Met Gly Ile
                20                  25                  30 tac tac ttt gta ttt agt ttc ttc ctt tca aac gaa act gtt tcg ggt     144
Tyr Tyr Phe Val Phe Ser Phe Phe Leu Ser Asn Glu Thr Val Ser Gly
            35                  40                  45 ccg tca atg cag cct acc ttt gaa aac aat gat cgt tta ata gca gta     192
Pro Ser Met Gln Pro Thr Phe Glu Asn Asn Asp Arg Leu Ile Ala Val
        50                  55                  60 cga cac ttt aat cct aaa cga aac gat atc gtt aat ttt aaa agc tcc     240
Arg His Phe Asn Pro Lys Arg Asn Asp Ile Val Asn Phe Lys Ser Ser
65                  70                  75                  80

<210> SEQ ID NO 147
<211> LENGTH: 80
<212> TYPE: PRT
<213> ORGANISM: Lactobacillus acidophilus

<400> SEQUENCE: 147

Met Val Glu Asn Leu Lys Lys Lys Lys Asp Asp Asn Glu Ser Ile Gly
1               5                   10                  15

Arg Phe Val Leu Asp Ile Val Ile Met Phe Ala Ile Leu Met Gly Ile
                20                  25                  30

Tyr Tyr Phe Val Phe Ser Phe Phe Leu Ser Asn Glu Thr Val Ser Gly
            35                  40                  45

Pro Ser Met Gln Pro Thr Phe Glu Asn Asn Asp Arg Leu Ile Ala Val
        50                  55                  60

Arg His Phe Asn Pro Lys Arg Asn Asp Ile Val Asn Phe Lys Ser Ser
65                  70                  75                  80

<210> SEQ ID NO 148
<211> LENGTH: 5
<212> TYPE: PRT
<213> ORGANISM: Artificial sequence
<220> FEATURE:
<223> OTHER INFORMATION: Consensus peptide sequence
<220> FEATURE:
<221> NAME/KEY: misc_feature
<222> LOCATION: (3)..(4)
<223> OTHER INFORMATION: Xaa can be any naturally occurring amino
      acid

<400> SEQUENCE: 148

His Glu Xaa Xaa His
1               5
```

<210> SEQ ID NO 149
<211> LENGTH: 7
<212> TYPE: PRT
<213> ORGANISM: Artificial
<220> FEATURE:
<223> OTHER INFORMATION: Consensus peptide sequence
<220> FEATURE:
<221> NAME/KEY: misc_feature
<222> LOCATION: (2)..(3)
<223> OTHER INFORMATION: Xaa can be any naturally occurring amino
      acid
<220> FEATURE:
<221> NAME/KEY: misc_feature
<222> LOCATION: (5)..(6)
<223> OTHER INFORMATION: Xaa can be any naturally occurring amino
      acid

<400> SEQUENCE: 149

His Xaa Xaa Glu Xaa Xaa His
1               5

<210> SEQ ID NO 150
<211> LENGTH: 4
<212> TYPE: PRT
<213> ORGANISM: Artificial
<220> FEATURE:
<223> OTHER INFORMATION: Consensus peptide sequence
<220> FEATURE:
<221> NAME/KEY: misc_feature
<222> LOCATION: (4)..(4)
<223> OTHER INFORMATION: Xaa can be any naturally occurring amino
      acid

<400> SEQUENCE: 150

Cys Ala Ala Xaa
1

<210> SEQ ID NO 151
<211> LENGTH: 4
<212> TYPE: PRT
<213> ORGANISM: Artificial
<220> FEATURE:
<223> OTHER INFORMATION: Consensus peptide sequence
<220> FEATURE:
<221> NAME/KEY: misc_feature
<222> LOCATION: (3)..(4)
<223> OTHER INFORMATION: Xaa can be any naturally occurring amino
      acid

<400> SEQUENCE: 151

Lys Lys Xaa Xaa
1

<210> SEQ ID NO 152
<211> LENGTH: 5
<212> TYPE: PRT
<213> ORGANISM: Artificial
<220> FEATURE:
<223> OTHER INFORMATION: Consensus peptide sequence
<220> FEATURE:
<221> NAME/KEY: misc_feature
<222> LOCATION: (2)..(4)
<223> OTHER INFORMATION: Xaa can be any naturally occurring amino
      acid

<400> SEQUENCE: 152

Glu Xaa Xaa Xaa Asp
1               5

<210> SEQ ID NO 153
<211> LENGTH: 5

```
-continued
<212> TYPE: PRT
<213> ORGANISM: Artificial
<220> FEATURE:
<223> OTHER INFORMATION: Consensus peptide sequence

<400> SEQUENCE: 153

Tyr Ser Ile Arg Lys
1               5

<210> SEQ ID NO 154
<211> LENGTH: 5
<212> TYPE: PRT
<213> ORGANISM: Artificial
<220> FEATURE:
<223> OTHER INFORMATION: Consensus peptide sequence
<220> FEATURE:
<221> NAME/KEY: misc_feature
<222> LOCATION: (2)..(3)
<223> OTHER INFORMATION: Xaa can be any naturally occurring amino
      acid

<400> SEQUENCE: 154

His Xaa Xaa Glu His
1               5
```

LACTOBACILLUS ACIDOPHILUS NUCLEIC ACID SEQUENCES ENCODING PROTEASE HOMOLOGUES AND USES THEREFORE

CROSS REFERENCE TO RELATED APPLICATIONS

This application is a divisional of U.S. application Ser. No. 11/062,665 (issued as U.S. Pat. No. 7,455,992 on Nov. 25, 2008), filed Feb. 22, 2005, which claims the benefit of U.S. Provisional Application Ser. No. 60/546,745, filed Feb. 23, 2004, the contents of which are herein incorporated by reference in their entirety. Furthermore, the entire contents of the compact disk filed in duplicate herewith and containing one file entitled "5051.692 Sequence Listing" (603 kb; created Feb. 22, 2005) is incorporated by reference herein.

FIELD OF THE INVENTION

This invention relates to polynucleotides isolated from lactic acid bacteria, namely *Lactobacillus acidophilus*, and polypeptides encoded by them, as well as methods for using the polypeptides and microorganisms expressing them.

BACKGROUND OF THE INVENTION

*Lactobacillus acidophilus* is a Gram-positive, rod-shaped, non-spore forming, homofermentative bacterium that is a normal inhabitant of the gastrointestinal and genitourinary tracts. Since its' original isolation by Moro (1900) from infant feces, the "acid loving" organism has been found in the intestinal tract of humans, breast-fed infants, and persons consuming high milk, lactose, or dextrin diets. Historically, *L. acidophilus* is the *Lactobacillus* species most often implicated as an intestinal probiotic capable of eliciting beneficial effects on the microflora of the gastrointestinal tract (Klaenhammer and Russell (2000) "Species of the *Lactobacillus acidophilus* complex," *Encyclopedia of Food Microbiology*, Volume 2, pp. 1151-1157. Robinson et al. eds. (Academic Press, San Diego, Calif.). *L. acidophilus* can ferment hexoses, including lactose and more complex oligosaccharides, to produce lactic acid and lower the pH of the environment where the organism is cultured. Acidified environments (e.g., food, vagina, and regions within the gastrointestinal tract) can interfere with the growth of undesirable bacteria, pathogens, and yeasts. The organism is well known for its acid tolerance, survival in cultured dairy products, and viability during passage through the stomach and gastrointestinal tract. Lactobacilli and other commensal bacteria, some of which are considered as probiotic bacteria that favor life, have been studied extensively for their effects on human health, particularly in the prevention or treatment of enteric infections, diarrheal disease, prevention of cancer, and stimulation of the immune system. Genetic characterization of other *Lactobacillus* species (e.g., *L johnsonii* and *L. rhamnosus*) has been described (see e.g., U.S. Pat. No. 6,476,209; U.S. Pat. No. 6,544,772; U.S. Patent Publication Nos. 20020159976, 2003013882 & 20040009490; PCT Publication No. WO 2004/031389; PCT Publication No. 2003/084989; PCT Publication No. WO 2004/020467).

Lactic acid bacteria are widely used for the production of fermented milk products. Their requirement for an exogenous source of amino acids or peptides necessitates having an efficient proteolytic system that can degrade the casein in milk into the necessary small peptides and single amino acids used for growth. The peptides and amino acids generated through proteolysis are also involved in the development of texture and flavor in dairy products. Enzymes of the proteolytic system include a cell wall-bound extracellular proteinase (CEP), which is responsible for the initial breakdown of casein, and various intracellular peptidases, which further degrade the oligopeptides thus formed. In addition, there are proteins involved in amino acid transport systems for the uptake of peptides and amino acids from the environment, and enzymes involved in converting amino acids into flavor compounds.

There are two main types of CEPs, designated PI and PIII (Visser et al. (1986) *Appl. Environ. Microbiol.* 52:1162; Siezen (1999) *Antonie Van Leeuwenhoek* 76:139-55). The multi-domain, cell-envelope proteinases encoded by the genes prtB of *Lactobacillus delbrueckii* subsp. *bulgaricus*, prtH of *Lactobacillus helveticus*, prtP of *Lactococcus lactis*, scpA of *Streptococcus pyogenes* and csp of *Streptococcus agalactiae* have been compared using multiple sequence alignment, secondary structure prediction and database homology searching methods. This comparative analysis has led to the prediction of a number of different domains in these cell-envelope proteinases, and their homology, characteristics and putative function are described. These domains include, starting from the N-terminus, a pre-pro-domain for secretion and activation, a serine protease domain (with a smaller inserted domain), two large middle domains A and B of unknown but possibly regulatory function, a helical spacer domain, a hydrophilic cell-wall spacer or attachment domain, and a cell-wall anchor domain. Not all domains are present in each cell-envelope proteinase, suggesting that these multi-domain proteins are the result of gene shuffling and domain swapping during evolution.

The CEPs differ in their cleavage specificity toward caseins, with PI preferentially degrading β-casein, not α- or κ-casein, and PIII degrading α-, β-, and κ-caseins (Pritchard and Coolbear (1993) *FEMS Micro. Rev.* 12:179-206). Less bitterness was generated from casein degraded by a PIII-type proteinase than by a PI-type proteinase (Visser et al. (1983) *Neth. Milk Dairy J.* 17:169-175). The domains mapped from various lactic acid bacteria CEPs include the pre-pro-domain for secretion and activation, a serine protease or catalytic domain, two large middle domains A and B which are thought to have a regulatory and stabilizing function, a helical spacer domain, a hydrophilic cell wall spacer domain, and a cell wall anchor domain (Siezen (1999) *Antonie Leeuwenhoek* 76:139-155). The cell wall anchor contains an LPXTG (SEQ ID NO:135) sequence that is cleaved after translocation, and the enzyme is thought to be covalently linked to the peptidoglycan layer. This anchor is not present in the CEPs of some *lactobacillus* species.

Peptidases include aminopeptidases, dipeptidases, proline-specific peptidases, tripeptidases, carboxypeptidases, and endopeptidases. The peptidases have overlapping substrate specificities, and three or more peptidases need to be disrupted simultaneously to observe an effect on growth rate in milk (Mierau et al. (1996) *J. Bacteriol.* 179:2794-2803). Aminopeptidases are capable of releasing single amino acid residues from oligopeptides, and are therefore important for flavor development in fermented milk products (Law and Haandrikman (1997) *Int. Dairy J.* 7:1-11). In cheese production, for example, it is thought that lysis of the starter bacteria releases peptidases into the curd, which then hydrolyze the casein-derived peptides into amino acids, resulting in enhanced flavor (Meijer et al. (1998) *Appl. Env. Micro.* 64:1950-1953).

Because of the roles peptidases play, peptidase gene sequences are needed for genetic modification of bacteria, particularly *Lactobacillus*.

BRIEF SUMMARY OF THE INVENTION

Compositions and methods for modifying *Lactobacillus* organisms are provided. Compositions of the invention include isolated nucleic acid molecules from *Lactobacillus acidophilus* encoding protease-like proteins, including proteinases and peptidases. Specifically, the present invention provides isolated nucleic acid molecules comprising, consisting essentially of and/or consisting of the nucleotide sequence found in SEQ ID NO:1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 and/or 146, and isolated nucleic acid molecules encoding the amino acid sequence found in SEQ ID NO:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 and/or 147. Also provided are isolated or recombinant polypeptides comprising, consisting essentially of and/or consisting of an amino acid sequence as set forth in SEQ ID NO:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 and/or 147, and/or encoded by a nucleic acid molecule described herein. Variant nucleic acid molecules and polypeptides sufficiently identical to the nucleotide and amino acid sequences set forth in the sequence listing are encompassed by the present invention. Additionally, fragments and sufficiently identical fragments of the nucleotide and amino acid sequences are encompassed. Nucleotide sequences that are complementary to a nucleotide sequence of the invention, or that hybridize to a sequence or its complement of the invention are also encompassed.

Compositions further include vectors and cells for recombinant expression of the nucleic acid molecules described herein, as well as transgenic microbial populations comprising the vectors of this invention. Also included in the invention are methods for the recombinant production of the polypeptides of the invention, and methods for their use. Further included are methods and kits for detecting the presence of a nucleic acid or polypeptide sequence of the invention in a sample, and antibodies that bind to a polypeptide of the invention.

The protease-like molecules of the present invention are useful in the selection and production of recombinant bacteria, particularly the production of bacteria with improved fermentative abilities. Such bacteria include, but are not limited to, those able to produce more, or improved, products for human or animal health, bacteria producing enhanced flavors, textures, or odors of fermented products, and bacteria that permit more efficient or more economic fermentation procedures.

The following embodiments are encompassed by the present invention:

1. An isolated nucleic acid molecule selected from the group consisting of:

a) a nucleic acid molecule comprising a nucleotide sequence as set forth in SEQ ID NO:1, 3, 5, 7, 10, 12, 14, 16, 18, 20, 22, 24, 26, 28, 30, 32, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 146, or a complement thereof;

b) a nucleic acid molecule comprising a nucleotide sequence having at least 90% sequence identity to a nucleotide sequence as set forth in SEQ ID NO:1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 146, or a complement thereof;

c) a nucleic acid molecule that encodes a polypeptide comprising an amino acid sequence as set forth in SEQ ID NO:2, 4, 6, 8, 9, 11, 13, 15, 17, 19, 21, 23, 25, 27, 29, 31, 33, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94 96, 98, 100, 102, 104, 106, 108, 110, 112, 114, 116, 118, 120, 122, 124, 126, 128, 130, 132, 134, or 147;

d) a nucleic acid molecule comprising a nucleotide sequence that encodes a polypeptide having at least 90% amino acid sequence identity to an amino acid sequence as set forth in SEQ ID NO:2, 4, 6, 8, 9, 11, 13, 15, 17, 19, 21, 23, 25, 27, 29, 31, 33, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94 96, 98, 100, 102, 104, 106, 108, 110, 112, 114, 116, 118, 120, 122, 124, 126, 128, 130, 132, 134, or 147; and e) a nucleic acid molecule that hybridizes under stringent conditions to a nucleic acid molecule of (a)-(d).

2. A vector comprising the nucleic acid molecule of embodiment 1.

3. The vector of embodiment 2, further comprising a nucleic acid molecule encoding a heterologous polypeptide.

4. A cell that contains the vector of embodiment 2.

5. The cell of embodiment 4 that is a bacterial cell or a eukaryotic cell.

6. An isolated polypeptide selected from the group consisting of:

a) a polypeptide comprising an amino acid sequence of SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147;

b) a polypeptide comprising a fragment of an amino acid sequence of SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147; and, c) a polypeptide comprising an amino acid sequence having at least 90% sequence identity with an amino acid sequence of SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

7. The polypeptide of embodiment 6 further comprising a heterologous amino acid sequence.

8. An antibody that selectively binds to a polypeptide of embodiment 6.

9. A method for producing a polypeptide comprising culturing the host cell of embodiment 4 under conditions in which a nucleic acid molecule encoding the polypeptide is expressed, said polypeptide being selected from the group consisting of:

a) a polypeptide comprising an amino acid sequence of SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147;

b) a polypeptide comprising a fragment of an amino acid sequence of SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147;

c) a polypeptide comprising an amino acid sequence having at least 90% sequence identity with an amino acid sequence of SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147; and, d) a polypeptide encoded by a nucleotide sequence having at least 90% sequence identity to a nucleotide sequence of SEQ ID NO: 1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 or 146.

10. A method for detecting the presence of a polypeptide in a sample comprising contacting the sample with a compound that selectively binds to a polypeptide and determining whether the compound binds to the polypeptide in the sample; wherein said polypeptide is selected from the group consisting of:

a) a polypeptide encoded by a nucleic acid sequence of SEQ ID NO: 1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 or 146;

b) a polypeptide comprising a fragment of an amino acid sequence encoded by a nucleic acid sequence of SEQ ID NO: 1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 or 146;

c) a polypeptide encoded by a nucleotide sequence having at least 90% sequence identity to a nucleic acid sequence of SEQ ID NO: 1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 or 146; and, d) a polypeptide comprising an amino acid sequence having at least 90% sequence identity to an amino acid sequence of SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

11. The method of embodiment 10, wherein the compound that binds to the polypeptide is an antibody.

12. A kit comprising a compound for use in the method of embodiment 10 and instructions for use.

13. A method for detecting the presence of a nucleic acid molecule of embodiment 1 in a sample, comprising the steps of:

a) contacting the sample with a nucleic acid probe or primer that selectively hybridizes to the nucleic acid molecule; and, b) determining whether the nucleic acid probe or primer binds to a nucleic acid molecule in the sample.

14. The method of embodiment 13, wherein the sample comprises mRNA molecules and is contacted with a nucleic acid probe.

15. A kit comprising a compound that selectively hybridizes to a nucleic acid molecule of embodiment 1, and instructions for use.

16. A method for modulating the growth rate of a bacterium comprising introducing into said organism a vector comprising at least one nucleotide sequence selected from the group consisting of:

a) a nucleotide sequence of SEQ ID NO:1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 or 146;

b) a nucleotide sequence comprising a fragment of a nucleotide sequence of SEQ ID NO:1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 or 146, wherein said fragment encodes a polypeptide that retains activity;

c) a nucleotide sequence that is at least 90% identical to the nucleotide sequence of SEQ ID NO:1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 or 146, wherein said nucleotide sequence encodes a polypeptide that retains activity; and, d) a nucleotide sequence encoding a polypeptide comprising an amino acid sequence having at least 90% sequence identity to an amino acid sequence of SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147, wherein said polypeptide retains activity; and measuring the growth rate of said bacterium.

17. A method for modulating the acidification rate of a milk product fermented by lactic acid bacteria comprising introducing into said organism a vector comprising at least one nucleotide sequence selected from the group consisting of:

a) a nucleotide sequence of SEQ ID NO: 1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 or 146;

b) a nucleotide sequence comprising a fragment of a nucleotide sequence of SEQ ID NO: 1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 or 146, wherein said fragment encodes a polypeptide that retains activity;

c) a nucleotide sequence that is at least 90% identical to the sequence of SEQ ID NO: 1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 or 146, wherein said nucleotide sequence encodes a polypeptide that retains activity; and, d) a nucleotide sequence encoding a polypeptide comprising an amino acid sequence having at least 90% sequence identity to an amino acid sequence of SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132 134 or 147, wherein said polypeptide retains activity; and measuring the acidification rate of said milk product.

18. A method for modifying the cleavage specificity of a *Lactobacillus acidophilus* protease comprising:

a) constructing a plasmid comprising a hybrid protease containing fragments of protease genes from more than one species of lactic acid bacteria, at least one of which is a nucleotide sequence from *Lactobacillus acidophilus* that encodes an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147;

b) introducing said hybrid protease into a bacterial cell; and, c) determining the cleavage specificity of said hybrid protease, wherein the specificity of the hybrid protease differs from a wild-type *Lactobacillus acidophilus* protease.

19. A method for modifying the substrate cleavage rate of a *Lactobacillus acidophilus* protease comprising:

a) constructing a plasmid comprising a hybrid protease enzyme containing fragments of protease genes from more than one species of lactic acid bacteria, at least one of which is a nucleotide sequence from *Lactobacillus acidophilus* that encodes an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147;

b) introducing the hybrid protease into a bacterial cell; and, c) determining the substrate cleavage rate of the hybrid enzyme, wherein the substrate cleavage rate of the hybrid enzyme is different than the wild-type protease.

20. A method for modifying the cleavage specificity of a *Lactobacillus acidophilus* protease comprising mutating a wild-type *Lactobacillus acidophilus* protease to create a mutein with a different cleavage specificity from said wild-type protease wherein said protease has an amino acid sequence as found in SEQ ID NO: 2, 4, 6, 8, 9, 11, 13, 45, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

21. The method of embodiment 20, wherein the method used to mutate said wild type protease is site-directed mutagenesis.

22. The method of embodiment 20, wherein the method used to mutate said wild-type protease is domain knockout.

23. A mutein of a *Lactobacillus acodiphilus* with an amino acid sequence having at least 90% sequence identity to SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147, and wherein said mutein has an altered cleavage specificity.

24. A method for modifying the cleavage rate of a *Lactobacillus acidophilus* protease comprising mutating a wild-type *Lactobacillus acidophilus* protease to create a mutein with a different cleavage rate from said wild-type protease, wherein said protease has an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

25. The method of embodiment 24, wherein the method used to mutate said wild-type protease is site-directed mutagenesis.

26. The method of embodiment 24, wherein the method used to mutate said wild-type protease is domain knockout.

27. A mutein of a *Lactobacillus acidophilus* protease with an amino acid sequence having at least 90% sequence identity to SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147, wherein said mutein has an altered cleavage rate.

28. A method for modulating the rate of cheese ripening comprising fermenting milk used for cheese in the presence of a mutein of embodiment 27, wherein said mutein has an increased cleavage rate compared to a wild-type *Lactobacillus acidophilus* protease.

29. A method for modulating flavor diversification of fermented milk products comprising:

a) modifying a *Lactobacillus acidophilus* protease having an amino acid sequence found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147, such that the flavor of said products is different from the flavor of products produced by said wild-type *Lactobacillus acidophilus* protease;

b) introducing said modified protease into a host cell; and c) fermenting milk used for cheese with said host cell.

30. A method for enhancing the stability of a *Lactobacillus acidophilus* protease comprising mutating a wild-type *Lactobacillus acidophilus* protease having an amino acid sequence found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147 to create a mutein with an enhanced stability compared to said wild-type protease.

31. A method for modifying the functional properties of a bacterial cell, comprising:

a) transforming said bacterial cell with a vector comprising a fusion protein comprising a *Lactobacillus acidophilus* cell wall-bound proteinase having a nucleotide sequence encoding an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147, operably linked to a heterologous protein or fragment; and b) culturing said bacterial cell under conditions that allow for expression of the fusion protein, wherein the heterologous protein or fragment is expressed on the surface of said bacteria and provides a function that is not present in a wild-type bacteria.

32. The method of embodiment 31, wherein the heterologous protein or fragment thereof is an antibody.

33. The method of embodiment 31, wherein the heterologous protein or fragment thereof is an enzyme.

34. The method of embodiment 31, wherein the heterologous protein or fragment thereof is a vaccine antigen.

35. The method of embodiment 31, wherein the heterologous protein or fragment thereof has a bactericidal activity.

36. The method of embodiment 31, wherein the heterologous protein or fragment thereof has receptor-binding activity.

37. A method for modulating a host immune response after ingesting *L. acidophilus* products, comprising:
   a) modifying a wild-type *Lactobacillus acidophilus* protease having an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147, such that the immune response to said protease is different from the immune response to a protease produced by said wild-type *Lactobacillus acidophilus*;
   b) introducing said modified protease into host cells; and
   c) feeding said host cells to a host organism.

38. A *Lactobacillus acidophilus* bacterial strain with an increased growth rate compared to a wild-type *Lactobacillus acidophilus*, wherein said increased growth rate is due to overexpression of at least one protease, wherein said protease has an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

39. A *Lactobacillus acidophilus* bacterial strain having an increased acidification rate for a milk product fermented by a lactic acid bacteria, wherein said increased acidification rate is due to overexpression of at least one protease, wherein said protease has an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

40. A *Lactobacillus acidophilus* bacterial strain comprising a protease with a modified cleavage specificity, wherein said strain contains at least one mutation in the nucleotide sequence encoding said protease, wherein said protease has an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

41. A *Lactobacillus acidophilus* bacterial strain comprising a protease with a modified substrate cleavage rate, wherein said strain contains at least one mutation in the nucleotide sequence encoding said protease, wherein said protease has an amino acid sequence as found in SEQ ID NO: 2, 4, 6, 8, 9, 11; 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

42. A *Lactobacillus acidophilus* bacterial strain having a modified rate of cheese ripening, wherein said strain contains at least one mutation in the nucleotide sequence encoding said protease, wherein said protease has an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

43. A *Lactobacillus acidophilus* bacterial strain having increased flavor diversification, wherein said strain contains at least one mutation in the nucleotide sequence encoding said protease, wherein said protease has an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

44. A *Lactobacillus acidophilus* bacterial strain having a mutein of a wild-type protease, wherein said mutein has enhanced stability compared to said wild-type protease, wherein said protease has an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

45. A *Lactobacillus acidophilus* bacterial strain with modified functional properties, wherein said strain comprises a protease fusion protein, wherein said fusion protein provides a functional property not present in a wild-type *Lactobacillus acidophilus* strain, wherein said protease has an amino acid sequence as found in SEQ ID NO: 2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134 or 147.

46. The strain of embodiment 44, wherein the fusion protein comprises an antibody.

47. The strain of embodiment 44, wherein the fusion protein comprises an enzyme.

48. The strain of embodiment 44, wherein the fusion protein comprises a vaccine antigen.

49. The strain of embodiment 44, wherein the fusion protein comprises a protein or fragment with bactericidal activity.

50. The strain of embodiment 44, wherein the fusion protein comprises a protein or fragment with receptor-binding activity.

DETAILED DESCRIPTION OF THE INVENTION

The present invention relates to protease-like molecules from *Lactobacillus acidophilus*. Nucleotide and amino acid sequences of the protease-like molecules are provided. The sequences are useful for modifying organisms for enhanced properties.

As used herein, "a," "an" and "the" can be plural or singular as used throughout the specification and claims. For example "a" cell can mean a single cell or a multiplicity of cells.

Also as used herein, "and/or" refers to and encompasses any and all possible combinations of one or more of the associated listed items, as well as the lack of combinations when interpreted in the alternative ("or").

By "protease-like molecules" or "protease" is intended an enzyme that catalyzes the splitting of proteins into smaller peptide fractions and amino acids by cleavage of their peptide bonds. The protease-like molecules include proteinases as well as peptidases. See Tables 1 and 2 for examples, and Table 3 for specific sequences of the invention. The full-length gene sequences or fragments thereof are referred to as protease-like sequences, showing that they have similarity to protease genes. The invention further provides fragments and variants of these protease-like sequences, which can be used to practice the methods of the present invention.

As used herein, the terms "gene" and "recombinant gene" refer to nucleic acid molecules comprising an open reading frame particularly those encoding a protease-like protein. Isolated nucleic acid molecules of the present invention comprise nucleic acid sequences encoding protease-like proteins, nucleic acid sequences encoding the amino acid sequences set forth in SEQ ID NOS:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and/or 147; the nucleic acid sequences set forth in SEQ ID NOS:1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, and/or 146, and variants and fragments thereof. The present invention also encompasses antisense nucleic acid molecules, as described below.

In addition, isolated polypeptides and proteins having protease-like activity, and variants and fragments thereof, are encompassed, as well as methods for producing those polypeptides. For purposes of the present invention, the terms "protein" and "polypeptide" are used interchangeably. The polypeptides of the present invention have protease-like activity. Protease-like activity refers to a biological or functional activity as determined in vivo or in vitro according to standard assay techniques. In one embodiment, the activity is catalyzing the splitting of proteins into smaller peptide fractions and amino acids by cleavage of their peptide bonds. Protease-like activity encompasses the activity of peptidases, including endopeptidases and exopeptidases, and proteinases.

Peptidases are enzymes that break the peptide bonds linking the amino group of one amino acid with the carboxy group (acid group) of an adjacent amino acid in a peptide chain. The two main families of peptidases are endopeptidases and exopeptidases. Exopeptidases cleave amino acids from the N- or C-terminus of a peptide chain, releasing free amino acids or short (di- and tripeptides). Types of exopeptidases include aminopeptidases, which release a free amino acid from the N-terminus of a peptide chain, dipeptidyl-peptidases, which release a dipeptide from the N-terminus of a peptide chain, tripeptidyl-peptidases, which release a tripeptide from the N-terminus of a peptide chain, carboxypeptidases, which release a free amino acid from the C-terminus of a peptide chain, peptidyl-dipeptidases, which release a dipeptide from the C-terminus of a peptide chain, dipeptidases, which release two free amino acids from a dipeptide, and tripeptidases, which release a free amino acid and a dipeptide from a tripeptide. Specific exopeptidases of the present invention can be found in SEQ ID NOS:2, 6, 8, 13, 15, 25, 27, 29, 31, 37, 43, 45, 50, 54, 58, 60, 62, 66, 72, 98, 104, 120, and 126.

Endopeptidases hydrolyze internal peptide bonds and are classified on the basis of their mode of catalysis. They include serine-endopeptidases, which depend on serine (or threonine) as the nucleophile in the catalytic reaction, cysteine-endopeptidases, which depend on the sulfhydryl group of cysteine as the nucleophile in the catalytic reaction, aspartic-endopeptidases, which contain aspartate residues that act as ligands for an activated water molecule which acts as the nucleophile in the catalytic reaction, and metallo-endopeptidases, which contain one or more divalent metal ions that activate the water molecule that acts as the nucleophile in the catalytic reaction. Specific endopeptidases of the present invention include SEQ ID NOS:4, 21, 23, 33, 39, 64, 86, 100, and 116.

The nucleic acid and protein compositions encompassed by the present invention are isolated or substantially purified. By "isolated" or "substantially purified" is intended that the nucleic acid or protein molecules, or biologically active fragments or variants, are substantially or essentially free from components normally found in association with the nucleic acid or protein in its natural state. Such components include other cellular material, culture media from recombinant production, and various chemicals used in chemically synthesizing the proteins or nucleic acids. Preferably, an "isolated" nucleic acid of the present invention is free of nucleic acid sequences that flank the nucleic acid of interest in the genomic DNA of the organism from which the nucleic acid was derived (such as coding sequences present at the 5' or 3' ends). However, the molecule may include some additional bases or moieties that do not deleteriously affect the basic characteristics of the composition. For example, in various embodiments, the isolated nucleic acid contains less than 5 kb, 4 kb, 3 kb, 2 kb, 1 kb, 0.5 kb, or 0.1 kb of nucleic acid sequence normally associated with the genomic DNA in the cells from which it was derived. Similarly, a substantially purified protein has less than about 30%, 20%, 10%, 5%, or 1% (by dry weight) of contaminating protein, or non-protease-like protein. When the protein is recombinantly produced, preferably culture medium represents less than 30%, 20%, 10%, or 5% of the volume of the protein preparation, and when the protein is produced chemically, preferably the preparations have less than about 30%, 20%, 10%, or 5% (by dry weight) of chemical precursors, or non-protease-like chemicals.

The compositions and methods of the present invention can be used to modulate the function of the protease-like molecules of *L. acidophilus*. By "modulate," "alter," or "modify" is intended the up- or down-regulation of a target activity. Proteins of the invention are useful in modifying the abilities of lactic acid bacteria, and also in modifying the nutritional or health-promoting characteristics of foods fermented by such bacteria. Nucleotide molecules of the invention are useful in modulating protease-like protein expression by lactic acid bacteria. Up- or downregulation of expression from a polynucleotide of the present invention is encompassed. Upregulation may be accomplished by providing multiple gene copies, modulating expression by modifying regulatory elements, promoting transcriptional or translational mechanisms, or other means. Overexpression is one form of upregulation. Downregulation may be accomplished by using known antisense and gene silencing techniques.

By "lactic acid bacteria" is intended bacteria from a genus selected from the following: *Aerococcus, Carnobacterium, Enterococcus, Lactococcus, Lactobacillus, Leuconostoc, Oenococcus, Pediococcus, Streptococcus, Melissococcus, Alloiococcus, Dolosigranulum, Lactosphaera, Tetragenococcus, Vagococcus*, and *Weissella* (Holzapfel et al. (2001) *Am. J. Clin. Nutr.* 73:365S-373S; *Bergey's Manual of Systematic Bacteriology*, Vol. 2 (Williams and Wilkins, Baltimore; 1986) pp. 1075-1079).

The polypeptides of the present invention or microbes expressing them are useful as nutritional additives or supplements, and as additives in dairy and fermentation processing. The polynucleotide sequences, encoded polypeptides, and microorganisms expressing them are useful in the manufacture of milk-derived products, such as cheeses, yoghurt, fermented milk products, sour milks, and buttermilk. Other food products that may be produced by bacteria expressing a polypeptide of the present invention are ice creams, fermented cereal based products, milk based powders, infant formulae, tablets, liquid bacterial suspensions, dried oral supplements, and liquid oral supplements. Microorganisms that express polypeptides of the invention may be probiotic organisms. By "probiotic" is intended a live microorganism that survives passage through the gastrointestinal tract and has a beneficial effect on the subject. By "subject" is intended an organism that comes into contact with a microorganism expressing a protein of the present invention. Subject may refer to humans and other animals.

The polynucleotides and polypeptides of the present invention are useful in modifying milk-derived products. These uses include, but are not limited to, modulating the growth rate of a bacterium, modulating the acidification rate of a milk product fermented by lactic acid bacteria, modulating the protease cleavage specificity or rate, modulating the rate of cheese ripening, modulating flavor diversification of fermented milk products, enhancing the stability of a protease, and modifying the functional properties of a bacterial cell.

In addition to the protease-like nucleotide sequences disclosed herein, and fragments and variants thereof, the isolated nucleic acid molecules of the current invention also encompass homologous DNA sequences identified and isolated from other organisms or cells by hybridization with entire or partial sequences obtained from the protease-like nucleotide sequences disclosed herein, or variants and fragments thereof.

Fragments and Variants

The invention provides isolated nucleic acid molecules comprising nucleotide sequences encoding protease-like proteins, as well as the protease-like proteins encoded thereby. By "protease-like protein" is intended proteins having the amino acid sequences set forth in SEQ ID NOS:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 147. Fragments and variants of these nucleotide sequences and encoded proteins are also provided. By "fragment" of a nucleotide sequence or protein is intended a portion of the nucleotide or amino acid sequence.

Fragments of the nucleic acid molecules disclosed herein can be used as hybridization probes to identify protease-like-encoding nucleic acids, or can be used as primers in PCR amplification or mutation of protease-like nucleic acid molecules. Fragments of nucleic acids can also be bound to a physical substrate to comprise what may be considered a macro- or microarray (for example, U.S. Pat. No. 5,837,832; U.S. Pat. No. 5,861,242; WO 89/10977; WO 89/11548; WO 93/17126; U.S. Pat. No. 6,309,823). Such arrays or "chips" of nucleic acids may be used to study gene expression or to identify nucleic acid molecules with sufficient identity to the target sequences.

The present invention further provides a nucleic acid array or chip, i.e., a multitude of nucleic acids (e.g., DNA) as molecular probes precisely organized or arrayed on a solid support, which allow for the sequencing of genes, the study of mutations contained therein and/or the analysis of the expression of genes, as such arrays and chips are currently of interest given their very small size and their high capacity in terms of number of analyses.

The function of these nucleic acid arrays/chips is based on molecular probes, mainly oligonucleotides, which are attached to a carrier having a size of generally a few square centimeters or more, as desired. For an analysis, the carrier, such as in a DNA array/chip, is coated with DNA probes (e.g., oligonucleotides) that are arranged at a predetermined location or position on the carrier. A sample containing a target nucleic acid and/or fragments thereof to be analyzed, for example DNA or RNA or cDNA, that has been labeled beforehand, is contacted with the DNA array/chip leading to the formation, through hybridization, of a duplex. After a washing step, analysis of the surface of the chip allows any hybridizations to be located by means of the signals emitted by the labeled target. A hybridization fingerprint results, which, by computer processing, allows retrieval of information such as the expression of genes, the presence of specific fragments in the sample, the determination of sequences and/or the identification of mutations.

In one embodiment of this invention, hybridization between target nucleic acids and nucleic acids of the invention, used in the form of probes and deposited or synthesized in situ on a DNA chip/array, can be determined by means of fluorescence, radioactivity, electronic detection or the like, as are well known in the art.

In another embodiment, the nucleotide sequences of the invention can be used in the form of a DNA array/chip to carry out analyses of the expression of *Lactobacillus acidophilus* genes. This analysis is based on DNA array/chips on which probes, chosen for their specificity to characterize a given gene or nucleotide sequence, are present. The target sequences to be analyzed are labeled before being hybridized onto the chip. After washing, the labeled complexes are detected and quantified, with the hybridizations being carried out at least in duplicate. Comparative analyses of the signal intensities obtained with respect to the same probe for different samples and/or for different probes with the same sample, allows, for example, for differential transcription of RNA derived from the sample.

In yet another embodiment, arrays/chips containing nucleotide sequences of the invention can comprise nucleotide sequences specific for other microorganisms, which allows for serial testing and rapid identification of the presence of a microorganism in a sample.

In a further embodiment, the principle of the DNA array/chip can also be used to produce protein arrays/chips on which the support has been coated with a polypeptide and/or an antibody of this invention, or arrays thereof, in place of the nucleic acid. These protein arrays/chips make it possible, for example, to analyze the biomolecular interactions induced by the affinity capture of targets onto a support coated, e.g., with proteins, by surface plasma resonance (SPR). The polypeptides or antibodies of this invention, capable of specifically binding antibodies or polypeptides derived from the sample to be analyzed, can be used in protein arrays/chips for the detection and/or identification of proteins and/or peptides in a sample.

Thus, the present invention provides a microarray or microchip comprising various nucleic acids of this invention in any combination, including repeats, as well as a microarray comprising various polypeptides of this invention in any combination, including repeats. Also provided is a microarray comprising antibodies that specifically react with various polypeptides of this invention, in any combination, including repeats.

By "nucleic acid molecule" is intended DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. A fragment of a nucleic acid molecule encoding a protease-like protein may encode a protein fragment that is biologically active, or it may be used as a hybridization probe or PCR primer as described below. A biologically active fragment of a polypeptide disclosed herein can be prepared by isolating a portion of one of the nucleotide sequences of the invention, expressing the encoded portion of the protease-like protein (e.g., by recombinant expression in vitro), and assessing the activity of the encoded portion of the protease-like protein. Fragments of nucleic acid molecules encoding protease-like nucleic acid molecules comprise at least about 15, 20, 50, 75, 100, 200, 250, 300, 350, 400, 450, 500, 550, 600, 650, 700, 800, 900, 1000, 1500, 2000, 2500, 3000, 3500, 4000, or 4500 nucleotides or up to the total number of nucleotides present in a full-length protease-like nucleotide sequence as disclosed herein (for example, 879 for SEQ ID NO: 1, 1974 for SEQ ID NO: 3, etc.).

Fragments of amino acid sequences include polypeptide fragments suitable for use as immunogens to raise anti-protease-like antibodies. Fragments include peptides comprising amino acid sequences sufficiently identical to or derived from the amino acid sequence of a protease-like protein, or partial-length protein, of the invention and exhibiting at least one activity of a protease-like protein, but which include fewer amino acids than the full-length protease-like proteins disclosed herein. Typically, biologically active portions comprise a domain or motif with at least one activity of the protease-like protein. A biologically active portion of a protease-like protein can be a polypeptide that is, for example, 10, 25, 50, 100, 150, 200 contiguous amino acids in length, or up to the total number of amino acids present in a full-length protease-like protein of the current invention (for example, 293 for SEQ ID NO: 2, 658 for SEQ ID NO: 4, etc.). Such biologically active portions can be prepared by recombinant techniques and evaluated for one or more of the functional activities of a native protease-like protein. As used here, a fragment comprises at least 5 contiguous amino acids of any of SEQ ID NOS:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 147. The invention encompasses other fragments, however, such as any fragment in the protein greater than 6, 7, 8, or 9 amino acids.

Variants of the nucleotide and amino acid sequences are encompassed in the present invention. By "variant" is intended a sufficiently identical sequence. Accordingly, the invention encompasses isolated nucleic acid molecules that are sufficiently identical to the nucleotide sequences encoding protease-like proteins in SEQ ID NOS:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 147, or nucleic acid molecules that hybridize to a nucleic acid molecule of SEQ ID NOS:1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131 or 133, and 146, or a complement thereof, under stringent conditions. Variants also include polypeptides encoded by the variant nucleotide sequences of the present invention. In addition, polypeptides of the current invention have an amino acid sequence that is sufficiently identical to an amino acid sequence put forth in SEQ ID NOS:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 147. By "sufficiently identical" is intended that one amino acid or nucleotide sequence contains a sufficient or minimal number of equivalent or identical amino acid residues as compared to a second amino acid or nucleotide sequence, thus providing a common structural domain and/or indicating a common functional activity. Conservative variants include those sequences that differ due to the degeneracy of the genetic code.

In general, amino acids or nucleotide sequences that have at least about 45%, 55%, or 65% identity, preferably at least about 70% or 75% identity, more preferably at least about 80%, 85% or 90%, most preferably at least about 91%, 92%, 93%, 94%, 95%, 96%, 97%, 98%, or 99% sequence identity to any of the amino acid sequences of SEQ ID NOS:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 147, or any of the nucleotide sequences of SEQ ID NOS:1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131 or 133, and 146 respectively, are defined herein as sufficiently identical. Variant proteins encompassed by the present invention are biologically active, that is they retain the desired biological activity of the native protein, that is, protease activity as described herein. A biologically active variant of a protein of the invention may differ from that protein by as few as 1-15 amino acid residues, as few as 1-10, such as 6-10, as few as 5, as few as 4, 3, 2, or even 1 amino acid residue.

Naturally occurring variants may exist within a population (e.g., the *L. acidophilus* population). Such variants can be identified by using well-known molecular biology techniques, including amplification techniques such as the polymerase chain reaction (PCR), and hybridization as described below. Synthetically derived nucleotide sequences, for example, sequences generated by site-directed mutagenesis or PCR-mediated mutagenesis, that still encode a protease-like protein, are also included as variants. One or more nucleotide or amino acid substitutions, additions, or deletions can be introduced into a nucleotide or amino acid sequence disclosed herein, such that the substitutions, additions, or deletions are introduced into the encoded protein. The additions (insertions) or deletions (truncations) may be made at the N-terminal or C-terminal end of the native protein, or at one or more sites in the native protein. Similarly, a substitution of one or more nucleotides or amino acids may be made at one or more sites in the native protein.

For example, conservative amino acid substitutions may be made at one or more predicted, preferably nonessential amino acid residues. A "nonessential" amino acid residue is a residue that can be altered from the wild-type sequence of a protein without altering the biological activity, whereas an "essential" amino acid is required for biological activity. A "conservative amino acid substitution" is one in which the amino acid residue is replaced with an amino acid residue with a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), betabranched side chains (e.g., threonine, valine, isoleucine) and aromatic side chains (e.g., tyrosine, phenylalanine, tryptophan, histidine).

Amino acid substitutions can be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues.

Alternatively, mutations can be made randomly along all or part of the length of the protease-like coding sequence, such as by saturation mutagenesis. The mutants can be expressed recombinantly, and screened for those that retain biological activity by assaying for protease-like activity using standard assay techniques. Methods for mutagenesis and nucleotide sequence alterations are known in the art. See, for example, Kunkel (1985) *Proc. Natl. Acad. Sci. USA* 82:488-492; Kunkel et al. (1987) *Methods in Enzymol. Molecular Biology* (MacMillan Publishing Company, New York) and the references sited therein. Obviously the mutations made in the DNA encoding the variant must not disrupt the reading frame and preferably will not create complimentary regions that could produce secondary mRNA structure. See, EP Patent Application Publication No. 75,444. Guidance as to appropriate amino acid substitutions that do not effect biological activity of the protein of interest may be found in the model of Dayhoff et al. (1978) *Atlas of Protein Sequence and Structure* (Natl. Biomed. Res. Found., Washington, D.C.), herein incorporated by reference.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity of peptidases can be evaluated by measuring hydrolyzing activity (see, for example, Sasaki et al. (1995) *J. Dairy Res.* 62:601-610, and Machuga and Ives (1984) *Biochim. Biophys. Acta* 789:26-36, herein incorporated by reference). The activity of proteinases can be evaluated by measuring proteolytic activity (see, for example, Fernandez-Espla et al. (2000) *Appl. Environ. Micro.* 66:4772-4778; Tuler et al. (2002) *J. Dairy Sci.* 85:2438-2450).

Variant nucleotide and amino acid sequences of the present invention also encompass sequences derived from mutagenic and recombinogenic procedures such as DNA shuffling. With such a procedure, one or more different protease-like protein coding regions can be used to create a new protease-like protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the protease-like gene of the invention and other known protease-like genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Variants of the protease-like proteins can function as either protease-like agonists (mimetics) or as protease-like antagonists. An agonist of the protease-like protein can retain substantially the same, or a subset, of the biological activities of the naturally occurring form of the protease-like protein. An antagonist of the protease-like protein can inhibit one or more of the activities of the naturally occurring form of the protease-like protein by, for example, competitively binding to a downstream or upstream member of a cellular signaling cascade that includes the protease-like protein.

Variants of a protease-like protein that function as either agonists or antagonists can be identified by screening combinatorial libraries of mutants, e.g., truncation mutants, of a protease-like protein for protease-like protein agonist or antagonist activity. In one embodiment, a variegated library of protease-like variants is generated by combinatorial mutagenesis at the nucleic acid level and is encoded by a variegated gene library. A variegated library of protease-like variants can be produced by, for example, enzymatically ligating a mixture of synthetic oligonucleotides into gene sequences such that a degenerate set of potential protease-like sequences is expressible as individual polypeptides, or alternatively, as a set of larger fusion proteins (e.g., for phage display) containing the set of protease-like sequences therein. There are a variety of methods that can be used to produce libraries of potential protease-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential protease-like sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acids Res.* 11:477).

In addition, libraries of fragments of a protease-like protein coding sequence can be used to generate a variegated population of protease-like fragments for screening and subsequent selection of variants of a protease-like protein. In one embodiment, a library of coding sequence fragments can be generated by treating a double-stranded PCR fragment of a protease-like coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the protease-like protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of protease-like proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify protease-like variants (Arkin and Yourvan (1992) *Proc. Natl. Acad. Sci. USA* 89:7811-7815; Delgrave et al. (1993) *Protein Engineering* 6(3):327-331).

Sequence Identity

The protease-like sequences are members of multiple families of molecules, with conserved functional features. By "family" is intended two or more proteins or nucleic acid molecules having sufficient nucleotide or amino acid sequence identity. A family that contains deeply divergent groups may be divided into subfamilies. A clan is a group of families that are thought to have common ancestry. Members of a clan often have a similar tertiary structure. Peptidases in the same family will have at least one domain with sequence identity, usually that domain responsible for catalytic activity. Families of peptidases differ in their catalytic mechanism, and may be serine-type, threonine-type, cysteine-type, aspartic-type, metallo-type or unknown type.

By "sequence identity" is intended the nucleotide or amino acid residues that are the same when aligning two sequences for maximum correspondence over at least one specified comparison window. By "comparison window" is intended a contiguous segment of the two nucleotide or amino acid sequences for optimal alignment, wherein the second sequence may contain additions or deletions (i.e., gaps) as compared to the first sequence. Generally, for nucleic acid alignments, the comparison window is at least 20 contiguous nucleotides in length, and optionally can be 30, 40, 50, 100, or longer. For amino acid sequence alignments, the comparison window is at least 6 contiguous amino acids in length, and optionally can be 10, 15, 20, 30, or longer. Those of skill in the art understand that to avoid a high similarity due to inclusion of gaps, a gap penalty is typically introduced and is subtracted from the number of matches.

Family members may be from the same or different species, and can include homologues as well as distinct proteins. Often, members of a family display common functional characteristics. Homologues can be isolated based on their identity to the *L. acidophilus* protease-like nucleic acid sequences disclosed herein using the cDNA, or a portion thereof, as a hybridization probe according to standard hybridization techniques under stringent hybridization conditions as disclosed below.

To determine the percent identity of two amino acid or nucleotide sequences, an alignment is performed. Percent identity of the two sequences is a function of the number of identical residues shared by the two sequences in the comparison window (i.e., percent identity=number of identical residues/total number of residues×100). In one embodiment, the sequences are the same length. Methods similar to those mentioned below can be used to determine the percent identity between two sequences. The methods can be used with or without allowing gaps. Alignment may also be performed manually by inspection.

When amino acid sequences differ in conservative substitutions, the percent identity may be adjusted upward to correct for the conservative nature of the substitution. Means for making this adjustment are known in the art. Typically the conservative substitution is scored as a partial, rather than a full mismatch, thereby increasing the percentage sequence identity.

Mathematical algorithms can be used to determine the percent identity of two sequences. Non-limiting examples of mathematical algorithms are the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877; the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; and the search-for-local-alignment method of Pearson and Lipman (1988) *Proc. Natl. Acad. Sci. USA* 85:2444-2448.

Various computer implementations based on these mathematical algorithms have been designed to enable the determination of sequence identity. The BLAST programs of Altschul et al. (1990) *J. Mol. Biol.* 215:403 are based on the algorithm of Karlin and Altschul (1990) supra. Searches to obtain nucleotide sequences that are homologous to nucleotide sequences of the present invention can be performed with the BLASTN program, score=100, wordlength=12. To obtain amino acid sequences homologous to sequences encoding a protein or polypeptide of the current invention, the BLASTX program may be used, score=50, wordlength=3. Gapped alignments may be obtained by using Gapped BLAST (in BLAST 2.0) as described in Altschul et al. (1997) *Nucleic Acids Res.* 25:3389. To detect distant relationships between molecules, PSI-BLAST can be used. See, Altschul et al. (1997) supra. For all of the BLAST programs, the default parameters of the respective programs can be used.

Another program that can be used to determine percent sequence identity is the ALIGN program (version 2.0), which uses the mathematical algorithm of Myers and Miller (1988) supra. A PAM120 weight residue table, a gap length penalty of 12, and a gap penalty of 4 can be used with this program when comparing amino acid sequences.

In addition to the ALIGN and BLAST programs, the BESTFIT, GAP, FASTA and TFASTA programs are part of the GCG Wisconsin Genetics Software Package, Version 10 (available from Accelrys Inc., 9685 Scranton Rd., San Diego, Calif., USA), and can be used for performing sequence alignments. The preferred program is GAP version 10, which used the algorithm of Needleman and Wunsch (1970) supra. Unless otherwise stated the sequence identity similarity values provided herein refer to the value obtained using GAP Version 10 with the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 Scoring Matrix; or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Alignment of a sequence in a database to a queried sequence produced by BLASTN, FASTA, BLASTP or like algorithm is commonly described as a "hit." Hits to one or more database sequences by a queried sequence produced by BLASTN, FASTA, BLASTP or a similar algorithm, align and identify similar portions of a sequence. A hit to a database sequence generally represents an overlap over a fraction of the sequence length of the queried sequence, i.e., a portion or fragment of the queried sequence. However, the overlap can represent the entire length of the queried sequence. The hits in an alignment to a queried sequence produced by BLASTN, FASTA, or BLASTP algorithms to sequences in a database are commonly arranged in order of the degree of similarity and the length of sequence overlap.

Polynucleotide and polypeptide hits aligned by BLASTN, FASTA, or BLASTP algorithms to a queried sequence produce "Expect" values. The Expect value (E value) indicates the number of hits one can "expect" to see over a certain number of contiguous sequences at random when searching a database of a certain size. The Expect value is used as a significance threshold for determining whether the hit to a database, such as the GenBank or the EMBL database, indicates actual similarity. For example, an E value of 0.1 assigned to a polynucleotide hit is interpreted as meaning that in a database of the size of the GenBank database, one might expect to see 0.1 matches over the aligned portion of the sequence with a similar score randomly. By this criterion, the aligned and matched portions of the polynucleotide sequences then have a probability of 90% of being the same. For sequences having an E value of 0.01 or less over aligned and matched portions, the probability of finding a match randomly in the GenBank database is 1% or less, using the BLASTN or FASTA algorithm.

According to an embodiment of this invention, "variant" polynucleotides and polypeptides of this invention, comprise sequences producing an E value of about 0.01 or less when compared to the polynucleotide or polypeptide sequences of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA, or BLASTP algorithms set at parameters described herein. In other embodiments, a variant polynucleotide is a sequence having the same number of, or fewer nucleic acids than a polynucleotide of the present invention that has at least a 99% probability of being the same as the polynucleotide of the present invention, measured as having an E value of 0.01 or less using the BLASTN or FASTA algorithms set at parameters described herein. Similarly, a variant polypeptide is a sequence having the same number of, or fewer amino acids than a polypeptide of the present invention that has at least a 99% probability of being the same as a polypeptide of the present invention, measured as having an E value of 0.01 or less using the BLASTP algorithm set at the parameters described herein.

As noted above, the percentage identity is determined by aligning sequences using one of the BLASTN, FASTA, or BLASTP algorithms, set at the running parameters described herein, and identifying the number of identical nucleic acids or amino acids over the aligned portions; dividing the number of identical nucleic acids or amino acids by the total number of nucleic acids or amino acids of the polynucleotide or polypeptide sequence of the present invention; and then multiplying by 100 to determine the percent identity. For example, a polynucleotide of the present invention having 220 nucleic acids has a hit to a polynucleotide sequence in the GenBank database having 520 nucleic acids over a stretch of 23 nucleotides in the alignment produced by the BLASTN algorithm using the parameters described herein. The 23 nucleotide hit includes 21 identical nucleotides, one gap and one different nucleotide. The percent identity of the polynucleotide of the present invention to the hit in the GenBank library is thus 21/220 times 100, or 9.5%. The polynucleotide sequence in the GenBank database is thus not a variant of a polynucleotide of the present invention.

Identification and Isolation of Homologous Sequences

Protease-like nucleotide sequences identified based on their sequence identity to the protease-like nucleotide sequences set forth herein, or to fragments and variants thereof, are encompassed by the present invention. Methods such as PCR or hybridization can be used to identify sequences from a cDNA or genomic library, for example that are substantially identical to sequence of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, New York). Methods for construction of such cDNA and genomic libraries are generally known in the art and are also disclosed in the above reference.

In hybridization techniques, the hybridization probes may be genomic DNA fragments, cDNA fragments, RNA fragments, or other oligonucleotides, and may consist of all or part of a known nucleotide sequence disclosed herein. In addition, they may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the nucleotide sequences disclosed herein. Degenerate primers designed on the basis of conserved nucleotides or amino acid residues in a known protease-like nucleotide sequence or encoded amino acid sequence can additionally be used. The hybridization probe typically comprises a region of nucleotide sequence that hybridizes under stringent conditions to at least about 10, preferably about 20, more preferably about 50, 75, 100, 125, 150, 175, 200, 250, 300, 350, or 400 consecutive nucleotides of a protease-like nucleotide sequence of the invention or a fragment or variant thereof. To achieve specific hybridization under a variety of conditions, such probes include sequences that are unique among protease-like protein sequences. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

In one embodiment, the entire nucleotide sequence encoding a protease-like protein is used as a probe to identify novel protease-like sequences and messenger RNAs. In another embodiment, the probe is a fragment of a nucleotide sequence disclosed herein. In some embodiments, the nucleotide sequence that hybridizes under stringent conditions to the probe can be at least about 300, 325, 350, 375, 400, 425, 450, 500, 550, 600, 650, 700, 800, 900, 1000, 1500, 2000, 2500, 3000, 3500, 4000, or 4500 nucleotides in length.

Substantially identical sequences will hybridize to each other under stringent conditions. By "stringent conditions" is intended conditions under which a probe will hybridize to its target sequence to a detectably greater degree than to other sequences (e.g., at least 2-fold over background). Generally, stringent conditions encompass those conditions for hybridization and washing under which nucleotides having at least about 60%, 65%, 70%, preferably 75% sequence identity typically remain hybridized to each other. Stringent conditions are known in the art and can be found in *Current Protocols in Molecular Biology* (John Wiley & Sons, New York (1989)), 6.3.1-6.3.6. Hybridization typically occurs for less than about 24 hours, usually about 4 to about 12 hours.

Stringent conditions are sequence dependent and will differ in different circumstances. Full-length or partial nucleic acid sequences may be used to obtain homologues and orthologs encompassed by the present invention. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

When using probes, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

The post-hybridization washes are instrumental in controlling specificity. The two critical factors are ionic strength and temperature of the final wash solution. For the detection of sequences that hybridize to a full-length or approximately full-length target sequence, the temperature under stringent conditions is selected to be about 5° C. lower than the thermal melting point ($T_m$) for the specific sequence at a defined ionic strength and pH. However, stringent conditions would encompass temperatures in the range of 1° C. to 20° C. lower than the $T_m$, depending on the desired degree of stringency as otherwise qualified herein. For DNA-DNA hybrids, the $T_m$ can be determined using the equation of Meinkoth and Wahl (1984) *Anal. Biochem.* 138:267-284: $T_m$=81.5° C.+16.6 (logM)+0.41 (% GC)−0.61 (% form)−500/L; where M is the molarity of monovalent cations, % GC is the percentage of guanosine and cytosine nucleotides in the DNA, % form is the percentage of form amide in the hybridization solution, and L is the length of the hybrid in base pairs. The $T_m$ is the temperature (under defined ionic strength and pH) at which 50% of a complementary target sequence hybridizes to a perfectly matched probe.

The ability to detect sequences with varying degrees of homology can be obtained by varying the stringency of the hybridization and/or washing conditions. To target sequences that are 100% identical (homologous probing), stringency conditions must be obtained that do not allow mismatching. By allowing mismatching of nucleotide residues to occur, sequences with a lower degree of similarity can be detected (heterologous probing). For every 1% of mismatching, the $T_m$ is reduced about 1° C.; therefore, hybridization and/or wash conditions can be manipulated to allow hybridization of sequences of a target percentage identity. For example, if sequences with >90% sequence identity are preferred, the $T_m$ can be decreased by 10° C. Two nucleotide sequences could be substantially identical, but fail to hybridize to each other under stringent conditions, if the polypeptides they encode are substantially identical. This situation could arise, for example, if the maximum codon degeneracy of the genetic code is used to create a copy of a nucleic acid.

Exemplary low stringency conditions include hybridization with a buffer solution of 30-35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., Eds. (1995) *Current Protocols in Molecular Biology*, Chapter 2 (Greene Publishing and Wiley-Interscience, New York). See, Sambrook et al. (1989) *Molecular Cloning: A Laboratory Manual* (2d ed.; Cold Spring Harbor Laboratory Press, Plainview, N.Y.).

In a PCR approach, oligonucleotide primers can be designed for use in PCR reactions to amplify corresponding DNA sequences from cDNA or genomic DNA extracted from any organism of interest. PCR primers are preferably at least about 10 nucleotides in length, and most preferably at least about 20 nucleotides in length. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., Eds. (1990) *PCR Protocols: A Guide to Methods and Applications* (Academic Press, New York); Innis and Gelfand, Eds. (1995) *PCR Strategies* (Academic Press, New York); and Innis and Gelfand, Eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

Assays

Diagnostic assays to detect expression of the disclosed polypeptides and/or nucleic acid molecules as well as their disclosed activity in a sample are disclosed. An exemplary method for detecting the presence or absence of a disclosed nucleic acid or protein comprising the disclosed polypeptide in a sample involves obtaining a sample from a food/dairy/feed product, starter culture (mother, seed, bulk/set, concentrated, dried, lyophilized, frozen), cultured food/dairy/feed product, dietary supplement, bioprocessing fermentate, or a subject that has ingested a probiotic material, and contacting the sample with a compound or an agent capable of detecting the disclosed polypeptides or nucleic acids (e.g., an mRNA or genomic DNA comprising the disclosed nucleic acid or fragment thereof) such that the presence of the disclosed sequence is detected in the sample. Results obtained with a sample from the food, supplement, culture, product, or subject may be compared to results obtained with a sample from a control culture, product, or subject.

One agent for detecting the mRNA or genomic DNA comprising a disclosed nucleotide sequence is a labeled nucleic acid probe capable of hybridizing to the disclosed nucleotide sequence of the mRNA or genomic DNA. The nucleic acid probe can be, for example, a disclosed nucleic acid molecule, such as the nucleic acid of SEQ ID NOS:1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131 or 133, and 146, or a portion thereof, such as a nucleic acid molecule of at least 10, 15, 20, 25, 30, 40, 50, 60, 70, 80, 90, 100, 200, 250, 300, 400 or 500 nucleotides in length and sufficient to specifically hybridize under stringent conditions to the mRNA or genomic DNA comprising the disclosed nucleic acid sequence. Other suitable probes for use in the diagnostic assays of the invention are described herein.

One agent for detecting a protein comprising a disclosed polypeptide sequence is an antibody capable of binding to the disclosed polypeptide, preferably an antibody with a detectable label. Antibodies can be polyclonal, or more preferably, monoclonal. An intact antibody, or a fragment thereof (e.g., Fab or F(abN)$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "sample" is intended to include tissues, cells, and biological fluids present in or isolated from a subject, as well as cells from starter cultures or food products carrying such cultures, or derived from the use of such cultures. That is, the detection method of the invention can be used to detect mRNA, protein, or genomic DNA comprising a disclosed sequence in a sample both in vitro and in vivo. In vitro techniques for detection of mRNA comprising a disclosed sequence include Northern hybridizations and in situ hybridizations. In vitro techniques for detection of a protein comprising a disclosed polypeptide include enzyme linked immunosorbent assays (ELISAs), Western blots, immunoprecipitations, and immunofluorescence. In vitro techniques for detection of genomic DNA comprising the disclosed nucleotide sequences include Southern hybridizations. Furthermore, in vivo techniques for detection of a protein comprising a disclosed polypeptide include introducing into a subject a labeled antibody against the disclosed polypeptide. For example, the antibody can be labeled with a radioactive marker whose presence and location in a subject can be detected by standard imaging techniques.

In one embodiment, the sample contains protein molecules from a test subject that has consumed a probiotic material. Alternatively, the sample can contain mRNA or genomic DNA from a starter culture.

The invention also encompasses kits for detecting the presence of disclosed nucleic acids or proteins comprising disclosed polypeptides in a sample. Such kits can be used to determine if a microbe expressing a specific polypeptide of the invention is present in a food product or starter culture, or in a subject that has consumed a probiotic material. For example, the kit can comprise a labeled compound or agent capable of detecting a disclosed polypeptide or mRNA in a sample and means for determining the amount of a the disclosed polypeptide in the sample (e.g., an antibody that recognizes the disclosed polypeptide or an oligonucleotide probe that binds to DNA encoding a disclosed polypeptide, e.g., SEQ ID NOS:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 147). Kits can also include instructions detailing the use of such compounds.

For antibody-based kits, the kit can comprise, for example: (1) a first antibody (e.g., attached to a solid support) that binds to a disclosed polypeptide; and, optionally, (2) a second, different antibody that binds to the disclosed polypeptide or the first antibody and is conjugated to a detectable agent. For oligonucleotide-based kits, the kit can comprise, for example: (1) an oligonucleotide, e.g., a detectably labeled oligonucleotide, that hybridizes to a disclosed nucleic acid sequence or (2) a pair of primers useful for amplifying a disclosed nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for use.

In one embodiment, the kit comprises multiple probes in an array format, such as those described, for example, in U.S. Pat. Nos. 5,412,087 and 5,545,531, and International Publication No. WO 95/00530, herein incorporated by reference. Probes for use in the array may be synthesized either directly onto the surface of the array, as disclosed in International Publication No. WO 95/00530, or prior to immobilization onto the array surface (Gait, ed. (1984) Oligonucleotide Synthesis a Practical Approach IRL Press, Oxford, England). The probes may be immobilized onto the surface using techniques well known to one of skill in the art, such as those described in U.S. Pat. No. 5,412,087. Probes may be a nucleic acid or peptide sequence, preferably purified, or an antibody.

The arrays may be used to screen organisms, samples, or products for differences in their genomic, cDNA, polypeptide, or antibody content, including the presence or absence of specific sequences or proteins, as well as the concentration of those materials. Binding to a capture probe is detected, for example, by signal generated from a label attached to the nucleic acid molecule comprising the disclosed nucleic acid sequence, a polypeptide comprising the disclosed amino acid sequence, or an antibody. The method can include contacting the molecule comprising the disclosed nucleic acid, polypeptide, or antibody with a first array having a plurality of capture probes and a second array having a different plurality of capture probes. The results of each hybridization can be compared to analyze differences in expression between a first and second sample. The first plurality of capture probes can be from a control sample, e.g., a wild type lactic acid bacteria, or control subject, e.g., a food, dietary supplement, starter culture sample, or a biological fluid. The second plurality of capture probes can be from an experimental sample, e.g., a mutant type lactic acid bacteria, or subject that has consumed a probiotic material, e.g., a starter culture sample or a biological fluid.

These assays may be especially useful in microbial selection and quality control procedures where the detection of unwanted materials is essential. The detection of particular nucleotide sequences or polypeptides may also be useful in determining the genetic composition of food, fermentation products, or industrial microbes, or microbes present in the digestive system of animals or humans that have consumed probiotics.

Antisense Nucleotide Sequences

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire protease-like coding strand, or to only a portion thereof, e.g., all or part of the protein coding region (or open reading frame). An antisense nucleic acid molecule can be antisense to a noncoding region of the coding strand of a nucleotide sequence encoding a protease-like protein. The noncoding regions are the 5' and 3' sequences that flank the coding region and are not translated into amino acids. Antisense nucleotide sequences are useful in disrupting the expression of the target gene. Antisense constructions having 70%, preferably 80%, more preferably 85% sequence identity to the corresponding sequence may be used.

Given the coding-strand sequence encoding a protease-like protein disclosed herein (e.g., SEQ ID NOS:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 147), antisense nucleic acids of the invention can be designed according to the rules of Watson and Crick base pairing. The antisense nucleic acid molecule can be complementary to the entire coding region of a protease-like mRNA, but more preferably is an oligonucleotide that is antisense to only a portion of the coding or noncoding region of a protease-like mRNA. For example, the antisense oligonucleotide can be complementary to the region surrounding the translation start site of a protease-like mRNA. An antisense oligonucleotide can be, for example, about 5, 10, 15, 20, 25, 30, 35, 40, 45, or 50 nucleotides in length, or it can be 100 or 200 nucleotides, or greater in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

An antisense nucleic acid molecule of the invention can be an α-anomeric nucleic acid molecule. An α-anomeric nucleic acid molecule forms specific double-stranded hybrids with complementary RNA in which, contrary to the usual n-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585-591)) can be used to catalytically cleave protease-like mRNA transcripts to thereby inhibit translation of protease-like mRNA. A ribozyme having specificity for a protease-like-encoding nucleic acid can be designed based upon the nucleotide sequence of a protease-like cDNA disclosed herein (e.g., SEQ ID NOS:1, 3, 5, 7, 10, 12, 14, 16, 18, 20, 22, 24, 26, 28, 30, 32, 34, 36, 38, 40, 42, 44, 46, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131 or 133, and 146). See, e.g., Cech et al., U.S. Pat. No. 4,987,071; and Cech et al., U.S. Pat. No. 5,116, 742. Alternatively, protease-like mRNA can be used to select a catalytic RNA having a specific ribonuclease activity from a pool of RNA molecules. See, e.g., Bartel and Szostak (1993) *Science* 261:1411-1418.

The invention also encompasses nucleic acid molecules that form triple helical structures. For example, protease-like gene expression can be inhibited by targeting nucleotide sequences complementary to the regulatory region of the protease-like protein (e.g., the protease-like promoter and/or enhancers) to form triple helical structures that prevent transcription of the protease-like gene in target cells. See generally, Helene (1991) *Anticancer Drug Des.* 6(6):569; Helene (1992) *Ann. N.Y. Acad. Sci.* 660:27; and Maher (1992) *Bioassays* 14(12):807.

In some embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see, Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described, for example, in Hyrup et al. (1996) supra; Perry-O'Keefe et al. (1996) *Proc. Natl. Acad. Sci. USA* 93:14670.

PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996) supra); or as probes or primers for DNA sequence and hybridization (Hyrup (1996) supra; Perry-O'Keefe et al. (1996) supra).

In another embodiment, PNAs of a protease-like molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357-63; Mag et al. (1989) *Nucleic Acids Res.* 17:5973; and Peterson et al. (1975) *Bioorganic Med. Chem. Lett.* 5:1119.

Fusion Proteins

The invention also includes protease-like chimeric or fusion proteins. A protease-like "chimeric protein" or "fusion protein" comprises a protease-like polypeptide operably linked to a non-protease-like polypeptide. A "protease-like polypeptide" refers to a polypeptide having an amino acid sequence corresponding to a protease-like protein, whereas a "non-protease-like polypeptide" refers to a polypeptide having an amino acid sequence corresponding to a protein that is not substantially identical to the protease-like protein, and which is derived from the same or a different organism. Within a protease-like fusion protein, the protease-like polypeptide can correspond to all or a portion of a protease-like protein, preferably including at least one biologically active portion of a protease-like protein. Within the fusion protein, the term "operably linked" is intended to indicate that the protease-like polypeptide and the non-protease-like polypeptide are fused in-frame to each other. The non-protease-like polypeptide can be fused to the N-terminus or C-terminus of the protease-like polypeptide.

Expression of the linked coding sequences results in two linked heterologous amino acid sequences that form the fusion protein. The carrier sequence (the non-protease-like polypeptide) can encode a carrier polypeptide that potentiates or increases expression of the fusion protein in the bacterial host. The portion of the fusion protein encoded by the carrier sequence, i.e., the carrier polypeptide, may be a protein fragment, an entire functional moiety, or an entire protein sequence. The carrier region or polypeptide may additionally be designed to be used in purifying the fusion protein, either with antibodies or with affinity purification specific for that carrier polypeptide. Likewise, physical properties of the carrier polypeptide can be exploited to allow selective purification of the fusion protein.

Particular carrier polypeptides of interest include superoxide dismutase (SOD), maltose-binding protein (MBP), glutathione-S-transferase (GST), an N-terminal histidine (His) tag, and the like. This list is not intended to be limiting, as any carrier polypeptide that potentiates expression of the protease-like protein as a fusion protein can be used in the methods of the invention.

In one embodiment, the fusion protein is a GST-protease-like fusion protein in which the protease-like sequences are fused to the C-terminus of the GST sequences. In another embodiment, the fusion protein is a protease-like-immunoglobulin fusion protein in which all or part of a protease-like protein is fused to sequences derived from a member of the immunoglobulin protein family. The protease-like-immunoglobulin fusion proteins of the invention can be used as immunogens to produce anti-protease-like antibodies in a subject, to purify protease-like ligands, and in screening assays to identify molecules that inhibit the interaction of a protease-like protein with a protease-like ligand.

In one embodiment of the invention, the fusion protein has the ability to modify the functional properties of a bacterial cell. By "functional properties" is intended a bacterium's ability to perform certain non-native functions, such as those related to adhesion, immune stimulation, or lysis. The non-protease-like protein may include, but is not limited to, an antibody, an enzyme, a vaccine antigen, a protein with bactericidal activity, or a protein with receptor-binding activity. By "bactericidal activity" is intended the ability to kill one or more bacteria. By "receptor-binding activity" is intended the ability to bind to a receptor on a cell membrane, cell surface, or in solution. Methods for constructing and testing fusion vectors that contain the LPXTG motif (SEQ ID NO:135) and a heterologous protein are well known in the art (see, for example, Leenhouts et al. (1999) *Antonie van Leeuwenhoek* 76:367-376; Steidler et al. (1998) *Appl. Environ. Microbiol.* 64:342-345). Methods to assess the ability of a fusion protein expressed on the surface of Gram-positive bacteria to be used as a vaccine are known in the art (see, for example, Fischetti et al. (1996) *Curr. Opin. Biotechnol.* 7:659-666; Pouwels et al. (1998) *Int. J. Food Microbiol.* 41:155-167).

One of skill in the art will recognize that the particular carrier polypeptide is chosen with the purification scheme in mind. For example, His tags, GST, and maltose-binding protein represent carrier polypeptides that have readily available affinity columns to which they can be bound and eluted. Thus, where the carrier polypeptide is an N-terminal His tag such as hexahistidine ($His_6$ tag), the protease-like fusion protein can be purified using a matrix comprising a metal-chelating resin, for example, nickel nitrilotriacetic acid (Ni-NTA), nickel iminodiacetic acid (Ni-IDA), and cobalt-containing resin (Co-resin). See, for example, Steinert et al. (1997) *QIAGEN News* 4:11-15, herein incorporated by reference in its entirety. Where the carrier polypeptide is GST, the protease-like fusion protein can be purified using a matrix comprising glutathione-agarose beads (Sigma or Pharmacia Biotech); where the carrier polypeptide is a maltose-binding protein (MBP), the protease-like fusion protein can be purified using a matrix comprising an agarose resin derivatized with amylose.

Preferably, a chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and re-amplified to generate a chimeric gene sequence (see, e.g., Ausubel et al., eds. (1995) *Current Protocols in Molecular Biology* (Greene Publishing and Wiley-Interscience, New York). Moreover, a protease-like-encoding nucleic acid can be cloned into a commercially available expression vector such that it is linked in-frame to an existing fusion moiety.

The fusion protein expression vector is typically designed for ease of removing the carrier polypeptide to allow the protease-like protein to retain the native biological activity associated with it. Methods for cleavage of fusion proteins are known in the art. See, for example, Ausubel et al., Eds. (1998) *Current Protocols in Molecular Biology* (John Wiley & Sons, Inc.). Chemical cleavage of the fusion protein can be accomplished with reagents such as cyanogen bromide, 2-(2-nitrophenylsulphenyl)-3-methyl-3'-bromoindolenine, hydroxylamine, or low pH. Chemical cleavage is often accomplished under denaturing conditions to cleave otherwise insoluble fusion proteins.

Where separation of the protease-like polypeptide from the carrier polypeptide is desired and a cleavage site at the junction between these fused polypeptides is not naturally occurring, the fusion construct can be designed to contain a specific protease cleavage site to facilitate enzymatic cleavage and removal of the carrier polypeptide. In this manner, a linker sequence comprising a coding sequence for a peptide that has a cleavage site specific for an enzyme of interest can be fused in-frame between the coding sequence for the carrier polypeptide (for example, MBP, GST, SOD, or an N-terminal His tag) and the coding sequence for the protease-like polypeptide. Suitable enzymes having specificity for cleavage sites include, but are not limited to, factor Xa, thrombin, enterokinase, remin, collagenase, and tobacco etch virus (TEV) protease. Cleavage sites for these enzymes are well known in the art. Thus, for example, where factor Xa is to be used to cleave the carrier polypeptide from the protease-like polypeptide, the fusion construct can be designed to comprise a linker sequence encoding a factor Xa-sensitive cleavage site, for example, the sequence IEGR (see, for example, Nagai and Thøgersen (1984) *Nature* 309:810-812, Nagai and Thøgersen (1987) *Meth. Enzymol.* 153:461-481, and Pryor and Leiting (1997) *Protein Expr. Purif.* 10(3):309-319, herein incorporated by reference). Where thrombin is to be used to cleave the carrier polypeptide from the protease-like polypeptide, the fusion construct can be designed to comprise a linker sequence encoding a thrombin-sensitive cleavage site, for example the sequence LVPRGS or VIAGR (see, for example, Pryor and Leiting (1997) *Protein Expr. Purif.* 10(3):309-319, and Hong et al. (1997) *Chin. Med. Sci. J.* 12(3):143-147, respectively, herein incorporated by reference). Cleavage sites for TEV protease are known in the art. See, for example, the cleavage sites described in U.S. Pat. No. 5,532,142, herein incorporated by reference in its entirety. See also the discussion in Ausubel et al., Eds. (1998) *Current Protocols in Molecular Biology* (John Wiley & Sons, Inc.), Chapter 16.

Antibodies

An isolated polypeptide of the present invention can be used as an immunogen to generate antibodies that specifically bind protease-like proteins, or stimulate production of antibodies in vivo. The full-length protease-like protein can be used as an immunogen or, alternatively, antigenic peptide fragments of protease-like proteins as described herein can be used. The antigenic peptide of a protease-like protein comprises at least 8, preferably 10, 15, 20, or 30 amino acid residues of an amino acid sequence as found in SEQ ID NOS:2, 4, 6, 8, 9, 11, 13, 15, 17, 19, 21, 23, 25, 27, 29, 31, 33, 35, 37, 39, 41, 43, 45, 47, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 147, and encompasses an epitope of an protease-like protein such that an antibody raised against the peptide forms a specific immune complex with the protease-like protein. Preferred epitopes encompassed by the antigenic peptide are regions of a protease-like protein that are located on the surface of the protein, e.g., hydrophilic regions.

Recombinant Expression Vectors

The nucleic acid molecules of the present invention may be included in vectors, preferably expression vectors. "Vector" refers to a nucleic acid molecule capable of transporting another nucleic acid to which it has been linked. Expression vectors include one or more regulatory sequences and direct the expression of genes to which they are operably linked. By "operably linked" is intended that the nucleotide sequence of interest is linked to the regulatory sequence(s) such that expression of the nucleotide sequence is allowed (e.g., in an in vitro transcription/translation system or in a host cell when the vector is introduced into the host cell). The term "regulatory sequence" is intended to include controllable transcriptional promoters, operators, enhancers, transcriptional terminators, and other expression control elements such as translational control sequences (e.g., Shine-Dalgarno consensus sequence, initiation and termination codons). These regulatory sequences will differ, for example, depending on the host cell being used.

The vectors can be autonomously replicated in a host cell (episomal vectors), or may be integrated into the genome of a host cell, and replicated along with the host genome (non-episomal mammalian vectors). Integrating vectors typically contain at least one sequence homologous to the bacterial chromosome that allows for recombination to occur between homologous DNA in the vector and the bacterial chromosome. Integrating vectors may also comprise bacteriophage or transposon sequences. Episomal vectors, or plasmids are circular double-stranded DNA loops into which additional DNA segments can be ligated. Plasmids capable of stable maintenance in a host are generally the preferred form of expression vectors when using recombinant DNA techniques.

The expression constructs or vectors encompassed in the present invention comprise a nucleic acid construct of the invention in a form suitable for expression of the nucleic acid in a host cell. Expression in prokaryotic host cells is encompassed in the present invention. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., protease-like proteins, mutant forms of protease-like proteins, fusion proteins, etc.).

Regulatory sequences include those that direct constitutive expression of a nucleotide sequence as well as those that direct inducible expression of the nucleotide sequence only under certain environmental conditions. A bacterial promoter is any DNA sequence capable of binding bacterial RNA polymerase and initiating the downstream (3') transcription of a coding sequence (e.g., structural gene) into mRNA. A promoter will have a transcription initiation region, which is usually placed proximal to the 5' end of the coding sequence. This transcription initiation region typically includes an RNA polymerase binding site and a transcription initiation site. A bacterial promoter may also have a second domain called an operator, which may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence.

An example of a gene activator protein is the catabolite activator protein (CAP), which helps initiate transcription of the lac operon in *Escherichia coli* (Raibaud et al. (1984) *Annu. Rev. Genet.* 18:173). Regulated expression may therefore be either positive or negative, thereby either enhancing or reducing transcription. Other examples of positive and negative regulatory elements are well known in the art. Various promoters that can be included in the protein expression system include, but are not limited to, a T7/LacO hybrid promoter, a trp promoter, a T7 promoter, a lac promoter, and a bacteriophage lambda promoter. Any suitable promoter can be used to carry out the present invention, including the native promoter or a heterologous promoter. Heterologous promoters may be constitutively active or inducible. A non-limiting example of a heterologous promoter is given in U.S. Pat. No. 6,242,194 to Kullen and Klaenhammer.

Sequences encoding metabolic pathway enzymes provide particularly useful promoter sequences. Examples include promoter sequences derived from sugar metabolizing enzymes, such as galactose, lactose (lac) (Chang et al. (1987) *Nature* 198:1056), and maltose. Additional examples include promoter sequences derived from biosynthetic enzymes such as tryptophan (trp) (Goeddel et al. (1980) *Nucleic Acids Res.* 8:4057; Yelverton et al. (1981) *Nucleic Acids Res.* 9:731; U.S. Pat. No. 4,738,921; EPO Publication Nos. 36,776 and 121, 775). The beta-lactamase (bla) promoter system (Weissmann, (1981) "The Cloning of Interferon and Other Mistakes," in *Interferon* 3 (ed. I. Gresser); bacteriophage lambda PL (Shimatake et al. (1981) *Nature* 292:128); the arabinose-inducible araB promoter (U.S. Pat. No. 5,028,530); and T5 (U.S. Pat. No. 4,689,406) promoter systems also provide useful promoter sequences. See also Balbas (2001) *Mol. Biotech.* 19:251-267, where *E. coli* expression systems are discussed.

In addition, synthetic promoters that do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac (Amann et al. (1983) *Gene* 25:167; de Boer et al. (1983) *Proc. Natl. Acad. Sci.* 80:21) and trc (Brosius et al. (1985) *J. Biol. Chem.* 260:3539-3541) promoters are hybrid trp-lac promoters comprised of both trp promoter and lac operon sequences that are regulated by the lac repressor. The tac promoter has the additional feature of being an inducible regulatory sequence. Thus, for example, expression of a coding sequence operably linked to the tac promoter can be induced in a cell culture by adding isopropyl-1-thio-β-D-galactoside (IPTG). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al. (1986) *J. Mol. Biol.* 189:113; Tabor et al. (1985) *Proc. Natl. Acad. Sci.* 82:1074). In addition, a hybrid promoter can also be comprised of a bacteriophage promoter and an *E. coli* operator region (EPO Publication No. 267, 851).

The vector may additionally contain a gene encoding the repressor (or inducer) for that promoter. For example, an inducible vector of the present invention may regulate transcription from the Lac operator (LacO) by expressing the gene encoding the Lad repressor protein. Other examples include the use of the lexA gene to regulate expression of pRecA, and the use of trpO to regulate ptrp. Alleles of such genes that increase the extent of repression (e.g., lacIq) or that modify the manner of induction (e.g., λCI857, rendering λpL thermo-inducible, or λCI+, rendering λ.pL chemo-inducible) may be employed.

In addition to a functioning promoter sequence, an efficient ribosome-binding site is also useful for the expression of the fusion construct. In prokaryotes, the ribosome binding site is called the Shine-Dalgarno (SD) sequence and includes an initiation codon (ATG) and a sequence 3-9 nucleotides in length located 3-11 nucleotides upstream of the initiation codon (Shine et al. (1975) *Nature* 254:34). The SD sequence is thought to promote binding of mRNA to the ribosome by the pairing of bases between the SD sequence and the 3' end of bacterial 16S rRNA (Steitz et al. (1979) "Genetic Signals and Nucleotide Sequences in Messenger RNA," in *Biological Regulation and Development: Gene Expression* (ed. R. F. Goldberger, Plenum Press, NY).

Protease-like proteins can also be secreted from the cell by creating chimeric DNA molecules that encode a protein comprising a signal peptide sequence fragment that provides for secretion of the protease-like polypeptides in bacteria (U.S. Pat. No. 4,336,336). The signal sequence fragment typically encodes a signal peptide comprised of hydrophobic amino acids that direct the secretion of the protein from the cell. The protein is either secreted into the growth media (Gram-positive bacteria) or into the periplasmic space, located between the inner and outer membrane of the cell (Gram-negative bacteria). Preferably there are processing sites, which can be cleaved either in vivo or in vitro, encoded between the signal peptide fragment and the protease-like protein.

DNA encoding suitable signal sequences can be derived from genes for secreted bacterial proteins, such as the *E. coli* outer membrane protein gene (ompA) (Masui et al. (1983) FEBS Lett. 151(1):159-164; Ghrayeb et al. (1984) *EMBO J.* 3:2437-2442) and the *E. coli* alkaline phosphatase signal sequence (phoA) (Oka et al. (1985) *Proc. Natl. Acad. Sci.* 82:7212). Other prokaryotic signals include, for example, the signal sequence from penicillinase, Ipp, or heat stable enterotoxin II leaders.

Bacteria such as *L. acidophilus* generally utilize the start codon ATG, which specifies the amino acid methionine (which is modified to N-formylmethionine in prokaryotic organisms). Bacteria also recognize alternative start codons, such as the codons GTG and TTG, which code for valine and leucine, respectively. When they are used as the initiation codon, however, these codons direct the incorporation of methionine rather than of the amino acid they normally encode. *Lactobacillus acidophilus* NCFM recognizes these alternative start sites and incorporates methionine as the first amino acid.

Typically, transcription termination sequences recognized by bacteria are regulatory regions located 3' to the translation stop codon and thus, together with the promoter, flank the coding sequence. These sequences direct the transcription of an mRNA that can be translated into the polypeptide encoded by the DNA. Transcription termination sequences frequently include DNA sequences (of about 50 nucleotides) that are capable of forming stem loop structures that aid in terminating transcription. Examples include transcription termination sequences derived from genes with strong promoters, such as the trp gene in *E. coli* as well as other biosynthetic genes.

The expression vectors will have a plurality of restriction sites for insertion of the protease-like sequence so that it is under transcriptional regulation of the regulatory regions. Selectable marker genes that ensure maintenance of the vector in the cell can also be included in the expression vector. Preferred selectable markers include those that confer resistance to drugs such as ampicillin, chloramphenicol, erythromycin, kanamycin (neomycin), and tetracycline (Davies et al. (1978) *Annu. Rev. Microbiol.* 32:469). Selectable markers may also allow a cell to grow on minimal medium, or in the presence of toxic metabolite and may include biosynthetic genes, such as those in the histidine, tryptophan, and leucine biosynthetic pathways.

The regulatory regions may be native (homologous), or may be foreign (heterologous) to the host cell and/or the nucleotide sequence of the invention. The regulatory regions may also be natural or synthetic. Where the region is "foreign" or "heterologous" to the host cell, it is intended that the region is not found in the native cell into which the region is introduced. Where the region is "foreign" or "heterologous" to the protease-like nucleotide sequence of the invention, it is intended that the region is not the native or naturally occurring region for the operably linked protease-like nucleotide sequence of the invention. For example, the region may be derived from phage. While it may be preferable to express the sequences using heterologous regulatory regions, native regions may be used. Such constructs would be expected in some cases to alter expression levels of protease-like proteins in the host cell. Thus, the phenotype of the host cell could be altered.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to protease-like mRNA. Regulatory sequences operably linked to a nucleic acid cloned in the antisense orientation can be chosen to direct the continuous or inducible expression of the antisense RNA molecule. The antisense expression vector can be in the form of a recombinant plasmid or phagemid in which antisense nucleic acids are produced under the control of a high efficiency regulatory region, the activity of which can be determined by the cell type into which the vector is introduced. For a discussion of the regulation of gene expression using antisense genes; see, Weintraub et al. (1986) *Reviews—Trends in Genetics*, Vol. 1(1).

Alternatively, some of the above-described components can be put together in transformation vectors. Transformation vectors are typically comprised of a selectable market that is either maintained in a replicon or developed into an integrating vector, as described above.

Microbial or Bacterial Host Cell's

The production of bacteria containing the nucleic acid sequences or proteins designated, the preparation of starter cultures of such bacteria, and methods of fermenting substrates, particularly food substrates such as milk, may be carried out in accordance with known techniques. (See, for example, Gilliland, S. E. (ed) Bacterial Starter Cultures for Food, CRC press, 1985, 205 pp.; Read, G. (Ed.). Prescott and Dunn's Industrial Microbiology, 4$^{th}$ Ed. AVI Publishing Company, Inc. 1982, 883 pp.; Peppler, J. J. and Perlman, D. (Eds.). Microbial Technology: Volume II, Fermentation Technology. Academic Press, 1979, 536 pp.)

By "fermenting" is intended the energy-yielding, metabolic breakdown of organic compounds by microorganisms that generally proceeds under anaerobic conditions and with the evolution of gas.

By "introducing" as it pertains to nucleic acid molecules is intended introduction into prokaryotic cells via conventional transformation or transfection techniques, or by phage-mediated infection. As used herein, the terms "transformation," "transduction," conjugation, and protoplast fusion are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals. By "introducing" as it pertains to polypeptides or microorganisms of the invention, is intended introduction into a host by ingestion, topical application, nasal, urogenital, suppository, or oral application of the polypeptide or microorganism.

Bacterial cells used to produce the protease-like polypeptides of this invention are cultured in suitable media, as described generally in Sambrook et al. (1989) *Molecular Cloning, A Laboratory Manual* (2d ed., Cold Spring Harbor Laboratory Press, Plainview, N.Y.).

Methods of Use

Methods are provided wherein properties of microbes used in fermentation are modified to provide strains able to produce more, or improved, products for human or animal health, strains producing enhanced flavors, textures, or odors of fermented products, and strains which permit more efficient or more economic fermentation procedures. The polypeptides of the invention may be introduced into a microorganism that does not naturally express the polypeptide, or the polypeptide may be expressed in a microorganism that already expresses the polypeptide. In this way, the polypeptide of the invention is a heterologous polypeptide. By "heterologous" is intended a sequence that originates from a foreign species, or, if from the same species, is substantially modified from its native form in composition and/or genomic locus by deliberate human intervention.

In one embodiment, a polypeptide of the invention may modulate the growth rate of a bacterium. By "growth rate" is intended a measure of the rate of growth of an organism or culture. When a microorganism is grown in continuous liquid culture at an exponential growth rate, the increase in cell mass can be expressed in terms of the specific growth rate constant ($\mu$: $dP/dt = \mu \times P$, where P is the cell mass and t is the time. The polypeptide of the invention may be expressed or overexpressed in a bacterium. By "overexpressing" is intended that the protein of interest is produced in an increased amount in the modified bacterium compared to its production in a wild-type bacterium. Assays to measure the growth rate of bacteria are known in the art (see, for example, Bruinenberg et al. (1992) *Appl. Environ. Microbiol.* 58:78-84).

In another embodiment, the polypeptide of the invention may modulate the acidification rate of a milk product fermented by lactic acid bacteria. By "acidification rate" is intended the rate at which the pH is lowered during fermentation. Assays to measure the acidification rate in fermentation are known in the art (see, for example, Bruinenberg et al. (1992) *Appl. Environ. Microbiol.* 58:78-84).

The polypeptides of the invention, when introduced into a fermentative organism, may also affect the cleavage specificity or cleavage rate of a culture used for fermentation, thereby affecting the rate of proteolysis.

In still other embodiments, fragments of a polynucleotide or polypeptide of the invention, in combination with protease fragments from species other than *L. acidophilus*, can be constructed to form a hybrid protease with modified cleavage specificity or cleavage rate (Siezen (1999) *Antonie Van Leeuwenhoek* 76:139-155). By "cleavage specificity" is intended the degree of selectivity shown by an enzyme with respect to the number and types of substrates the enzyme cleaves. By "substrate cleavage rate" is intended the rate at which the enzyme cleaves its substrate. By "constructing" is intended that the sequence is assembled using molecular biological techniques, and is not isolated from a wild-type cell. By "hybrid protease" is intended that the protease is constructed using one or more fragments of a protease gene from more than one species. Assays to measure the cleavage specificity and rate of an enzyme are well known in the art (see, for example, Vos et al. (1991) *Protein Eng.* 4:479-484; Siezen et al. (1993) *Protein Eng.* 6:927-937).

In alternative embodiments, a mutein of a polypeptide of the invention may have a modified cleavage specificity or rate compared to a wild-type *L. acidophilus* protease. By "mutein" is intended a mutant protein. Methods used to mutate wild-type proteases include site-directed mutagenesis and domain knock-out. By "domain knock-out" is intended a method wherein one or more domains of the protein are removed. Site-directed mutagenesis and domain knock-out are well known techniques (see, for example, Sambrook et al. (1989) *Molecular Cloning: A Laboratory Manual* (2d ed., Cold Spring Harbor Laboratory Press, Plainview, N.Y.; Siezen (1999) *Antonie Van Leewenhoek* 76:139-155).

In another embodiment, a polynucleotide or polypeptide of the invention may modulate the rate of cheese ripening. Cheese ripening is a very complex biochemical process. Each variety of cheese requires unique ripening conditions depending on the amount of proteolysis required to create its characteristic flavor. The flavors and textures unique to each cheese type are a result of glycolysis, lipolysis, and especially proteolysis (Fox et al. (1996) *Antonie Van Leeuwenhoek* 70:271-297). Since proteolysis is the rate-limiting step, the acceleration of proteolysis would be of great economic importance. Alternatively, a decreased proteolytic rate may allow for more flexible processing of fermented products. Variants of a polypeptide sequence of the current invention may have an altered cleavage rate. Methods to assay proteolytic rates are known in the art (see, for example, Vos et al. (1991) *Protein Eng.* 4:479-484).

In another embodiment, a polynucleotide or polypeptide of the invention may increase flavor diversification of fermented milk products. By "flavor diversification" is intended the variety of flavors present in a fermented product. Methods for the organoleptic evaluation of cheese are well known in the art (see, for example, Meijer et al. (1998) *Appl. Environ. Micro.* 64:1950-1953).

In yet another embodiment, a polynucleotide or polypeptide of the invention may enhance the stability of a microorganism, including *L. acidophilus*. By "stability" is intended the ability of a microorganism to withstand stress. By "enhancing" is intended an increase in the ability. Assays to measure bacterial stability are well known in the art (see, for example, (Gilliland, S. E. (ed.) Bacterial Starter Cultures for Foods, CRC Press, 1985. 205 pp.).

Proteases and Peptidases

Peptidases are grouped into clans and families. Clans are groups of families for which there is evidence of common ancestry. Families are grouped by their catalytic type, with the first character representing the catalytic type: S, serine; T, threonine; C, cysteine; A, aspartic; M, metallo and U, unknown. A clan that contains families of more than one type is described as being of type P. The serine, threonine and cysteine peptidases utilize the catalytic part of an amino acid as a nucleophile and form an acyl intermediate—these peptidases can also readily act as transferases. In the case of aspartic and metallopeptidases, the nucleophile is an activated water molecule.

Serine Peptidases

Proteolytic enzymes that exploit serine in their catalytic activity are ubiquitous, being found in viruses, bacteria and eukaryotes. They include a wide range of peptidase activity, including exopeptidase, endopeptidase, oligopeptidase and omega-peptidase activity. Over 20 families (denoted S1-S27) of serine protease have been identified, these being grouped into 6 clans (SA, SB, SC, SE, SF and SG) on the basis of structural similarity and other functional evidence (Rawlings and Barrett (1994) *Methods Enzymol.* 244:461-86). Structures are known for four of the clans (SA, SB, SC and SE): these appear to be totally unrelated, suggesting at least four evolutionary origins of serine peptidases and possibly many more. Notwithstanding their different evolutionary origins, there are similarities in the reaction mechanisms of several peptidases. Chymotrypsin, subtilisin and carboxypeptidase C clans have a catalytic triad of serine, aspartate and histidine in common: serine acts as a nucleophile, aspartate as an electrophile, and histidine as a base (Rawlings and Barrett, 1994, supra). The geometric orientations of the catalytic residues are similar between families, despite different protein folds (Rawlings and Barrett, 1994, supra). The linear arrangements of the catalytic residues commonly reflect clan relationships. For example the catalytic triad in the chymotrypsin clan (SA) is ordered HDS, but is ordered DHS in the subtilisin clan (SB) and SDH in the carboxypeptidase clan (SC) (Rawlings and Barrett (1993) *Biochem. J.* 290:205-18).

SEQ ID NO:58 is a member of the D-alanyl-D-alanine carboxypeptidase family (PFAM Accession No. PF00768). This group of serine peptidases belongs to MEROPS peptidase family S11 (D-Ala-D-Ala carboxypeptidase A family, clan SE). There are three families of serine-type D-Ala-D-Ala peptidase, which are also known as low molecular weight penicillin-binding proteins. Family S11 contains only D-Ala-D-Ala peptidases. The protein fold of the peptidase domain for members of this family resembles that of D-Ala-D-Ala-carboxypeptidase B, the type example for clan SE. D-Ala-D-Ala carboxypeptidase A is involved in the metabolism of cell components (Ghuysen (1991) *Annu. Rev. Microbiol.* 45:37-67); it is synthesized with a leader peptide to target it to the cell membrane (Rawlings and Barrett, 1994, supra). After cleavage of the leader peptide, the enzyme is retained in the membrane by a C-terminal anchor. Methods for measuring serine carboxypeptidase activity are well known in the art (see, for example, Ramirez-Zavala et al. (2004) *Int. J. Food Microbiol.* 91:245-52).

SEQ ID NOS:41 and 70 are members of the Peptidase S24-like family (PFAM Accession No. PF00717). This signature is associated with serine peptidases that belong to MEROPS peptidase families S24 (LexA family, clan SF), S26A (signal peptidase I) and S26B (signalase). The S24 family, of which SEQ ID NO:41 is a member, includes: the lambda repressor C1/C2 family and related bacterial prophage repressor proteins; LexA, the repressor of genes in the cellular SOS response to DNA damage; MucA and the related UmuD proteins, which are lesion-bypass DNA polymerases, induced in response to mitogenic DNA damage; and RulA, a component of the rulAB locus that confers resistance to UV. All of these proteins, with the possible exception of RulA, interact with RecA, which activates self cleavage either derepressing transcription in the case of CI and LexA or activating the lesion-bypass polymerase in the case of UmuD and MucA. The S26A and B families are signal peptidases (Spases), also known as leader peptidases, which remove signal peptides from secretory proteins. SEQ ID NO:70 is an S26 protein. In prokaryotes three types of SPases are known: type I (gene lepB) which is responsible for the processing of the majority of exported pre-proteins; type II (gene lsp) which only process lipoproteins, and a third type involved in the processing of pili subunits. Methods to measure serine-type peptidase activity are well known in the art (see, for example, van Dijl et al. (1995) *J. Biol. Chem.* 270:3611-8).

SEQ ID NO:41 is also a member of the LexA DNA binding domain family (PFAM Accession No. PF01726). This is the DNA binding domain of the LexA SOS regulon repressor that prevents expression of DNA repair proteins in bacteria. This domain is found associated with Peptidase_S24 (PFAM Accession No. PF00717), the auto-proteolytic domain of LexA (EC: 3.4.21.88). Methods to measure repressor LexA activity are well known in the art (see, for example, Little et al. (1981) *Proc. Natl. Acad. Sci. U.S.A.* 78:4199-203).

SEQ ID NO:52 is a member of the Subtilase family (PFAM Accession No. PF00082). This group of serine peptidases belongs to the MEROPS peptidase families S8 (subfamilies S8A (subtilisin) and S8B (kexin)) and S53 (sedolisin), both of which are members of clan SB. The subtilisin family is the second largest serine protease family characterized to date. It is widespread, being found in eubacteria, archaebacteria, eukaryotes and viruses (Rawlings and Barrett, 1994, supra). The vast majority of the family members are endopeptidases, although there is an exopeptidase and a tripeptidyl peptidase. Structures have been determined for several members of the subtilisin family: they exploit the same catalytic triad as the chymotrypsins, although the residues occur in a different order (HDS in chymotrypsin and DHS in subtilisin). Based on sequence homology, a subdivision into six families has been proposed (Siezen and Leunissen (1997) *Protein Sci.* 6:501-23). Methods for measuring subtilase activity are well known in the art (see, for example, Kim and Choi (2000) *Biosci. Biotechnol. Biochem.* 64:1722-1725).

SEQ ID NO:50 is a member of the X-Pro dipeptidyl-peptidase (S15 family) (PFAM Accession No. PF02129). This family of sequences is made up of serine peptidases belonging to MEROPS peptidase family S15 (clan SC) (Rawlings and Barrett, 1994, supra). The type example is X-Pro dipeptidyl-peptidase of *Lactococcus lactis*. These proteins, which have similar specificity to mammalian dipeptidyl-peptidase IV, cleave Xaa-Pro-releasing N-terminal dipeptides. The penultimate residue must be proline. In *L. lactis* the proteins exist as cytoplasmic homodimers. In lactobacilli, X-Pro dipeptidyl-peptidase is involved in the casein-degradation pathway, providing essential amino acids to the lactobacilli (Yüksel and Steele (1996) *Appl. Microbiol. Biotechnol* 44:766-773). Methods for measuring X-Pro aminopeptidase activity are well known in the art (see, for example, Yüksel and Steele, 1996, supra).

Cysteine Peptidases

Cysteine peptidases have characteristic molecular topologies, which can be seen not only in their three-dimensional structures, but commonly also in the two-dimensional structures. The peptidase domain is responsible for peptide bond hydrolysis; in Merops this is termed the peptidase unit. These are peptidases in which the nucleophile is the sulfhydryl group of a cysteine residue. Cysteine proteases are divided into clans (proteins which are evolutionarily related), and further sub-divided into families, on the basis of the architecture of their catalytic dyad or triad (Barrett and Rawlings (2001) *Biol. Chem.* 382:727-33). Clan CA contains the families of papain (C1), calpain (C2), streptopain (C10) and the ubiquitin-specific peptidases (C12, C19), as well as many families of viral cysteine endopeptidases. Clan CD contains the families of clostripain (C11), gingipain R (C25), legumain (C13), caspase-1 (C14) and separin (C50). These enzymes have specificities dominated by the interactions of the S1 subsite. Clan CE contains the families of adenain (C5) from adenoviruses, the eukaryotic Ulp1 protease (C48) and the bacterial YopJ proteases (C55). Clan CF contains only pyroglutamyl peptidase I (C15). Clan PA contains the picornains (C3), which have probably evolved from serine peptidases and which form the majority of enzymes in this clan. Clans PB and CH contain the autolytic cysteine peptidases.

SEQ ID NOS:8, 9, 11, 19, 29, 114, and 118 are members of the Peptidase C1-like family (PFAM Accession No. PF03051). This group of proteins belongs to the peptidase family C1, sub-family C1B (bleomycin hydrolase, clan CA). This family is closely related to the Peptidase_C1 family (PFAM Accession No. PF00112), containing several prokaryotic and eukaryotic aminopeptidases and bleomycin hydrolases. Methods to measure cysteine-type peptidase activity are well known in the art (see, for example, Chapot-Chartier et al. (1994) *Eur. J. Biochem.* 224:497-506).

SEQ ID NOS:13, 15, 60, 66, 98, 120, and 126 are members of the Peptidase U34 family (PFAM Accession No. PF03577). This group of peptidases belongs to MEROPS peptidase family C69 (dipeptidase A family, clan PB), which appear to be mainly dipeptidases (Vesanto et al. (1996) *Appl. Microbiol. Biotechnol.* 45:638-45). Methods to measure dipeptidase activity are well known in the art (see, for example, Vesanto, 1996, supra).

SEQ ID NO:6 is a member of the Pyroglutamyl peptidase family (PFAM Accession No. PF01470). This group of cysteine peptidases belongs to MEROPS peptidase family C15 (pyroglutamyl peptidase I, clan CF). Peptidase family C15 contains omega peptidases that release an N-terminal pyroglutamate (pGlu) residue. Pyroglutamyl/pyrrolidone carboxyl peptidase (Pcp or PYRase) is an exopeptidase that hydrolytically removes the pGlu from pGlu-peptides or pGlu-proteins (Awade et al. (1994) *Proteins* 20:34-51; Awade et al. (1992) *FEBS Lett.* 305:67-73). PYRase has been found in prokaryotes and eukaryotes, where at least two different classes have been characterized: the first containing bacterial and animal type I PYRases, and the second containing animal type II and serum PYRases. Type I and bacterial PYRases are soluble enzymes, while type II PYRases are membrane-bound. The conserved residues Cys-144 and His-168 have been identified by inhibition and mutagenesis studies (Awade et al., 1994, supra; Gonzales and Robert-Baudouy (1994) *J. Bacteriol.* 176:2569-76). Methods to measure pyroglutamyl-peptidase I activity are well known in the art (see, for example, Awade et al., 1994, supra).

Metalloproteases

Metalloproteases are the most diverse of the four main types of protease, with more than 30 families identified to date. In these enzymes, a divalent cation, usually zinc, activates the water molecule. The metal ion is held in place by amino acid ligands, usually three in number. The known metal ligands are His, Glu, Asp or Lys and at least one other residue is required for catalysis, which may play an electrophilic role. Of the known metalloproteases, around half contain a His-Glu-Xaa-Xaa-His (SEQ ID NO:148, or "HEXXH") motif, which has been shown in crystallographic studies to form part of the metal-binding site (Rawlings and Barrett (1995) *Methods Enzymol.* 248:183-228). The HEXXH motif is relatively common, but can be more stringently defined for metalloproteases as abXHEbbHbc (SEQ ID NO:136), where 'a' is most often valine or threonine and forms part of the S1' subsite in thermolysin and neprilysin, 'b' is an uncharged residue, and 'c' is a hydrophobic residue. Proline is never found in this site, possibly because it would break the helical structure adopted by this motif in metalloproteases (Rawlings and Barrett, 1995, supra).

SEQ ID NOS:21 and 23 are members of the glycoprotease family (PFAM Accession No. PF00814). This group of metallopeptidases belongs to MEROPS peptidase family M22 (clan MK). Peptidase family M22 contains an endopeptidase that cleaves only proteins that are O-sialoglycosylated. The Peptidase M22 proteins are part of the HSP70-actin superfamily. The region represented here is an insert into the fold and is not found in the rest of the family (beyond the Peptidase M22 family). This region also contains the histidine dyad believed to coordinate the metal ion and hence provide catalytic activity. The zinc-binding and catalytic residues of this family have not been determined, although the motif HMEGH (SEQ ID NO:137) may be a zinc-binding region (Rawlings and Barrett, 1995, supra). The nature of the active site is unknown, but it has been suggested that an HXXEXXH (SEQ ID NO:149) motif, conserved in some members of the family, is akin to the HEXXH motif found in clan MA, in which the histidines are zinc ligands and the glutamate is a catalytic residue. Methods to measure O-sialoglycoprotein endopeptidase activity are well known in the art (see, for example, Mellors and Lo (1995) *Methods Enzymol.* 248:728-40).

SEQ ID NO:86 is a member of the Insulinase (Peptidase M16) family (PFAM Accession No. PF00675). Members in this family are metalloendopeptidases and non-peptidase homologs belonging to MEROPS peptidase family M16 (clan ME), subfamilies M16A, M16B and M16C. These proteins share some regions of sequence similarity in the N-terminal section. This region includes a conserved histidine followed two residues later by a glutamate and another histidine (His-Xaa-Xaa-Glu-His, SEQ ID NO:154, or "HXXEH" motif). In pitrilysin, it has been shown (Fujita et al. (1994) *Nature* 372:567-70) that this HXXEH motif is involved in enzymatic activity; the two histidines bind zinc and the glutamate is necessary for catalytic activity. Methods for measuring metalloendopeptidase activity are well known in the art (see, for example, Yan et al. (1987) *Eur. J. Biochem.* 163:259-65).

SEQ ID NO:134 is a member of the Peptidase M16 inactive domain family (PFAM Accession No. PF05193). Peptidase M16 consists of two structurally related domains. One is the active peptidase, whereas the other is inactive. The two domains hold the substrate like a clamp (Taylor et al. (2001) *Structure (Camb)* 9:615-25). These metallopeptidases belong to MEROPS peptidase family M16 (clan ME).

SEQ ID NO:102 is a member of the M42 glutamyl aminopeptidase family (PFAM Accession No. PF05343). This group of metallopeptidases belongs to MEROPS peptidase family M42 (glutamyl aminopeptidase family, clan MH). These peptidases are co-catalytic metallopeptidases, typically binding two atoms of zinc or cobalt. For members of this family and family M28, the predicted metal ligands occur in the same order in the sequence: HDE(D/E)H (SEQ ID NO:138); and the active site residues occur in the motifs HXD and EE. Some of the enzymes exhibit typical aminopeptidase specificity, whereas others are also able to hydrolyze acylated N-terminal residues, the so-called "N-terminal deblocking activity." Characteristics commonly reported are exceptional thermal stability and a requirement for cobalt ions for maximal activity. Methods for measuring glutamyl aminopeptidase activity are well known in the art (see, for example, Ando et al. (1999) *FEBS Lett.* 447:25-8).

SEQ ID NOS:25, 27, and 45 are members of the metallopeptidase M24 family (PFAM Accession No. PF00557). This group of metallopeptidases and non-peptidase homologs belongs to MEROPS peptidase family M24 (clan MG). It includes the enzymes proline dipeptidase and methionine aminopeptidase. Peptidase family M24 contains exopeptidases that require co-catalytic ions of cobalt or manganese. The methionyl aminopeptidases of subfamily M24A are essential for the removal of the initiating methionine of many proteins, acting co-translationally in association with the ribosomes (Chang and Lee (1992) *J. Biol. Chem.* 267:3952-3958). The X-Pro dipeptidase found in eukaryotes has a role in the cleavage of Xaa-Pro linkages found in dipeptides associated with collagen recycling. Methods for measuring metalloexopeptidase activity are well known in the art (see, for example, Chang and Lee, 1992, supra).

SEQ ID NOS:56 and 68 are members of the Peptidase M1 family (PFAM Accession No. PF01433). This group of metallopeptidases belongs to the MEROPS peptidase family M1 (clan MA(E)). The peptidases of family M1 are dependent on a single zinc ion for activity and all members of the family act on the N-terminus of polypeptides, many of them being aminopeptidases. The members differ widely in specificity, hydrolyzing acidic, basic or neutral N-terminal residues. In the active site, a catalytic zinc ion is bound by two histidines and a glutamate. The histidines are within an HEXXH motif on one long helix with the glutamate on another antiparallel helix. The catalytic mechanism is believed to involve activation of a water molecule by the zinc ion. The glutamate of the HEXXH motif is known to be important for catalysis and a tyrosine may also be involved. Membrane alanine aminopeptidase (EC:3.4.11.2) is part of the HEXXH$^+$E group (SEQ ID NO:139); it consists entirely of aminopeptidases, spread across a wide variety of species (Rawlings and Barrett, 1995, supra). Methods to measure membrane alanyl aminopeptidase activity are well known in the art (see, for example, Ferracci and Maroux (1980) *Biochim. Biophys. Acta* 599:448-63).

SEQ ID NOS:4, 39 and 116 are members of the Peptidase M13 family (PFAM Accession No. PF01431). This group of metallopeptidases belongs to the MEROPS peptidase family M13 (neprilysin family, clan MA(E)). Peptidase family M13 contains metalloendopeptidases restricted to action on substrates smaller than proteins. In the active site, there is an HEXXCH motif, in which the His residues are ligands of a zinc atom and the Glu has a catalytic role. There is also a more C-terminal Glu residue that is the third ligand of the zinc atom. The protein fold of the peptidase unit for members of this family resembles that of thermolysin, the type example for clan MA. Methods for measuring metallopeptidase activity are well known in the art (see, for example, Yan et al. (1987) *Eur. J. Biochem.* 163:259-65).

SEQ ID NOS:31, 37, 54, and 104 are members of the Peptidase M20/M25/M40 family (PFAM Accession No. PF01546). This group of proteins contains the metallopeptidases and non-peptidase homologues that belong to the MEROPS peptidase family M20 (clan MH) (Rawlings and Barrett, 1995, supra). This family includes a range of zinc metallopeptidases belonging to several families in the peptidase classification. Peptidase family M20 contains exopeptidases: carboxypeptidases, dipeptidases and a specialized aminopeptidase. Peptidase family M25 contains X-His dipeptidases. The peptidases of this clan have two catalytic zinc ions at the active site, bound by His/Asp, Asp, Glu, Asp/Glu and His (SEQ ID NO:140). The catalyzed reaction involves the release of an N-terminal amino acid, usually neutral or hydrophobic, from a polypeptide. The peptidases are of the 'co-catalytic' type, binding two metal ions per monomer of protein. There are five metal-ligand residues, because one ligates both metal ions, and the general arrangement of these is: (H/D)DE(E/D)H (SEQ ID NO:140). With the addition of two catalytic residues (bold), the full set of active site residues becomes: (H/D)DDEE(E/D)H (SEQ ID NO:141), but there are variations in the individual subfamilies. Peptidase T (M20.003) acts only on tripeptide substrates and has therefore been termed a tripeptidase. Methods for measuring metallopeptidase activity are well known in the art (see, for example, Chang and Lee, 1992, supra).

SEQ ID NO:64 is a member of the Peptidase M3 family (PFAM Accession No. PF01432). This group of metallopeptidases belongs to MEROPS peptidase family M3 (clan MA(E)), subfamilies M3A and M3B. This is the Thimet oligopeptidase family, a large family of mammalian and bacterial oligopeptidases that cleave medium sized peptides. The peptidases of family M3 are high-molecular-mass (about 80 kDa) zinc metalloendopeptidases. They contain the HEXXH motif that forms the active site in conjunction with a C-terminally-located Glu residue. A single zinc ion is ligated by the side chains of the two His residues, and the more C-terminal Glu. Both thimet oligopeptidase (M03.001) and neurolysin (M03.002) are oligopeptidases, acting only on substrates of less than about 19 amino acid residues, with a particular preference for cleaving near the C-terminus (Knight et al. (1995) *Biochem. J.* 308:145-150). Methods for measuring metalloendopeptidase activity are well known in the art (see, for example, Yan et al. (1987) *Eur. J. Biochem.* 163:259-65).

SEQ ID NO:100 is a member of the Peptidase M48 family (PFAM Accession No. PF01435). This group of metallopeptidases belongs to MEROPS peptidase family M48 (Step 24 endopeptidase family, clan M-); members of both subfamily are represented. The members of this set of proteins are homologs of protease htpX (EC:3.4.24) or CAAX (Cys-Ala-Ala-Xaa, SEQ ID NO:150) prenyl protease 1, which proteolytically removes the C-terminal three residues of farnesylated proteins. They are integral membrane proteins associated with the endoplasmic reticulum and Golgi complex, binding one zinc ion per subunit. In *Saccharomyces cerevisiae* Step 24p is required for the first NH2-terminal proteolytic processing event within the a-factor precursor, which takes place after COOH-terminal CAAX (SEQ ID NO:150) modification is complete. The Step 24p contains multiple predicted membrane spans, a zinc metalloprotease motif (HEXXH, SEQ ID NO:148), and a COOH-terminal ER retrieval signal (KKXX; SEQ ID NO:151). The HEXXH protease motif is critical for Step 24p activity, since Step 24p fails to function when conserved residues within this motif are mutated. The Step 24p homologues occur in a diverse group of organisms, including *Escherichia coli, Schizosaccharomyces pombe, Haemophilus influenzae*, and *Homo sapiens*, which indicates that the gene is highly conserved throughout evolution. Step 24p and the proteins related to it define a subfamily of proteins that are likely to function as intracellular, membrane-associated zinc metalloproteases (Fujimura-Kamada et al. (1997) *J. Cell Biol.* 136:271-285). Methods for measuring metalloendopeptidase activity are well known in the art (see, for example, Yan et al. (1987) *Eur. J. Biochem.* 163:259-65).

SEQ ID NOS:106, 108, and 110 are members of the Peptidase propeptide and YPEB domain family (PFAM Accession No. PF03413). This signature, PepSY, is found in the propeptide of members of the MEROPS peptidase family M4 (clan MA(E)), which contains the thermostable thermolysins (EC:3.4.24.27), and related thermolabile neutral proteases (bacillolysins) (EC:3.4.24.28) from various species of *Bacillus*. Many extracellular bacterial proteases are produced as proenzymes. The propeptides usually have a dual function, i.e., they function as an intramolecular chaperone required for the folding of the polypeptide and as an inhibitor, preventing premature activation of the enzyme. Analysis of the propeptide region of the M4 family of peptidases reveals two regions of conservation, the PepSY domain and a second domain, proximal to the N terminus, the FTP domain (PFAM Accession No. PF07504), which is also found in isolation in the propeptide of eukaryotic peptidases belong to MEROPS peptidase family M36. All peptidases in the family bind a single, catalytic zinc ion. As in many other families of metallopeptidases, there is an HEXXH motif, in which the histidines are zinc ligands and the glutamate (Glu375) is an active site residue. This common motif was refined by Jongeneel et al. ((1989) *FEBS Lett.* 242:211-214). The Jongeneel consensus identifies most mono-catalytic zinc metallopeptidases from a number of families. The zinc is bound by a glutamate (Glu398), 20-33 residues C-terminal to the HEXXH motif. Metallopeptidases in which the zinc is bound by HEXXH plus Glu (SEQ ID NO:139) are known as "Glu-zincins." A zinc ion is tetrahedrally co-ordinated, and the fourth ligand is activated water that forms the nucleophile in catalysis. Residues found to be essential for catalysis are Tyr389, Asp402, Asp458 and His463. Asp402 is completely conserved amongst all active members of the family and forms a hydrogen bond with His463 (Argos et al. (1978) *J. Mol. Biol.* 126:141-158); the EXXXD (SEQ ID NO:152) is a second useful motif for detecting members of the family. Most members of the family are endopeptidases active at neutral pH. Proteins and peptides are degraded with a preference for cleavage of Xaa+Yaa, in which Xaa is a hydrophobic residue and Yaa is Leu, Phe, Ile, or Val. Thermolysin has a two-domain structure with the active site between the domains.

The N-terminal domain includes a distinctive six-strand beta sheet with two helices, one of which carries the HEXXH (SEQ ID NO:148) zinc-binding motif. The C-terminal domain, which is unique for the family, is predominantly helical and carries the third zinc ligand. Thermolysin is the type-example of clan MA. Other families in clan MA, such as M10 and M12, share a similar core structure to the thermolysin N-terminal domain, but the C-terminal domains are unrelated. Most members of the family are secreted enzymes that degrade extracellular proteins and peptides for bacterial nutrition, especially prior to sporulation. Methods to measure zinc ion binding are well known in the art (see, for example, Tang et al. (2003) *Biochem. Biophys. Res. Commun.* 301: 1093-8).

Aspartic Endopeptidases

Aspartic endopeptidases (EC:3.4.23) of vertebrate, fungal and retroviral origin have been characterized (Szecsi et al. (1992) *Scand. J. Clin. Lab. Invest. Suppl.* 210:5-22). Aspartate peptidases are so named because Asp residues are the ligands of the activated water molecule in all examples where the catalytic residues have been identified, although at least one viral enzyme is believed to have an Asp and an Asn as its catalytic dyad. All or most aspartate peptidases are endopeptidases. These enzymes have been assigned into clans (proteins which are evolutionary related), and further sub-divided into families, largely on the basis of their tertiary structure.

SEQ ID NO:17 is a member of the Bacterial Peptidase A24 N-terminal domain family (PFAM Accession No. PF06750). This family is found at the N-terminus of the prepilin peptidases family (PFAM Accession No. PF01478). Some of the family members have been characterized as bifunctional (Strom et al. (1993) *J. Biol. Chem.* 268:15788-94), and this domain may contain the N-methylation activity (EC:2.1.1.-). The domain consists of an intracellular region between a pair of transmembrane domains. This intracellular region contains an invariant proline and two almost fully conserved disulfide bridges, hence the name DiS-P-DiS. These four conserved cysteines are arranged in a two-pair motif, with the Cys residues of a pair separated (usually) by two amino acids and with each pair separated by 21 largely hydrophilic residues; they have been shown to be essential to the overall function of the enzyme (Strom et al., 1993, supra). SEQ ID NO:17 is a prepilin peptidase (EC 3.4.99.-), which processes the N-terminus of the prepilins (Albers et al. (2003) *J. Bacteriol.* 185:3918-25). The processing is essential for the correct formation of the pseudopili of type IV bacterial protein secretion. Prepilin leader peptidases are found on the cytosolic membrane surface, where they have dual activity, involving cleavage of glycine-phenylalanine bonds and methylation of the newly-revealed N-terminal phenylalanine. The consensus sequence for the site of proteolytic cleavage is GFT(L/I) (SEQ ID NO:142), in which the Gly P1 residue is essential (Rawlings and Barrett, 1994, supra). Methods to measure cysteine-type peptidase activity are well known in the art (see, for example, Strom et al., 1993, supra).

SEQ ID NO:33 is a member of the Signal peptidase (SPase) II family (PFAM Accession No. PF01252). This group of aspartic peptidases belongs to the MEROPS peptidase family A8 (signal peptidase II family, clan AC). The catalytic residues have not been identified, but three conserved aspartates can be identified from sequence alignments. Two aspartate residues have been shown by site-directed mutagenesis to be essential for activity (Tjalsma et al. (1999) *J. Biol. Chem.* 274:28191-28197). These occur in the motifs GNXXDRX (SEQ ID NO:143) and FNXAD (SEQ ID NO:144) where X is a hydrophobic residue. The type example is the *Escherichia* coli lipoprotein signal peptidase or SPase II (EC:3.4.23.36). This enzyme recognizes a conserved sequence and cuts in front of a cysteine residue to which a glyceride-fatty acid lipid is attached. SPase II is an integral membrane protein that is anchored in the membrane. Bacterial cell walls contain large amounts of murein lipoprotein, a small protein that is both N-terminally bound to lipid and attached to membrane peptidoglycan (murein) through the epsilon-amino group of its C-terminal lysine residue (Rawlings and Barrett, 1995, supra). Secretion of this lipoprotein is facilitated by the action of lipoprotein signal peptidase (also known as leader peptidase II), located in the inner membrane (Tokunaga et al. (1984) *J. Biol. Chem.* 259:3825-30; Rawlings and Barrett, 1995, supra). Methods to measure aspartic-type endopeptidase activity are well known in the art (see, for example, Tjalsma et al., 1999, supra).

Other Peptidases

The prolyl aminopeptidases of the present invention (SEQ ID NOS:2, 62, 72, and 128) are members of the alpha/beta hydrolase fold domain family (PFAM Accession No. PF00561). The alpha/beta hydrolase fold (Ollis is et al. (1992) *Protein Eng.* 5:197-211) is common to a number of hydrolytic enzymes of widely differing phylogenetic origin and catalytic function. The core of each enzyme is an alpha/beta-sheet (rather than a barrel), containing eight beta-sheets connected by alpha-helices (Ollis is et al., 1992, supra). The enzymes are believed to have diverged from a common ancestor, preserving the arrangement of the catalytic residues. All have a catalytic triad, the elements of which are borne on loops, which are the best conserved structural features of the fold.

SEQ ID NO:82 is a member of the ATPase family associated with various cellular activities (AAA) (PFAM Accession No. PF00004). AAA family proteins often perform chaperone-like functions that assist in the assembly, operation, or disassembly of protein complexes (Confalonieri and Duguet (1995) *Bioessays* 17:639-50). A key feature of this family is that the members share a conserved region of about 220 amino acids that contains an ATP-binding site. The proteins that belong to this family either contain one or two AAA domains. It is proposed that, in general, the AAA domains in these proteins act as ATP-dependent protein clamps (Confalonieri and Duguet, 1995, supra). In addition to the ATP-binding 'A' and 'B' motifs, which are located in the N-terminal half of this domain, there is a highly conserved region located in the central part of the domain.

SEQ ID NOS:74, 76, 80, 92, and 130 are members of the CAAX (SEQ ID NO:150) amino terminal protease family (PFAM Accession No. PF02517). These proteins contain a highly conserved Glu-Glu motif at the amino end of the alignment. The alignment also contains two histidine residues that may be involved in zinc binding.

SEQ ID NOS:78 and 132 are members of the Patatin-like phospholipase family (PFAM Accession No. PF01734). This family consists of various patatin glycoproteins from plants. The patatin protein accounts for up to 40% of the total soluble protein in potato tubers (Banfalvi et al. (1994) *Mol. Gen. Genet.* 245:517-22). Patatin is a storage protein but it also has the enzymatic activity of lipid acyl hydrolase, catalyzing the cleavage of fatty acids from membrane lipids (Banfalvi et al., 1994, supra). Members of this family have been found also in vertebrates.

SEQ ID NO:96 is a member of the YSIRK (SEQ ID NO:153) type signal peptide family (PFAM Accession No. PF04650). Many surface proteins found in *Streptococcus, Staphylococcus*, and related lineages share apparently homologous signal sequences. A motif resembling [YF] SIRKxxxGxxS[VIA] (SEQ ID NO:145) appears at the start of the transmembrane domain. The GxxS motif appears perfectly conserved, suggesting a specific function and not just homology. There is a strong correlation between proteins carrying this region at the N-terminus and those carrying the Gram-positive anchor domain with the LPXTG (SEQ ID NO:135) sortase processing site at the C-terminus.

SEQ ID NO:122 is a member of the amidohydrolase family (PFAM Accession No. PF01979). This family of enzymes comprises a large metal dependent hydrolase superfamily whose members catalyze the hydrolysis of various bonds. Methods to measure hydrolase activity are well known in the art (see, for example, Park et al. (2004) *Arch. Biochem. Biophys.* 429:224-30).

The following examples are offered by way of illustration and not by way of limitation.

EXPERIMENTAL

Example 1

Gapped BlastP Results for Amino Acid Sequences

A Gapped BlastP sequence alignment showed that SEQ ID NO:2 (293 amino acids) has about 88% identity from amino acids 1-293 with a protein from *Lactobacillus helveticus* that is a proline iminopeptidase (PIP) (prolyl aminopeptidase) (PAP) (Accession No. sp|P52278|PIP_LACHE), about 61% identity from amino acids 1-293 with a protein from *Lactobacillus delbrueckii* that is a proline iminopeptidase (PIP) (prolyl aminopeptidase) (PAP) (Accession No. sp|P465-42|PIP_LACDL), about 61% identity from amino acids 1-293 with a protein from *Lactobacillus delbrueckii* that is a proline iminopeptidase (Accession Nos. gb|AAA61596.1; L10712), about 61% identity from amino acids 1-293 with a protein from *Lactobacillus delbrueckii* that is a proline iminopeptidase (PIP) (prolyl aminopeptidase) (PAP) (Accession No. sp|P46544|PIP_LACDE), and about 63% identity from amino acids 1-269 with a protein from *Lactobacillus delbrueckii* that is a prolyl aminopeptidase (EC 3.4.11.5) (Accession No. pir||S44282).

A Gapped BlastP sequence alignment showed that SEQ ID NO:4 (658 amino acids) has about 62% identity from amino acids 11-658 with a protein from *Lactobacillus helveticus* that is an endopeptidase O2 (Accession Nos. gb|AAL73136.1; AF321529), about 59% identity from amino acids 9-658 with a protein from *Lactobacillus helveticus* that is a neutral endopeptidase (Endopeptidase O) (Accession No. sp|O52071|PEPO_LACHE), about 44% identity from amino acids 29-658 with a protein from *Lactococcus lactis* subsp. *lactis* that is a neutral endopeptidase (Accession Nos. NP_267960.1; NC_002662), about 44% identity from amino acids 29-658 with a protein from *Lactococcus lactis* subsp. *lactis* that is a p endopeptidase PepO (EC 3.4.-.-) (Accession No. pir||F53290), and about 44% identity from amino acids 29-658 with a protein from *Lactococcus lactis* subsp. *cremoris* that is a neutral endopeptidase (endopeptidase O) (Accession No. sp|Q09145|PEPO_LACLC).

A Gapped BlastP sequence alignment showed that SEQ ID NO:6 (200 amino acids) has about 60% identity from amino acids 1-198 with a protein from *Lactococcus lactis* subsp. *cremoris* that is a pyrrolidone carboxyl peptidase (Accession Nos. emb|CAA11699.1; AJ223962), about 60% identity from amino acids 1-198 with a protein from *Lactococcus lactis* subsp. *cremoris* that is a pyrrolidone-carboxylate peptidase (5-oxoprolyl-peptidase) (Accession No. sp|O87765|PCP_LACLC), about 52% identity from amino acids 1-199 with a protein from *Streptococcus pneumoniae* that is a pyrrolidone-carboxylate peptidase (Accession Nos. NP_345348.1; NC_003028), about 52% identity from amino acids 1-199 with a protein from *Streptococcus pyogenes* that is homologous to a pyrrolidone carboxyl peptidase (Accession Nos. NP_606760.1; NC_003485), and about 52% identity from amino acids 1-199 with a protein from *Streptococcus pyogenes* that is homologous to a pyrrolidone carboxyl peptidase (Accession Nos. NP_268785.1; NC_002737).

A Gapped BlastP sequence alignment showed that SEQ ID NO:8 (124 amino acids) has about 55% identity from amino acids 10-118 with a protein from *Lactobacillus delbrueckii* that is an aminopeptidase G (Accession No. sp|P94869|PEPG_LACDL), about 55% identity from amino acids 10-118 with a protein from *Lactobacillus helveticus* that is an aminopeptidase E (Accession No. sp|P94870|PEPE_LACHE), about 51% identity from amino acids 10-118 with a protein from *Lactobacillus delbrueckii* that is an aminopeptidase W (Accession No. sp|P94868|PEPW_LACDL), about 44% identity from amino acids 10-118 with a protein from *Lactobacillus delbrueckii* that is an aminopeptidase C (bleomycin hydrolase) (Accession No. sp|Q48543|PEPC_LACDL), and about 45% identity from amino acids 10-118 with a protein from *Lactobacillus helveticus* that is an aminopeptidase C (bleomycin hydrolase) (Accession No. sp|Q10744|PEPC_LACHE).

A Gapped BlastP sequence alignment showed that SEQ ID NO:9 (306 amino acids) has about 53% identity from amino acids 6-306 with a protein from *Lactobacillus helveticus* that is an aminopeptidase E (Accession No. sp|P94870|PEPE_LACHE), about 51% identity from amino acids 7-306 with a protein from *Lactobacillus delbrueckii* that is an aminopeptidase G (Accession No. sp|P94869|PEPG_LACDL), about 50% identity from amino acids 6-305 with a protein from *Lactobacillus delbrueckii* that is an aminopeptidase W (Accession No. sp|P94868|PEPW_LACDL), about 43% identity from amino acids 4-305 with a protein from *Lactobacillus helveticus* that is an aminopeptidase C (bleomycin hydrolase) (Accession No. sp|Q10744|PEPC_LACHE), and about 43% identity from amino acids 4-305 with a protein from *Lactobacillus delbrueckii* that is an aminopeptidase C (bleomycin hydrolase) (Accession No. sp|Q48543|PEPC_LACDL).

A Gapped BlastP sequence alignment showed that SEQ ID NO:11 (445 amino acids) has about 91% identity from amino acids 8-445 with a protein from *Lactobacillus helveticus* that is an aminopeptidase E (Accession No. sp|P94870|PEPE_LACHE), about 72% identity from amino acids 8-445 with a protein from *Lactobacillus delbrueckii* that is an aminopeptidase G (Accession No. sp|P94869|PEPG_LACDL), about 61% identity from amino acids 8-444 with a protein from *Lactobacillus delbrueckii* that is an aminopeptidase W (Accession No. sp|P94868|PEPW_LACDL), about 41% identity from amino acids 8-444 with a protein from *Lactobacillus delbrueckii* that is an aminopeptidase C (bleomycin hydrolase) (Accession No. sp|Q48543|PEPC_LACDL), and about 42% identity from amino acids 8-429 with a protein from *Lactobacillus helveticus* that is an aminopeptidase C (bleomycin hydrolase) (Accession Nos. gb|AAA25250.1; L26223).

A Gapped BlastP sequence alignment showed that SEQ ID NO:13 (194 amino acids) has about 95% identity from amino acids 1-194 with a protein from *Lactobacillus helveticus* that is a dipeptidase (Accession Nos. emb|CAA86210.1; Z38063), about 95% identity from amino acids 1-194 with a protein from *Lactobacillus helveticus* that is a dipeptidase A (Accession No. sp|Q48558|PEDA_LACHE), about 45% identity from amino acids 2-194 with a protein from *Lactococcus lactis* subsp. *lactis* that is a dipeptidase (Accession Nos. NP_267714.1; NC_002662), about 42% identity from amino acids 2-194 with a protein from *Lactococcus lactis* subsp. *lactis* that is a dipeptidase (Accession Nos. NP_266408.1; NC_002662), and about 41% identity from amino acids 2-194 with a protein from *Streptococcus pyogenes* that is homologous to a dipeptidase (Accession Nos. NP_606948.1; NC_003485).

A Gapped BlastP sequence alignment showed that SEQ ID NO:15 (280 amino acids) has about 93% identity from amino acids 1-252 with a protein from *Lactobacillus helveticus* that is a dipeptidase (Accession Nos. emb|CAA86210.1; Z38063), about 93% identity from amino acids 1-252 with a protein from *Lactobacillus helveticus* that is a dipeptidase A (Accession No. sp|Q48558|PEDA_LACHE), about 61% identity from amino acids 2-251 with a protein from *Lactococcus lactis* subsp. *lactis* that is a dipeptidase (Accession Nos. NP_267714.1; NC_002662), about 65% identity from amino acids 6-252 with a protein from *Lactococcus lactis* subsp. *lactis* that is a dipeptidase (Accession Nos. NP_266408.1; NC_002662), and about 54% identity from amino acids 1-252 with a protein from *Streptococcus pyogenes* that is homologous to a dipeptidase (Accession Nos. NP_606948.1; NC_003485).

A Gapped BlastP sequence alignment showed that SEQ ID NO:17 (229 amino acids) has about 38% identity from amino acids 30-113 with a protein from *Caulobacter crescentus* that is a prepilin peptidase (Accession Nos. NP_419003.1; NC_002696), about 27% identity from amino acids 1-198 with a protein from *Clostridium perfringens* that is homologous to a prepilin peptidase (Accession Nos. NP_563203.1; NC_003366), about 27% identity from amino acids 4-219 with a protein from *Thermotoga maritima* that is a type IV prepilin peptidase (Accession Nos. NP_229496.1; NC_000853), about 32% identity from amino acids 6-115 with a protein from *Aquifex aeolicus* that is a type 4 prepilin peptidase (Accession Nos. NP_214100.1; NC_000918), and about 24% identity from amino acids 36-226 with a protein from *Escherichia coli* that is a prepilin peptidase (Accession Nos. gb|AAL10690.1; AY056599).

A Gapped BlastP sequence alignment showed that SEQ ID NO:19 (449 amino acids) has about 90% identity from amino acids 1-449 with a protein from *Lactobacillus helveticus* that is an aminopeptidase C (bleomycin hydrolase) (Accession No. sp|Q10744|PEPC_LACHE), about 90% identity from amino acids 1-434 with a protein from *Lactobacillus helveticus* that is an aminopeptidase C (Accession Nos. gb|AAA25250.1; L262236), about 76% identity from amino acids 1-449 with a protein from *Lactobacillus delbrueckii* that is an aminopeptidase C (bleomycin hydrolase) (Accession No. sp|Q48543|PEPC_LACDL), about 51% identity from amino acids 5-446 with a protein from *Streptococcus thermophilus* that is an aminopeptidase C (bleomycin hydrolase) (Accession No. sp|Q56115|PEPC_STRTR), and about 52% identity from amino acids 23-446 with a protein from *Streptococcus pyogenes* that is homologous to a cysteine aminopeptidase C (Accession Nos. NP_269696.1; NC_002737).

A Gapped BlastP sequence alignment showed that SEQ ID NO:21 (244 amino acids) has about 40% identity from amino acids 1-182 with a hypothetical protein from *Enterococcus faecalis* (Accession Nos. emb|CAA76861.1; Y17797), about 32% identity from amino acids 1-244 with a protein from *Streptococcus pyogenes* that is homologous to a glycoprotein endopeptidase (Accession Nos. NP_607937.1;

NC_003485), about 33% identity from amino acids 1-244 with a protein from *Streptococcus pyogenes* that is homologous to a glycoprotein endopeptidase (Accession Nos. NP_269867.1; NC_002737), about 32% identity from amino acids 1-234 with a conserved hypothetical protein from *Streptococcus pneumoniae* (Accession Nos. NP_357723.1; NC_003098), and about 30% identity from amino acids 1-234 with a conserved hypothetical protein from *Streptococcus pneumoniae* (Accession Nos. NP_344673.1; NC_003028).

A Gapped BlastP sequence alignment showed that SEQ ID NO:23 (349 amino acids) has about 57% identity from amino acids 5-339 with a protein from *Streptococcus pneumoniae* that is a secreted metalloendopeptidase Gcp (Accession Nos. NP_357725.1; NC_003098), about 57% identity from amino acids 5-339 with a protein from *Streptococcus pneumoniae* that is a glycoprotease family protein (Accession Nos. NP_344675.1; NC_003028), about 56% identity from amino acids 4-341 with a protein from *Listeria monocytogenes* that is homologous to a glycoprotein endopeptidase (Accession Nos. NP_465599.1; NC_003210), about 56% identity from amino acids 4-341 with a protein from *Listeria innocua* that is homologous to a glycoprotein endopeptidase (Accession Nos. NP_471514.1; NC_003212), and about 56% identity from amino acids 6-339 with a protein from *Streptococcus pyogenes* that is homologous to a glycoprotein endopeptidase (Accession Nos. NP_607935.1; NC_003485).

A Gapped BlastP sequence alignment showed that SEQ ID NO:25 (368 amino acids) has about 92% identity from amino acids 1-368 with a protein from *Lactobacillus helveticus* that is a Xaa-Pro dipeptidase (X-Pro dipeptidase) (proline dipeptidase) (Accession No. sp|O84913|PEPQ_LACHE), about 73% identity from amino acids 1-368 with a protein from *Lactobacillus delbrueckii* that is a Xaa-Pro (X-Pro dipeptidase) (proline depeptidase) (Accession No. sp|P46545|PEPQ_LACDL), about 73% identity from amino acids 1-368 with a protein from *Lactobacillus delbrueckii* subsp. *bulgaricus* that is an Xaa-Pro dipeptidase (X-Pro dipeptidase) (Proline dipeptidase) (Accession No. sp|Q9S6S1|PEPQ_LACDE), about 72% identity from amino acids 1-368 with a protein from *Lactobacillus delbrueckii* that is a prolidase (Accession Nos. emb|CAB07978.1; Z93944), and about 57% identity from amino acids 3-366 with a protein from *Lactobacillus pentosus* that is a PepQ (Accession Nos. gb|AAD53120.1; AF176799).

A Gapped BlastP sequence alignment showed that SEQ ID NO:27 (275 amino acids) has about 52% identity from amino acids 1-261 with a protein from *Listeria innocua* that is homologous to a methionine aminopeptidase (Accession Nos. NP_471156.1; NC_003212), about 50% identity from amino acids 1-261 with a protein from *Listeria monocytogenes* that is homologous to a methionine aminopeptidase (Accession Nos. NP_465234.1; NC_003210), about 47% identity from amino acids 1-257 with a protein from *Streptococcus pneumoniae* that is a methionine aminopeptidase, type I (Accession Nos. NP_345557.1; NC_003028), about 45% identity from amino acids 1-257 with a protein from *Lactococcus lactis* subsp. *lactis* that is a methionine aminopeptidase (Accession Nos. NP_266768.1; NC_002662), and about 44% identity from amino acids 1-257 with a protein from *Streptococcus pyogenes* that is homologous to a methionine aminopeptidase (Accession Nos. NP_269461.1; NC_002737).

A Gapped BlastP sequence alignment showed that SEQ ID NO:29 (437 amino acids) has about 64% identity from amino acids 7-436 with a protein from *Lactobacillus helveticus* that is a aminopeptidase E (Accession No. sp|P94870|PEPE_LACHE), about 63% identity from amino acids 7-436 with a protein from *Lactobacillus delbrueckii* that is an aminopeptidase G (Accession No. sp|P94869|PEPG_LACDL), about 55% identity from amino acids 4-436 with a protein from *Lactobacillus delbrueckii* that is an aminopeptidase W (Accession No. sp|P94868|PEPW_LACDL), about 42% identity from amino acids 4-437 with a protein from *Lactobacillus delbrueckii* that is an aminopeptidase C (bleomycin hydrolase) (Accession No. sp|Q48543|PEPC_LACDL), and about 42% identity from amino acids 4-418 with a protein from *Lactobacillus helveticus* that is an aminopeptidase C (Accession Nos. gb|AAA25250.1; L26223).

A Gapped BlastP sequence alignment showed that SEQ ID NO:31 (467 amino acids) has about 86% identity from amino acids 1-467 with a protein from *Lactobacillus helveticus* that is a carnosinase (Accession Nos. gb|AAC24967.1; AF012085), about 73% identity from amino acids 1-466 with a protein from *Lactobacillus delbrueckii* that is an Xaa-His dipeptidase (X-His dipeptidase) (Aminoacyl-histidine) (Accession No. sp|P45494|PEPV_LACDL), about 47% identity from amino acids 3-465 with a protein from *Streptococcus pyogenes* that is homologous to a dipeptidase (Accession Nos. NP_269236.1; NC_002737), about 47% identity from amino acids 3-465 with a protein from *Streptococcus pyogenes* that is homologous to a dipeptidase (Accession Nos. NP_607175.1; NC_003485), and about 46% identity from amino acids 3-449 with a protein from *Streptococcus pneumoniae* that is a dipeptidase (Accession Nos. NP_345135.1; NC_003028).

A Gapped BlastP sequence alignment showed that SEQ ID NO:33 (167 amino acids) has about 49% identity from amino acids 17-156 with a protein from *Streptococcus pyogenes* that is homologous to a prolipoprotein signal peptidase (Accession Nos. NP_269038.1; NC_002737), about 49% identity from amino acids 17-156 with a protein from *Streptococcus pyogenes* that is homologous to a prolipoprotein signal peptidase (Accession Nos. NP_607041.1; NC_003485), about 43% identity from amino acids 15-165 with a protein from *Lactococcus lactis* subsp. *lactis* that is a lipoprotein signal peptidase (EC 3.4.23.36) (Accession Nos. NP_267153.1; NC_002662), about 40% identity from amino acids 20-157 with a protein from *Streptococcus pneumoniae* that is a lipoprotein signal peptidase (Accession Nos. NP_345412.1; NC_003028), and about 37% identity from amino acids 15-165 with a protein from *Lactococcus lactis* subsp. *cremoris* that is a lipoprotein signal peptidase (prolipoprotein signal peptidase) (Accession No. sp|Q48729|LSPA_LACLC).

A Gapped BlastP sequence alignment showed that SEQ ID NO:37 (415 amino acids) has about 93% identity from amino acids 1-413 with a protein from *Lactobacillus helveticus* that is a tripeptidase (Accession Nos. emb|CAB72938.1; AJ243321), about 55% identity from amino acids 1-413 with a protein from *Lactococcus lactis* that is a peptidase T (aminotripeptidase) (tripeptidase) (Accession No. sp|P42020|PEPT_LACLC), about 55% identity from amino acids 1-410 with a protein from *Lactococcus lactis* subsp. *lactis* that is a tripeptidase (Accession Nos. NP_267967.1; NC_002662), about 53% identity from amino acids 1-402 with a protein from *Streptococcus pneumoniae* that is a aminotripeptidase (tripeptidase) (Accession Nos. NP_358507.1; NC_003098), and about 53% identity from amino acids 1-402 with a protein from *Streptococcus pneumoniae* that is a peptidase T (Accession Nos. NP_345484.1; NC_003028).

A Gapped BlastP sequence alignment showed that SEQ ID NO:39 (647 amino acids) has about 85% identity from amino acids 1-647 with a protein from *Lactobacillus helveticus* that is a neutral endopeptidase (endopeptidase O) (Accession No. sp|O52071|PEPO_LACHE), about 57% identity from amino acids 7-647 with a protein from *Lactobacillus helveticus* that is an endopeptidase O₂ (Accession Nos. gb|AAL73136.1; AF321529), about 39% identity from amino acids 24-647 with a protein from *Lactococcus lactis* subsp. *lactis* that is an endopeptidase PepO (EC 3.4.-.-) (Accession No. pir||F53290), about 38% identity from amino acids 24-647 with a protein from *Lactococcus lactis* subsp. *lactis* that is a neutral endopeptidase (Accession Nos. NP_267960.1; NC_002662), and about 37% identity from amino acids 24-647 with a protein from *Streptococcus pneumoniae* that is an endopeptidase 0 (Accession Nos. NP_359084.1; NC_003098).

A Gapped BlastP sequence alignment showed that SEQ ID NO:41 (208 amino acids) has about 61% identity from amino acids 9-204 with a protein from *Bacillus subtilis* that is a transcriptional regulator (Accession Nos. NP_389668.1; NC_000964), about 58% identity from amino acids 9-205 with a protein from *Listeria innocua* that is homologous to an SOS response regulator (lexA) (Accession Nos. NP_470676.1; NC_003212), about 57% identity from amino acids 9-205 with a protein from *Listeria monocytogenes* that is homologous to an SOS response regulator (lexA) (Accession Nos. NP_464827.1; NC_003210), about 59% identity from amino acids 9-204 with a protein from *Staphylococcus aureus* that is a LexA repressor (Accession No. sp|Q9L4P1|LEXA_STAAU), and about 59% identity from amino acids 9-204 with a protein from *Staphylococcus aureus* that is a LexA protein (Accession Nos. gb|AAK52314.1; AY033082).

A Gapped BlastP (version) sequence alignment showed that SEQ ID NO:43 (487 amino acids) has about 50% identity from amino acids 17-487 with a protein from *Lactobacillus sakei* that is homologous to a dipeptidase (Accession No. sp|Q48841|PEPD_LACSK), about 41% identity from amino acids 20-485 with a protein from *Lactococcus lactis* subsp. *lactis* that is a dipeptidase (Accession Nos. NP_267714.1; NC_002662), about 42% identity from amino acids 21-483 with a protein from *Lactobacillus helveticus* that is a dipeptidase (Accession Nos. emb|CAA86210.1; Z38063), 42% identity from amino acids 21-483 with a protein from *Lactobacillus helveticus* that is a dipeptidase A (Accession No. sp|Q48558|PEDA_LACHE) and 38% identity from amino acids 20-485 with a protein from *Streptococcus pyogenes* that is homologous to a dipeptidase (Accession Nos. NP_606948.1; NC_003485).

A Gapped BlastP sequence alignment showed that SEQ ID NO:45 (369 amino acids) has about 40% identity from amino acids 13-366 with a protein from *Bacillus halodurans* that is a Xaa-Pro dipeptidase (Accession Nos. NP_243666.1; NC_002570), about 41% identity from amino acids 13-363 with a protein from *Thermotoga maritima* that is homologous to an aminopeptidase P (Accession Nos. NP_227858.1; NC_000853), about 41% identity from amino acids 13-367 with a protein from *Staphylococcus aureus* subsp. *aureus* that is an Xaa-Pro dipeptidase (Accession Nos. NP_374643.1; NC_002745), about 37% identity from amino acids 14-367 with a protein from *Bacillus subtilis* that is homologous to an Xaa-Pro dipeptidase (Accession Nos. NP_390326.1; NC_000964), and about 38% identity from amino acids 13-367 with a protein from *Listeria innocua* that is homologous to an aminopeptidase P (Accession Nos. NP_470727.1; NC_003212).

A Gapped BlastP sequence alignment showed that SEQ ID NO:47 (193 amino acids) has about 28% identity from amino acids 3-193 with a protein from *Bacillus halodurans* that is an aryldialkylphosphatase (Accession Nos. NP_243801.1; NC_002570), about 31% identity from amino acids 49-193 with a protein from Methanothermobacter thermautotrophicus that is homologous to an aryldialkylphosphatase (Accession Nos. NP_276647.1; NC_000916), about 35% identity from amino acids 49-193 with a protein from *Caulobacter crescentus* that is homologous to an Xaa-Pro dipeptidase (Accession Nos. NP_421471.1; NC_002696), about 30% identity from amino acids 32-193 with a protein from *Sulfolobus solfataricus* that is an prolidase (Xaa-Pro dipeptidase) (Accession Nos. NP_343867.1; NC_002754), and about 30% identity from amino acids 18-193 with a protein from *Sulfolobus solfataricus* that is a prolidase (Xaa-Pro dipeptidase) (Accession Nos. NP_343436.1; NC_002754).

A Gapped BlastP sequence alignment showed that SEQ ID NO:48 (198 amino acids) has about 36% identity from amino acids 3-186 with a protein from *Caulobacter crescentus* that is homologous to an Xaa-Pro dipeptidase (Accession Nos. NP_419119.1; NC_002696), about 37% identity from amino acids 2-185 with a protein from *Caulobacter crescentus* that is homologous to an Xaa-Pro dipeptidase (Accession Nos. NP_421471.1; NC_002696), about 33% identity from amino acids 1-198 with a protein from *Bacillus halodurans* that is an aryldialkylphosphatase (Accession Nos. NP_243801.1; NC_002570), about 37% identity from amino acids 2-188 with a protein from *Caulobacter crescentus* that is homologous to an Xaa-Pro dipeptidase (Accession Nos. NP_421919.1; NC_002696), and about 35% identity from amino acids 2-195 with a protein from *Sulfolobus solfataricus* that is a prolidase (Xaa-Pro dipeptidase) (Accession Nos. NP_343867.1; NC_002754).

A Gapped BlastP sequence alignment showed that SEQ ID NO:50 (793 amino ACIDS) has about 69% identity from amino acids 1-793 with a protein from *Lactobacillus delbrueckii* subsp. *lactis* that is an Xaa-Pro dipeptidyl-peptidase (X-Pro dipeptidyl-peptidase) (Accession No. sp|P40334|PEPX_LACDL), about 68% identity from amino acids 7-793 with a protein from *Lactobacillus delbrueckii* that is an X-prolyl dipeptidyl aminopeptidase (Accession Nos. emb|CAB38074.1; AJ012302), about 91% identity from amino acids 1-793 with a protein from *Lactobacillus helveticus* that is a PepX protein (Accession Nos. gb|AAB50275.1; U22900), about 91% identity from amino acids 1-793 with a protein from *Lactobacillus helveticus* that is an X-prolyl dipeptidyl aminopeptidase (Accession Nos. emb|CAA88273.1; Z48236), and about 40% identity from amino acids 1-788 with a protein from *Lactobacillus rhamnosus* that is an X-Pro dipeptidyl-peptidase (EC 3.4.14.11) (Accession No. pir||T46737).

A Gapped BlastP sequence alignment showed that SEQ ID NO:52 (1627 amino acids) has about 30% identity from amino acids 364-979 with a protein from *Lactococcus lactis* subsp. *cremoris* that is a PrtP precursor (Accession No. gb|AAK27981.1; AF247159), about 30% identity from amino acids 350-979 with a protein from *Lactobacillus paracasei* that is an PII-type proteinase precursor (lactocepin) (cell wall-associated serine proteinase) (Accession No. sp|Q02470|P2P_LACPA), about 30% identity from amino acids 350-979 with a protein from *Lactococcus lactis* subsp. *cremoris* that is a PII-type proteinase precursor (lactocepin) (cell wall-associated serine proteinase) (Accession No. sp|P15293|P2P_LACLC), about 30% identity from amino acids 350-979 with a protein from *Lactococcus lactis* subsp. *cremoris* that is a PI-type proteinase precursor (cell wall-associated serine proteinase) (Accession No. sp|P16271|PIP_LACLC), and about 30% identity from amino acids 350-979 with a protein from *Lactococcus lactis* subsp. *cremoris* that is a lactocepin (EC 3.4.21.96) precursor (Accession No. pir||B45764).

A Gapped BlastP sequence alignment showed that SEQ ID NO:54 (427 amino acids) has about 48% identity from amino acids 9-408 with a protein from *Fusobacterium nucleatum* subsp. *nucleatum* that is a peptidase T (Accession Nos. NP_603630.1; NC_003454), about 44% identity from amino acids 11-408 with a protein from *Clostridium acetobutylicum* that is a peptidase T (aminotripeptidase) (Accession Nos. NP_347116.1; NC_003030), about 45% identity from amino acids 6-408 with a protein from *Clostridium perfringens* that is homologous to an aminotripeptidase (Accession Nos. NP_560941.1; NC_003366), about 45% identity from amino acids 9-408 with a protein from *Streptococcus pneumoniae* that is an aminotripeptidase (tripeptidase) (Accession Nos. NP_358507.1; NC_003098), and about 45% identity from amino acids 9-407 with a protein from *Streptococcus pneumoniae* that is a peptidase T (Accession Nos. NP_345484.1; NC_003028).

A Gapped BlastP sequence alignment showed that SEQ ID NO:56 (510 amino acids) has about 31% identity from amino acids 127-376 with a protein from *Streptomyces coelicolor* that is homologous to a metallopeptidase (Accession Nos. emb|CAC16707.1; AL450289), about 24% identity from amino acids 235-484 with a protein from *Rattus norvegicus* that is a leucyl-specific aminopeptidase PILS (Accession Nos. NP_110463.1; NM_030836), about 22% identity from amino acids 287-498 with a protein from *Xylella fastidiosa* that is an aminopeptidase N (Accession Nos. NP_298777.1; NC_002488), about 24% identity from amino acids 235-484 with a protein from *Rattus norvegicus* that is an aminopeptidase PILS (Accession Nos. gb|AAF73106.1; AF148323), and about 25% identity from amino acids 306-495 with a protein from *Caenorhabditis elegans* that is a peptidase (Accession Nos. NP_502335.1; NM_069934).

A Gapped BlastP sequence alignment showed that SEQ ID NO:58 (432 amino acids) has about 39% identity from amino acids 5-430 with a protein from *Bacillus subtilis* that is a D-alanyl-D-alanine carboxypeptidase (penicillin-binding protein) (Accession Nos. NP_387891.1; NC_000964), about 37% identity from amino acids 46-430 with a protein from *Bacillus stearothermophilus* that is a D-alanyl-D-alanine carboxypeptidase precursor (DD-peptidase) (Accession No. sp|Q05523|DACA_BACST), about 34% identity from amino acids 8-389 with a protein from *Bacillus halodurans* that is a serine-type D-Ala-D-Ala carboxypeptidase (Accession Nos. NP_240887.1; NC_002570), about 40% identity from amino acids 56-430 with a protein from *Bacillus subtilis* that is a penicillin binding protein (Accession No. pir||I39830), and about 37% identity from amino acids 12-382 with a protein from *Lactococcus lactis* subsp. *lactis* that is a D-alanyl-D-alanine carboxypeptidase (Accession Nos. NP_268420.1; NC_002662).

A Gapped BlastP sequence alignment showed that SEQ ID NO:60 (475 amino acids) has about 45% identity from amino acids 6-475 with a protein from *Lactobacillus sakei* that is homologous to a dipeptidase (Accession No. sp|Q48841|PEPD_LACSK), about 42% identity from amino acids 2-473 with a protein from *Lactococcus lactis* subsp. *lactis* that is a dipeptidase (Accession No. NP_267714.1; NC_002662), about 39% identity from amino acids 6-473 with a protein from *Lactococcus lactis* subsp. *lactis* that is a dipeptidase (Accession Nos. NP_266408.1; NC_002662), about 37% identity from amino acids 1-473 with a protein from *Streptococcus pyogenes* that is homologous to a dipeptidase (Accession Nos. NP_606948.1; NC_003485), and about 37% identity from amino acids 1-473 with a protein from *Streptococcus pyogenes* that is homologous to a dipeptidase (Accession Nos. NP_268945.1; NC_002737).

A Gapped BlastP sequence alignment showed that SEQ ID NO:62 (305 amino acids) has about 96% identity from amino acids 1-304 with a protein from *Lactobacillus helveticus* that is a prolinase (Accession Nos. gb|AAA19050.1; U05214), about 96% identity from amino acids 1-304 with a protein from *Lactobacillus helveticus* that is a prolyl aminopeptidase (EC 3.4.11.5) (Accession No. pir||B59088), about 96% identity from amino acids 1-302 with a protein from *Lactobacillus helveticus* that is a prolinase (Accession No. pir||S47276), about 67% identity from amino acids 1-301 with a protein from *Lactobacillus rhamnosus* that is a prolinase (Accession Nos. emb|CAA06029.1; AJ003247), and about 50% identity from amino acids 5-273 with a protein from *Lactobacillus delbrueckii* that is a leucyl aminopeptidase (Accession No. pir||S52201).

A Gapped BlastP sequence alignment showed that SEQ ID NO:64 (598 amino acids) has about 49% identity from amino acids 3-598 with a protein from *Bacillus licheniformis* that is a thimet oligopeptidase (EC 3.4.24.15) (Accession No. pir||T44581), about 49% identity from amino acids 3-598 with a protein from *Bacillus subtilis* that is homologous to an oligoendopeptidase (Accession Nos. NP_389036.1; NC_000964), about 51% identity from amino acids 6-598 with a protein from *Streptococcus pneumoniae* that is a group B oligopeptidase (Accession Nos. NP_358476.1; NC_003098), about 51% identity from amino acids 6-598 with a protein from *Streptococcus pneumoniae* that is an oligoendopeptidase F (Accession Nos. NP_345460.1; NC_003028), and about 49% identity from amino acids 6-598 with a protein from *Lactococcus lactis* that is a oligoendopeptidase F (Accession No. sp|P54124|PEF1_LACLC).

A Gapped BlastP sequence alignment showed that SEQ ID NO:66 (473 amino acids) has about 39% identity from amino acids 12-473 with a protein from *Lactobacillus sakei* that is homologous to a dipeptidase (Accession No. sp|Q48841|PEPD_LACSK), about 35% identity from amino acids 11-470 with a protein from *Lactococcus lactis* subsp. *lactis* that is a dipeptidase (Accession Nos. NP_267714.1; NC_002662), about 34% identity from amino acids 13-470 with a protein from *Lactococcus lactis* subsp. *lactis* that is a dipeptidase (Accession Nos. NP_266408.1; NC_0026628), about 34% identity from amino acids 9-469 with a protein from *Streptococcus pyogenes* that is homologous to a dipeptidase (Accession Nos. NP_606948.1; NC_003485), and about 34% identity from amino acids 9-469 with a protein from *Streptococcus pyogenes* that is homologous to a dipeptidase (Accession Nos. NP_268945.1; NC_002737).

A Gapped BlastP sequence alignment showed that SEQ ID NO:68 (844 amino acids) has about 91% identity from amino acids 1-844 with a protein from *Lactobacillus helveticus* that is a membrane alanyl aminopeptidase (EC 3.4.11.2) (Accession No. pir||S47274), about 91% identity from amino acids 1-844 with a protein from *Lactobacillus helveticus* that is an aminopeptidase N (lysyl aminopeptidase) (Accession No. sp|Q10730|AMPN_LACHE), about 71% identity from amino acids 1-832 with a protein from *Lactobacillus delbrueckii* that is an aminopeptidase N (lysyl aminopeptidase) (Accession No. sp|P37896|AMPN_LACDL), about 49% identity from amino acids 1-839 with a protein from *Lactococcus lactis* that is an aminopeptidase N (lysyl aminopeptidase) (Accession No. sp|P37897|AMPN_LACLC), and about 49% identity from amino acids 1-839 with a protein from *Lactococcus lactis* subsp. *cremoris* that is a lysine aminopeptidase (EC 3.4.11.-) (Accession No. pir∥JN0324).

A Gapped BlastP sequence alignment showed that SEQ ID NO:70 (210 amino acids) has about 33% identity from amino acids 15-208 with a protein from *Staphylococcus aureus* that is a type-1 signal peptidase 1B (Accession Nos. NP_371489.1; NC_002758), about 35% identity from amino acids 21-209 with a protein from *Listeria monocytogenes* that is homologous to a signal peptidase I (Accession Nos. NP_464796.1; NC_003210), about 32% identity from amino acids 5-209 with a protein from *Staphylococcus carnosus* that is a type-I signal peptidase SipB (Accession Nos. gb∥AAD09011.1; AF089862), about 33% identity from amino acids 1-208 with a protein from *Clostridium acetobutylicum* that is a signal peptidase I (Accession Nos. NP_349253.1; NC_003030), and about 34% identity from amino acids 9-210 with a protein from *Lactococcus lactis* subsp. *lactis* that is a signal peptidase I (EC 3.4.21.89) (Accession Nos. NP_268415.1; NC_002662).

A Gapped BlastP sequence alignment showed that SEQ ID NO:72 (301 amino acids) has about 73% identity from amino acids 3-270 with a protein from *Lactobacillus delbrueckii* that is a leucyl aminopeptidase (Accession No. pir∥S52201), about 52% identity from amino acids 6-298 with a protein from *Lactobacillus rhamnosus* that is a prolinase (Accession Nos. emb∥CAA06029.1; AJ003247), about 51% identity from amino acids 6-301 with a protein from *Lactobacillus helveticus* that is a prolyl aminopeptidase (EC 3.4.11.5) (Accession No. pir∥B59088), about 51% identity from amino acids 6-301 with a protein from *Lactobacillus helveticus* that is a prolinase (Accession Nos. gb∥AAA19050.1; U05214), and about 51% identity from amino acids 6-301 with a protein from *Lactobacillus helveticus* that is a prolinase (Accession No. pir∥S47276).

A Gapped BlastP sequence alignment showed that SEQ ID NO:74 (485 amino acids) has about 29% identity from amino acids 101-476 with a protein from *Lactobacillus gasseri* that is homologous to a metal-dependent membrane protease (Accession No. ref∥ZP_00047041.1), about 28% identity from amino acids 101-482 with a protein from *Lactobacillus johnsonii* (Accession No. ref∥NP_964632.1), about 26% identity from amino acids 120-485 with a protein from *Lactobacillus gasseri* that is homologous to a metal-dependent membrane protease (Accession No. ref∥ZP_00046861.1), about 29% identity from amino acids 98-478 with a protein from *Lactobacillus johnsonii* (Accession No. ref∥NP_965449.1), and about 26% identity from amino acids 141-475 with a protein from *Lactobacillus plantarum* that is a membrane-bound protease, CAAX family (Accession No. ref∥NP_786255.1).

A Gapped BlastP sequence alignment showed that SEQ ID NO:76 (264 amino acids) has about 23% identity from amino acids 115-231 with a protein from *Clostridium acetobutylicum* that is homologous to a CAAX-like membrane endopeptidase (Accession Nos. NP_149219.1; NC_001988), about 29% identity from amino acids 78-260 with a protein from *Lactobacillus plantarum* that is a PlnI protein (Accession Nos. emb∥CAA64208.1; X94434), about 21% identity from amino acids 17-217 with a protein from *Clostridium acetobutylicum* that is homologous to a CAAX-like membrane endopeptidase (Accession Nos. NP_347123.1; NC_003030), about 29% identity from amino acids 116-218 with a protein from *Streptomyces coelicolor* that is homologous to a transmembrane protein (Accession No. pir∥T34651), and about 25% identity from amino acids 39-217 with a putative protein from *Arabidopsis thaliana* (Accession Nos. NP_568928.1; NM_125468).

A Gapped BlastP sequence alignment showed that SEQ ID NO:78 (286 amino acids) has about 41% identity from amino acids 5-284 with a protein from *Fusobacterium nucleatum* subsp. *nucleatum* that is a serine protease (Accession Nos. NP_603405.1; NC_003454), about 38% identity from amino acids 5-284 with a protein from *Pasteurella multocida* (Accession Nos. NP_245575.1; NC_002663), about 34% identity from amino acids 8-284 with a protein from *Clostridium acetobutylicum* that is homologous to a phosphoesterase (Accession Nos. NP_349039.1; NC_003030), about 50% identity from amino acids 9-269 with a conserved hypothetical protein from *Clostridium perfringens* (Accession Nos. NP_562255.1; NC_003366), and about 29% identity from amino acids 9-284 with a putative protein from *Corynebacterium glutamicum* that is homologous to an esterase of the alpha-beta hydrolase superfamily (Accession Nos. NP_600371.1; NC_003450).

A Gapped BlastP sequence alignment showed that SEQ ID NO:80 (402 amino acids) has about 25% identity from amino acids 257-392 with a protein from *Lactobacillus plantarum* that is a PlnI protein (Accession Nos. emb∥CAA64208.1; X94434), about 24% identity from amino acids 150-337 with a protein from *Clostridium acetobutylicum* that is homologous to a CAAX-like (SEQ ID NO: 150) membrane endopeptidase (Accession Nos. NP_149219.1; NC_001988), about 26% identity from amino acids 237-339 with a protein from *Yersinia pestis* that is homologous to a membrane protein (Accession Nos. NP_404750.1; NC_003143), about 28% identity from amino acids 225-339 with a conserved hypothetical protein from *Clostridium perfringens* (Accession Nos. NP_561049.1; NC_003366), and about 24% identity from amino acids 261-333 with a protein from *Lactobacillus plantarum* that is a PlnP protein (Accession Nos. emb∥CAA64202.1; X94434).

A Gapped BlastP sequence alignment showed that SEQ ID NO:82 (728 amino acids) has about 62% identity from amino acids 1-728 with a protein from *Lactococcus lactis* subsp. *lactis* that is an ATP-dependent protease ATP-binding subunit (Accession Nos. NP_266713.1; NC_002662), about 62% identity from amino acids 1-728 with a protein from *Lactococcus lactis* that is an ATP-dependent clp protease ATP-binding subunit clpE (Accession No. sp∥Q9S5Z2∥CLPE_LACLC), about 60% identity from amino acids 1-719 with a protein from *Streptococcus pyogenes* that is homologous to an ATP-dependent protease (Accession Nos. NP_607597.1; NC_003485), about 60% identity from amino acids 1-719 with a protein from *Streptococcus pyogenes* that is homologous to an ATP-dependent protease (Accession Nos. NP_269585.1; NC_002737), and about 60% identity from amino acids 1-713 with a protein from *Streptococcus pneumoniae* that is an ATP dependent protease (Accession Nos. NP_358319.1; NC_003098).

A Gapped BlastP sequence alignment showed that SEQ ID NO:84 (410 amino acids) has about 21% identity from amino acids 5-350 with a hypothetical protein from *Staphylococcus aureus* subsp. *aureus* (Accession Nos. NP_371802.1; NC_002758), about 21% identity from amino acids 11-373 with a conserved protein from *Bacillus halodurans* (Accession Nos. NP_243259.1; NC_002570), about 21% identity from amino acids 16-373 with a conserved hypothetical protein from *Streptococcus pneumoniae* (Accession Nos. NP_359621.1; NC_003098), about 25% identity from amino acids 127-352 with a protein from *Mesorhizobium loti* that is a processing protease (Accession Nos. NP_107814.1; NC_002678), and about 21% identity from amino acids 16-373 with a conserved hypothetical protein from *Streptococcus pneumoniae* (Accession Nos. NP_346633.1; NC_003028).

A Gapped BlastP sequence alignment showed that SEQ ID NO:86 (417 amino acids) has about 28% identity from amino acids 26-393 with a protein from *Lactococcus lactis* subsp. *lactis* that is a protease (Accession Nos. NP_268129.1; NC_002662), about 27% identity from amino acids 2-367 with a conserved hypothetical protein from *Streptococcus pneumoniae* (Accession Nos. NP_359620.1; NC_003098), about 25% identity from amino acids 6-414 with a protein from *Streptococcus pneumoniae* that is a peptidase (Accession Nos. NP_346632.1; NC_003028), about 25% identity from amino acids 13-327 with a protein from *Bacillus subtilis* that is homologous to a processing protease (Accession Nos. NP_389568.1; NC_000964), and about 31% identity from amino acids 1-200 with a hypothetical protein from *Staphylococcus aureus* subsp. *aureus* (Accession Nos. NP_371803.1; NC_002758).

A Gapped BlastP sequence alignment showed that SEQ ID NO:88 (197 amino acids) has about 39% identity from amino acids 76-130 with a protein from *Homo sapiens* that is homologous to a YME1-like protein (Accession Nos. XP_064907.1; XM_064907), about 35% identity from amino acids 80-156 with a protein from *Lactobacillus plantarum* that is a PlnI protein (Accession Nos. emb|CAA64208.1; X94434), about 31% identity from amino acids 59-156 with a protein from *Lactobacillus plantarum* that is a PlnP protein (Accession Nos. emb|CAA64202.1; X94434), about 39% identity from amino acids 29-98 with a protein from *Arabidopsis thaliana* (Accession Nos. NP_182197.1; NM_130240), and about 37% identity from amino acids 78-130 with a protein from *Homo sapiens* that is homologous to a YME1-like 1 protein (Accession Nos. gb|AAH07795.1; AAH07795; BC007795).

A Gapped BlastP sequence alignment showed that SEQ ID NO:90 (398 amino acids) has about 35% identity from amino acids 256-360 with a protein from *Lactobacillus plantarum* that is a PlnP protein (Accession Nos. emb|CAA64202.1; X94434), and about 25% identity from amino acids 279-350 with a protein from *Arabidopsis thaliana* (Accession Nos. NP_565483.1; NM_127637).

A Gapped BlastP sequence alignment showed that SEQ ID NO:92 (217 amino acids) has about 24% identity from amino acids 2-216 with a conserved hypothetical protein from *Streptococcus pneumoniae* (Accession Nos. NP_357859.1; NC_003098), about 25% identity from amino acids 5-216 with a conserved hypothetical protein from *Streptococcus pneumoniae* (Accession Nos. NP_344826.1; NC_003098), about 29% identity from amino acids 77-216 with a hypothetical protein from *Streptococcus pneumoniae* (Accession Nos. NP_358420.1; NC_003098), about 29% identity from amino acids 77-216 with a conserved hypothetical protein from *Streptococcus pneumoniae* (Accession Nos. NP_345409.1; NC_003028), and about 31% identity from amino acids 90-217 with a conserved domain protein from *Streptococcus pneumoniae* (Accession Nos. NP_346535.1; NC_003028).

A Gapped BlastP sequence alignment showed that SEQ ID NO:94 (180 amino acids) has about 30% identity from amino acids 53-173 with a protein from *Lactobacillus helveticus* that is a cell envelope-associated proteinase (PrtH) (Accession Nos. gb|AAD50643.1; AF133727), about 26% identity from amino acids 40-172 with a protein from *Lactobacillus helveticus* that is a surface layer protein (Accession Nos. emb|CAB46990.1; AJ388564), about 26% identity from amino acids 40-172 with a protein from *Lactobacillus helveticus* that is a surface layer protein (Accession Nos. emb|CAB46988.1; AJ388562), about 26% identity from amino acids 40-172 with a protein from *Lactobacillus helveticus* that is a surface layer protein (Accession Nos. emb|CAA63409.1; X92752), and about 26% identity from amino acids 40-172 with a protein from *Lactobacillus helveticus* that is a surface layer protein (Accession Nos. emb|CAB46986.1; AJ388560).

A Gapped BlastP sequence alignment showed that SEQ ID NO:96 (66 amino acids) has about 47% identity from amino acids 13-52 with a protein from *Streptococcus thermophilus* that is a cell envelope proteinase (Accession Nos. gb|AAG09771.1; AF243528), about 47% identity from amino acids 17-58 with a protein from *Streptococcus gordonii* that is a surface-associated protein cshA precursor (Accession No. pir||S61441), about 51% identity from amino acids 18-66 with a protein from *Staphylococcus aureus* that is a biofilm-associated surface protein (Accession Nos. gb|AAK38834.1; AF288402), about 53% identity from amino acids 18-59 with a protein from *Staphylococcus aureus* that is a bone sialoprotein-binding protein (Accession Nos. emb|CAB75732.1; Y18653), and about 66% identity from amino acids 18-41 with a protein from *Staphylococcus epidermidis* that is an accumulation-associated protein (Accession Nos. emb|CAB77251.1; AJ249487).

A Gapped BlastP sequence alignment showed that SEQ ID NO:98 (466 amino acids) has about 50% identity from amino acids 3-466 with a protein from *Lactobacillus plantarum* that is a dipeptidase (Accession No. ref|NP_784672.1), about 49% identity from amino acids 3-466 with a protein from *Lactococcus lactis* subsp. *lactis* that is a dipeptidase (Accession No. ref|NP_267714.1), about 49% identity from amino acids 3-466 with a protein from *Pediococcus pentosaceus* that is a dipeptidase (Accession No. ref|ZP_00322734.1), about 53% identity from amino acids 3-438 with a protein from *Oenococcus oeni* that is a dipeptidase (Accession No. ref|ZP_00319585.1), and about 50% identity from amino acids 3-466 with a protein from *Lactobacillus helveticus* that is a dipeptidase (Accession No. emb|CAA86210.1).

A Gapped BlastP sequence alignment showed that SEQ ID NO:100 (298 amino acids) has about 72% identity from amino acids 1-298 with a protein from *Lactobacillus johnsonii* that is homologous to a protease htpX-like protein (Accession No. ref|NP_964092.1), about 72% identity from amino acids 1-298 with a protein from *Lactobacillus gasseri* that is a Zn-dependent protease with chaperone function (Accession No. ref|ZP_00047067.1), about 58% identity from amino acids 1-298 with a protein from *Lactobacillus plantarum* that is a cell surface zinc metalloproteinase (Accession No. ref|NP_784296.1), about 59% identity from amino acids 1-298 with a protein from *Pediococcus pentosaceus* that is a Zn-dependent protease with chaperone function (Accession No. ref|ZP_00323762.1), and about 56% identity from amino acids 1-298 with a protein from *Leuconostoc mesenteroides* subsp. *mesenteroides* that is a Zn-dependent protease with chaperone function (Accession No. ref|ZP_00063838.1).

A Gapped BlastP sequence alignment showed that SEQ ID NO:102 (360 amino acids) has about 91% identity from amino acids 1-358 with a protein from *Lactobacillus johnsonii* (Accession No. ref|NP_964579.1), about 46% identity from amino acids 1-356 with a protein from *Enterococcus faecalis* that is a peptidase, M42 family (Accession No. ref|NP_816356.1), about 32% identity from amino acids 9-352 with a protein from *Staphylococcus epidermidis* that is an endo-1,4-beta-glucanase (Accession No. ref|NP_765585.1), about 32% identity from amino acids 5-358 with a protein from Symbiobacterium thermophilum that is an endo-1,4-beta-glucanase (Accession No. ref|YP_076504.1), and about 33% identity from amino acids 5-358 with a protein from Listeria monocytogenes that is homologous to a peptidase (Accession No. ref|YP_013825.1).

A Gapped BlastP sequence alignment showed that SEQ ID NO:104 (383 amino acids) has about 62% identity from amino acids 9-382 with a protein from Pediococcus pentosaceus that is a Metal-dependent amidase/aminoacylase/carboxypeptidase (Accession No. ref|ZP_00323382.1), about 58% identity from amino acids 3-381 with a protein from Lactobacillus plantarum that is an amino acid amidohydrolase (Accession No. ref|NP_785749.1), about 56% identity from amino acids 3-382 with a protein from Oenococcus oeni that is a Metal-dependent amidase/aminoacylase/carboxypeptidase (Accession No. ref|ZP_00319187.1), about 50% identity from amino acids 4-382 with a protein from Leuconostoc mesenteroides subsp. mesenteroides that is a Metal-dependent amidase/aminoacylase/carboxypeptidase (Accession No. ref|ZP_00063246.1), and about 52% identity from amino acids 4-378 with a protein from Enterococcus faecalis that is a peptidase, M20/M25/M40 family (Accession No. ref|NP_814864.1).

A Gapped BlastP sequence alignment showed that SEQ ID NO:106 (180 amino acids) has about 43% identity from amino acids 5-180 with a protein from Lactobacillus johnsonii (Accession No. ref|NP_964990.1), about 41% identity from amino acids 25-180 with a protein from Lactobacillus gasseri that is homologous to a membrane protein (Accession No. ref|ZP_00046788.2), about 40% identity from amino acids 41-175 with a protein from Lactobacillus helveticus (Accession No. dbj|BAC00953.1), about 41% identity from amino acids 6-180 with a protein from Lactobacillus johnsonii (Accession No. ref|NP_964071.1), and about 38% identity from amino acids 23-180 with a protein from Lactobacillus plantarum that is a lipoprotein precursor (Accession No. ref|NP_785142.1).

A Gapped BlastP sequence alignment showed that SEQ ID NO:108 (202 amino acids) has about 43% identity from amino acids 12-202 with a protein from Lactobacillus gasseri that is homologous to a membrane protein (Accession No. ref|ZP_00046788.2), about 39% identity from amino acids 2-202 with a protein from Lactobacillus johnsonii (Accession No. ref|NP_964071.1), about 32% identity from amino acids 2-202 with a protein from Enterococcus faecalis that is homologous to a lipoprotein (Accession No. ref|NP_816666.1), about 40% identity from amino acids 50-202 with a protein from Lactobacillus johnsonii (Accession No. ref|NP_964990.1), and about 32% identity from amino acids 60-196 with a protein from Lactobacillus helveticus (Accession No. dbj|BAC00953.1).

A Gapped BlastP sequence alignment showed that SEQ ID NO:110 (193 amino acids) has about 53% identity from amino acids 1-193 with a protein from Lactobacillus helveticus (Accession No. dbj|BAC00953.1), about 30% identity from amino acids 16-193 with a protein from Lactobacillus gasseri that is homologous to a membrane protein (Accession No. ref|ZP_00046788.2), about 37% identity from amino acids 54-193 with a protein from Lactobacillus johnsonii (Accession No. ref|NP_964071.1), about 33% identity from amino acids 42-193 with a protein from Lactobacillus johnsonii (Accession No. ref|NP_964990.1), and about 29% identity from amino acids 43-193 with a protein from Lactobacillus plantarum that is a lipoprotein precursor (Accession No. ref|NP_785142.1).

A Gapped BlastP sequence alignment showed that SEQ ID NO:112 (300 amino acids) has about 71% identity from amino acids 1-296 with a protein from Lactobacillus johnsonii that is a protease maturation protein precursor (Accession No. ref|NP_965480.1), about 72% identity from amino acids 1-296 with a protein from Lactobacillus gasseri that is a Parvulin-like peptidyl-prolyl isomerase (Accession No. ref|ZP_00046709.1), about 52% identity from amino acids 5-299 with a protein from Pediococcus pentosaceus that is a Parvulin-like peptidyl-prolyl isomerase (Accession No. ref|ZP_00323213.1), about 50% identity from amino acids 1-299 with a protein from Lactobacillus lactis subsp. cremoris (Accession No. emb|CAA32349.1), and about 49% identity from amino acids 1-299 with a protein from Lactococcus lactis subsp. cremoris that is a PrtM precursor (Accession No. gb|AAK27980.1).

A Gapped BlastP sequence alignment showed that SEQ ID NO:114 (437 amino acids) has about 92% identity from amino acids 1-437 with a protein from Lactobacillus helveticus that is an endopeptidase E2 (Accession No. gb|AAQ72431.1), about 82% identity from amino acids 1-437 with a protein from Lactobacillus johnsonii that is an aminopeptidase C (Accession No. ref|NP_964192.1), about 82% identity from amino acids 1-437 with a protein from Lactobacillus gasseri that is an aminopeptidase C (Accession No. ref|ZP_00047232.2), about 57% identity from amino acids 1-437 with a protein from Lactobacillus gasseri that is an aminopeptidase C (Accession No. ref|ZP_00047230.1), and about 56% identity from amino acids 1-437 with a protein from Lactobacillus johnsonii that is an aminopeptidase C (Accession No. ref|NP_964194.1).

A Gapped BlastP sequence alignment showed that SEQ ID NO:116 (650 amino acids) has about 74% identity from amino acids 7-650 with a protein from Lactobacillus gasseri that is homologous to a metalloendopeptidase (Accession No. ref|ZP_00046938.1), about 73% identity from amino acids 5-650 with a protein from Lactobacillus johnsonii that is an endopeptidase 0 (Accession No. ref|NP_964163.1), about 73% identity from amino acids 5-650 with a protein from Lactobacillus helveticus that is an endopeptidase O3 (Accession No. gb|AAQ72429.1), about 62% identity from amino acids 3-650 with a protein from Lactobacillus helveticus that is an endopeptidase O2 (Accession No. gb|AAL73136.1), and about 59% identity from amino acids 1-650 with a protein from Lactobacillus helveticus that is an endopeptidase O (Accession No. gb|AAC35997.1).

A Gapped BlastP sequence alignment showed that SEQ ID NO:118 (438 amino acids) has about 91% identity from amino acids 1-438 with a protein from Lactobacillus helveticus that is an endopeptidase (Accession No. gb|AAB52540.1), about 72% identity from amino acids 1-438 with a protein from Lactobacillus delbrueckii that is a cysteine aminopeptidase (Accession No. emb|CAA96465.1), about 70% identity from amino acids 1-438 with a protein from Lactobacillus gasseri that is an aminopeptidase C (Accession No. ref|ZP_00047230.1), about 69% identity from amino acids 1-438 with a protein from Lactobacillus johnsonii that is an aminopeptidase C (Accession No. ref|NP_964194.1), and about 63% identity from amino acids 5-437 with a protein from Lactobacillus johnsonii that is an aminopeptidase C (Accession No. ref|NP_965376.1). A Gapped BlastP (version)) sequence alignment showed that SEQ ID NO:120 (473 amino acids) has about 85% identity from amino acids 1-473 with a protein from Lactobacillus gasseri that is a dipeptidase (Accession No. ref|ZP_00047305.1), about 85% identity from amino acids 1-473 with a protein from Lactobacillus johnsonii that is a dipeptidase (Accession No. ref|NP_965320.1), about 58% identity from amino acids 6-473 with a protein from Pediococcus pentosaceus that is a dipeptidase (Accession No. ref|ZP_00323606.1), 57% identity from amino acids 6-473 with a protein from *Lactobacillus plantarum* that is a dipeptidase (Accession No. ref|NP_784146.1) and 50% identity from amino acids 3-473 with a protein from *Pediococcus pentosaceus* that is a dipeptidase (Accession No. ref|ZP_00323346.1).

A Gapped BlastP sequence alignment showed that SEQ ID NO:122 (193 amino acids) has about 40% identity from amino acids 3-190 with a protein from *Leuconostoc mesenteroides* subsp. *mesenteroides* that is in the Imidazolonepropionase and related amidohydrolases COG1228 (Accession No. ref|ZP_00063494.1), about 39% identity from amino acids 2-189 with a protein from *Lactobacillus plantarum* (Accession No. ref|NP_786871.1), about 41% identity from amino acids 9-175 with a protein from *Oceanobacillus iheyensis* that is homologous to an aryldialkylphosphatase (Accession No. ref|NP_691226.1), about 37% identity from amino acids 3-181 with a protein from *Caulobacter crescentus* that is homologous to an Xaa-Pro dipeptidase (Accession No. ref|NP_419119.1), and about 34% identity from amino acids 4-193 with a protein from *Bacillus halodurans* that is an aryldialkylphosphatase (Accession No. ref|NP_243801.1).

A Gapped BlastP sequence alignment showed that SEQ ID NO:124 (505 amino acids) has about 27% identity from amino acids 3-481 with a protein from *Thermoanaerobacter tengcongensis* that is an aminopeptidase N (Accession No. ref|NP_624209.1), about 33% identity from amino acids 122-369 with a protein from *Streptomyces avermitilis* that is homologous to a metallopeptidase (Accession No. ref|NP_821429.1), about 31% identity from amino acids 122-371 with a protein from *Streptomyces coelicolor* that is homologous to a metallopeptidase (Accession No. ref|NP_631646.1), about 24% identity from amino acids 11-480 with a protein from *Chloroflexus aurantiacus* that is an aminopeptidase N (Accession No. ref|ZP_00358219.1), and about 23% identity from amino acids 122-468 with a protein from *Moorella thermoacetica* that is an aminopeptidase N (Accession No. ref|ZP_00329919.1).

A Gapped BlastP sequence alignment showed that SEQ ID NO:126 (470 amino acids) has about 76% identity from amino acids 3-470 with a protein from *Lactobacillus johnsonii* that is homologous to a dipeptidase (Accession No. ref|NP_965710.1), about 76% identity from amino acids 6-470 with a protein from *Lactobacillus gasseri* that is a dipeptidase (Accession No. ref|ZP_00046618.2), about 59% identity from amino acids 9-470 with a protein from *Lactobacillus johnsonii* (Accession No. ref|NP_964598.1), about 49% identity from amino acids 9-470 with a protein from *Lactobacillus plantarum* that is a dipeptidase (Accession No. ref|NP_785290.1), and about 48% identity from amino acids 66-470 with a protein from *Pediococcus pentosaceus* that is a dipeptidase (Accession No. ref|ZP_00323315.1).

A Gapped BlastP sequence alignment showed that SEQ ID NO:128 (299 amino acids) has about 73% identity from amino acids 1-268 with a protein from *Lactobacillus delbrueckii* that is a leucyl aminopeptidase (Accession No. emb|CAA84382.1), about 52% identity from amino acids 4-296 with a protein from *Lactobacillus plantarum* that is a prolyl aminopeptidase (Accession No. ref|NP_784587.1), about 52% identity from amino acids 4-296 with a protein from *Lactobacillus rhamnosus* that is a prolinase (Accession No. emb|CAA06029.1), about 50% identity from amino acids 4-297 with a protein from *Lactobacillus sakei* that is a PepR (Accession No. gb|AAM88886.1), and about 51% identity from amino acids 4-299 with a protein from *Lactobacillus helveticus* that is a prolinase (Accession No. emb|CAA83195.1).

A Gapped BlastP sequence alignment showed that SEQ ID NO:130 (252 amino acids) has about 31% identity from amino acids 15-249 with a protein from *Lactobacillus gasseri* that is homologous to a metal-dependent membrane protease (Accession No. ref|ZP_00047281.1), about 32% identity from amino acids 18-206 with a protein from *Lactobacillus johnsonii* (Accession No. ref|NP_964551.1), about 23% identity from amino acids 103-219 with a protein from *Clostridium acetobutylicum* that is homologous to a CAAX-like membrane endopeptidase (Accession No. ref|NP_149219.1), about 28% identity from amino acids 70-205 with a protein from *Oenococcus oeni* that is homologous to a metal-dependent membrane protease (Accession No. ref|ZP_00320199.1), and about 27% identity from amino acids 43-205 with a protein from *Methanosarcina barkeri* str. *fusaro* that is homologous to a metal-dependent membrane protease (Accession No. ref|ZP_00296469.1).

A Gapped BlastP sequence alignment showed that SEQ ID NO:132 (282 amino acids) has about 59% identity from amino acids 1-282 with a protein from *Lactobacillus johnsonii* (Accession No. ref|NP_964640.1), about 59% identity from amino acids 1-282 with a protein from *Lactobacillus gasseri* that is homologous to an esterase of the alpha-beta hydrolase superfamily (Accession No. ref|ZP_00045972.1), about 41% identity from amino acids 1-280 with a protein from *Streptococcus agalactiae* (Accession No. ref|NP_689045.1), about 41% identity from amino acids 1-280 with a protein from *Mannheimia succiniciproducens* that is an RssA protein (Accession No. ref|YP_087337.1), and about 41% identity from amino acids 1-280 with a protein from *Fusobacterium nucleatum* subsp. *vincentii* that is a serine protease (Accession No. ref|ZP_00143830.1).

A Gapped BlastP sequence alignment showed that SEQ ID NO:134 (404 amino acids) has about 39% identity from amino acids 4-404 with a protein from *Lactobacillus johnsonii* (Accession No. ref|NP_964689.1), about 40% identity from amino acids 4-404 with a protein from *Lactobacillus gasseri* that is homologous to a Zn-dependent peptidase (Accession No. ref|ZP_00047325.1), about 19% identity from amino acids 26-403 with a protein from *Staphylococcus epidermidis* that is homologous to a processing proteinase-like protein (Accession No. ref|NP_764510.1), about 21% identity from amino acids 5-344 with a protein from *Staphylococcus aureus* subsp. *aureus* (Accession No. ref|YP_040665.1), and about 21% identity from amino acids 5-344 with a protein from *Staphylococcus aureus* subsp. *aureus* that is homologous to a processing proteinase (Accession No. ref|NP_645978.1).

A Gapped BlastP sequence alignment showed that SEQ ID NO:147 (80 amino acids) has about 55% identity from amino acids 6-79 with a protein from *Lactobacillus johnsonii* that is a signal peptidase I (Accession No. ref|NP_965146.1), about 52% identity from amino acids 6-75 with a protein from *Lactobacillus gasseri* that is a signal peptidase I (Accession No. ref|ZP_00045871.1), about 52% identity from amino acids 7-75 with a protein from *Lactobacillus gasseri* that is a signal peptidase I (Accession No. ref|ZP_00047480.1), about 50% identity from amino acids 7-75 with a protein from *Lactobacillus johnsonii* that is a signal peptidase I (Accession No. ref|NP_965313.1), and about 31% identity from amino acids 3-79 with a protein from *Enterococcus faecalis* that is a signal peptidase I (Accession No. ref|NP_814596.1).

Example 2

PFAM Results for Amino Acid Sequences

Table 4 shows the top PFAM results for the amino acid sequences of the invention.

All publications, patents and patent applications mentioned in the specification are indicative of the level of those skilled in the art to which this invention pertains. All publications, patents and patent applications are herein incorporated by reference to the same extent as if each individual publication, patent or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

TABLE 1

Proteinases of dairy lactic acid bacteria[a]

| Strain | MW[b] | Substrate | References[c] |
|---|---|---|---|
| *Lc. lactis* subsp. *cremoris* WG2 | 181 | κ-, β-casein | Kok et al. (1988) |
| *Lc. lactis* subsp. *cremoris* HP (1987a) | | κ-, β-casein | Exterkate and De Veer |
| *Lc. lactis* subsp. *cremoris* SK11 | 187 | $\alpha_{s1}$-, κ-, β-casein | Vos et al. (1989) |
| *Lc. lactis* subsp. *cremoris* AC1 | | $\alpha_{s1}$-, κ-, β-casein | Bockelmann et al. (1989) |
| *Lc. lactis* subsp. *cremoris* AM1 | | $\alpha_{s1}$-, κ-, β-casein | Visser et al. (1991) |
| *Lc. lactis* subsp. *cremoris* H2 | 180 | κ-, β-casein | Coolbear et al. (1992) |
| *Lc. lactis* subsp. *cremoris* NCDO763 | 181 | $\alpha_{s1}$-, κ-, β-casein | Kiwaki et al. (1989) |
| *Lb. casei* subsp. *casei* HN1 | | β-casein | Kojic et al. (1991) |
| *Lb. casei* subsp. *casei* NCDO 151 | 181 | | Holck and Naes (1992) |
| *Lb. delbrueckii* subsp. *bulgaricus* CNRZ 397 | 170 | $\alpha_{s1}$-, β-casein | Laloi et al. (1991) |
| *Lb. helveticus* CNRZ 303 | | $\alpha_{s1}$-, β-casein | Zevaco and Gripon (1988) |
| *Lb. helveticus* CP790 | 45 | $\alpha_{s1}$-, β-casein | Yamamoto et al. (1993) |
| *Lb. helveticus* L89 (1994) | 180 | $\alpha_{s1}$-, β-casein | Martin-Hernandez et al. |

[a]Source: Kunji et al. (1996a)
[b](kDa)
[c]Only key references are cited

TABLE 2

Peptidases of lactic acid bacteria[a]

| Peptidase | Strain | MW[b] | Structure | Class[c] | References |
|---|---|---|---|---|---|
| Glutamyl Aminopeptidase (PepA) | *Lc. lactis* | 40 | hexamer | M | Bacon et al. (1994) |
| | *Lc. lactis* | 43 | trimer | M | Exterkate and De Veer (1987b) |
| | *Lc. lactis* | 38 | | | l'Anson et al. (1995) |
| | *Lc. lactis* | 41 | hexamer | M | Niven (1991) |
| | *S. thermophilus* | 45 | octamer | M | Rul et al. (1995) |
| Cysteine Aminopeptidase (PepC) | *Lb. delbrueckii* | 54 | tetramer | C | Wohlrab and Bockelmann (1993) |
| | *Lb. delbrueckii* | 51 | | C | Klein et al. (1994a) |
| | *Lb. helveticus* | 49 | | C | Fernandez et al. (1994) |
| | *Lb. helveticus* | 51 | | C | Vesanto et al. (1994) |
| | *Lb. helveticus* | 50 | tetramer | C | Fernandez de Palencia et al. (1997) |
| | *Lc. lactis* | 50 | hexamer | C | Neviani et al. (1989) |
| | *Lc. lactis* | 50 | | C | Chapot-Chartier et al. (1993) |
| | *Lc. lactis* | 50 | hexamer | | Mistou et al. (1994) |
| | *S. thermophilus* | 50 | hexamer | C | Chapot-Chartier et al. (1994) |
| Aminopeptidase (PepN) | *Lb. casei* | 95 | monomer | M | Fernandez de Palencia et al. (1997) |
| | *Lb. casei* | 87 | monomer | M | Arora and Lee (1992) |
| | *Lb. delbrueckii* | 98 | monomer | M | Tsakalidou et al. (1993) |
| | *Lb. delbrueckii* | 95 | | M | Bockelmann et al. (1992) |
| | *Lb. delbrueckii* | 95 | monomer | M | Klein et al. (1993) |
| | *Lb. helveticus* | 97 | monomer | M | Khalid and Marth (1990a) |
| | *Lb. helveticus* | 96 | | M | Christensen et al. (1995b) |
| | *Lb. helveticus* | 97 | monomer | M | Blanc et al. (1993) |
| | *Lb. helveticus* | 92 | monomer | M | Miyakawa et al. (1992) |
| | *Lb. helveticus* | 95 | monomer | M | Sasaki et al. (1996) |
| | *Lb. helveticus* | 96 | | M | Varmanen et al. (1994) |
| | *Lb. lactis* | 78 | monomer | M | Eggimann and Bachmann (1980) |
| | *Lb. rhamnosus* | 89 | monomer | M | Arora and Lee (1994) |
| | *Lb. sanfranciso* | 75 | monomer | M | Gobbetti et al. (1996) |
| | *Lc. lactis* | 95 | | M | Exterkate et al. (1992) |
| | *Lc. lactis* | 95 | monomer | M | Van Alen-Boerrigter et al. (1991) |
| | *Lc. lactis* | 95 | | M | Stroman (1992) |
| | *Lc. lactis* | 95 | monomer | M | Tan and Konings (1990) |
| | *Lc. lactis* | 95 | | M | Tan et al. (1992) |

TABLE 2-continued

Peptidases of lactic acid bacteria[a]

| Peptidase | Strain | MW[b] | Structure | Class[c] | References |
|---|---|---|---|---|---|
| | Lc. lactis | 85 | | M | Desmazeaud and Zevaco (1979) |
| | S. thermophilus | 92 | monomer | M | Tsakalidou and Kalantzopoulos (1992) |
| | S. thermophilus | 97 | monomer | M | Rul et al. (1994) |
| | S. thermophilus | 98 | monomer | M | Midwinter and Pritchard (1994) |
| | S. thermophilus | 89 | monomer | M | Tsakalidou et al. (1993) |
| Aminopeptidase (PepS) | S. thermophilus | 45 | monomer | M | Fernandez-Espla and Rul (1999) |
| X-Prolyl-Dipeptidyl Aminopeptidase (PepXP) | Lb. acidophilus | 95 | dimer | S | Bockelmann et al. (1991) |
| | Lb. casei | 79 | monomer | S | Habibi-Najafi and Lee (1994) |
| | Lb. curvatus | 98 | dimer | | Magboul and McSweeney (2000) |
| | Lb. delbrueckii | 95 | dimer | S | Bockelmann et al. (1991) |
| | Lb. delbrueckii | 82 | | S | Atlan et al. (1990) |
| | Lb. delbrueckii | 90 | trimer | S | Miyakawa et al. (1991) |
| | Lb. delbrueckii | 88 | monomer | S | Meyer-Barton et al. (1993) |
| | Lb. helveticus | 72 | monomer | S | Khalid and Marth (1990b) |
| | Lb. helveticus | 90 | | S | Yuksel and Steele (1996) |
| | Lb. helveticus | 87 | monomer | S | Miyakawa et al. (1994) |
| | Lb. helveticus | 91 | dimer | S | Vesanto et al. (1995) |
| | Lb. rhamnosus | | | | Varmanen et al. (2000) |
| | Lc. lactis | 90 | dimer | S | Meyer and Jordi (1987) |
| | Lc. lactis | 117 | | S | Booth et al. (1990b) |
| | Lc. lactis | 88 | dimer | | Chich et al. (1995) |
| | Lc. lactis | 88 | | | Nardi et al. (1991) |
| | Lc. lactis | 85 | dimer | S | Zevaco et al. (1990) |
| | Lc. lactis | 88 | dimer | S | Yan et al. (1991) |
| | Lc. lactis | 90 | dimer | S | Kiefer-Partsch et al. (1989) |
| | Lc. lactis | 88 | | | Mayo et al. (1991) |
| | Lc. lactis | 82 | dimer | S | Lloyd and Pritchard (1991) |
| | S. thermophilus | 80 | dimer | S | Tsakalidou et al. (1998) |
| | S. thermophilus | 80 | dimer | S | Meyer and Jordi (1987) |
| Aminopeptidase (PepP) | Lc. lactis | 43 | monomer | M | Mars and Monnet (1995) |
| | Lc. lactis | 46 | | M | Matos et al. (1998) |
| Iminopeptidase (PepI) | Lb. delbrueckii | 33 | | S | Atlan et al. (1994) |
| | Lb. delbrueckii | 34 | trimer | S | Gilbert et al. (1994) |
| | Lb. delbrueckii | 33 | | S | Klein et al. (1994b) |
| | Lb. helveticus | 34 | dimer | S | Varmanen et al. (1996a) |
| | Lc. lactis | 50 | dimer | M | Baankreis and Exterkate (1991) |
| Prolidase (PepQ) | Lb. casei | 41 | monomer | M | Fernandez-Espla and Martin-Hernandez (1997) |
| | Lb. delbrueckii | 41 | dimer | | Morel et al. (1999) |
| | Lb. delbrueckii | 41 | | M | Rantanen and Palva (1997) |
| | Lb. delbrueckii | 41 | | M | Stucky et al. (1995) |
| | Lb. helveticus | 41 | | | Yuksel and Steele (1997a) |
| | Lc. lactis | 42 | | M | Booth et al. (1990a) |
| | Lc. lactis | 43 | | M | Kaminogawa et al. (1984) |
| Prolinase (PepR) | Lb. helveticus | 35 | | | Dudley and Steele (1994) |
| | Lb. helveticus | 33 | tetramer | S | Shao et al. (1997) |
| | Lb. helveticus | 35 | | | Varmanen et al. (1996b) |
| | Lb. rhamnosus | 34 | | | Varmanen et al. (1998) |
| | Lb. curvatus | 32 | dimer | | Magboul and McSweeney (1998) |
| Dipeptidase (Pep D) (PepV) | Lb. helveticus | 53 | | | Dudley et al. (1996) |
| | Lb. helveticus | 53 | octamer | C | Vesanto et al. (1996) |
| | Lb. casei | 46 | monomer | M | Fernandez-Espla and Martin-Hernandez (1997) |
| | Lb. delbrueckii | 51 | monomer | M | Wohlrab and Bockelmann (1992) |
| | Lb. delbrueckii | 52 | monomer | M | Vongerichten et al. (1994) |
| | Lb. helveticus | 51 | | | Yuksel and Steele (1997b) |
| | Lb. helveticus | 50 | | M | Tan et al. (1995) |
| | Lb. sake | 50 | monomer | M | Montel et al. (1995) |
| | Lb. sanfrancisco | 65 | monomer | M | Gobbetti et al. (1996) |
| | Lc. lactis | 100 | | M | Hwang et al. (1981) |
| | Lc. lactis | 51 | | M | Hellendoorn et al. (1997) |
| | Lc. lactis | 49 | monomer | M | Van Boven et al. (1988) |
| | Lc. lactis | 50 | | M | Desmazeaud and Zevaco (1977) |

TABLE 2-continued

Peptidases of lactic acid bacteria[a]

| Peptidase | Strain | MW[b] | Structure | Class[c] | References |
|---|---|---|---|---|---|
| Tripeptidase (PepT) | Lc. lactis | 55 | dimer | M | Bacon et al. (1994) |
| | Lc. lactis | 46 | | | Mierau et al. (1994) |
| | Lc. lactis | 52 | dimer | M | Bosman et al. (1990) |
| Unclassified | Lb. delbrueckii | 29 | trimer | M | Bockelmann et al. (1995) |
| | Lb. delbrueckii | 38 | dimer | M | Bockelmann et al. (1997) |
| | Lb. sake | 55 | monomer | M | Sanz and Toldra (1998) |
| | Lc. lactis | 23 | trimer | | Sahlstrom et al. (1993) |
| | Lc. lactis | 75 | | M | Desmazeaud and Zevaco (1979) |
| | P. pentosaceus | 45 | dimer | M | Simitsopoulou et al. (1997) |
| Endopeptidase (PepO) | Lb. helveticus | 71 | | M | Chen and Steele (1998) |
| | Lc. lactis | 71 | | M | Lian et al. (1996) |
| | Lc. lactis | 71 | | M | Mierau et al. (1993) |
| | Lc. lactis | 70 | monomer | M | Pritchard et al. (1994) |
| | Lc. lactis | 71 | | M | Tynkkynen et al. (1993) |
| (PepE) | Lb. helveticus | 52 | | C | Fenster et al. (1997) |
| (PepF1) | Lc. lactis | 70 | monomer | M | Monnet et al. (1994) |
| | Lc. lactis | 70 | | | Nardi et al. (1997) |
| (PepF2) | Lc. lactis | 70 | | | Nardi et al. (1997) |
| Unclassified | Lb. delbrueckii | 68 | monomer | M | Bockelmann et al. (1996) |
| | Lb. paracasei | 30 | multimer | M | Tobiassen et al. (1997) |
| | Lc. lactis | 98 | monomer | M | Yan et al. (1987) |
| | Lc. lactis | 180 | multimer | M | Baankreis et al. (1995) |
| | Lc. lactis | 40 | dimer | M | Yan et al. (1987) |
| | Lc. lactis | 70 | monomer | M | Baankreis et al. (1995) |
| | Lc. lactis | 70 | monomer | M | Stepaniak and Fox (1995) |
| | Lc. lactis | 52 | multimer | M | Stepaniak et al. (1998) |
| | Lc. lactis | 93 | | M | Muset et al. (1989) |
| | Lc. lactis | 70 | monomer | M | Tan et al. (1991b) |
| | Lc. lactis | 140 | | M | Ohmiya and Sato (1975) |
| | Lc. lactis | 50 | | M | Desmazeaud and Zevaco (1976) |

[a]Source: Christensen et al. (1999)
[b](kDa)
[c]C — cysteine-peptidase; M — metallopeptidase; S — serine-peptidase

TABLE 3

Proteases/Peptidases of the Present Invention

| SEQ ID NO: | ORF NO. | FUNCTION | COG |
|---|---|---|---|
| 1, 2 | 92 | Prolyl aminopeptidase (EC 3.4.11.5) | 0596 |
| 3, 4 | 165 | Neutral endopeptidase (EC 3.4.-.-) | 3590 |
| 5, 6 | 186 | Pyrrolidone carboxyl peptidase (EC 3.4.19.3) | 2039 |
| 7, 8, 9 | 194, 195 | Aminopeptidase G | 3579 |
| 10, 11 | 204 | Aminopeptidase E | 3579 |
| 12, 13 | 235 | Dipeptidase (EC 3.4.13.18) | 4690 |
| 14, 15 | 236 | Dipeptidase (EC 3.4.13.18) | 4690 |
| 16, 17 | 286 | Prepilin peptidase (EC 3.4.99.-) | 1989 |
| 18, 19 | 343 | Aminopeptidase C | 3579 |
| 20, 21 | 388 | Glycoprotein endopeptidase | 1214 |
| 22, 23 | 390 | Endopeptidase (EC 3.4.24.57) | 0533 |
| 24, 25 | 430 | Xaa-pro dipeptidase (EC 3.4.13.9) | 0006 |
| 26, 27 | 623 | Methionine aminopeptidase (ampM) (EC 3.4.11.18) | 0024 |
| 28, 29 | 911 | Aminopeptidase | 3579 |
| 30, 31 | 994 | Aminoacyl-histidine dipeptidase (PepD) (EC 3.4.13.3) | 0624 |
| 32, 33 | 1152 | Lipoprotein signal peptidase A (LspA) (EC3.4.23.36) | 0597 |
| 34, 35 | 1182 | Peptidase | |
| 36, 37 | 1190 | Amino tripeptidase T (EC 3.4.11.-) | 2195 |
| 38, 39 | 1275 | Neutral endopeptidase O (PepO) (EC 3.4.-.-) | 3590 |
| 40, 41 | 1280 | Transcriptional repressor | 1974 |
| 42, 43 | 1294 | Dipeptidase (EC 3.4.13.18) | 4690 |
| 44, 45 | 1336 | X-Pro dipeptidase (EC 3.4.13.9) | 0006 |
| 46, 47, 48 | 1344, 1343 | Aryldialkylphosphatase (PepQ) | 1228 |
| 49, 50 | 1373 | X-Pro dipeptidyl-peptidase (PepX) (EC 3.4.14.11) | |
| 51, 52 | 1512 | PrtP | 1404 |
| 53, 54 | 1515 | Peptidase T | 2195 |
| 55, 56 | 1567 | Aminopeptidase | 0308 |
| 57, 58 | 1603 | d-alanyl-d-alanine carboxypeptidase | |
| 59, 60 | 1646 | Dipeptidase (EC 3.4.13.18) | 4690 |
| 61, 62 | 1658 | Prolyl aminopeptidase (EC 3.4.11.5) | 0596 |
| 63, 64 | 1763 | Oligopeptidase (EC 3.4.24.15) | 1164 |
| 65, 66 | 1837 | Dipeptidase (EC 3.4.13.18) | 4690 |
| 67, 68 | 1849 | Aminopeptidase N (EC 3.4.11.2) | 0308 |
| 69, 70 | 1909 | Signal peptidase I | 0681 |
| 71, 72 | 1957 | Prolyl aminopeptidase (EC 3.4.11.5) | 0596 |
| 73, 74 | 87 | Metal-dependent membrane protease | 1266 |
| 75, 76 | 553 | Metal-dependent membrane protease (PlnI) | 1266 |
| 77, 78 | 601 | Serine protease | 4667 |
| 79, 80 | 604 | Metal-dependent membrane protease (PlnI) | 1266 |
| 81, 82 | 638 | ATPase (ClpE) | 0542 |
| 83, 84 | 660 | Zn-dependent peptidase | 0612 |
| 85, 86 | 661 | Zn-dependent peptidase | 0612 |
| 87, 88 | 1808 | Metal-dependent membrane protease | 1266 |
| 89, 90 | 1810 | Metal-dependent membrane protease | 1266 |
| 91, 92 | 1937 | Metal-dependent membrane protease | 1266 |
| 93, 94 | 1235 | S-layer protein | |
| 95, 96 | 1378 | Biofilm-associated surface protein | |
| 97, 98 | 35 | Dipeptidase (EC 3.4.13.18) | 4690 |
| 99, 100 | 96 | HtpX (EC:3.4.24.-) | 0501 |

TABLE 3-continued

Proteases/Peptidases of the Present Invention

| SEQ ID NO: | ORF NO. | FUNCTION | COG |
|---|---|---|---|
| 101, 102 | 569 | Endo-1,4-beta-glucanase, amino-peptidase (EC3.4.11.-) | 1363 |
| 103, 104 | 853 | Metal-dependent amidase/aminoacylase/carboxypeptidase | 1473 |
| 105, 106 | 1661 | Peptidase | 3212 |
| 107, 108 | 1662 | Peptidase | 3212 |
| 109, 110 | 1667 | Peptidase | 3212 |
| 111, 112 | 1588 | PrtM | 0760 |
| 113, 114 | 195 | Aminopeptidase G | 3579 |
| 115, 116 | 165 | Neutral endopeptidase (EC 3.4.-.-) | 3590 |
| 117, 118 | 204 | Aminopeptidase E | 3579 |
| 119, 120 | 1294 | Dipeptidase (EC 3.4.13.18) | 4690 |
| 121, 122 | 1343 | Aryldialkylphosphatase (PepQ) | 1228 |
| 123, 124 | 1567 | Aminopeptidase | 0308 |
| 125, 126 | 1837 | Dipeptidase (EC 3.4.13.18) | 4690 |
| 127, 128 | 1957 | Prolyl aminopeptidase (EC 3.4.11.5) | 0596 |
| 129, 130 | 553 | Metal-dependent membrane protease (PlnI) | 1266 |
| 131, 132 | 601 | Serine protease | 4667 |
| 133, 134 | 660 | Zn-dependent peptidase | 0612 |
| 146, 147 | 1182 | Signal peptidase I | 0681 |

TABLE 4

PFAM Results for Amino Acid Sequences

| SEQ ID NO: | ORF | Domain | Amino Acid Range Start, Stop | Family | PFAM Accession No. |
|---|---|---|---|---|---|
| 2 | 92 | Abhydrolase_1 | 55, 287 | alpha/beta hydrolase fold | PF00561 |
| 116 | 165 | Peptidase_M13_N | 22, 401 | Peptidase family M13 | PF05649 |
| 116 | 165 | Peptidase_M13 | 458, 647 | Peptidase family M13 | PF01431 |
| 6 | 186 | Peptidase_C15 | 1, 200 | Pyroglutamyl peptidase | PF01470 |
| 114 | 195 | Pept_C1-like | 4, 437 | Peptidase C1-like family | PF03051 |
| 118 | 204 | Pept_C1-like | 4, 438 | Peptidase C1-like family | PF03051 |
| 13 | 235 | Peptidase_U34 | 1, 128 | Peptidase family U34 | PF03577 |
| 15 | 236 | Peptidase_U34 | 5, 280 | Peptidase family U34 | PF03577 |
| 17 | 286 | DiS_P_DiS | 11, 94 | Bacterial Peptidase A24 N-terminal domain | PF06750 |
| 19 | 343 | Pept_C1-like | 4, 443 | Peptidase C1-like family | PF03051 |
| 21 | 388 | Peptidase_M22 | 24, 110 | Glycoprotease family | PF00814 |
| 23 | 390 | Peptidase_M22 | 46, 134 | Glycoprotease family | PF00814 |
| 25 | 430 | Peptidase_M24 | 293, 355 | metallopeptidase family M24 | PF00557 |
| 27 | 623 | Peptidase_M24 | 165, 255 | metallopeptidase family M24 | PF00557 |
| 29 | 911 | Pept_C1-like | 3, 437 | Peptidase C1-like family | PF03051 |
| 31 | 994 | Peptidase_M20 | 20, 465 | Peptidase family M20/M25/M40 | PF01546 |
| 33 | 1152 | Peptidase_A8 | 16, 165 | Signal peptidase (SPase) II | PF01252 |
| 37 | 1190 | Peptidase_M20 | 10, 410 | Peptidase family M20/M25/M40 | PF01546 |
| 39 | 1275 | Peptidase_M13_N | 22, 401 | Peptidase family M13 | PF05649 |
| 39 | 1275 | Peptidase_M13 | 455, 644 | Peptidase family M13 | PF01431 |
| 41 | 1280 | LexA_DNA_bind | 3, 67 | LexA DNA binding domain | PF01726 |
| 41 | 1280 | Peptidase_S24 | 124, 193 | Peptidase S24-like | PF00717 |
| 120 | 1294 | Peptidase_U34 | 6, 405 | Peptidase family U34 | PF03577 |
| 45 | 1336 | Peptidase_M24 | 296, 359 | metallopeptidase family M24 | PF00557 |
| 122 | 1343 | Amidohydro_1 | 1, 168 | Amidohydrolase family | PF01979 |
| 50 | 1373 | Peptidase_S15 | 200, 789 | X-Pro dipeptidyl-peptidase (S15 family) | PF02129 |
| 52 | 1512 | Peptidase_S8 | 192, 531 | Subtilase family | PF00082 |
| 52 | 1512 | DUF1034 | 565, 678 | Domain of Unknown Function (DUF1034) | PF06280 |
| 54 | 1515 | Peptidase_M20 | 13, 412 | Peptidase family M20/M25/M40 | PF01546 |
| 58 | 1603 | Peptidase_S11 | 27, 296 | D-alanyl-D-alanine carboxypeptidase | PF00768 |
| 60 | 1646 | Peptidase_U34 | 5, 407 | Peptidase family U34 | PF03577 |
| 62 | 1658 | Abhydrolase_1 | 56, 291 | alpha/beta hydrolase fold | PF00561 |
| 64 | 1763 | Peptidase_M3 | 202, 584 | Peptidase family M3 | PF01432 |
| 126 | 1837 | Peptidase_U34 | 10, 401 | Peptidase family U34 | PF03577 |
| 68 | 1849 | Peptidase_M1 | 6, 379 | Peptidase family M1 | PF01433 |
| 70 | 1909 | Peptidase_S24 | 41, 107 | Peptidase S24-like | PF00717 |
| 128 | 1957 | Abhydrolase_1 | 53, 286 | alpha/beta hydrolase fold | PF00561 |
| 130 | 553 | Abi | 106, 212 | CAAX amino terminal protease family | PF02517 |
| 132 | 601 | Patatin | 5, 172 | Patatin-like phospholipase | PF01734 |
| 82 | 638 | AAA | 139, 331; 467, 682 | ATPase family associated with various cellular activities (AAA) | PF00004 |
| 134 | 660 | Peptidase_M16_C | 170, 344 | Peptidase M16 inactive domain | PF05193 |
| 86 | 661 | Peptidase_M16 | 19, 158 | Insulinase (Peptidase family M16) | PF00675 |
| 92 | 1937 | Abi | 124, 217 | CAAX amino terminal protease family | PF02517 |
| 96 | 1378 | YSIRK_signal | 13, 39 | YSIRK type signal peptide | PF04650 |
| 98 | 35 | Peptidase_U34 | 2, 404 | Peptidase family U34 | PF03577 |
| 100 | 96 | Peptidase_M48 | 85, 298 | Peptidase family M48 | PF01435 |
| 102 | 569 | Peptidase_M42 | 47, 341 | M42 glutamyl aminopeptidase | PF05343 |
| 104 | 853 | Peptidase_M20 | 6, 381 | Peptidase family M20/M25/M40 | PF01546 |
| 106 | 1661 | PepSY | 119, 178 | Peptidase propeptide and YPEB domain | PF03413 |
| 108 | 1662 | PepSY | 62, 121; 141, 199 | Peptidase propeptide and YPEB domain | PF03413 |

TABLE 4-continued

PFAM Results for Amino Acid Sequences

| SEQ ID NO: | ORF | Domain | Amino Acid Range Start, Stop | Family | PFAM Accession No. |
|---|---|---|---|---|---|
| 110 | 1667 | PepSY | 59, 118; 137, 193 | Peptidase propeptide and YPEB domain | PF03413 |
| 56 | 1567 | Peptidase_M1 | 31, 416 | Peptidase family M1 | PF01433 |
| 74 | 87 | Abi | 327, 433 | CAAX amino terminal protease family | PF02517 |
| 80 | 604 | Abi | 255, 343 | CAAX amino terminal protease family | PF02517 |
| 4 | 165 | Peptidase_M13 | 466, 655 | Peptidase family M13 | PF01431 |
| 8 | 194 | Pept_C1-like | 13, 118 | Peptidase C1-like family | PF03051 |
| 9 | 195 | Pept_C1-like | 1, 306 | Peptidase C1-like family | PF03051 |
| 11 | 204 | Pept_C1-like | 11, 445 | Peptidase C1-like family | PF03051 |
| 72 | 1957 | Abhydrolase_1 | 55, 290 | Alpha/beta hydrolase fold | PF00561 |
| 76 | 553 | Abi | 118, 224 | CAAX amino terminal protease family | PF02517 |
| 78 | 601 | Patatin | 9, 176 | Patatin-like phospholipase | PF01734 |

That which is claimed:

1. An isolated nucleic acid molecule comprising a nucleotide sequence that encodes a polypeptide having at least 95% amino acid sequence identity to the full length amino acid sequence of SEQ ID NO: 56, wherein said polypeptide has aminopeptidase activity.

2. A plasmid comprising a nucleotide sequence that encodes a polypeptide having at least 95% amino acid sequence identity to the full length amino acid sequence of SEQ NO: 56, wherein said polypeptide has aminopeptidase activity.

3. The plasmid of claim 2, further comprising a nucleotide sequence encoding a heterologous polypeptide.

4. A microbial host cell comprising the plasmid of claim 2.

5. The microbial host cell of claim 4, wherein said microbial host cell is a bacterial cell.

6. The microbial host cell of claim 5, wherein said bacterial cell is a lactic acid bacterium.

7. A method for producing a polypeptide, comprising culturing a microbial host cell comprising a heterologous nucleic acid molecule that encodes the polypeptide under conditions in which the nucleic acid molecule is expressed, wherein the polypeptide encoded comprises an amino acid sequence having at least 95% sequence identity to the full length amino acid sequence of SEQ ID NO:56, and wherein the polypeptide has aminopeptidase activity.

8. The isolated nucleic acid molecule of claim 1, wherein said nucleic acid molecule comprises a nucleotide sequence having at least 95% sequence identity to the full length nucleotide sequence of SEQ ID NO: 55.

9. The isolated nucleic acid molecule of claim 1, wherein said nucleic acid molecule comprises the full length nucleotide sequence of SEQ ID NO: 55.

10. The isolated nucleic acid molecule of claim 1, wherein said nucleic acid molecule comprises a nucleotide sequence that encodes a polypeptide having the amino acid sequence set forth in SEQ ID NO: 56.

11. An isolated nucleic acid molecule comprising a nucleotide sequence that hybridizes under stringent conditions to the full length complement of SEQ ID NO:55, wherein said nucleic acid molecule encodes a polypeptide having aminopeptidase activity, wherein said stringent conditions comprise hybridization in 50% formamide, 1M NaCL, 1% SDS at 37° C. and a wash in 0.1×SSC at 60° C. to 65° C.

12. The plasmid of claim 2, wherein said nucleic acid molecule comprises the nucleotide sequence of SEQ ID NO: 55.

13. The plasmid of claim 2, wherein said nucleic acid molecule comprises a nucleotide sequence haying at least 95% sequence identity to the nucleotide sequence of SEQ ID NO: 55.

14. The plasmid of claim 2, wherein said nucleic acid molecule comprises a nucleotide sequence that encodes a polypeptide comprising the amino acid sequence of SEQ ID NO: 56.

15. The microbial host cell of claim 4, wherein said nucleic acid molecule comprises a nucleotide sequence having at least 95% sequence identity to the full length nucleotide sequence of SEQ ID NO: 55.

16. The microbial host cell of claim 4, wherein said nucleic acid molecule comprises the full length nucleotide sequence of SEQ ID NO: 55.

17. The microbial host cell of claim 4, wherein said nucleic acid molecule encodes a polypeptide having the amino acid sequence set forth in SEQ ID NO: 56.

18. A microbial host cell comprising a heterologous nucleic acid molecule that encodes a polypeptide comprising an amino acid sequence having at least 95% sequence identity to the amino acid sequence of SEQ ID NO: 56, wherein said polypeptide has aminopeptidase activity.

19. The microbial host cell of claim 18, wherein said microbial host cell is a bacterial host cell.

20. The microbial host cell of claim 19, wherein said bacterial host cell is a lactic acid bacterium.

21. The microbial host cell of claim 20, wherein said lactic acid bacterium is *Lactobacillus acidophilus*.

22. The microbial host cell of claim 19, wherein said nucleic acid molecule comprises the nucleotide sequence of SEQ ID NO: 55.

23. The microbial host cell of claim 18, wherein said nucleic acid molecule comprises a nucleotide sequence having at least 95% sequence identity to the nucleotide sequence of SEQ ID NO: 55.

24. The microbial host cell of claim 18, wherein said nucleic acid molecule comprises a nucleotide sequence that encodes a polypeptide comprisinng the amino acid sequence of SEQ ID NO: 56.

25. The method of claim 7, wherein said nucleic acid molecule comprises the nucleotide sequence of SEQ ID NO: 55.

26. The method of claim 7, wherein said nucleic acid molecule comprises a nucleotide sequence having at least 95% sequence identity to the nucleotide sequence of SEQ ID NO: 55.

27. The method of claim 7, wherein said nucleic acid molecule comprises a nucleotide sequence that encodes a polypeptide comprising the amino acid sequence of SEQ ID NO: 56.

28. The method of claim 7, wherein said microbial host cell is a bacterial host cell.

29. The method of claim 28, wherein said bacterial host cell is a lactic acid bacterium.

30. The method of claim 29, wherein said lactic acid bacterium is *Lactobacillus acidophilus*.

31. The microbial host cell of claim 6, wherein said lactic acid bacterium is *Lactobacillus acidophilus*.

\* \* \* \* \*